(12) United States Patent
Routier et al.

(10) Patent No.: US 10,906,900 B2
(45) Date of Patent: Feb. 2, 2021

(54) COMPOUNDS FOR USING IN IMAGING AND PARTICULARLY FOR THE DIAGNOSIS OF NEURODEGENERATIVE DISEASES

(71) Applicants: CENTRE NATIONAL DE LA RECHERCHE SCIENTIFIQUE, Paris (FR); UNIVERSITE D'ORLEANS, Orleans (FR); UNIVERSITE DE TOURS, Tours (FR); CENTRE HOSPITALIER REGIONAL UNIVERSITAIRE DE TOURS, Tours (FR); INSERM (INSTITUT NATIONAL DE LA SANTE ET DE LA MEDICALE), Paris (FR)

(72) Inventors: Sylvain Routier, Tigy (FR); Franck Suzenet, La Chapelle St Mesmin (FR); Sylvie Chalon, Saint-Cyr-sur-Loire (FR); Frederic Buron, Orleans (FR); Johnny Vercouillie, Amboise (FR); Ronald Melki, Verseilles (FR); Liliana Boiaryna, Olivet (FR); Denis Guilloteau, Saint-Cyr-sur-Loire (FR); Laura Pieri, Orsay (FR)

(73) Assignees: CENTRE NATIONAL DE LA RECHERCHE SCIENTIFIQUE, Paris (FR); UNIVERSITE D'ORLEANS, Orleans (FR); UNIVERSITE DE TOURS, Tours (FR); CENTRE HOSPITALIER REGIONAL UNIVERSITAIRE DE TOURS, Tours (FR); INSERM (INSTITUT NATIONAL DE LA SANTE ET DE LA RECHERCHE MEDICALE), Paris (FR)

( * ) Notice: Subject to any disclaimer, the term of this patent is extended or adjusted under 35 U.S.C. 154(b) by 0 days.

(21) Appl. No.: 16/336,309

(22) PCT Filed: Sep. 26, 2017

(86) PCT No.: PCT/FR2017/052592
§ 371 (c)(1),
(2) Date: Mar. 25, 2019

(87) PCT Pub. No.: WO2018/055316
PCT Pub. Date: Mar. 29, 2018

(65) Prior Publication Data
US 2019/0211011 A1    Jul. 11, 2019

(30) Foreign Application Priority Data

Sep. 26, 2016  (FR) ..................................... 16 59033
Mar. 10, 2017  (FR) ..................................... 17 52001

(51) Int. Cl.
*C07D 471/04*    (2006.01)

(52) U.S. Cl.
CPC ................................ *C07D 471/04* (2013.01)

(58) Field of Classification Search
CPC ........................... C07D 471/04; C07D 471/14
See application file for complete search history.

(56) References Cited

U.S. PATENT DOCUMENTS

| | | | |
|---|---|---|---|
| 8,491,869 B2* | 7/2013 | Gangadharmath | .. C07D 401/04 424/1.89 |
| 2007/0129364 A1 | 6/2007 | Dong | |
| 2008/0009514 A1 | 1/2008 | Stoit | |
| 2010/0063041 A1 | 3/2010 | Moon | |
| 2011/0144105 A1 | 6/2011 | Berthel | |

FOREIGN PATENT DOCUMENTS

| | | |
|---|---|---|
| WO | 2004031188 A1 | 10/2002 |
| WO | 2005097129 A2 | 4/2004 |
| WO | 2008003736 A2 | 7/2006 |
| WO | 2010111303 A2 | 3/2009 |
| WO | 2011119565 A1 | 3/2010 |

OTHER PUBLICATIONS

Barghorn et al., "Purification of Recombinant Tau Protein and Preparation of Alzheimer-Paired Helical Filaments In Vitro," From: Methods in Molecular Biology, vol. 299: Amyloid Proteins: Methods and Protocols, pp. 35-51.
Chaulet et al., "Desulfonylation of Indoles and 7-Azaindoles Using Sodium tert-Butoxide," Synlett, No. 10, pp. 1481-1484, 2010.
Cheng et al., "Relationship Between the Inhibition Constant (K1) and the Connection of Inhibitor Which Causes 50 Per Cent Inhibition (I50) of an Enzymatic Reaction," Biochemical Pharmacology, vol. 22, pp. 3099-3108, 1973.
Desarbre et al., "Synthesis of 2-Substituted-1H-Pyrrolo[2,3-b]Pyridines: Preparation of 7-Azaolivacine Analogue and 7-Azaindolopyridopyrimidine Derivatives," Tetrahedron, vol. 53, No. 10, pp. 3637-3648, 1997.
Fillaut et al., "Design and Synthesis of Ruthenium Oligothienylacetylide Complexes. New Materials for Acoustically Induced Nonlinear Optics," Organometallics 2005, 24, 687-695.
Ghee et al., "PA700, the regulatory complex of the 26S proteasome, interferes with α-synuclein assembly," FEBS Journal 272 (2005) 4023-4033.
Hands et al., "A Convenient Method for the Preparation of 5-, 6- and 7-Azaindoles and Their Derivatives," Synthesis, Jul. 1996, 877-882.
Herbert et al., "Manipulating the Diastereoselectivity of Ortholithiation in Planar Chiral Ferrocenes," Organic Letters, 2013, vol. 15, No. 12, 3334-3337.

(Continued)

*Primary Examiner* — Michael G. Hartley
*Assistant Examiner* — Jagadishwar R Samala
(74) *Attorney, Agent, or Firm* — Nixon & Vanderhye

(57) ABSTRACT

The invention relates to compounds of formula (II) for using in imaging and particularly for the diagnosis of neurodegenerative diseases.

12 Claims, 2 Drawing Sheets

(56) References Cited

OTHER PUBLICATIONS

Hirose et al., "Self-assembly of amphiphilic fluorescent dyes showing aggregate-induces enhanced emission: temperature dependence of molecular alignment and intermolecular interaction in aqueous environment," Chem. Commun., 2009, 5832-5834.

Joseph et al., "Synthesis of Pyrido[2,3-b]indole Derivatives via Diels-Alder Reactions of 2- and 3-Vinylpyrrolo[2,3-b] pyridines," Tetrahedron 56 (2000) 3189-3196.

Lefoix et al., "Regioselective Metallative Functionalization of 5-Azaindole," Synfacts 2006, 3, 0203-0203.

Levine, "Thioflavine T interaction with synthetic Alzheimer's disease β-amyloid peptides: Detection of amyloid aggregation in solution," Protein Science (1993), 2, 404-410.

Liu et al., "Syntheses, Structures, and Electroluminescence of New Blue/Green Luminescent Chelate Compounds: Zn(2-py-in)2(THF), BPh2(2-py-in), Be(2-py-in)2, and BPh2(2-py-aza) [2-py-in=2-(2-pyridyl)indole; 2-py-aza=2-(2-pyridyl)-7-azaindole]," J. Am. Chem. Soc. 2000, 122, 3671-3678.

Liu et al., "Design, synthesis and biological evaluation of 1H-pyrrolo[2,3-b]pyridine and 1H-pyrazolo[3,4-b]pyridine derivatives as c-Met inhibitors," Bioorganic Chemistry, 2016.

Maia et al., "Longitudinal and Parallel Monitoring of Neuroinflammation and Neurodegeneration in a 6-Hydroxydopamine Rat Model of Parkinson's Disease," Synapse 2012.

Minakata et al., "Regioselective Functionalization of 1H-Pyrrolo[2,3-b]pyridine via Its N-Oxide," Synthesis, Jul. 1992, pp. 661-663.

Ouach et al., "Design of α7 nicotinic acetylcholine receptor ligands using the (het) Aryl-1,2,3-triazole core: Synthesis, in vitro evaluation and SAR studies," European Journal of Medicinal Chemistry 107 (2016) 1536-164.

Sakai et al., "Colorimetric Detection of Anions in Aqueous Solution Using Poly(phenylacetylene) with Sulfonamide Receptors Activated by Electron Withdrawing Group," Macromolecules, 2012, 45, pp. 8221-8227.

Serriere et al., "In vivo PET quantification of the dopamine transported in rat brain with [18F]LBT-999," Nuclear Medicine and Biology 41 (2014) 106-113.

Serriere et al., "Amyloid load and TSPO in APPswePS1-dE9 mice: a longitudinal study," Neurobiology of Aging 2015.

Stoit et al., "7-Azaindole derivatives as potential partial nicotinic agonists," Bioorganic & Medicinal Chemistry Letters 18 (2008) 188-193.

Tung et al., "Scaffold-Hopping Strategy: Synthesis and Biological Evaluation of 5,6-Fused Bicyclic Heteroaromatics to Identify Orally Bioavailable Anticancer Agents," Journal of Medicinal Chemistry 2011, 54, 3076-3080.

Udenfriend et al., "Fluorescamine: A Reagent for Assay of Amino Acids, Peptides, and Primary Amines in the Picomole Range," Science, vol. 178, pp. 871-872, 1972.

Walsh et al., "A facile method for expression and purification of the Alzheimer's disease-associated amyloid β-peptide," FEBS Journal 276 (2009) 1266-1281.

International Search Report, dated Nov. 16, 2017, from corresponding PCT/FR2017/052592 application.

* cited by examiner

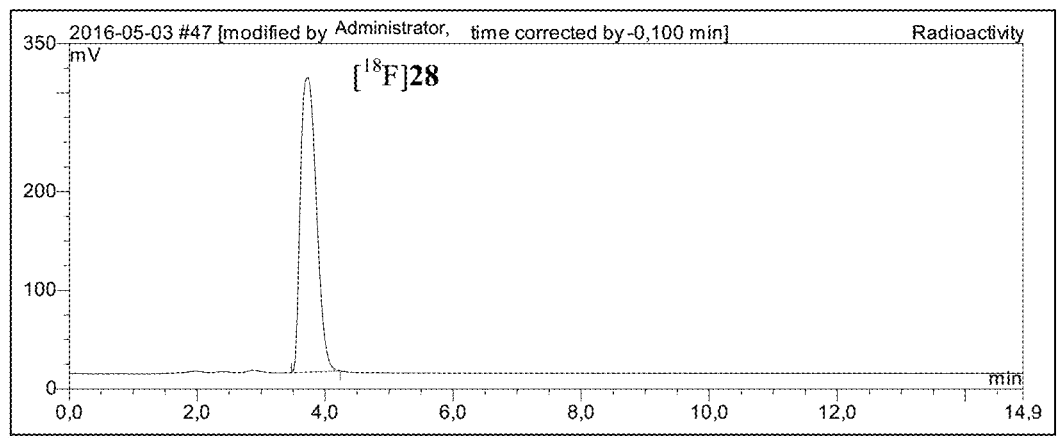
FIG. 3A
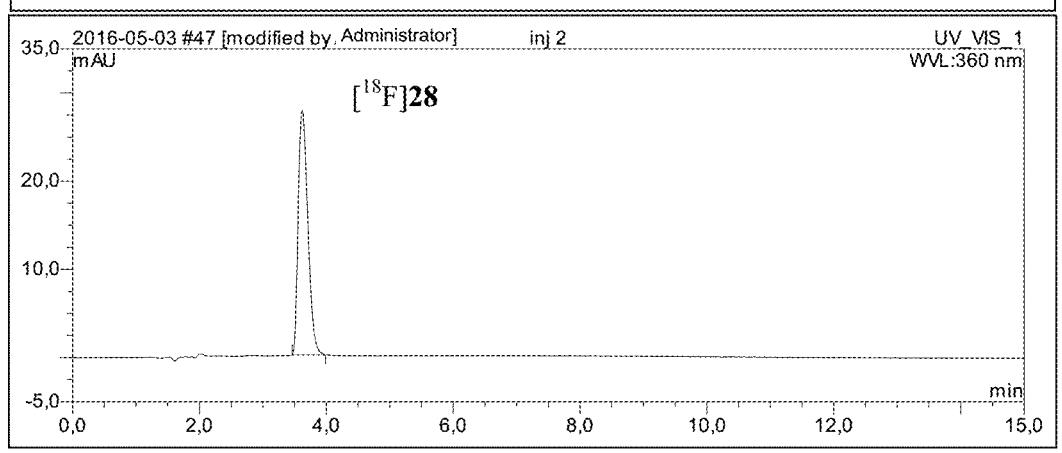
FIG. 3B
FIG. 4
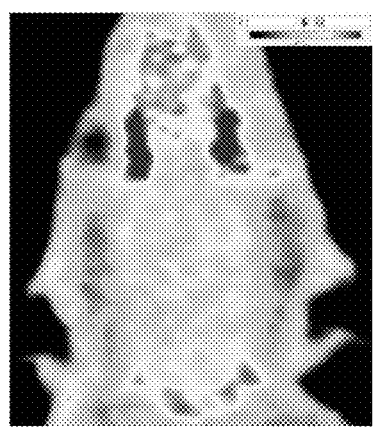

COMPOUNDS FOR USING IN IMAGING AND PARTICULARLY FOR THE DIAGNOSIS OF NEURODEGENERATIVE DISEASES

The invention relates to compounds for use in imaging and in particular for the diagnosis of neurodegenerative diseases.

The aggregation of abnormal proteins is a common feature of several neurodegenerative disorders. The propagation of these aggregates from an initial brain area to other areas anatomically connected appears as a major process of progressive neuronal death. These aggregates or deposits are found, in particular, abnormal tau protein, amyloïd-beta, and alpha-synuclein aggregates.

The pathologies concerned by this type of deposit are directly related to the protein. Thus, neurodegenerative diseases associated with abnormal aggregates of protein tau, beta-amyloïd and alpha-synuclein are named respectively taupathies, amyloïdopathies and synucleinopathies. More particularly, these neurodegenerative diseases include Alzheimer's and Parkinson's diseases.

Deposits of alpha-synuclein protein (α-syn) are, in particular, major synucleinopathies markers and especially of Parkinson's disease (PD). The a-syn is a 14 kDa protein localized in neurons, in the cytoplasm and nuclei but especially synaptic buttons. Under physiological conditions, the precise roles of this protein is still unclear (it seems to interact with presynaptic vesicles). In some pathological conditions, the α-syn adopts conformations oligomeric and/ or fibrillar. Aggregates (or body of Lewy) can then be formed and induce alterations in the release of neurotransmitters (especially dopamine), and affect mitochondrial function, vesicle transport, and some protein degradation process, the entire of these processes can lead to neuronal death.

Currently, diagnosis of PD is based primarily on clinical criteria that are beginning to be supported by exploration in molecular imaging in single photon emission computed tomographySPECT (SPECT) or positron emission tomography (PET) of the dopamine transporter whose reduction is an index of the disease.

However, aggregates of α-syn appearing in the early stages of PD, their detection is a key element of early diagnosis. One method of choice in this context is molecular imaging PET or SPECT, which allows to explore in vivo targets such as receptors, transporters, or protein clusters. This method requires the use of tracers or radiopharmaceuticals, radiation emitters β+ or γ and specific for the target to explore. To date, no specific PET tracer or TEMP of the α-syn is available.

Therefore, one of the aims of the invention is the use of a compound of the Invention as an in vivo imaging agent. In particular, another object of the invention is to provide a PET or SPECT imaging agent for detecting and quantifying the in vivo aggregates of alpha-synuclein, β-amyloïd or abnormal tau.

Another object of the invention is to develop a radiolabeled tracer, for example fluorine-18 ($^{18}$F), for clinical use on a large population, to improve early diagnosis, monitoring and developing treatments of synucleinopathies such as PD.

Another object of the invention is to provide a compound having an affinity for alpha-synuclein, β-amyloïd peptide and/or tau fibers.

Another object of the invention is to provide a compound for use in a in vivo method of diagnosis or imaging.

Another object of the invention is to provide a pharmaceutical composition comprising the compound of the Invention.

Another object of the invention is to provide a compound for use as a pharmaceutical or radiopharmaceutical drug.

The present invention thus relates to a compound of formula I

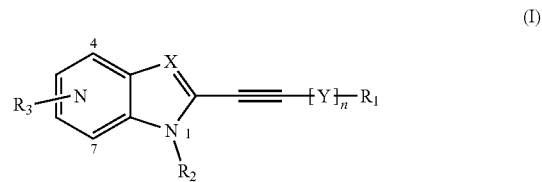

X being selected from N or C—R$_4$

Y being selected from an alkene or an alkyne, an aryl or a heteroaryl, an alkane comprising from 1 to 7 carbon atoms, n being an integer equal to 0 or 1;

R$_1$ being selected from aryl or heteroaryl selected from phenyl, pyrimidine, pyridine, thiophene, furan, triazole, oxazole, (aza)indole, (aza)indoline, (aza)benzimidazole optionally substituted at one or more positions with a group selected from:

Halogen, NO$_2$, CN, dimethyltriazene, trimethylammonium, aryliodonium,

NR$^a$R$^b$, SO$_2$NR$^a$R$^b$, CONR$^a$R$^b$, NR$^c$SO$_2$NR$^a$R$^b$, NR$^c$CONR$^a$R$^b$, NR$^a$COR$^b$;

R$^a$, R$^b$ and R$^c$ are independently of each other H, (C$_1$-C$_7$)alkyl, aryl, heteroaryl, (C$_3$-C$_7$)carbocyclyl, (C$_1$-C$_7$)alkyl-aryl, (C$_1$-C$_7$)alkyl-heteroaryl, or R$^a$ and R$^b$ together form a (C$_3$-C$_7$)heterocyclyl;

Sn(Alkyl)$_3$, Alkyl being selected from methyl or n-butyl;

B(OH)$_2$, B(pinacol);

R$^d$, CH$_2$R$^d$;

R$^d$ represents H, (C$_1$-C$_7$)alkyl, aryl, heteroaryl, (C$_3$-C$_7$) heterocyclyl, (C$_3$-C$_7$)carbocyclyl, (C$_1$-C$_7$)alkyl-aryl, (C$_1$-C$_7$)alkyl-heteroaryl, (C$_1$-C$_7$)alkyl-(C$_3$-C$_7$)heterocyclyl, [(C$_1$-C$_7$) alkyl]$_n$-Z or [(C$_1$-C$_7$) alkyl-Z]$_n$ Z being a heteroatom selected from N, O or S, in particular selected from NR$^a$R$^b$ or OR$^e$, and n being an integer comprised from 1 to 7;

OR$^e$, OAc, OTs, OTf, SR$^e$, SO$_2$R$^e$, COR$^e$, NR$^e$SO$_2$R$^e$, NHCOOR$^e$;

R$^e$ is H, (C$_1$-C$_7$)alkyl, aryl, heteroaryl, (C$_3$-C$_7$)heterocyclyl, (C$_3$-C$_7$)carbocyclyl, (C$_1$-C$_7$)alkyl-aryl, (C$_1$-C$_7$)alkyl-heteroaryl or (C$_1$-C$_7$) alkyl-(C$_3$-C$_7$)heterocyclyl;

R$_2$ being selected from:
H, SO$_2$Ph, COR$^e$, NR$^c$CONR$^a$R$^b$, COOR$^e$, OH, R$^d$;

R$_3$ being selected from:
Halogen, NO$_2$, CN, dimethyltriazene, trimethylammonium, aryliodonium,
NR$^a$R$^b$, SO$_2$NR$^a$R$^b$, CONR$^a$R$^b$, NR$^c$SO$_2$NR$^a$R$^b$, NR$^c$CONR$^a$R$^b$, NR$^a$COR$^b$;
Sn(Alkyl)$_3$, Alkyl being selected from methyl or n-butyl;
B(OH)$_2$, B (pinacol);
R$^d$, CH$_2$R$^d$;
OR$^e$, OAc, OTs, OTf, O(heteroaryl), especially O(HOBt), SR$^e$, SO$_2$R$^e$, COR$^e$, NR$^a$SO$_2$R$^e$, NHCOOR$^e$;

$R_4$ being selected from:

Halogen, $CH_2NR^aR^b$, $R^a$, $COOR^e$, CHO, $CH_2OR^e$;

wherein at least one of the substituents $R_1$, $R_2$, $R_3$ or $R_4$ optionally comprises a radioelement selected from $^{18}F$, $^{11}C$, $^{123}I$ and $^{124}I$.

When at least one of the substituents $R_1$ and $R_3$ is trimethylammonium, the counterion is selected from $I^-$, $Cl^-$, $OTs^-$ and $OMs^-$ Within the meaning of the present invention, the term "aryliodonium" is defined as the cation of an iodine atom bearing an aryl group. Examples, without limitation, of aryliodonium include [trimethyl-2,4,6 phenyl] $I^+$, [4-tert-butylphenyl] $I^+$ and [2,6-dimethyl-4-tertbutylphenyl] $I^+$ whose counterion is para-toluenesulfonate.

Within the meaning of the invention, the term "($C_1$-$C_7$) alkyl" refers to an acyclic carbon chain, saturated, linear or branched, comprising 1 to 7 carbon atoms. Group examples of ($C_1$-$C_7$)alkyl include methyl, ethyl, propyl, butyl, pentyl, hexyl or heptyl. The definition of propyl, butyl, pentyl, hexyl, heptyl or include all possible isomers. For example, the term butyl includes "n-butyl, iso-butyl, sec-butyl and ter-butyl. ($C_1$-$C_7$)alkyl may be substituted by one more groups such as halogen, hydroxyl, alkoxyl, amino, amido, cyano, aryl, trifluoromethyl, pentafluorosulfur, carboxylic acid or carboxylic ester. Preferably, the group ($C_1$-$C_7$)alkyl may be substituted by halogen, hydroxyl or an alkoxyl, or more particularly by one fluoro, chloro, hydroxyl or alkoxyl such as OMs or OTs groups respectively representing the methane sulfonate and para-toluene groups. In particular the group ($C_1$-$C_7$) alkyl may be of the form $(CH_2)_n$—$CH_2F$, n being from 0 to 6.

Thus, within the meaning of the present invention, a group

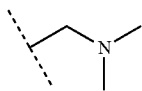

is included in the definition of an alkyl group substituted with an amine, the amine being in this case an (N, N-dimethyl)-amine.

Within the meaning of the invention, the term "($C_3$-$C_7$) carbocyclyl" refers to a mono-, bi- or tricyclic saturated or partially saturated ring containing 3 to 7 carbon atoms. Examples of ($C_3$-$C_7$)carbocyclyl groups include cyclopropyl, cyclobutyl, cyclopentyl, cyclohexyl or cycloheptyl. The cycloalkyl may be substituted by one or more groups such as fluoro, chloro, bromo, iodo, amino or alkoxyl. The "($C_3$-$C_7$)carbocyclyl" may also form a spirocycle with another "($C_3$-$C_7$)carbocyclyl" or "($C_3$-$C_7$)heterocyclyl".

Within the meaning of the invention, the term "($C_3$-$C_7$) heterocyclyl" means a saturated heterocycle comprising 3, 4, 5, 6, or 7 ring atoms of which 1, 2 or 3 heteroatoms selected from O, S or N, replace respectively 1, 2 or 3 carbon atoms. Examples of "($C_3$-$C_7$) heterocyclyl" include pyrrolidinyl, piperidinyl, piperazinyl and morpholinyl. The heterocyclyl may be substituted by one or more groups such as amino, alkoxyl, methyl, cyclohexyl, cyclopentyl, aryl, halogen, or ($C_1$-$C_3$) alkyl halogen. The "($C_3$-$C_7$)carbocyclyl" may also form a spirocycle with a "($C_3$-$C_7$) carbocyclyl" or another "($C_3$-$C_7$)heterocyclyl".

Within the meaning of the invention by expression means "($C_1$-$C_3$) alkyl-halogen", an acyclic carbon chain, saturated, linear or branched, comprising 1 to 3 carbon atoms, substituted on one or more positions with a halogen group such as fluoro, chloro, bromo or iodo.

In general, in the sense of the present invention, when a group comprises two or more subunits, their commitment is noted "-". Thus, it is meant by the terms "($C_1$-$C_7$)alkyl-aryl", "($C_1$-$C_7$)alkyl-heteroaryl" or "($C_1$-$C_7$) alkyl-($C_3$-$C_7$)heterocyclyl", a chain ($C_1$-$C_7$)alkyl as defined in the present Invention linked to an aryl group respectively, heteroaryl or ($C_3$-$C_7$)heterocyclyl as defined in the present invention.

Within the meaning of the invention, the term "$R^a$ and $R^b$ together form a ($C_3$-$C_7$) heterocyclyl" means that the nitrogen, $R^a$ and $R^b$ together represent a heterocyclic ring. For example, $R^a$ and $R^b$ may be connected together via a chain $C_4$-alkyl, forming a pyrrolidin ring with the nitrogen atom through which they are connected.

The term "aryl" means an aromatic mono-ring comprising from 5 to 6 carbon atoms, which may itself be fused with a second saturated, unsaturated or aromatic. The term aryl includes, without limitation, phenyl. The aryl group may be substituted by one or more groups independently selected from the groups alk the, halogen, ($C_1$-$C_3$)alkyl-halogen, hydroxyl, alkoxy, amino, amido, nitro, cyano, trifluoromethyl, pentafluorosulfur, carboxylic acid or ester carboxylic acid. Examples of substituted aryls include, without limitation, 2-, 3- or 4-(N,N-dimethylamino)phenyl, 2-, 3- or 4-cyanophenyl, 2-, 3- or 4-nitrophenyl, 2-, 3- or 4-fluoro-, chloro-, bromo- or iodo-phenyl, 2-, 3- or 4-methoxyphenyl.

Within the meaning of the invention is meant by the expression "($C_1$-$C_3$)alkyl-halogen", an acyclic carbon chain, saturated, linear or branched, comprising 1 to 3 carbon atoms, substituted at one or more positions by halogen such as fluoro, chloro, bromo or iodo.

Within the meaning of the present invention, the term "heteroaryl" means a mono- or polycyclic aryl as described above, wherein one or more carbon atoms have been replaced by one or more heteroatoms selected from N, O or S. the term heteroaryl includes all possible isomers. Examples of heteroaryls include furanyl, thienyl, pyrrolyl, N-alkyl pyrrolyl, indolyl, aza-indolyl, benzofuranyl, benzothiophenyl, pyridyl, oxazolyl, thiazolyl, imidazolyl, pyrimidyl, pyrazinyl, triazolyl, N-alkyl triazolyl, thiadiazolyl, oxadiazolyl, tetrazolyl and N-alkyl tetrazolyl. The heteroaryl group may be further substituted by one or more groups independently selected from alkyl, ($C_1$-$C_3$)alkyl-halogen, alkoxy, halogen, hydroxyl, amino, amido, nitro, cyano, trifluoromethyl, pentafluorosulfur, carboxylic acid or carboxylic ester.

Within the meaning of the present invention, the term "halogen" represents fluorine, chlorine, bromine or iodine.

Within the meaning of the present invention, the terms "alkoxyl" and "alkoxy" means a hydroxyl or an alkyl chain of which at least one of the carbon atoms is replaced by an oxygen atom. The alkyl chain may be further substituted. In particular, it may be substituted by an aryl group or halogen. Thus, alkoxyl examples within the meaning of the invention include OH, OMe, O—$(CH_2)_n$—F, O—$(CH_2)_n$—O—$(CH_2)_m$—F, n and m being independently one of the other integer from 0 to 6 inclusive, O—$(CH_2)_n$-aryl, in particular

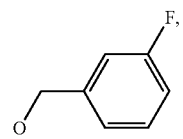

O—$(CH_2)_2$—F, O—$(CH_2)_2$—O—$(CH_2)_2$—F.

The term "at least one of the substituents $R_1$, $R_2$, $R_3$ or $R_4$ optionally comprises a radioelement selected from $^{18}F$, $^{11}C$, $^{123}I$ and $^{124}I$" means within the meaning of the invention that one of the atoms of at least one of the substituents $R_1$, $R_2$, $R_3$ or $R_4$ is optionally substituted by a radioelement.

The molecules of the invention bind to these deposits with various affinities and selectivities.

The present invention is based on the observation made by the inventors, the affinity of the compounds of formula I for the alpha-synuclein, β-amyloïd and/or tau fibers.

The present invention relates also to a compound of formula Ibis

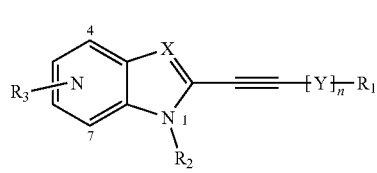

(Ibis)

X being selected from N or C—$R_4$

Y being selected from an alkane, alkene or alkyne comprising from 1 to 7 carbon atoms, or aryl or heteroaryle, n being an integer equal to 0 or 1;

$R_1$ being selected from aryl or heteroaryle selected from phenyl, pyrimidine, pyridine, thiophene, furan, triazole, oxazole, (aza)indole, (aza)indoline, (aza)benzimidazole optionally substituted at one or more positions with a group selected from:

Halogen, $NO_2$, CN, dimethyltriazene, $NR^aR^b$, $SO_2NR^aR^b$, $CONR^aR^b$, $NR^cSO_2NR^aR^b$, $NR^c$-$CONR^aR^b$, $NR^aCOR^b$;

$R^a$, $R^b$ and $R^c$ are independently of each other H, $(C_1-C_7)$alkyl, aryl, heteroaryl, $(C_3-C_7)$carbocyclyl, $(C_1-C_7)$alkyl-aryl $(C_1-C_7)$alkyl-heteroaryl, or $R^a$ and $R^b$ together form a $(C_3-C_7)$ heterocyclyl;

$R^d$, $CH_2R^d$;

$R^d$ is H, $(C_1-C_7)$alkyl, aryl, heteroaryl, $(C_3-C_7)$heterocyclyl, $(C_3-C_7)$carbocyclyl, $(C_1-C_7)$alkyl-aryl, $(C_1-C_7)$alkyl-heteroaryl, $(C_1-C_7)$alkyl-$(C_3-C_7)$ heterocyclyl, $[(C_1-C_7)Alkyl]_n$-Z or a $[(C_1-C_7)Alkyl$-Z]. Z being a heteroatom selected from N, O or S, in particular selected from $NR^aR^c$ or $OR^e$ and n being an integer comprised from 1 to 7;

$OR^e$, $SR^e$, $SO_2R^e$, $COR^e$, $NR^aSO_2R^e$, $NHCOOR^e$;

$R^e$ is H, $(C_1-C_7)$alkyl, aryl, heteroaryl, $(C_3-C_7)$heterocyclyl, $(C_3-C_7)$carbocyclyl, $(C_1-C_7)$alkyl aryl, $(C_1-C_7)$alkyl-heteroaryl, or $(C_1-C_7)$alkyl-$(C_3-C_7)$heterocyclyl;

$R_2$ being selected from:

H, $SO_2Ph$, $COR^e$, $NR^cCONR^aR^b$, $COOR^e$, OH, $R^d$;

$R_3$ being selected from:

Halogen, $NO_2$, CN, dimethyltriazene, $NR^aR^b$, $SO_2NR^aR^b$, $CONR^aR^b$, $NR^cSO_2NR^aR^b$, $NR^c$-$CONR^aR^b$, $NR^aCOR^b$;

$R^d$, $CH_2R^d$, $OR^e$, $SR^e$, $SO_2R^e$, $COR^e$, $NR^aSO_2R^e$, $NHCOOR^e$;

$R_4$ being selected from:

Halogen, $CH_2NR^aR^b$, $R^a$, $COOR^e$, CHO, $CH_2OR^e$;

wherein at least one of the substituents R, $R_2$, $R_3$ or $R_4$ optionally comprises a radioelement selected from $^8F$, $^{11}C$, $^{123}I$ and $^{124}I$.

The substituents trimethylammonium aryliodonium, Sn(alkyl)$_3$, B(OH)$_2$, B(pinacol), OAc, OMs, OTs, OTf and O(HOBt) correspond to synthesis of intermediates for the formation of compounds of formula Ibis.

The present Invention is based on the observation made by the inventors, of the affinity of compounds of formula Ibis for alpha-synuclein, β-amyloïd and/or tau fibers.

According to one embodiment, the compound of the invention, wherein at least one of substituents $R_1$, $R_2$, $R_3$ or $R_4$ comprises a radioelement selected from $^{18}F$, $^{11}C$, $^{123}I$ and $^{124}I$, is of formula II.

The substituents X, Y, $R_1$, $R_2$, $R_3$ or $R_4$ for compounds of formula II have the same meaning as in formula I, provided that at least one of $R_1$, $R_2$, $R_3$ or $R_4$ comprises a radioelement selected from $^{18}F$, $^{11}C$, $^{123}I$ and $^{124}I$.

Preferably, the radioelement is $^{18}F$ because its half-life (110 minutes) is sufficiently long to allow use of the radiolabelled compound, both in preclinical and clinical in a PET imaging system dedicated and located distance cyclotron needed to produce the radioelement and thus the radiolabeled compound.

According to one embodiment, the compound of the invention, wherein at least one of substituents $R_1$, $R_2$, $R_3$ or $R_4$ comprises a radioelement selected from $^{18}F$, $^{11}C$, $^{123}I$ and $^{124}I$, is of formula IIbis.

According to another embodiment, the compound of the invention, wherein none of the substituents $R_1$, $R_2$, $R_3$ or $R_4$ comprise radioelement is of formula III.

According to an advantageous embodiment, the compound of the invention is of the general formula Ia or IIa:

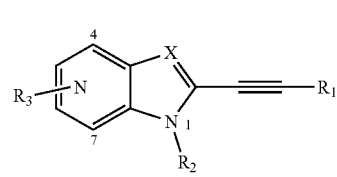

(Ia) or (IIa)

X, $R_1$, $R_2$, and $R_3$ being as defined above in formula I or II respectively. According to an advantageous embodiment, the compound of the invention is of general formula Ib or IIb:

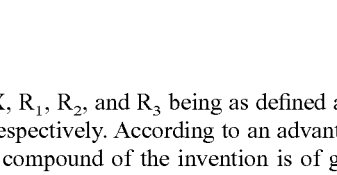

(Ib) or (IIb)

Y being selected from phenyl, thienyl or furanyl.

X, $R_1$, $R_2$, $R_3$ being as defined above in formula I or II.

According to an advantageous embodiment, the compound of the invention is of general formula I-1

(I-1)

R₁, R₂, R₃ and R₄ being as defined previously in formula I,

According to an advantageous embodiment, the compound of the invention is of general formula II-1

(II-1)

R₁, R₂, R₃ and R₄ being as defined previously in formula I or II;

wherein at least one of the substituents R₁, R₂, R₃ or R₄ comprises a radioelement selected from $^{18}F$, $^{11}C$, $^{123}I$ and $^{124}I$.

According to an advantageous embodiment, the compound of the invention is of general formula III-1

(III-1)

R₁, R₂, R₃ and R₄ being as previously defined in formula I;

wherein none of the substituents R₁, R₂, R₃ and R₄ comprises a radioelement.

According to an advantageous embodiment, the compound of the invention is of general formula I-1a or II-1a:

(I-1a) or (II-1a)

R₁, R₂, R₃ and R₄ being as previously defined in formula I or II respectively.

According to an advantageous embodiment, the compound of the invention is of general formula I-1b or the II-1b:

(I-1b) or (II-1b)

R₁, R₂, R₃ and R₄ being as previously defined in formula I or II respectively.

According to an advantageous embodiment, the compound of the invention is of general formula I-1c or II-1c:

(I-1c) or (II-1c)

R₁, R₂, R₃ and R₄ being as previously defined in formula I or II respectively.

According to an advantageous embodiment, the compound of the invention is of general formula I-1d or II-1d:

(I-1d) or (II-1d)

R₁, R₂, R₃ and R₄ being as previously defined in formula I or II respectively.

According to an advantageous embodiment, the compound of the invention is of the formula I-1 or II-1:

(I-1) or (II-1)

R₂, R₃ and R₄ being as previously defined in formula I or II respectively;

R₁ being optionally labeled and is selected from

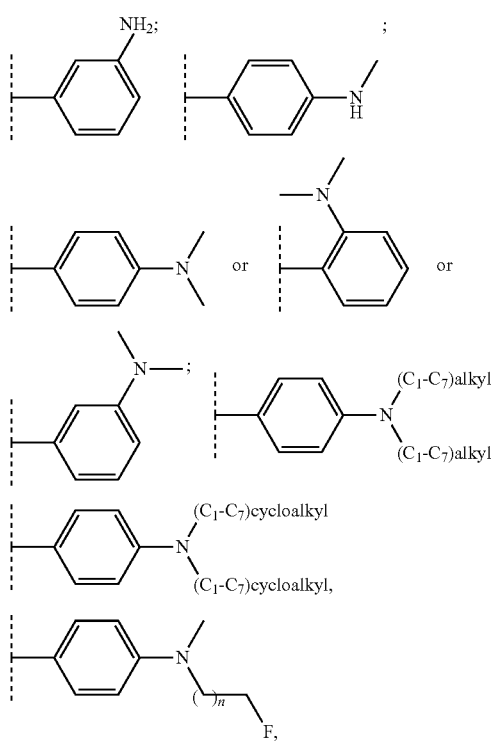
n being in particular from 0 to 6;
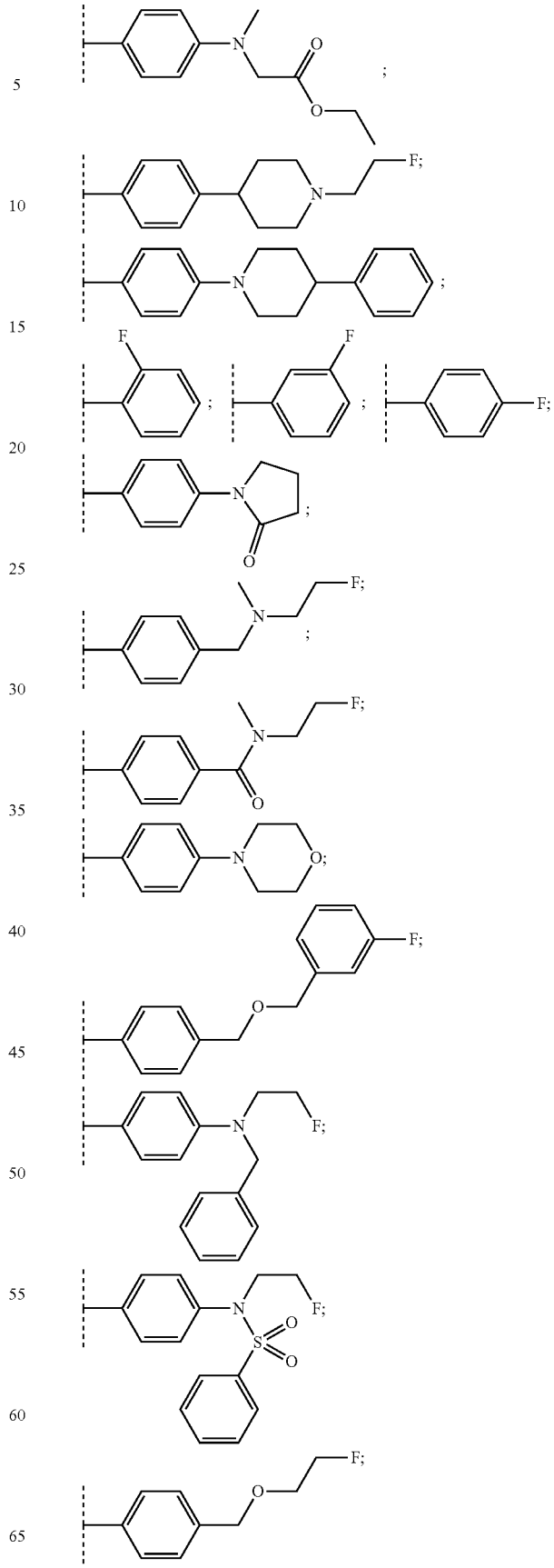

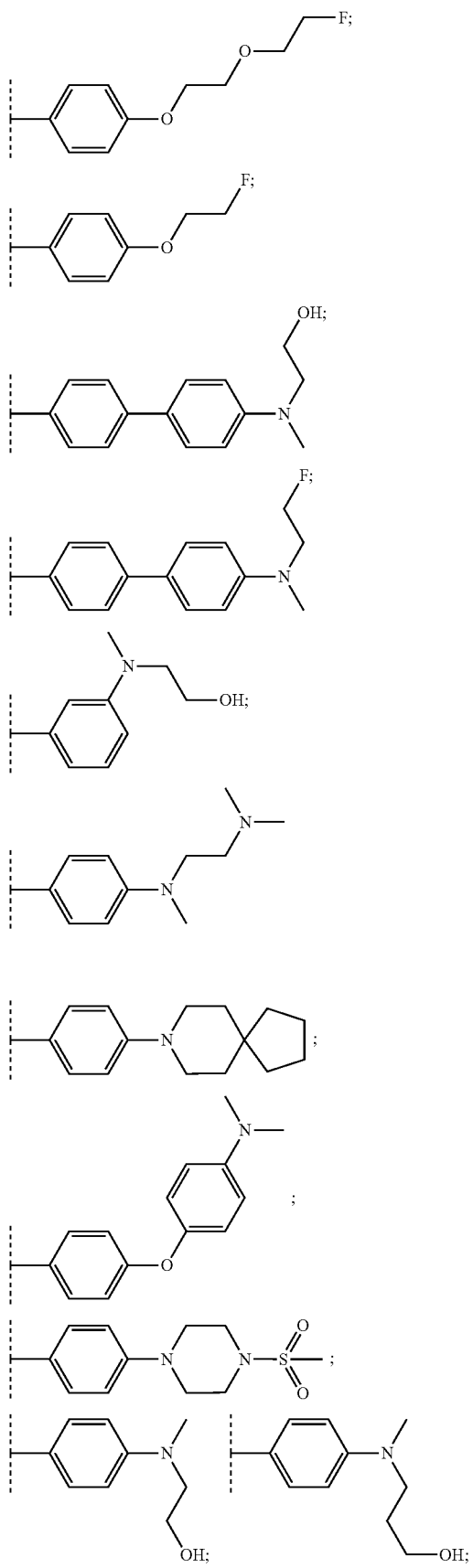

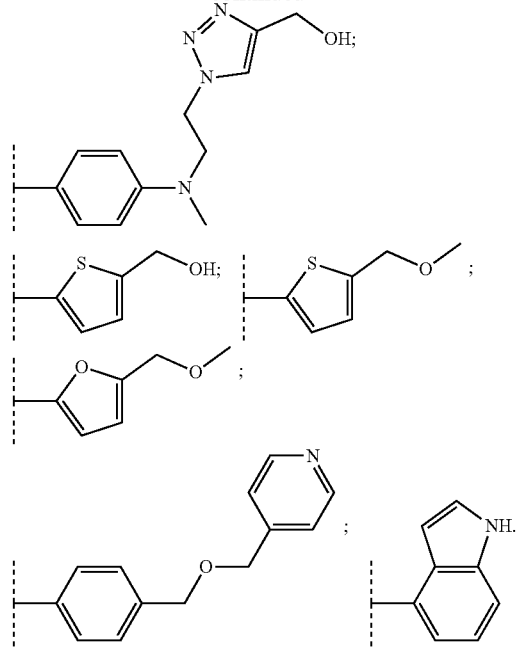

The term "optionally labeled" indicates that the substituent in question potentially includes a radioelement. Thus, the compounds of formula II-1 include a radioelement selected from $^{18}F$, $^{11}C$, $^{123}I$ and $^{124}I$ on at least one of the substituents $R_1$, $R_2$, $R_3$ or $R_4$.

According to an advantageous embodiment, the compound of the invention is of the formula I-1 or II-1:

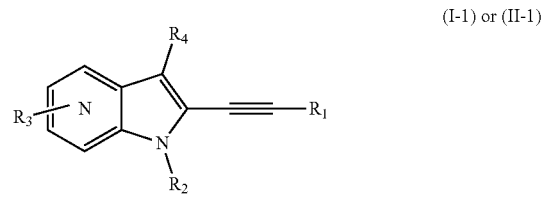

(I-1) or (II-1)

$R_1$, $R_3$ and $R_4$ being as previously defined in formula I or II respectively;
$R_2$ being optionally labeled and is selected from
H;
$(CH_2CH_2O)_n$—$CH_2CH_2F$, n being an integer equal to 0, 1 or 2;
—$SO_2Ph$;
$COO^tBu$;
$CH_2OCH_3$;
$CH_2O(CH_2)_2OCH_3$,
$COCH_3$;

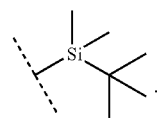

The compounds of formula II-1 comprise a radioelement selected from $^{18}F$, $^{11}C$, $^{123}I$ and $^{124}I$ on at least one of substituents $R_1$, $R_2$, $R_3$ or $R_4$.

According to an advantageous embodiment, the compound of general formula I-1 or II-1

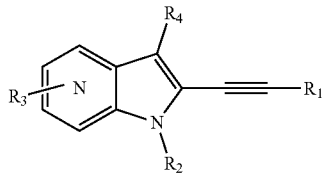
(I-1) or (II-1)

$R_1$, $R_2$ and $R_4$ being as previously defined in formula I or II respectively;
$R_3$ being optionally labeled and is selected from
6-Cl;
6-F;
5-F;
4-F;
6-(2-thienyl);
6-(3-thienyl);
6-(6-fluoro-3-pyridyl);
5-OMe;
6-morpholino;
5-morpholino;
6-Br;
4-Br;
4-Bpin;
5-Bpin.

The compounds of formula II-1 comprise a radioelement selected from $^{18}F$, $^{11}C$, $^{123}I$ and $^{124}I$ on at least one of the substituents $R_1$, $R_2$, $R_3$ ou $R_4$.

According to an advantageous embodiment, the compound of the invention is of the formula I-1 or II-1:

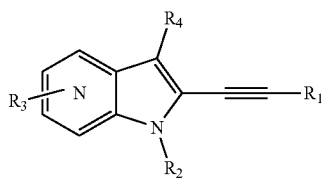
(I-1) or (II-1)

$R_1$, $R_2$ et $R_3$ being as previously defined in formula I or II respectively;
$R_4$ being selected from
H;
$(CH_2)_n$—N-alkyl, n being an integer equal to 0, 1 or 2.

The compounds of formula II-1 comprise a radioelement selected from $^{18}F$, $^{11}C$, $^{123}I$ and $^{124}I$ on at least one of the substituents $R_1$, $R_2$ or $R_3$.

According to an advantageous embodiment, the compound of the invention is of the general formula I-1a or II-1a:

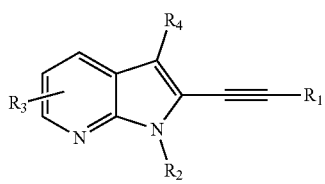
(I-1a) or (II-1a)

$R_2$, $R_3$ and $R_4$ being as previously defined in formula I or II respectively;

$R_1$ being optionally labeled and is selected from

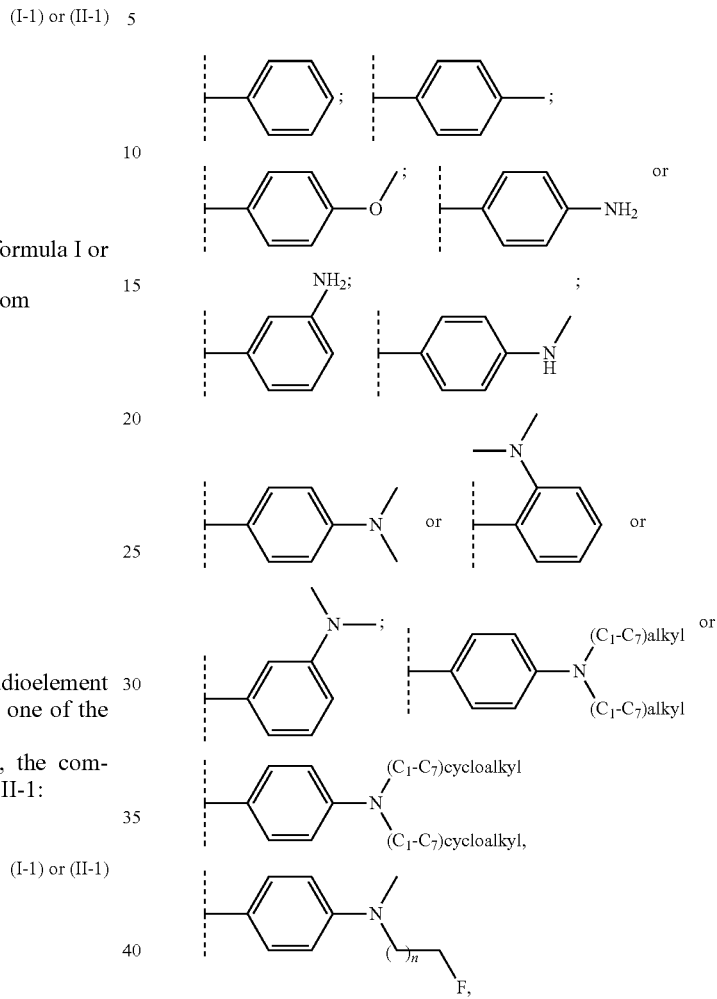

n being in particular from 0 to 6

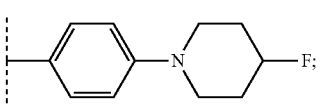

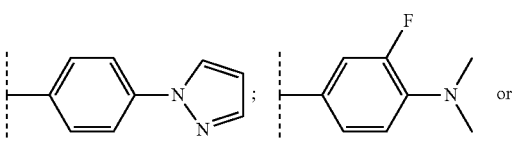

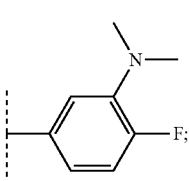

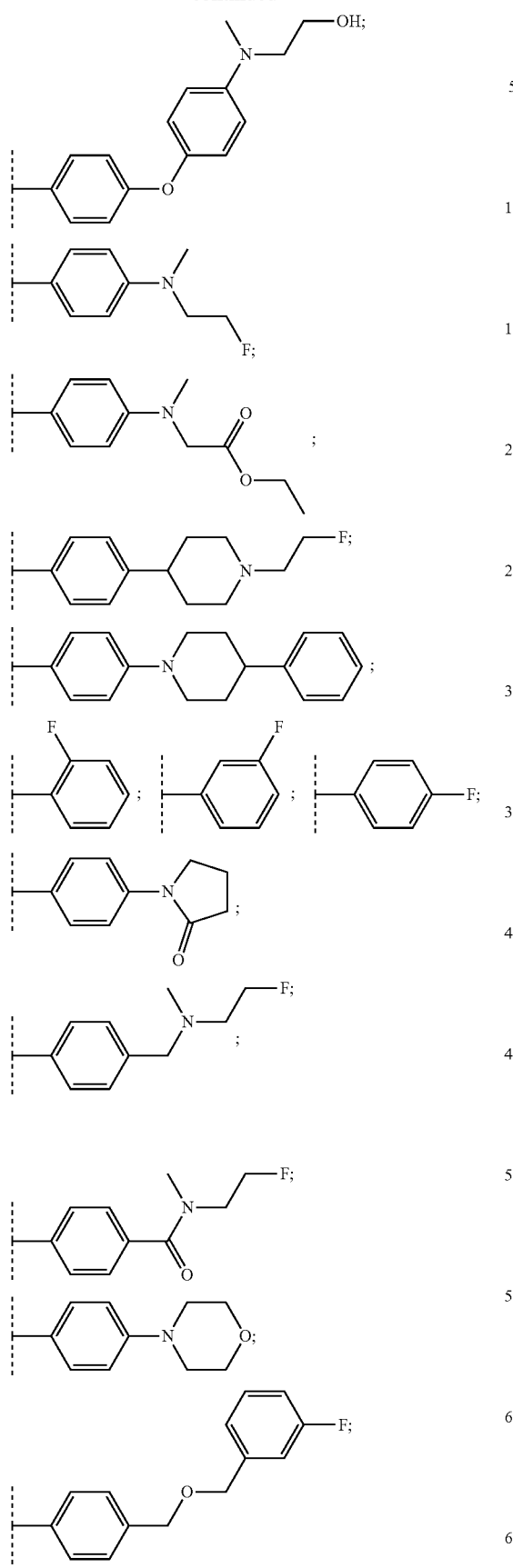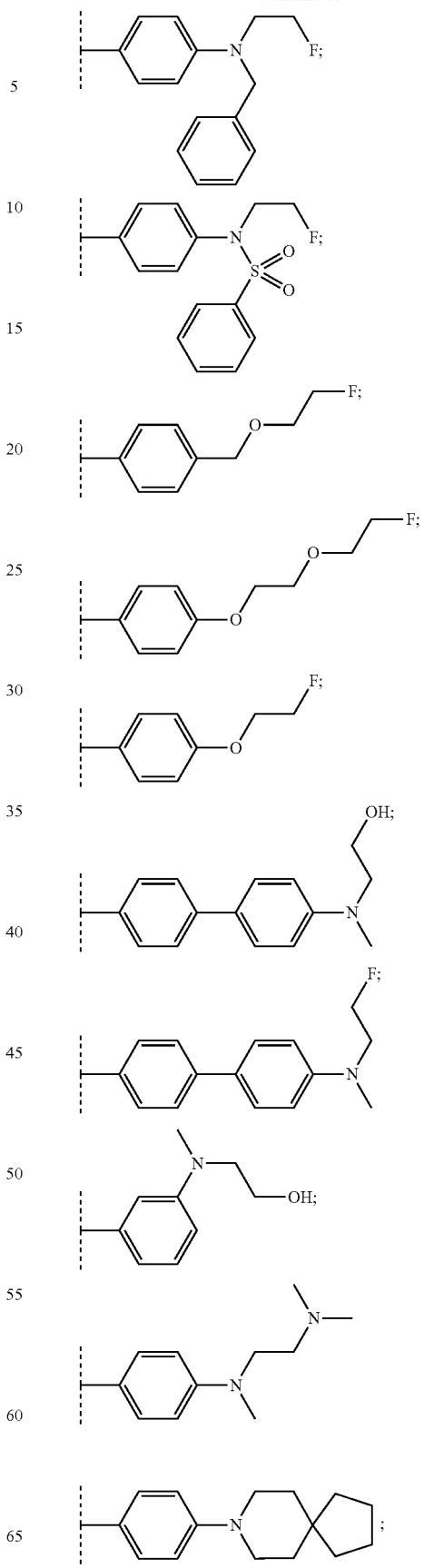

17

-continued

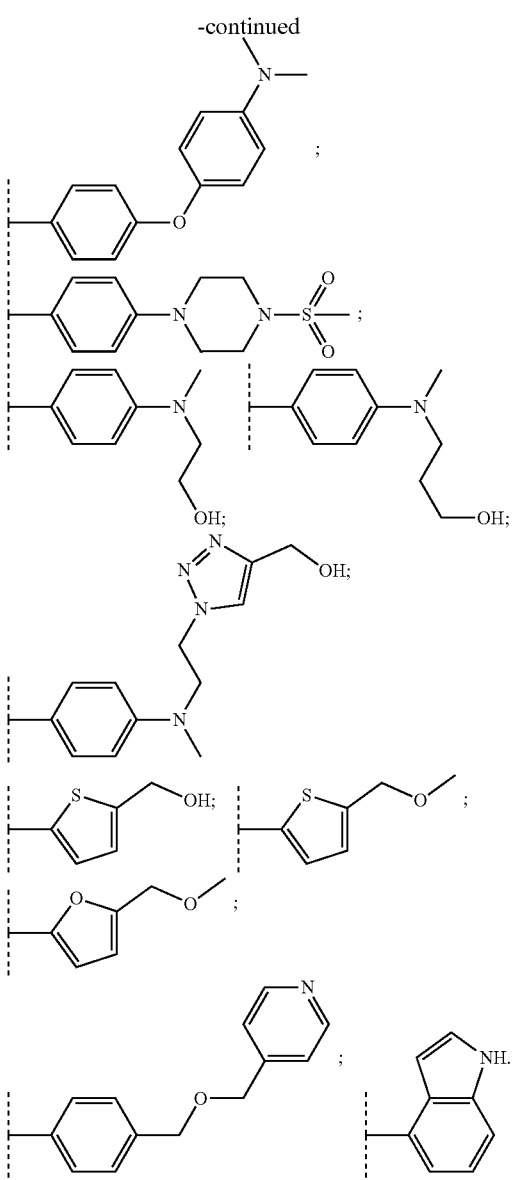

The compounds of formula II-1a comprise a radioelement selected from $^{18}F$, $^{11}C$, $^{123}I$ and $^{124}I$ on at least one of substituents $R_1$, $R_2$, $R_3$ ou $R_4$.

According to an advantageous embodiment, the compound of the invention is of general formula I-1a or II-1a:

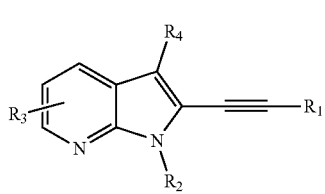

(I-1a) or (II-1a)

$R_1$, $R_3$ and $R_4$ being as previously defined in formula I or II respectively;
$R_2$ being optionally labeled and is selected from
H;
$(CH_2CH_2O)_n$—$CH_2CH_2F$, n being an integer equal to 0, 1 or 2;

18

$SO_2Ph$;
$COO^tBu$;
$CH_2OCH_3$;
$CH_2O(CH_2)_2OCH_3$
$COCH_3$;

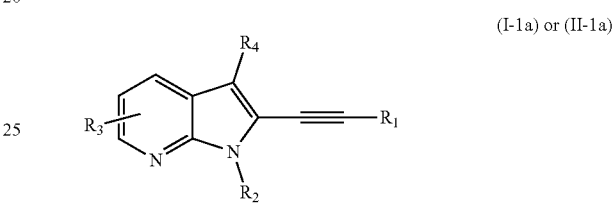

The compounds of formula II-1a comprise a radioelement selected from $^{18}F$, $^{11}C$, $^{123}I$ and $^{124}I$ on at least one of the substituents $R_1$, $R_2$, $R_3$ or $R_4$.

According to an advantageous embodiment, the compound of the invention is of general formula I-1a or II-1a:

(I-1a) or (II-1a)

$R_1$, $R_2$ and $R_4$ being as previously defined in formula I or II respectively;
$R_3$ being optionally labeled and is selected from
6-Cl;
6-F;
5-F
4-F;
6-(2-thienyl);
6-(3-thienyl);
6-(6-fluoro-3-pyridyl);
5-OMe
6-morpholino;
5-morpholino;
6-Br;
4-Br;
4-Bpin;
5-Bpin.

The compounds of formula II-1a comprise a radioelement selected from $^{18}F$, $^{11}C$, $^{123}I$ and $^{124}I$ on at least one of the substituents $R_1$, $R_2$, $R_3$ or $R_4$.

According to an advantageous embodiment, the compound of the invention is of general formula I-1a or II-1a:

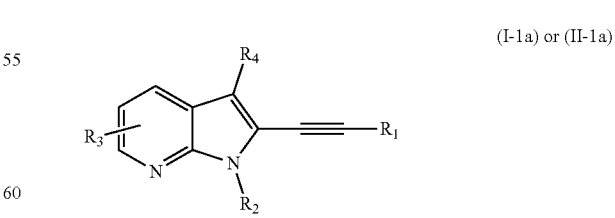

(I-1a) or (II-1a)

$R_1$, $R_2$ and $R_3$ being as previously defined in formula I or II respectively;
$R_4$ being selected from
H;
$(CH_2)_n$—N-alkyl, n being an integer equal to 0, 1 or 2.

The compounds of formula II it comprises a radioelement selected from $^{18}F$, $^{11}C$, $^{123}I$ and $^{124}I$ on at least one of the substituents $R_1$, $R_2$, or $R_3$.

According to an advantageous embodiment, the compound of the invention is of general formula I-1a or II-1a:

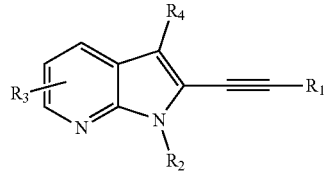
(I-1a) or (II-1a)

$R_3$ and $R_4$ being as previously defined in formula I or II respectively;

$R_1$, being optionally labeled and is selected from

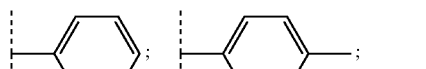
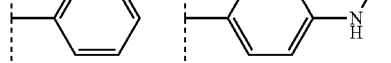
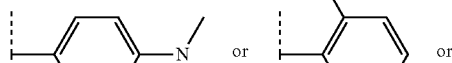
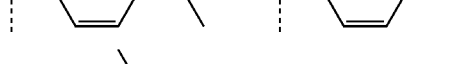
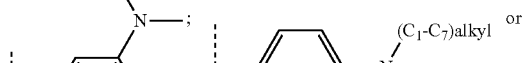
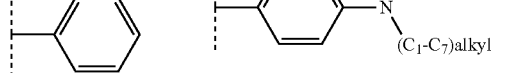

n being in particular from 0 to 6;

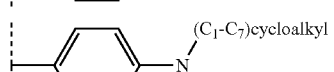

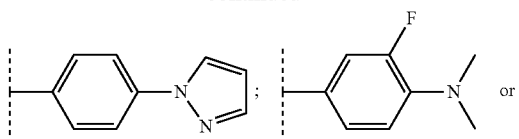

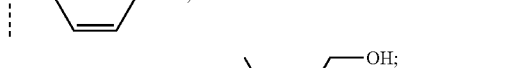

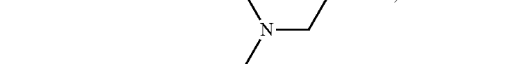

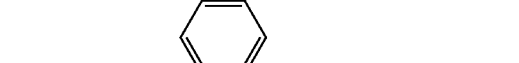

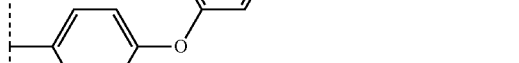

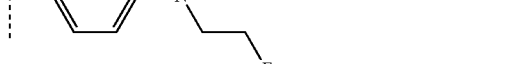

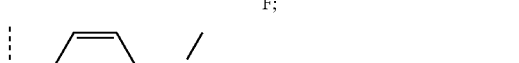

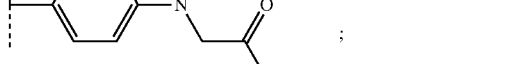

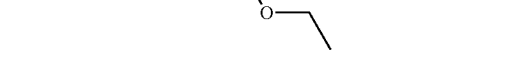

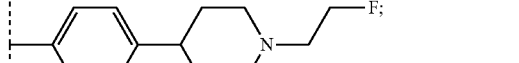

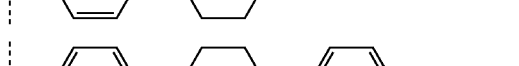

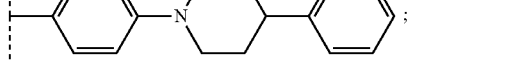

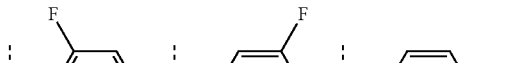

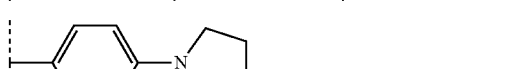

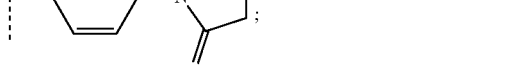

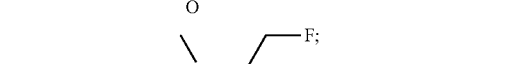

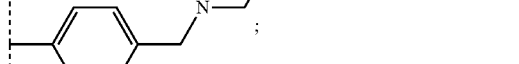

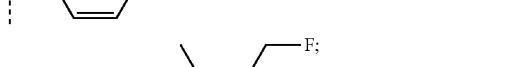

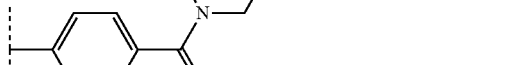

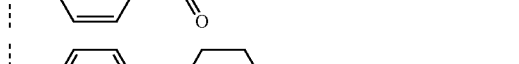

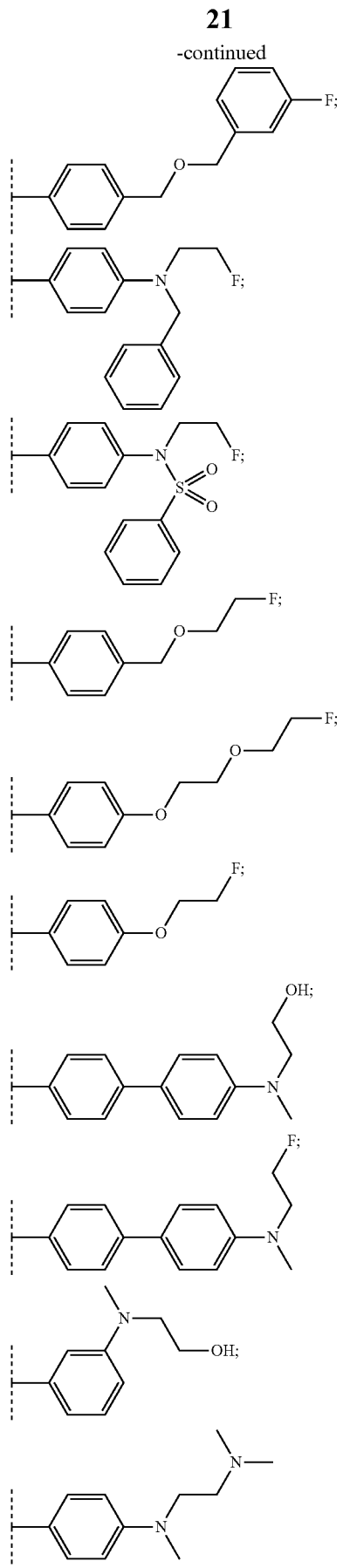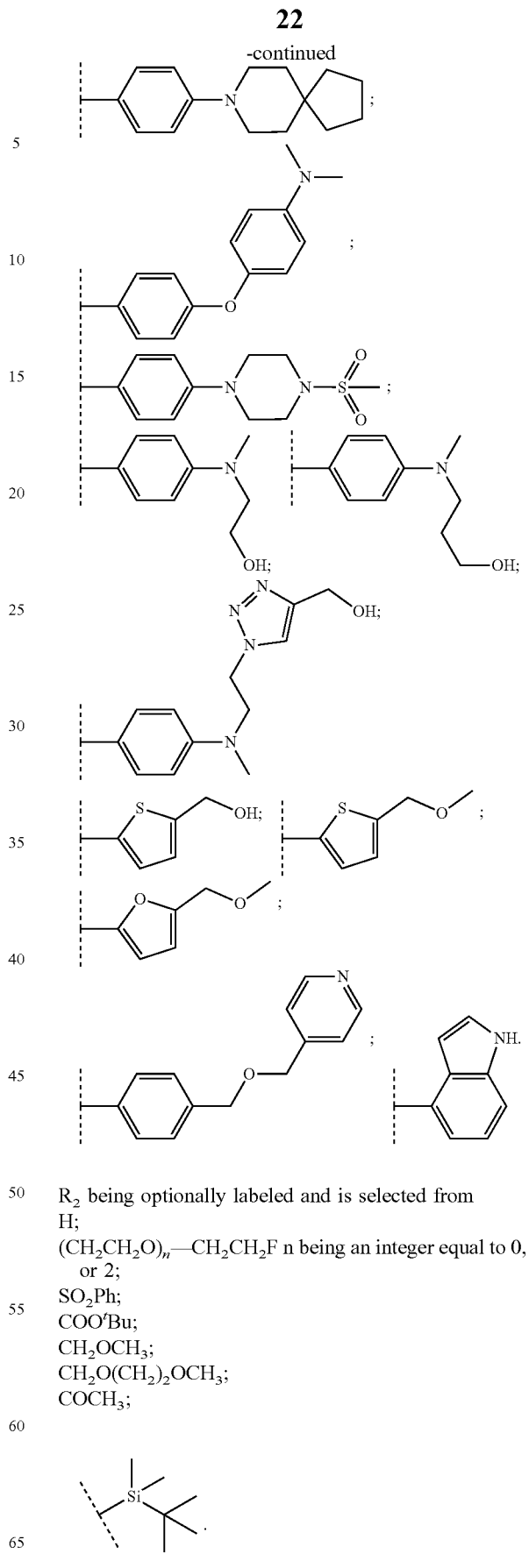
$R_2$ being optionally labeled and is selected from
H;
$(CH_2CH_2O)_n$—$CH_2CH_2F$ n being an integer equal to 0, 1 or 2;
$SO_2Ph$;
$COO^tBu$;
$CH_2OCH_3$;
$CH_2O(CH_2)_2OCH_3$;
$COCH_3$;

The compounds of formula II-1a comprise a radioelement selected from $^{18}F$, $^{11}C$, $^{123}I$ and $^{124}I$ on at least one of the substituents $R_1$, $R_2$, $R_3$ or $R_4$.

According to an advantageous embodiment, the compound of the invention is of general formula I-1a or II-1a:

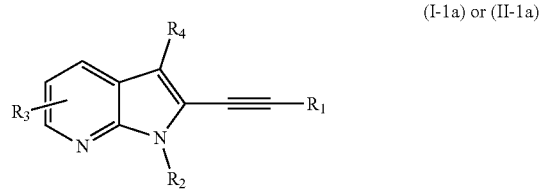

(I-1a) or (II-1a)

$R_2$ and $R_4$ being as previously defined in formula I or II respectively;

$R_1$ being optionally labeled and is selected from

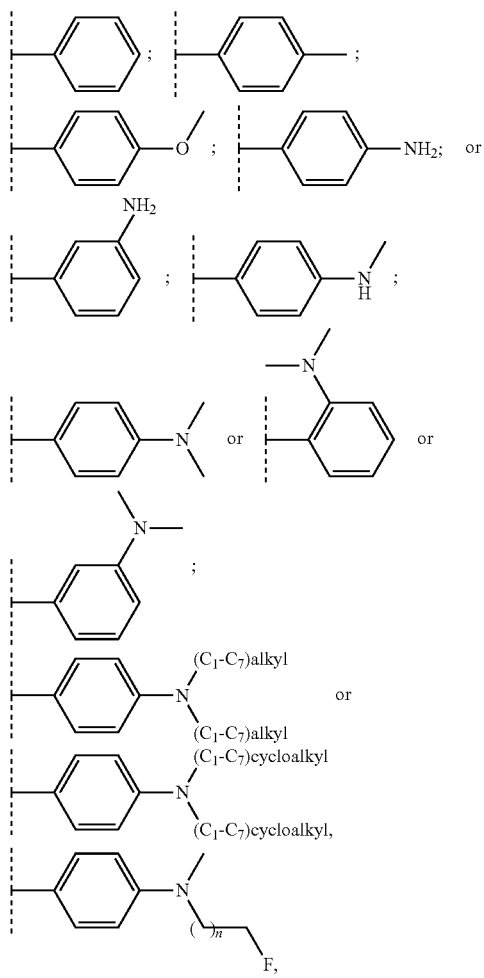

n being in particular from 0 to 6;

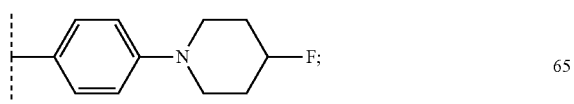

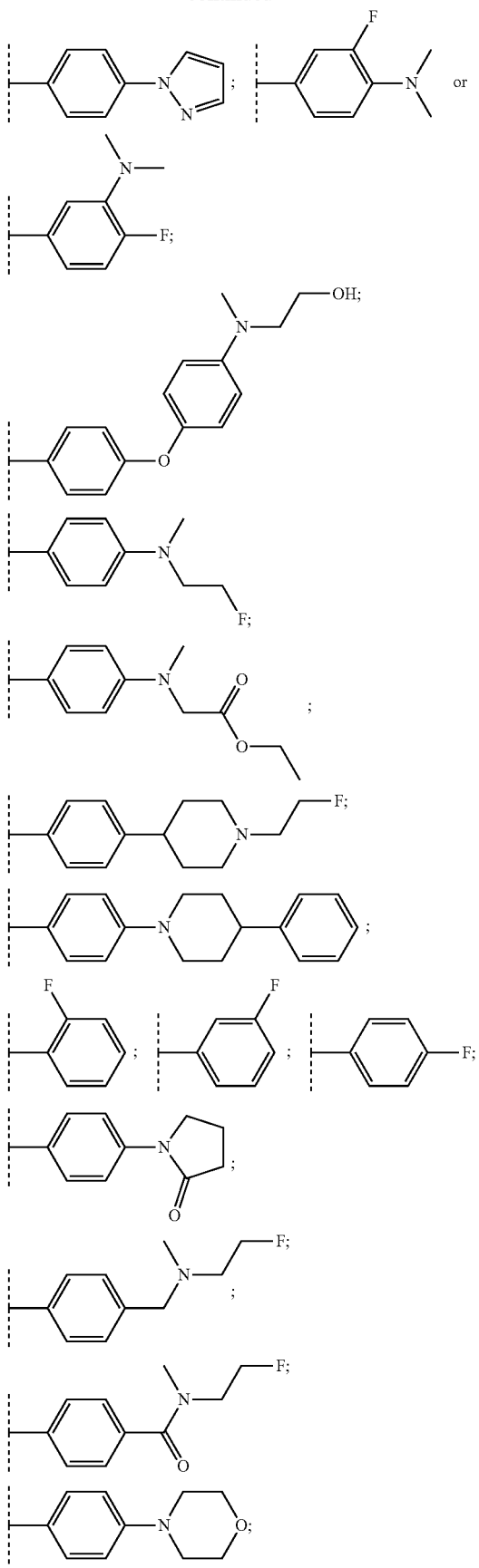

-continued
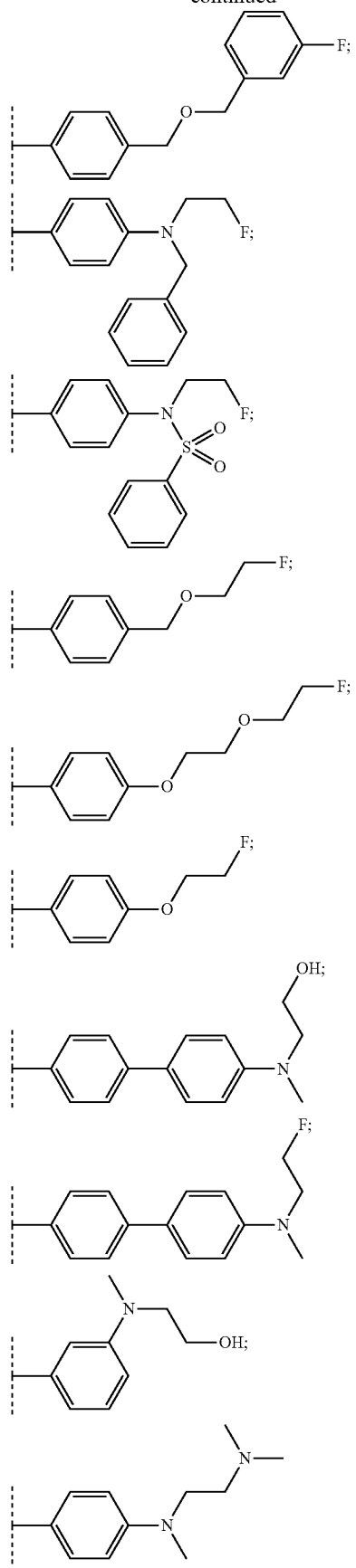
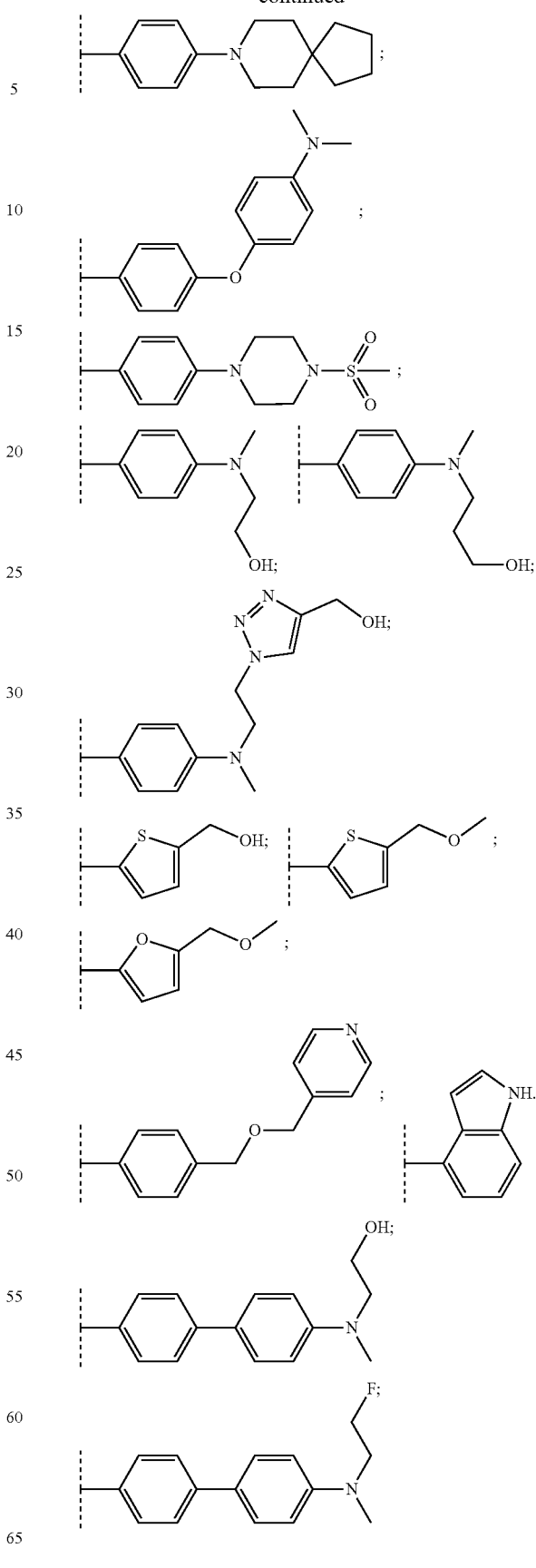

-continued

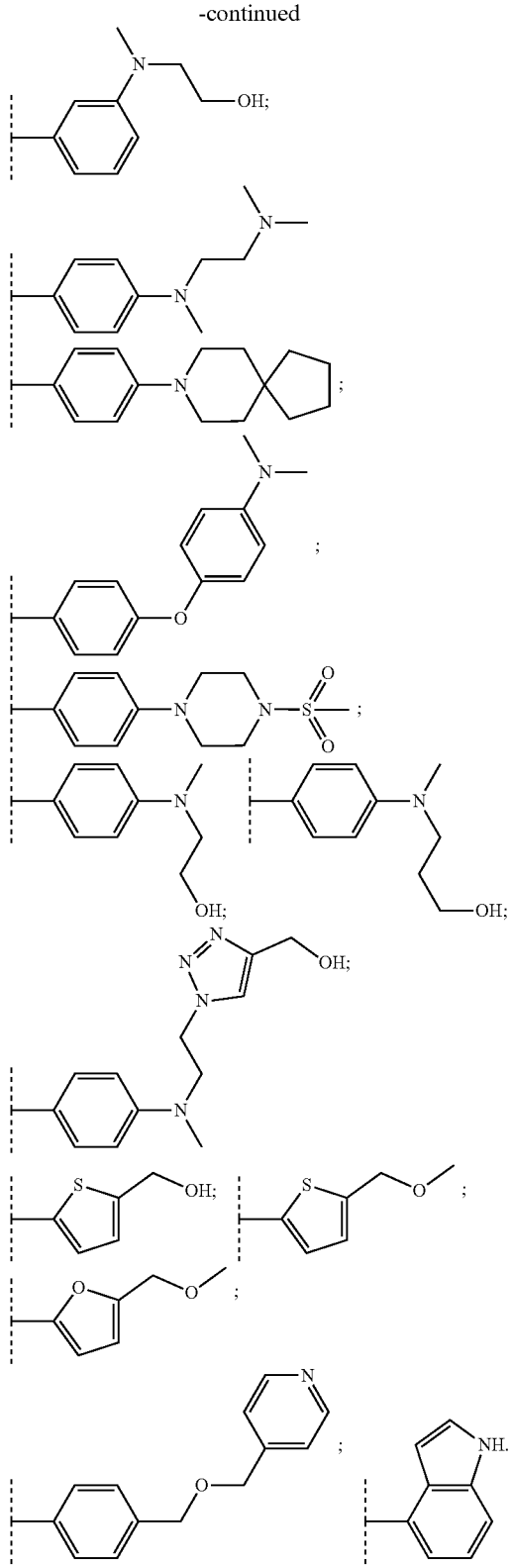

$R_3$ being optionally labeled and is selected from
6-Cl;
6-F;
5-F;
4-F;
6-(2-thienyl);

6-(3-thienyl);
6-(6-fluoro-3-pyridyl);
5-OMe;
6-morpholino;
5-morpholino;
6-Br;
4-Br;
4-Bpin;
5-Bpin.

The compounds of formula II-1a comprise a radioelement selected from $^{18}F$, $^{11}C$, $^{123}I$ and $^{124}I$ on at least one of the substituents $R_1$, $R_2$, $R_3$ or $R_4$.

According to an advantageous embodiment, the compound of the invention is of general formula I-1a or II-1a:

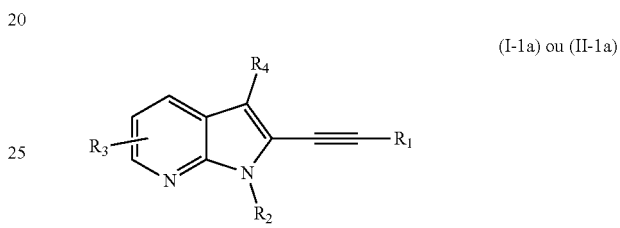

(I-1a) ou (II-1a)

$R_2$ and $R_3$ being as previously defined in formula I or II respectively;

$R_1$ being optionally labeled and is selected from

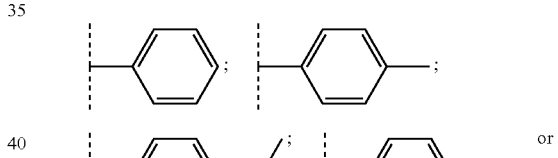

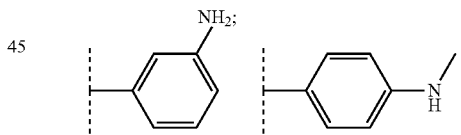

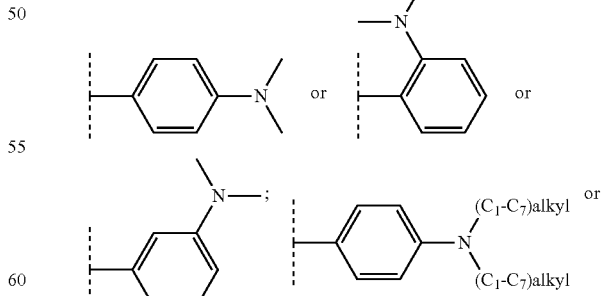

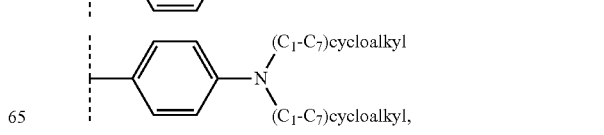

-continued
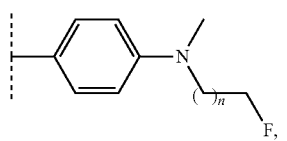
n being in particular from 0 to 6;
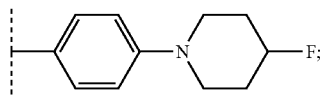
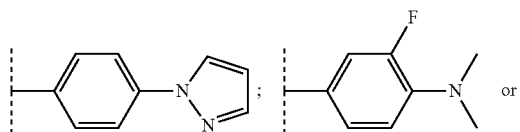
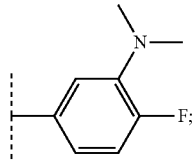
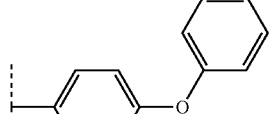
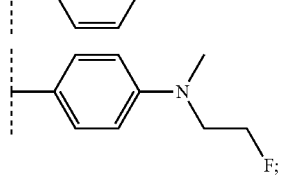
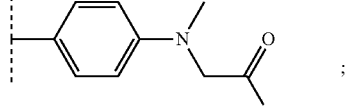
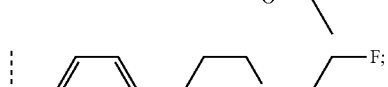
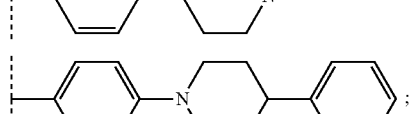
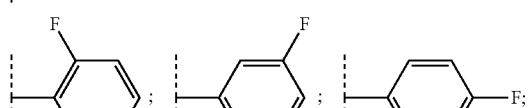
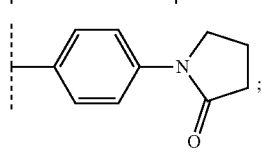
-continued
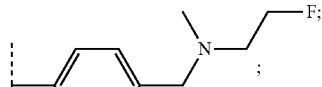
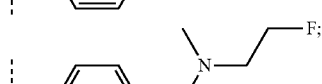
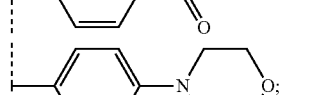
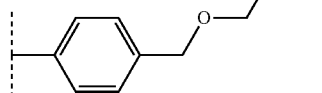
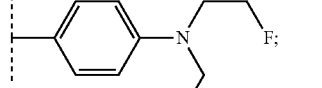
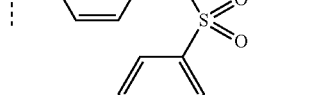
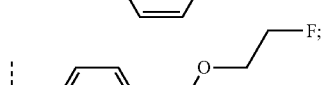
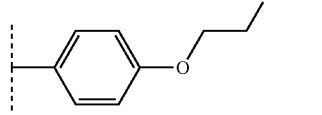
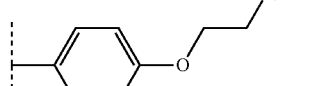

$R_4$ being selected from
H;
$(CH_2)_n$—N-alkyl, n being an integer equal to 0, 1 or 2.

The compounds of formula II-1a comprise a radioelement selected from $^{18}F$, $^{11}C$, $^{123}I$ and $^{124}I$ on at least one of the substituents $R_1$, $R_2$ or $R_3$.

According to an advantageous embodiment, the compound of the invention is of the general formula I-1a or II-1a:

(I-1a) or (II-1a)

$R_1$ and $R_4$ are as previously defined in formula I or II respectively;

$R_2$ being optionally labeled and is selected from
H;
$(CH_2CH_2O)_n$—$CH_2CH_2F$, n being an integer equal to 0, 1 or 2;
$SO_2Ph$;
$COO^tBu$;
$CH_2OCH_3$;
$CH_2O(CH_2)_2OCH_3$;
$COCH_3$;

$R_3$ being optionally labeled and is selected from
6-Cl;
6-F;
5-F;
4-F;
6-(2-thienyl);
6-(3-thienyl);
6-(6-fluoro-3-pyridyl);
5-OMe;
6-morpholino;
5-morpholino;
6-Br;
4-Br;
4-Bpin;
5-Bpin.

The compounds of formula II-1a comprise a radioelement selected from $^{18}F$, $^{11}C$, $^{123}I$ and $^{124}I$ on at least one of the substituents $R_1$, $R_2$, $R_3$ or $R_4$ According to an advantageous embodiment, the compound of the invention is of general formula I-1a or II-1a:

(I-1a) or (II-1a)

$R_1$ and $R_3$ being as defined above in formula I or II respectively;

R₂ being optionally labeled and is selected from
H;
(CH₂CH₂O)ₙ—CH₂CH₂F, n being an integer equal to 0, 1 or 2;
SO₂Ph;
COO'Bu;
CH₂OCH₃;
CH₂O(CH₂)₂OCH₃
COCH₃

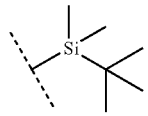

R₄ being selected from
H;
(CH₂)ₙ—N-alkyl, n being an integer equal to 0, 1 or 2.

The compounds of formula II-1a comprise a radioelement selected from ¹⁸F, ¹¹C, ¹²³I and ¹²⁴I on at least one of the substituents R₁, R₂ or R₃.

According to an advantageous embodiment, the compound of the invention is of the general formula I-1a or II-1a:

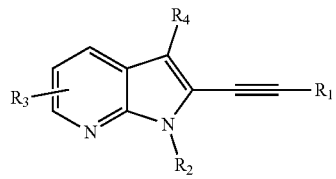

(I-1a) or (II-1a)

R₁ and R₂ being as previously defined in formula I or II respectively;
R₃ being optionally labeled and is selected from
6-Cl;
6-F;
5-F;
4-F;
6-(2-thienyl);
6-(3-thienyl);
6-(6-fluoro-3-pyridyl);
5-OMe;
6-morpholino;
5-morpholino;
6-Br;
4-Br;
4-Bpin;
5-Bpin.

R₄ is selected from
H;
(CH₂)ₙ—N-alkyl, n being an integer equal to 0, 1 or 2.

The compounds of formula II-1a it comprises a radioelement selected from ¹⁸F, ¹¹C, ¹²³I and ¹²⁴I on at least one of the substituents R₁, R₂ or R₃.

According to an advantageous embodiment, the compound of the invention is of the general formula I-1a or II-1a

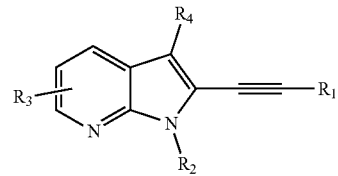

(I-1a) or (II-1a)

R₄ being as previously defined in formula I or II respectively;
R₁ being optionally labeled and is selected from

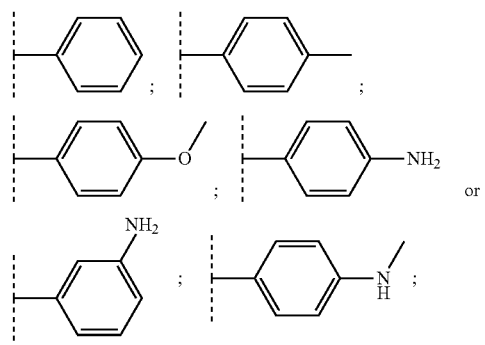

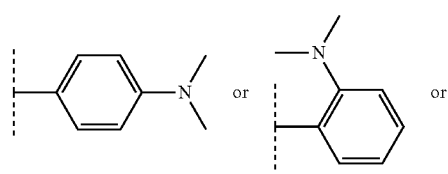

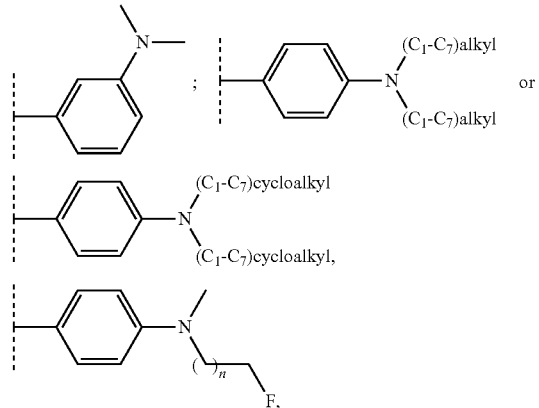

n being in particular from 0 to 6;

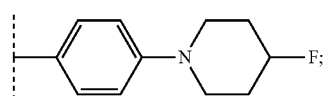

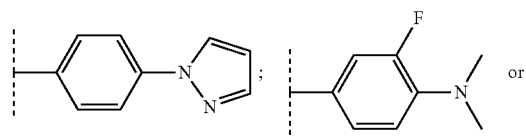

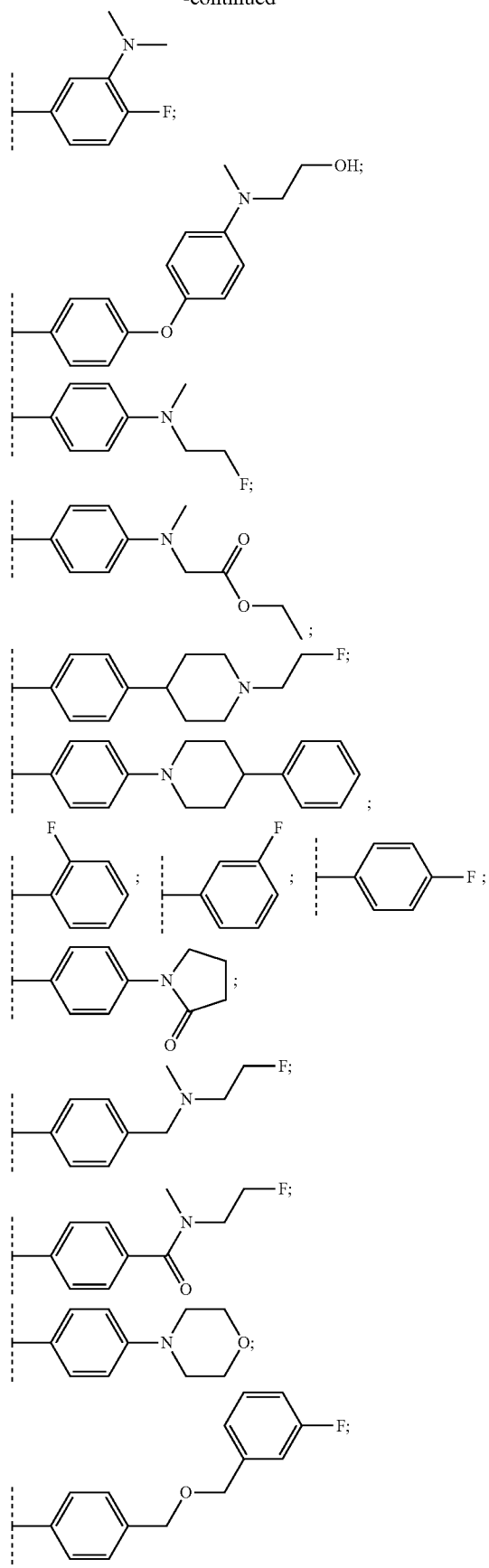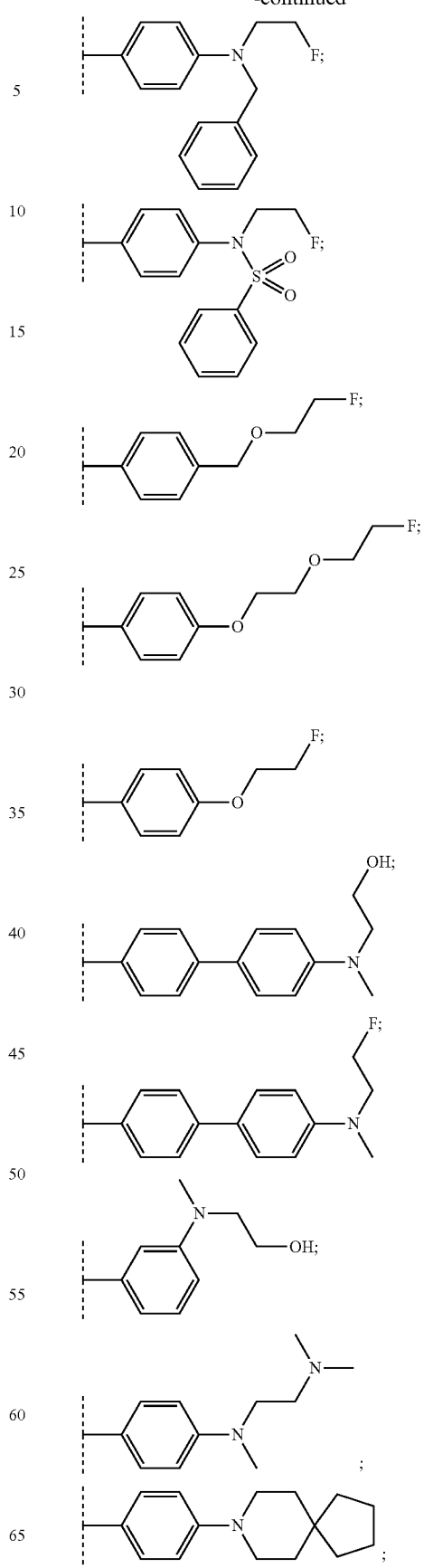

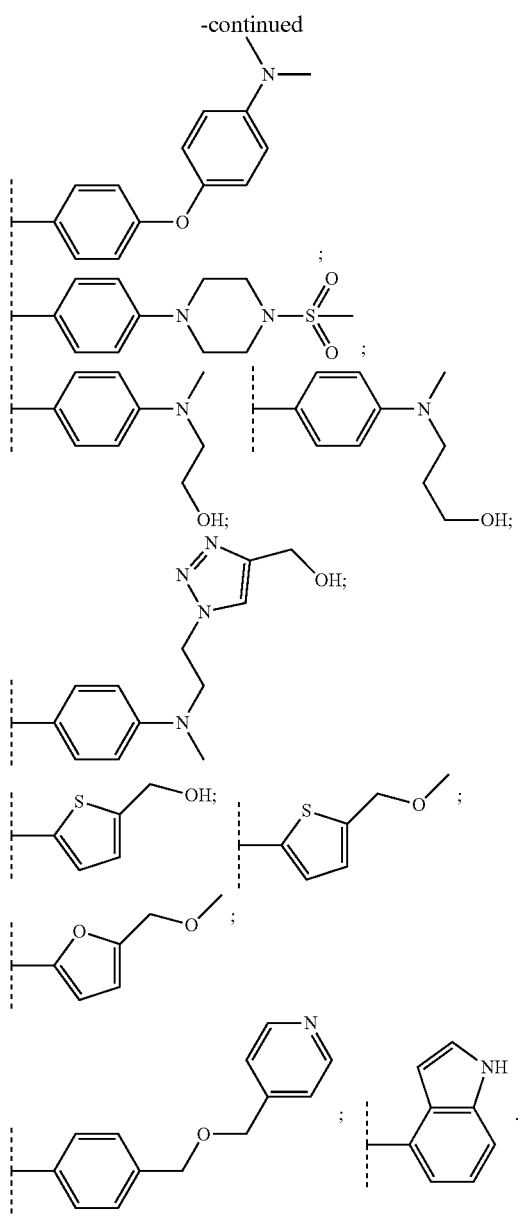

R₂ being optionally labeled and is selected from
H;
(CH₂CH₂O)$_n$—CH₂CH₂F, n being an integer equal to 0, 1 or 2;
SO₂Ph;
COO$^t$Bu;
CH₂OCH₃;
CH₂O(CH₂)₂OCH₃
COCH₃,

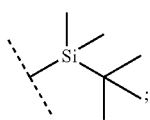

R₃ being optionally labeled and is selected from
6-Cl;
6-F;
5-F;
4-F;
6-(2-thienyl);
6-(3-thienyl);
6-(6-fluoro-3-pyridyl);
5-OMe;
6-morpholino;
5-morpholino;
6-Br;
4-Br;
4-Bpin;
5-Bpin.

The compounds of formula II-1a comprise a radioelement selected from $^{18}F$, $^{11}C$, $^{123}I$ and $^{124}I$ on at least one of the substituents R₁, R₂, R₃ or R₄.

According to an advantageous embodiment, the compound of the invention is of general formula I-1a-1 or II-1a-1

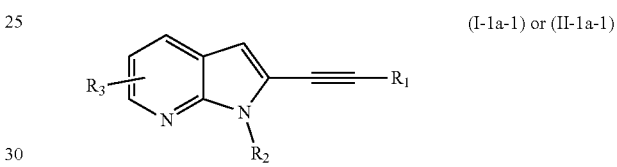

(I-1a-1) or (II-1a-1)

R₃ being as previously defined in formula I or II respectively;
R₁ being optionally labeled and is selected from

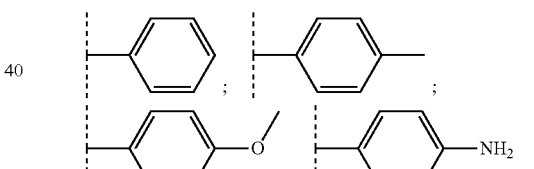

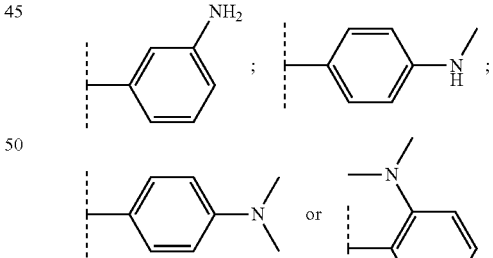

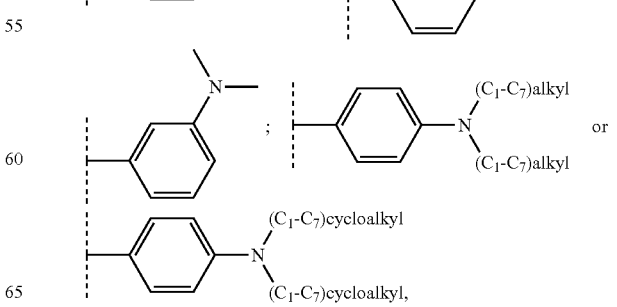

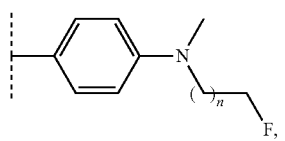
n being in particular from 0 to 6;
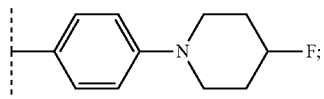
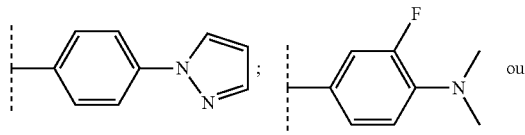 ou
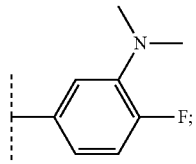
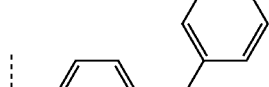
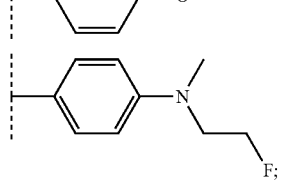
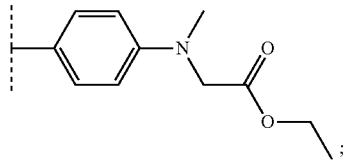
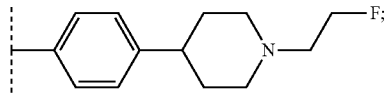
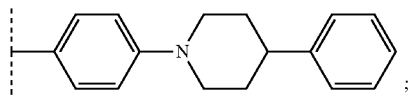
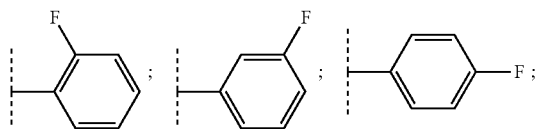
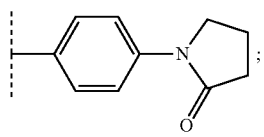
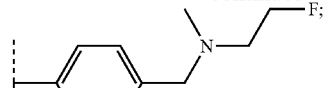
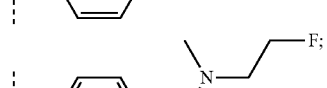
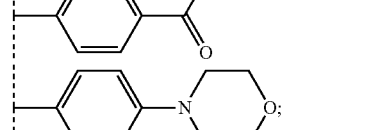
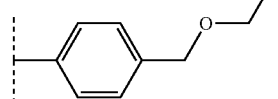
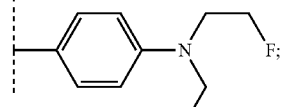
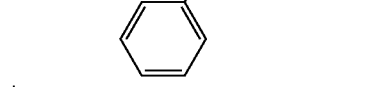
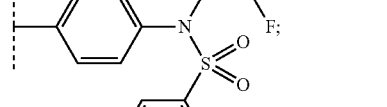
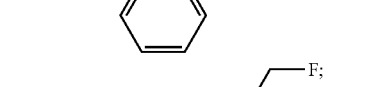
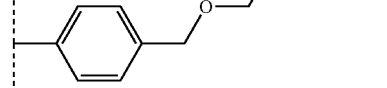
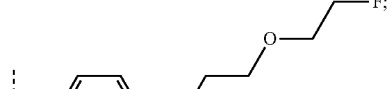
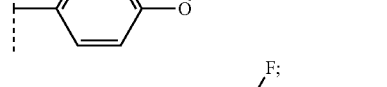
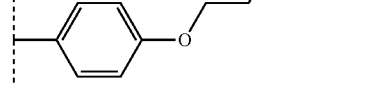

-continued

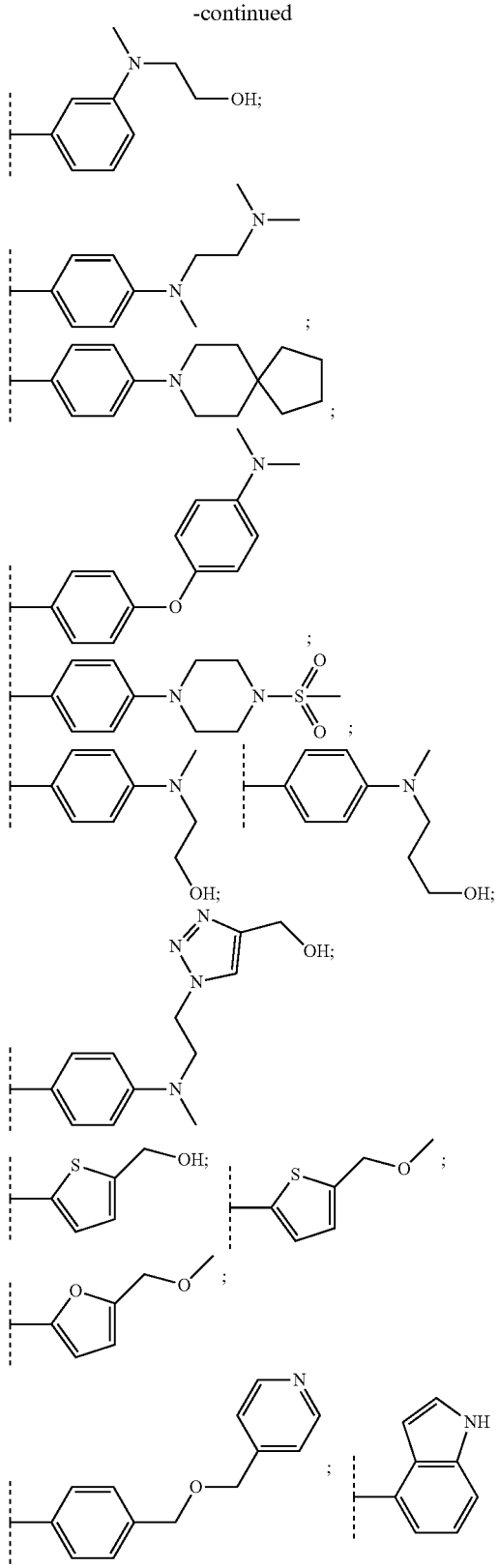

R₂ being optionally labeled and is selected from
H;
(CH₂CH₂O)ₙ—CH₂CH₂F, n being an integer equal to 0, 1 or 2;

SO₂Ph;
COOᵗBu;
CH₂OCH₃;
CH₂O(CH₂)₂OCH₃
COCH₃,

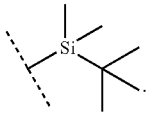

The compounds of formula II-1a-1 comprise a radioelement selected from $^{18}$F, $^{11}$C, $^{123}$I and $^{124}$I on at least one of the substituents R₁, R₂, or R₃

According to an advantageous embodiment, the compound of the invention is of general formula I-1a-1 or II-1a-1

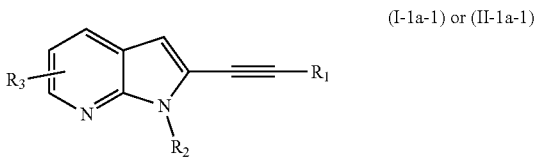
(I-1a-1) or (II-1a-1)

R₂ being as previously defined in formula I or II respectively;

R₁ being optionally labeled and is selected from

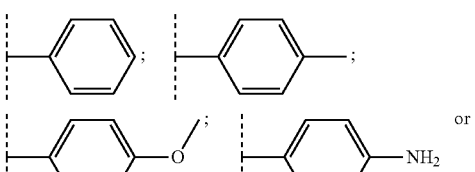
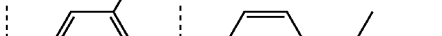
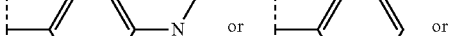
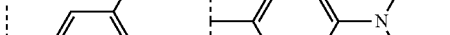
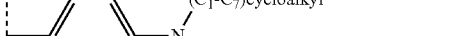
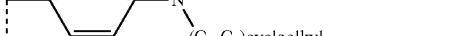
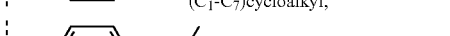
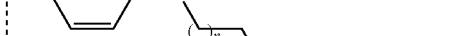
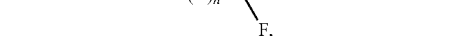

n being in particular from 0 to 6;
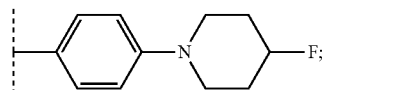
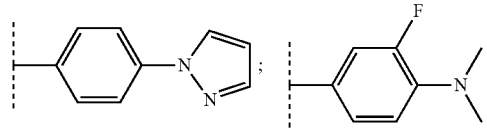 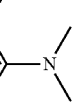 or
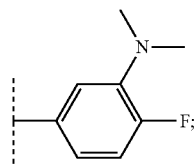
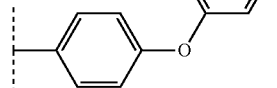
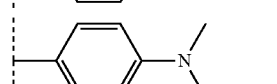
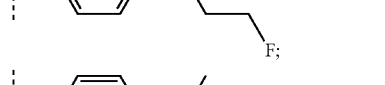
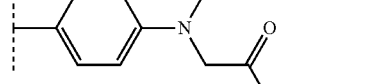
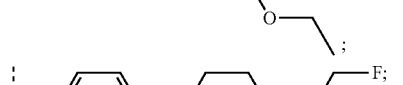
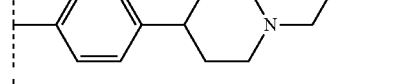
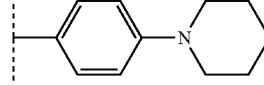
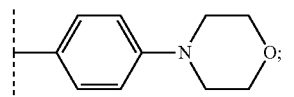
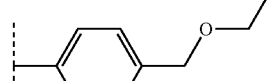
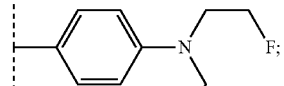
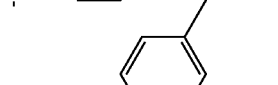
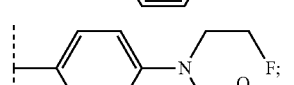
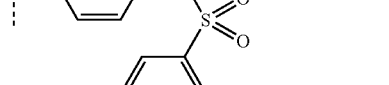
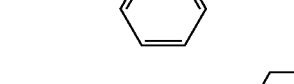
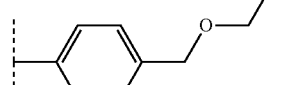
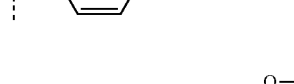
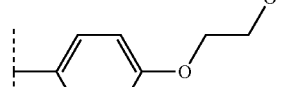
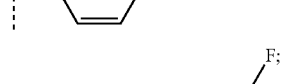
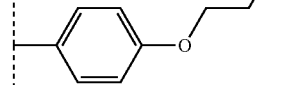
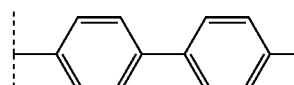
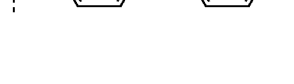
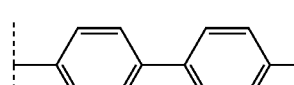
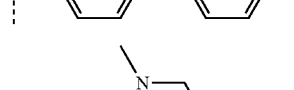

-continued

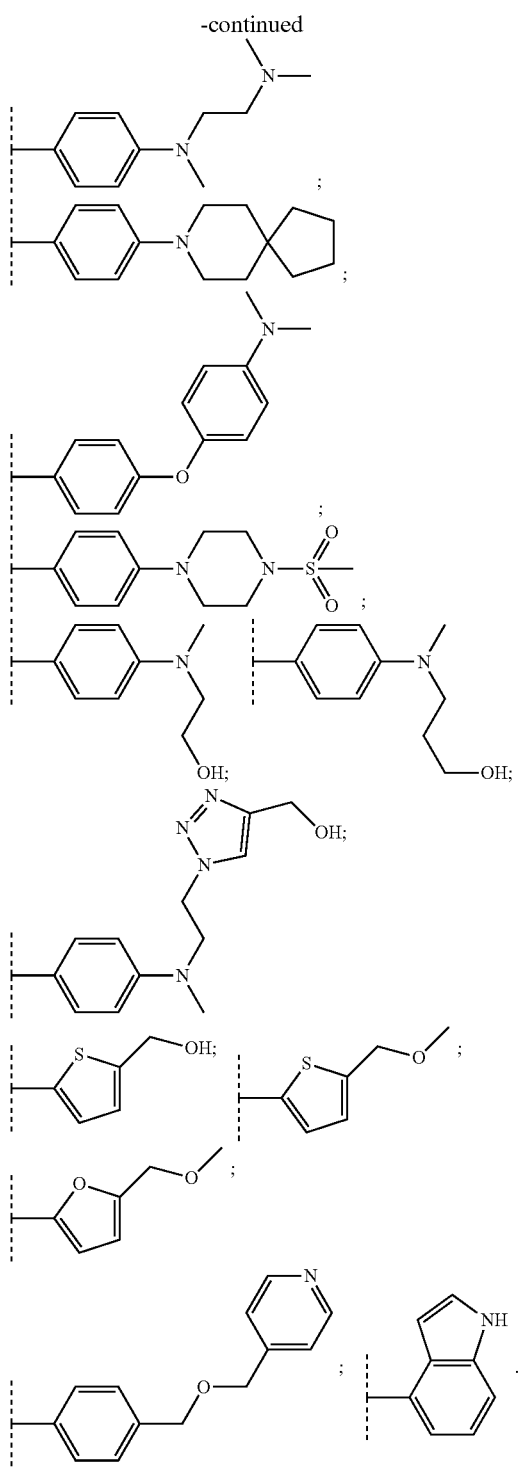

$R_3$ being optionally labeled and is selected from
6-Cl;
6-F;
5-F;
4-F;
6-(2-thienyl);
6-(3-thienyl);
6-(6-fluoro-3-pyridyl);
5-OMe;
6-morpholino;
5-morpholino;
6-Br;
4-Br;
4-Bpin;
5-Bpin.

The compounds of formula II-1a-1 comprise a radioelement selected from $^{18}F$, $^{11}C$, $^{123}I$ and $^{124}I$ on at least one of the substituents $R_1$, $R_2$, or $R_3$.

According to an advantageous embodiment, the compound of the invention is of general formula I-1a-1 or II-1a-1

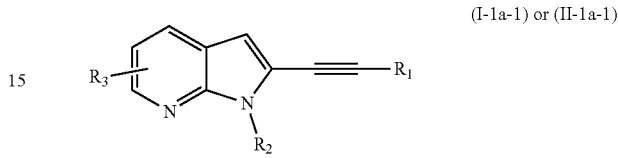
(I-1a-1) or (II-1a-1)

$R_1$ being as previously defined in formula I or II respectively;
$R_2$ being optionally labeled and is selected from
H;
$(CH_2CH_2O)_n$—$CH_2CH_2F$, n being an integer equal to 0, 1 or 2;
$SO_2Ph$;
$COO^tBu$;
$CH_2OCH_3$;
$CH_2O(CH_2)_2OCH_3$
$COCH_3$

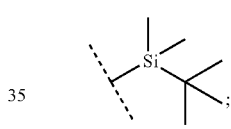

$R_3$ being optionally labeled and is selected from
6-Cl;
6-F;
5-F;
4-F;
6-(2-thienyl);
6-(3-thienyl);
6-(6-fluoro-3-pyridyl);
5-OMe;
6-morpholino;
5-morpholino;
6-Br;
4-Br;
4-Bpin;
5-Bpin.

The compounds of formula II-1a-1 comprise a radioelement selected from $^{18}F$, $^{11}C$, $^{123}I$ and $^{124}I$ on at least one of the substituents $R_1$, $R_2$, or $R_3$ According to an advantageous embodiment, the compound of the invention is of general formula I-1a-1 or II-1a-1

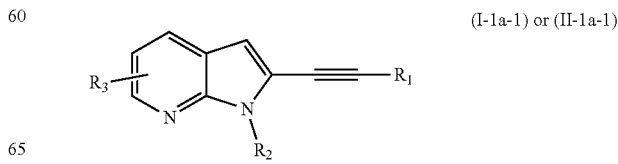
(I-1a-1) or (II-1a-1)

$R_1$ being optionally labeled and is selected from
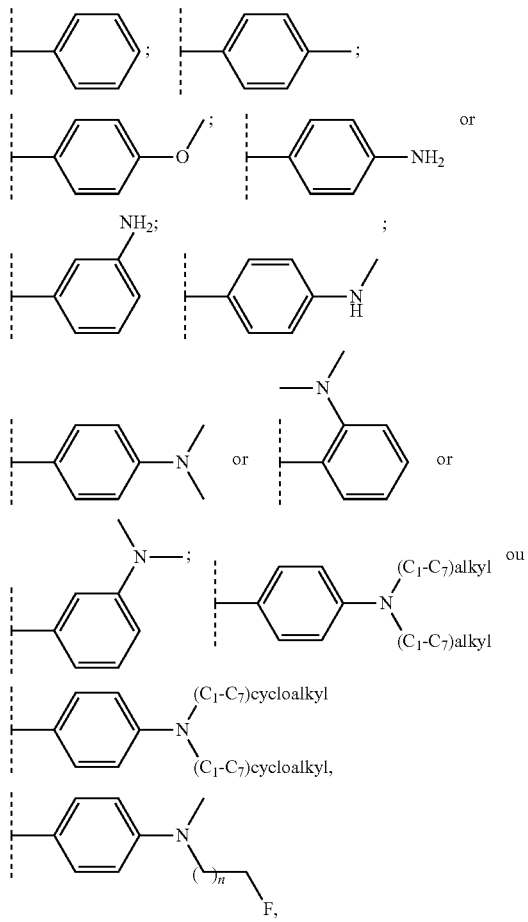
n being in particular from 0 to 6;
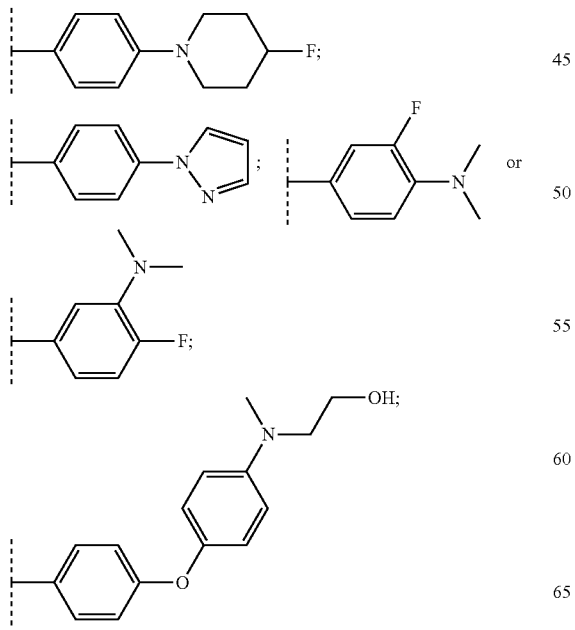
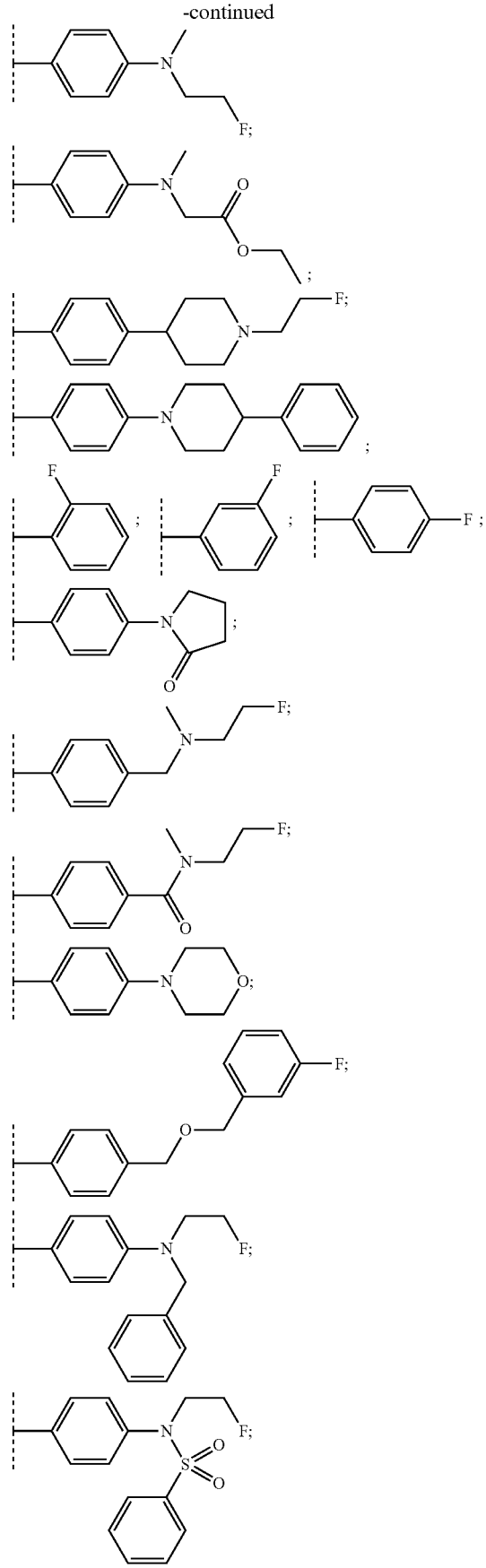

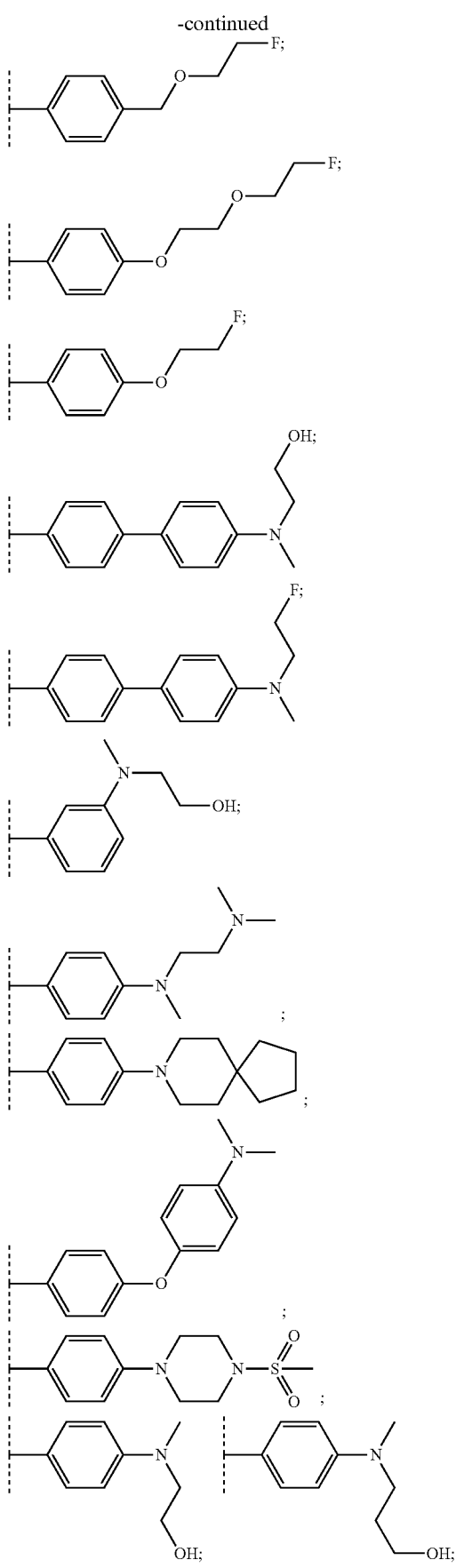

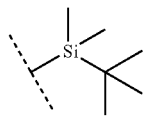

$R_2$ being optionally labeled and is selected from
H;
$(CH_2CH_2O)_n$—$CH_2CH_2F$, n being an integer equal to 0, 1 or 2;
$SO_2Ph$;
$COO^tBu$;
$CH_2OCH_3$;
$CH_2O(CH_2)_2OCH_3$
$COCH_3$;

$R_3$ being optionally labeled and is selected from
6-Cl;
6-F;
5-F;
4-F;
6-(2-thienyl);
6-(3-thienyl);
6-(6-fluoro-3-pyridyl);
5-OMe;
6-morpholino;
5-morpholino;
6-Br;
4-Br;
4-Bpin;
5-Bpin.

The compounds of formula II-1a-1 comprise a radioelement selected from $^{18}F$, $^{11}C$, $^{123}I$ and $^{124}I$ on at least one of the substituents $R_1$, $R_2$, or $R_3$.

According to an advantageous embodiment, the compound of the invention is of general formula I-1a-2 or II-1a-2

(I-1a-2) or (II-1a-2)
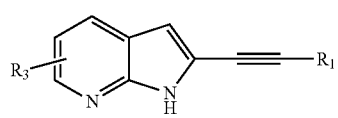
$R_3$ being as previously defined in formula I or II respectively;
$R_1$ being optionally labeled and is selected from
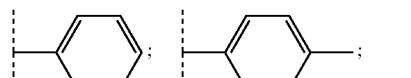
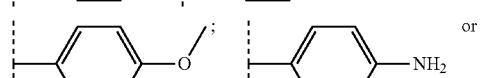
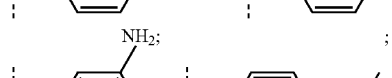
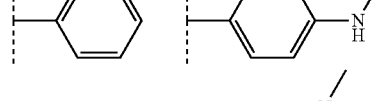
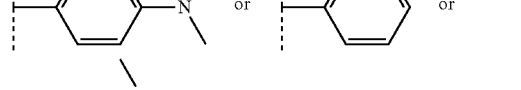
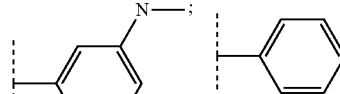
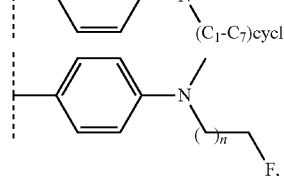
n being in particular from 0 to 6;
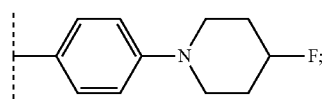
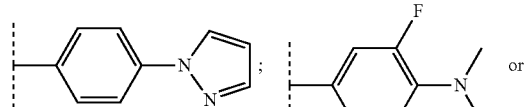
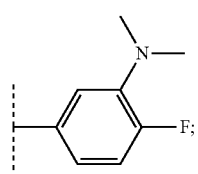
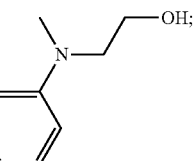
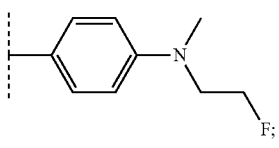
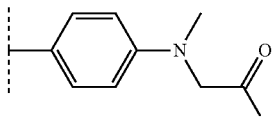
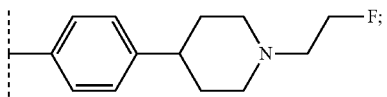
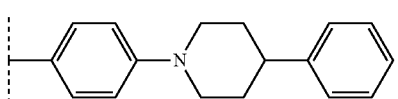
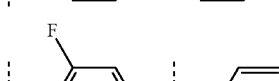
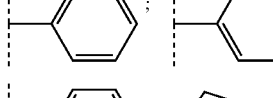
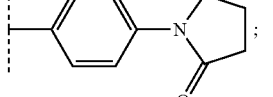
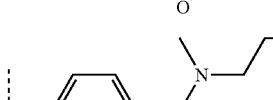
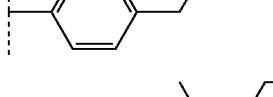
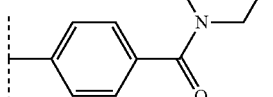
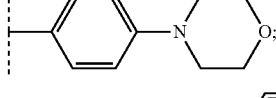
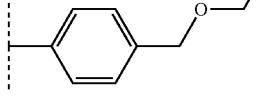

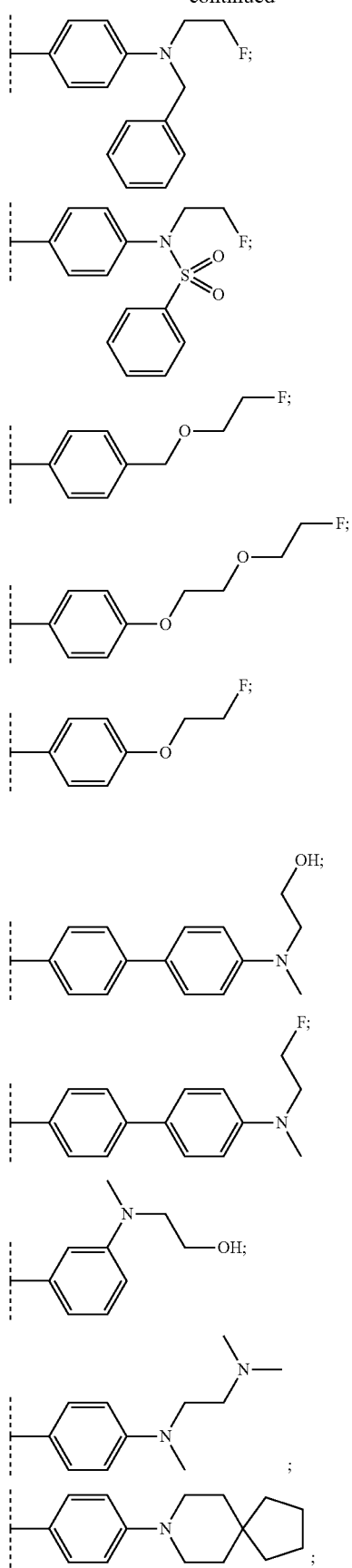

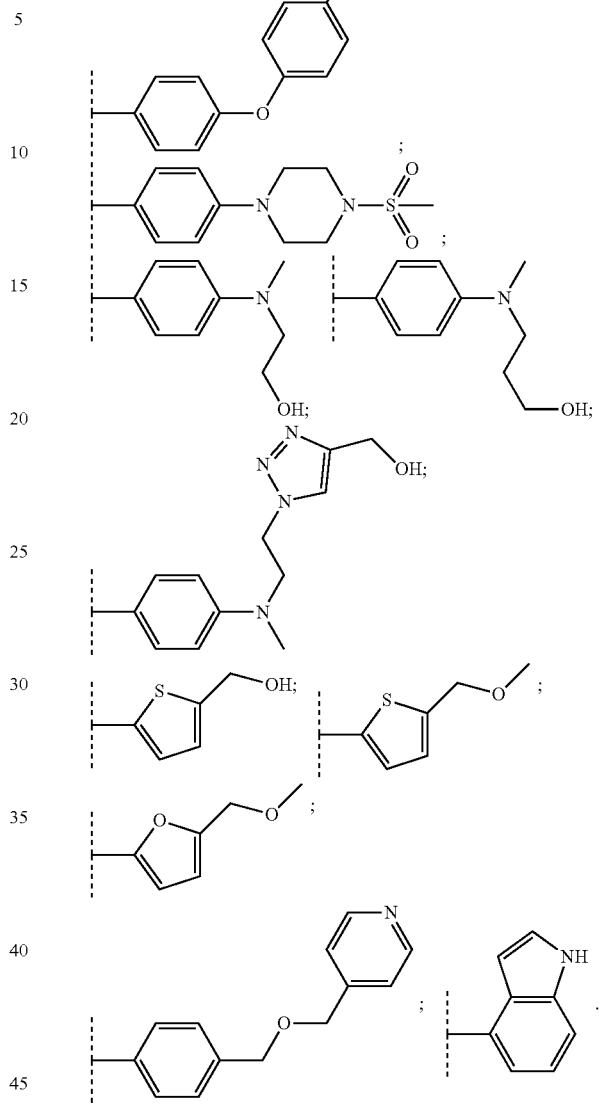

The compounds of formula II-1a-2 comprise a radioelement selected from $^{18}F$, $^{11}C$, $^{123}I$ and $^{124}I$ on at least one of the substituents $R_1$ or $R_3$.

According to an advantageous embodiment, the compound of the invention is of general formula I-1a-2 or II-1a-2

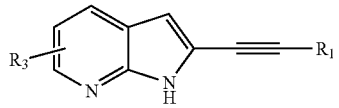

(I-1a-2) ou (II-1a-2)

$R_1$ being as previously defined in formula I or II respectively;

$R_3$ being optionally labeled and is selected from
6-Cl;
6-F;
5-F;
4-F;

6-(2-thienyl);
6-(3-thienyl);
6-(6-fluoro-3-pyridyl);
5-OMe;
6-morpholino;
5-morpholino;
6-Br;
4-Br;
4-Bpin;
5-Bpin.

The compounds of formula II-1a-2 comprise a radioelement selected from $^{18}F$, $^{11}C$, $^{123}I$ and $^{124}I$ on at least one of the substituents $R_1$ or $R_3$.

According to an advantageous embodiment, the compound of the invention is of general formula I-1a-2 or II-1a-2

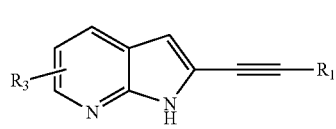

(I-1a-2) or (II-1a-2)

$R_1$ being optionally labeled and is selected from

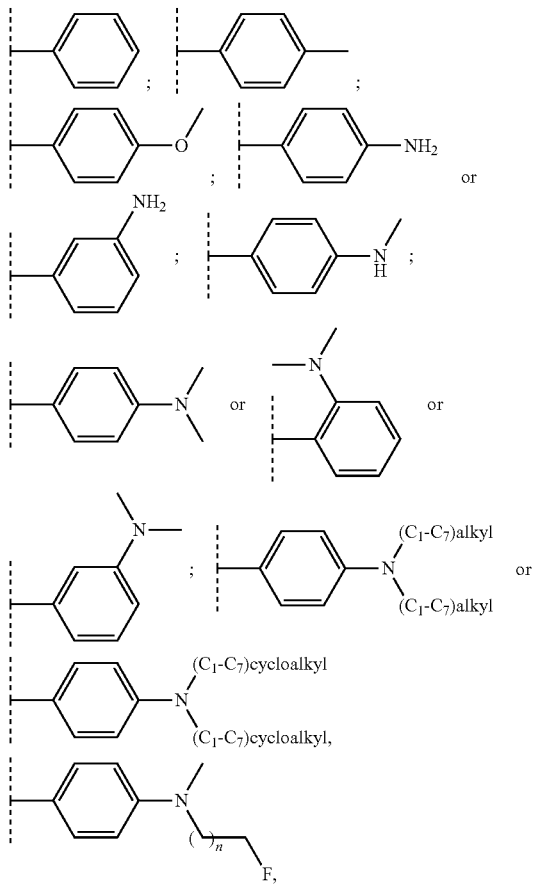

n being in particular from de 0 to 6;

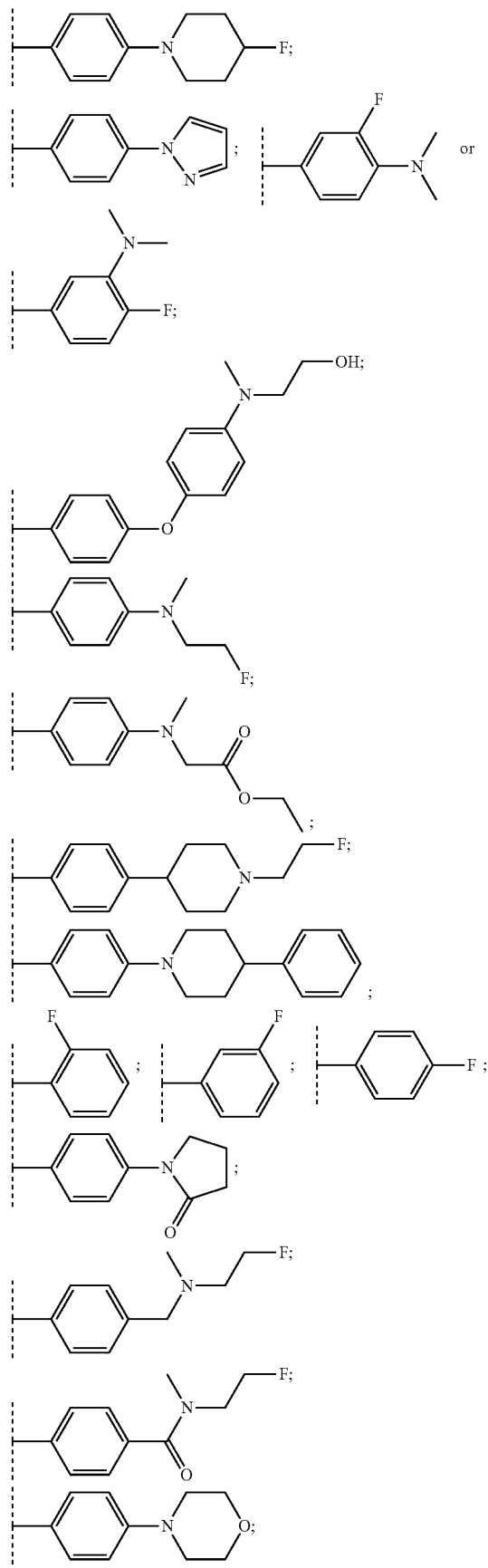

-continued
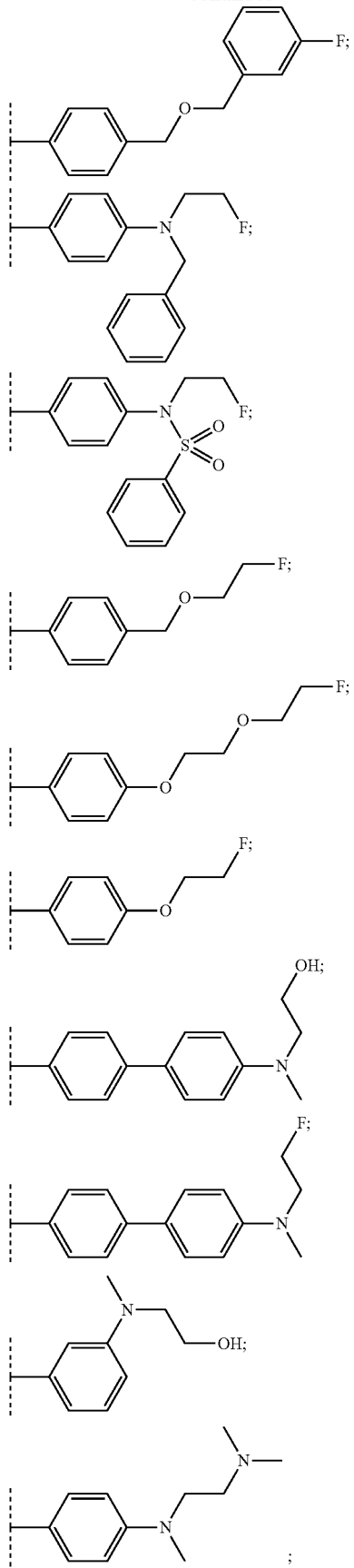
-continued
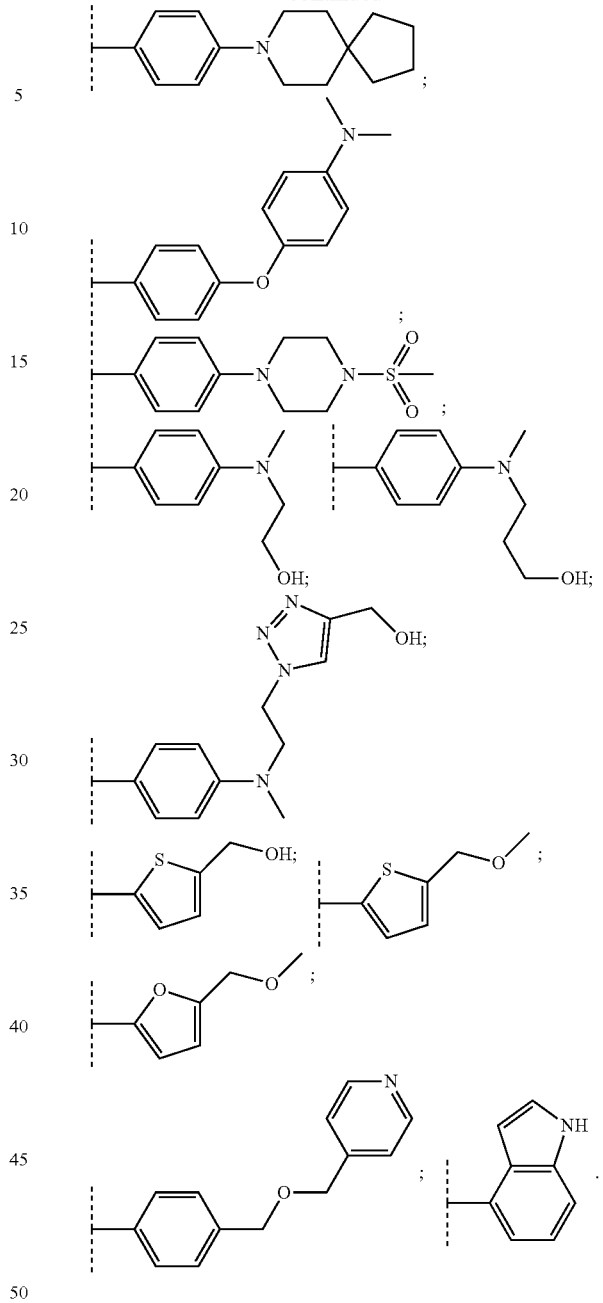
R₃ being optionally labeled and is selected from
6-Cl;
6-F;
5-F;
4-F;
6-(2-thienyl);
6-(3-thienyl);
6-(6-fluoro-3-pyridyl);
5-OMe;
6-morpholino;
5-morpholino;
6-Br;
4-Br;
4-Bpin;
5-Bpin.

The compounds of formula II-1a-2 comprise a radioelement selected from $^{18}F$, $^{11}C$, $^{123}I$ and $^{124}I$ on at least one of the substituents $R_1$ or $R_3$.

According to an advantageous embodiment, the compound of the invention is of general formula I-1a-2-A or II-1a-2-A:

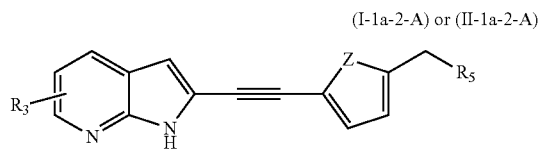

(I-1a-2-A) or (II-1a-2-A)

$R_3$ being as previously defined in formula I or II respectively;

Z being O or S;

$R_5$ being optionally labeled and is selected from $NR^aR^b$, $R^a$ and $R^b$ being as previously defined in formula I or II respectively;

$OR^e$, $R^e$ being as previously defined in formula I or II respectively.

The compounds of the formula II-2-A comprise a radioelement selected from $^{18}F$, $^{11}C$, $^{123}I$ and $^{124}I$ on at least one of the substituents $R_5$ or $R_3$. In the context of the formulas (I-1a-2-A) and (II-1a-2-A), the group $R_1$ in formulas I and II respectively is a heteroaryl substituted by an alkyl, said alkyl itself substituted with an amine or an alkoxyl. In particular, in this case, the heteroaryl is selected from thiophenyl or furanyl, substituted by a $C_1$ alkyl, itself substituted by an amino or alkoxyl.

According to another advantageous embodiment, the compound of the invention is of the general formula I-1a-2-A or II-1a-2-A:

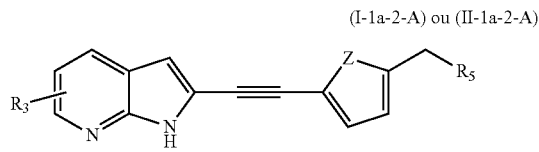

(I-1a-2-A) ou (II-1a-2-A)

$R_3$ being as previously defined in formula I or II respectively;

Z being O;

$R_5$ being optionally labeled and is selected from $NR^aR^b$;

$OR^e$.

The compounds of formula II-1a-2-A comprise a radioelement selected from $^{18}F$, $^{11}C$, $^{123}I$ and $^{124}I$ on at least one of the substituents $R_5$ or $R_3$.

According to another advantageous embodiment, the compound of the invention is of general formula I-1a-2-A or II-1a-2-A:

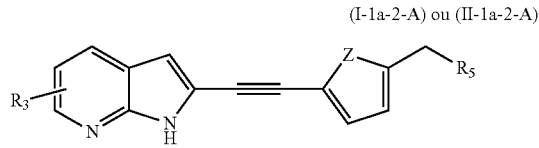

(I-1a-2-A) ou (II-1a-2-A)

$R_3$ being as previously defined in formula I or II respectively;

Z being S;

$R_5$ being optionally labeled and is selected from $NR^aR^b$;

$OR^e$.

The compounds of the formula II-1a-2-A comprise a radioelement selected from $^{18}F$, $^{11}C$, $^{123}I$ and $^{124}I$ on at least one of the substituents $R_5$ or $R_3$.

According to a mode more advantageous embodiment, the compound of the invention is of general formula I-1a-2-A or II-1a-2-A:

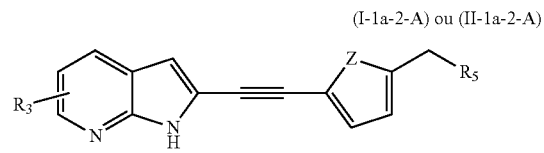

(I-1a-2-A) ou (II-1a-2-A)

$R_3$ being as previously defined in formula I or II respectively;

Z being O or S;

$R_5$ being optionally labeled and is selected from $N(CH_3)_2$;

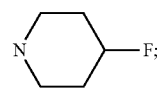

OH $OCH_3$.

The compounds of the formula II-1a-2-A comprise a radioelement selected from $^{18}F$, $^{11}C$, $^{123}I$ and $^{124}I$ on at least one of the substituents $R_5$ or $R_3$, Within the meaning of the invention, the group

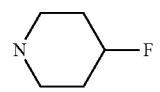

is an amine $NR^aR^b$ in which $R^a$ and $R^b$ form together a $(C_3-C_7)$heterocyclyl, said $(C_3-C_7)$heterocyclyl in this case a $C_5$-heterocyclyl substituted by halogen, fluorine.

According to another more preferred embodiment, the compound of the invention is of general formula I-1a-2-A or II-1a-2-A:

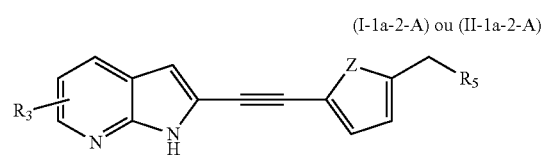

(I-1a-2-A) ou (II-1a-2-A)

$R_3$ being as previously defined in formula I or II respectively

Z being O;

R₃ being optionally labeled and is selected from N(CH₃)₂;

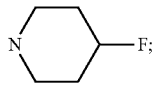

OH
OCH₃.

The compounds of formula II-1a-2-A comprise a radio-element selected from ¹⁸F, ¹¹C, ¹²³I and ¹²⁴I on at least one of the substituents R₅ or R₃.

In another more advantageous embodiment, the compound of the invention is of general formula I-1a-2-A or II-1a-2-A:

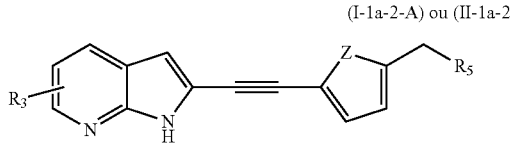

(I-1a-2-A) ou (II-1a-2-A)

R₃ being as previously defined in formula I or II respectively;
Z being S;
R₅ being optionally labeled and is selected from N(CH₃)₂;

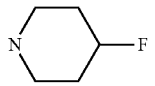

OH
OCH₃.

The compounds of the formula II-1a-2-A comprise a radioelement selected from ¹⁸F, ¹¹C, ¹²³I and ¹²⁴I on at least one of the substituents R₅ or R₃.

According to a particularly advantageous embodiment, the compound of the invention of formula I is selected from:

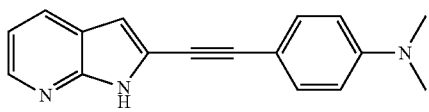
22a

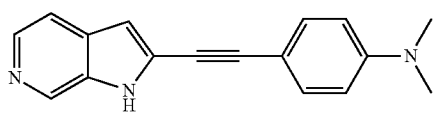
22b

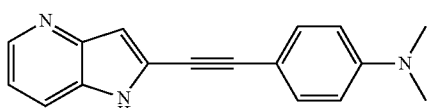
22c

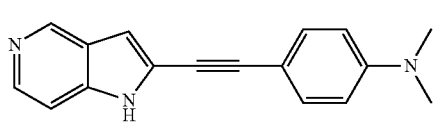
22d

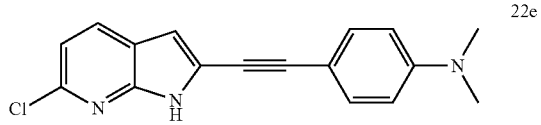
22e

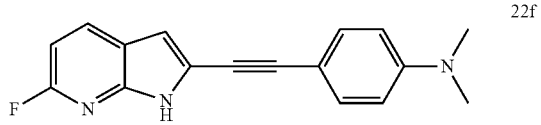
22f

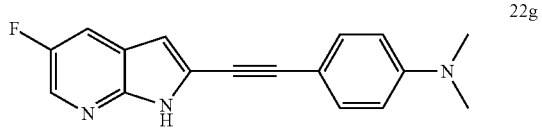
22g

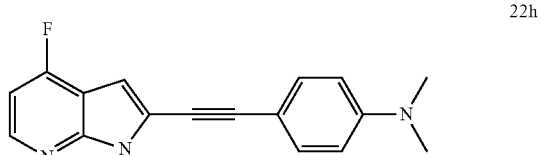
22h

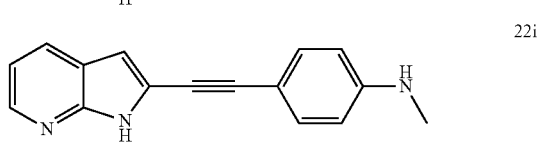
22i

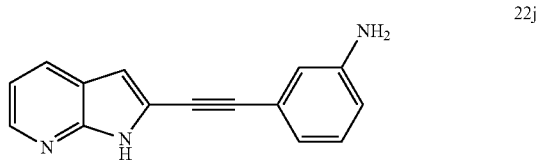
22j

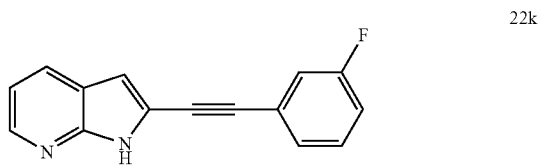
22k

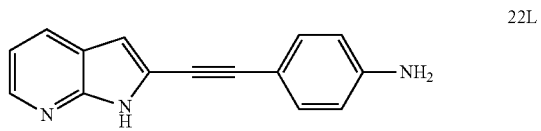
22L

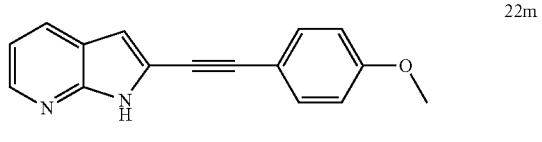
22m

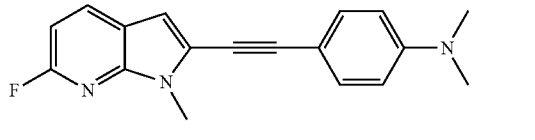
22n

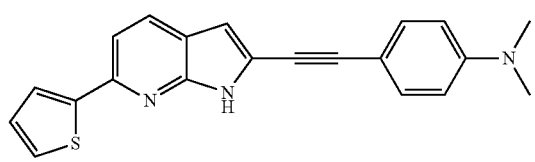
25a

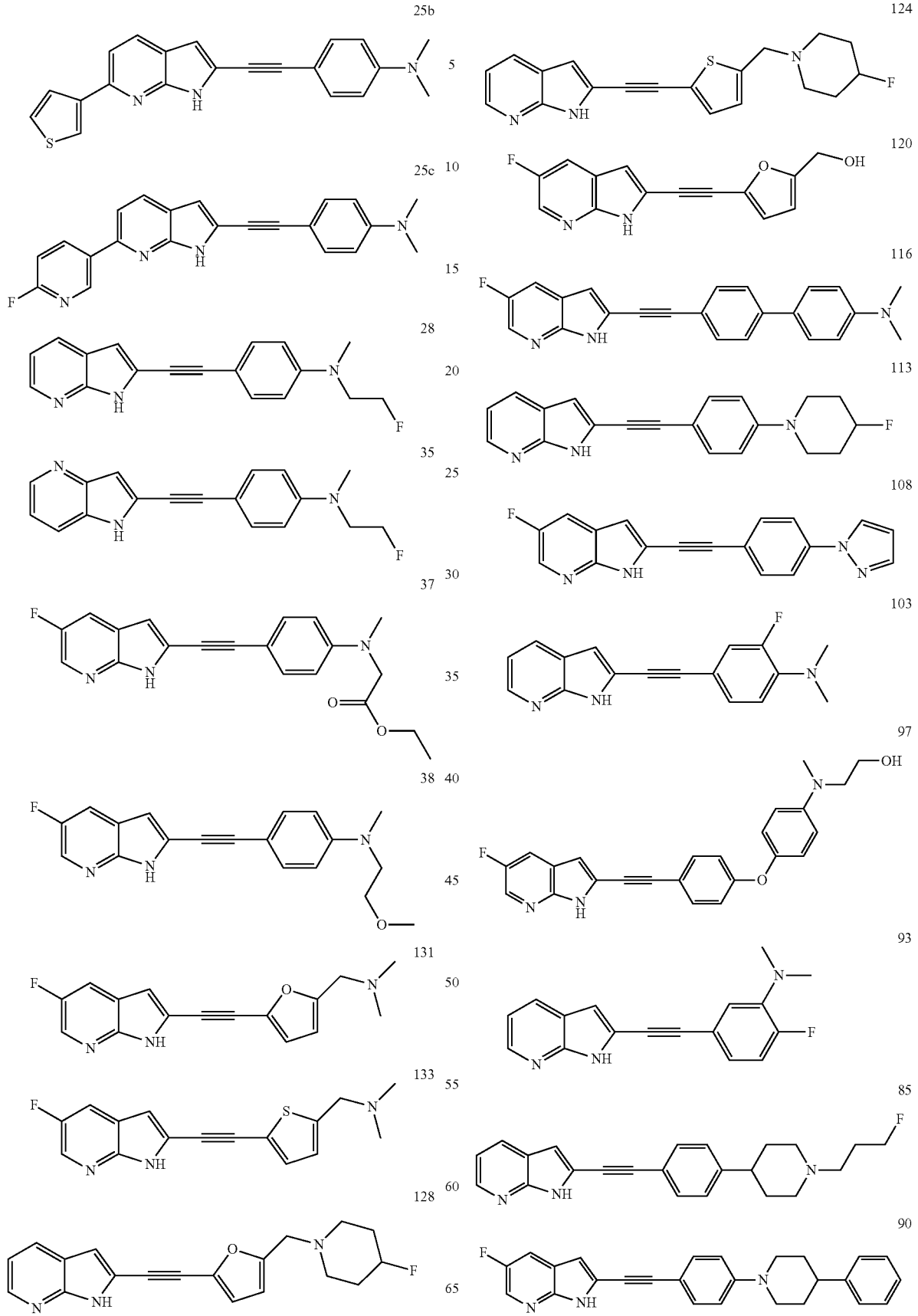

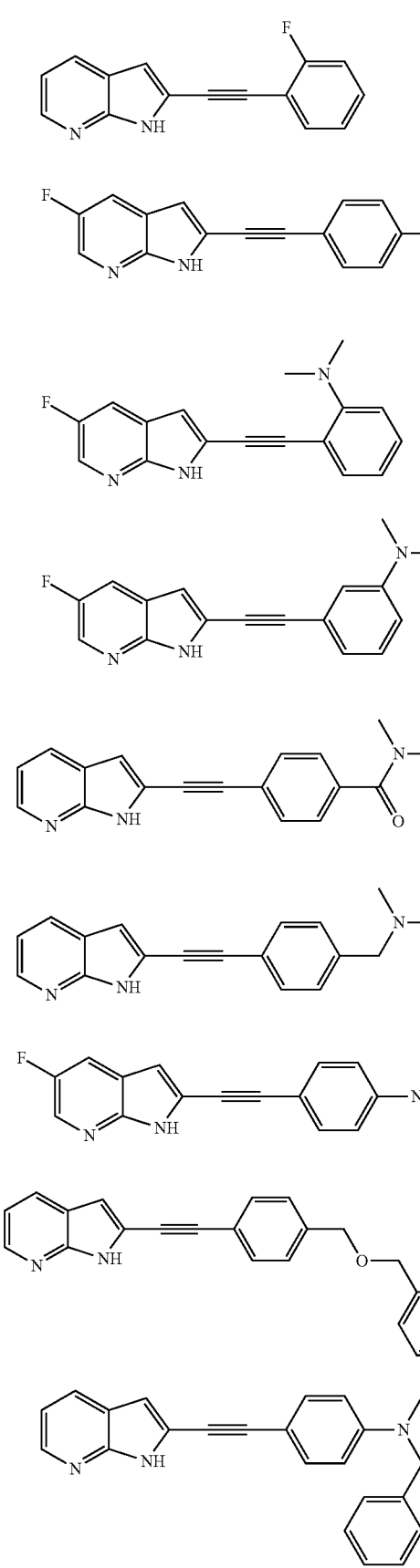
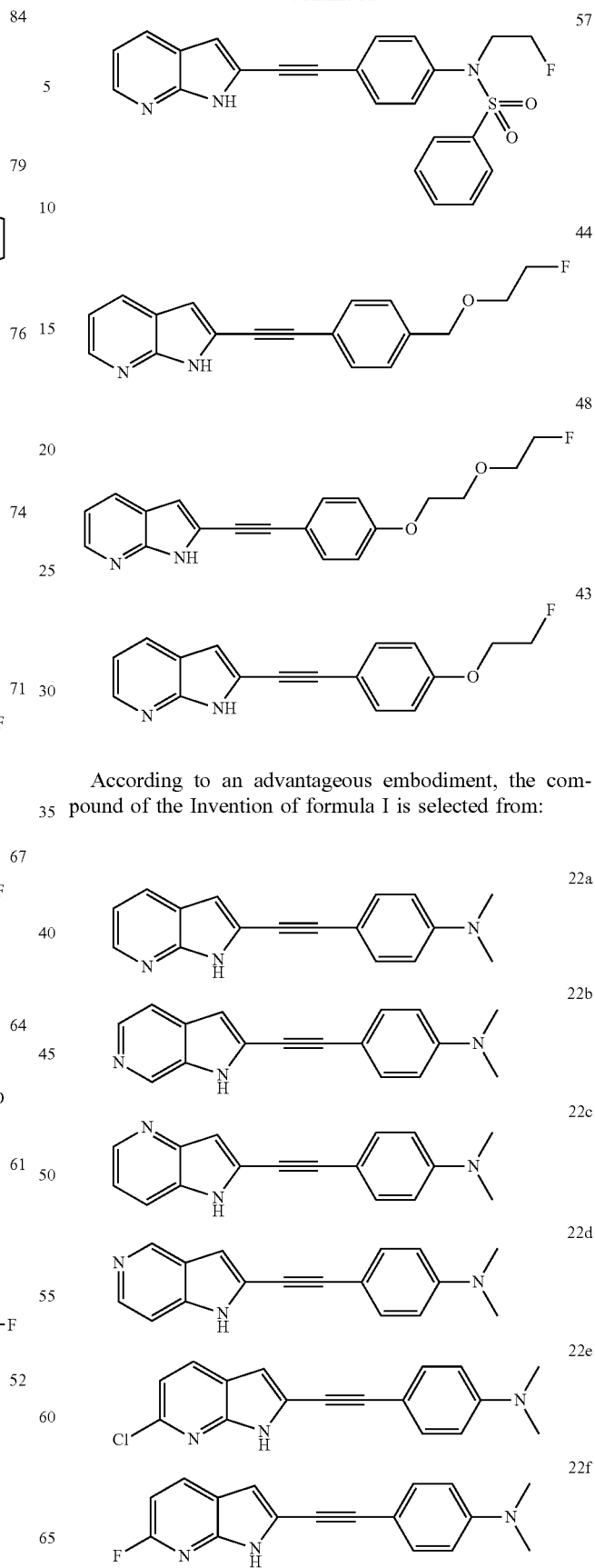
According to an advantageous embodiment, the compound of the Invention of formula I is selected from:

22g 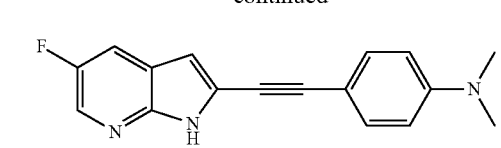
22h 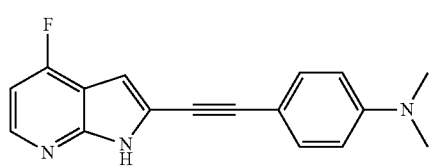
22i 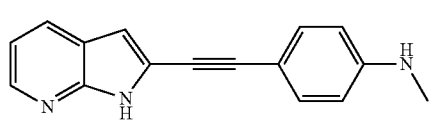
22k 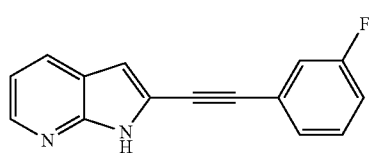
22m 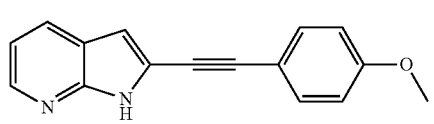
22n 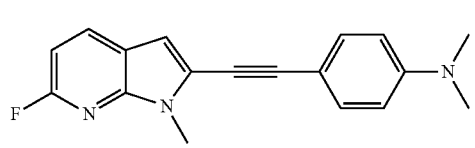
25a 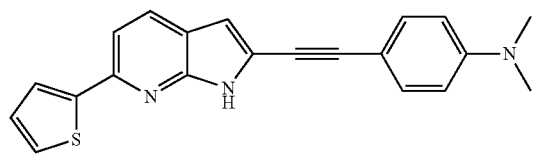
25b 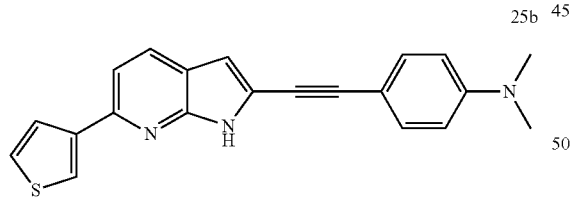
25c 
28 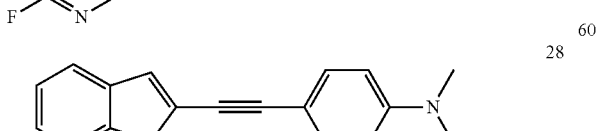
35 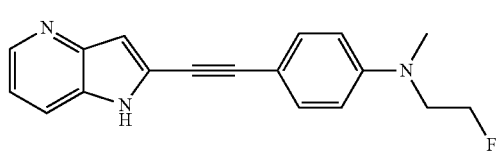
37 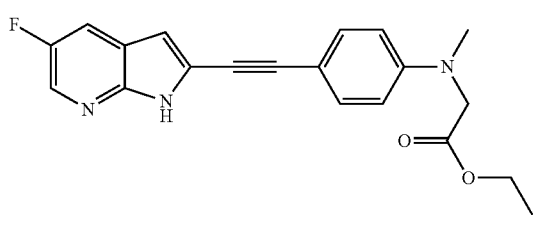
38 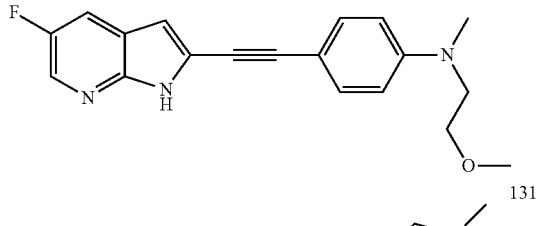
131 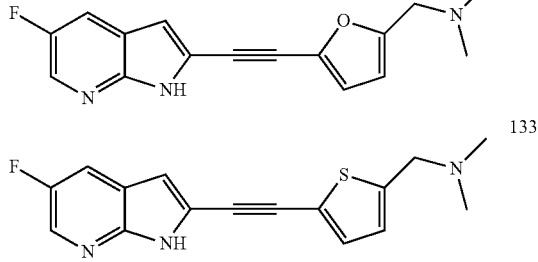
133 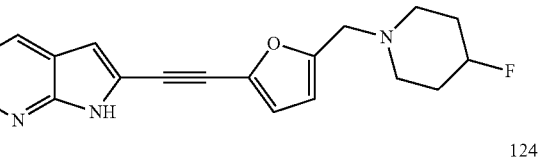
128 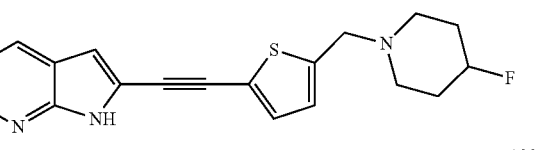
124 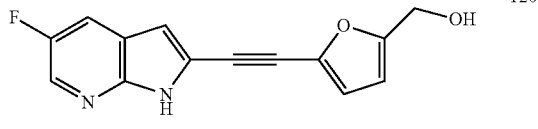
120 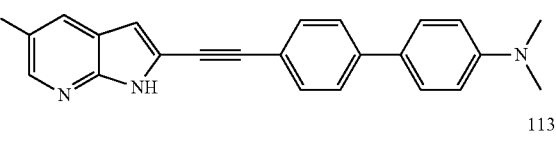
116 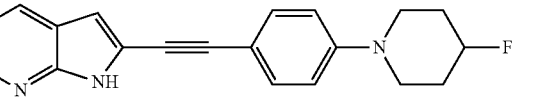
113

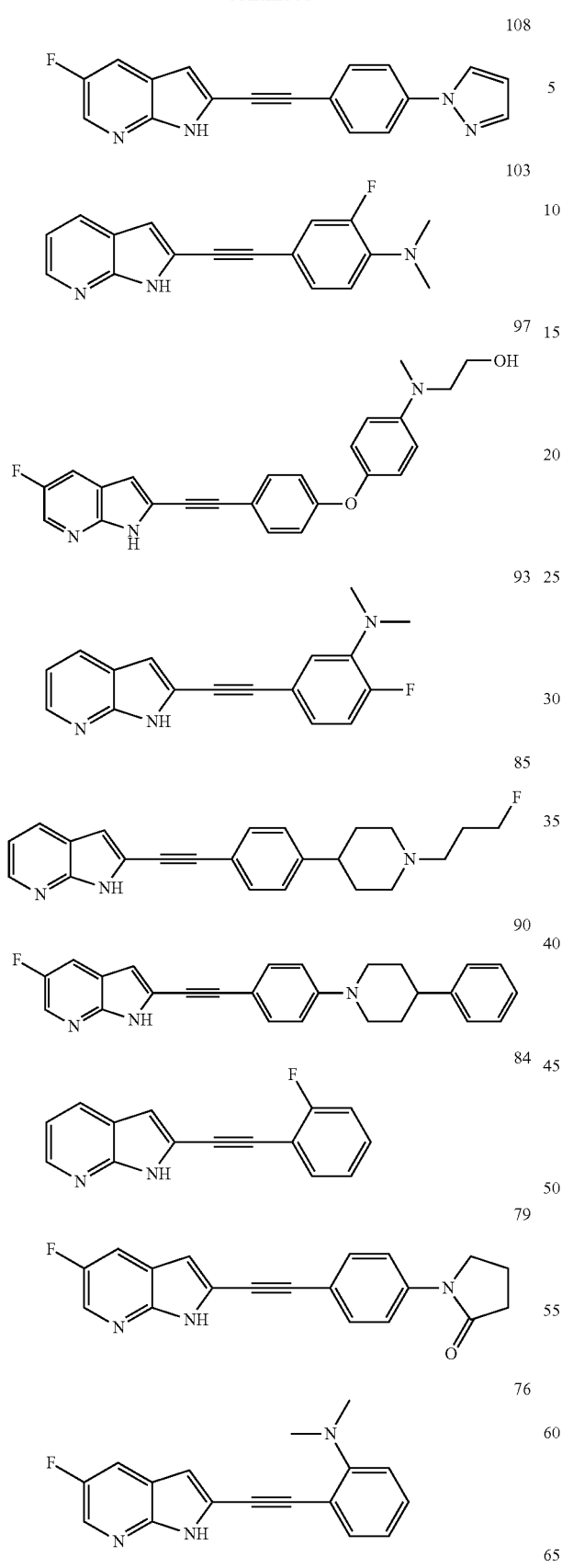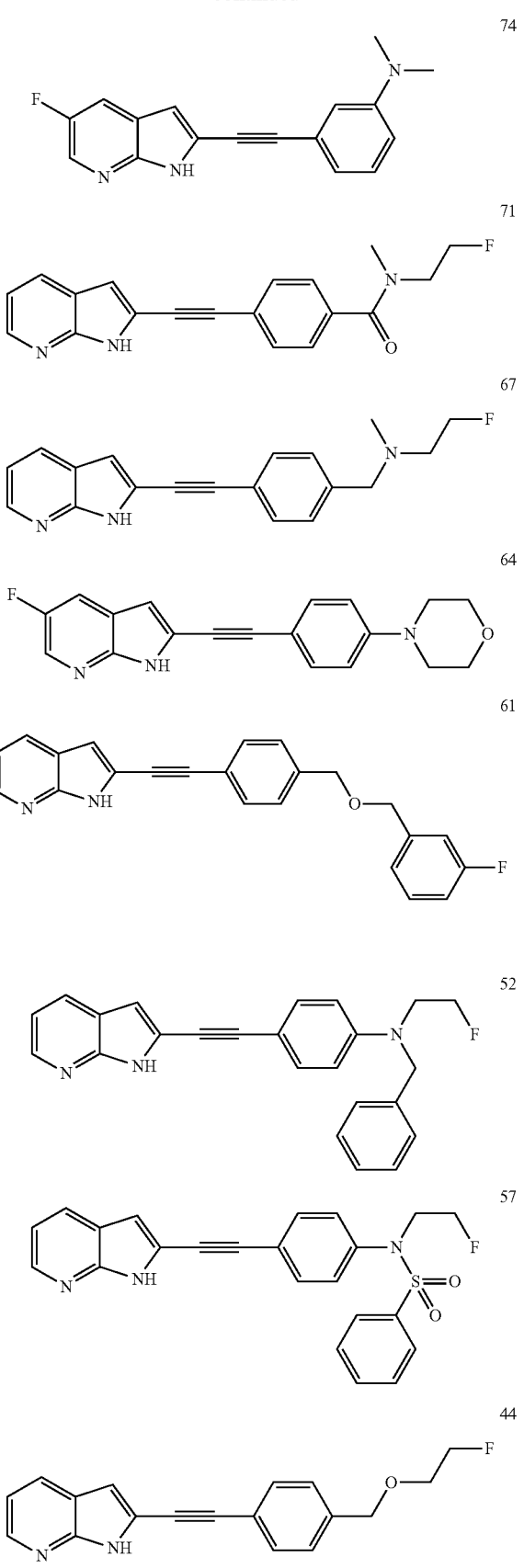

-continued
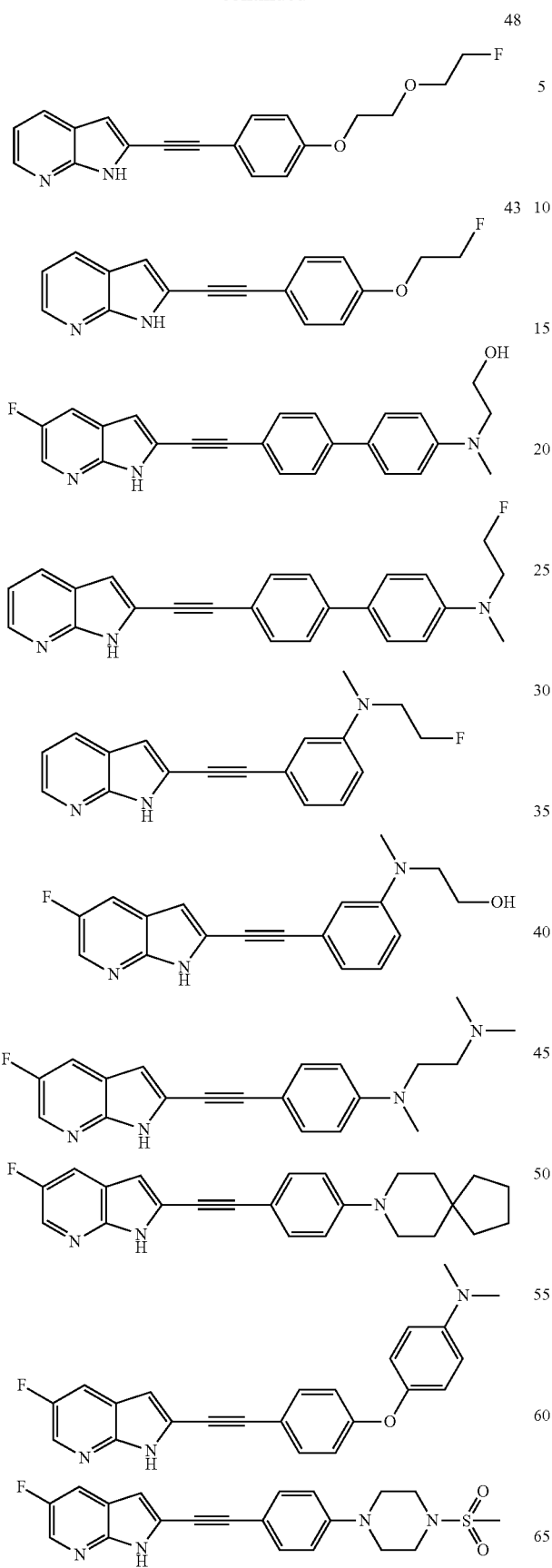
-continued
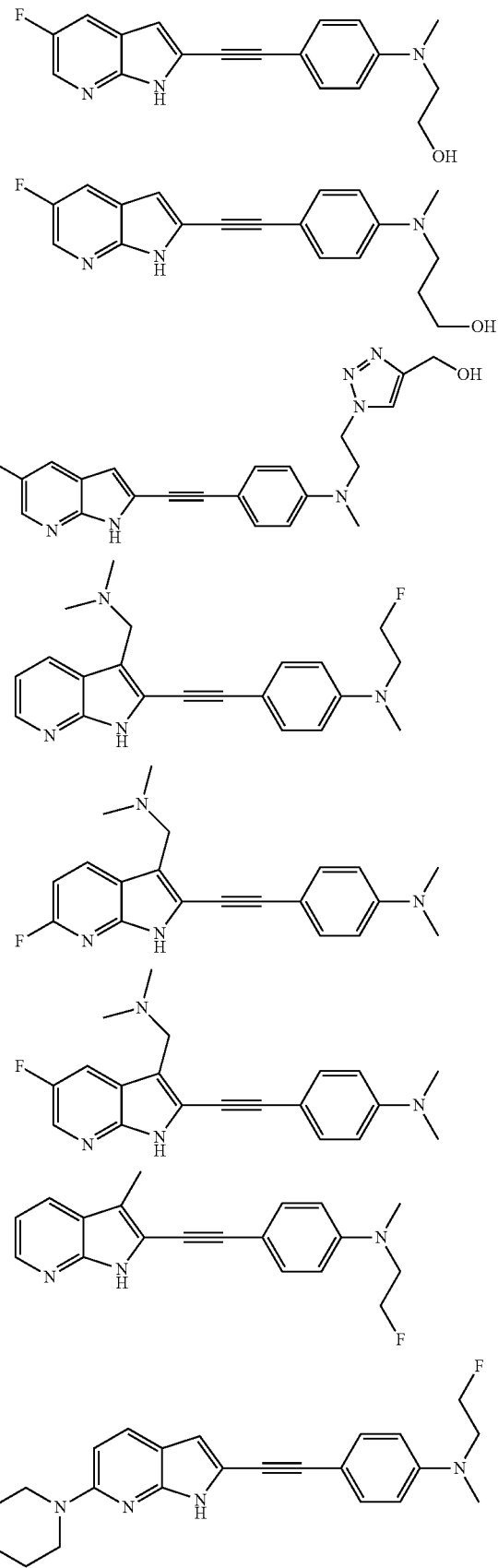

-continued
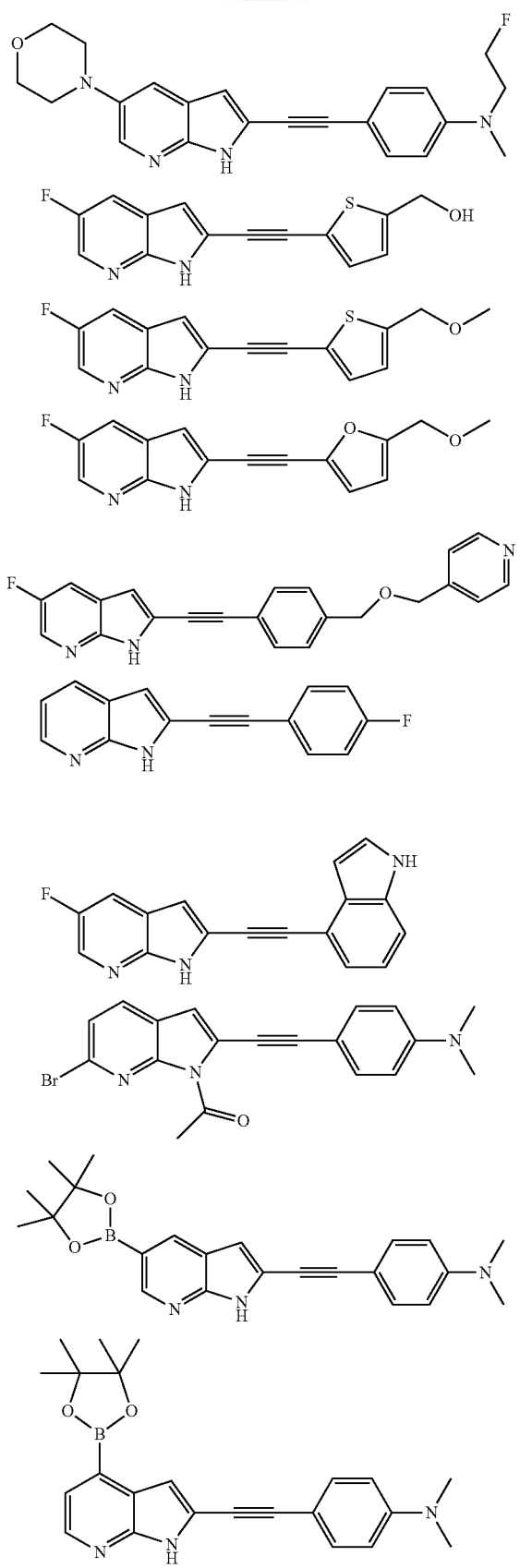
-continued
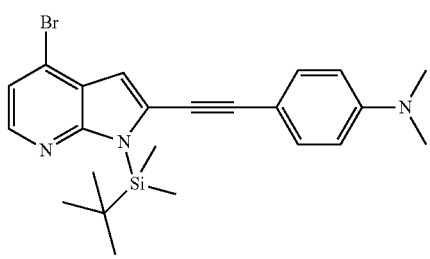
According to a particularly advantageous embodiment, the compound of the Invention of formula II is:
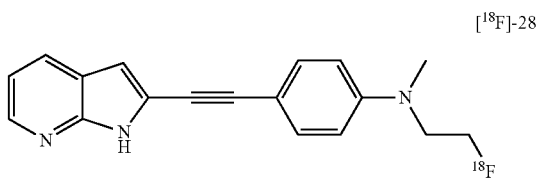 [SMILES: CN(CC[18F])c1ccc(C#Cc2cc3cccnc3[nH]2)cc1]
According to an embodiment, the compound of the Invention is selected from:
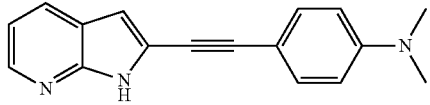
22a
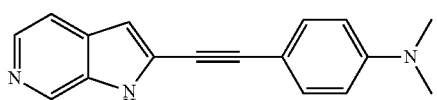
22b
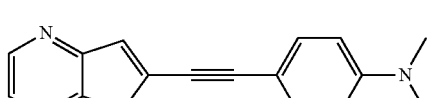
22c
22d
22e
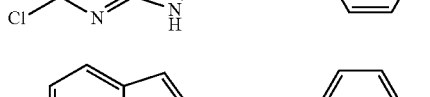
22f
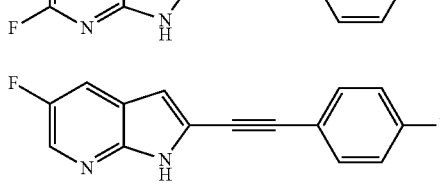
22g

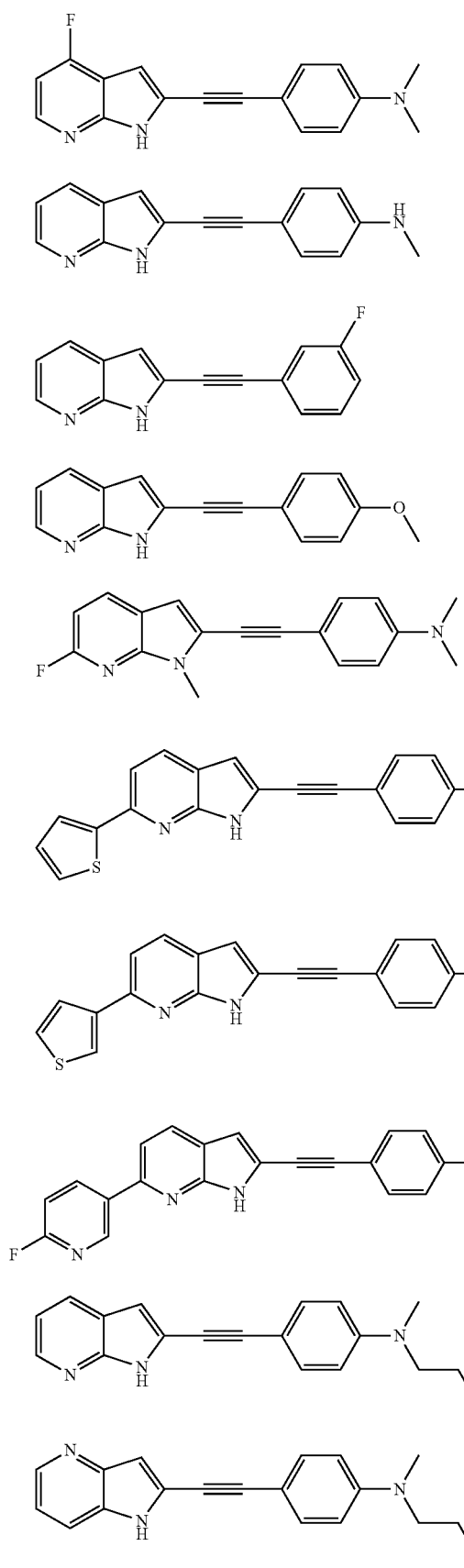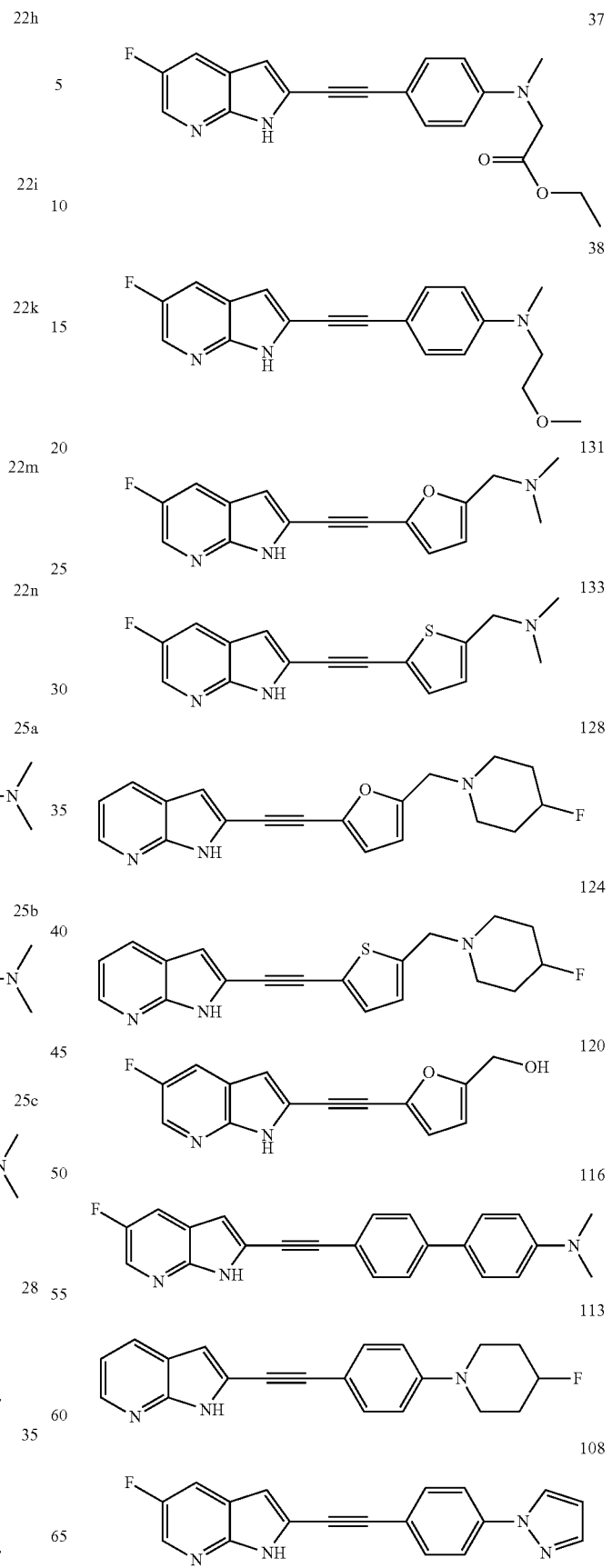

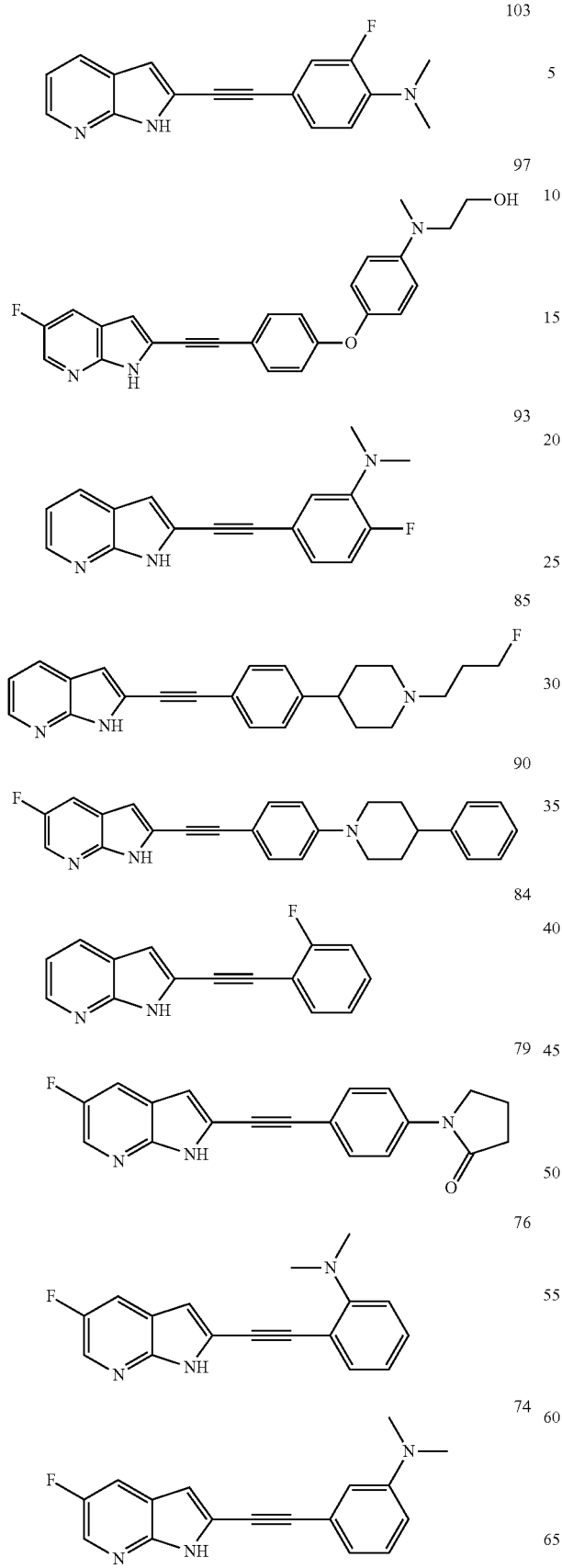
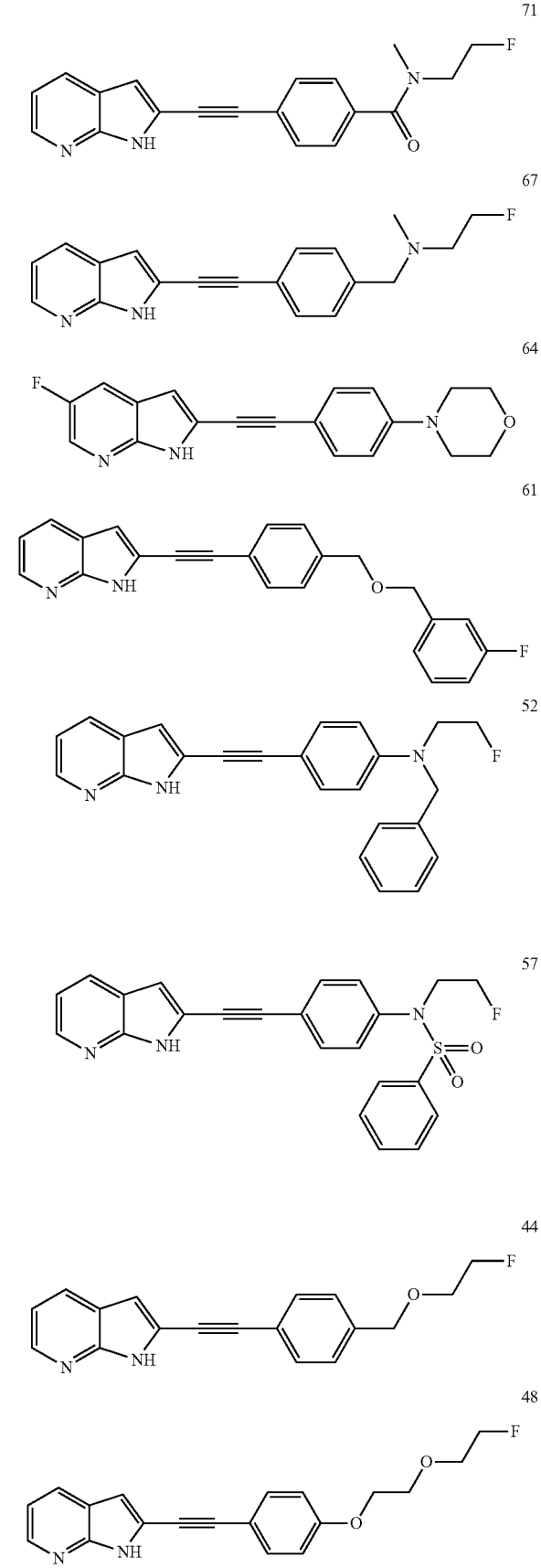

-continued

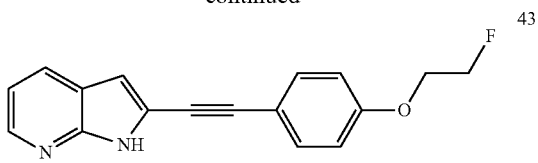

43

In a radiolabeled state;
In particular, said compound of formula II being:

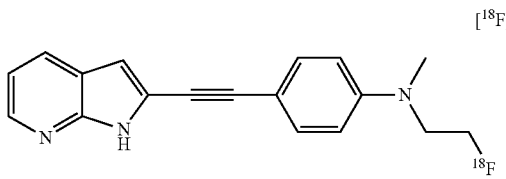

[$^{18}$F]-28

According to another advantageous embodiment, the compound of the invention is of general formula I-2

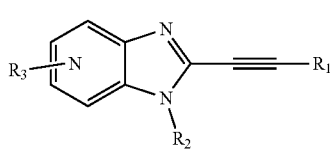

(I-2)

$R_1$, $R_2$ and $R_3$ being as previously defined in formula I.

According to one advantageous embodiment, the compound of the invention is of the formula II-2

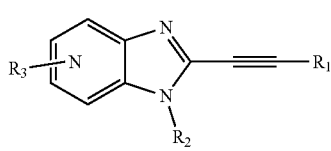

(II-2)

$R_1$, $R_2$ or $R_3$ being as previously defined in formula II;
wherein at least one of the substituents $R_1$, $R_2$ or $R_3$ comprises a radioelement selected from $^{18}$F, $^{11}$C, $^{123}$I and $^{124}$I.

According to an advantageous embodiment, the compound of the invention is of general formula III-2

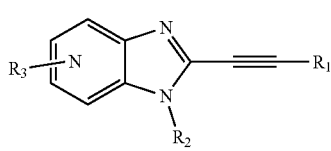

(III-2)

$R_1$, $R_2$ and $R_3$ being as defined previously in the formula III;
wherein the substituents $R_1$, $R_2$ and $R_3$ do not comprise a radioelement.

According to an advantageous embodiment, the compound of the Invention is of general formula I-2a or II-2a:

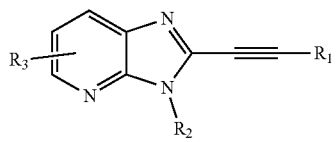

(I-2a) ou (II-2a)

$R_1$, $R_2$ and $R_3$ being as previously defined in formula I or II respectively.

The compounds of formula II-2a comprise a radioelement selected from $^{18}$F, $^{11}$C, $^{123}$I and $^{124}$I on at least one of the substituents $R_1$, $R_2$ and $R_3$.

According to an advantageous embodiment, the compound of the invention is of general formula I-2a or II-2a:

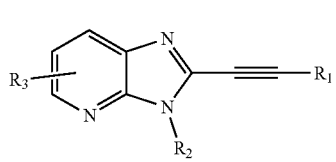

(I-2a) ou (II-2a)

$R_2$ and $R_3$ are as previously defined in formula I or II respectively;
$R_1$ being optionally labeled and is selected from
phenyl;
p-N(CH$_3$)$_2$-phenyl;
p-N(CH$_3$)(CH$_2$CH$_2$F)-phenyl.

The compounds of formula II-2a comprise a radioelement selected from $^{18}$F, $^{11}$C, $^{123}$I and $^{124}$I on at least one of the substituents $R_1$, $R_2$ and $R_3$.

According to an advantageous embodiment, the compound of the invention is of general formula I-2a or II-2a:

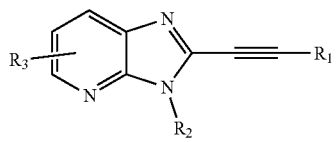

(I-2a) ou (II-2a)

$R_1$ and $R_3$ being as previously defined in formula I or II respectively;
$R_2$ being optionally labeled and is selected from
H;
(CH$_2$CH$_2$O)$_n$—CH$_2$CH$_2$F, n being an integer equal to 0, 1 or 2;
SO$_2$Ph;
COO$^t$Bu;
CH$_2$OCH$_3$,
CH$_2$O(CH$_2$)$_2$OCH$_3$
COCH$_3$

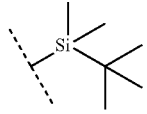

The compounds of formula II-2a comprise a radioelement selected from $^{18}$F, $^{11}$C, $^{123}$I and $^{124}$I on at least one of the substituents $R_1$, $R_2$ and $R_3$.

According to an advantageous embodiment, the compound of the invention is of general formula I-2a or II-2a:

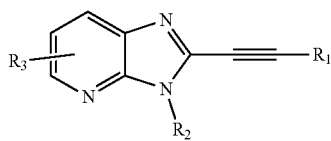
(I-2a) ou (II-2a)

R₃ being as defined precedes ment in formula I or II respectively;
R₁ being optionally labeled and selected from
phenyl;
p-N(CH₃)₂-phenyl;
p-N(CH₃)(CH₂CH₂F)-phenyl.
R₂ being optionally labeled and is selected from
H;
$(CH_2CH_2O)_n$—$CH_2CH_2F$, n being an integer equal to 0, 1
SO₂Ph;
COOtBu;
CH₂OCH₃,
CH₂O(CH₂)₂OCH₃
COCH₃

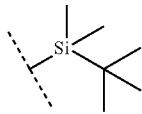

The compounds of formula II-2a comprise a radioelement selected from $^{18}F$, $^{11}C$, $^{123}I$ and $^{124}I$ on at least one of the substituents R₁, R₂ and R₃.

The invention also relates to a compound of formula III for the preparation of compounds of formula II, IIbis, IIa, IIb, II-1, II-2, II-1a, II-1b, II-1c, II-id, II-1a-1, II-1a-2, II-1a-2-A, or II-2a.

The invention also relates to a compound, as defined above in formulas II, IIbis, IIa, IIb, II-1, II-2, II-1a, II-1b, II-1c, II-1d, II-1a-1, II-1a-2, II-1a-2-A, or II-2a, wherein at least one of substituents R₁, R₂, R₃ or R₄ comprises a radioelement is selected from $^{18}F$, $^{11}C$, $^{123}I$ and $^{124}I$ for use in a method of diagnosis or in vivo imaging of a subject with a neurodegenerative disease, wherein said method of diagnosis or imaging comprises administering said compound.

According to one embodiment, the invention relates to the compound of formula II, IIbis, IIa, IIb, II-1, II-2, II-1a, II-1b, II-1c, II-id, II-1a-1, II-1a-2, II-1a-2-A, or II-2a for use in a method of diagnosis or in vivo imaging of a subject with a neurodegenerative disease, said disease neuro-degenerative being a amyloïdopathy, alpha-synucleinopathy or a tauopathy.

For the purposes of the present invention, the term "neurodegenerative disease" refers to a group of progressive diseases related to metabolic dysfunction in the nervous tissue, leading to neuronal death and destruction of the nervous system.

By "amyloïdopathy" is understood within the meaning of the invention, a neurodegenerative disease having a fiber aggregation of abnormal β-amyloïd peptides in the brain.

The term "alpha-synucleionopathy" is understood within the meaning of the invention, a neurodegenerative disease having an aggregation of α-synuclein protein fibers in the brain. In particular, alpha-synucleinopathy concerned by the invention are Parkinson's disease, dementia with Lewy bodies and multiple system atrophy.

By "tauopathy" is understood, in the sense of the invention, a neurodegenerative disease with an abnormal tau fiber aggregation in the brain.

The subject compounds have affinity for at least two of the β-amyloïd proteins, α-synuclein and tau fibrils but are not selective vis-à-vis one of them.

The term "affinity" in the sense of the invention, refers to the ability of a compound of the invention to bind to β-amyloïd protein, α-synuclein and tau fibrils. Affinity is indirectly determined by the value of the inhibition constant $K_i$, obtained by competitive measures with other ligands, such thioflavin T, directly or, more specifically, by measuring $K_d$. Within the meaning of the invention, a compound is considered to have good affinity for the fibrillar protein under consideration when the value of $K_i$ is less than or equal to 50 nM and/or the value of $K_d$ is less than or equal to 20 n. Above a $K_d$ threshold of 20 nM compound is considered to have a low affinity for the reporting protein fibrils. In other words, the affinity is then insufficient for the compound to be potentially used as a selective radiotracer of the protein target.

A compound is said "selective" for one of β-amyloïd protein, α-synuclein or tau fibrils, within the meaning of the invention, since it exhibits good affinity for this protein and that its affinity for this protein or at least two times greater than that for at least one of the two other proteins.

By way of example, according to one embodiment, and according to the analysis of $K_i$ presented in Table 5,
α-syn-selective compounds are 22a, 22b, 22e, 22f, 22 g, 22 h
Tau selective compounds are 22a, 22b, 22c, 22e.
By way of example, according to another embodiment, and according to the analysis of $K_d$ presented in Tables 6 and 7,
Tau selective compounds are 22a, 22b, 22c, 28
α-syn-selective compounds are 22a, 22b, 22d, 22f, 25a, 25b, 25c
A Aβ selective compound is 28.

According to one embodiment, the invention relates to the compound of formula II, IIbis, IIa, IIb, II-1, II-2, II-1a, II-1b, II-1c, II-id, II-1a-1, II-1a-2, II-1a-2-A, or II-2a for use in a method of diagnosis or in vivo imaging of a subject with a neurodegenerative disease, said neurodegenerative disease being a amyloïdopathy.

According to one embodiment, the invention relates to the compound of formula II, IIbis, IIa, IIb, II-1, II-2, II-1a, II-1b, II-1c, II-id, II-1a-1, II-1a-2, II-1a-2-A, or II-2a for use in a method of diagnosis or in vivo imaging of a subject with a neurodegenerative disease, said neurodegenerative disease being an alpha-synucleinopathy.

According to one embodiment, the invention relates to the compound of formula II, IIbis, IIa, IIb, II-1, II-2, II-1a, II-1b, II-1c, II-id, II-1a-1, II-1a-2, II-1a-2-A, or II-2a for use in a method of diagnosis or in vivo imaging of a subject with a neurodegenerative disease, said neurodegenerative disease is a tauopathy.

According to one embodiment, the invention relates to the compound of formula II, IIbis, IIa, IIb, II-1, II-2, II-1a, II-1b, II-1c, II-id, II-1a-1, II-1a-2, II-1a-2-A, or II-2a for use in a method of diagnosis or in vivo imaging of a subject with a neurodegenerative disease, wherein the method of in vivo imaging is the positron emission tomography or the single photon emission tomography.

The positron emission tomography (PET) and the single photon emission tomography (SPET) are non-invasive medical imaging techniques used to diagnose certain diseases, monitoring of the evolution of these diseases and the evaluation of the effectiveness of treatments. The images are obtained by injection into the body of a radiotracer (radioactive molecule), recording its transportation in the body thanks to PET or SPECT cameras and computer data processing.

The exploration by imaging of the α-syn represents a major advance for example in the diagnosis of Parkinson's disease in which aggregates of this protein appear in the early stages. Furthermore, this type of exploration permits to assess the effects of Parkinson's disease treatments by acting on the aggregates of α-syn.

The Invention also relates to the use of the compound of formula II, IIbis, IIa, IIb, II-1, II-2, II-1a, II-Ib, II-1c, II-1d, II-1a-1, II-1a-2, II-1a-2-A, or II-2a, wherein at least one of the substituents $R_1$, $R_2$, $R_3$ or $R_4$ comprises a radioelement selected from $^{18}F$, $^{11}C$, $^{123}I$ and $^{124}I$ as a marker for the in vivo diagnosis of a neurodegenerative disease.

The invention also relates to the use of the compound of formula II, IIbis, IIa, IIb, II-1, II-2, II-1a, II-1b, II-1c, II-1d, II-1a-1, II-1a-2, II-1a-2-A, or II-2a, wherein at least one of the substituents $R_1$, $R_2$, $R_3$ or $R_4$ comprises a radioelement selected from $^{18}F$, $^{11}C$, $^{123}I$ and $^{124}I$ as a marker for the in vivo or in vitro diagnosis of a neurodegenerative disease.

The invention also relates to the use of the compound of formula II, IIbis, IIa, IIb, II-1, II-2, II-1a, II-1b, II-1c, II-1d, II-1a-1, II-1a-2, II-1a-2-A, or II-2a, wherein at least one of the substituents $R_1$, $R_2$, $R_3$ or $R_4$ comprises a radioelement selected from $^{18}F$, C, $^{123}I$ and $^{124}I$, as an in vivo imaging agent to a subject afflicted with a neurodegenerative disease.

According to an advantageous embodiment, in the use of the compound of formula II, IIbis, IIa, IIb, II-1, II-2, II-1a, II-1b, II-1c, II-id, II-1a-1, II-1a-2, II-1a-2-A, or II-2a of the Invention as an in vivo imaging agent, the in vivo imaging is the positron emission tomography or the tomography of single photon emission.

Within the meaning of the present invention, the term "radiolabelled PET derived" means that the considered compound comprises at least one radioelement selected from $^{18}F$, $^{11}C$, or $^{124}I$, by substitution of an unlabeled element. For example, compound [$^{18}F$]-28 is a $^{18}F$ radiolabeled derivative of compound 28. For the purposes of the present invention, the term "radiolabeled derivatives TEMP" means that the considered compound comprises at least one radioelement as $^{123}I$ by substituting an unlabeled element.

The invention also relates to a pharmaceutical or radiopharmaceutical which comprises as active substance the compound of formula I, II, III, Ibis, IIbis, Ia, Ib, IIa, IIb, I-1, I-2, II-1, II-2, III-1, III-2, I-1a, I-1b, I-1c, I-1d, II-1a, II-1b, II-1c, II-1d, I-1a-1, I-1a-2, I-1a-2-A, II-1a-1, II-1a-2, II-1a-2-A, I-2a or II-2a described previously, optionally in association with a biocompatible carrier.

In particular, the radiopharmaceutical composition comprises as active substance a labeled compound of formula II, IIbis, IIa, IIb, II-1, II-2, II-1a, II-1b, II-1c, II-1d, II-1a-1, II-1a-2, II-1a-2-A, or II-2a.

The Invention also relates to a compound of formula I, II, III, Ibis, IIbis, Ia, Ib, IIa, IIb, I-1, I-2, II-1, II-2, III-1, III-2, I-1a, I-1b, I-1c, I-1d, II-1a, II-1b, II-1c, II-1d, I-1a-1, I-1a-2, I-1a-2-A, II-1a-1, II-1a-2, II-1a-2-A, I-2a or II-2a as described previously for use as a pharmaceutical or radiopharmaceutical drug, optionally in association with a biocompatible carrier.

According to one embodiment, the compound of the invention for use as a pharmaceutical or radiopharmaceutical medicament is administered parenterally, especially intravenously, at a dose of about 3 MBq/kg body weight of the individual. The dose will be determined based on the individual.

The activity of the administered dose is at least 200 MBq to be observable in the brain but a maximum of 450 MBq of patient radiation protection reasons.

The invention also provides a method for diagnosing or monitoring a neuro degenerative disease in a human or animal comprising:
a step of administering a compound of formula II, IIa, IIa, IIb, II-1, II-2, II-1a, II-1b, II-1c, II-1d, II-1a-1, II-1a-2, II-1a-2-A or II-2a comprising a radioelement to a human or animal subject; a human brain imaging step or animal body by the positron emission tomography or the single photon emission tomography.

The animal if possible in particular to verify the in vivo tracer uptake on target. The animal is thus used as a model. This is, for example, of an animal to which the aggregates were injected into the brain, or of a genetically modified animal which expresses in its human brain aggregates.

In vivo quantification of aggregation of β-amyloïd protein, α-synuclein and/or tau fibrils in a patient is beneficial not only for early diagnosis of diseases resulting but also to monitor these diseases and evaluate treatments.

Diagnostic methods suitable for use of ligands of β-amyloïd proteins, α-synuclein and/or tau fibrils of the invention are PET and SPECT. PET and SPECT using biologically active molecules, previously labeled with an isotope to short-lived positron emitter, or gamma emitters at concentrations of micromolar or nanomolar. The physical characteristics of isotopes and molecular selectivity of labeled molecules, combined with the high scanners detection efficiency used for these scintigtaphiques methods provide sensitivity for indicating in vivo measurements of concentrations which is of several orders of magnitude, higher than other imaging methods.

The administration to a subject the compound labeled with a positron emitting isotope or gamma emitters takes place intravenously. The subject is scanned and the axial tomographic sections of the brain region in which the labeled compound has accumulated is obtained. The accumulation of the compound may be linked to brain metabolism, blood flow or concentration of binding sites using appropriate mathematical models. Thus, the use of a labeled compound with a positron emitting isotope having a high affinity and selectivity for one of the β-amyloïd, α-synuclein proteins and/or tau fibrils allows the quantification of the level of aggregation of these proteins and their location. This approach not only to improve the diagnosis of neurodegenerative diseases such as PD, but also provide a tool to monitor these diseases and the effectiveness of treatment, and to improve understanding of the progression of these diseases.

According to one embodiment of the Invention, in the method of the Invention, the neurodegenerative disease is a synucleinopathy, an amyloïdopathy or tauopathy.

According to one embodiment of the invention, in the method of the Invention the neurodegenerative disease is a synucleinopathy.

According to one embodiment of the invention, in the method of the Invention the neurodegenerative disease is an amyloïdopathy.

According to one embodiment of the invention, in the method of the invention the neurodegenerative disease is a tauopathy.

According to one embodiment of the invention, in the method of the invention the radioelement is selected from $^{18}F$, $^{11}C$, $^{123}I$ and $^{124}I$.

FIGURES

FIG. 3 shows the quality control chromatograms of the compound [$^{18}F$]28 with a double detection, A) radioactive signal) and B) ultraviolet at 360 nm.

FIG. 4 shows the image obtained after the experiment described in Example 19.6 in PET/CT imaging, it is the cross section of the head of a rat after iv injection of the tracer and the sum of acquisitions between 50 and 180 min post-injection.

EXAMPLES

General Procedures

Figure 1A:
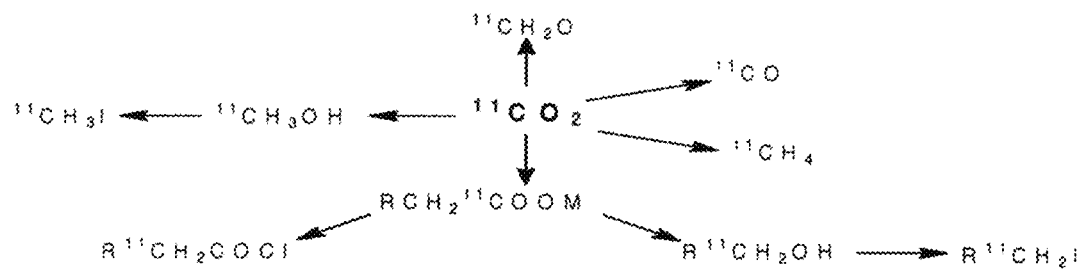
FIG. 1a shows the preparation of synthons radiolabeled with carbon-11 1a) from carbon dioxide labeled with carbon-11 and 1b) from methane labeled with carbon-11.

Example 1 Procedure A (Protection of Azaindole with a Benzenesulfonyl Group)

Example 1.1

A1: To a solution of NaH (2 eq.) in THF under argon and at 0° C. was added slowly a solution of azaindole (1 eq.) in THF (1 M). The mixture was stirred at room temperature for 30 min. After returning to 0° C., benzenesulfonyl chloride (1.2 eq.) was added dropwise. After stirring overnight at room temperature, the mixture was poured into a beaker with ice. After allowing to warm to room temperature, the phases were separated. The aqueous phase was extracted with ethyl acetate. The combined organic phases were washed with NaCl, dried over $MgSO_4$ and concentrated under reduced pressure. The protected product was isolated either by filtration followed by washing the precipitate with diethyl ether or by flash column chromatography on silicagel.

Example 1.2

A2: To a solution of azaindole (1 eq.) in 2-butanone (0.1 M) was added potassium carbonate (4 eq.) and benzenesulfonyl chloride (1.5 eq.). The mixture was stirred at 80° C. for 2 hours. The mixture was concentrated under reduced pressure and water and ethyl acetate were added. After phase separation, the aqueous phase was further extracted with ethyl acetate (3 times). The combined organic phases were washed with NaCl, dried over $MgSO_4$ and concentrated under reduced pressure. The protected product was isolated either by filtration followed by washing the precipitate with diethyl ether or by flash column chromatography on silicagel.

Example 2. Procedure B (Lodation in C-2 Position of the Azaindole)

Example 2.1

B1 (E. DESARBRE S. Coudret, C. Meheust, J Y Merour, *Tetrahedron*, 1997, 53 (10) 3637-3648; Joseph B., H. Da Costa J Y Merour, Ldonce S., *Tetrahedron*, 2000, 56, 3189-3196): Under argon atmosphere, to a solution of phenylsulfonylazaindole (1 eq) and TMEDA (1.05 eq) in THF (0.1 M), cooled to −25. ° C., was added dropwise a solution of LDA in THF (2M, 2 eq.). After 30 min, a solution of iodine (1M, 2 eq.) in THF was slowly added to the reaction medium via cannula. The reaction was followed by $^1H$ NMR and once the starting material was consumed, addition of water and extraction with ethyl acetate (3 times) were performed. The combined organic phase was dried over $MgSO_4$ and concentrated under reduced pressure and purified by flash column chromatography on silicagel.

Example 2.2

B2: Under argon atmosphere, to a solution phenylsulfonylazaindole (1 eq.) and TMEDA (1.1 eq) in THF (0.1M), cooled to −70° C., was added dropwise a solution of LDA (2M in THF, 1.7 eq.). After 30 min, a solution of iodine (2.2 eq.) in THF (1M) was slowly added to the reaction medium via cannula. The reaction was monitored by $^1H$ NMR After consumption of the starting material, water is added, and the aqueous phase was extracted with ethyl acetate (3 times). The combined organic phase was then dried over $MgSO_4$, concentrated under reduced pressure and purified by flash column chromatography on silicagel.

Example 3: Procedure C (Sonogashira Coupling)

3.1 Example C

The catalyst [$Pd(PPh_3)_4$] (5 mol %) was added to a degassed solution of iodine azaindole derivative (1.0 eq.), alkyne (1.2 eq.) and CuI (10 mol %) in a mixture of $Et_3N$/THF (1:1) at a concentration of 0.1 M. The mixture was heated at 50-60° C. for 4 h under argon atmosphere. After returning to room temperature, the mixture was poured into an aqueous solution of (10%) $NH_4Cl$. After phase separation, the aqueous phase was further extracted with ethyl acetate (3 times 20 ml) and the combined organic phases were washed with NaCl, dried over $MgSO_4$, filtered, concentrated under reduced pressure and purified by flash column chromatography on silicagel.

3.1 Example C2

The catalyst [$Pd(PPh_3)_2Cl_2$] (5 mol %) was added to a degassed solution of iodine azaindole derivative (1.0 eq.), alkyne (1.2 eq.), CuI (10% mol) and $Et_3N$ (2.2 eq) in THF (C=0.1 M). The mixture was stirred at room temperature for 16 h under argon. The reaction mixture was concentrated under reduced pressure before being purified by flash column chromatography on silicagel.

Example 4. Procedure D (Desulfonylation of the Azaindole)

(C. Chaulet, C. Cross, J. Basset, M.-D. Pujol, M.-C. Viaud-Massuard, *Synlett.* 2010, 10, 1481-1484)

A dioxane solution containing the azaindole derivative (1 eq.) protected by a sulfonyl benzene group, was added sodium tert-butoxyde (1.5 eq.). The mixture was heated at 80° C. for 18 hours. The medium was concentrated under reduced pressure and the residue was dissolved in ethyl acetate and water. After decantation, the aqueous phase was extracted with ethyl acetate (3 times). The combined organic phases were dried over $MgSO_4$ and concentrated under reduced pressure, prior to purifying the crude reaction product by flash column chromatography on silicagel.

Example 5. Procedure E (Protection of Azaindole with a Boc)

A solution of azaindole (1 eq.), di-tert-butyl dicarbonate (1.5 eq.) and 4-DMAP (0.2 eq.) in THF (0.2 M) was stirred at room temperature overnight. The mixture was concentrated under reduced pressure and purified by flash column chromatography on silicagel.

Example 6. Procedure F (Deprotection of Boc)

To a dichloromethane solution (0.05 M) containing the azaindolique product protected by the Boc group (1 eq.), cooled to 0° C. was added dropwise TFA (ratio TFA/dichloromethane=1/2), stirring at 0° C. was carried out with TLC monitoring. At the end of the reaction, the reaction mixture was neutralized with saturated aqueous $NaHCO_3$. After decantation, the aqueous phase was extracted with dichloromethane (2 times). The combined organic phases were dried over $MgSO_4$, concentrated under reduced pressure and purified by flash column chromatography on silicagel.

Example 7. Procedure G (Suzuki Couplings)

Example 7.1 G1

A halogenated compound (1 eq.) was dissolved in dioxane under argon and the boronic acid (1.2 eq.), $Cs_2CO_3$ (1.2 eq.), as well as $[Pd_2(dba)_3]$ (5 mol-%) and ligand $P(t-Bu)_3$ (10 mol %) were added. The reaction mixture was stirred and irradiated under microwave conditions at 100° C. for 1 hour. After cooling, the mixture was concentrated under reduced pressure and the residue was purified by flash column chromatography.

Example 7.2 G2

A halogenated compound (1 eq.) Was dissolved in a mixture $DME/H_2O$ (2/1) under argon, and the boronic acid (1.2 eq.), $Na_2CO_3$ (2 eq.) and $[Pd(PPh_3)_4]$ (5 mol %) were added. The reaction mixture was stirred and irradiated under microwave conditions at 120° C. for 30 min. After cooling, water was added, and the compound was extracted with dichloromethane (3 times). The organic phase was dried over $MgSO_4$ and concentrated under reduced pressure before the residue was purified by flash column chromatography.

Preparation of the Acetylenic Azaindole Derivatives
General Scheme:

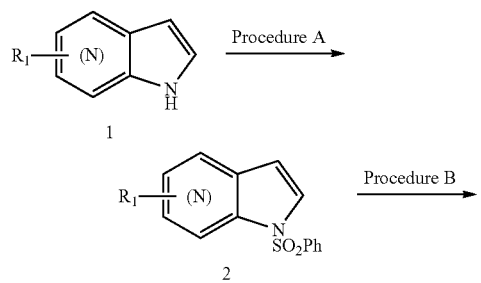

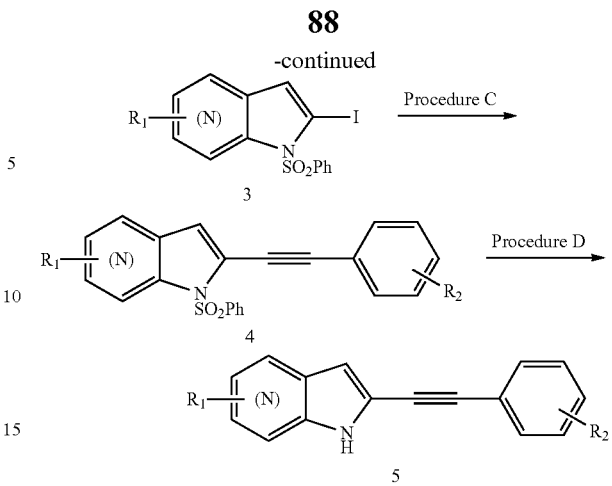

Example 8. Synthesis of the Starting Azaindoles

Among the various azaindoles, some were synthesized by preparation methods described in the literature. This is particularly the case of 4-azaindole (Ia), 6-azaindole (Ib), 6-chloro-7-azaindole (Ic) and 6-fluoro-7-azaindole (Id)

TABLE 1

Starting Azaindoles 1a
global yield
78%

1b
global yield
50%

1c
global yield
33%

1d
global yield
5%

Example 8.1 Preparation of 4-azaindole 4-azaindole was prepared from 4-amino-2-bromopyridine in a two steps sequence:

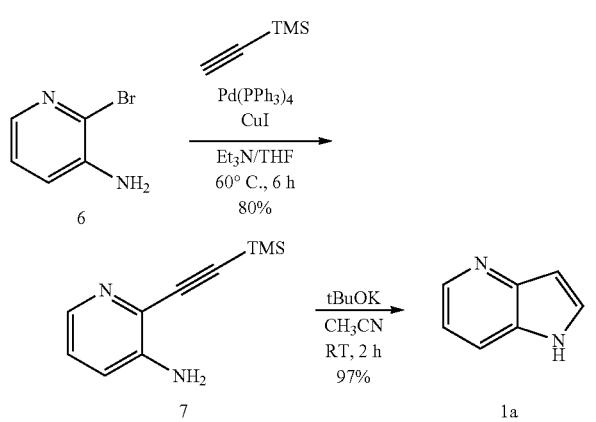

Preparation of 2-((trimethylsilyl ethynyl pyridin-3-amine 7

Product 7 was obtained starting from 3-amino-2-bromopyridine 6 according to procedure C by stirring the mixture at 60° C. for 6 hours and was isolated with a yield of 80% by flash column chromatography (ethyl acetate/petroleum ether=5/95).

Preparation of 4-azaindole 1a

Product 7 (1.96 g, 10.3 mtnol, 1 eq.) was subjected to a cyclization reaction in the presence of a 1M THF solution potassium-tert-butoxide (10.3 ml, 10.3 mmol, 1 eq.) in $CH_3CN$ (15 ml) at room temperature for 2 hours. The mixture was then diluted with ethyl acetate and hydrolyzed with water. After decantation, the organic phase was washed with saturated aqueous NaCl solution, dried over $MgSO_4$ and concentrated under reduced pressure. 4-azaindole was isolated by flash column chromatography on silicagel (ethyl acetate/petroleum ether=1/1) with a yield of 97%.

Example 8.2 Preparation of 6-azaindole 1b 6-azaindole was prepared from 3-amino-4-methylpyridine by a 3-step sequence described by Hands (D. Hands, B. Bishop, M. Cameron, J S Edwards, I F Cottrell, S H B Wright, *Synthesis*, 1996, 7, 877-882)

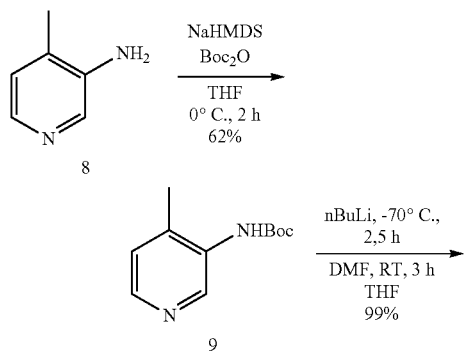

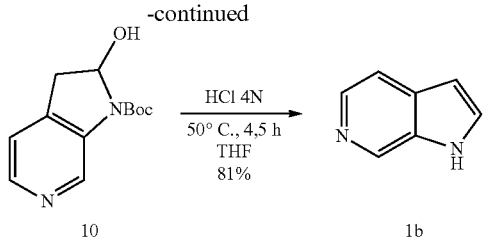

Preparation of tert-butyl (4-methylpyridin-3-yl) carbamate 9

To a solution of 3-amino-4-methylpyridine (2 g, 18.5 mmol, 1 eq.) in THF (35 ml) under argon at 0° C., was slowly added a 1M solution of NaHMDS/THF (40.7 ml, 40.7 mmol, 2.2 eq.). $Boc_2O$ (4.8 g, 22.2 mmol, 1.2 eq.) Was added and the ice bath was removed. The mixture was stirred 1 h30 at room temperature, the solvent was evaporated, and the residue was taken up in dichloromethane and washed with an aqueous HCl solution (50 ml), followed by a saturated NaCl solution. The organic phase was dried over $MgSO_4$ and concentrated under reduced pressure, prior to isolation of 9 (2.4 g) after flash column chromatography on silicagel (ethyl acetate/petroleum ether=30/70) with a 62% yield.

tert-butyl Preparation of 2-hydroxy-2,3-dihydro-1H-pyrrolo[2,3-c]pyridine-1-carboxylate 10

To a solution of tert-butyl(4-methylpyridin-3-yl) carbamate 9 (2.4 g, 11.5 mmol, 1 eq.) in THF (100 ml), cooled to −70° C., was added dropwise a solution 2.2 M nBuLi/hexanes (1 1.5 ml, 25.4 mmol, 2.2 eq.). After addition, the temperature was allowed to rise to −30° C. and maintained at that temperature with stirring for 2 h30. Then, DMF (1.34 ml, 17.3 mmol, 1.5 eq.) was added and the mixture was allowed to return to room temperature. After stirring for 3 hours at room temperature, water (100 ml) was added and the product was extracted with ethyl acetate (100 ml). The combined organic phases were washed with saturated NaCl solution, dried over $MgSO_4$ and concentrated under reduced pressure before being purified by flash column chromatography on silicagel (ethyl acetate/petroleum ether=1/1) affording the desired product 10 in 99% yield (2.68 g).

Preparation of 6-azaindole 1b

To a solution of t tert-butyl 2-hydroxy-2,3-dihydro-pyrrolo[2,3-c]pyridine-1-carboxylate 10 (2.68 g, 1 1.3 mmol, 1 eq.) in THF (45 ml) was added a 4N HCl solution in dioxane (15.6 ml, 62.4 mmol, 5.5 eq.). The mixture was stirred at 50° C. for 4 h30. The reaction mixture was neutralized with 5M aqueous NaOH solution (15.8 ml, 79.4 mmol, 7 eq.) and the aqueous phase was extracted with ethyl acetate (3 times). The combined organic phases were dried over $MgSO_4$, concentrated under reduced pressure and purified by flash column chromatography on silicagel (solvent used: ethyl acetate) to give the desired product Ib in a yield of 81% (1.09 g).

Example 8.3 Preparation of 6-chloro-7-azaindole

The 6-chloro-7-azaindole was prepared by a 3-step sequence described by Minakata (S. Minakata, M. omatsu, Y. Ohshiro, *Synthesis*, 1992, 7, 661-663):

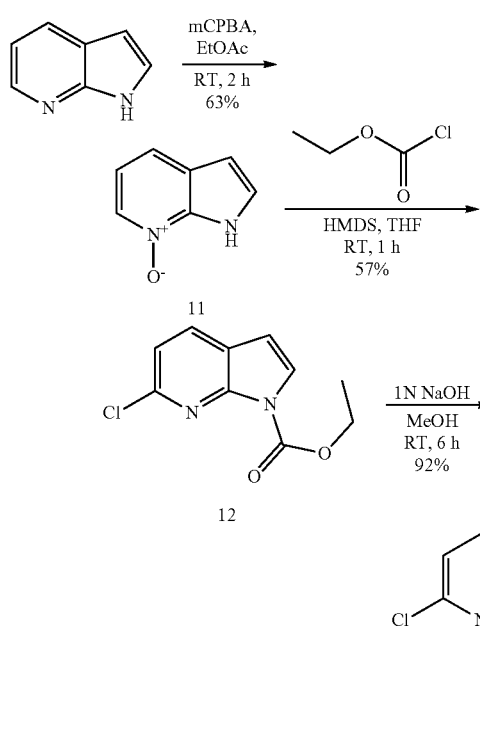

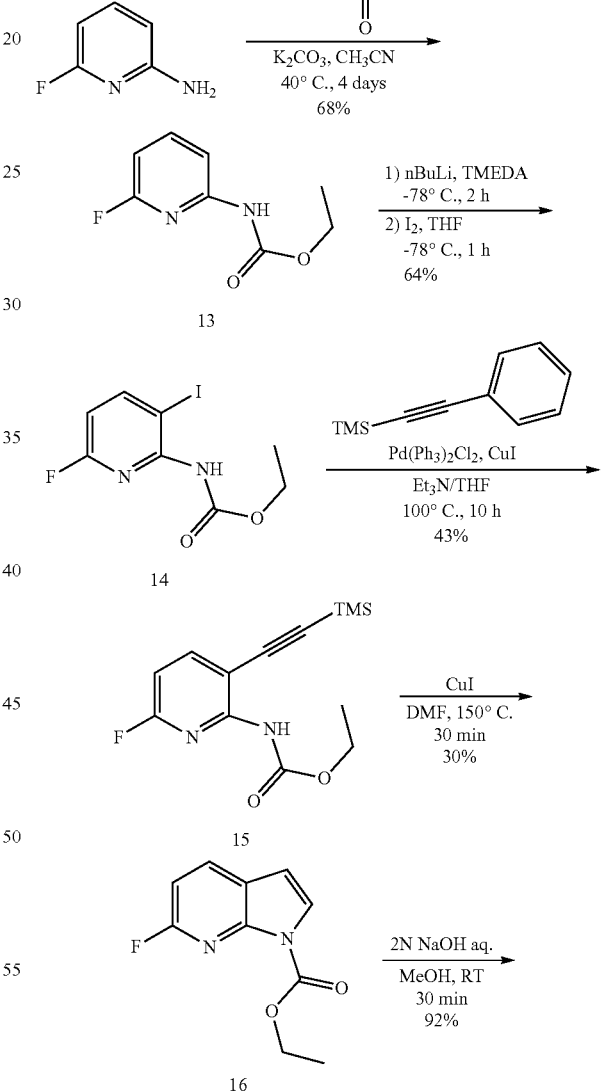

Example 8.4 Preparation of 6-fluoro-7-azaindole Id 6-fluoro-7-azaindole Id was prepared by a 5-step method from 2-amino-6-fluoropyridine (A. Stoit, H. K. A. C. Coolen, M. A. W. Van Der Neut, C. G. Kruse, Preparation of azaindoles with a combination of partial nicotinic acetylcholine receptor agonism and dopamine reuptake inhibitory activity PCT Int. Appl. 2008, WO 2008003736 A1 Jan. 10, 2008)

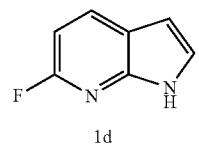

Preparation of N-Oxide 11

To a solution of 7-azaindole (2 g, 16.9 mmol, 1 eq.) in ethyl acetate (60 ml) at 0° C., mCPBA (6.3 g, 25.6 mmol, 1.5 eq.) was added. The medium was stirred at room temperature for 2 hours. The reaction mixture was then put in an ice bath and the formed precipitate was isolated by filtration and washed with diethyl ether. Then, water was added to the tan solid and the medium was basified to pH=9 with a saturated solution of $K_2CO_3$. The mixture was placed in the refrigerator and filtered cold the next day. The filtrate was concentrated and cooled to repeat the operation to give after assembling the different batches, a white solid with a yield of 63% (1.43 g).

Preparation of ethyl 6-chloro-1H-pyrrolo[2,3-b]pyridine-1-carboxylate 12

To a solution of 11 (3.05 g, 22.7 mmol, 1 eq.) and HMDS (3.67 g, 22.7 mmol, 1 eq.) in THF was added dropwise methyl chloroformate (5.42 ml, 56.8 mmol, 2.5 eq.). The medium was stirred for 1 hour at room temperature and concentrated under reduced pressure. The residue obtained was dissolved in ethyl acetate, the organic phase is washed with a saturated solution of $NaHCO_3$, dried over $MgSO_4$ and concentrated under reduced pressure. The residue was purified by flash column chromatography on gel silica (ethyl acetate/petroleum ether=1/1) to give the desired product 12 with a 99% yield (2.68 g).

Preparation of 6-chloro-7-azaindole

To a solution of 12 (0.302 g, 1.4 mmol, 1 eq.) in MeOH (25 ml) was added a 1N solution of NaOH (1 1 ml). The mixture was stirred at room temperature for 6 hours, neutralized with a saturated solution of $NaHCO_3$ and concentrated under reduced pressure. The precipitate was washed with water, filtered and dried under reduced pressure to give with 92% yield (0.2 g).

Preparation of ethyl (6-fluoropyridin-2-yl) carbamate 13

To a solution containing 2-amino-6-fluoropyridine (5 g, 44.6 mmol, 1 eq.) in $CH_3CN$ (110 ml) were added $K_2CO_3$ (18.5 g, 133.8 mmol, 3 eq.) and ethyl chloroformate (4.3 ml, 44.6 mmol, 1 eq.). The mixture was stirred at 40° C. for 4 days. Then, an additional portion of ethyl chloroformate (4.3 ml, 44.6 mmol, 1 eq.) was added and the mixture was stirred at 40° C. for 2 days. After returning to room temperature, ethyl acetate was added and the organic phase was washed with a saturated solution of $NaHCO_3$, dried over $MgSO_4$, filtered and concentrated under reduced pressure. The residue was purified by flash column chromatography on silicagel (ethyl acetate/petroleum ether=10/90) to afford the desired product 13 in a yield of 68% (5.62 g). $^1H$ NMR (400 MHz, $CDCl_3$, 20° C.) δ 7.83 (dd, J=8.0 Hz, J=2.0 Hz, 1H), 7.77 (m, 1H), 7.45 (bs, 1H), 6.59 (m, 1H), 4.25 (q, J=8.0 Hz, 2H), 1.32 (t, J=8.0 Hz, 3H).

Preparation of ethyl (6-fluoro-3-iodopyridin-2-yl) carbamate 14

To a solution of 13 (5.6 g, 30.4 mmol, 1 eq.) in THF (80 ml), TMEDA (11.3 ml, 76.0 mmol, 2.5 eq.) was added and the mixture was cooled to −78° C. under argon. Then, a solution of n-BuLi (1.6 M in THF, 50 ml, 79.1 mmol, 2.6 eq.) was slowly added and the mixture was stirred at −78° C. for 2 hours. A solution of iodine (18 g, 70.9 mmol, 2.3 eq.) in THF (20 ml) was added via cannula. After stirring for stirring at −78° C., a saturated aqueous solution of $Na_2S_2O_3$ was added. After returning to room temperature, ethyl acetate was added and the separated organic phase was washed with a saturated aqueous solution of $NaHCO_3$, dried over $MgSO_4$ and concentrated under reduced pressure before the residue was purified by flash column chromatography on silicagel (ethyl acetate/petroleum ether=10/90) to provide the desired product 14 with a 64% yield (6.03 g). $^1H$ NMR (400 MHz, $CDCl_3$, 20° C.) δ 8.07 (t, J=8.0 Hz, 1H), 7.19 (bs, 1H), 6.49 (dd, J=8.0 Hz, J=3.0 Hz, 1H), 4.29 (q, J=8.0 Hz, 2H), 1.35 (t, J=8 Hz, 3H).

Preparation of ethyl (6-fluoro-3-((trimethylsilyl) ethynyl)pyridin-2-yl)carbamate 15

$[Pd(PPh_3)_2]Cl_2$ (0.68 g, 0.97 mmol, 0.05 eq.) was added to a degassed solution containing derivative 14 (6.03 g, 19.5 mmol, 1 eq.), allyltrimethylsilane (4.9 ml, 35.0 mmol, 1.2 eq) and CuI (0.37 g, 1.95 mmol, 0.1 eq) in a mixture of 20 ml of $Et_3N$/DMF (1/1). The mixture was heated at 100° C. for 30 hours under argon. After returning to room temperature, the mixture was poured into an ethyl acetate solution and $H_2O$. After decantation, the organic was washed with $H_2O$, dried over $MgSO_4$ and concentrated under reduced pressure before being purified by flash column chromatography on silicagel (ethyl acetate/petroleum ether=5/95) and providing compound 15 in a yield of 15 43% (2.32 g). $^1H$ NMR (250 MHz, $CDCl_3$, 20° C.) δ 7.76 (t, J=8.0 Hz, 1H), 7.64 (is, 1H), 6.56 (dd, J=8.0 Hz, J=3.0 Hz, 1H), 4.29 (q, J=8.0 Hz, 2H), 1.34 (t, J=8.0 Hz, 3H), 0.3 (s, 9H).

Preparation of ethyl 6-fluoro-1H-pyrrolo[2,3-b]pyridine-1-carboxylate 16

A mixture of derivative 15 (2.32 g, 8.3 mmol, 1 eq.) and CuI (3.15 g, 16.5 mmol, 2 eq) in DMF (40 ml) was degassed under argon for 30 minutes. Then, the reaction mixture was heated at 150° C. for 30 minutes. After cooling, the mixture was diluted with ethyl acetate and filtered. The residue is washed with $H_2O$, dried over $MgSO_4$, filtered and concentrated under reduced pressure before being purified by flash column chromatography on silicagel (ethyl acetate/diethyl ether=1/1) to provide 16 with a 30% yield (0.52 g). $^1H$ NMR (250 MHz, $CDCl_3$, 20° C.) δ 7.95 (t, J=8.0 Hz, 1H), 7.69 (d, J=4.0 Hz, 1H), 6.87 (dd, J=8.0 Hz, J=2.0 Hz, 1H), 6.57 (d, J=4.0 Hz, 1H), 4.55 (q, J=8.0 Hz, 2H), 1.49 (t, J=8.0 Hz, 3H).

Preparation of 6-fluoro-7-azaindole Id

To a solution of 16 (1.3 g, 6.2 mmol, 1 eq.) in MeOH (25 ml) was added a 2N aqueous solution of NaOH (10 ml). The mixture was stirred for 30 minutes at room temperature and ethyl acetate was added. After decantation, the organic phase was washed with a 5% solution of $NaHCO_3$, dried over $MgSO_4$), filtered and concentrated under reduced pressure to provide Id with a 99% yield (0.84 g). $^1H$ NMR (400 MHz, $CDCl_3$, 20° C.) δ 9.6 (bs, 1H), 7.95 (t, J=8.0 Hz, 1H), 7.29 (m, 1H), 6.75 (dd, J=8.0 Hz, J=2.0 Hz, 1H), 6.53 (m, 1H).

Example 9. Synthesis of N-Benzenesulfonyl Azaindole

Example 9.1 Synthesis of Derivatives of N-Benzenesulfonyl Azaindol Described in the Literature Commercial azaindoles and those prepared above were protected by the benzenesulfonyl group as described in one of two alternative general methods (A1 and A2). Table 2 below includes the compounds 1-(phenylsulfonyl)-1H-pyrrolo[2,3-b] pyridine 2a (S.-F. Liu, Q. Wu, H. L. Schmider H. Aziz, N.-X. Hu, Z. Popovic, S. Wang, *J Am. Chem. Soc.* 2000, 122, 3671-3678), 1-(phenylsulfonyl)-1H-pyrrolo[3,2-c] pyridine 2b (Mr. Lefoix, J.-P. Daillant S. Road, J Y Meour I. Gillaizeau G. Coudert, *Synthesis,* 2005, 20, 3581-3588), 1-(phenylsulfonyl)-1H-pyrrolo[3,2-b] pyridine 2c (D. C. Brookings, R. J. Cubbon, J. M. Davis, B. J. Langham. Preparation of pyrrolo[3,2-b]pyridines as p38 kinase inhibitors. PCT Int. Appl., 2004031188, 15 Apr. 2004), 1-(phenylsulfonyl)-1H-pyrrolo[2,3-c] pyridine 2d (Y. Horiguchi, H. Imoto, M. A. Wolf. Preparation of 6-azaindoles as IκB kinase inhibitors for treating diabetes and inflammatory diseases. PCT Int. Appl., 2005097129, 20 Oct. 2005), 6-chloro-1-(phenylsulfonyl)-1H-[2,3-b]pyridine 2e (Y.-S. Tung, M. S. Coumar, Y.-S. Wu, H.-Y. Shiao, J.-Y. Chang, J.-P. Liou, P. Shukla, C.-W. Chang, C.-Y. Chang, C.-C. Kuo, T.-K. Yeh, C.-Y. Lin, J.-S. Wu, S.-Y. Wu, C.-C. Liao, H.-P. Hsieh, *J. Med. Chem.* 2011, 54, 3076-3080), 6-fluoro-1-(phenylsulfonyl)-1H-pyrrolo[2,3-b]pyridine 2f (A. R. Stoit, A. P. den Hartog, H. Mons, S. van Schaik, N. Barkhuijsen, C. Stroomer, H. K. A. C. Coolen, J. H. Reinders, T. J. P. Adolfs, M. van der Neut, H. Keizer, C. G. Kruse, *Bioorg. Med. Chem. Lett.* 2008, 18, 188-193), 5-fluorouracil-1-(phenylsulfonyl)-1H-pyrrolo[2,3-i] pyridin 2 g (S. J. Berthel, L. Chen, W. L. Corbett, L. C. Feng, N.-E. Haynes, R. F. Kester, S. S. So, J. Wright Tilley. Azaindole derivatives as glucokinase activators and their preparation and use in the treatment of metabolic disorders. U.S. Pat. Appl. Publ., 20110144105, 16 Jun. 2011), 6-bromo-1-(phenylsulfonyl)-1H-pyrrolo[2,3-b]pyridine 2i (A. Stoit, H. K. A. C. Coolen, M. A. W. Van Der Neut, C. G. Kruse, Azaindole derivatives with a combination of partial nicotinic acetylcholine receptor agonism and dopamine reuptake inhibition, US 2008/

0009514 A1 Jan. 10, 2008), 5-bromo-1-(phenylsulfonyl)-1H-pyrrolo[2,3-b] pyridine 2j (N. Liu, Y Wang, G. Huang, C. Ji. W. Fan, H. Li, Y. Cheng, H. Tian, *Bioorg. Chem.* 2016, 65, 146-158) and 4-chloro-1-(phenylsulfonyl)-IH-pyrrolo[2,3-b]pyridine 2k (H.-Q. Dong, K. Foreman, A.-H. Li, M. J. Mulvihill, B. Panicker, A. G. Steinig, K. M. Stolz, Q. Weng, M. Jin, B. Volk, J. Wang, T. Wang, J. D. Beard, Pyrrolopyridine kinase inhibiting compounds, US 2007/0129364 A1 Jun. 7, 2007)

TABLE 2

N-benzenesulfonyl azaindoles

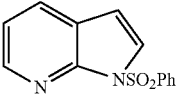

2a, 90%
Procedure A1

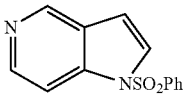

2b, 92%
Procedure A2

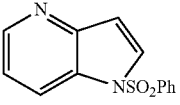

2c, 79%
Procedure A2

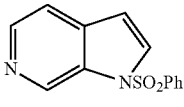

2d, 85%
Procedure A2

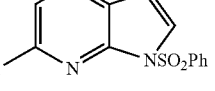

2e, 96%
Procedure A2

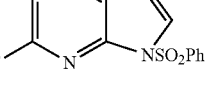

2f, 89%
Procedure A1

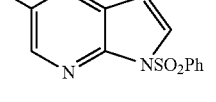

2g, 80%
Procedure A1

TABLE 2-continued

N-benzenesulfonyl azaindoles

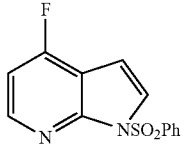

2h, 98%
Procedure A1

2i, 97%
Procedure A1

2j, 91%
Procedure A1

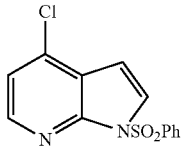

2k, 96%
Procedure A1

Example 10. Synthesis Iodated Azaindole Derivatives

The different iodated derivatives were prepared by appropriate general procedures. The compounds 2-iodo-1-(phenylsulfonyl)-1H-pyrrolo[2,3-b] pyridine 3a, 2-iodo-1-(phenylsulfonyl)-1H-pyrrolo[3,2-c]pyridine 3b, were obtained good yields of 83 and 60% respectively

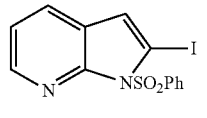

3a, 83%
Procedure B1

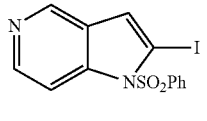

3b, 60%
Procedure B1

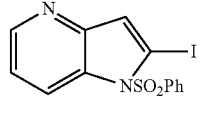

3c, 70%
Procedure B1

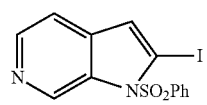

3d, 67%
Procedure A2

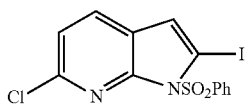

3e, 65%
Procedure B2

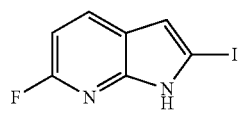 [SMILES: Fc1ccc2cc(I)[nH]c2n1]

18f
56% 2 steps
Procedures B2/D

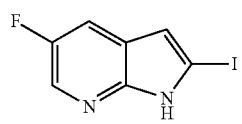

18g
48% 2 steps
Procedures B2/D

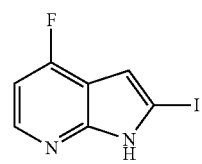 [SMILES: Fc1ccnc2[nH]c(I)cc12]

18h
73% 2 steps
Procedure B2/D

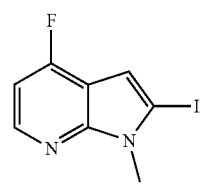

18i, 90%

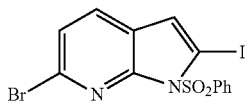

3j, 93%
Procedure B2

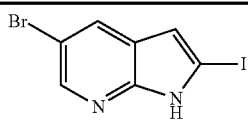

18k
3% 2 steps
Procedures B1/D

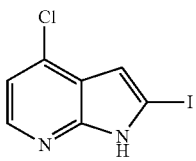 [SMILES: Clc1ccnc2[nH]c(I)cc12]

18l
58% 2 steps
Procedure B1/D 2-iodo-1-(phenylsulfonyl)-1H-pyrrolo[3,2-b]pyridine 3c was prepared following procedure B1, however, under the same conditions its isomer 2-iodo-1-(phenylsulfonyl)-1H-pyrrolo[2,3-c] pyridine 3d led to the formation of a non-separable mixture of the desired product 3d and di-iodated product 17d. the mixture was isolated by extraction and engaged in a desulfonylation reaction according to procedure D to afford the product 18d with a 47% yield over 2 steps. The latter was protected according to procedure A2 to obtain the desired product 3d

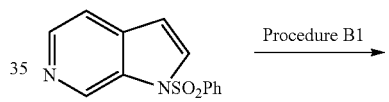

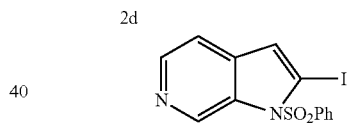

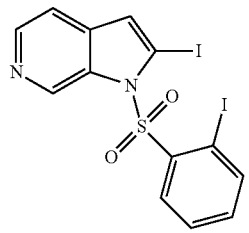

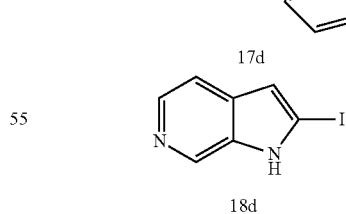

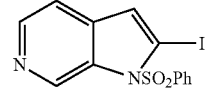

The iodated derivative of 6-chloro-7-azaindole 3 was prepared according to procedure B1 with a moderate yield of 46%, which was improved to 65% using procedure B2. But its brominated 3d was obtained with an excellent yield of 93% according to procedure B2.

Procedure B2 starting from compounds 2f-h provided fluorinated derivatives of 7-azaindole 3f-h in a mixture with with di-iodated products 17f and 19f-h. After application of desulfonylation procedure D, derivatives 18f-h were isolated alone and used directly in Sonogashira coupling reactions.

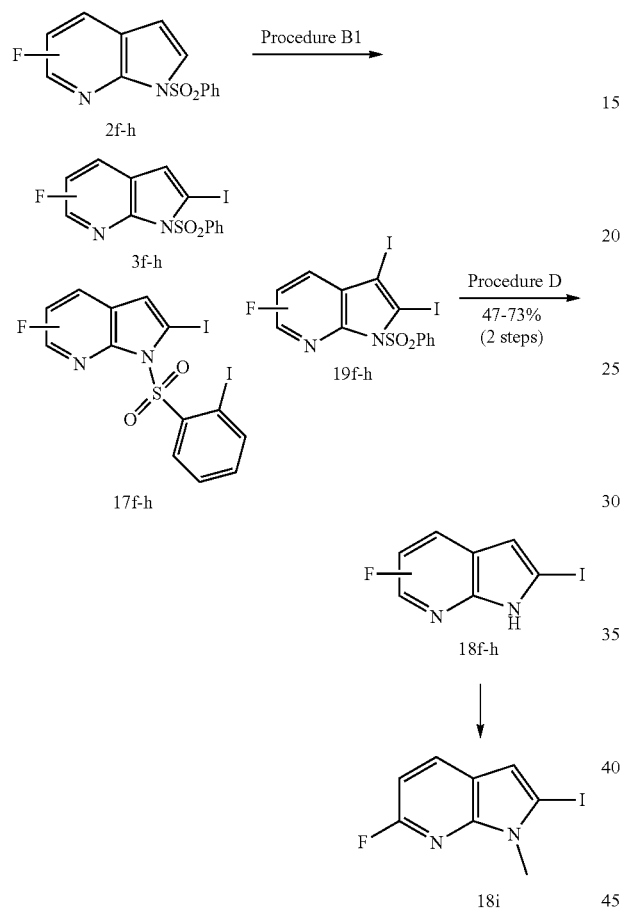

The desulfonylation of type 3 azaindoles has been completed according to procedure D, the type 18 products have then undergone a protection step by a protective group Boc generating 20 (E procedure)

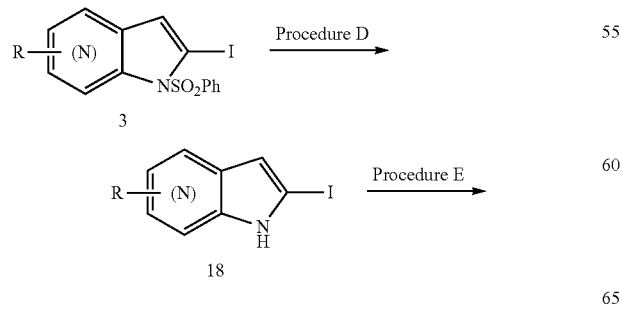

-continued

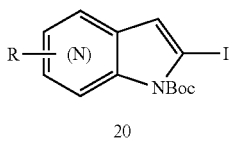

R = H, Cl

TABLE 4

Iiodated derivatives of azaindoles obtained according to procedures D or E.

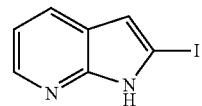

18a, 85%
Procedure D

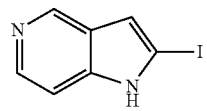

18b, 65%
Procedure D

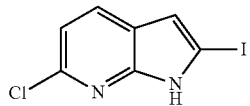 [SMILES: Clc1ccc2cc(I)[nH]c2n1]

18e, 61%
Procedure D

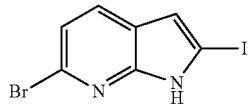

18j, 87%
Procedure D

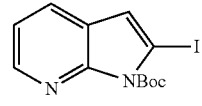 [SMILES: CC(C)(C)OC(=O)n1c(I)cc2cccnc21]

20a, 94%
Procedure E

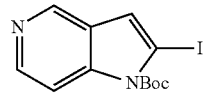

20b, 88%
Procedure E

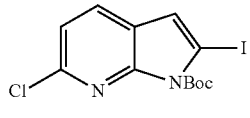

20e, 99%
Procedure E

TABLE 4-continued

Iiodated derivatives of azaindoles obtained according to procedures D or E.

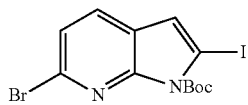 [SMILES: CC(C)(C)OC(=O)n1c(I)cc2ccc(Br)nc21]

20j, 99%
Procedure E

Example 10.1 2-Iodo-1-(phenylsulfonyl)-LH-pyrrolo[3,2-d] pyridine 3c

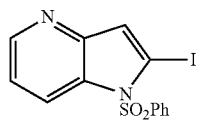

C$_{13}$H$_9$IN$_2$O$_2$S
MW: 384,19 g.mol$^{-1}$

The compound was prepared according to procedure B1 and purified by flash chromatography column on silicagel (ethyl acetate/petroleum ether=25/75). Yellow solid (70%), mp 138-140° C., R$_s$=0.27 (ethyl acetate/petroleum ether=30/70). IR (v, cm$^{-1}$, neat) 3704, 3061, 2360, 1566, 1502, 1479, 1450, 1405, 1375, 1268, 1213, 1191, 1166, 1125, 1090, 998, 802, 781, 756, 724, 682, 668, 584, 558, 524, 509. $^1$H NMR (250 MHz, CDCl$_3$, 20° C.) δ 8.59-8.45 (m, 2H), 7.95-7.83 (m, 2H), 7.61 (m, 1H), 7.52-7.40 (m, 2H), 7.21 (m, 2H). $^{13}$C NMR (63 MHz, CDCl$_3$, 20° C.) δ 149.1 (Cq), 146.6 (CH), 137.9 (Cq), 134.5 (CH), 132.3 (Cq), 129.4 (2×CH), 127.3 (2×CH), 124.8 (CH), 122.5 (CH), 119.3 (CH), 81.0 (Cq). HRMS (+ESI) calculated for C$_{13}$H$_{10}$IN$_2$O$_2$S (M+H+): 384.9502, found: 384.9503.

Example 10.2 2-Iodo-1-(phenylsulfonyl)-LH-pyrrolo[2,3-c] pyridine 3d

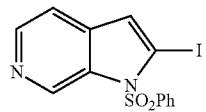

C$_{13}$H$_9$IN$_2$O$_2$S
MW: 384,19 g.mol$^{-1}$

The compound was prepared according to procedure A2 and purified by flash column chromatography on silicagel (ethyl acetate/petroleum ether=30/70). Yellow solid (67%), mp 149 151° C., Rf=0.34 (ethyl acetate/petroleum ether=1/1). IR (v, cm$^{-1}$, neat) 3091, 2919, 2842, 2735, 1639, 1612, 1592, 1540, 1480, 1450, 1416, 1379, 1319, 1272, 1205, 1170, 1124, 1109, 1091, 1049, 1031, 1014, 996, 899, 834, 819, 755, 725, 684, 668, 607, 559, 514. $^1$H NMR (250 MHz, CDCl$_3$, 20° C.) δ 9.53 (t, J=0.9 Hz, 1H), 8.39 (d, J=5.3 Hz, 1H), 8.03-7.86 (m, 2H), 7.61 (m, 1H), 7.55-7.41 (m, 2H), 7.35 (dd, J=5.3 Hz, J=1.1 Hz, 1H), 7.00 (d, J=0.8 Hz, 1H). $^{13}$C NMR (63 MHz, CDCl$_3$, 20° C.) δ 142.8 (CH), 137.7 (Cq), 137.2 (CH), 136.7 (Cq), 135.6 (Cq), 134.5 (CH), 129.4 (2×CH), 127.4 (2×CH), 122.4 (CH), 113.7 (CH), 81.9 (Cq). HRMS (+ESI) calculated for C$_{13}$H$_{10}$IN$_2$O$_2$S (M+H+): 384.9502, found: 384.9507.

Example 10.3 3 6-Chloro-2-iodo-1-(phenylsulfonyl)-1H-pyrrolo[2,3-b]pyridine 3e

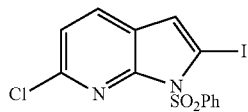

C$_{13}$H$_8$ClIN$_2$O$_2$S
MW: 418,64 g.mol$^{-1}$

The compound was prepared according to procedure B2 and purified by flash column chromatography on silicagel (ethyl acetate/petroleum ether=10/90). White solid (46%), mp 176-178° C., Rf=0.39 (ethyl acetate/petroleum ether=10/90). IR (v, cm$^{-1}$, neat) 3115, 2954, 1907, 1570, 1486, 1435, 1374, 1336, 1277, 1240, 1207, 1177, 1126, 1089, 1012, 928, 825, 756, 724, 684, 631, 588, 558, 545, 521. $^1$H NMR (250 MHz, CDCl$_3$, 20° C.) δ 8.32-8.19 (m, 2H), 7.70-7.41 (m, 4H), 7.14 (d, J=8.2 Hz, 1H), 6.95 (s, 1H). $^{13}$C NMR (63 MHz, CDCl$_3$, 20° C.) δ 147.7 (Cq), 146.1 (Cq), 138.1 (Cq), 134.4 (CH), 129.6 (CH), 129.0 (2×CH), 128.5 (2×CH), 122.2 (Cq), 119.7 (CH), 119.4 (CH), 75.9 (Cq). HRMS (+ESI) calculated for C$_{13}$H$_9$C$_1$N$_2$O$_2$S (M+H+): 418.9113, found: 418.9111.

Example 10.4 10.4 6-Bromo-2-iodo-1-(phenylsulfonyl)-1H-pyrrolo[2,3-b]pyridine 3j

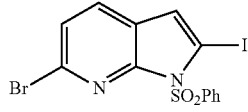

C$_{13}$H$_8$BrIN$_2$O$_2$S
MW: 463,09 g.mol$^{-1}$

The compound was prepared according to procedure B2 and purified by chromatography column on silicagel under pressure (the ratio of solvents used: ethyl acetate/petroleum ether=10/90). White solid (93%), mp 205-207° C., Rf=0.43 (ethyl acetate/petroleum ether=10/90). IR (v, cm$^{-1}$, neat) 3383, 2359, 1635, 1588, 1567, 1485, 1449, 1430, 1370, 1333, 1275, 1235, 1207, 1175, 1129, 1114, 1087, 1011, 918, 826, 755, 723, 697, 684, 623, 585, 557, 537, 502. $^1$H NMR (250 MHz, CDCl$_3$, 20° C.) δ 8.35-8.01 (m, 2H), 7.69-7.37 (m, 4H), 7.25 (m, 1H), 6.91 (s, 1H). 13C NMR (63 MHz, CDCl$_3$, 20° C.) δ 148.0 (Cq), 138.1 (Cq), 136.1 (Cq), 134.4 (CH), 129.4 (CH), 129.0 (2*CH), 128.7 (2×CH), 123.3 (CH), 122.4 (Cq), 119.5 (CH), 76.0 (Cq). HRMS (+ESI) calculated for C$_3$H$_9$ strand$_2$ 0$_2$ S (M HI+): 464.8587, found: 464.8581.

Example 10.5 2-Iodo-1H-pyrrolo[2,3-b]pyridine 18a

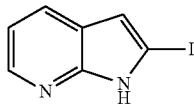

C₇H₅IN₂
MW: 244,03 g.mol⁻¹

The compound was prepared according to procedure D and purified by flash column chromatography on silicagel (ethyl acetate/petroleum ether=10/90). White solid (85%), mp 189-191° C., Rf=0.43 (ethyl acetate/petroleum ether=20/80). IR (v, cm⁻¹, neat) 2790, 1580, 1481, 1431, 1403, 1336, 1308, 1275, 911, 812, 762, 622, 510. ¹H NMR (400 MHz, DMSO-d₆, 20° C.) δ 12.20 (s, 1H), 8.13 (dd, J=4.7 Hz, J=1.6 Hz, 1H), 7.86 (dd, J=7.8 Hz, J=1.6 Hz, 1H), 7.02 (dd, J=7.8 Hz, J=4.7 Hz, 1H), 6.70 (s, 1H). ¹³C NMR (101 MHz, DMSO-d₆, 20° C.) δ 151.0 (Cq), 142.9 (CH), 126.9 (CH), 122.1 (Cq), 116.3 (CH), 110.0 (CH), 81.1 (Cq). HRMS (+ESI) calculated for C₇H61N₂ (M+H+): 244.9570, found: 244.9570.

Example 10.6 2-Iodo-1H-pyrrolo[3,2-c] pyridine 18b

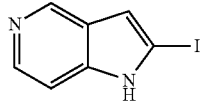

C₇H₅IN₂
MW: 244,03 g.mol⁻¹

The compound was prepared according to procedure D and isolated by precipitation in Et₂0 with a filtration. White solid (65%), mp 247-249° C., Rf=0.19 (ethyl acetate/petroleum ether=30/70) IR (v, cm⁻¹, neat) 3349, 3120, 3080, 3044, 2930, 2770, 2733, 2690, 2644, 1668, 1606, 1574, 1504, 1447, 1423, 1324, 1292, 1248, 1201, 1182, 1168, 1101, 1028, 948, 908, 838, 808, 796, 753, 629, 604, 537, 522, 518, 514, 511. ¹H NMR (400 MHz, DMSO-d₆, 20° C.) δ 12.08 (s, 1H), 8.73 (s, 1H), 8.09 (d, J=5.6 Hz, 1H), 7.29 (d, J=5.6 Hz, 1H), 6.81 (s, 1H). ¹³C NMR (101 MHz, DMSO-d₆, 20° C.) δ ¹³C NMR (101 MHz, DMSO) δ 142.3 (Cq), 141.6 (CH), 140.6 (CH), 127.0 (Cq), 110.3 (CH), 106.3 (CH), 81.5 (Cq). HRMS (+ESI) calculated for C₇H61N₂ (M+H+): 244.9570, found: 244.9568.

Example 10.7 2-Iodo~1H-pyrrolo[3,2-b] pyridine 18c

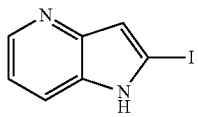

C₇H₅IN₂
MW: 244,03 g.mol⁻¹

The compound was prepared according to procedure D and purified by flash column chromatography on silicagel (acetone/dichloromethane=3/97). White solid (73%), mp 192-1° C. 4, Rf=0.31 (acetone/dichloromethane=2/98). IR (v, cm⁻¹, neat) 3052, 2950, 2871, 2644, 1613, 1563, 1504, 1481, 1432, 1393, 1352, 1309, 1282, 1195, 1118, 908, 769, 622, 578, 512, 502. ¹H NMR (400 MHz, DMSO-d₆, 20° C.) δ 11.91 (s, 1H), 8.26 (dd, J=4.6 Hz, J=1.4 Hz, 1H), 7.68 (dd, J=8.3 Hz, J=1.4 Hz, 1H), 7.03 (dd, J=8.3 Hz, J=4.6 Hz, 1H), 6.80 (s, 1H). ¹³C NMR (101 MHz, DMSO-d₆, 20° C.) δ 147.7 (Cq), 143.2 (CH), 132.0 (Cq), 117.8 (CH), 116.8 (CH), 111.6 (CH), 84.6 (Cq). HRMS (+ESI) calculated for C₇H₆IN₂ (M+H+): 244.9570, found: 244.9573.

Example 10.8 2-Iodo-1H-pyrrolo[2,3-c] pyridine 18d

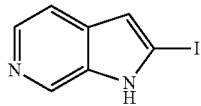

C₇H₅IN₂
MW: 244,04 g.mol⁻¹

The compound was prepared according to procedure B1 and procedure I and purified by flash column chromatography on silicagel (ethyl acetate). yellow solid (47% over 2 steps), mp 210-212° C., Rf=0.26 (ethyl acetate/petroleum ether=1/1). IR (v, cm⁻¹, neat) 2583, 1611, 1516, 1433, 1400, 1297, 1218, 1155, 1031, 910, 817, 630, 598, 512. ¹H NMR (400 MHz, DMSO-d₆, 20° C.) δ 12.21 (large s, 1H), 8.64 (s, 1H), 8.04 (m, 1H), 7.45 (d, J=5.3 Hz, 1H), 6.73 (s, 1H). ¹³C NMR (101 MHz, DMSO-d₆, 20° C.) δ 138.5 (Cq), 136.7 (Cq), 134.0 (Cq), 133.4 (CH), 113.5 (CH), 110.5 (2×CH).
HRMS (+ESI) calculée pour C₇H₆IN₂ (M+H+): 244.9570, trouvée: 244.9573

Example 10.9 6-Chloro-2-iodo-1H-pyrrolo[2,3-b] pyridine 18e

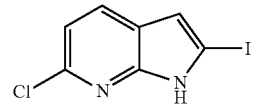

C₇H₄ClIN₂
MW: 278,48 g.mol⁻¹

The compound was prepared according to procedure D and purified by flash column chromatography on silicagel (ethyl acetate/petroleum ether=3/97). White solid (61%), mp 208-210° C., Rf=0.40 (ethyl acetate/petroleum ether=3/97). IR (v, cm⁻¹, neat) 3103, 3024, 2938, 2852, 2806, 1596, 1575, 1474, 1409, 1387, 1332, 1285, 1265, 1124, 1111, 1092, 965, 933, 812, 752, 690, 630, 607, 517, 506. ¹H NMR (400 MHz, DMSO-d₆, 20° C.) δ 12.44 (s, 1H), 7.92 (d, J=8.2 Hz, 1H), 7.09 (d, J=8.2 Hz, 1H), 6.76 (s, 1H). ¹³C NMR (101 MHz, DMSO-d₆, 20° C.) δ 149.6 (Cq), 143.5 (Cq), 130.1 (CH), 121.0 (Cq), 116.2 (CH), 110.4 (CH), 81.8 (Cq). HRMS (+ESI) calculated for C₇H₅ClIN₂ (M+H+): 278.9181, found 278.9177.

Example 10.10 6-Fluoro-2-iodo-1H-pyrrolo[2,3-b]pyridine 18f

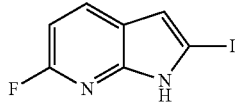

C$_7$H$_4$FIN$_2$
MW: 262,02 g.mol$^{-1}$

The compound was prepared according to procedure B2 and procedure D and purified by flash column chromatography on silicagel (ethyl acetate/petroleum ether=3/97). White solid (56% over 2 steps), mp 172-174° C., Rf=0.34 (ethyl acetate/petroleum ether=5/95). IR (v, cm$^{-1}$, neat) 3134, 1589, 1424, 1343, 1272, 1199, 1105, 995, 811, 757, 614. $^1$H NMR (250 MHz, DMSO-d$_6$, 20° C.) δ 12.34 (s, 1H), 8,02 (t, J=8.3 Hz, 1H), 6.79 (d, J=8.3 Hz, 1H), 6.76 (s, 1H). $^{13}$C NMR (63 MHz, DMSO-d$_6$, 20° C.) δ 161.3 (Cq), 147.0 (d, J=18.8 Hz, Cq), 132.2 (d, J=9.4 Hz, CH), 120.2 (Cq), 110.5 (CH), 101.6 (d, J=38.9 Hz, CH), 79.4 (Cq). $^{19}$F NMR (376 MHz, DMSO-d$_6$, 20° C.) δ −76.0.
HRMS (+ESI) calculated for C$_7$H$_5$FIN$_2$ (M+H+): 262.9476, found: 262.9475.

Example 10.11 5-Fluoro-2-iodo-1H-pyrrolo[2,3-b]pyridine 18 g

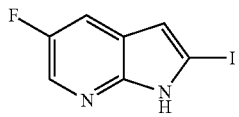

C$_7$H$_4$FIN$_2$
MW: 262,02 g.mol$^{-1}$

The compound was prepared according to procedure B2 and procedure D and purified by flash column chromatography on silicagel (ethyl acetate/petroleum ether=5/95). White solid (48% over 2 steps), mp 199-201° C., Rf=0.32 (ethyl acetate/petroleum ether=10/90). IR (v, cm$^{-1}$, neat) 3105, 3038, 2952, 2911, 2863, 2786, 2738, 2709, 2361, 1759, 1609, 1586, 1565, 1500, 1425, 1387, 1321, 1290, 1237, 1194, 1093, 1009, 978, 897, 877, 802, 760, 630, 590, 541, 505. RMN $^1$H (250 MHz, DMSO-d$_6$, 20° C.) δ 12.38 (s, 1H), 8.13 (m, 1H), 7.77 (dd, J=9.3 Hz, J=2.4 Hz, 1H), 6.71 (m, 1H). $^{13}$C NMR (101 MHz, DMSO-d$_6$, 20° C.) δ 155.3 (d, J=239.7 Hz, Cq), 147.9 (Cq), 131.0 (d, J=29.0 Hz, CH), 122.0 (d, J=7.3 Hz, Cq), 112.5 (d, J=20.9 Hz, CH), 110.0 (d, J=4.0 Hz, CH), 83.9 (Cq). $^{19}$F NMR (376 MHz, DMSO-d$_6$, 20° C.) δ −139.0. HRMS (+ESI) calculated for C$_7$H$_5$FIN$_2$ (M+H+): 262.9476, found: 262.9473.

Example 10.12 4-fluoro-2-iodo-1H-pyrrolo[2,3-b]pyridine 18 h

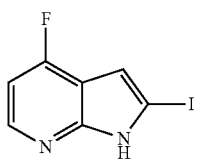

C$_7$H$_4$FIN$_2$
MW: 262,02 g.mol$^{-1}$

The compound was prepared according to the sequence of procedures B2 and D and purified by flash column chromatography on silicagel (ethyl acetate/petroleum ether=20:80) Solid. white (73% over 2 steps), mp 218-220° C., Rf 0.26 (ethyl acetate/petroleum ether=20:80). IR (v, cm$^{-1}$, neat) 2724, 1628, 1570, 1511, 1479, 1432, 1395, 1336, 1311, 1273, 1253, 1113, 1049, 874, 806, 746, 616, 511. $^1$H NMR (400 MHz, DMSO-d$_6$, 20° C.) δ 12.57 (s, 1H), 8.14 (s, 1H), 6.92 (d, J=4.0 Hz, 1H), 6.78 (s, 1H). RMN $^{13}$C (101 MHz, DMSO-d$_6$, 20° C.) δ 159.67 (d, J=260.5 Hz, Cq), 154.4 (d, J=11.4 Hz, Cq), 145.0 (d, J=6.1 Hz, CH), 110.9 (d, J=18.0 Hz, Cq), 105.6 (CH), 102.8 (d, J=14.8 Hz, CH), 81.6 (Cq). $^{19}$F NMR (376 MHz, DMSO-d$_6$, 20° C.) δ −112.3. HRMS (+ESI) calculated for C$_7$H$_5$FIN$_2$ (M+H+): 262.9476, found: 262.9475.

Example 10.13 6-Fluoro-2-iodo-1-methyl-1H-pyrrolo[2,3-b]pyridine 18i

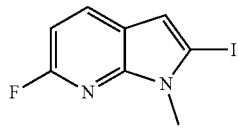

C$_8$H$_6$FIN$_2$
MW: 276,05 g.mol$^{-1}$

The compound was prepared according to procedure C and purified by flash column chromatography on silicagel (ethyl acetate/petroleum ether=1/99). White solid (90%), mp 94-96° C., Rf=0.27 (ethyl acetate/petroleum ether=5/95). IR (v, cm$^{-1}$, neat) 3111, 1602, 1574, 1472, 1441, 1404, 1333, 1301, 1265, 1230, 1125, 1091, 1041, 973, 820, 777, 748, 690, 580, 564, 516, 506, 503. $^1$H NMR (400 MHz, CDCl$_3$, 20° C.) δ 7.84 (m, 1H), 6.79 (s, 1H), 6.66 (dd, J=8.4 Hz, J=1.1 Hz, 1H), 3.78 (s, 3H). $^{13}$C NMR (101 MHz, CDCl$_3$, 20° C.) δ 159.9 (d, J=237.5 Hz, Cq), 145.1 (d, J=17.5 Hz, Cq), 131.7 (d, J=9.4 Hz, CH), 119.5 (d, J=2.9 Hz, Cq), 110.3 (CH), 101.6 (d, J=38.8 Hz, CH), 83.4 (d, J=4.1 Hz, Cq), 32.6 (CH$_3$). $^{19}$F NMR (376 MHz, CDCl$_3$, 20° C.) δ −75.0. HRMS (+ESI) calculated for C$_5$H$_7$FIN$_2$ (M+H+): 276.9633, found: 276.9633.

Example 10.14 6-Bromo-2-iodo-1H-pyrrolo[2,3-b]pyridine 18j

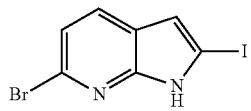

C$_7$H$_4$BrIN$_2$
MW: 322,93 g.mol$^{-1}$

The compound was prepared according to procedure D and purified by pressurized silicagel column chromatography (the ratio of solvents used: ethyl acetate/petroleum ether=5/95). White solid (81%), mp 238-240° C., Rf 0.24 (ethyl acetate/petroleum ether=5/95). IR (v, cm$^{-1}$, neat) 3898, 3851, 3819, 3800, 3749, 3742, 3731, 3687, 3674, 3668, 3646, 3627, 3565, 3099, 3019, 2930, 2844, 2798, 2588, 2216, 1912, 1595, 1567, 1473, 1406, 1382, 1330, 1282, 1263, 1206, 1120, 1098, 964, 953, 920, 813, 751, 670, 621, 603, 536, 524, 517, 506. $^1$H NMR (400 MHz, DMSO-$d_6$, 20° C.) δ 12.46 (s, 1H), 7.83 (d, J=8.2 Hz, 1H), 7.21 (d, J=8.2 Hz, 1H), 6.76 (s, 1H). $^{13}$C NMR (101 MHz, DMSO-$d_6$, 20° C.) δ 150.1 (Cq), 134.0 (Cq), 129.9 (CH), 121.2 (Cq), 119.7 (CH), 110.5 (CH), 81.9 (Cq). HRMS (+ESI) calculated for $C_7H_5BrN_2$ (M+H+): 324.8655, found: 324.8652.

Example 10.15: 5-Bromo-2-iodo-1H-pyrrolo[2,3-b]pyridine 18k

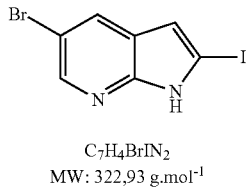 [SMILES: Brc1cnc2[nH]c(I)cc2c1]

$C_7H_4BrIN_2$
MW: 322,93 g.mol$^{-1}$

The compound was prepared according to the sequence of procedures BI and D and purified by column chromatography on silicagel under pressure (the ratio of solvent used (methanol/dichloromethane=5/95), white solid (3% over 2 steps), mp 253-255° C., Rf 0.57 (methanol/dichloromethane=5/95). IR (v, cm$^{-1}$, neat) 2687, 1567, 1467, 1416, 1390, 1326, 1278, 1229, 924, 882, 805, 753, 683. (400 MHz, DMSO-$d_6$, 20° C.) δ 12.46 (s, 1H), 8.19 (s, 1H), 8.11 (s, 1H), 6.69 (s, 1H). $^{13}$C NMR (101 MHz, DMSO-$d_6$, 20° C.) δ 149.4 (Cq), 142.8 (CH), 128.8 (CH), 123.8 (Cq), 111.6 (Cq), 109.7 (CH), 83.8 (Cq). HRMS (+ESI) calculated for $C_7H_5BrIN_2$ (M+H+): 322.8675, found: 322.8675.

Example 10.16 4-Chloro-2-iodo-1H-pyrrolo[2,3-b]pyridine 18l

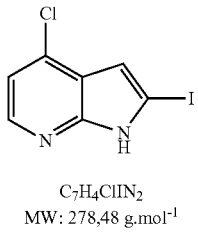 [SMILES: Clc1ccnc2[nH]c(I)cc12]

$C_7H_4ClIN_2$
MW: 278,48 g.mol$^{-1}$

The compound was prepared according to the sequence of procedures BI and D and purified by precipitation from $Et_2O$. White solid (58% over 2 steps), mp 231-233° C., IR (v, cm$^{-1}$, neat) 2722, 1602, 1568, 1480, 1428, 1387, 1326, 1307, 1265, 1183, 961, 905, 850, 801, 740, 664, 615, 522, 510, 508. $^1$H NMR (250 MHz, DMSO-$d_6$, 20° C.) δ 12.60 (s, 1H), 8.10 (d, J=5.2 Hz, 1H), 7.16 (d, J=5.2 Hz, 1H), 6.75 (s, 1H). $^{13}$C NMR (63 MHz, DMSO-$d_6$, 20° C.) δ 151.1 (Cq), 143.2 (CH), 132.0 (Cq), 120.5 (Cq), 115.7 (CH), 107.5 (CH), 82.5 (Cq). HRMS (+ESI) calculated for $C_7H_5ClIN_2$ (M+H+): 278.9181, found: 278.9184.

Example 10.17 tert-Butyl 2-iodo-1H-pyrrolo[2,3-b]pyridine-1-carboxylate 20a

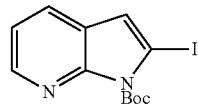

$C_{12}H_{13}IN_2O_2$
MW: 344,15 g.mol$^{-1}$

The compound was prepared following procedure E and purified by flash column chromatography on silicagel (ethyl acetate/petroleum ether=10/90). White solid (99%), mp 74-76° C., Rf=0.40 (ethyl acetate/petroleum ether=20/80). IR (v, cm$^{-1}$, neat) 3067, 2981, 1725, 1572, 1504, 1460, 1392, 1369, 1345, 1324, 1304, 1252, 1206, 1154, 1132, 1106, 1066, 1044, 912, 839, 805, 765, 665, 611, 589, 517, 511. $^1$H NMR (400 MHz, CDCl$_3$, 20° C.) δ 8.36 (dd, J=4.8 Hz, J=1.6 Hz, 1H), 7.72 (dd, J=7.8 Hz, J=1.6 Hz, 1H), 7.08 (dd, J=7.8 Hz, J=4.8 Hz, 1H), 6.87 (s, 1H), 1.70 (s, 9H). $^{13}$C NMR (101 MHz, CDCl$_3$, 20° C.) δ 149.7 (Cq), 147.7 (Cq), 144.7 (CH), 127.3 (CH), 123.3 (Cq), 118.6 (CH), 118.0 (CH), 85.8 (Cq), 77.0 (Cq), 28.2 (3×CH$_3$). HRMS (+ESI) calculated for $C_{12}H_{14}IN_2O_2$ (M+H+): 345.0095, found: 345.0094.

Example 10.18 tert-Butyl 2-iodo-1H-pyrrolo[3,2-c]pyridine-1-carboxylate 20b

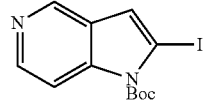

$C_{12}H_{13}IN_2O_2$
MW: 344,15 g.mol$^{-1}$

The compound was prepared following procedure E and purified by flash column chromatography on silicagel (ethyl acetate/petroleum ether=20/80). white solid (88%), mp 82-84° C., Rf=0.19 (ethyl acetate/petroleum ether=20/80). IR (v, cm$^{-1}$, neat) 3041, 2983, 1733, 1592, 1504, 1479, 1447, 1432, 1394, 1367, 1331, 1316, 1271, 1254, 1178, 1150, 1056, 914, 844, 816, 768, 746, 644, 595, 544, 521, 505. $^1$H NMR (250 MHz, CDCl$_3$, 20° C.) δ 8.66 (d, J=1.0 Hz, 1H), 8.27 (dd, J=5.9 Hz, J=1.0 Hz, 1H), 7.81 (dd, J=5.9 Hz, J=0.9 Hz, 1H), 6.92 (t, J=0.9 Hz, 1H), 1.62 (s, 9H). $^{13}$C NMR (63 MHz, CDCl$_3$, 20° C.) δ 148.6 (Cq), 144.0 (CH), 142.0 (CH), 141.6 (Cq), 127.6 (Cq), 120.0 (CH), 110.2 (CH), 86.5 (Cq), 28.3 (3×CH$_3$). HRMS (+ESI) calculated for $C_{12}H_{14}IN_2O_2$ (M+H+): 345.0095, found: 345.0093.

Example 10.19 tert-Butyl 6-chloro-2-iodo-1H-pyrrolo[2,3-b]pyridine-1-carboxylate 20e

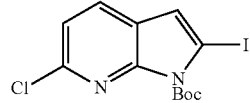

$C_{12}H_{12}ClIN_2O_2$
MW: 378,59 g.mol$^{-1}$

The compound was prepared following procedure E and purified by flash column chromatography on silica gef (ethyl acetate/petroleum ether=1/99). White solid (99%), mp 81-83° C., Rf=0.16 (ethyl acetate/petroleum ether=1/99). IR (v, cm$^{-1}$, neat) 2986, 2973, 2929, 1746, 1592, 1568, 1493, 1474, 1457, 1436, 1392, 1367, 1352, 1311, 1276, 1251, 1157, 1127, 1101, 1068, 1037, 937, 844, 817, 772, 749, 738, 712, 640, 627, 589, 551, 517, 509, 503. $^1$H NMR (400 MHz, CDCl$_3$, 20° C.) δ 7.69 (d, J=8.2 Hz, 1H), 7.15 (d, J=8.2 Hz, 1H), 6.91 (s, 1H), 1.72 (s, 9H). $^{13}$C NMR (101 MHz, CDCl$_3$, 20° C.) δ 147.8 (Cq), 147.6 (Cq), 146.1 (Cq), 129.4 (CH), 121.9 (Cq), 119.1 (CH), 117.6 (CH), 86.1 (Cq), 77.1 (Cq), 28.1 (3×CH$_3$). HRMS (+ESI) calculated for C$_7$H$_5$ClIN$_2$ (M+H+): 378.9705, found: 378.9704.

Example 10.20 tert-butyl 6-bromo-2-iodo-1H-pyrrolo[2,3-b]pyridine-1-carboxylate 20j

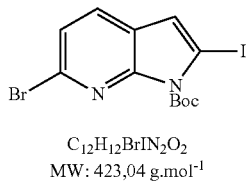

C$_{12}$H$_{12}$BrIN$_2$O$_2$
MW: 423,04 g.mol$^{-1}$

The compound was prepared following procedure E and purified by column chromatography on silicagel under pressure (the ratio of solvents used: ethyl acetate/petroleum ether=1/99). Orange solid (81%), mp 69-71° C., Rf=0.38 (ethyl acetate/petroleum ether=1/99). IR (v, cm$^{-1}$, neat) 2972, 1746, 1588, 1561, 1489, 1431, 1390, 1367, 1349, 1308, 1275, 1250, 1156, 1136, 1096, 1065, 924, 843, 816, 771, 749, 734, 695, 517, 505, 503. $^1$H NMR (400 MHz, CDCl$_3$, 20° C.) δ 7.60 (d, J=8.1 Hz, 1H), 7.29 (d, J=8.1 Hz, 1H), 6.89 (s, 1H), 1.72 (s, 9H). $^{13}$C NMR (101 MHz, CDCl$_3$, 20° C.) δ 148.0 (Cq), 147.7 (Cq), 136.3 (Cq), 129.1 (CH), 122.6 (Cq), 122.1 (CH), 117.7 (CH), 86.1 (Cq), 77.2 (Cq), 28.1 (3×CH$_3$). HRMS (+ESI) calculated for C$_{12}$H$_{13}$BrIN$_2$O$_2$ (M+H+): 424.9180, found: 424.9178.

Example 11. Synthesis of Final Compounds and Analogue Protected Compounds

The final products of type 22 were prepared by three different methods:
either by coupling Sonogasbira from iodated derivatives protected by a benzenesulfonyl of type 3 and with a deprotection of the intermediate 21 (method 1);
or by the Sonogashira coupling directly from unprotected iodated derivatives of type 18 (method 2); or by the Sonogashira coupling from iodated derivatives protected by a teri-butoxycarbonyl of type 20 and with a deprotection of the intermediate product 23 (Method 3)

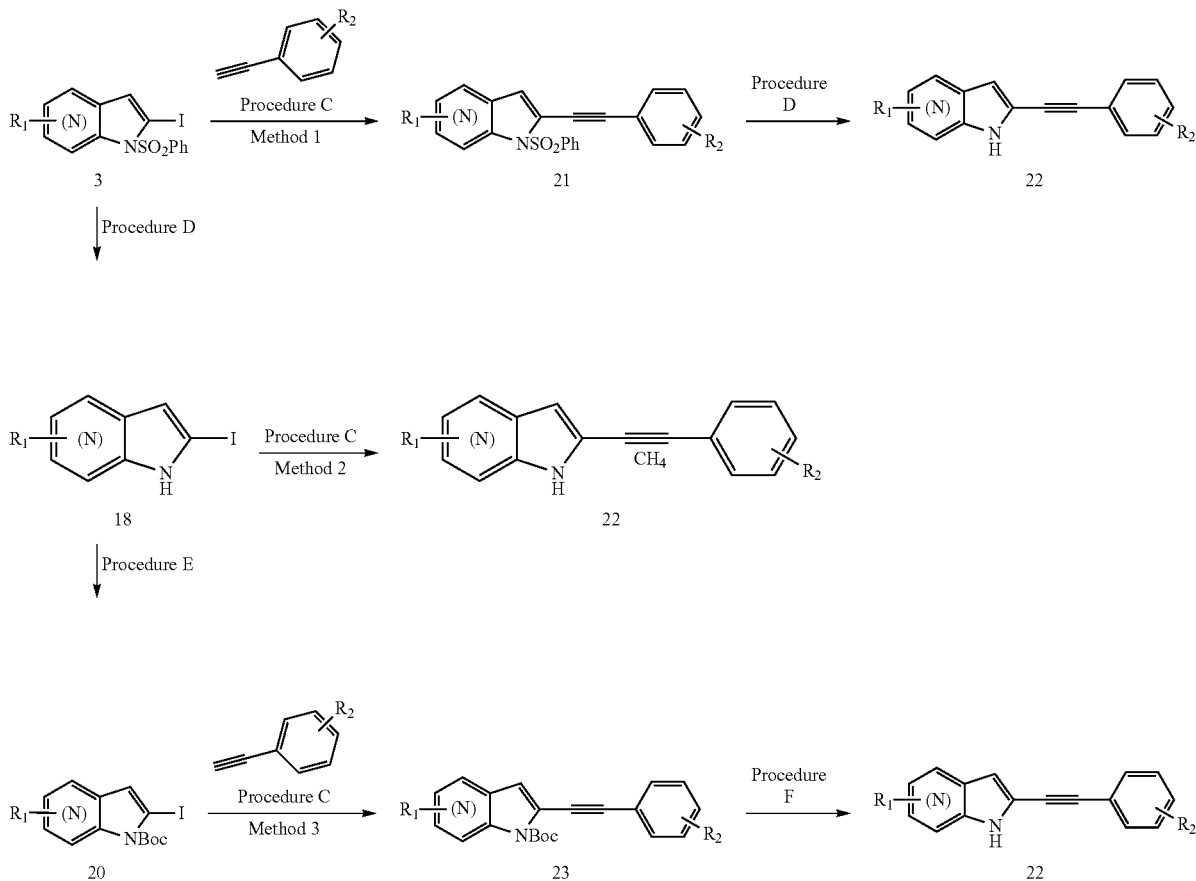

Example 11.1 N,N-Dimethyl-4-((1-(phenylsulfonyl)-1H-pyrrolo[2,3-b] pyridin-2-yl)ethynyl)aniline 21a

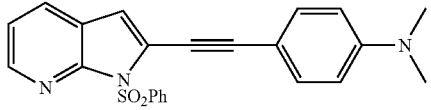

C₂₃H₁₉N₃O₂S
MW: 401,48 g.mol⁻¹

The compound was prepared according to procedure C2 and purified by flash column chromatography on silicagel (ethyl acetate/petroleum ether=10/90). Yellow solid (62%), mp 185-187° C., Rf=0.18 (ethyl acetate/petroleum ether=10/90). IR (v, cm⁻¹, neat) 2918, 2194, 1732, 1605, 1578, 1545, 1517, 1474, 1447, 1398, 1374, 1311, 1267, 1226, 1183, 1128, 1114, 1089, 1071, 1054, 1036, 997, 941, 871, 829, 811, 726, 683, 661, 626. ¹H NMR (250 MHz, CDCl₃, 20° C.) δ 8.47 (dd, J=4.8 Hz, J=1.6 Hz, 1H), 8.28-8.17 (m, 2H), 7.73 (dd, J=7.9 Hz, J=1.6 Hz, 1H), 7.57-7.48 (m, 3H), 7.47-7.37 (m, 2H), 7.16 (dd, J=7.9 Hz, J=4.8 Hz, 1H), 6.75 (s, 1H), 6.73-6.63 (m, 2H), 3.02 (s, 6H). ¹³C NMR (63 MHz, CDCl₃, 20° C.) δ 150.7 (Cq), 148.3 (CH), 145.3 (Cq), 139.2 (Cq), 133.8 (CH), 132.9 (2×CH), 129.0 (2×CH), 128.6 (CH), 127.8 (2×CH), 122.6 (Cq), 121.8 (Cq), 119.4 (CH), 111.8 (2×CH), 111.5 (CH), 108.7 (Cq), 99.7 (Cq), 78.6 (Cq), 40.15 (2×CH₃). HRMS (+ESI) calculated for C₂₃H₂₀N₃O₂S (M+H+): 402.1271, found: 402.1274.

Example 11.2 N,N-Dimethyl-4-((1-(phenylsulfonyl)-1H-pyrrolo[3,2-b] pyridin-2-yl)ethynyl)aniline 21c

C₂₃H₁₉N₃O₂S
MW: 401,48 g.mol⁻¹

The compound was prepared according to procedure C2 and purified by flash column chromatography on silicagel (etliyle acetate/petroleum ether=30/70). Brown oil (98%), Rf_0.22 (ethyl acetate/petroleum ether=30/70). IR (v, cm⁻¹, neat) 2924, 2200, 1733, 1605, 1566, 1549, 1516, 1446, 1405, 1367, 1268, 1225, 1169, 1127, 1089, 1043, 945, 816, 727, 685, 583, 559, 506, 503. ¹H NMR (400 MHz, CDCl₃, 20° C.) δ 8.56 (dd, J=4.7 Hz, J=1.1 Hz, 1H), 8.51 (d, J=8.4 Hz, 1H), 8.01-7.96 (m, 2H), 7.60-7.51 (m, 3H), 7.43 (m, 2H), 7.29 (m, 1H), 7.04 (m, 1H), 6.72 (d, J=9.0 Hz, 2H), 3.06 (s, 6H). ¹³C NMR (101 MHz, CDCl₃, 20° C.) δ 150.8 (Cq), 147.3 (Cq), 146.9 (CH), 138.4 (Cq), 134.2 (CH), 133.0 (2×CH), 130.3 (Cq), 129.2 (2×CH), 127.2 (2×CH), 125.3 (Cq), 121.7 (CH), 119.5 (CH), 115.4 (CH), 111.8 (2×CH), 108.2 (Cq), 101.3 (Cq), 78.2 (Cq), 40.1 (2×CH₃). HRMS (+ESI) calculated for C₂₃H₂₀N₃O₂S (M+H+): 402.1271, found: 402.1271.

Example 11.3 N,N-Diméthyl-4-((1-(phenylsulfonyl)-1H-pyrrolo[2,3-c] pyridin-2-yl)ethynyl)aniline 21d

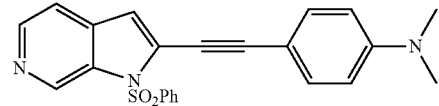

C₂₃H₁₉N₃O₂S
MW: 401,48 g.mol⁻¹

The compound was prepared according to procedure C and purified by flash column chromatography on silicagel (ethyl acetate/petroleum ether=30/70). Brown solid (80%), mp 168-170° C., Rf=0.34 (ethyl acetate/petroleum ether=30/70). IR (v, cm⁻¹, neat) 3058, 2205, 1679, 1603, 1536, 1446, 1428, 1351, 1272, 1224, 1183, 1123, 1088, 1050, 836, 817, 729, 680, 654, 574, 556, 512. ¹H NMR (250 MHz, CDCl₃, 20° C.) δ 9.55 (s, 1H), 8.43 (d, J=5.1 Hz, 1H), 8.12-7.96 (m, 2H), 7.64-7.50 (m, 3H), 7.47-7.37 (m, 3H), 6.79 (s, 1H), 6.72 (d, J=8.9 Hz, 2H), 3.05 (s, 6H). ¹³C NMR (63 MHz, CDCl₃, 20° C.) δ 150.9 (Cq), 142.9 (Cq), 138.3 (Cq), 136.7 (CH), 134.8 (Cq), 134.2 (CH), 133.1 (2×CH), 129.3 (2×CH), 127.3 (2×CH), 125.2 (Cq), 114.9 (CH), 113.2 (CH), 111.7 (2×CH), 107.9 (Cq), 101.0 (Cq), 78.0 (Cq), 40.1 (2×CH₃). HRMS (+ESI) calculated for C₂₃H₂₀N₃O₂S (M+H+): 402.1271, found: 402.1273.

Example 11.4 4-((6-chloro-1-(phenylsulfonyl)-1H-pyrrolo[2,3-b]pyridin-2-yl)ethynyl)-N,N-dimethylaniline 21e

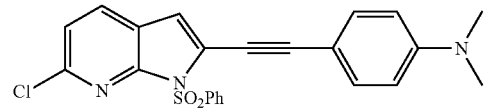

C₂₃H₁₈ClN₃O₂S
MW: 435,93 g.mol⁻¹

The compound was prepared according to procedure C and purified by flash column chromatography on silicagel (ethyl acetate/petroleum ether=5/95). Brown solid (99%), mp 195-197° C., Rf=0.41 (ethyl acetate/petroleum ether=10/90). IR (v, cm⁻¹, neat) 2204, 1608, 1567, 1544, 1439, 1379, 1361, 1312, 1279, 1246, 1180, 1111, 1093, 1042, 812, 736, 686, 617, 577, 561, 515, 506, 503. ¹H NMR (250 MHz, CDCl₃, 20° C.) δ 8.22 (m, 2H), 7.63 (dd, J=8.2 Hz, J=1.1 Hz, 1H), 7.57-7.38 (m, 5H), 7.13 (dd, J=8.2 Hz, J=1.1 Hz, 1H), 6.74-6.55 (m, 3H), 2.99 (s, 6H). ¹³C NMR (101 MHz, CDCl₃, 20° C.) δ 6 150.7 (Cq), 146.7 (Cq), 146.6 (Cq), 138.8 (Cq), 134.1 (CH), 133.0 (2×CH), 130.5 (CH), 129.0 (2×CH), 128.2 (2×CH), 123.0 (Cq), 120.1 (Cq), 119.9 (CH), 111.8 (2×CH), 110.7 (CH), 108.6 (Cq), 100.0 (Cq), 78.3 (Cq), 40.2 (2×CH₃). HRMS (+ESI) calculated for C₂₃H₁₉ClN₃O₂S (M+H+): 436.0881, found: 436.0881.

Example 11.5 3-((1-(phenylsulfonyl)-1H-pyrrolo[2,3-b]pyridin-2-yl)ethynyl)aniline 21f

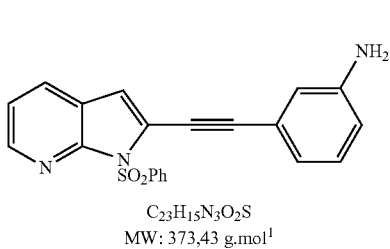

C$_{23}$H$_{15}$N$_3$O$_2$S
MW: 373,43 g.mol$^{-1}$

The compound was prepared according to procedure C and puriffe by flash column chromatography on silicagel (ethyl acetate/petroleum ether=10/90). Brown solid (94%), mp 156-158° C., Rf=0.32 (ethyl acetate/petroleum ether=10:90). IR (v, cm$^{-1}$, neat) 3431, 3325, 3228, 3061, 2360, 2210, 1637, 1598, 1575, 1486, 1447, 1394, 1377, 1333, 1262, 1176, 1127, 1088, 1033, 993, 916, 860, 822, 782, 764, 724, 683, 570, 553, 509. $^1$H NMR (400 MHz, CDCl$_3$, 20° C.) δ 8.52 (dd, J=4.8 Hz, J=1.6 Hz, 1H), 8.25 (dd, J=8.4 Hz, J=1.4 Hz, 2H), 7.80 (dd, J=7.9 Hz, J=1.6 Hz, 1H), 7.58 (m, 1H), 7.48 (dd, J=8.5 Hz, J=7.1 Hz, 2H), 7.21 (ddd, J=7.8 Hz, J=6.3 Hz, J=1.4 Hz, 2H), 7.09 (dt, J=7.7 Hz, J=1.2 Hz, 1H), 7.02 (t, J=1.9 Hz, 1H), 6.87 (s, 1H), 6.76 (ddd, J=7.9 Hz, J=2.4 Hz, J=1.0 Hz, 1H), 3.79 (s, 2H). $^{13}$C NMR (101 MHz, CDCl$_3$, 20° C.) δ 148.5 (Cq), 146.6 (Cq), 146.1 (CH), 139.2 (Cq), 134.1 (CH), 129.6 (CH), 129.2 (2×CH), 129.1 (CH), 128.0 (2×CH), 123.2 (Cq), 122.1 (CH), 121.9 (Cq), 121.6 (Cq), 119.7 (CH), 117.8 (CH), 116.3 (CH), 113.1 (CH), 98.2 (Cq), 79.7 (Cq). HRMS (+ESI) calculated for C$_{21}$H$_{16}$N$_3$O$_2$S (M+H+): 374.0958, found: 374.0957.

Example 11.6 4-((1H-Pyrrolo[2,3-b]pyridin-2-yl)ethynyl)-N,N-dimethylaniline 22a

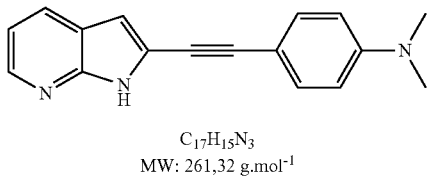 [SMILES: CN(C)c1ccc(C#Cc2cc3cccnc3[nH]2)cc1]

C$_{17}$H$_{15}$N$_3$
MW: 261,32 g.mol$^{-1}$

The compound was prepared following procedure E and purified by flash column chromatography on silicagel (ethyl acetate/petroleum ether=15/85). Yellow solid (92%), mp 229-231° C., Rf=0.36 (ethyl acetate/petroleum ether=30/70). IR (v, cm$^{-1}$, neat) 3055, 2886, 2796, 2198, 1603, 1584, 1538, 1509, 1433, 1405, 1354, 1326, 1281, 1223, 1186, 1165, 1118, 1061, 976, 945, 918, 807, 763, 699, 645, 625. $^1$H NMR (400 MHz, DMSO-d$_6$, 20° C.) δ 12.07 (s, 1H), 8.20 (m, 1H), 7.92 (dd, J=7.8 Hz, J=1.7 Hz, 1H), 7.39 (d, J=8.4 Hz, 2H), 7.08 (dd, J=7.8 Hz, J=4.6 Hz, 1H), 6.84-6.46 (m, 3H), 2.97 (s, 6H). $^{13}$C NMR (100 MHz, DMSO-d$_6$, 20° C.) δ 150.8 (Cq), 148.8 (Cq), 144.3 (CH), 132.9 (2×CH), 128.4 (CH), 120.6 (Cq), 120.2 (Cq), 116.6 (CH), 112.4 (2×CH), 108.0 (Cq), 105.4 (CH), 94.9 (Cq), 80.5 (Cq), 40.1 (2×CH$_3$). HRMS (+ESI) calculated for C$_{17}$H$_{16}$N$_3$ (M+H+): 262.1339, found: 262.1340.

Example 11.7 4-((1H-Pyrrolo[2,3-c]pyridin-2-yl)ethynyl)-N,N-dimethylaniline 22b

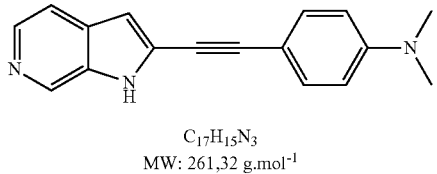 [SMILES: CN(C)c1ccc(C#Cc2cc3ccncc3[nH]2)cc1]

C$_{17}$H$_{15}$N$_3$
MW: 261,32 g.mol$^{-1}$

The compound was prepared according to procedure D and purified by flash column chromatography on silicagel (ethyl acetate/petroleum ether=20/80). Yellow solid (88%), mp 242-244° C., Rf=0.27 (ethyl acetate/petroleum ether=30/70). IR (v, cm$^{-1}$, neat) 2669, 2207, 1609, 1573, 1535, 1361, 1303, 1224, 1187, 906, 811, 598, 515. $^1$H NMR (250 MHz, DMSO-d$_6$, 20° C.) δ 12.08 (large s, 1H), 8.67 (s, 1H), 8.10 (d, J=5.5 Hz, 1H), 7.49 (dd, J=5.5 Hz, J=1.0 Hz, 1H), 7.45-7.36 (m, 2H), 6.79-6.71 (m, 3H), 2.98 (s, 6H). $^{13}$C NMR (63 MHz, DMSO-d$_6$, 20° C.) δ 151.0 (Cq), 138.6 (CH), 134.4 (CH), 133.0 (2×CH), 132.2 (Cq), 123.6 (Cq), 112.4 (2×CH), 107.5 (Cq), 105.8 (CH), 95.1 (Cq), 80.1 (Cq), 40.1 (2×CH$_3$). HRMS (+ESI) calculated for C$_{17}$H$_{16}$N$_3$ (M+H+): 262.1339, found: 262.1338.

Example 11.8 4-((1H-Pyrrolo[3,2-b]pyridin-2-yl)ethynyl)-N,N-dimethylaniline 22c

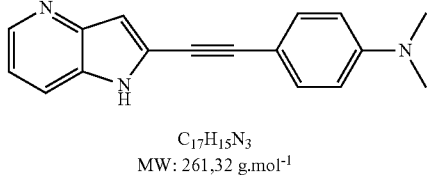 [SMILES: CN(C)c1ccc(C#Cc2cc3ncccc3[nH]2)cc1]

C$_{17}$H$_{15}$N$_3$
MW: 261,32 g.mol$^{-1}$

The compound was prepared following procedure E and purified by flash column chromatography on silicagel (ethyl acetate/petroleum ether=30/70). Orange solid (87%), mp 191-193° C., Rf=0.24 (ethyl acetate/petroleum ether=30/70). IR (v, cm$^{-1}$, neat) 3064, 2889, 2806, 2703, 2199, 1673, 1606, 1570, 1537, 1512, 1406, 1355, 1286, 1223, 1186, 1122, 943, 913, 814, 778, 623, 558, 514. $^1$H NMR (400 MHz, DMSO-d$_6$, 20° C.) δ 11.82 (s, 1H), 8.35 (dd, J=4.6 Hz, J=1.2 Hz, 1H), 7.69 (d, J=8.1 Hz, 1H), 7.40 (t, J=8.9 Hz, 2H), 7.14 (dd, J=8.2 Hz, J=4.6 Hz, 1H), 6.81 (d, J=0.9 Hz, 1H), 6.75 (d, J=8.9 Hz, 2H), 2.97 (s, 6H). $^{13}$C NMR (101 MHz, DMSO-d$_6$, 20° C.) δ 150.9 (Cq), 145.9 (Cq), 143.8 (CH), 132.9 (2×CH), 129.7 (Cq), 123.2 (Cq), 118.4 (CH), 117.8 (CH), 112.4 (2×CH), 107.8 (Cq), 106.8 (CH), 95.4 (Cq), 80.4 (Cq), 40.1 (2×CH$_3$). HRMS (+ESI) calculated for C$_{17}$H$_{16}$N$_3$ (M+H+): 262.1339, found: 262.1342.

Example 11.9 4-((1H-Pyrrolo[3,2-c]pyridin-2-yl)ethynyl)-N,N-dimethylaniline 22d

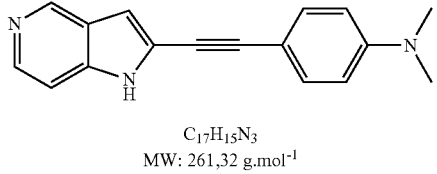

C$_{17}$H$_{15}$N$_3$
MW: 261,32 g.mol$^{-1}$

The compound was prepared according to procedure F and purified by flash column chromatography on silicagel (ethyl acetate). Orange solid (47%), mp 250-252° C., Rf=0.22 (ethyl acetate). IR (v, cm$^{-1}$, neat) 2899, 2623, 2203, 1605, 1543, 1517, 1369, 1292, 1233, 1182, 814, 762, 519, 506. $^1$H NMR (400 MHz, DMSO-d$_6$, 20° C.) δ 11.99 (s, 1H), 8.80 (s, 1H), 8.19 (d, J=5.7 Hz, 1H), 7.43-7.36 (m, 2H), 7.29 (dt, J=5.8 Hz, J=1.0 Hz, 1H), 6.84 (s, 1H), 6.78-6.68 (m, 2H), 2.97 (s, 6H). $^{13}$C NMR (101 MHz, DMSO-d$_6$, 20° C.) δ 150.86, 143.51 (CH), 141.58 (CH), 139.88, 132.91 (2×CH), 125.03, 121.04, 112.37 (2×CH), 107.83, 106.77 (CH), 105.86 (CH), 94.44, 80.12, 40.12 (2×CH$_3$). HRMS (+ESI) calculated for C$_{17}$H$_{16}$N$_3$ (M+H+): 262.1339, found: 262.1340.

Example 11.10 4-((6-Chloro-1H-pyrrolo[2,3-b]pyridin-2-yl)ethynyl)-N,N-dimethylaniline 22e

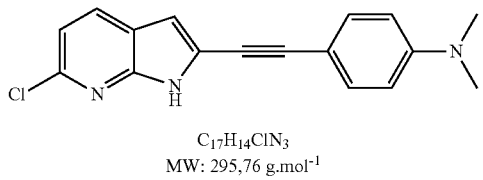 [SMILES: CN(C)c1ccc(C#Cc2cc3ccc(Cl)nc3[nH]2)cc1]

C$_{17}$H$_{14}$ClN$_3$
MW: 295,76 g.mol$^{-1}$

The compound was prepared according to procedure D (32%) or by procedure F (35%) and purified by flash chromatography column on silicagel (ethyl acetate/petroleum ether=5/95). Yellow solid. mp 241-243° C., Rf=0.32 (ethyl acetate/petroleum ether=10/90). IR (v, cm$^{-1}$, neat) 2895, 2121, 1600, 1514, 1440, 1360, 1224, 1160, 942, 815, 510. $^1$H NMR (250 MHz, DMSO-d$_6$, 20° C.) δ 12.27 (s, 1H), 7.93 (d, J=8.2 Hz, 1H), 7.42-7.25 (m, 2H), 7.09 (d, J=8.2 Hz, 1H), 6.75-6.64 (m, 3H), 2.92 (s, 6H). $^{13}$C NMR (63 MHz, DMSO-d$_6$, 20° C.) δ 150.9 (Cq), 147.5 (Cq), 144.6 (Cq), 132.9 (2×CH), 131.5 (CH), 121.2 (Cq), 119.2 (Cq), 116.5 (CH), 112.4 (2×CH), 107.7 (Cq), 105.7 (CH), 95.4 (Cq), 80.1 (Cq), 40.1 (2×CH$_3$). HRMS (+ESI) calculated for C$_{17}$H$_{15}$ClN$_3$ (M+H+): 296.0949, found: 296.0946.

Example 11.11 4-((6-Fluoro-1H-pyrrolo[2,3-b]pyridin-2-yl)ethynyl)-N,N-dimethylaniline 22f

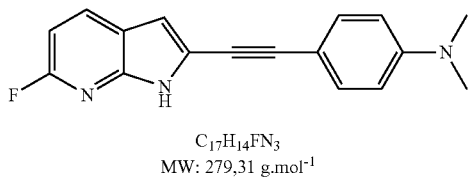 [SMILES: CN(C)c1ccc(C#Cc2cc3ccc(F)nc3[nH]2)cc1]

C$_{17}$H$_{14}$FN$_3$
MW: 279,31 g.mol$^{-1}$

The compound was prepared according to procedure C and purified by flash column chromatography on silicagel (ethyl acetate/petroleum ether=10/90). Yellow solid (62%), mp 232-234° C., Rf=0.33 (ethyl acetate/petroleum ether=10/90). IR (v, cm$^{-1}$, neat) 3157, 3072, 2893, 2205, 1605, 1541, 1511, 1432, 1273, 1224, 1183, 809, 763, 507. $^1$H NMR (400 MHz, DMSO-d$_6$, 20° C.) δ 12.23 (s, 1H), 8.08 (t, J=8.2 Hz, 1H), 7.38 (d, J=8.3 Hz, 2H), 6.84 (d, J=8.3 Hz, 1H), 6.78-6.57 (m, 3H), 2.97 (s, 6H). $^{13}$C NMR (63 MHz, DMSO-d$_6$, 20° C.) δ 160.6 (d, J=233.8 Hz, Cq), 150.8 (Cq), 145.2 (d, J=19.3 Hz, Cq), 133.7 (d, J=9.5 Hz, CH), 132.9 (2×CH), 120.2 (d, J=4.5 Hz, Cq), 118.1 (d, J=2.7 Hz, Cq), 112.4 (2×CH), 107.9 (Cq), 105.9 (CH), 102.04 (d, J=38.8 Hz, CH), 94.7 (Cq), 80.1 (Cq), 40.1 (2×CH$_3$). $^{19}$F NMR (376 MHz, DMSO-d$_6$, 20° C.) δ −74.40. HRMS (+ESI) calculated for C$_{17}$H$_{15}$FN$_3$ (M+H+): 280.1245, found: 280.1243.

Example 11.12 4-((5-Fluoro-1H-pyrrolo[2,3-b]pyridin-2-yl)ethynyl)-N,N-dimethylaniline 22 g

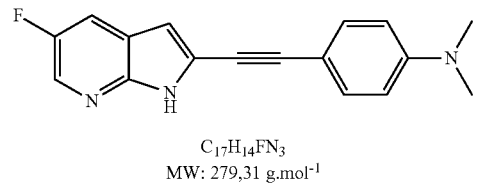 [SMILES: CN(C)c1ccc(C#Cc2cc3cc(F)cnc3[nH]2)cc1]

C$_{17}$H$_{14}$FN$_3$
MW: 279,31 g.mol$^{-1}$

The compound was prepared according to procedure C and purified by flash column chromatography on silicagel (ethyl acetate/petroleum ether=15/85). Yellow solid (68%), mp 255-257° C., Rf=0.25 (ethyl acetate/petroleum ether=20/80). IR (v, cm$^{-1}$, neat) 3120, 2987, 2897, 2801, 2360, 2209, 1609, 1583, 1541, 1503, 1447, 1399, 1362, 1345, 1293, 1230, 1189, 1151, 1109, 1066, 976, 944, 875, 817, 761, 559, 519, 509. $^1$H NMR (400 MHz, DMSO-d$_6$, 20° C.) δ 12.23 (s, 1H), 8.20 (m, 1H), 7.80 (dd, J=9.5 Hz, J=2.8 Hz, 1H), 7.39 (d, J=8.4 Hz, 2H), 6.75 (d, J=8.4 Hz, 2H), 6.67 (m, 1H), 2.98 (s, 6H). $^{13}$C NMR (101 MHz, DMSO, 20° C.) δ 155.7 (d, J=239.5 Hz, Cq), 150.9 (Cq), 145.6 (Cq), 132.9 (2×CH), 132.4 (d, J=29.0 Hz, CH), 122.9 (Cq), 120.3 (d, J=7.5 Hz, Cq), 113.7 (d, J=20.7 Hz, CH), 112.4 (2×CH), 107.7 (Cq), 105.4 (d, J=4.5 Hz, CH), 95.5 (Cq), 80.2 (Cq), 40.1 (2×CH$_3$). $^{19}$F NMR (376 MHz, DMSO-d$_6$, 20° C.) δ −138.76. HRMS (+ESI) calculated for C$_{17}$H$_{15}$FN$_3$ (M+H+): 280.1245, found: 280.1243.

Example 11.13 4-((4-Fluoro-1H-pyrrolo[2,3-b]pyridin-2-yl)ethynyl)-N,N-dimethylaniline 22 h

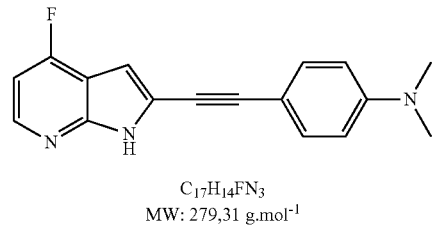 [SMILES: CN(C)c1ccc(C#Cc2cc3c(F)ccnc3[nH]2)cc1]

C$_{17}$H$_{14}$FN$_3$
MW: 279,31 g.mol$^{-1}$

The compound was prepared according to procedure C and purified by flash column chromatography on silicagel (ethyl acetate/petroleum ether=20/80). White solid (73%), mp 248-250° C., Rf=0.31 (ethyl acetate/petroleum ether=20/80). IR (v, cm$^{-1}$, neat) 3066, 2900, 2803, 2359, 2201, 1604, 1540, 1510, 1441, 1362, 1345, 1326, 1299, 1274, 1250, 1231, 1185, 1170, 1078, 1058, 980, 946, 881, 796, 753, 618, 594, 530, 510. $^1$H NMR (400 MHz, DMSO-d$_6$, 20° C.) δ 12.45 (s, 1H), 8.25 (dd, J=8.2 Hz, J=5.3 Hz, 1H), 7.40 (d, J=8.3 Hz, 2H), 6.98 (dd, J=10.3 Hz, J=5.4 Hz, 1H), 6.82-6.67 (m, 3H), 2.97 (s, 6H). $^{13}$C NMR (101 MHz, DMSO-d$_6$, 20° C.) δ 161.2 (d, J=260.9 Hz, Cq), 152.0 (d, J=11.4 Hz, Cq), 150.92 (Cq), 146.3 (d, J=6.1 Hz, CH), 133.0 (2×CH), 120.9 (Cq), 112.4 (2×CH), 109.2 (d, J=18.1 Hz, Cq), 107.6

(Cq), 102.9 (d, J=14.6 Hz, CH), 100.9 (CH), 95.2 (Cq), 79.8 (Cq), 40.1 (2×CH₃). ¹⁹F NMR (376 MHz, DMSO-d₆, 20° C.) δ −111.96. HRMS (+ESI) calculated for $C_{17}H_{15}FN_3$ (M+H+): 280.1245, found: 280.1246.

Example 11.14 4-((1H-pyrrolo[2,3-b]pyridin-2-yl)ethynyl)-N-methylaniline 22i

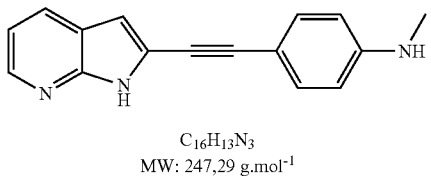 [SMILES: CNc1ccc(C#Cc2cc3cccnc3[nH]2)cc1]

$C_{16}H_{13}N_3$
MW: 247,29 g.mol⁻¹

The compound was prepared according to procedure C and purified by flash column chromatography on silicagel (ethyl acetate/petroleum ether=20/80). Beige solid (87%), mp 208-210° C., Rf=0.19 (ethyl acetate/petroleum ether=20/80). IR (v, cm⁻¹, neat) 3409, 3056, 2195, 1602, 1532, 1509, 1478, 1431, 1406, 1358, 1324, 1282, 1177, 1157, 1123, 917, 823, 802, 764, 625, 550, 542, 527, 519, 512, 506. ¹H NMR (400 MHz, DMSO-d₆, 20° C.) δ 12.04 (s, 1H), 8.23 (d, J=3.6 Hz, 1H), 7.91 (d, J=7.6 Hz, 1H), 7.31 (d, J=8.5 Hz, 2H), 7.07 (dd, J=7.7 Hz, J=3.6 Hz, 1H), 6.69 (d, J=1.1 Hz, 1H), 6.57 (d, J=8.5 Hz, 2H), 6.23 (d, J=4.9 Hz, 1H), 2.72 (d, J=4.9 Hz, 3H). ¹³C NMR (101 MHz, DMSO-d₆, 20° C.) δ 150.9 (Cq), 148.7 (Cq), 144.2 (CH), 133.0 (2×CH), 128.3 (CH), 120.7 (Cq), 120.2 (Cq), 116.6 (CH), 112.0 (2×CH), 107.6 (Cq), 105.3 (CH), 95.2 (Cq), 80.0 (Cq), 29.7 (CH₃). HRMS (+ESI) calculated for $C_{16}H_{14}N_3$ (M+H+): 248.1182, found: 248.1183.

Example 11.15 3-((1H-pyrrolo[2,3-b]pyridin-2-yl)ethynyl)aniline 22j

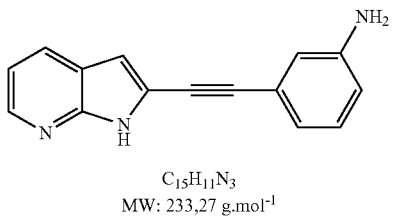 [SMILES: Nc1cccc(C#Cc2cc3cccnc3[nH]2)c1]

$C_{15}H_{11}N_3$
MW: 233,27 g.mol⁻¹

The compound was prepared following procedure E and purified by flash column chromatography on silicagel (ethyl acetate/petroleum ether=30/70). White solid (67%), mp 196-198° C., Rf=0.14 (ethyl acetate/petroleum ether=30/70). IR (v, cm⁻¹, neat) 3465, 3373, 3201, 3075, 3053, 2975, 2895, 2817, 2746, 1601, 1579, 1535, 1488, 1448, 1430, 1407, 1361, 1312, 1283, 1190, 1169, 1115, 992, 916, 852, 801, 767, 735, 681, 634, 621, 570, 526, 513, 503. ¹H NMR (250 MHz, DMSO-d₆, 20° C.) δ 12.17 (s, 1H), 8.28 (d, J=3.8 Hz, 1H), 7.95 (d, J=7.7 Hz, 1H), 7.11 (d, J=7.8 Hz, 2H), 6.91-6.45 (m, 4H), 5.31 (s, 2H). ¹³C NMR (63 MHz, DMSO-d₆, 20° C.) δ 149.4 (Cq), 148.8 (Cq), 144.7 (CH), 129.8 (CH), 128.8 (CH), 122.3 (Cq), 20.0 (Cq), 119.7 (Cq), 119.1 (CH), 116.8 (CH), 116.4 (CH), 115.4 (CH), 106.4 (CH), 94.2 (Cq), 81.2 (Cq). HRMS (+ESI) calculated for $C_{15}H_{12}N_3$ (M+H+): 234.1026, found: 234.1025.

Example 11.16 2-((3-fluorophenyl)ethynyl)-1H-pyrrolo[2,3-b]pyridine 22k

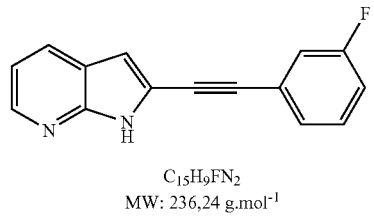 [SMILES: Fc1cccc(C#Cc2cc3cccnc3[nH]2)c1]

$C_{15}H_9FN_2$
MW: 236,24 g.mol⁻¹

The compound was prepared according to procedure C and purified by flash column chromatography on silicagel (ethyl acetate/petroleum ether=20/80). White solid (64%), mp 220-222° C., Rf=0.24 (ethyl acetate/petroleum ether=20/80). IR (v, cm⁻¹, neat) 3056, 2817, 1607, 1577, 1481, 1434, 1406, 1360, 1283, 1174, 1112, 917, 807, 767, 676, 572, 517, 507. ¹H NMR (400 MHz, DMSO-d₆, 20° C.) δ 12.26 (s, 1H), 8.30 (dd, J=4.6 Hz, J=1.4 Hz, 1H), 7.97 (dd, J=7.9 Hz, J=1.4 Hz, 1H), 7.51 (dd, J=14.1 Hz, J=7.7 Hz, 1H), 7.46-7.39 (m, 2H), 7.37-7.28 (m, 1H), 7.11 (dd, J=7.9 Hz, J=4.7 Hz, 1H), 6.86 (s, 1H). ¹³C-NMR (101 MHz, DMSO-d₆, 20° C.) δ 162.4 (d, J=244.9 Hz), 148.8 (Cq), 145.2 (CH), 131.5 (d, J=8.9 Hz, CH), 129.1 (CH), 128.2 (d, J=2.9 Hz, CH), 124.1 (d, J=9.7 Hz, Cq), 119.9 (Cq), 118.8 (Cq), 118.3 (d, J=23.1 Hz, CH), 117.0 (d, J=21.1 Hz, CH), 116.9 (CH), 107.3 (CH), 91.9 (d, J=3.4 Hz, Cq), 83.6 (Cq). ¹⁹F NMR (376 MHz, DMSO-d₆, 20° C.) δ −112.1.

HRMS (+ESI) calculated for $C_{15}H_{10}FN_2$ (M+H+): 237.0823, found: 237.0821.

Example 11.17 4-((1H-pyrrolo[2,3-b]pyridin-2-yl)ethynyl)aniline 22l

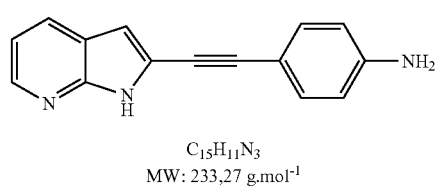 [SMILES: Nc1ccc(C#Cc2cc3cccnc3[nH]2)cc1]

$C_{15}H_{11}N_3$
MW: 233,27 g.mol⁻¹

The compound was prepared according to procedure C and purified by flash column chromatography on silicagel (ethyl acetate/petroleum ether=40/60). Yellow solid (87%), mp 244-246° C., Rf=0.19 (Ethyl acetate/petroleum ether=40/60). IR (v, cm⁻¹, neat) 3471, 3375, 3052, 2879, 2199, 1616, 1603, 1585, 1538, 1503, 1405, 1356, 1299, 1278, 1175, 917, 818, 761, 626, 568, 514, 511, 507, 503. ¹H NMR (400 MHz, DMSO-d₆, 20° C.) δ 12.04 (s, 1H), 8.23 (dd, J=4.6 Hz, J=1.4 Hz, 1H), 7.90 (m, 1H), 7.24 (d, J=8.5 Hz, 2H), 7.07 (dd, J=7.9 Hz, J=4.7 Hz, 1H), 6.68 (d, J=1.7 Hz, 1H), 6.59 (d, J=8.5 Hz, 2H), 5.65 (s, 2H). ¹³C NMR (101 MHz, DMSO-d₆, 20° C.) δ 150.3 (Cq), 148.7 (Cq), 144.2 (CH), 133.0 (2×CH), 128.3 (CH), 120.6 (Cq), 120.1 (Cq), 116.6 (CH), 114.1 (2×CH), 107.7 (Cq), 105.2 (CH), 95.2 (Cq), 79.7 (Cq). HRMS (+ESI) calculated for $C_{15}H_{12}N_3$ (M+H+): 234.1026, found: 234.1025.

Example 11.18 2-((4-methoxyphenyl)ethynyl)-1H-pyrrolo[2,3-b]pyridine 22m

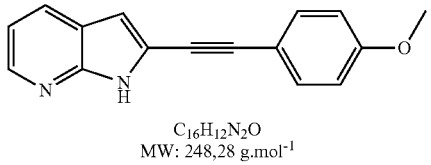 [SMILES: COc1ccc(C#Cc2cc3cccnc3[nH]2)cc1]

C₁₆H₁₂N₂O
MW: 248,28 g.mol⁻¹

The compound was prepared according to Procedure C and purified by flash column chromatography on silicagel (ethyl acetate/petroleum ether=30/70). Yellow solid (83%), mp 193-195° C., Rf=0.26 (ethyl acetate/petroleum ether=30/70). IR (ν, cm⁻¹, neat) 3054, 2976, 2832, 1600, 1583, 1536, 1501, 1436, 1404, 1358, 1280, 1242, 1171, 1107, 1027, 917, 812, 768, 723, 625, 562, 537, 507, 503. $^1$H NMR (400 MHz, DMSO-d₆, 20° C.) δ 12.15 (s, 1H), 8.27 (dd, J=4.7 Hz, J=1.4 Hz, 1H), 7.95 (dd, J=7.9 Hz, J=1.2 Hz, 1H), 7.53 (d, J=8.8 Hz, 2H), 7.09 (dd, J=7.9 Hz, J=4.7 Hz, 1H), 7.03 (d, J=8.8 Hz, 2H), 6.78 (d, J=1.6 Hz, 1H), 3.82 (s, 3H). $^{13}$C NMR (101 MHz, DMSO-d₆, 20° C.) δ 160.3 (Cq), 148.8 (Cq), 144.7 (CH), 133.4 (2×CH), 128.7 (CH), 120.0 (Cq), 119.8 (Cq), 116.8 (CH), 115.0 (2×CH), 114.0 (Cq), 106.2 (CH), 93.3 (Cq), 81.3 (Cq), 55.8 (CH₃). HRMS (+ESI) calculated for C₁₆H₁₃N₂O (M+H+): 249.1022, found: 249.1021.

Example 11.19 4-((6-fluoro-1-methyl-1H-pyrrolo[2,3-b] pyridin-2-yl)ethynyl)-N,N-dimethylaniline 22n

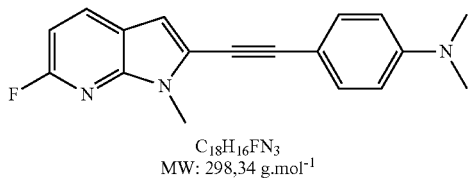 [SMILES: CN(C)c1ccc(C#Cc2cc3ccc(F)nc3n2C)cc1]

C₁₈H₁₆FN₃
MW: 298,34 g.mol⁻¹

The compound was prepared according to procedure C and purified by flash column chromatography on silicagel (ethyl acetate/petroleum ether=2/98). Greyish solid (72%), mp 194-196° C., Rf=0.24 (ethyl acetate/petroleum ether=4/96). IR (ν, cm⁻¹, neat) 2896, 2202, 1606, 1577, 1539, 1505, 1445, 1406, 1358, 1316, 1278, 1230, 1191, 1092, 985, 947, 804, 760, 581, 517, 506, 502. $^1$H NMR (400 MHz, CDCl₃, 20° C.) δ 7.90 (t, J=8.0 Hz, 1H), 7.46 (d, J=8.1 Hz, 2H), 6.84-6.65 (m, 4H), 3.90 (s, 3H), 3.04 (s, 6H). $^{13}$C NMR (101 MHz, CDCl₃, 20° C.) δ 160.9 (d, J=237.3 Hz, Cq), 150.6 (Cq), 144.8 (d, J=18.0 Hz, Cq), 132.8 (2×CH), 132.8 (CH), 123.5 (d, J=4.8 Hz, Cq), 117.6 (d, J=2.7 Hz, Cq), 111.9 (2×CH), 108.8 (Cq), 104.5 (CH), 101.7 (d, J=38.8 Hz, CH), 97.6 (Cq), 78.3 (Cq), 40.3 (2×CH₃), 29.5 (CH₃). $^{19}$F NMR (376 MHz, CDCl₃, 20° C.) δ −74.2. HRMS (+ESI) calculated for C₁₈H₁₇FN₃ (M+H+): 294.1401, found: 294.1401.

Example 11.20 tert-Butyl-2-((4-(dimethylamino)phenyl)ethynyl)-1H-pyrrolo[2,3-b]pyridine-1-carboxylate 23a

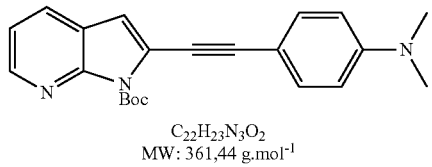 [SMILES: CN(C)c1ccc(C#Cc2cc3cccnc3n2C(=O)OC(C)(C)C)cc1]

C₂₂H₂₃N₃O₂
MW: 361,44 g.mol⁻¹

The compound was prepared according to procedure C2 and purified by flash column chromatography on silicagel (ethyl acetate/petroleum ether=15/85). Yellow solid (91%), mp 188-190° C., Rf=0.39 (ethyl acetate/petroleum ether=20/80). IR (ν, cm⁻¹, neat) 3064, 2982, 2906, 2194, 1738, 1604, 1572, 1542, 1515, 1444, 1399, 1363, 1253, 1142, 1114, 1089, 974, 942, 840, 826, 813, 788, 773, 751, 697, 517, 504. $^1$H NMR (250 MHz, CDCl₃, 20° C.) δ 8.53 (dd, J=4.8 Hz, J=1.6 Hz, 1H), 7.83 (dd, J=7.8 Hz, J=1.6 Hz, 1H), 7.50-7.39 (m, 2H), 7.19 (dd, J=7.8 Hz, J=4.8 Hz, 1H), 6.82 (s, 1H), 6.76-6.62 (m, 2H), 3.03 (s, 6H), 1.71 (s, 9H). $^{13}$C NMR (63 MHz, CDCl₃, 20° C.) δ 150.4 (Cq), 148.6 (Cq), 148.1 (Cq), 145.7 (CH), 132.7 (2×CH), 128.3 (CH), 122.0 (Cq), 121.6 (Cq), 118.8 (CH), 111.8 (2×CH), 111.6 (CH), 109.2 (Cq), 97.1 (Cq), 84.6 (Cq), 79.7 (Cq), 40.1 (2×CH₃), 28.2 (3×CH₃). HRMS (+ESI) calculated for C₂₂H₂₄N₃O₂ (M+H+): 362.1863, found: 362.1862.

Example 11.21 tert-Butyl-2-((4-(dimethylamino)phenyl)ethynyl)-1H-pyrrolo[3,2-c]pyridine-1-carboxylate 23b

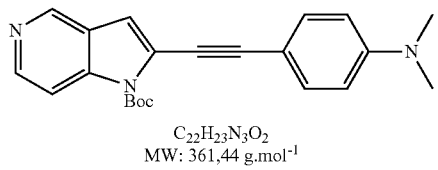 [SMILES: CN(C)c1ccc(C#Cc2cc3cnccc3n2C(=O)OC(C)(C)C)cc1]

C₂₂H₂₃N₃O₂
MW: 361,44 g.mol⁻¹

The compound was prepared according to procedure C and purified by flash column chromatography on silicagel (ethyl acetate/petroleum ether=10/90). Yellow solid (99%), mp 162-164° C., Rf=0.44 (ethyl acetate/petroleum ether=10/90). IR (ν, cm⁻¹, neat) 2983, 2205, 1733, 1604, 1549, 1517, 1456, 1338, 1317, 1247, 1149, 1092, 814, 507. $^1$H NMR (400 MHz, CDCl₃, 20° C.) δ 8.82 (s, 1H), 8.45 (d, J=5.8 Hz, 1H), 8.00 (d, J=5.8 Hz, 1H), 7.43 (d, J=7.9 Hz, 2H), 6.93 (s, 1H), 6.67 (d, J=8.0 Hz, 2H), 3.00 (s, 6H), 1.69 (s, 9H). $^{13}$C NMR (101 MHz, CDCl₃, 20° C.) δ 150.4 (Cq), 149.1 (Cq), 144.6 (CH), 143.2 (CH), 140.3 (Cq), 132.8 (2×CH), 125.4 (Cq), 122.8 (Cq), 112.9 (CH), 111.7 (2×CH), 110.3 (CH), 109.1 (Cq), 97.3 (Cq), 85.1 (Cq), 79.3 (Cq), 40.1 (2×CH₃), 28.2 (3×CH₃). HRMS (+ESI) calculated for C₂₂H₂₄N₃O₂ (M+H+): 362.1863, found: 362.1862.

Example 11.22 tert-Butyl-6-chloro-2-((4-(dimethylamino)phenyl)ethynyl)-1H-pyrrolo[2,3-b] pyridine-1-carboxylate 23e

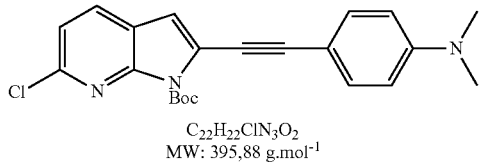 [SMILES: CN(C)c1ccc(C#Cc2cc3ccc(Cl)nc3n2C(=O)OC(C)(C)C)cc1]

C$_{22}$H$_{22}$ClN$_3$O$_2$
MW: 395,88 g.mol$^{-1}$

The compound was prepared according to procedure C and purified by flash column chromatography on silicagel (ethyl acetate/petroleum ether=10/90). Yellow solid (93%), mp 160-162° C., Rf=0.38 (ethyl acetate/petroleum ether=20/80). IR (v, cm$^{-1}$, neat) 2923, 2853, 2196, 1740, 1611, 1567, 1546, 1517, 1439, 1397, 1368, 1334, 1306, 1268, 1245, 1186, 1152, 1140, 1110, 944, 881, 842, 813, 770, 744, 722, 602, 529. $^1$H NMR (250 MHz, CDCl$_3$, 20° C.) δ 7.71 (d, J=8.3 Hz, 1H), 7.40 (d, J=9.0 Hz, 2H), 7.17 (d, J=8.2 Hz, 1H), 6.75 (s, 1H), 6.64 (d, J=9.0 Hz, 2H), 2.99 (s, 6H), 1.67 (s, 9H). $^{13}$C NMR (101 MHz, CDCl$_3$, 20° C.) δ 150.5 (Cq), 147.6 (Cq), 147.0 (Cq), 146.9 (Cq), 132.8 (2×CH), 130.3 (CH), 122.6 (Cq), 120.1 (Cq), 119.3 (CH), 111.7 (2×CH), 110.9 (CH), 108.9 (Cq), 97.8 (Cq), 85.0 (Cq), 79.3 (Cq), 40.1 (2×CH$_3$), 28.2 (3×CH$_3$). HRMS (+ESI) calculated for C$_{22}$H$_{23}$ClN$_3$O$_2$ (M+H+): 396.1473, found: 396.1474.

Example 11.23 tert-Butyl-2-((4-(methylamino)phenyl)ethynyl)-1H-pyrrolo[2,3-b]pyridine-1-carboxylate 23i

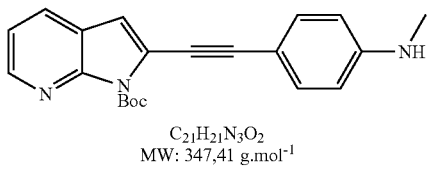 [SMILES: CNc1ccc(C#Cc2cc3cccnc3n2C(=O)OC(C)(C)C)cc1]

C$_{21}$H$_{21}$N$_3$O$_2$
MW: 347,41 g.mol$^{-1}$

The compound was prepared according to procedure C and purified by flash column chromatography on silicagel (ethyl acetate/petroleum ether=20/80). Yellow solid (91%), mp 166-168° C., Rf=0.34 (ethyl acetate/petroleum ether=20/80). IR (v, cm$^{-1}$, neat) 3368, 3066, 2983, 2936, 2815, 2198, 1742, 1607, 1575, 1545, 1521, 1472, 1404, 1367, 1339, 1308, 1251, 1177, 1154, 1112, 1087, 876, 847, 826, 772, 640, 599, 561, 532, 515. $^1$H NMR (400 MHz, CDCl$_3$, 20° C.) δ 8.53 (d, J=3.9 Hz, 1H), 7.83 (d, J=7.7 Hz, 1H), 7.40 (d, J=8.3 Hz, 2H), 7.19 (dd, J=7.5 Hz, J=4.9 Hz, 1H), 6.81 (s, 1H), 6.59 (d, J=8.3 Hz, 2H), 4.02 (1s, 1H), 2.89 (s, 3H), 1.70 (s, 9H). $^{13}$C NMR (101 MHz, CDCl$_3$, 20° C.) δ 149.6 (Cq), 148.6 (Cq), 148.1 (Cq), 145.7 (CH), 132.9 (2×CH), 128.3 (CH), 122.0 (Cq), 121.6 (Cq), 118.8 (CH), 112.0 (2×CH), 111.6 (CH), 110.2 (Cq), 97.0 (Cq), 84.6 (Cq), 79.5 (Cq), 30.3 (CH$_3$), 28.2 (3×CH$_3$). HRMS (+ESI) calculated for C$_{21}$H$_{22}$N$_3$O$_2$ (M+H+): 348.1707, found: 348.1705.

Example 11.24 tert-butyl-6-bromo-2-((4-(dimethylamino)phenyl)ethynyl)-1H-pyrrolo[2,3-b] pyridine-1-carboxylate 23j

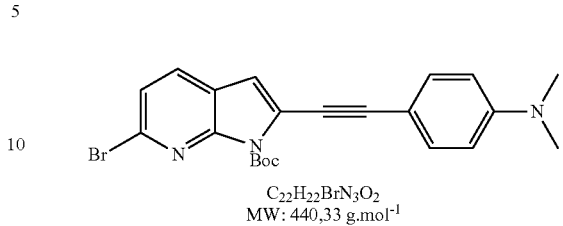

C$_{22}$H$_{22}$BrN$_3$O$_2$
MW: 440,33 g.mol$^{-1}$

The compound was prepared according to procedure C and purified by column chromatography on silicagel under pressure (the ratio of solvents used: ethyl acetate/dichloromethane/petroleum ether=7/3/90). Yellow solid (68%), mp 170-172° C., Rf=0.27 (ethyl acetate/dichloromethane/petroleum ether=3/7/90). IR (v, cm$^{-1}$, neat) 2983, 2200, 1752, 1606, 1561, 1542, 1434, 1394, 1367, 1353, 1332, 1306, 1240, 1153, 1137, 1103, 875, 832, 815, 802, 768, 518, 502. $^1$H NMR (400 MHz, CDCl$_3$, 20° C.) δ 7.64 (d, J=8.2 Hz, 1H), 7.46-7.39 (m, 2H), 7.33 (d, J=8.2 Hz, 1H), 6.75 (s, 1H), 6.70-6.57 (m, 2H), 3.01 (s, 6H), 1.69 (s, 9H). $^{13}$C NMR (101 MHz, CDCl$_3$, 20° C.) δ 150.5 (Cq), 147.6 (Cq), 147.2 (Cq), 137.0 (Cq), 132.8 (2×CH), 130.0 (CH), 122.9 (CH), 122.5 (Cq), 120.3 (Cq), 111.7 (2×CH), 110.9 (CH), 108.9 (Cq), 98.0 (Cq), 84.9 (Cq), 79.3 (Cq), 40.1 (2×CH$_3$), 28.2 (3×CH$_3$). HRMS (+ESI) calculated for C$_{22}$H$_{23}$BrN$_3$O$_2$ (M+H+): 440.0968, found: 440.0967.

Example 12. Synthesis of Final Compounds Functionalized at the C-6 Position of 7-Azaindole to prepare the functionalized compounds on position 6, a Suzuki coupling was carried out starting from compound 23e to give compound 24 which then deprotected according to procedure F

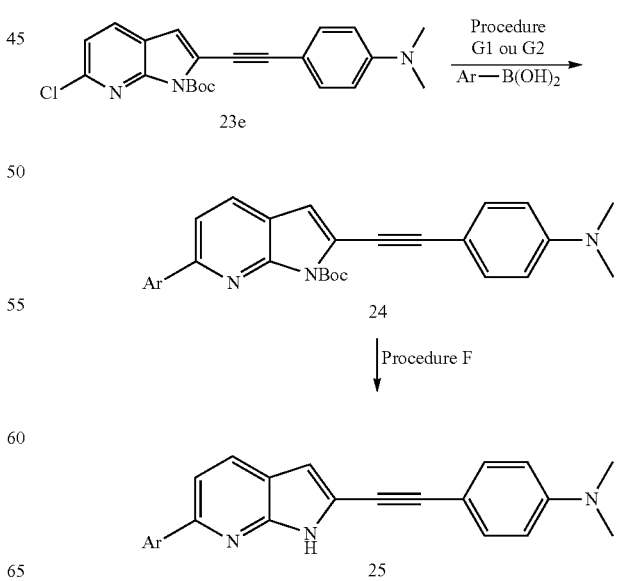

Example 12.1 tert-Butyl 2-((4-(dimethylamino)phenyl)ethynyl)-6-(thiophen-2-yl)-1H-pyrrolo[2,3-b]pyridine-1-carboxylate 24a

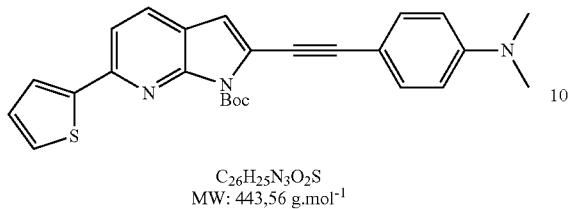

$C_{26}H_{25}N_3O_2S$
MW: 443,56 g.mol$^{-1}$

The compound was prepared according to procedure G2 and purified by flash column chromatography on silicagel (ethyl acetate/petroleum ether=5/95). Yellow solid (37%), mp 173-175° C., Rf=0.42 (ethyl acetate/petroleum ether=10/90). IR (v, cm$^{-1}$, neat) 2927, 2197, 1744, 1593, 1365, 1258, 1154, 829, 696, 508. $^1$H NMR (400 MHz, CDCl$_3$, 20° C.) δ 7.79 (d, J=8.1 Hz, 1H), 7.64 (m, 1H), 7.59 (d, J=8.2 Hz, 1H), 7.48 (d, J=7.7 Hz, 2H), 7.38 (d, J=4.8 Hz, 1H), 7.12 (m, 1H), 6.79 (s, 1H), 6.70 (d, J=7.7 Hz, 2H), 3.03 (s, 6H), 1.80 (s, 9H). $^{13}$C NMR (101 MHz, CDCl$_3$, 20° C.) δ 150.4 (Cq), 148.4 (Cq), 147.8 (Cq), 146.0 (Cq), 132.9 (2×CH), 128.6 (CH), 127.9 (CH), 127.0 (CH), 126.4 (Cq), 124.3 (CH), 122.4 (Cq), 120.4 (Cq), 114.6 (CH), 111.8 (2×CH), 111.2 (CH), 109.4 (Cq), 97.9 (Cq), 84.3 (Cq), 79.9 (Cq), 40.2 (2×CH$_3$), 28.4 (3×CH$_3$). HRMS (+ESI) calculated for C$_{26}$H$_{26}$N$_3$O$_2$S (M+H+): 444.1740, found: 444.1742.

Example 12.2 N,N-Dimethyl-4-((6-(thiophen-2-yl)-1H-pyrrol[2,3-b]pyridin-2-yl)ethynyl)aniline 25a

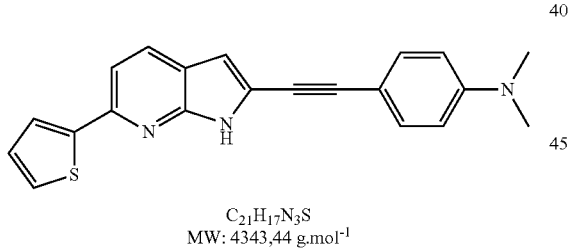

$C_{21}H_{17}N_3S$
MW: 4343,44 g.mol$^{-1}$

The compound was prepared according to procedure F and purified by flash column chromatography on silicagel (ethyl acetate/petroleum ether=10/90). Yellow solid (38%), mp 231-233° C., Rf=0.55 (ethyl acetate/petroleum ether=20/80). IR (v, cm$^{-1}$, neat) 3066, 1597, 1535, 1416, 1278, 821, 705. $^1$H NMR (250 MHz, DMSO-d$_6$, 20° C.) δ 12.16 (s, 1H), 7.95 (d, J=8.3 Hz, 1H), 7.77 (dd, J=3.7 Hz, J=1.1 Hz, 1H), 7.67 (d, J=8.3 Hz, 1H), 7.58 (dd, J=5.1 Hz, J=1.1 Hz, 1H), 7.39 (d, J=8.9 Hz, 2H), 7.16 (dd, J=5.1 Hz, J=3.7 Hz, 1H), 6.75 (d, J=8.9 Hz, 2H), 6.71 (d, J=2.0 Hz, 1H), 2.98 (s, 6H). $^{13}$C NMR (63 MHz, DMSO-d$_6$, 20° C.) δ 150.8 (Cq), 148.3 (Cq), 147.0 (Cq), 146.1 (Cq), 132.6 (2×CH), 129.2 (CH), 128.8 (CH), 127.7 (CH), 124.9 (CH), 120.9 (Cq), 119.4 (Cq), 112.8 (CH), 112.4 (2×CH), 108.0 (Cq), 105.9 (Cq), 95.3 (Cq), 80.6 (Cq), 40.1 (2×CH$_3$). HRMS (+ESI) calculated for C$_{21}$H$_{18}$N$_3$S (M+H+): 344.1216, found: 344.1216.

Example 12.3 tert-butyl 2-((4-(dimethylamino)phenyl)ethynyl)-6-(thiophen-3-yl)-1H-pyrrolo[2,3-b]pyridine-1-carboxylate 24b

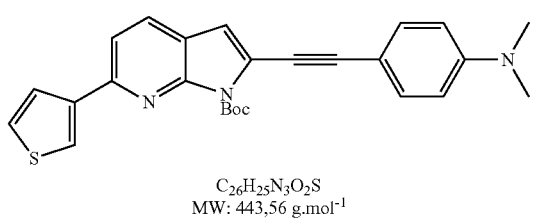 [SMILES: CN(C)c1ccc(C#Cc2cc3ccc(-c4ccsc4)nc3n2C(=O)OC(C)(C)C)cc1]

$C_{26}H_{25}N_3O_2S$
MW: 443,56 g.mol$^{-1}$

The compound was prepared according to procedure GI and purified by flash column chromatography on silicagel (ethyl acetate/petroleum ether=10/90). Yellow solid (57%), mp 163-165° C., Rf=0.29 (ethyl acetate/petroleum ether=20/80). IR (v, cm$^{-1}$, neat) 1743, 1607, 1257, 1154, 769, 507. $^1$H NMR (250 MHz, CDCl$_3$, 20° C.) δ 7.98 (dd, J=3.0 Hz, J=1.2 Hz, 1H), 7.86-7.78 (m, 2H), 7.57 (d, J=8.2 Hz, 1H), 7.52-7.44 (m, 2H), 7.41 (dd, J=5.1 Hz, J=3.0 Hz, 1H), 6.81 (s, 1H), 6.74-6.65 (m, 2H), 3.03 (s, 6H), 1.77 (s, 9H). $^{13}$C NMR (63 MHz, CDCl$_3$, 20° C.) δ 150.3 (Cq), 149.4 (Cq), 148.3 (Cq), 148.2 (Cq), 143.0 (Cq), 132.8 (2×CH), 128.7 (CH), 126.6 (CH), 125.9 (CH), 123.0 (CH), 122.3 (Cq), 120.1 (Cq), 115.9 (CH), 111.8 (2×CH), 111.4 (CH), 109.4 (Cq), 97.6 (Cq), 84.1 (Cq), 80.0 (Cq), 40.2 (2×CH$_3$), 28.4 (3×CH$_3$). HRMS (+ESI) calculated for C$_{26}$H$_{26}$N$_3$O$_2$S (M+H+): 444.1740, found: 444.1738.

Example 12.4 N,N-Dimethyl-4-((6-(thiophen-3-yl)-1H-pyrrol[2,3-b]pyridin-2-yl)ethynyl)aniline 25b

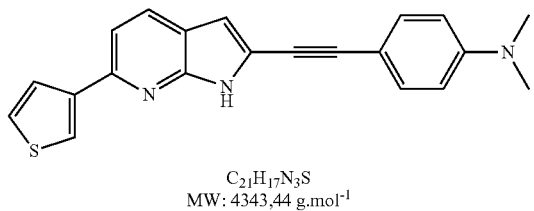 [SMILES: CN(C)c1ccc(C#Cc2cc3ccc(-c4ccsc4)nc3[nH]2)cc1]

$C_{21}H_{17}N_3S$
MW: 4343,44 g.mol$^{-1}$

The compound was prepared according to procedure F and purified by flash column chromatography on silicagel (ethyl acetate/petroleum ether=3/97). Yellow solid (66%), mp 220-222° C., Rf=0.46 (ethyl acetate/petroleum ether=10/90). IR (v, cm$^{-1}$, neat) 3103, 2211, 1768, 1596, 1536, 1501, 1422, 1328, 1269, 1163, 1138, 1054, 935, 864, 821, 769, 691, 603, 564, 520. $^1$H NMR (250 MHz, DMSO-d$_6$, 20° C.) δ 12.09 (s, 1H), 8.11 (d, J=1.7 Hz, 1H), 7.95 (d, J=8.2 Hz, 1H), 7.79 (d, J=4.1 Hz, 1H), 7.63 (m, 2H), 7.39 (d, J=8.8 Hz, 2H), 6.75 (d, J=8.9 Hz, 2H), 6.71 (d, J=1.8 Hz, 1H), 2.98 (s, 6H). $^{13}$C NMR (63 MHz, DMSO-d$_6$, 20° C.) δ 150.8 (Cq), 148.6 (Cq), 148.1 (Cq), 143.2 (Cq), 132.9 (2×CH), 129.2 (CH), 127.2 (CH), 126.9 (CH), 123.2 (CH), 120.8 (Cq), 119.1 (Cq), 114.2 (CH), 112.4 (2×CH), 108.1 (Cq), 105.7 (CH), 95.1 (Cq), 80.7 (Cq), 40.1 (2×CH$_3$). HRMS (+ESI) calculated for C$_{21}$H$_{18}$N$_3$S (M+H+): 344.1216, found: 344.1216.

Example 12.5 tert-Butyl-2-((4-(dimethylamino)phenyl)ethynyl)-6-(6-fluoropyridin-3-yl)-1H-pyrrolo[2,3-b]pyridine-1-carboxylate 24c

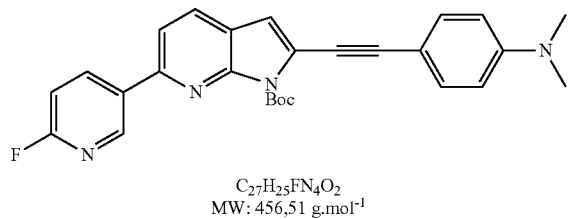 [SMILES: CN(C)c1ccc(C#Cc2cc3ccc(-c4ccc(F)nc4)nc3n2C(=O)OC(C)(C)C)cc1]

C$_{27}$H$_{25}$FN$_4$O$_2$
MW: 456,51 g.mol$^{-1}$

The compound was prepared according to procedure GI and purified by flash column chromatography on silicagel (ethyl acetate/petroleum ether=10/90). Yellow solid (46%), mp 168-170° C., Rf=0.49 (ethyl acetate/petroleum ether=20/80). IR (v, cm$^{-1}$, neat) 2925, 2196, 1740, 1612, 1567, 1546, 1439, 1398, 1369, 1335, 1306, 1269, 1245, 1154, 1110, 841, 813, 770, 508. $^1$H NMR (250 MHz, CDCl$_3$, 20° C.) δ 8.91 (d, J=2.4 Hz, 1H), 8.58 (td, J=8.4, 2.4 Hz, 1H), 7.87 (d, J=8.2 Hz, 1H), 7.62 (d, J=8.2 Hz, 1H), 7.45 (d, J=8.9 Hz, 2H), 7.03 (dd, J=8.5 Hz, J=2.9 Hz, 1H), 6.81 (s, 1H), 6.67 (d, J=8.9 Hz, 2H), 3.01 (s, 6H), 1.74 (s, 9H). $^{13}$C NMR (63 MHz, CDCl$_3$, 20° C.) δ 163.8 (d, J=240.1 Hz, Cq), 150.5 (Cq), 149.0 (Cq), 148.3 (Cq), 148.1 (Cq), 146.1 (d, J=15.2 Hz, CH), 139.9 (d, J=8.1 Hz, CH), 133.7 (d, J=4.7 Hz, Cq), 132.9 (2×CH), 129.0 (CH), 123.3 (Cq), 121.0 (Cq), 115.4 (CH), 111.8 (2×CH), 111.0 (CH), 109.4 (d, J=37.4 Hz, CH), 98.3 (Cq), 84.4 (2×Cq), 79.7 (Cq), 40.1 (2×CH$_3$), 28.3 (3×CH$_3$). $^{19}$F NMR (376 MHz, CDCl$_3$, 20° C.) δ −72.03. HRMS (+ESI) calculated for C$_{27}$H$_{25}$FN$_4$O$_2$ (M+H+): 457.2034, found: 457.2036.

Example 12.6 4-((6-(6-Fluoropyridin-3-yl)-1H-pyrrolo[2,3-b]pyridin-2-yl)ethynyl)-N,N-dimethylaniline 25c

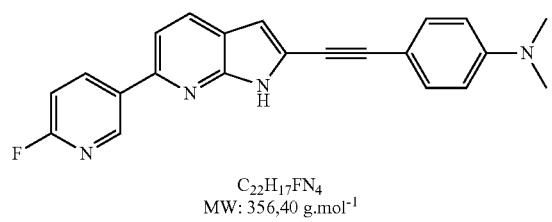 [SMILES: CN(C)c1ccc(C#Cc2cc3ccc(-c4ccc(F)nc4)nc3[nH]2)cc1]

C$_{22}$H$_{17}$FN$_4$
MW: 356,40 g.mol$^{-1}$

The compound was prepared according to procedure F and purified by flash column chromatography on silicagel (ethyl acetate/petroleum ether=10/90). Yellow solid (68%), mp 251-253° C., Rf=0.19 (ethyl acetate/petroleum ether=10/90). IR (v, cm$^{-1}$, neat) 3140, 2899, 2197, 1610, 1540, 1470, 1415, 1371, 1291, 1273, 1187, 1140, 1065, 1019, 948, 814, 761, 699, 645, 567, 520. $^1$H NMR (250 MHz, 20° C.) δ 12.24 (s, 1H), 8.94 (d, J=2.4 Hz, 1H), 8.65 (td, J=8.4 Hz, J=2.7 Hz, 1H), 8.06 (d, J=8.3 Hz, 1H), 7.77 (d, J=8.3 Hz, 1H), 7.41 (d, J=8.9 Hz, 2H), 7.31 (dd, J=8.7 Hz, J=2.7 Hz, 1H), 6.83-6.68 (m, 3H), 2.98 (s, 6H). $^{13}$C NMR (63 MHz, DMSO-d$_6$, 20° C.) δ 159.8 (d, J=222.0 Hz, Cq), 150.7 (Cq), 148.8 (Cq), 147.6 (Cq), 146.0 (d, J=15.7 Hz, CH), 140.4 (d, J=8.0 Hz, CH), 134.2 (d, J=4.5 Hz, Cq), 132.9 (2×CH), 129.5 (CH), 121.7 (Cq), 120.0 (Cq), 113.9 (CH), 112.4 (2×CH), 110.0 (d, J=37.7 Hz, CH), 107.9 (Cq), 105.6 (CH), 95.5 (Cq), 80.5 (Cq), 40.1 (2×CH$_3$). $^{19}$F NMR (376 MHz, DMSO-d$_6$, 20° C.) δ −70.25. HRMS (+ESI) calculated for C$_{22}$H$_{18}$FN$_4$ (M+H+): 357.1510, found: 357.1507.

Example 13. Synthesis of the Final Fluorinated Alkyl Compounds

The derivatives of 7-azaindole, having a fluoroethyl group on the amine of the N-methylaniline were obtained by two different methods.

Method 1

The first method consists of performing a nucleophilic substitution reaction of the secondary amine intermediate 23i. The product 26 was obtained in a yield of 31%. Alcohol 26 was then converted to fluoro derivative 27 in the presence of DAST in a yield of 27%. This compound was deprotected with a solution of TFA in CH$_2$Cl$_2$ to give the final product 28 with a yield of 26%.

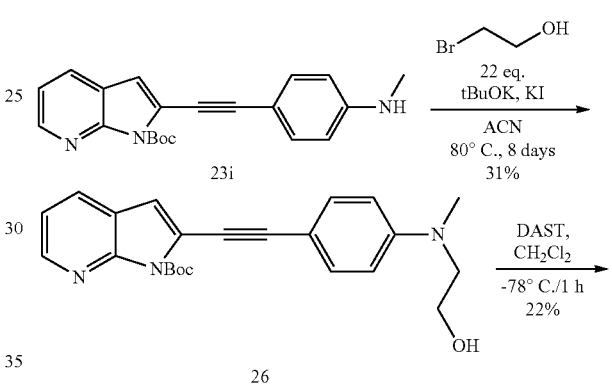

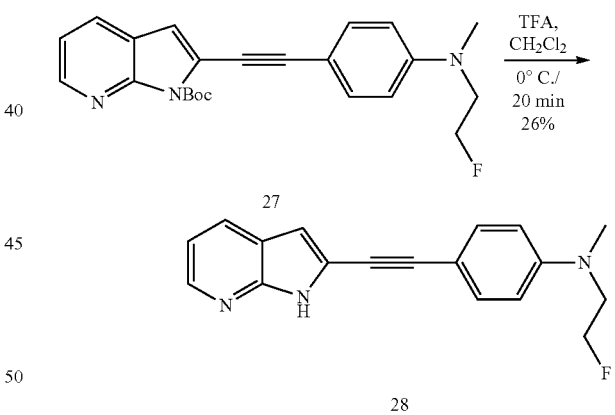

To prepare compounds radiolabeled with $^{18}$F, O-tosyl derivative 29 was prepared from 26

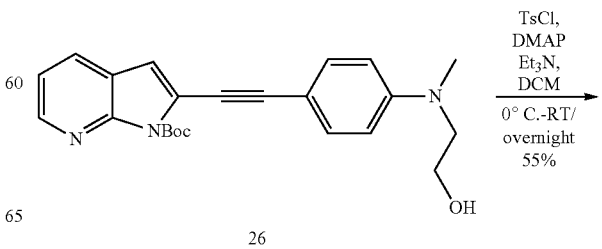

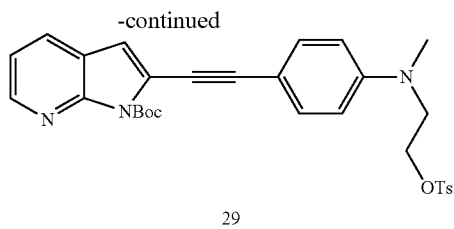

29

Example 13.1 tert-Butyl-2-((4-((2-hydroxyethyl)(methyl)amino)phenyl)ethynyl)-1H-pyrrolo[2,3-b]pyridine-1-carboxylate 26

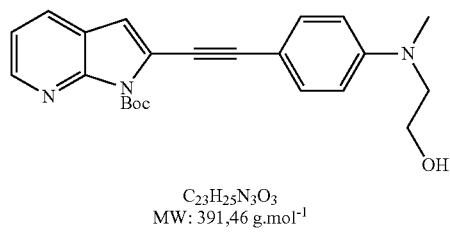 [SMILES: CN(CCO)c1ccc(C#Cc2cc3cccnc3n2C(=O)OC(C)(C)C)cc1]

$C_{23}H_{25}N_3O_3$
MW: 391,46 g.mol$^{-1}$

To a solution containing derivative 23i (0.6 g, 1.73 mmol, 1 eq.), 2-bromoethanol (0.55 ml, 7.77 mmol, 4.5 eq.) and KI (0.06 g, 0.35 mmol, 0.2 eq.) in acetonitrile (30 ml) was added a solution of t-BuOK (1M in THF, 3.8 ml, 3.80 mmol, 2.2 eq.). The mixture was stirred at reflux for 8 days (TLC monitoring) with adding 4 eq. 2-bromoethanol every 24 hours. At the end of the reaction water was added to the reaction mixture, the phases were separated, and the aqueous phase was extracted with ethyl acetate. The combined organic phases were washed with water, a saturated NaCl solution and dried over MgSO$_4$ before being concentrated under reduced pressure. The compound was purified by flash column chromatographie on silicagel (ethyl acetate/petroleum ether=50/50+1% MeOH). yellow solid (31%), mp 154-156° C., Rf=0.22 (ethyl acetate/petroleum ether=40/60). IR (v, cm$^{-1}$, neat) 3386, 2980, 2926, 2206, 1747, 1603, 1546, 1517, 1473, 1408, 1384, 1343, 1305, 1249, 1194, 1154, 1117, 1085, 980, 847, 831, 814, 776, 746, 643, 525. $^1$H NMR (250 MHz, CDCl$_3$, 20° C.) δ 8.50 (dd, J=4.8 Hz, J=1.7 Hz, 1H), 7.81 (dd, J=7.8 Hz, J=1.7 Hz, 1H), 7.46-7.34 (m, 2H), 7.17 (dd, J=7.8 Hz, J=4.8 Hz, 1H), 6.80 (s, 1H), 6.79-6.64 (m, 2H), 3.85 (t, J=5.7 Hz, 2H), 3.54 (t, J=5.7 Hz, 2H), 3.04 (s, 3H), 1.82 (1s, 1H), 1.68 (s, 9H). $^{13}$C NMR (63 MHz, CDCl$_3$, 20° C.) δ 149.8 (Cq), 148.6 (CH), 148.1 (Cq), 145.7 (Cq), 132.8 (2×CH), 128.3 (CH), 121.9 (Cq), 121.6 (Cq), 118.8 (CH), 112.1 (2×CH), 111.7 (CH), 109.9 (Cq), 96.9 (Cq), 84.6 (Cq), 79.8 (Cq), 60.2 (CH$_2$), 54.8 (CH$_2$), 38.9 (CH$_3$), 28.2 (3×CH$_3$). HRMS (+ESI) calculated for $C_{23}H_{26}N_3O_3$ (M+H+): 392.1969, found: 392.1968.

Example 13.2 tert-Butyl-2-((4-(methyl(2-(tosyloxy)ethyl)amino)phenyl)ethynyl)-1H-pyrrol[2,3-b] pyridine-1-carboxylate 29

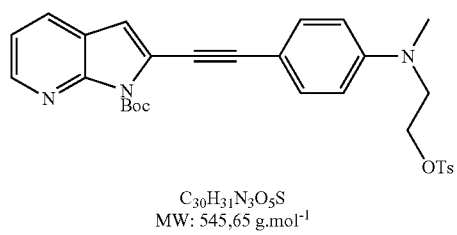 [SMILES: Cc1ccc(S(=O)(=O)OCCN(C)c2ccc(C#Cc3cc4cccnc4n3C(=O)OC(C)(C)C)cc2)cc1]

$C_{30}H_{31}N_3O_5S$
MW: 545,65 g.mol$^{-1}$

To a solution of TsCl (0.12 g, 0.63 mmol, 1.2 eq.), triethylamine (0.15 ml, 1.05 mmol, 2 eq.) and DMAP (0.013 g, 0.3 1 mmol, 0.2 eq.) in THF (11 ml), cooled to 0° C., was added a solution of 26 (0.21 g, 0.53 mmol, 1 eq.) in THF (6 ml). The mixture was stirred at room temperature overnight, concentrated under reduced pressure and purified by flash column chromatography on silicagel (ethyl acetate/petroleum ether=30/70). Yellow solid (55%), mp 171-173° C., Rf=0.38 (ethyl acetate/petroleum ether=40/60). IR (v, cm$^{-1}$, neat) 2986, 2360, 2198, 1749, 1605, 1544, 1514, 1407, 1348, 1306, 1253, 1187, 1170, 1114, 1092, 1010, 972, 900, 804, 776, 663, 556, 508. $^1$H NMR (250 MHz, CDCl$_3$, 20° C.) δ 8.48 (dd, J=4.8, 1.7 Hz, 1H), 7.78 (dd, J=7.8 Hz, J=1.7 Hz, 1H), 7.73-7.52 (m, 2H), 7.39-7.26 (m, 2H), 7.30-7.17 (m, 2H), 7.14 (dd, J=7.8 Hz, J=4.8 Hz, 1H), 6.78 (s, 1H), 6.56-6.42 (m, 2H), 4.16 (t, J=5.8 Hz, 2H), 3.62 (t, J=5.8 Hz, 2H), 2.90 (s, 3H), 2.39 (s, 3H), 1.66 (s, 9H). $^{13}$C NMR (101 MHz, CDCl$_3$, 20° C.) δ 148.6 (Cq), 148.3 (Cq), 148.1 (Cq), 145.8 (CH), 145.0 (Cq), 132.8 (2×CH), 132.6 (Cq), 129.8 (2×CH), 128.3 (CH), 127.8 (2×CH), 121.9 (Cq), 121.5 (Cq), 118.9 (CH), 111.8 (CH), 111.6 (2×CH), 110.0 (Cq), 96.7 (Cq), 84.6 (Cq), 79.9 (Cq), 66.7 (CH$_2$), 51.0 (CH$_2$), 39.0 (CH$_3$), 28.2 (3×CH$_3$), 21.7 (CH$_3$). HRMS (+ESI) calculated for $C_{30}H_{32}N_3O_5S$ (M+H+): 546.2057, found: 546.2053.

Example 13.3 tert-Butyl-2-((4-((2-fluoroethyl)(methyl)amino)phenyl)ethynyl)-1H-pyrrolo[2,3-b]pyridine-1-carboxylate 27

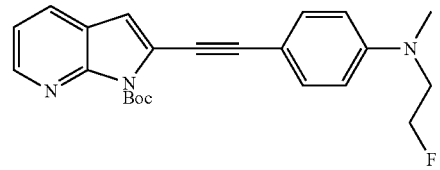

$C_{23}H_{24}FN_3O_2$
MW: 393,45 g.mol$^{-1}$

To a solution containing compound 26 (0.1 5 g, 0.29 mmol, 1 eq.) in dichloromethane (3 ml) and cooled to −78° C. was added dropwise DAST (0.077 ml, 0.59 mmol, 2 eq.). The reaction mixture was stirred for 1 h at −78° C. After returning to room temperature, water and dichloromethane were added and the phases were separated. The aqueous phase was extracted with dichloromethane (2 times), the combined organic phases were dried over MgSO$_4$ and concentrated under reduced pressure. The compound was purified by flash column chromatography on silicagel (ethyl acetate/petroleum ether=20/80). White solid (22%), mp 151-153° C., Rf=0.31 (ethyl acetate/petroleum ether=20/80). IR (v, cm$^{-1}$, neat) 2979, 2204, 1742, 1605, 1573, 1544, 1517, 1355, 1306, 1253, 1189, 1154, 1115, 1089, 1041, 979, 813, 774, 527, 510, 508, 504. $^1$H NMR (250 MHz, CDCl$_3$, 20° C.) δ 8.48 (dt, J=4.8 Hz, J=1.6 Hz, 1H), 7.78 (dt, J=7.9 Hz, J=1.6 Hz, 1H), 7.44-7.34 (m, 2H), 7.15 (ddd, J=7.8 Hz, J=4.8 Hz, J=1.4 Hz, 1H), 6.78 (s, 1H), 6.66 (d, J=8.8 Hz, 2H), 4.69 (t, J=5.1 Hz, 1H), 4.50 (t, J=5.1 Hz, 1H), 3.72 (t, J=5.2 Hz, 1H), 3.62 (t, J=5.2 Hz, 1H), 3.04 (m, 3H), 1.66 (s, 9H). $^{13}$C NMR (101 MHz, CDCl$_3$, 20° C.) δ 149.1 (Cq), 148.7 (Cq), 148.2 (Cq), 145.9 (CH), 133.0 (2×CH), 128.5 (CH), 122.1 (Cq), 121.7 (Cq), 119.0 (CH), 111.9 (2×CH), 111.8 (CH), 109.9 (Cq), 96.9 (Cq), 84.7 (Cq), 81.8 (d, J=170.3 Hz, CH$_2$), 80.0 (Cq), 52.5 (d, J=21.2 Hz, CH$_2$), 39.1 (CH$_3$), 28.3 (3×CH$_3$). $^{19}$F NMR (235 MHz, CDCl$_3$, 20° C.)

δ −222.2. HRMS (+ESI) calculated for $C_{23}H_{25}FN_3O_2$ (M+H+): 394.1925, found: 394.1925.

Example 13.4 4-((1H-Pyrrolo[2,3-b]pyridin-2-yl)ethynyl)-N-(2-fluoroethyl)-N-methylaniline 28

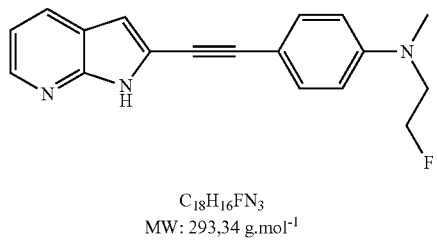 [SMILES: CN(CCF)c1ccc(C#Cc2cc3cccnc3[nH]2)cc1]

$C_{18}H_{16}FN_3$
MW: 293,34 g.mol$^{-1}$

The compound was prepared according to procedure F (26%), or according to procedure C (83% see Method 2, described below) and purified by flash column chromatography on silicagel (ethyl acetate/petroleum ether=10/90). Yellow solid (83%), mp 242-244° C., Rf=0.28 (ethyl acetate/petroleum ether=20/80). IR (v, cm$^{-1}$, neat) 3113, 3057, 2977, 2892, 2808, 2360, 2202, 1601, 1536, 1510, 1432, 1405, 1378, 1353, 1324, 1278, 1236, 1214, 1187, 1137, 1076, 1042, 1012, 977, 916, 810, 766, 692, 624, 552, 515. $^1$H NMR (400 MHz, DMSO-d$_6$, 20° C.) δ 12.07 (s, 1H), 8.24 (m, 1H), 7.90 (m, 1H), 7.39 (d, J=8.4 Hz, 2H), 7.08 (dd, J=7.9 Hz, J=4.6 Hz, 1H), 6.78 (d, J=8.4 Hz, 2H), 6.71 (d, J=1.7 Hz, 1H), 4.66 (t, J=5.0 Hz, 1H), 4.54 (t, J=5.0 Hz, 1H), 3.76 (t, J=5.1 Hz, 1H), 3.69 (t, J=5.1 Hz, 1H), 3.00 (s, 3H). $^{13}$C NMR (101 MHz, DMSO-d$_6$, 20° C.) δ 149.7 (Cq), 148.8 (Cq), 144.3 (CH), 133.0 (2×CH), 128.4 (CH), 120.5 (Cq), 120.2 (Cq), 116.6 (CH), 112.4 (2×CH), 108.3 (Cq), 105.5 (CH), 94.7 (Cq), 82.4 (d, J=166.2 Hz, CH$_2$), 80.5 (Cq), 51.9 (d, J=19.8 Hz, CH$_2$), 38.9 (CH$_3$). $^{19}$F NMR (235 MHz, DMSO-d$_6$) δ −221.2 (tt, J=47.5 Hz, J=26.2 Hz). HRMS (+ESI) calculated for $C_{18}H_{17}FN_3$ (M+H+): 294.1401, found: 294.1401.

Example 14. Synthesis of Final Fluorinated Alkyl Compounds

Method 2:

Compound 30, obtained by reductive amination of ethynylaniline, was engaged in an alkylation reaction with ethyl bromoacetate to give the derivative 31, which is then reduced with LiAlH$_4$ to provide amino alcohol 32. The latter was transformed to tosylate 33 and subsequently substituted with fluorine in the presence of TBAF to give alkyne 34, which is used for the Sonogashira coupling to give the desired product 28 or its analogue 35

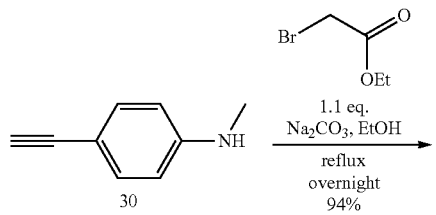

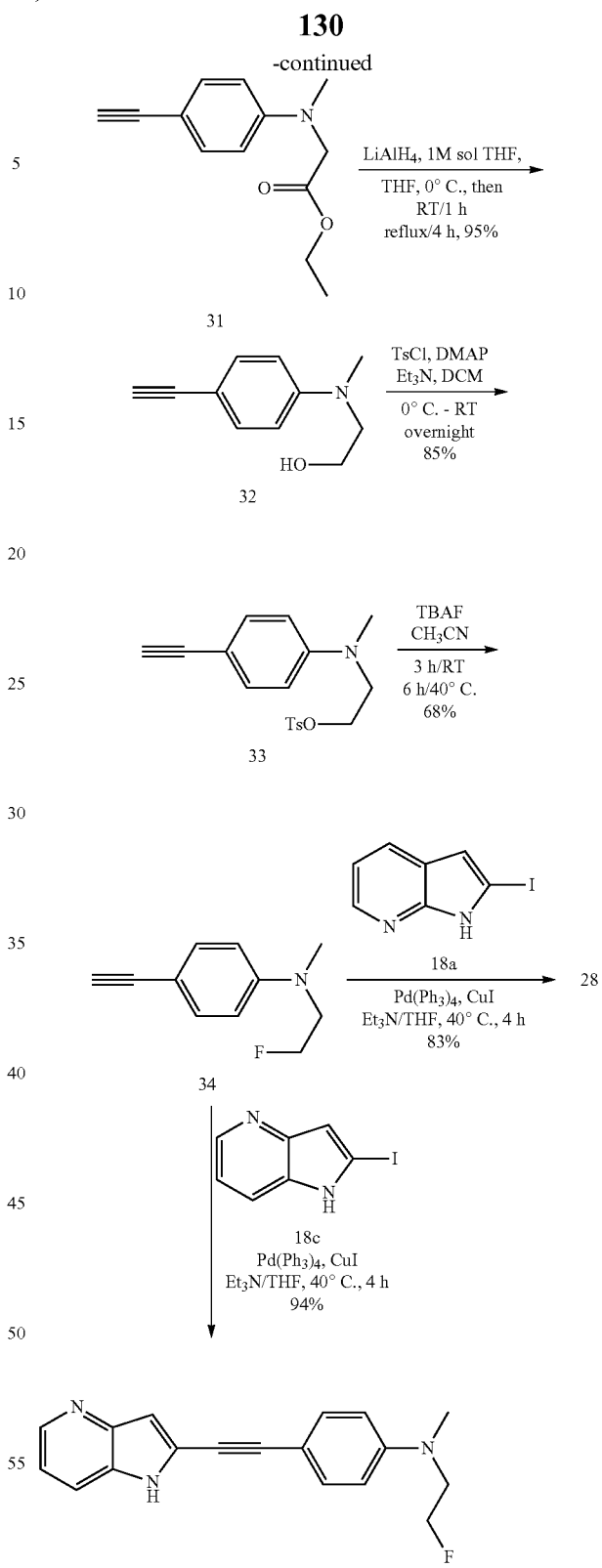

Thereafter, the alkynes 31 and 36 (methylated analogues of 32) were used to exemplify the group of 5-fluoro-1H-pyrrolo[2,3-b]pyridine. Thus, the products 37 and 38, obtained from the Sonogashira coupling with the derivative 18 g were obtained with yields of 93% and 80% respectively

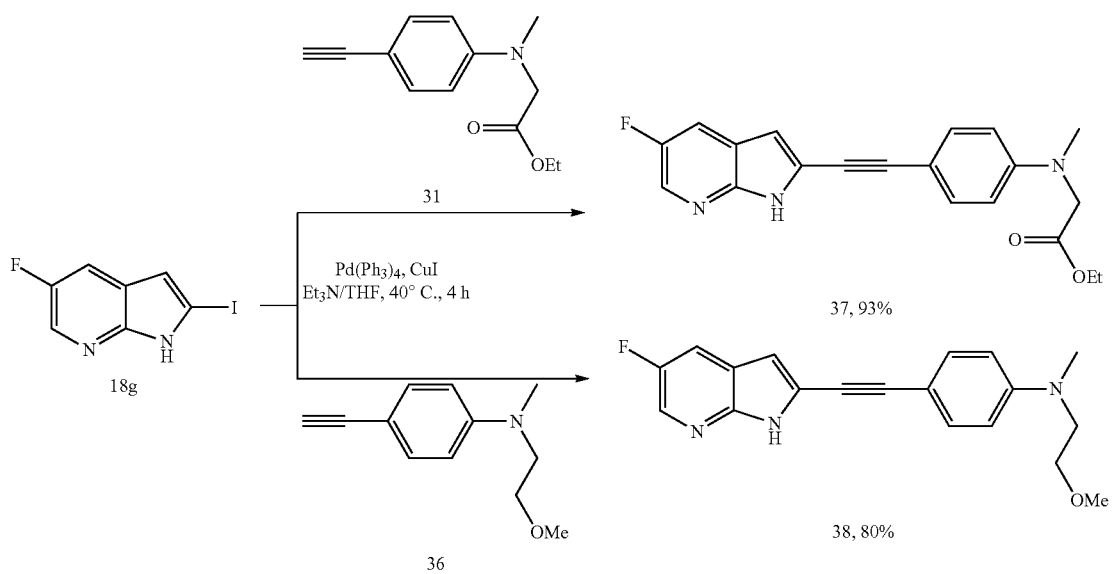 [SMILES: Fc1cnc2[nH]c(I)cc2c1 ; C#Cc1ccc(N(C)CCOC)cc1 ; C#Cc1ccc(N(C)CC(=O)OCC)cc1 ; COCCN(C)c1ccc(C#Cc2cc3cc(F)cnc3[nH]2)cc1 ; CCOC(=O)CN(C)c1ccc(C#Cc2cc3cc(F)cnc3[nH]2)cc1]

Example 14.1 Ethyl 2-((4-ethynylphenyl)(methyl)amino)acetate 31

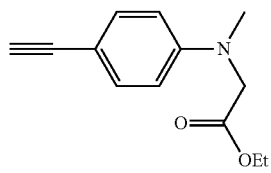

C₁₃H₁₅NO₂
MW: 217,26 g.mol⁻¹

4-ethynyl-N-methylaniline (2.05 g, 15.6 mmol, 1 eq.) and Na$_2$CO$_3$ (2.49 g, 23.4 mmol, 1.5 eq.) were dissolved in EtOH (30 ml), and ethyl bromoacetate (1.83 ml, 17.19 mmol, 1.1 eq.) was slowly added. the reaction medium was at reflux for 1 day. After cooling, water (70 ml) and ethyl acetate (40 ml) were added and the compound was extracted with ethyl acetate (3 times). The organic phase was dried over MgSO$_4$ and concentrated under reduced pressure before being purified by flash column chromatography on silicagel (ethyl acetate/petroleum ether=5/95). transparent liquid (3.18 g, 94%), Rf=0.34 (ethyl acetate/petroleum ether=5/95). IR (v, cm⁻¹, neat) 3282, 2981, 2099, 1741, 1607, 1515, 1476, 1370, 1250, 1181, 1115, 1026, 946, 816, 662, 538, 505. $^1$H NMR (400 MHz, CDCl$_3$, 20° C.) δ 7.42-7.34 (m, 2H), 6.65-6.56 (m, 2H), 4.20 (q, J=7.1 Hz, 2H), 4.08 (s, 2H), 3.09 (s, 3H), 2.99 (s, 1H), 1.26 (t, J=7.1 Hz, 3H). $^{13}$C NMR (101 MHz, CDCl$_3$, 20° C.) δ 170.5 (Cq), 149.0 (Cq), 133.3 (2×CH), 111.8 (2×CH), 110.0 (Cq), 84.6 (Cq), 75.0 (CH), 61.1 (CH$_2$), 54.2 (CH$_2$), 39.5 (CH$_3$), 14.2 (CH$_3$). HRMS (+ESI) calculated for C$_{13}$H$_{16}$NO$_2$ (M+H+): 218.1176, found: 218.1175.

Example 14.2 2-((4-Ethynylphenyl)(methyl)amino)ethanol 32

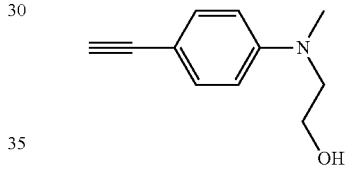

C₁₁H₁₃NO
MW: 175,23 g.mol⁻¹

To a solution of 31 (0.518 g, 2.38 mmol, 1 eq.) in THF (2.4 ml) was slowly added a 1M solution of LiAlH$_4$ in THF (4.8 ml, 4.76 mmol, 2 eq.). The mixture was stirred at room temperature for 1 hour and then for 4 hours at reflux. After cooling to 0° C., were added water, a saturated aqueous solution of NaCl and Et$_2$O. The suspension was filtered over celite and washed with Et$_2$O. The filtrate was separated into two phases and the aqueous phase was washed 3 times with Et$_2$O. The combined organic layers were dried over MgSO$_4$ and concentrated in reduced pressure. The crude product was purified by flash column chromatography on silicagel (ethyl acetate/petroleum ether=20/80). White solid (0.36 g, 85%), mp 73-75° C., Rf=0.36 (ethyl acetate/petroleum ether=30/70). IR (v, cm⁻¹, neat) 3293, 3271, 2907, 2871, 2094, 1606, 1518, 1454, 1378, 1349, 1268, 1222, 1176, 1125, 1059, 977, 908, 852, 814, 803, 644, 581, 524, 509. $^1$H NMR (250 MHz, CDCl$_3$, 20° C.) δ 7.37-7.28 (m, 2H), 6.70-6.60 (m, 2H), 3.79 (q, J=5.6 Hz, 2H), 3.48 (t, J=5.6 Hz, 2H), 2.97 (s, 3H), 2.95 (s, 1H), 1.62 (1s, 1H). $^{13}$C NMR (63 MHz, CDCl$_3$, 20° C.) δ 149.8 (Cq), 133.3 (2×CH), 112.0 (2×CH), 109.4 (Cq), 84.6 (Cq), 75.0 (CH), 60.2 (CH$_2$), 54.8 (CH$_2$), 38.8 (CH$_3$). HRMS (+ESI) calculated for C$_{11}$H$_{14}$NO (M+H+): 176.1070, found: 176.1071.

Example 14.3
2-((4-Ethynylphenyl)(methyl)amino)ethyl 4-methylbenzenesulfonate 33

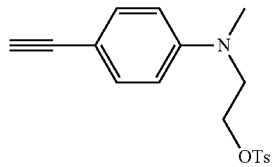

C$_{18}$H$_{19}$NO$_3$S
MW: 329,41 g.mol$^{-1}$

To a solution of TsCl (0.30 g, 1.55 mmol, 1.2 eq.), triethylamine (0.36 ml, 2.58 mmol, 2 eq.) and DMAP (0.032 g, 0.26 mmol, 0.2 eq.) in THF (27 ml), cooled to 0° C., was added a solution of 32 (0.23 g, 1.29 mmol, 1 eq.) in THF (15 ml). The mixture was stirred at room temperature overnight, concentrated under reduced pressure and purified by flash column chromatography on silicagel (ethyl acetate/petroleum ether=10/90). White solid (85%), mp 99-101° C., Rf=0.38 (ethyl acetate/petroleum ether=20/80). IR (v, cm$^{-1}$, neat) 3278, 2991, 2920, 2099, 1608, 1519, 1351, 1293, 1268, 1240, 1217, 1172, 1145, 1093, 1078, 1015, 959, 918, 898, 842, 817, 777, 692, 658, 578, 556, 523. $^1$H NMR (250 MHz, CDCl$_3$, 20° C.) δ 7.75-7.53 (m, 2H), 7.36-7.07 (m, 4H), 6.55-6.18 (m, 2H), 4.14 (t, J=5.8 Hz, 2H), 3.59 (t, J=5.8 Hz, 2H), 2.95 (s, 1H), 2.87 (s, 3H), 2.39 (s, 3H). $^{13}$C NMR (63 MHz, CDCl$_3$, 20° C.) δ 148.2 (Cq), 145.0 (Cq), 133.3 (2×CH), 132.5 (Cq), 129.8 (2×CH), 127.8 (2×CH), 111.5 (2×CH), 109.5 (Cq), 84.5 (Cq), 75.1 (Cq), 66.7 (CH$_2$), 50.9 (CH$_2$), 39.0 (CH$_3$), 21.6 (CH$_3$). HRMS (+ESI) calculated for C$_{18}$H$_{20}$NO$_3$S (M+H+): 330.1158, found: 330.1158.

Example 14.4
4-Ethynyl-N-(2-fluoroethyl)-N-methylaniline 34

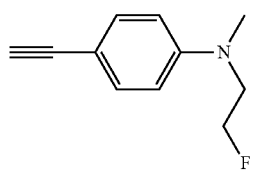

C$_{11}$H$_{12}$FN
MW: 177,22 g.mol$^{-1}$

To a solution of 33 (0.21 g, 0.65 mmol, 1 eq.) In CH$_3$CN (5 ml) was added a solution of TBAF 1M in THF (1.30 ml, 1.29 mmol, 2 eq.). The mixture was stirred at room temperature overnight, and 4 hours at 40° C. before being concentrated under reduced pressure and purified by flash column chromatography on silicagel (ethyl acetate/petroleum ether=5/95). transparent liquid (68%), Rf=0.39 (ethyl acetate/petroleum ether=5/95). IR (v, cm$^{-1}$, neat) 3291, 2896, 2098, 1606, 1515, 1479, 1373, 1267, 1209, 1179, 1133, 1075, 1040, 1006, 979, 907, 846, 816, 845, 537, 520. $^1$H NMR (250 MHz, CDCl$_3$, 20° C.) δ 7.39-7.27 (m, 2H), 6.67-6.45 (m, 2H), 4.66 (t, J=5.2 Hz, 1H), 4.47 (t, J=5.2 Hz, 1H), 3.68 (t, J=5.2 Hz, 1H), 3.58 (t, J=5.2 Hz, 1H), 3.00 (s, 3H), 2.96 (s, 1H). $^{13}$C NMR (63 MHz, CDCl$_3$, 20° C.) δ 148.9 (Cq), 133.4 (2×CH), 111.6 (2×CH), 109.3 (Cq), 84.6 (CH), 81.6 (d, J=170.1 Hz, CH$_2$), 75.0 (CH), 52.4 (d, J=21.2 Hz, CH$_2$), 39.0 (CH$_3$). $^{19}$F NMR (235 MHz, CDCl$_3$, 20° C.) δ −50.0. HRMS (+ESI) calculated for C$_{11}$H$_{13}$FN (M+H+): 178.1027, found: 178.1026.

Example 14.5 4-((1H-Pyrrolo[3,2-b]pyridin-2-yl)ethynyl)-N-(2-fluoroethyl)-N-methylaniline 35

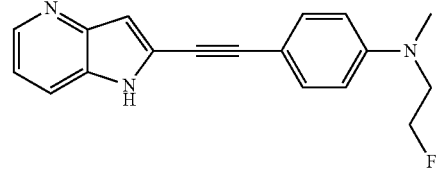

C$_{18}$H$_{16}$FN$_3$
MW: 293,34 g.mol$^{-1}$

The compound was prepared according to Procedure C and purified by column chromatography on silicagel under pressure (ethyl acetate/petroleum ether=20/80). Yellow solid (94%), mp 232-234° C., Rf=0.24 (ethyl acetate/petroleum ether=20/80). IR (v, cm$^{-1}$, neat) 3066, 2952, 2890, 2820, 2703, 2202, 1606, 1571, 1538, 1513, 1405, 1376, 1354, 1285, 1247, 1189, 1124, 1040, 982, 913, 815, 776, 623, 583, 557, 529, 515, 506. $^1$H NMR (400 MHz, DMSO-d$_6$, 20° C.) δ 11.83 (s, 1H), 8.35 (d, J=4.6 Hz, 1H), 7.69 (m, 1H), 7.50-7.31 (m, 2H), 7.14 (dd, J=8.2 Hz, J=4.6 Hz, 1H), 6.89-6.69 (m, 3H), 4.67 (t, J=4.9 Hz, 1H), 4.55 (t, J=4.9 Hz, 1H), 3.76 (t, J=5.0 Hz, 1H), 3.70 (t, J=5.0 Hz, 1H), 3.00 (s, 3H). $^{13}$C NMR (101 MHz, DMSO-d$_6$, 20° C.) δ 149.7 (Cq), 145.9 (Cq), 143.8 (CH), 133.0 (2×CH), 129.7 (Cq), 123.1 (Cq), 118.4 (CH), 117.8 (CH), 112.4 (2×CH), 108.1 (Cq), 106.8 (CH), 95.2 (Cq), 82.4 (d, J=166.2 Hz, CH$_2$), 80.4 (Cq), 51.9 (d, J=19.8 Hz, CH$_2$), 38.8 (CH$_3$). $^{19}$F NMR (376 MHz, DMSO-d$_6$, 20° C.) δ 15.8. HRMS (+ESI) calculated for C$_{18}$H$_{17}$FN$_3$ (M+H+): 294.1401, found: 294.1404.

Example 14.6
4-Ethynyl-N-(2-methoxyethyl)-N-methylaniline 36

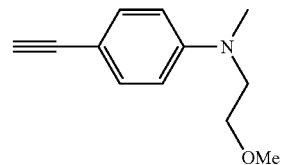

C$_{12}$H$_{15}$NO
MW: 189,26 g.mol$^{-1}$

To a solution of 32 (0.25 g, 1.43 mmole, 1 eq.) in THF (3 ml) was slowly added a 1M solution of tBuOK in THF (2.85 ml, 2.85 mmol, 2 eq.). The mixture was stirred under ultrasound conditions for 5 minutes, cooled to 0° C. and methyl iodide was added dropwise. The reaction medium was stirred at room temperature for 16 h and concentrated in vacuo. The residue was taken up in ethyl acetate and the insoluble precipitate was filtered. To the filtrate was added water and the phases were separated. The aqueous phase was extracted with ethyl acetate (2 times). The combined organic phases were washed with a saturated NaCl solution, dried over MgSO$_4$ and concentrated under reduced pressure. The product was purified by pressurized silicagel column chromatography (the ratio of solvents used: ethyl acetate/petroleum ether=5/95). Transparent liquid (0.22 g, 81%), Rf=0.21 (ethyl acetate/petroleum ether=2/98). IR (v, cm$^{-1}$, neat) 3286, 2877, 2097, 1606, 1515, 1451, 1375, 1274, 1193, 1179, 1110, 1067, 1018, 815, 644, 530, 514, 506, 503. $^1$H NMR (400 MHz, CDCl$_3$, 20° C.) δ 6 7.38 (d, J=9.0 Hz, 2H), 6.65 (d, J=9.0 Hz, 2H), 3.56 (t, J=3.1 Hz, 4H), 3.37 (s, 3H), 3.02 (s, 3H), 3.00 (s, 1H). $^{13}$C NMR (101 MHz, CDCl$_3$, 20° C.) δ 149.3 (Cq), 133.3 (2×CH), 111.5 (2×CH), 108.7 (Cq), 84.8 (CH), 74.8 (CH), 70.1 (CH$_2$), 59.1 (CH$_3$), 52.1 (CH$_2$), 38.9 (CH$_3$). HRMS (+ESI) calculated for C$_{12}$H$_{16}$NO (M+H$^+$): 190.1226, found: 190.1225.

Example 14.7 2-((4-((5-Fluoro-1H-pyrrolo[2,3-b]pyridin-2-yl)ethynyl)phenyl) (methyl)amino)acetate d'ethyle 37

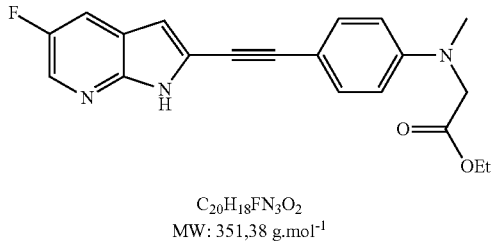 [SMILES: CCOC(=O)CN(C)c1ccc(C#Cc2cc3cc(F)cnc3[nH]2)cc1]

C$_{20}$H$_{18}$FN$_3$O$_2$
MW: 351,38 g.mol$^{-1}$

The compound was prepared according to Procedure C and purified by column chromatography on silicagel under pressure (ethyl acetate/petroleum ether=15/85). White solid (93%), mp 186-188° C., Rf=0.24 (ethyl acetate/petroleum ether=10/90). IR (v, cm$^{-1}$, neat) 2984, 2208, 1729, 1608, 1585, 1540, 1508, 1372, 1295, 1254, 1190, 1154, 1109, 1030, 948, 871, 805, 765, 526, 514, 506, 503. $^1$H NMR (400 MHz, CDCl$_3$, 20° C.) δ 10.59 (s, 1H), 8.25 (t, J=2.3 Hz, 1H), 7.60 (dd, J=8.9 Hz, J=2.6 Hz, 1H), 7.52-7.42 (m, 2H), 6.80-6.49 (m, 3H), 4.23 (q, J=7.1 Hz, 2H), 4.12 (s, 2H), 3.14 (s, 3H), 1.28 (t, J=7.1 Hz, 3H). $^{13}$C NMR (101 MHz, CDCl$_3$, 20° C.) δ 170.4 (Cq), 155.9 (d, J=241.9 Hz), 149.3 (Cq), 145.0 (Cq), 133.0 (2×CH), 131.9 (d, J=29.8 Hz, CH), 122.0 (Cq), 120.9 (d, J=7.3 Hz, Cq), 114.0 (d, J=21.0 Hz, CH), 112.0 (2×CH), 109.8 (Cq), 105.4 (d, J=4.4 Hz, CH), 95.3 (Cq), 79.3 (Cq), 61.2 (CH$_2$), 54.2 (CH$_2$), 39.5 (CH$_3$), 14.2 (CH$_3$). $^{19}$F NMR (376 MHz, CDCl$_3$, 20° C.) δ -138.3.

HRMS (+ESI) calculated for C$_{20}$H$_{19}$FN$_3$O$_2$ (M+H+): 352.1456, found: 352.1457.

Example 14.8 4-((5-Fluoro-1H-pyrrolo[2,3-b]pyridin-2-yl)ethynyl)-N-(2-methoxyethyl)-N-methylaniline 38

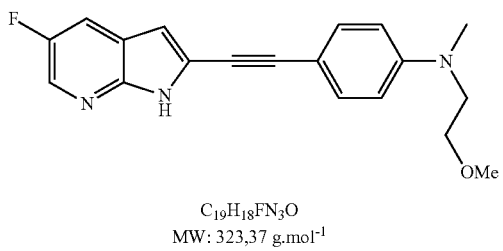 [SMILES: COCCN(C)c1ccc(C#Cc2cc3cc(F)cnc3[nH]2)cc1]

C$_{19}$H$_{18}$FN$_3$O
MW: 323,37 g.mol$^{-1}$

The compound was prepared according to Procedure C and purified by column chromatography on silicagel under pressure (ethyl acetate/petroleum ether=20/80). White solid (80%), mp 160-162° C., Rf=0.35 (ethyl acetate/petroleum ether=30/70). IR (v, cm$^{-1}$, neat) 3066, 2882, 2203, 1602, 1534, 1507, 1372, 1346, 1293, 1218, 1189, 1155, 1106, 1019, 984, 895, 876, 821, 760, 553, 514, 506, 502. $^1$H NMR (400 MHz, CDCl$_3$, 20° C.) δ 10.46 (s, 1H), 8.22 (t, J=2.3 Hz, 1H), 7.57 (dd, J=8.9 Hz, J=2.6 Hz, 1H), 7.47-7.41 (m, 2H), 6.74-6.67 (m, 2H), 6.65 (d, J=2.0 Hz, 1H), 3.58 (s, 4H), 3.37 (s, 3H), 3.04 (s, 3H). $^{13}$C NMR (101 MHz, CDCl$_3$, 20° C.) δ 155.9 (d, J=241.7 Hz, Cq), 149.5 (Cq), 145.1 (Cq), 133.0 (2×CH), 131.9 (d, J=29.7 Hz, CH), 123.1 (Cq), 120.9 (d, J=7.2 Hz, Cq), 113.9 (d, J=20.9 Hz, CH), 111.7 (2×CH), 108.4 (Cq), 105.2 (d, J=4.4 Hz, CH), 95.7 (Cq), 79.1 (Cq), 70.1 (CH$_2$), 59.1 (CH$_3$), 52.1 (CH$_2$), 38.9 (CH$_3$). $^{19}$F NMR (376 MHz, CDCl$_3$, 20° C.) δ -138.4. HRMS (+ESI) calculated for C$_{19}$H$_{19}$FN$_3$O (M+H+): 324.1507, found: 324.1507.

Example 15. Production of Fluorinated Ligands Labeled $^{18}$F by Nucleophilic Substitution Step: Production of Fluoride Ions and Assessment of their Reactivity

[$^{18}$F] ions were produced by nuclear transmutation $^{18}$O(p,n)$^{18}$F. The ion solution [$^{18}$F] was passed over an QMA® anion exchange cartridge for fixing the fluoride ions. This cartridge was pre-conditioned with 10 ml of K$_2$CO$_3$ and then rinsed with 10 ml of water. [$^{18}$F] ions were eluted from the QMA® cartridge with an aqueous solution of K$_2$CO$_3$ and Kyptofix$_{2.2.2}$ dissolved in MeCN. This solution was transferred into a reactor and dried twice by azeotropic distillation with the addition of 1 ml MeCN each time. At the end of the drying, the complex with fluoride ions was ready for the next step of radiofluorination.

Step: Nucleophilic Substitution (Aliphatic, Aromatic, Heteroaromatic)

The syntheses are carried from (hetero)aromatic aryliodonium compounds, of electronically impoverished (heteroaryl)nitro, of (hetero)aryltrimethylammonium, of (hetero)aromatic boronic esters or acids, but also halogenated aliphatic compounds (Cl, Br, I), triflates or mesylates. The precursor, dissolved in a solvent (MeCN, DMSO, DMF or the like), was added to the reactor containing the complex with fluoride ions. For aliphatic substitutions MeCN was mainly used but, if necessary, solvents with higher boiling points can be used for the (hetero)aromatics substitutions, which typically require solvents such as DMSO or DMF. The reaction medium was thermally heated to between 5 and 30 min or by microwave, and then the solution was cooled to room temperature. This was diluted with water and possibly hydrolyzed, depending on the nature of the precursor used (removal of a protecting group). The approach described above is direct. An indirect approach depending on the accessibility of the molecule, the precursor may be considered. For example, the [$^{18}$F] fluoroethyltosylate ([$^{18}$F] FETos) was prepared from ethylene ditosylate, followed by an N, O or S alkylation of the precursor to give the desired product.

Step: Purification and Formulation

The crude reaction mixture was passed through a pre-purification cartridge and rinsed with water. The radiotracer was eluted from the cartridge with MeCN and the solution was loaded onto a semi-preparative column. The radiolabelled product of interest was collected and dissolved in water and trapped on a cartridge. It was rinsed and the radiopharmaceutical was eluted with injectable ethanol. The formulation was completed by addition of NaCl 0.9% so that no more than 10% ethanol, by weight, was present in the radiopharmaceutical medicine solution. The solution was passed through a sterilizing filter and dispensed into sterile and pyrogenic vials before being dispensed.

Example 16. Production of Carbon-11 Radiolabeled Ligands

Step: production of reactive synthons labeled with Carbon-11

[$^{11}$C] ions were produced by nuclear transmutation $^{11}$C (p,☐)$^{15}$N. This transmutation occurs in the presence of a few ppm of hydrogen or oxygen to lead to the formation of carbon-11 radiolabeled methane or carbon dioxide respectively. These two building blocks will pave the way for the production of many other building blocks radiolabeled with carbon-11 which will serve as reaction intermediates for incorporation in the molecule of interest. Among the most common compounds, methyl iodide or methyl triflate can be cited.

Figure 1B:
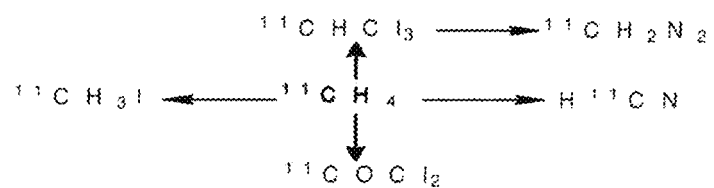

FIG. 1a depicts the preparation of synthons from carbon dioxide radiolabeled with carbon-11 while FIG. 1b shows the preparation of synthons from methane radiolabeled with carbon-11.

Figure 2:
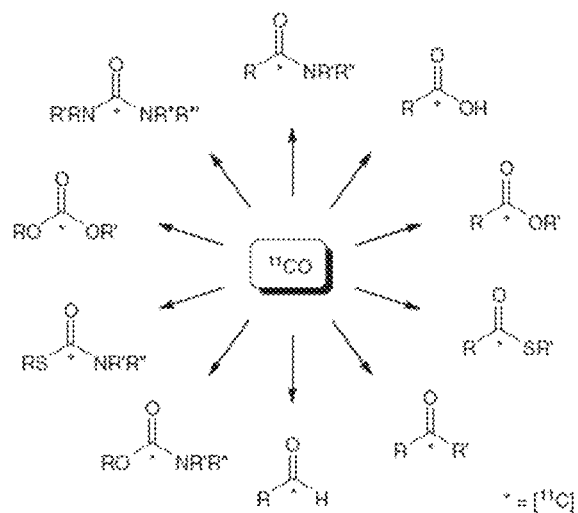
FIG. 2 shows the chemical functionalities radiolabeled with carbon-11 accessible via carbonylation reactions.

Step: Incorporating the Building Block to the Molecule of Interest.

methyl iodide or methyl triflate radiolabeled with carbon-11 can be used in common reactions of O, N and S alkylation. The solvents used are: MeCN, DMSO, DMF or NMP. Coupling reactions with organometallic reagents can be used for these radiolabeled synthons: Stille, Suzuki, Sonogashira. Moreover, [$^{11}$C]CO$_2$ may be subject to attack from a Grignard reagent or be transformed into Grignard reagent. It can also be reduced by carbon monoxide, [$^{11}$C] CO, and provide access to many chemical functions. FIG. 2 shows the chemical functionalities accessible via carbonylation reactions. The Carbon-11 labeling reactions are therefore mostly multistep reactions.

Step: Purification and Formulation

The crude reaction mixture was passed through a pre-purification cartridge then rinsed with water. The radiotracer was eluted from the cartridge with MeCN and the solution was loaded onto a semi-preparative column. The radiolabelled product of interest was collected and then dissolved in water and trapped on a cartridge. It was rinsed and the radiopharmaceutical was eluted with injectable ethanol and the formulation was completed by addition of NaCl 0.9% so that no more than 10% ethanol, by weight, was present in the radiopharmaceutical medicine solution. The solution was passed through a sterilizing filter and dispensed into sterile and pyrogenic vials before being dispensed.

Example 17. Production of Ligands Radiolabeled with Iodine-123

The commercial solution of Na$^{123}$I was acidified with ethanolic hydrogen chloride or sulfuric acid and then were added:
  ethanolic aromatic or heteroaromatic stannyl precursor (SnBu$_3$ or SnMe$_3$)
  a solution of oxidizing agent (Chloramine T, hydrogen peroxide or iodo-bead)

The mixture was then stirred at room temperature for a few minutes (2-30 min). The solution was basified by addition of a solution NH$_4$OH or NaHCO$_3$. The reaction medium was purified by HPLC, the radiolabelled product of interest was collected and dissolved in water and trapped on a cartridge. It was rinsed and the radiopharmaceutical was eluted with injectable ethanol and the formulation was completed by addition of NaCl 0.9% so that no more than 10% ethanol, by weight, was present in the radiopharmaceutical medicine solution. The solution was passed through a sterilizing filter and dispensed into sterile and pyrogenic vials before being dispensed.

A similar approach can be applied for compounds radiolabeled with other isotopes of iodine (124, 125, 131).

Example 18. Radiosynthesis

Example 18.1

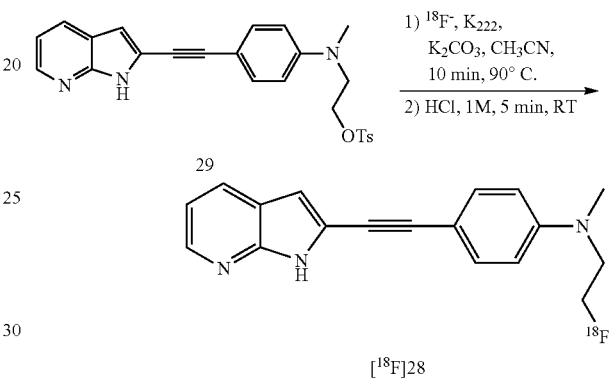

The radiosynthesis of 28 was carried out using a FXFN-pro (GE Healthcare) equipment. [$^{18}$F] ions were produced by $^{18}$O(p,n)$^{18}$F nuclear transmutation using a cyclotron PETtrace (GE Healthcare). The activity produced was transferred to the radiosynthesis automate and trapped on a QMA® anion exchange cartridge (Waters) for fixing the fluoride ions. This cartridge was previously conditioned with 10 ml of K$_2$CO$_3$ and rinsed with 10 ml of water. [$^{18}$F] ions were eluted from the QMA cartridge with an aqueous solution of K$_2$CO$_3$ and Kyptofix$_{2,2,2}$ dissolved in MeCN (7.2 g of K$_{2.2.2\ 2}$+715 µl MeCN and 3.8 mg of K$_2$CO$_3$+285 µl H$_2$O). This solution was transferred into a reactor and dried twice by azeotropic distillation with the addition each time of 1 ml MeCN. At the end of drying the complex with the fluoride ions was ready for the next step of radiofluorination. 2 mg of precursor 29 having the tosyl function, dissolved in 700 of MeCN are added to the fluoride ions. The reaction mixture was maintained at 90° C. for 10 min. The solution was then brought to room temperature before adding 500 µl of 1M HCl. The reaction was stirred 5 min at room temperature before being quenched by the addition of 8 ml of water. The mixture was then pre-purified on a preconditioned tC 18plus cartridge (Waters). The cartridge was washed with 5 ml of water prior to eluting the crude product of interest with 2 ml of MeCN to which were added 2 ml of 0.1 M ammonium acetate.

The collected 4 ml were then loaded into a HPLC loop and injected onto a semi-preparative column Zorbax Eclipse XDB-C18 9,4×250 mm 5 g (Agilent) with a MeCN/0.1M ammonium acetate 50:50 mobile phase at a rate of 5 ml/min. Under these conditions, the product of interest, [$^{18}$F]28, was collected with a retention time of about 23 min. The collected product was dissolved in 25 ml of water and then trapped on a previously conditioned tC18light cartridge (Waters). The cartridge was rinsed with 5 ml of water. [$^{18}$F]28 was eluted from the cartridge with 1 ml of injectable ethanol. The formulation was completed by the addition of 9 ml of 0.9% NaCl.

For future injection to man the mother solution thus obtained must be aseptic according to GMP guidelines, with a double sterile filtration and filling the vials in a suitable environment under class A laminaRflow.

[$^{18}$F]28 was obtained in 85±5 min in a yield of 32±3% (corrected for decay). The specific activity determined from the calibration curve with the cold standard is of the order of 128 GBq/µmole.

FIG. 3 shows a quality control chromatogram of compound [$^{18}$F]28.

Example 19. Biological Studies

These are studies to determine the affinity and selectivity of the new compounds for α-synuclein fibers. In order to identify better selectivity/affinity, the binding of molecules synthesized to the alpha-synuclein fibers is compared to their binding to the fibers of the β-amyloid peptide (Aβ1-42) and/or Tau. They are made by in vitro binding study on preparations of synthetic fibers of α-synuclein (α-syn), of (β-amyloid peptide (Aβ1-42) or Tau in two ways: 1/competition between the new compound and thioflavin T (ThT), and measuring fluorescence from the bound ThT, 2/direct binding of the new compound and measuring fluorescence from the bound fraction.

Example 19.1 Expression and Purification of α-Syn, AβI-42 and Tau Recombinant Proteins The α-syn and Aβ1-42 native proteins are expressed in *E. coli* (strain BL21 (DE3), (Stratagene, La Jolla, Calif.)) and purified according to described methods (Ghee M., Melki R., Michot N., Mallet J. PA700, the regulatory complex of the 26S proteasome, interferes with α-synuclein assembly. *FEBS J.* 2005, 272:4023-4033; Walsh D M, Thulin E, Minogue A M, Gustavsson N, Pang E, Teplow D B, Linse S. A facile method for expression and purification of the Alzheimer's disease-associated amyloid beta-peptide. *FEBS J.* 2009, 276:1266-1281). The α-syn concentration is determined by measuring the absorbance at 280 nm with a molar extinction coefficient of 5960 $M^{-1}$ $cm^{-1}$. For Aβ1-42, the concentration is determined by fluorimetric method with the fluorescamine reagent (Sigma) which reacts with primary amines to form a fluorescent product (Udenfriend S, Stein S, Böhlen P, Dairman W, Leimgruber W, Weigele M. Fluorescamine: a reagent for assay of amino acids, peptides, proteins, and primary amines in the picomolar range. *Science* 1972, 178:871-872).

Human Tau protein (isoform h2N4RTau) is expressed in the vector pET11d in *E. Coli* (strain BL21 (DE3), (Stratagene, La Jolla, Calif.)) and purified according to the described method (Barghorn S, Biernat J, Mandelkow E. (2005) Methods Mol Biol. 299:35-51). The Tau purified concentration is determined by measuring the absorbance at 280 nm using a molar extinction coefficient of 7450 $M^{-1}$ $cm^{-1}$.

Example 19.2 Production and Characterization of α-Syn, Aβ1-42 and Tau Fibers

To obtain fiber assembly, α-syn is incubated in Tris-HCl 50 mM pH7.5, KCl 150 mM at 37° C. under continuous agitation during 4 days. The lyophilized Aβ1-42 was dissolved in 1,1,1,3,3,3-Hexafluoro-2-propanol (HFIP) at 0.2 mg/mL and incubated for 24 h at 37° C. to obtain the complete solubilization. The HFIP is evaporated under nitrogen stream to obtain a dry product. To start the fiber assembly, the dry peptide is resuspended in PBS pH7.4, 10% (v/v) DMSO and incubated at 37° C. for 3 days without agitation.

The assembly process is followed by measuring the binding of Thioflavin T (ThT) to the fibres (LeVine, H 3rd. Thioflavine T interaction with synthetic Alzheimer's disease beta-amyloid peptides: detection of amyloid aggregation in solution. *Protein Sci.* 1993, 2: 404-410). At regular intervals, 10 µL protein aliquots are collected and mixed with 400 µL of ThT (10 µM) in water. The fluorescence of ThT is measured using a Cary Eclipse Spectrofluorometer (Varian Inc., Palo Alto, USA) (excitation: 440 nm, emission: 480 nm). Protein fibers are systematically observed by electron microscopy (Jeol 1400). The images are recorded with a CCD camera (Gatan Orius). Finally, the percentage of α-syn and Aβ1-42 aggregated into fibers is checked on the pellet after centrifugation at 40000×g for 20 min and determination of the concentration of soluble protein/peptide remaining in the supernatant.

Tau protein in PBS buffer containing 1 mM DTT is assembled into fiber in the presence of one twelfth of a molar equivalent of heparin at 37° C. under stirring.

Example 19.3 In Vitro Inhibition of ThT Binding and Determination of $K_i$

Fresh solutions of the test compounds (2.5 mM in DMSO) are diluted in PBS pH7.4, at concentrations between 0.5 nM and 5 µM in the presence of α-syn (200 nM), Aβ1-42 (500 nM) or Tau (200 nM) fibres and ThT 500 nM in a final 2 mL volume. The samples are incubated for 1 h at room temperature (RT) to reach equilibrium. The binding of ThT to α-syn, Aβ1-42 or Tau fibres is measured by fluorescence (excitation: 440 nm, emission: 480 nm). Inhibition of ThT binding by increasing concentrations of each test compound is measured by fluorescence reduction. Due to the partial superposition between the emission spectra of some compounds and ThT, the compounds are also incubated with α-syn, Aβ1-42 or Tau fibers in the absence of ThT. For each concentration, the fluorescence values in the absence of ThT are subtracted from those in the presence of ThT. The results are expressed as a percentage of the maximum fluorescence value of the ThT measured in the absence of a competitor (100% bind). From each curve, the $IC_{50}$ value is measured using the following equation:

$$Y = \min + (\max - \min)/1 + (Y/IC_{50})^{slope}$$

The Ki was then determined using the method of Cheng and Prusoff (Cheng Y, Prusoff W H. Relationship between the inhibition constant (K1) and the concentration of inhibitor which causes 50 percent inhibition (I50) of an enzymatic reaction. *Biochem Pharmacol* 1973, 22:3099-3108).

$$Ki = IC_{50}/(1 + [ThT]/Kd_{ThT})$$

The equation takes into account the concentration of ThT used (500 nM) and its affinity ($Kd_{ThT}$) for for α-syn, Aβ1-42 and/or Tau fibers, namely 700 nM, 500 nM, and 350 nM, respectively.

The results obtained are summarized in Table 5.

TABLE 5

| | Ki vs Thioflavin T measurement | | | |
|---|---|---|---|---|
| Reference | Structure | Ki Aβ (nM) | Ki αsyn (nM) | Ki Tau (nM) |
| AV45 | | 2.2 ± 1 | 76.6 ± 44 | 30.6 ± 9 |
| FDDNP | | 4.6 ± 3 | 25.1 ± 5 | 9.5 ± 1 |
| 22a | 7-azaindole-C≡C-C6H4-N(CH3)2 | 24.5 ± 9 | 4.7 ± 2 | 4.61 ± 0.2 |
| 22b | 6-azaindole isomer-C≡C-C6H4-N(CH3)2 | 91.5 ± 11 | 28.7 ± 8 | 8.4 ± 2 |
| 22c | 4-azaindole isomer-C≡C-C6H4-N(CH3)2 | 21.3 ± 7 | 26.0 ± 16 | 12.0 ± 1 |
| 22d | 5-azaindole isomer-C≡C-C6H4-N(CH3)2 | | | |
| 22e | 6-Cl-7-azaindole-C≡C-C6H4-N(CH3)2 | 909 ± 143 | 49.9 ± 12 | 25.1 ± 8 |
| 22f | 6-F-7-azaindole-C≡C-C6H4-N(CH3)2 | 349 ± 256 | 14.8 ± 7 | |
| 22g | 5-F-7-azaindole-C≡C-C6H4-N(CH3)2 | 318.2 ± 95 | 19.0 ± 8 | |
| 22h | 4-F-7-azaindole-C≡C-C6H4-N(CH3)2 | 244.1 ± 84 | 20.7 ± 9 | |
| 22i | 7-azaindole-C≡C-C6H4-NHCH3 | | | |
| 22j | 7-azaindole-C≡C-C6H4-NH2 (meta) | | | |

TABLE 5-continued
| | Ki vs Thioflavin T measurement | | | |
|---|---|---|---|---|
| Reference | Structure | Ki Aβ (nM) | Ki αsyn (nM) | Ki Tau (nM) |
| 22k | 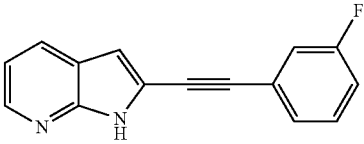 [SMILES: Fc1cccc(C#Cc2cc3cccnc3[nH]2)c1] | | | |
| 22L | 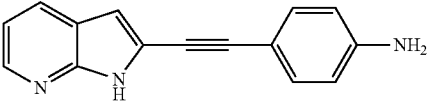 [SMILES: Nc1ccc(C#Cc2cc3cccnc3[nH]2)cc1] | | | |
| 22m | 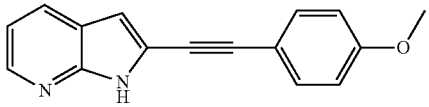 [SMILES: COc1ccc(C#Cc2cc3cccnc3[nH]2)cc1] | | | |
| 22n | 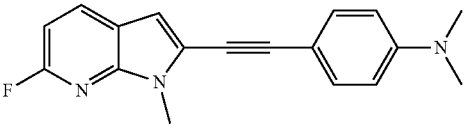 [SMILES: CN(C)c1ccc(C#Cc2cc3ccc(F)nc3n2C)cc1] | | | |
| 25a | 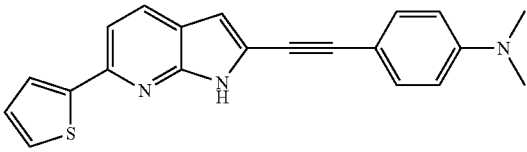 [SMILES: CN(C)c1ccc(C#Cc2cc3ccc(-c4cccs4)nc3[nH]2)cc1] | | | |
| 25b | 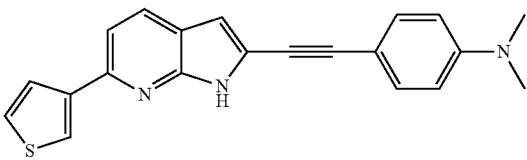 [SMILES: CN(C)c1ccc(C#Cc2cc3ccc(-c4ccsc4)nc3[nH]2)cc1] | | | |
| 25c | 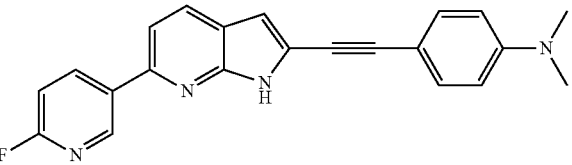 [SMILES: CN(C)c1ccc(C#Cc2cc3ccc(-c4ccc(F)nc4)nc3[nH]2)cc1] | | | |
| 28 | 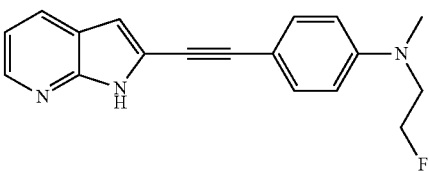 [SMILES: CN(CCF)c1ccc(C#Cc2cc3cccnc3[nH]2)cc1] | | | |
| 35 | 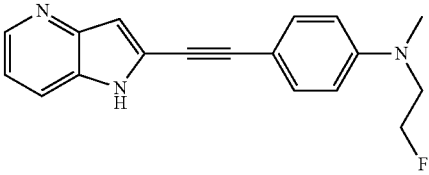 [SMILES: CN(CCF)c1ccc(C#Cc2cc3ncccc3[nH]2)cc1] | | | |

TABLE 5-continued

Ki vs Thioflavin T measurement

| Reference | Structure | Ki Aβ (nM) | Ki αsyn (nM) | Ki Tau (nM) |
|---|---|---|---|---|
| 37 | [5-fluoro-7-azaindole connected via alkyne to phenyl-N(methyl)-CH2-C(=O)-O-ethyl] | | | |
| 38 | [5-fluoro-7-azaindole connected via alkyne to phenyl-N(methyl)-CH2CH2-O-methyl] | | | |

Example 19.4 In Vitro Direct Determination of Kd and Bmax by Fluorescence

For some of the compounds, the $IC_{50}$ could not be determined because their emission spectra were confused with that of ThT. For these compounds as well as those (azaindole series) that showed significant competition with ThT, direct fluorescence measurements were performed to determine their affinity (Kd) and the density of binding sites (Bmax) to the fibers.

Fresh solutions of each test compound (2.5 mM in DMSO) are diluted in PBS pH=7.4 at concentrations between 0.5 nM and 5 μM in the presence or absence of α-syn (200 nM), Aβ1-42 (500 nM) or Tau (200 nM) fibers in a final 2 mL volume. After 1 h of incubation at RT, the binding of each compound to α-syn, A131-42 or Tau fibers is measured by fluorescence using the spectral changes of the compounds during their binding to the fibers, using the appropriate excitation/emission wavelengths (those giving the highest fluorescence variation during binding to the fibres). For each concentration of compound added to the fibres, the bound and free fractions are measured by fluorescence according to the following equation:

$$F_m = F_B B + F_F \times (T-B)$$

Where $F_m$ is the fluorescence measured in the presence of fibers at a concentration T of the compound added to the fibers, $F_B$ is the specific fluorescence of the bound compound, $F_F$ is the specific fluorescence of the free compound, and B is the concentration of the fiber bound compound at a given concentration T (Bell, J. E., "Fluorescence; Solution Studies", Spectrometry in Biochemistry, vol. I, Bell, J. E., ed., CRC Press, Inc., Boca Raton, Fla., pp. 155-194 (1981)).

The value of $F_F$ is determined by measuring the fluorescence of known concentrations of compounds in the absence of fibres. The $F_B$ value is determined by measuring the maximum fluorescence of known concentrations of compounds in the presence of saturated concentrations of α-syn, Aβ1-42, or Tau fibers.

Thus, at each point, the concentration of bound compound B is determined according to the following equation:

$$B = (F_m - F_F \times T)/(F_B - F_F)$$

The values of B thus determined versus the concentrations of the free fractions (T-B) are analyzed according to the Michaelis-Menten equation. The affinity (Kd) and density of binding sites within the fibers of α-syn, Aβ1-42 or Tau (Bmax) are determined by Scatchard analysis, which also makes it possible to highlight multiple site classes.

The results obtained are shown in Tables 6 and 7.

TABLE 6

α-syn vs Aβ Kd & Bmax measurement

| Reference | Structure | Aβ Kd1 nM | Aβ Bmax1 nmol/μmol prot (number of sites/monomer) | αsyn Kd1 nM | αsyn Bmax1 nmol/μmol prot (number of sites/monomer) |
|---|---|---|---|---|---|
| AV45 | | 1.68 ± 0.2 | 3.33 ± 0.2 (1/300) | 24.3 ± 20 | 27.9 ± 19 (1/35) |
| FDDNP | | 4.2 ± 1 | 10.2 ± 1 (1/100) | 16.1 ± 6 | 39.5 ± 10 (1/25) |
| 22a | [7-azaindole-alkyne-phenyl-N(methyl)2] | 11.8 ± 3 | 3.04 ± 0.6 (1/300) | 0.53 ± 0.2 | 69.5 ± 20 (1/14) |

TABLE 6-continued
α-syn vs Aβ Kd & Bmax measurement
| Reference | Structure | Aβ Kd1 nM | Aβ Bmax1 nmol/μmol prot (number of sites/monomer) | αsyn Kd1 nM | αsyn Bmax1 nmol/μmol prot (number of sites/monomer) |
|---|---|---|---|---|---|
| 22b | 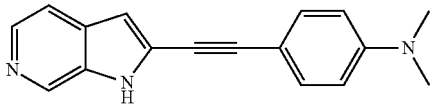 | 5.2 ± 3 | 2.3 ± 0.8 (1/400) | 1.4 ± 1 | 80.0 ± 42 (1/15) |
| 22c | 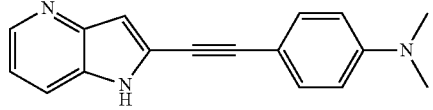 [SMILES: CN(C)c1ccc(C#Cc2cc3ncccc3[nH]2)cc1] | 2.9 ± 2 | 1.44 ± 0.6 (1/700) | 3.25 ± 0.2 | 82.5 ± 5 (1/12) |
| 22d | 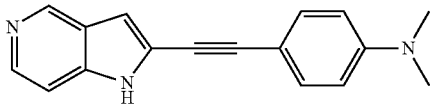 | 3.6 ± 2 | 2.4 ± 0.8 (1/400) | 1.0 ± 0.5 | 6.0 ± 1 (1/170) |
| 22f | 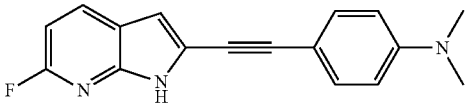 | 16.8 ± 2 | 21.6 ± 3 (1/50) | 0.79 ± 0.4 | 49.0 ± 15 (1/20) |
| 25a | 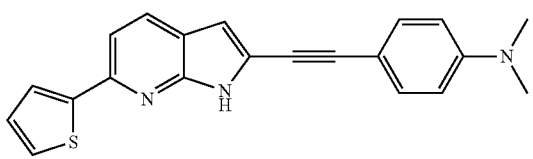 [SMILES: CN(C)c1ccc(C#Cc2cc3ccc(-c4cccs4)nc3[nH]2)cc1] | 4.9 ± 0.6 | 5.8 ± 0.32 (1/170) | 0.49 ± 0.2 | 53.5 ± 10 (1/20) |
| 25b | 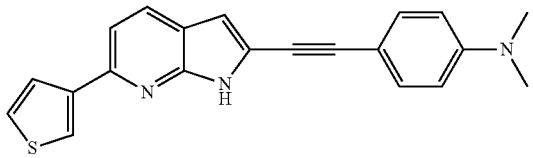 [SMILES: CN(C)c1ccc(C#Cc2cc3ccc(-c4ccsc4)nc3[nH]2)cc1] | 4.27 ± 0.6 | 11.0 ± 1 (1/90) | 0.73 ± 0.3 | 69.6 ± 23 (1/14) |
| 25c | 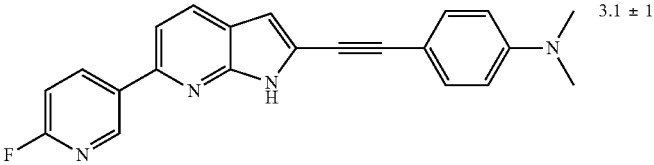 | 3.1 ± 1 | 11.0 ± 2 (1/90) | 1.27 ± 0.4 | 130 ± 30 (1/8) |
| 28 | 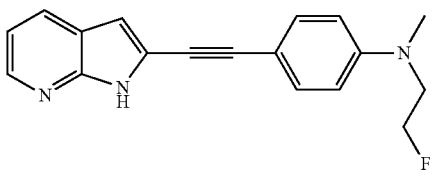 [SMILES: CN(CCF)c1ccc(C#Cc2cc3cccnc3[nH]2)cc1] | 1.2 ± 1 | 1.8 ± 0.6 (1/600) | 2.4 ± 1 | 141.5 ± 45 (1/7) |

TABLE 7

α-syn vs Tau Kd & Bmax measurement

| Reference | Structure | Tau Kd1 nM | Tau Bmax1 nmol/μmol prot (number of sites/monomer) | αsyn Kd1 nM | αsyn Bmax1 nmol/μmol prot (number of sites/monomer) |
|---|---|---|---|---|---|
| AV45 | | 19.6 ± 5 | 92.0 ± 20 (1/11) | 24.3 ± 20 | 27.9 ± 19 (1/35) |
| FDDNP | | 34.9 ± 6 | 138.5 ± 16 (1/7) | 16.1 ± 6 | 39.5 ± 10 (1/25) |
| 22a | 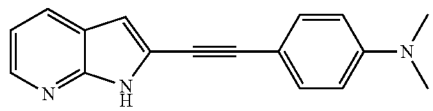 [SMILES: CN(C)c1ccc(C#Cc2cc3cccnc3[nH]2)cc1] | 0.44 ± 0.1 | 93.0 ± 15 (1/10) | 0.53 ± 0.2 | 69.5 ± 20 (1/14) |
| 22b | 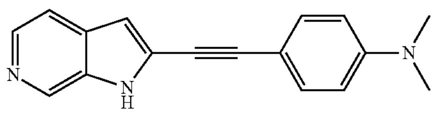 [SMILES: CN(C)c1ccc(C#Cc2cc3ccncc3[nH]2)cc1] | 0.49 ± 0.2 | 37.1 ± 10 (1/30) | 1.4 ± 1 | 80.0 ± 42 (1/15) |
| 22c | 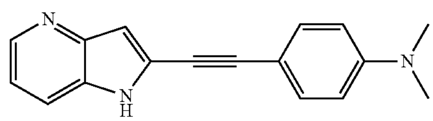 [SMILES: CN(C)c1ccc(C#Cc2cc3ncccc3[nH]2)cc1] | 0.13 ± 0.05 | 26.5 ± 5 (1/40) | 3.25 ± 0.2 | 82.5 ± 5 (1/12) |
| 22d | 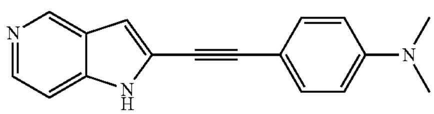 [SMILES: CN(C)c1ccc(C#Cc2cc3cnccc3[nH]2)cc1] | 2.4 ± 0.9 | 12.5 ± 5 (1/80) | 1.0 ± 0.5 | 6.0 ± 1 (1/170) |
| 25a | 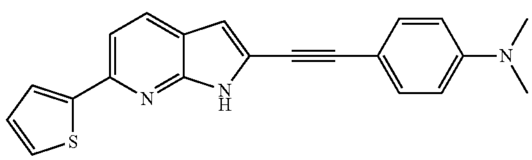 [SMILES: CN(C)c1ccc(C#Cc2cc3ccc(-c4cccs4)nc3[nH]2)cc1] | 1.67 ± 0.5 | 70.4 ± 4 (1/10) | 0.49 ± 0.2 | 53.5 ± 10 (1/20) |
| 28 | 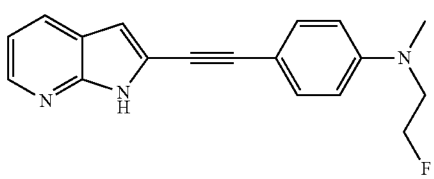 [SMILES: CN(CCF)c1ccc(C#Cc2cc3cccnc3[nH]2)cc1] | 0.97 ± 0.4 | 46.5 ± 5 (1/20) | 2.4 ± 1 | 141.5 ± 45 (1/7) |

Example 19.5 In Vivo Evaluation of a Fluorine-18-Labelled α-Syn Tracer

The objective is to determine whether the tracer binds in vivo to the α-syn fibers after intravenous injection.

Animal Model: Adult male rats of Wistar strain.

Preparation of fiber: α-syn fibers produced according to the protocol described in Example 19.2 were centrifuged at 16000×g for 20 min to twice and resuspended in PBS pH 7.4.

Preparation of the animals: the fibers are implanted by stereotactic surgery in the right striatum of anesthetized animal (Maia et al. Synapse 2012, 66:573-83).

In vivo study: the fiber-bearing animal receives an intravenous injection of the tracer to be tested. From the moment of injection, imaging is carried out using a dedicated system (eXplore VISTA/CT) which records the intracerebral accumulation of radioactivity for 70 minutes. The analysis of the images obtained can quantify the binding of the tracer implanted in the striatum compared to the control side (Sérrière et al. Nucl. Med. Biol. 2014, 41:103-13; Sérrière et al. Neurobiol. Aging 2015, 36:1639-52).

Example 19.6 In Vivo Evaluation of a Fluorine-18-Labelled α-Syn Tracer

The objective is to determine whether the tracer has the blood-brain barrier (BBB) crossing properties in sufficient quantities to be used as a PET imaging tracer. In addition, bone fixation can be qualified, which reflects the degree of defluorination of the tracer in vivo.

Animal Model: Adult male rats of Wistar strain.

In vivo study: the healthy animal receives an intravenous injection of the tracer test (molecule 28).

From the moment of injection, imaging is carried out using a dedicated system (PET/CT) which records the intracerebral accumulation of radioactivity (Sérrière et al. Nucl. Med. Biol. 2014, 41:103-13; Sérrière et al. Neurobiol. Aging 2015, 36:1639-52). At the end of the imaging, the animal is euthanized; the brain and a bone fragment (femur) are collected, weighed and their radioactivity is measured.

This method allows to precisely quantify the accumulation of the tracer in the tissues. The results are expressed as a percentage of the injected tracer dose/g of tissue (% DI/g).
Results:
Passing of the BBB (≈0.4% DI/g)
Weak binding to bone (0.3% DI/g)

Example 20. Procedure M (Buchwald Coupling)

Under argon, $Pd_2dba_3$ (0.05 eq.) and BINAP (0.075 mmol) are added to an anhydrous toluene degassed solution of 0.3 M concentration containing the amine (1.0 eq.), 1,4-dibromobenzene (1.0 eq.) and tBuONa (1.2 eq.). After 16 h at 80° C., the solvent was evaporated under reduced pressure. Then, the reaction mixture was concentrated under reduced pressure, before being purified by flash column chromatography on silicagel.

Example 21. Procedure I (Preparation of True Alkynes)

Example II 21.1

Under argon, $Pd(PPh_3)_2Cl_2$ (0.05 eq.) and CuI (0.1 mmol) are added to a degassed piperidine solution of 0.1 M concentration containing l'ethynyltrimethylsilane (4.0 eq.), the brominated derivative (1.0 eq.) and triphenylphosphine (0.2 eq.). After 16 h at 85° C., the solvent was evaporated under reduced pressure. Then, the reaction mixture was purified by flash column chromatography on silicagel. Then the alkyne intermediate is reacted with $K_2CO_3$ (1.5 eq.) in methanol (0.03 M). After 3 h at room temperature, the solvent was evaporated under reduced pressure. The crude is dissolved in 10 mL of ethyl acetate. Then the organic phase was washed with brine (3×10 mL). Then the organic phase is dried with $MgSO_4$, filtered through cotton and evaporated under reduced pressure. Finally, the crude is purified by flash column chromatography on silicagel with eluting agent (ethyl acetate/petroleum ether) to afford the true alkyne.

Example 21.2. 12

The catalyst [$Pd(PPh_3)_2Cl_2$] (0.025 eq.) was added to a degassed solution of the brominated 40 (1.0 eq.), Ethynyltrimethylsilane (1.4 eq.), CuI (0.05 eq.) in $THF/Et_3N$ (1/1). The mixture was stirred at room temperature for 20 h under argon. Then, the reaction mixture was concentrated under reduced pressure before being purified by flash column chromatography on silica gel with eluting agent (ethyl acetate/petroleum ether=2/98) to obtain the silylated intermediate which is reacted with KOH (2.0 eq.) in methanol. After 10 min stirring at room temperature, dichloromethane and water are added. The organic phases are extracted 3 times with dichloromethane. They are combined, dried over $MgSO_4$, filtered through cotton and evaporated to dryness to yield the expected alkyne.

Example 22. Procedure J (Desylilation)

At 0° C. under argon, a solution of TBAF in THF (C=1 M, 1.5 eq.) was added dropwise to the reaction mixture containing the silylated compound (1.0 eq.) diluted in THF. After 2 h at room temperature, water (20 ml) and ethyl acetate (20 ml) are successively added. The organic phases are extracted 3 times with ethyl acetate (20 ml), then they were combined, dried with MgSO filtered through cotton and evaporated under reduced pressure. Finally, the crude is purified by flash column chromatography on silica gel with eluting agent (methanol/dichloromethane) to yield the primary alcohol.

Example 23. Procedure (Reductive Amination)

The aldehyde (1.0 eq.) is reacted with an amine (6.0 eq.) in the presence of $NaBH(OAc)_3$ (10 eq.) and $Et_3N$ (11 equiv.) in DCE. After 4 h at room temperature, the mixture was evaporated to dryness and then 10 ml of a saturated solution of $NaHCO_3$ and 10 ml of ethyl acetate are added. The organic phase was extracted with ethyl acetate (3×10 ml). The organic phases are combined and washed with a saturated NaCl solution and then dried over $MgSO_4$, filtered through cotton and evaporated to dryness. The crude was purified by flash chromatography column on silica gel to yield the expected compound.

Example 24. 2-{2-[4-(2-fluoroethoxy)phenyl]ethynyl}-1H-pyrrolo[2,3-b]pyridine 43

2-{2-[4-(2-fluoroethoxy)phenyl]ethynyl}-1H-pyrrolo[2,3-b]pyridine was synthesized in 3 steps. Initially, the corresponding alkyne was prepared in 2 steps and then we did the Sonogashira reaction with the azaindole to obtain the final compound.

Example 24.1 Preparation of 1-ethynyl-4-f2-fluoroethoxy) benzene 39

The alkyne 39 was prepared in three steps by starting from 4-iodophenol 40. The first step has been described by Hirose et al. (Chemical Communications, 2009, 39 p 5832-.5834) and for the last two steps we used the method described by Ouach et al. (European Journal of Medicinal Chemistry, 2016, vol. 107, p. 153-164)

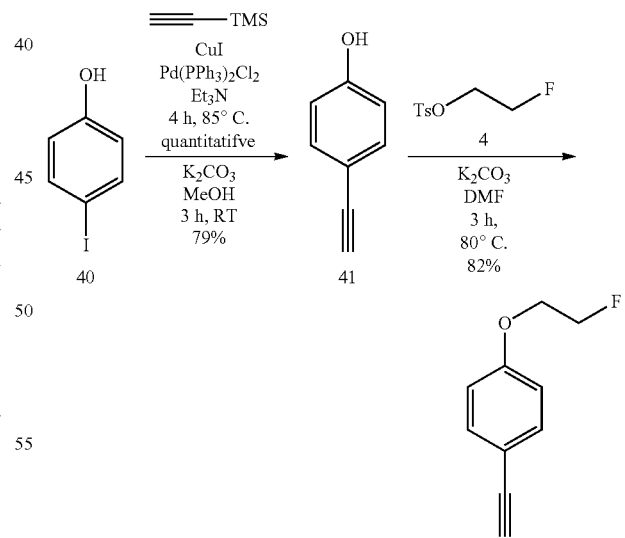

The catalyst [$Pd(PPh_3)_2Cl_2$] (39 mg, 0.055 mmol, 0.03 eq.) was added to a degassed solution of iodized 39 (400 mg, 1.82 mmol, 1.0 eq.), ethynyltrimethylsilane (0.386 ml, 2.73 mmol, 1.5 eq.), CuI (10.4 mg, 0.055 mmol, 0.03 eq.) in 6 ml of $Et_3$ N. The mixture was stirred at 85° C. room for 4 h under argon atmosphere. Then, the reaction mixture was concentrated under reduced pressure before being purified by flash column chromatography on silica gel with eluting agent (ethyl acetate/petroleum ether=20/80) to obtain 200 mg of the intermediate silyl which is reacted with K$_2$CO$_3$ (351 mg, 2.4 eq.) in 15 ml of methanol. After 3 h stirring at room temperature, the solution is filtered through cotton. After evaporation to dryness, the crude is purified by flash column chromatography on silica gel with eluting agent (ethyl acetate/petroleum ether=30/70) to obtain the alkyne 41 as a brown solid 79% yield over 2 steps.

This latter is reacted with the tosylated derivative 42 in the presence of K$_2$CO3 in DMF. After 3 h at 80° C., the reaction mixture was cooled and 10 ml of H$_2$O is introduced. The organic phase was extracted with ethyl acetate (3×10 ml). Then the organic phases are combined, dried with MgSO$_4$ and filtered over cotton. After evaporation under reduced pressure, the crude was purified by flash column chromatography on silica gel with eluting agent (ethyl acetate/petroleum ether=15/85) to obtain the alkyne 39 in form of a colorless oil with a yield of 82%.

Example 24.2 2-{2-[4-(2-fluoroethoxy)phenyl]ethynyl}-1H-pyrrolo[2,3-b]pyridine 43

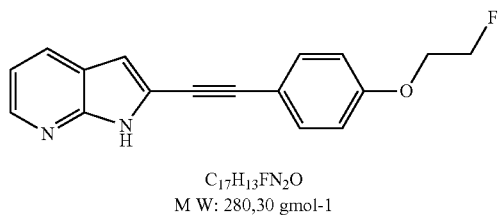 [SMILES: FCCOc1ccc(C#Cc2cc3cccnc3[nH]2)cc1]

C$_{17}$H$_{13}$FN$_2$O
M W: 280,30 gmol-1

The compound was prepared according to procedure C1 and purified by flash column chromatography on silica gel (ethyl acetate/petroleum ether=30/70). Beige solid (38%), mp 250-252° C., Rf=0.20 (ethyl acetate/petroleum ether=30/70). IR (v, cm$^{-1}$, neat) 3122, 3054, 2978, 2883, 2790, 1603, 1582, 1534, 1498, 1277, 1249, 1175, 1078, 1051, 921. $^1$H NMR (400 MHz, DMSO-d$_6$, 20° C.) δ 12.11 (s, 1H), 8.22 (s, 1H), 7.90 (d, J=7.9 Hz, 1H), 7.49 (d, J=8.6 Hz, 2H), 7.10-6.95 (m, 4H), 6.74 (s, 1H), 4.82 (t, J=6.2 Hz, 1H), 4.62 (t, J=6.2 Hz, 1H), 4.32 (t, J=5.7 Hz, 1H), 4.20 (t, J=5.7 Hz, 1H). $^{13}$C NMR (63 MHz, DMSO-d$_6$, 20° C.) δ 159.2 (Cq), 144.7 (CH), 133.5 (2×CH), 128.7 (CH), 120.0 (Cq), 119.7 (Cq), 116.8 (CH), 115.6 (2×CH), 114.4 (Cq), 106.2 (CH), 93.2 (Cq), 82.6 (d, J=151.0 Hz, CH$_2$), 81.4 (Cq), 67.8 (d, J=18.8 Hz, CH$_2$). $^{19}$F NMR (376 MHz, DMSO-d$_6$, 20° C.) δ -222.2. HRMS (+ESI) calculated for C$_{17}$H$_{13}$FN$_2$O (M+H+): 281.1084, found: 281.1085.

Example 25: 2-(2-{4-[(2-fluoroethoxy)methyl]phenyl}ethynyl)-1H-pyrrolo[2,3-b]pyridine 44

2-(2-{4-[(2-fluoroethoxy)methyl]phenyl}ethynyl)-1H-pyrrolo[2,3-b]pyridine 44 was synthesized in 2 steps. Initially, the corresponding alkyne 45 was prepared in one step and then we did the Sonogashira reaction with the azaindole to get the final compound.

Example 25.1 Synthesis of 1-ethynyl-4-((2-fluoroethoxy)methyl)benzene 45 (US2015/196672 A1)

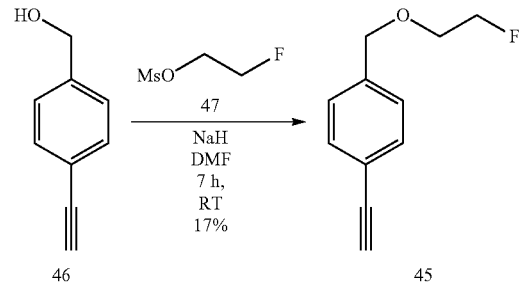

Under argon, 100 mg of alkyne 46 (0.756 mmol, 1.0 eq.) is dissolved in 5 ml of DMF. At 0° C., 51 mg of NaH (50% in mineral oil, 1.06 mmol, 1.4 eq.) was added portionwise and after 5 minutes, 118 mg of mesyl 47 (0.832 mmol, 1.1 eq.) is added drop by drop. After 7 h at room temperature, 10 ml of H$_2$O are added and the organic phase was extracted with ethyl acetate (3×10 ml). Then the organic phases are combined, dried and filtered over cotton. After evaporation under reduced pressure, the crude was purified by flash column chromatography on silica gel with eluting agent (ethyl acetate/petroleum ether=5/45) to obtain alkyne 45 as a colorless oil with a yield of 17%. $^1$H NMR (250 MHz, CDCl$_3$) δ 7.44 (d, J=8.2 Hz, 2H), 7.28 (d, J=8.2 Hz, 2H), 4.68-4.61 (m, 1H), 4.56 (s, 2H), 4.50-4.42 (m, 1H), 3.77-3.72 (m, 1H), 3.65-3.60 (m, 1H), 3.03 (s, 1H). CAS Number: 1562413-13-1.

Example 25.2 2-(2-{4-[(2-fluoroethoxy)methyl]phenyl}ethynyl)-1H-pyrrolo[2,3-b]pyridine 44

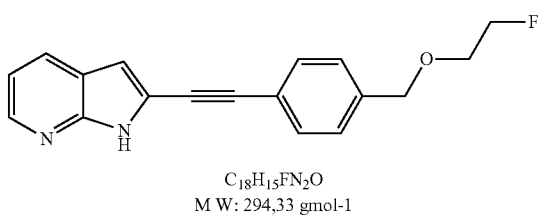 [SMILES: FCCOCc1ccc(C#Cc2cc3cccnc3[nH]2)cc1]

C$_{18}$H$_{15}$FN$_2$O
M W: 294,33 gmol-1

The compound was prepared according to procedure C1 and purified by flash column chromatography on silicagel (ethyl acetate/petroleum ether=30/70). Yellow solid (57%), mp 192-194° C., Rf=0.18 (ethyl acetate/petroleum ether=30/70). IR (v, cm$^{-1}$, neat) 3122, 3054, 2978, 2883, 2790, 1603, 1582, 1534, 1498, 1277, 1249, 1175, 1078, 1051, 921. $^1$H NMR (400 MHz, CDCl$_3$, 20° C.) δ 10.81 (s, 1H), 8.39 (s, 1H), 7.93 (s, 1H), 7.58 (s, 2H), 7.40 (s, 2H), 7.12 (s, 1H), 6.78 (s, 1H), 4.73-4.51 (m, 4H), 3.76 (d, J=29.5 Hz, 2H). $^{13}$C NMR (101 MHz, CDCl$_3$, 20° C.) δ 148.4 (Cq), 144.0 (CH), 138.3 (Cq), 131.7 (2×CH), 129.1 (CH), 127.7 (2×CH), 121.6 (Cq), 120.6 (Cq), 119.8 (Cq), 116.6 (CH), 106.6 (CH), 93.4 (Cq), 83.9 (d, J=169.4 Hz, CH$_2$) 81.5 (Cq), 72.9 (CH$_2$), 69.6 (d, J=19.7 Hz, CH$_2$). $^{19}$F NMR (376 MHz, DMSO-d$_6$, 20° C.) δ -221.4. HRMS (+ESI) calculated for C$_{18}$H$_{15}$FN$_2$O (M+H+): 295.1241, found: 295.1242.

Example 26: 2-(2-{4-[2-(2-fluoroethoxy)ethoxy]phenyl}ethynyl)-1H-pyrrolo[2,3-b]pyridine 48

2-(2-{4-[2-(2-fluoroethoxy)ethoxy]phenyl}ethynyl)-1H-pyrrolo[2,3-b]pyridine 48 was synthesized in 3 steps. Initially, the corresponding alkyne 49 was prepared in 2 steps from tosyl 50 and then we did the Sonogashira reaction with the azaindole to obtain the final compound.

Example 26.1 Synthesis of 1-ethynyl-4-[2-(2-fluoroethoxy)ethoxyl]benzene 49

The alkyne 49 was obtained in three steps starting from ditosyl 50 which was prepared according to the method of Herbert (Organic Letters, 2013, 15, 13 p 3334-. 3337)

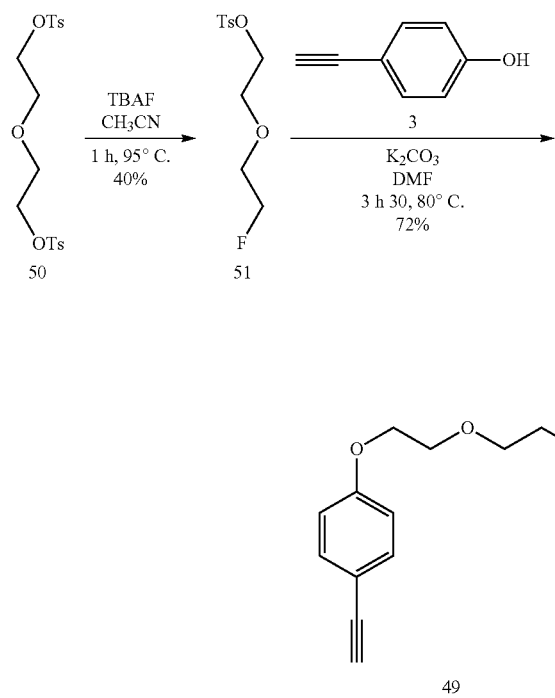

Synthesis of Fluorinated 51

Under argon, the compound 50 (300 mg, 0.724 mmol, 1.0 eq.) is dissolved in 17 ml of $CH_3CN$. Then TBAF (0.796 ml, 0.796 mmol, 1.1 eq.) was added drop by drop. At the end of 1 h at 95° C., the reaction mixture was cooled to room temperature and evaporated under reduced pressure. The crude was purified by flash column chromatography on silica gel with eluting agent (ethyl acetate/petroleum ether=2/4) to obtain the fluorinated 51 as a colorless oil with a yield of 40%. $^1$H NMR (400 MHz, $CDCl_3$) δ 7.83 (d, J=8.3 Hz, 2H), 7.37 (d, J=8.3 Hz, 2H), 4.61-4.52 (m, 1H), 4.47-4.43 (m, 1H), 4.24-4.14 (m, 2H), 3.78-3.70 (m, 3H), 3.68-3.63 (m, 1H), 2.47 (s, 3H). CAS Number: 1118567-11-5

Synthesis of alkyne 49

The alkyne 41 (43.4 mg, 0.367 mmol, 1.0 eq.) and the fluorinated 51 (107.0 mg, 0.408 mmol, 1.1 eq.) are placed in the presence of $K_2CO_3$ (101.3 mg, 0.734 mmol, 2.0 eq.) in 3 ml of DMF. After 3 h at 80° C., the reaction mixture was cooled and 10 ml of $H_2O$ is introduced. The organic phase was extracted with ethyl acetate (3×10 ml). Then the organic phases are combined, dried with MgSO4 and filtered through cotton. After evaporation under reduced pressure, the crude was purified by flash column chromatography on silica gel with eluting agent (ethyl acetate/petroleum ether=5/45) to give alkyne 49 as a colorless oil with a yield of 72%. Rf=0.65 (ethyl acetate/petroleum ether=20/80). IR (□, cm−1, neat) 3286, 2889, 2359, 2105, 1604, 1571, 1505, 1454, 1356, 1287, 1245, 1171, 1134, 1046, 927, 873. $^1$H NMR (250 MHz, $CDCl_3$, 20° C.) δ 7.39 (d, J=8.8 Hz, 2H), 6.83 (d, J=8.8 Hz, 2H), 4.70-4.40 (m, 2H), 4.15-4.08 (m, 2H), 3.90-3.80 (m, 3H), 3.76-3.68 (m, 1H), 2.97 (s, 1H). $^{13}$C NMR (63 MHz, $CDCl_3$, 20° C.) δ 159.0 (Cq), 133.6 (2×CH), 114.6 (2×CH), 114.5 (Cq), 83.1 (d, J=169.1 Hz, $CH_2$), 83.6 (Cq), 75.9 (CH), 70.6 (d, J=19.7 Hz, $CH_2$), 69.8 ($CH_2$), 67.5 ($CH_2$). $^{19}$F NMR (235 MHz, $CDCl_3$, 20° C.) δ −223.0. HRMS (+ESI) calculated for $C_{12}H_{13}FO_2$ (M+H+): 209.0972, found: 209.09714.

Example 26.2 2-(2-{4-[2-(2-fluoroethoxy)ethoxyl]phenyl}ethynyl)-1H-pyrrolo[2,3-b]pyridine 48

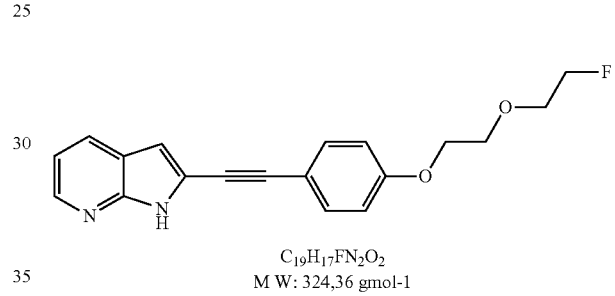

$C_{19}H_{17}FN_2O_2$
M W: 324,36 gmol-1

The compound was prepared according to procedure C1 and purified by flash column chromatography on silica gel (ethyl acetate/petroleum ether=10/90). yellowish solid (75%), mp 156-158° C., Rf=0.33 (ethyl acetate/petroleum ether=10/90). IR (v, cm$^{-1}$, neat) 3122, 3054, 2978, 2883, 2790, 1603, 1582, 1534, 1498, 1277, 1249, 1175, 1078, 1051, 92. $^1$H NMR (400 MHz, $CDCl_3$, 20° C.) δ 9.97 (s, 1H), 8.35 (d, J=4.7 Hz, 1H), 7.90 (dd, J=7.8, 1.5 Hz, 1H), 7.51 (d, J=8.7 Hz, 2H), 7.10 (dd, J=7.9, 4.7 Hz, 1H), 6.94 (d, J=8.7 Hz, 2H), 6.73 (s, 1H), 4.73-4.47 (m, 2H), 4.19 (m, 2H), 3.92 (m, 3H), 3.83 (m, 2H). $^{13}$C NMR (63 MHz, $CDCl_3$, 20° C.) 159.6 (Cq), 148.7 (Cq), 144.4 (CH), 138.2 (Cq), 133.6 (2×CH), 129.3 (CH), 120.5 (Cq) 116.9 (CH), 115.3 (2×CH), 115.12 (Cq), 106.8 (CH), 92.8 (Cq), 83.7 (d, J=177.2 Hz, $CH_2$), 80.7 (Cq), 71.1 (d, J=19.7 Hz, $CH_2$), 70.4 ($CH_2$), 67.7 ($CH_2$). $^{19}$F NMR (235 MHz, $CDCl_3$, 20° C.) δ. −223.0. HRMS (+ESI) calculated for $C_{19}H_{17}FN_2O_2$ (M+H+): 325.1326, found: 325.1347.

Example 27. 4-((1H-pyrrolo[2,3-b]pyridin-2-yl)ethynyl)-N-benzyl-N-(2-fluoroethyl)aniline 52

4-((1H-pyrrolo[2,3-b] pyridin-2-yl) ethynyl)-N-benzyl-N-(2-fluoroethyl) aniline was synthesized in 5 steps from the benzylamine 54. initially, the corresponding alkyne 53 was prepared in 4 steps from the benzylamine 54 and then we did the Sonogashira reaction with azaindole to obtain the final compound.

Example 27.1 Synthesis of N-benzyl-4-ethynyl-N-(2-fluoroethyl)aniline 53

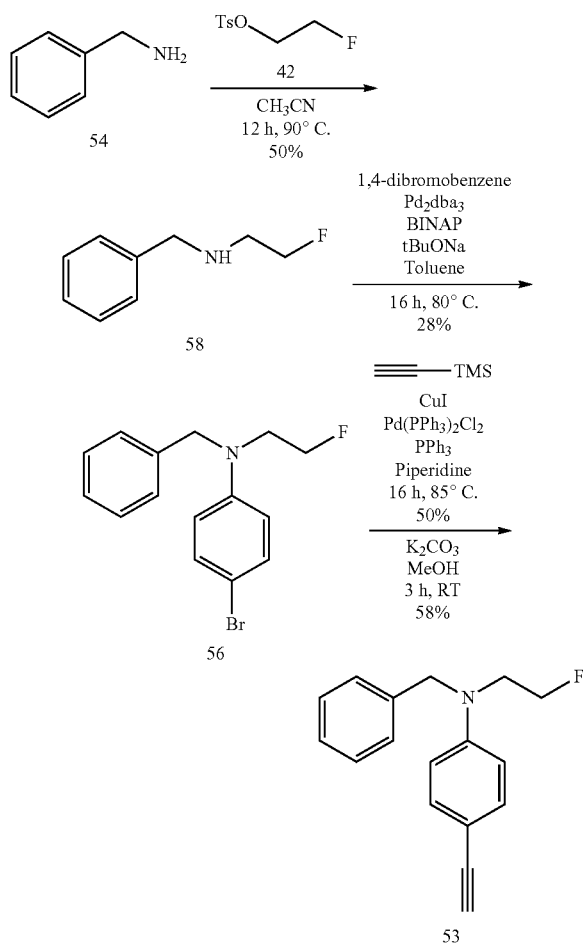

Synthesis of Amine 55

Under argon, 130 mg of compound 42 (0.985 mmol, 1.0 eq.) is dissolved in 3 ml of $CH_3CN$. After adding 0.40 ml of benzyl amine 54 (2.38 mmol, 4.0 eq.), the reaction mixture was heated at 90° C. for 12 h. After cooling the reaction mixture, 10 ml of a saturated solution of $NaHCO_3$ is added. Then, the organic phase is extracted with DCM (3×10 ml). Then the organic phases are combined, dried with $MgSO_4$ and filtered over cotton. After evaporation under reduced pressure, the crude was purified by flash column chromatography on silica gel with eluting agent (methanol/dichloromethane/$NH_4OH$=2/48/0.5) to afford the amine 55 as a colorless oil with a yield of 50%. $^1H$ NMR (250 MHz, $CDCl_3$) δ 7.31 (m, 5H), 4.69-4.32 (m, 2H), 3.82 (s, 2H), 3.02-2.73 (m, 2H). CAS Number: 122974-04-3.

Synthesis of Amine 56

Compound 56 was prepared according to procedure D and purified by flash column chromatography on silicagel (ethyl acetate/petroleum ether-1/49). Colorless oil (28%), Rf=0.50 (ethyl acetate/petroleum ether=5/45). IR (v, $cm^{-1}$, neat) 3028, 2951, 2359, 1591, 1493, 1451, 1386, 1352, 1228, 1193, 1173, 1101, 1080, 1046, 1003, 912, 882. $^1H$ NMR (250 MHz, $CDCl_3$, 20° C.) δ 7.39-7.19 (m, 7H), 6.66-6.57 (m, 2H), 4.71 (t, J=5.3 Hz, 1H), 4.66-4.55 (m, 3H), 3.76 (dt, J=23.5, 5.3 Hz, 2H). $^{13}C$ NMR (63 MHz, $CDCl_3$, 20° C.) δ 147.25 (Cq), 137.89 (Cq), 131.9 (2×CH), 128.7 (2×CH), 127.09 (Cq), 126.4 (2×CH), 114.2 (2×CH), 108.9 (Cq), 81.6 (d, J=21.5 Hz, $CH_2$), 55.0 ($CH_2$), 51.3 (d, J=21.5 Hz, $CH_2$). $^{19}F$ NMR (235 MHz, $CDCl_3$, 20° C.) δ. −221.7. HRMS (+ESI) calculated for $C_{15}H_{15}BrFN$ (M+H+): 308.0444, found: 308.0445.

Synthesis of Alkyne 53

The alkyne 11 was prepared according to procedure E and purified by flash column chromatography on silica gel (ethyl acetate/petroleum ether=2/48). Colorless oil (29% over two steps), Rf=0.50 (ethyl acetate/petroleum ether=2/48). IR (v, $cm^{-1}$, neat) 3028, 2951, 2359, 1591, 1493, 1451, 1386, 1352, 1228, 1193, 1173, 1101, 1080, 1046, 1003, 912, 882. $^1H$ NMR (400 MHz, $CDCl_3$, 20° C.) δ 7.37-7.10 (m, 7H), 6.68-6.54 (m, 2H), 4.62 (s, 2H), 4.61 (dt, J=47.1, 5.3 Hz, 2H), 3.74 (dt, J=23.3, 5.3 Hz, 2H), 2.93 (s, 1H), 4.76-4.58 (m, 3H). $^{13}C$ NMR (101 MHz, $CDCl_3$, 20° C.) δ 147.3 (Cq), 137.8 (Cq), 133.4 (2×CH), 128.7 (2×CH), 127.09 (Cq), 126.9 (2×CH), 112.0 (2×CH), 108.98 (Cq), 84.1 (Cq), 81.5 (d, J=21.5 Hz, $CH_2$), 75.0 (CH), 54.0 ($CH_2$), 50.9 (d, J=21.5 Hz, $CH_2$). $^{19}F$ NMR (376 MHz, $CDCl_3$, 20° C.) δ. −221.7. HRMS (+ESI) calculated for $C_{17}H_{16}FN$ (M+H+): 254.1339, found: 254.1344.

Example 27.2 4-((1H-pyrrolo[2,3-b]pyridin-2-yl)ethynyl)-N-benzyl-N-(2-fluoroethyl)aniline 52

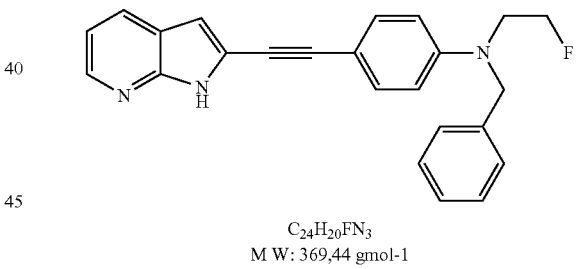

$C_{24}H_{20}FN_3$
M W: 369,44 gmol-1

The compound was prepared according to procedure C1 and purified by flash column chromatography on silica gel (ethyl acetate/petroleum ether=30/70). Yellow solid (66%), mp 184-186° C., Rf=0.20 (ethyl acetate/petroleum ether=30/70). IR (v, $cm^{-1}$, neat) 3054, 2885, 2201, 1601, 1538, 1508, 1401, 1355, 1279, 1236, 1189, 1050, 811. $^1H$ NMR (250 MHz, DMSO-$d_6$, 20° C.) δ 12.06 (s, 1H), 8.23 (m, 1H), 7.91 (d, J=7.9 Hz, 1H), 7.42-7.25 (m, 3H), 7.23 (t, J=7.6 Hz, 2H), 7.07 (dd, J=7.6, 4.7 Hz, 1H), 6.82-6.64 (m, 2H), 4.70 (s, 1H), 4.66 (dt, J=47.8, 5.2 Hz, 3H), 3.85 (dt, J=25.5, 5.2 Hz, 2H). $^{13}C$ NMR (63 MHz, DMSO-$d_6$, 20° C.) δ 150.5 (Cq), 148.5 (Cq), 144.2 (CH), 138.7 (Cq), 133.1 (2×CH), 129.2 (2×CH), 128.6 (CH), 127.5 (CH), 126.9 (2×CH), 120.4 (Cq), 120.2 (Cq), 116.6 (CH), 112.8 (2×CH), 108.4 (Cq), 105.2 (CH), 94.3 (Cq), 83.7 (Cq), 80.8 (d, J=168.8 Hz, $CH_2$), 53.7 ($CH_2$). $^{19}F$ NMR (235 MHz, DMSO-$d_6$, 20° C.) δ. −221.7. HRMS (+ESI) calculated for $C_{24}H_{20}FN_3$ (M+H+): 370.1714, found: 370.1413.

Example 28 N-(4-((1H-pyrrolo[2,3-b] pyridin-2-yl) ethynyl)phenyl)-N-(2-fluoroethyl)benzenesulfonamide 57

N-(4-((1H-pyrrolo[2,3-b] pyridin-2-yl) ethynyl) phenyl)-N-(2-fluoroethyl) benzenesulfonamide 57 was synthesized in 3 steps from alkyne 59. Initially, the corresponding alkyne 58 was prepared in 2 steps and then we did the Sonogashira reaction with azaindole to obtain the final compound.

Example 28.1 Synthesis of N-(4-ethynylphenyl)-N-(2-fluoroethyl)benzenesulfonamide 58

The synthesis of alkyne 58 is obtained in two steps starting from alkyne 59. The alkyne 60 was prepared using the conditions of Sakai et al. (Macromolecules, 2012, 45, 20 from 8221 to 8227.7).

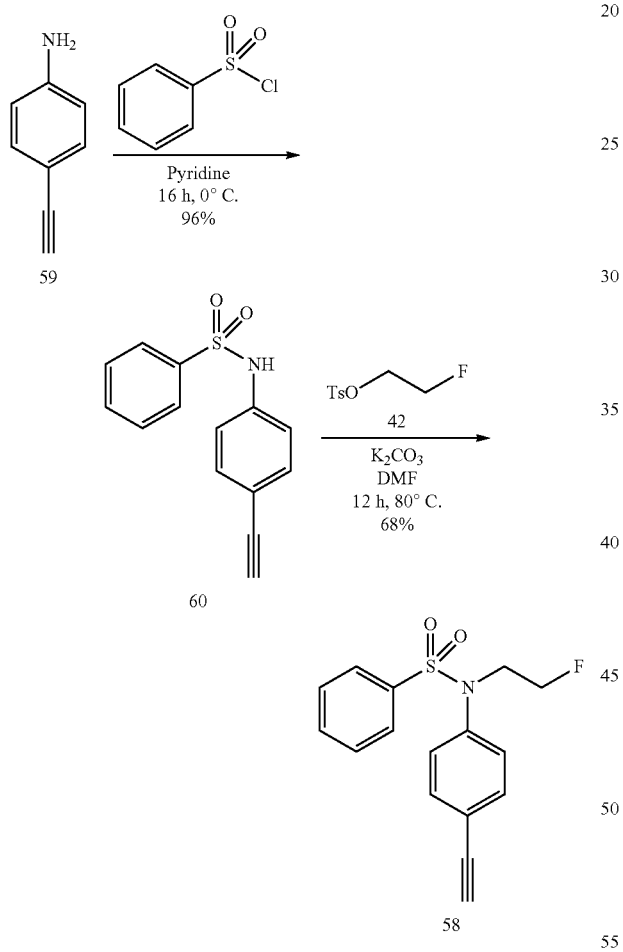

Synthesis of Alkyne 60

Under argon, alkyne 59 (100 mg, 0.854 mmol, 1.05 eq.) is dissolved in pyridine. At 0° C., benzenesulfonyl chloride (0.10 ml, 0.811 mmol, 1.0 eq.) is added dropwise. After 16 h at 0° C., 10 ml of a 1M HCl solution is added slowly. Then, the organic phase is extracted with ethyl acetate (3×10 ml). Then the organic phases are combined, dried with MgSO$_4$ and filtered over cotton. After evaporation under reduced pressure, the alkyne 60 is obtained without purification in a yield of 96% as a yellowish solid. $^1$H NMR (250 MHz, CDCl$_3$) δ 7.83-7.73 (m, 2H), 7.58-7.31 (m, 5H), 7.02 (d, J=8.6 Hz, 2H), 6.57 (sl, 1H), 3.05 (s, 1H). CAS Number: 383147-75-9.

Synthesis of N-(4-ethynylphenyl)-N-(2-fluoroethyl) benzenesulfonamide 58

The alkyne 60 (50.0 mg, 0.194 mmol, 1.0 eq.) and the fluorinated 42 (51 mg, 0.233 mmol, 1.2 eq.) are placed in the presence of K$_2$CO$_3$ (53.5 mg, 0.328 mmol, 2.0 eq.) in 2 ml of DMF. After 12 h at 80° C., the reaction mixture was cooled to room temperature. After evaporation under reduced pressure, the crude was purified by flash column chromatography on silicagel eluting (ethyl acetate/petroleum ether=20/80) to give alkyne 58 as a colorless oil with a yield of 68%. Rf=0.50 (ethyl acetate/petroleum ether=20/80). IR (n, cm−1, neat) 3285, 2959, 2360, 1601, 1500, 1446, 1347, 1265, 1228, 1164, 1080, 1046, 1017, 940, 903, 842. $^1$H NMR (250 MHz, CDCl$_3$, 20° C.) δ 7.66-7.42 (m, 7H), 7.11-6.97 (m, 2H), 4.53 (dt, J=46.8, 5.3 Hz, 2H), 4.51-4.43 (m, 1H), 4.62-4.55 (m, 1H), 3.90 (dt, J=22.1, 5.3 Hz, 2H), 3.14 (s, 1H). $^{13}$C NMR (63 MHz, CDCl$_3$, 20° C.) δ 139.7 (Cq), 138.1 (Cq), 133.0 (3×CH), 129.0 (2×CH), 128.9 (2×CH), 127.6 (2×CH), 122.2 (Cq), 82.6 (Cq), 81.3 (d, J=172.4 Hz), 78.6 (CH), 51.1 (d, J=22.7 Hz). $^{19}$F NMR (235 MHz, CDCl$_3$, 20° C.) δ −223.0. HRMS (+ESI) calculated for C$_{16}$H$_{14}$FNO$_2$S (M+H+): 304.0802, found: 304.0802.

Example 28.2 N-(4-((1H-pyrrolo[2,3-b] pyridin-2-yl)ethynyl)phenyl)-N-(2-fluoroethyl)benzenesulfonamide 57

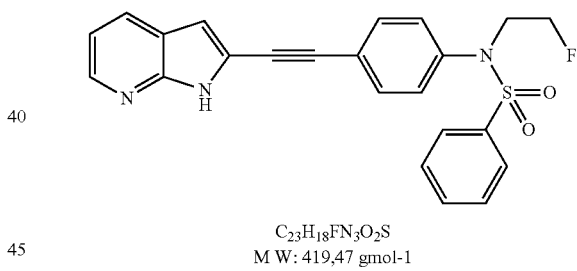

C$_{23}$H$_{18}$FN$_3$O$_2$S
M W: 419,47 gmol-1

The compound was prepared according to procedure C1 and purified by flash column chromatography on silica gel (ethyl acetate/petroleum ether=30/70). Yellow solid (51%), mp 202-204° C., Rf=0.33 (ethyl acetate/petroleum ether=10/90). IR (v, cm$^{-1}$, neat) 3124, 3058, 2962, 2890, 2358, 2219, 1581, 1537, 1496, 1446, 1329, 1286, 1229, 1155, 1123, 1084, 1050, 1017, 956, 937, 912, 836, 808, 762. $^1$H NMR (250 MHz, DMSO-d$_6$, 20° C.) δ 12.25 (s, 1H), 8.32-8.27 (m, 1H), 7.98 (d, J=7.9 Hz, 1H), 7.75-7.71 (m, 1H), 7.64-7.60 (m, 4H), 7.57 (d, J=8.2 Hz, 2H), 7.17 (d, J=8.2 Hz, 2H), 7.14-7.09 (m, 1H), 6.85 (s, 1H), 4.53-4.48 (m, 1H), 4.42-4.37 (m, 1H), 4.01-3.97 (m, 1H), 3.93 (m, 1H). $^{13}$C NMR (63 MHz, DMSO-d$_6$ 20° C.) δ 206.9 (Cq), 148.8 (Cq), 145.1 (CH), 139.7 (Cq), 137.9 (Cq), 133.9 (CH), 132.5 (2×CH), 129.9 (2×CH), 129.3 (CH), 129.02 (2×CH), 127.7 (CH), 121.6 (CH), 119.9 (Cq), 119.1 (Cq), 116.9 (CH), 107.0 (CH), 92.34 (Cq), 83.7 (Cq), 81.7 (d, J=168.8 Hz, CH$_2$), 51.0 (d, J=20.2 Hz, CH$_2$), $^{19}$F NMR (235 MHz, DMSO-d$_6$, 20° C.) δ. −222.0. HRMS (+ESI) calculated for C$_{23}$H$_{18}$FN$_3$O$_2$S (M+H+): 420.1176, found: 420.1174.

Example 29 2-((4-(((3-fluorobenzyl)oxy)methyl) phenyl)ethynyl)-1H-pyrrolo[2,3-b]pyridine 61

Example 29.2 2-((4-(((3-fluorobenzyl)ox)methyl) phenyl)ethynyl)-1H-pyrrolo[2,3-b]pyridine 61

2-((4-(((3-fluorobenzyl)oxy)methyl)phenyl)ethynyl)-1H-pyrrolo[2,3-b]pyridine was synthesized in 2 steps from the alkyne 46. Initially, the corresponding alkyne 62 was prepared in one step, and then we made the Sonogashira reaction with azaindole to obtain the final compound.

Example 29.1 Synthesis of 1-(((4-ethynylbenzyl)oxy)methyl)-3-fluorobenzene 62

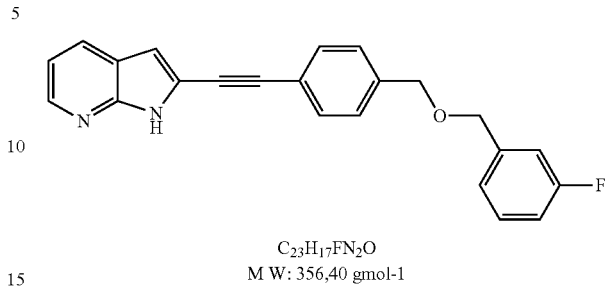

$C_{23}H_{17}FN_2O$
M W: 356,40 gmol-1

The compound was prepared according to procedure C1 and purified by flash column chromatography on silica gel (ethyl acetate/petroleum ether=30/70). Yellow solid (58%), mp 192-194° C., Rf=0.20 (ethyl acetate/petroleum ether=30/70). IR (v, cm$^{-1}$, neat) 3057, 2978, 2893, 2848, 1607, 1584, 1488, 1447, 1433, 1406, 1357, 1282, 1258, 1205, 1141, 1111, 1062, 1007, 934. $^1$H NMR (250 MHz, DMSO-d$_6$, 20° C.) δ 12.23 (s, 1H), 8.29 (s, 1H), 7.97 (d, J=9.8 Hz, 1H), 7.58 (s, 2H), 7.46 (d, J=7.9 Hz, 3H), 7.20 (m, 2H), 7.12 (d, J=7.9 Hz, 2H), 6.84 (s, 1H), 4.60 (s, 4H). $^{13}$C NMR (63 MHz, DMSO-d$_6$ 20° C.) δ 160.6 (d, J=276 Hz, Cq), 148.81 (Cq), 144.9 (CH), 141.8 (d, J=8.3 Hz, Cq), 139.9 (Cq), 131.8 (2×CH), 130.8 (d, J=8.3 Hz, CH), 128.9 (CH), 128.2 (2×CH), 123.8 (d, J=2 Hz, CH), 121.1 (Cq), 119.9 (Cq), 119.4 (Cq), 116.8 (CH), 114.7 (d, J=20.9 Hz, CH), 114.4 (d, J=20.9 Hz, CH), 106.8 (CH), 93.1 (Cq), 82.6 (Cq), 71.5 (CH$_2$), 71.3 (d, J=2 Hz, CH$_2$). $^{19}$F NMR (235 MHz, DMSO-d$_6$, 20° C.) δ. -113.4. HRMS (+ESI) calculated for $C_{23}H_{17}FN_2O$ (M+H$^+$) 357.1397, found: 357.1398.

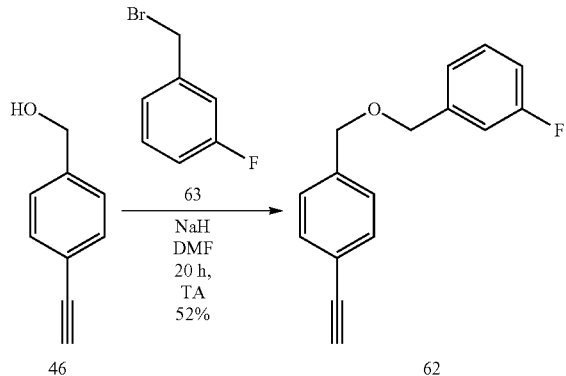

Under argon, 100 mg of alkyne 46 (0.756 mmol, 1.1 eq.) is dissolved in 2 mL of DMF. At 0° C., 48 mg of NaH (50% in mineral oil, 1.02 mmol, 1.5 eq.) was added portionwise, then after 1 h at room temperature, 0.084 ml bromine 63 (0.68 mmol, 1.0 eq.) is added drop by drop. After 20 h at room temperature, 10 ml of H$_2$O is added and the organic phase was extracted with ethyl acetate (3×10 ml). Then the organic phases are combined, dried and filtered over cotton. After evaporation under reduced pressure, the crude was purified by flash column chromatography on silica gel eluting (ethyl acetate/petroleum ether=2/48) to obtain 93 mg of the alkyne 62 as a colorless oil with a yield of 52%. Rf=0.80 (ethyl acetate/petroleum ether=10/90). IR (v, cm$^{-1}$, neat) 3291, 2858, 1698, 1607, 1590, 1507, 1487, 1449, 1412, 1359, 1267, 1204, 1174, 1138, 1094, 1070, 1017, 946, 859. $^1$H NMR (250 MHz, CDCl$_3$, 20° C.) 7.49 (d, J=7.9 Hz, 2H), 7.32 (d, J=7.9 Hz, 3H), 7.10 (m, 2H), 6.99 (m, 1H), 4.55 (2×s, 4H), 3.07 (s, 1H). $^{13}$C NMR (63 MHz, CDCl$_3$ 20° C.) δ 162.4 (d, J=246.4 Hz, Cq), 140.7 (d, J=7.9 Hz, Cq), 138.8 (Cq), 132.2 (2×CH), 129.9 (d, J=7.9 Hz, CH), 127.5 (2×CH), 123.0 (d, J=2.9 Hz, CH), 121.45 (Cq), 114.6 (d, J=12.8 Hz, CH), 114.38 (d, J=12.8 Hz, CH), 83.5 (Cq), 77.2 (CH), 71.8 (CH$_2$), 71.5 (d, J=2.0 Hz, CH$_2$). $^{19}$F NMR (235 MHz, DMSO-d$_6$, 20° C.) δ. -113.4. HRMS (+ESI) calculated for $C_{16}H_{13}FO$ (M+H$^+$): 241.1023, found: 241.1024.

Example 30. 4-[4-[2-(5-fluoro-1H-pyrrolo[2,3-b]pyridin-2-yl)ethynyl] phenyl]morpholine 64

4-[4-[2-(5-fluoro-1H-pyrrolo[2,3-b]pyridin-2-yl)ethynyl] phenyl]morpholine was synthesized in 4 steps from dibromobenzene. Initially, the corresponding alkyne 65 was prepared in 3 steps and then we did the Sonogashira reaction with azaindole to obtain the final compound.

Example 30.1 Preparation of 4-(4-ethynylphenyl)morpholine 65

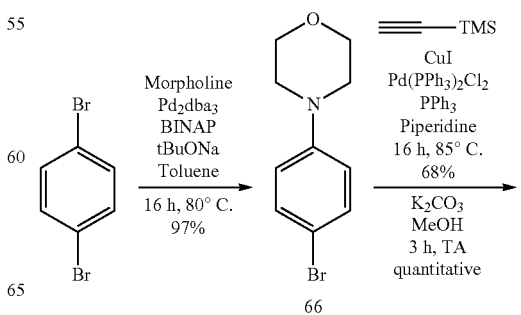

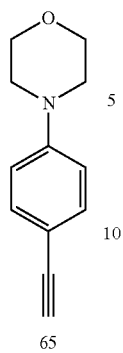

Synthesis Bromine 66

Compound 66 was prepared according to procedure D and purified by flash column chromatography on silica gel (ethyl acetate/petroleum ether=1/49). Colorless oil (97%). $^1$H NMR (250 MHz, CDCl$_3$) δ 7.40-7.22 (m, 2H), 6.82-6.68 (m, 2H), 3.90-3.72 (m, 4H), 3.17-3.03 (m, 4H). CAS Number: 30483-75-1.

Synthesis of True Alkyne 65

The alkyne 65 was prepared according to procedure E and purified by flash column chromatography on silica gel (ethyl acetate/petroleum ether=2/48). Colorless oil (68% over two steps). $^1$H NMR (250 MHz, CDCl$_3$) δ 7.47-7.38 (m, 4H), 6.88-6.80 (m, 4H), 3.91-3.84 (m, 4H), 3.25-3.18 (m, 4H), 3.01 (s, 1H). CAS Number: 41876-72-6.

Example 30.2 4-[4-[2-(5-fluoro-1H-pyrrolo[2,3-b]pyridin-2-yl)ethynyl]phenyl]morpholine 64

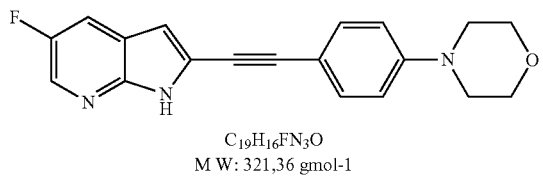 [SMILES: Fc1cnc2[nH]c(C#Cc3ccc(N4CCOCC4)cc3)cc2c1]

C$_{19}$H$_{16}$FN$_3$O
M W: 321,36 gmol-1

The compound was prepared according to procedure C1 and purified by flash column chromatography on silica gel (ethyl acetate/petroleum ether=40/60). Yellow solid (42%), mp>260° C., Rf=0.33 (ethyl acetate/petroleum ether=40/60). IR (v, cm$^{-1}$, neat) 3114, 3057, 2964, 2852, 2209, 1604, 1586, 1536, 1507, 1448, 1394, 1381, 1341, 1285, 1264, 1242, 1222, 1197, 1157, 1122, 1053, 922. $^1$H NMR (250 MHz, DMSO-d$_6$, 20° C.) δ 12.26 (s, 1H), 8.23 (s, 1H), 7.81 (m, 1H), 7.43 (d, J=8.7 Hz, 2H), 6.99 (d, J=8.7 Hz, 2H), 6.73 (s, 1H), 3.85-3.58 (m, 4H), 3.24-3.04 (m, 4H). $^{13}$C NMR (63 MHz, DMSO-d$_6$ 20° C.) δ 155.8 (d, J=239.2 Hz, Cq), 151.64 (Cq), 145.61 (Cq), 132.9 (2×CH), 132.7 (d, J=29.0 Hz, CH), 122.6 (Cq), 120.6 (d, J=7.5 Hz, Cq), 114.9 (2×CH), 113.8 (d, J=20.9 Hz, CH), 110.9 (Cq), 105.8 (d, J=4.4 Hz, CH), 94.8 (Cq), 80.6 (Cq), 66.4 (2×CH$_2$), 47.7 (2×CH$_2$). $^{19}$F NMR (235 MHz, DMSO-d$_6$, 20° C.) δ. -138.4. HRMS (+ESI) calculated for C$_{19}$H$_{16}$FN$_3$O (M+H+): 322.1350, found: 322.1354.

Example 31. N-(4-((1H-pyrrolo[2,3-b]pyridin-2-yl)ethynyl)benzyl)-2-fluoro-N-methylethan-1-amine 67

N-(4-((1H-pyrrolo[2,3-b]pyridin-2-yl)ethynyl)benzyl)-2-fluoro-N-methylethan-1-amine was synthesized in 2 steps from the alkyne 69. Initially, the corresponding alkyne 68 was prepared in one step and then we did the Sonogashira reaction with azaindole to obtain the final compound.

Example 31.1 Synthesis of N-[(4-ethynylphenyl)methyl]-2-fluoro-N-methyl-ethanamine 68

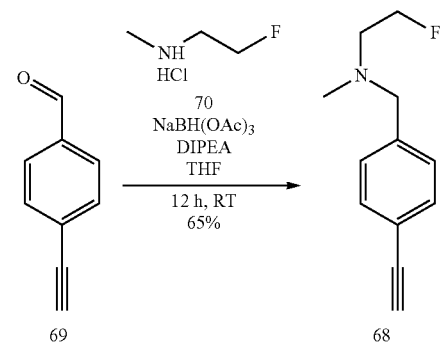

Under argon, 100 mg of aldehyde 69 (0.77 mmol, 1.0 eq.) and 98.5 mg of amine 70 (0.845 mmol, 1.1 eq.) are dissolved in 5 ml of THF. After the addition of 0.536 ml of DIPEA (3.08 mmol, 4.0 eq.) and 386.4 mg of NaBH (OAc)$_3$, the reaction mixture was stirred for 12 h at room temperature. Then 15 ml of a saturated solution of NaHCO$_3$ is added and the organic phase was extracted with ethyl acetate (3×15 ml). Then the organic phases are combined, dried and filtered over cotton. After evaporation under reduced pressure, the crude was purified by flash column chromatography on silica gel with eluting agent (ethyl acetate/petroleum ether=5/45) to obtain 95 mg of the alkyne 68 as a colorless oil with a yield of 65%, Rf=0.40 (ethyl acetate/petroleum ether=5/45). IR (v, cm$^{-1}$, neat) 3289, 2952, 2794, 2359, 2107, 1682, 1504, 1455, 1410, 1364, 1017, 846, 825. $^1$H NMR (250 MHz, CDCl$_3$, 20° C.) δ 7.40 (d, J=8.2 Hz, 2H), 7.24 (d, J=8.2 Hz, 2H), 4.51 (dt, J=47.6, 5.0 Hz, 2H), 3.53 (s, 2H), 3.01 (s, 1H), 2.68 (dt, J=27.0, 5.0 Hz, 2H), 2.25 (s, 3H). $^{13}$C NMR (63 MHz, CDCl$_3$ 20° C.) δ 139.8 (Cq), 132.1 (2×CH), 128.8 (2×CH), 120.8 (Cq), 83.8 (Cq), 82.4 (d, J=158.6 Hz, CH$_2$), 76.45 (CH), 62.3 (CH$_2$), 56.8 (d, J=20.1 Hz, CH$_2$), 42.7 (CH$_3$). $^{19}$F NMR (235 MHz, CDCl$_3$, 20° C.) δ. -219.2. HRMS (+ESI) calculated for C$_{12}$H$_{14}$FN (M+H+): 192.1183, found: 192.1185.

Example 31.2 N-(4-((1H-pyrrolo[2,3-b]pyridin-2-yl)ethynyl)benzyl)-2-fluoro-N-methylethan-1-amine 67

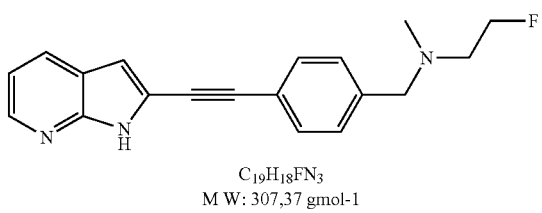 [SMILES: CN(CCF)Cc1ccc(C#Cc2cc3cccnc3[nH]2)cc1]

C$_{19}$H$_{18}$FN$_3$
M W: 307,37 gmol-1

The compound was prepared according to procedure C1 and purified by flash column chromatography on silica gel (ethyl acetate/petroleum ether=40/60). Yellow solid (60%), mp 160-162° C., Rf=0.18 (ethyl acetate/petroleum ether=40/60). IR (v, cm$^{-1}$, neat) 3055, 2951, 2779, 1583, 1536, 1497, 1433, 1405, 1359, 1283, 1115, 1014, 879. $^1$H NMR (250 MHz, CDCl$_3$, 20° C.) δ 11.78 (s, 1H), 8.41 (m, 1H), 7.93 (m, 1H), 7.56 (d, J=8.0 Hz, 2H), 7.38 (d, J=8.0 Hz, 2H), 7.20-7.05 (m, 1H), 6.78 (s, 1H), 4.58 (dt, J=47.6, 5.0 Hz, 2H), 3.62 (s, 2H), 2.76 (dt, J=27.1, 5.0 Hz, 2H), 2.33 (s, 3H). $^{13}$C NMR (63 MHz, CDCl$_3$ 20° C.) δ 148.6 (Cq), 143.6 (CH), 139.9 (Cq), 131.5 (2×CH), 129.1 (2×CH), 121.1 (Cq), 120.8 (Cq), 120.1 (Cq), 116.5 (CH), 106.3 (CH), 93.4 (Cq), 83.8 (Cq), 82.5 (d, J=167.6 Hz, CH$_2$), 62.3 (CH$_2$), 57.8 (d, J=20.0 Hz, CH$_2$), 42.7 (CH$_3$). $^{19}$F NMR (235 MHz, CDCl$_3$, 20° C.) δ. –219.1. HRMS (+ESI) calculated for C$_{19}$H$_{18}$FN$_3$ (M+H+): 308.1557, found: 308.1557.

Example 32. 4-((1H-pyrrolo[2,3-b]pyridin-2-yl)ethynyl)-N-(2-fluoroethyl)-N-methylbenzamide 71

4-((1H-pyrrolo[2,3-b]pyridin-2-yl)ethynyl)-N-(2-fluoroethyl)-N-methylbenzamide was synthesized in 2 steps from the alkyne 73. Initially the corresponding alkyne 72 was prepared in one step and then we did the Sonogashira reaction with azaindole to obtain the final compound.

Example 32.1 Synthesis of 4-ethynyl-N-(2-fluoroethyl)-N-methyl-benzamide 72

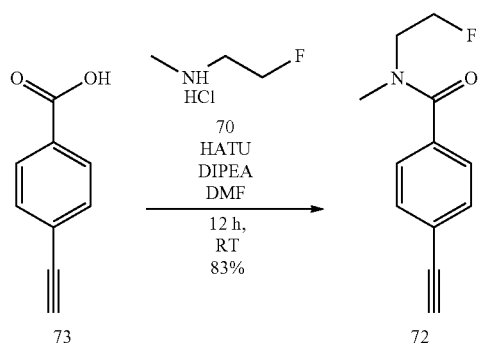

Under argon, 100 mg of the acid 73 (0.684 mmol, 1.0 eq.) and 85 mg of amine 70 (0.752 mmol, 1.1 eq.) are dissolved in 5 ml of DMF. After the addition of 0.571 ml of DIPEA (3.28 mmol, 4.8 eq.) and 312 mg of HATU (0.821 mmol, 1.2 eq.), the reaction mixture was stirred for 12 h at room temperature.

Then, 15 ml of H$_2$O is added and the organic phase was extracted with ethyl acetate (3×15 ml). Then the organic phases are combined, dried and filtered over cotton. After evaporation under reduced pressure, the crude was purified by flash chromatography column on silica gel with eluting agent (ethyl acetate/petroleum ether=30/70) to obtain 95 mg of the alkyne 72 as a colorless oil with a yield of 83%. Rf=0.25 (ethyl acetate/petroleum ether=30/70). IR (v, cm$^{-1}$, neat) 3290, 3225, 2929, 2359, 1625, 1508, 1482, 1400, 1303, 1177, 1074, 1036, 1017, 979, 847, 764, 668. $^1$H NMR (250 MHz, CDCl$_3$, 20° C.) δ 7.53 (d, J=7.9 Hz, 2H), 7.38 (d, J=7.2 Hz, 2H), 4.60 (m, 2H), 3.92-3.46 (m, 2H), 3.11 (m, 4H). $^{13}$C NMR (63 MHz, CDCl$_3$ 20° C.) δ 168.9 (Cq), 136.2 (Cq), 132.2 (2×CH), 127.0 (2×CH), 123.6 (Cq), 83.8 (d, J=167.6 Hz, CH$_2$), 82.8 (Cq), 78.6 (CH), 48.4 (d, J=20 Hz, CH$_2$), 39.4 (CH$_3$). $^{19}$F NMR (235 MHz, CDCl$_3$, 20° C.) δ. –222.2. HRMS (+ESI) calculated for C$_{12}$H$_{12}$FN (M+H+): 206.0975, found: 206.0976.

Example 32.2 4-((1H-pyrrolo[2,3-b]pyridin-2-yl)ethynyl)-N-(2-fluoroethyl)-N-methylbenzamide

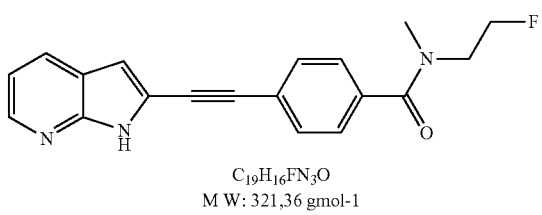 [SMILES: CN(CCF)C(=O)c1ccc(C#Cc2cc3cccnc3[nH]2)cc1]

C$_{19}$H$_{16}$FN$_3$O
M W: 321,36 gmol-1

The compound was prepared according to procedure C1 and purified by flash column chromatography on silica gel (ethyl acetate/petroleum ether=10/90). Yellow solid (34%), mp 192-194° C., Rf=0.33 (ethyl acetate/petroleum ether=10/90). IR (v, cm$^{-1}$, neat) 3055, 2951, 2779, 1583, 1536, 1497, 1433, 1405, 1359, 1283, 1115, 1014, 879. $^1$H NMR (250 MHz, CDCl$_3$, 20° C.) δ 8.40 (d, J=4.7 Hz, 1H), 7.95 (d, J=7.8 Hz, 1H), 7.63 (d, J=7.9 Hz, 2H), 7.47 (d, J=7.9 Hz, 2H), 7.13 (dd, J=7.8, 4.7 Hz, 1H), 6.81 (s, 1H), 4.74 (d, J=47.8 Hz, 2H), 3.86 (d, J=28.1 Hz, 2H), 3.13 (s, 3H). $^{13}$C NMR DEPT (63 MHz, CDCl$_3$ 20° C.) δ 144.2 (CH), 131.6 (2×CH), 129.2 (CH), 127.3 (2×CH), 116.7 (CH), 107.1 (CH), 84.8 (d, J=167.6 Hz, CH$_2$), 83.0 (Cq), 48.6 (d, J=20.0 Hz, CH$_2$), 39.6 (CH$_3$). $^{19}$F NMR (235 MHz, CDCl$_3$, 20° C.) δ. –222.5. HRMS (+ESI) calculated for C$_{19}$H$_{16}$FN$_3$O (M+H+): 322.1350, found: 322.1352.

Example 33. 3-((5-fluoro-1H-pyrrolo[2,3-b]pyridin-2-yl)ethynyl)-N,N-dimethylaniline 74

3-((5-fluoro-1H-pyrrolo[2,3-b]pyridin-2-yl)ethynyl)-N,N-dimethylaniline was synthesized in 3 steps from 3-bromoaniline. Initially, the corresponding alkyne 75 was prepared in 2 steps and then we did the Sonogashira reaction with azaindole to obtain the final compound.

Example 33.1 Synthesis of 3-ethynyl-N,N-dimethylaniline 75

To synthesize the alkyne 75, we use the method of Fang et coll. (Journal of Chemical Research, 2015, 39, 8, 487-491)

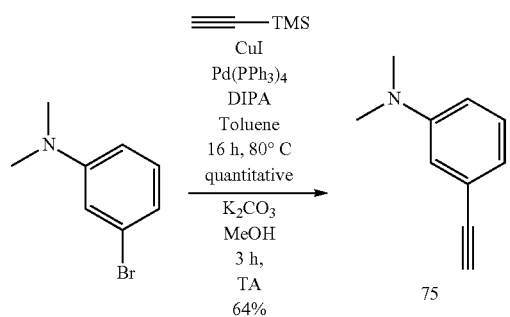

The catalyst [Pd(PPh₃)₄] (29 mg, 0.025 mmol, 5 mol %) was added to a degassed solution of bromine derivative 3-bromo-N,N-diméthylaniline (100 mg, 0.5 mmol, 1.0 eq.), of ethynyltrimethylsilane (0.083 ml, 0.6 mmol, 1.2 eq), CuI (5 mg, 0.025 mmol, 5 mol %) in a mixture of diisopropylamine/toluene (1:3) at a concentration of 0.1 M. The mixture was heated at 80° C. for 16 h under argon. After returning to room temperature, the mixture was concentrated under reduced pressure before being purified by flash column chromatography on silica gel with eluting agent (ethyl acetate/petroleum ether=1/49) to obtain 100 mg of the intermediate alkyne as a colorless oil with quantitative yield. This latter is reacted with K₂CO₃ (103 mg, 0.745, 1.5 eq.) in methanol. After 3 h stirring at room temperature, the solvent was evaporated. Then, the crude is solubilized in ethyl acetate OML. Then the organic phase is washed with brine (10 ml). Then the organic phase is dried with MgSO₄, filtered through cotton and evaporated under reduced pressure. The alkyne 75 is obtained with a yield of 64% without purification. ¹H NMR (250 MHz, CDCl₃) δ 7.22-7.11 (m, 1H), 6.93-6.82 (m, 2H), 6.72 (m, 1H), 3.48 (s, 6H), 3.3 (s, 1H). CAS Number: 52324-05-7.

Example 33.2 3-((5-fluoro-1H-pyrrolo[2,3-b]pyridin-2-yl)ethynyl)-N,N-dimethylaniline 74

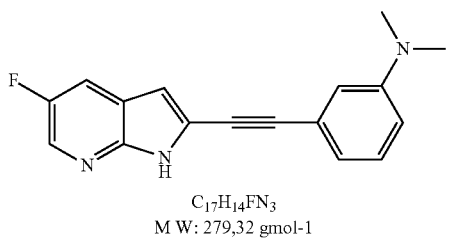 [SMILES: CN(C)c1cccc(C#Cc2cc3cc(F)cnc3[nH]2)c1]

C₁₇H₁₄FN₃
M W: 279,32 gmol-1

The compound was prepared according to procedure C2 and purified by flash column chromatography on silica gel (DCM=100). White solid (27%), mp 226-228° C., Rf=0.25 (dichloromethane=100). IR (□, cm⁻¹, neat) 3063, 2890, 2805, 1595, 1494, 1360, 1343, 1296, 1224, 1143, 767. ¹H NMR (250 MHz, DMSO-d₆, 20° C.) δ 11.91 (s, 1H), 7.83 (dd, J=2.8, 1.8 Hz, 1H), 7.41 (dd, J=8.0, 2.8 Hz, 1H), 6.82 (t, J=8.0 Hz, 1H), 6.48-6.32 (m, 4H), 2.50 (s, 6H). ¹³C NMR (63 MHz, DMSO-d₆ 20° C.) δ 155.8 (d, J=239.5 Hz, Cq), 150.7 (Cq), 145.6 (Cq), 133.1 (d, J=29.2 Hz, CH), 129.9 (CH), 122.1 (d, J=17.9 Hz, Cq), 120.1 (d, J=7.5 Hz, Cq), 119.4 (CH), 114.8 (CH), 114.1 (d, J=20.8 Hz, CH), 113.9 (CH), 106.5 (d, J=4.5 Hz, CH), 94.9 (Cq), 81.1 (Cq), 40.5 (2×CH₃). ¹⁹F NMR (235 MHz, DMSO-d₆, 20° C.) δ. -138.5. HRMS (+ESI) calculated for C₁₇H₁₄FN₃ (M+H+): 280.1244, found: 280.1245.

Example 34 2-((5-fluoro-1H-pyrrolo[2,3-b]pyridin-2-yl)ethynyl)-N,N-dimethylaniline 76

2-((5-fluoro-1H-pyrrolo[2,3-b]pyridin-2-yl)ethynyl)-N, N-dimethylaniline was synthesized in 4 steps from 2-iodoaniline. Initially, the corresponding alkyne 77 was prepared in 3 steps and then we did the Sonogashira reaction with azaindole to obtain the final compound.

Example 34.1 Synthesis of 2-ethynyl-N,N-dimethylaniline 77

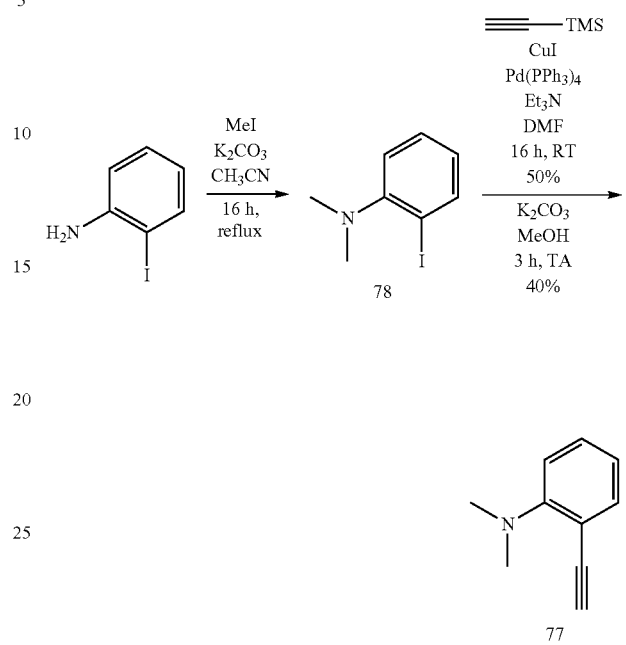

500 mg of 2-iodoaniline (2.28 mmol, 1.0 eq.) is dissolved in 10 ml of CH₃CN. Then 0.425 ml of iodomethane (6.84 mmol, 3.0 eq.) and 787 mg of K₂CO₃ (5.7 mmol, 2.5 eq.) are added successively. After 16 h at reflux, the reaction mixture is cooled. 20 ml of H₂O was added and the organic phase is extracted with ethyl acetate (3×15 ml). Then the organic phases are combined, dried and filtered over cotton. After evaporation under reduced pressure, the crude was purified by flash column chromatography on silica gel with eluting agent (ethyl acetate/petroleum ether=2/48) to obtain 434 mg of the iodated 78 with 2% monoalkylated.

Synthesis of 2-ethynyl-N,N-dimethylaniline 77

The catalyst [Pd(PPh₃)₄] (12 mg, 0.018 mmol, 1.0 mol %) was added to a degassed solution of iodine derivative 78, (434 mg, 1.75 mmol, 1.0 eq.), ethynyltrimethylsilane (0.365 ml, 2.6 mmol, 1.5 eq.), CuI (10 mg, 0.052 mmol, 3 mol %) and Et₃N (0.240 ml, 1.75 mmol, 1.0 eq.) in 1.5 ml of DMF. The mixture was stirred at room temperature for 16 h under argon. Then the mixture is concentrated under reduced pressure before being purified by flash column chromatography on silica gel with eluting agent (ethyl acetate/petroleum ether=1/49) to obtain 186 mg of the intermediate alkyne as a colorless oil with the yield of 50%. This latter is reacted with K₂CO₃ (177 mg, 1.28 mmol, 1.5 eq.) in 15 ml of methanol. After stirring for 3 h at room temperature, the solvent was evaporated. Then, the crude is dissolved in 10 ml of ethyl acetate. Then the organic phase is washed with brine (3×10 ml). Then the organic phase is dried, filtered through cotton and evaporated under reduced pressure. The alkyne 77 was obtained with the yield of 64% without purification. ¹H NMR (250 MHz, CDCl₃) δ 7.43 (m, 1H), 7.29-7.13 (m, 1H), 6.95-6.76 (m, 2H), 3.43 (s, 1H), 2.90 (s, 6H). CAS Number: 219605-52-4.

Example 34.2 2-((5-fluoro-1H-pyrrolo[2,3-b]pyridin-2-yl)ethynyl)-N,N-dimethylaniline 76

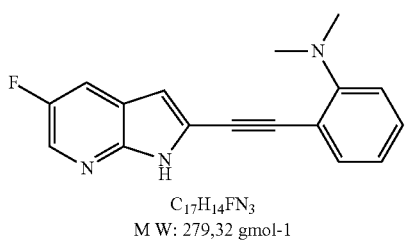 [SMILES: CN(C)c1ccccc1C#Cc1cc2cc(F)cnc2[nH]1]

C₁₇H₁₄FN₃
M W: 279,32 gmol-1

The compound was prepared according to procedure C2 and purified by flash column chromatography on silica gel (ethyl acetate/petroleum ether=10/90). White solid (27%), mp 146-148° C., Rf=0.30 (ethyl acetate/petroleum ether=15/85). IR (□, cm⁻¹, neat) 3058, 2837, 2789, 2203, 1588, 1533, 1504, 1487, 1451, 1430, 1397, 1345, 1322, 1291, 1272, 1189, 1113, 1046, 983, 943. ¹H NMR (400 MHz, CDCl₃, 20° C.) δ 10.73 (s, 1H), 8.32 (t, J=2.3 Hz, 1H), 7.59 (ddd, J=28.4, 8.2, 2.3 Hz, 2H), 7.38-7.29 (m, 1H), 7.04-6.92 (m, 2H), 6.75 (d, J=2.0 Hz, 1H), 3.04 (s, 6H). ¹³C NMR (101 MHz, CDCl₃, 20° C.) δ 155.9 (d, J=241.8 Hz, Cq), 155.2 (Cq), 145.1 (Cq), 134.3 (CH) 132.4 (d, J=29.2 Hz, CH), 130.1 (CH), 122.6 (Cq), 120.7 (d, J=7.3 Hz, Cq), 120.6 (CH) 117.1 (CH), 114.8 (Cq), 114.2 (d, J=20.8 Hz, CH), 105.8 (d, J=4.5 Hz, CH), 93.8 (Cq), 86.2 (Cq), 43.6. (2×CH₃). ¹⁹F NMR (376 MHz, CDCl₃, 20° C.) δ. –138.5. HRMS (+ESI) calculated for C₁₇H₁₄FN₃ (M+H+): 280.1244, found: 280.1245.

Example 35 1-[4-[2-(5-fluoro-1H-pyrrolo[2,3-b]pyridin-2-yl)ethynyl]phenyl]pyrrolidin-2-one 79

1-[4-[2-(5-fluoro-1H-pyrrolo[2,3-b]pyridin-2-yl)ethynyl]phenyl]pyrrolidin-2-one was synthesized in 3 steps. Initially, the corresponding alkyne 80 was prepared in 3 steps and then we did the Sonogashira reaction with azaindole to obtain the final compound.

Example 35.1 Synthesis of 1-(4-ethynylphenyl)pyrrolidin-2-one 80

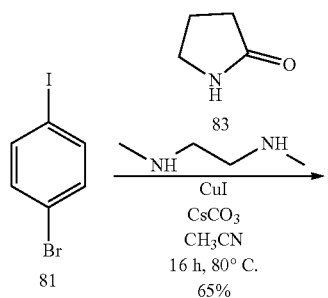

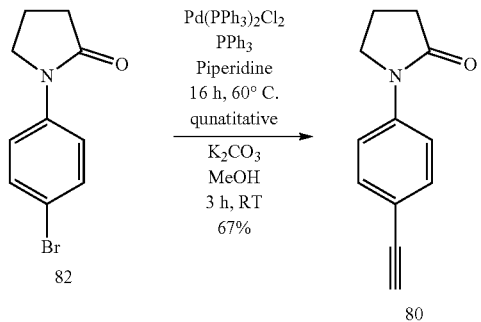

Synthesis of Bromine 82

CuI (12 mg, 0.282 mmol, 20 mol %) was added to a degassed solution of iodine derivative 81 (200 mg, 0.707 mmol, 1.0 eq.), amine 83 (0.056 ml, 0.742 mmol, 1.5 eq.), N,N-dimethylethylenediamine (0.026 ml, 0.282 mmol, 20% mol) and CsCO₃ (459 mg, 1.41 mmol, 2.0 eq) in 3.0 ml of CH₃CN. The mixture was stirred at 80° C. for 16 h under argon. Then the mixture was cooled and filtered through Celite®.

The filtrate is evaporated under reduced pressure before being purified by flash column chromatography on silicagel with eluting agent (ethyl acetate/petroleum ether=25/75) to give 110 mg of the bromine 82 as a colorless oil with the yield of 65%. ¹H NMR (250 MHz, CDCl₃, 20° C.) δ 7.57-7.37 (m, 4H), 3.81 (t, J=7.0 Hz, 2H), 2.58 (t, J=8.1 Hz, 2H), 2.14 (m, 2H). CAS Number: 7661-32-7.

Synthesis of 1-(4-ethynylphenyl)pyrrolidin-2-one 80

Under argon, Pd(PPh₃)₄ (24 mg, 0.021 mmol, 0.1 eq.) and CuI (4 mg, 0.021 mmol, 0.01 eq.) were added to a degassed solution of Et₃N (1 ml) containing ethynyltrimethylsilane (0.058 ml, 0.416 mmol, 2.0 eq.) and the bromine derivative 82 (50 mg, 0.21 mmol, 1.0 eq.). After 16 h at 60° C., the solvent was evaporated under reduced pressure. Then, the reaction mixture was purified by flash column chromatography on silicagel. Then, 56 mg of the intermediate alkyne was reacted with K₂CO₃ (45 mg, 0.217 mmol, 1.5 eq.) in 5 ml of methanol. After 3 h at room temperature, the solvent was evaporated under reduced pressure. The crude product was dissolved in 10 ml of ethyl acetate. Then the organic phase is washed with brine (3×10 ml). Then the organic phase is dried with MgSO₄, filtered through cotton and evaporated under reduced pressure to obtain alkyne 80 with a yield of 67% as a white solid. mp 136-138° C., Rf=0.5 (ethyl acetate/petroleum ether=50/50). IR (□, cm⁻¹, neat) 3292, 3031, 2915, 2099, 1605, 1514, 1494, 1451, 1395, 1355, 1233, 1177, 1100, 1046, 1003, 912, 883, 847, 815. ¹H NMR (250 MHz, CDCl₃, 20° C.) δ 7.60 (d, J=9.0 Hz, 2H), 7.48 (d, J=9.0 Hz, 2H), 3.86 (dd, J=7.4, 6.7 Hz, 2H), 3.33 (s, 1H), 2.69-2.55 (m, 2H), 2.25-2.08 (m, 2H). ¹³C NMR (63 MHz, CDCl₃ 20° C.) δ 174.8 (Cq), 140.3 (Cq), 133.2 (2×CH), 119.7 (2×CH), 118.2 (Cq), 83.4 (Cq), 77.3 (CH), 46.9 (CH₂), 33.27 (CH₂), 18.37 (CH₂). HRMS (+ESI) calculated for C₁₂H₁₂NO (M+H+): 186.0913, found: 186.0913.

Example 35.2 1-[4-[2-(5-fluoro-1H-pyrrolo[2,3-b]pyridin-2-yl)ethynyl]phenyl]pyrrolidin-2-one 79

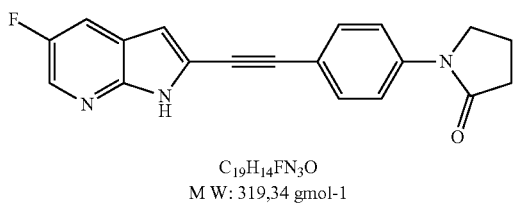 [SMILES: O=C1CCCN1c1ccc(C#Cc2cc3cc(F)cnc3[nH]2)cc1]

C$_{19}$H$_{14}$FN$_3$O
M W: 319,34 gmol-1

The compound was prepared according to procedure C2 and purified by flash column chromatography on silica gel (ethyl acetate/petroleum ether=10/90). White solid (27%), mp 256-258° C., Rf=0.30 (ethyl acetate/petroleum ether=15/85). IR (□, cm$^{-1}$, neat) 3058, 2837, 2789, 2203, 1588, 1533, 1504, 1487, 1451, 1430, 1397, 1345, 1322, 1291, 1272, 1189, 1113, 1046, 983, 943. $^1$H NMR (400 MHz, DMSO-d$_6$, 20° C.) δ 12.37 (s, 1H), 8.27 (s, 1H), 7.85 (d, J=9.8 Hz, 1H), 7.79 (d, J=7.4 Hz, 2H), 7.60 (d, J=7.4 Hz, 2H), 6.81 (s, 1H), 3.87 (m, 2H), 2.54 (m, 2H), 2.07 (m, 2H). $^{13}$C NMR (101 MHz, DMSO-d$_6$, 20° C.) δ 174.8 (Cq), 155.7 (d, J=240 Hz, Cq), 145.6 (Cq), 140.8 (Cq), 133.3 (d, J=28.9 Hz, CH), 132.4 (2×CH), 121.9 (Cq), 120.2 (d, J=7.5 Hz, Cq), 119.5 (2×CH), 116.6 (Cq), 114.1 (d, J=20.8 Hz, CH), 106.5 (d, J=3.5 Hz, Cq), 93.8 (Cq), 81.8 (Cq), 48.4 (CH$_2$), 32.9 (CH$_2$), 17.8 (CH$_2$). $^{19}$F NMR (376 MHz, DMSO-d$_6$, 20° C.) δ. −138.5. HRMS (+ESI) calculated for C$_{19}$H$_{14}$FN$_3$O (M+H+): 320.1192, found: 320.1193.

Example 36. 2-[2-(2-fluorophenyl)ethynyl]-1H-pyrrolo[2,3-b]pyridine 84

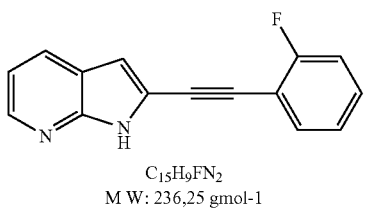 [SMILES: Fc1ccccc1C#Cc1cc2cccnc2[nH]1]

C$_{15}$H$_9$FN$_2$
M W: 236,25 gmol-1

The compound was prepared according to procedure C2 and purified by flash column chromatography on silica gel (ethyl acetate/petroleum ether=10/90). Yellowish solid (32%), mp 210-212° C., Rf=0.20 (ethyl acetate/petroleum ether=15/85). IR (□, cm$^{-1}$, neat) 3058, 2837, 2789, 2203, 1588, 1533, 1504, 1487, 1451, 1430, 1397, 1345, 1322, 1291, 1272, 1189, 1113, 1046, 983, 943. $^1$H NMR (400 MHz, CDCl$_3$, 20° C.) δ 11.55 (s, 1H), 8.46 (s, 1H), 7.95 (d, J=7.9 Hz, 1H), 7.59 (t, J=7.3 Hz, 1H), 7.43-7.34 (m, 1H), 7.17 (m, 3H), 6.83 (s, 1H). $^{13}$C NMR (101 MHz, CDCl$_3$, 20° C.) δ 163.7 (d, J=252.5 Hz, Cq), 148.5 (Cq), 144.1 (CH), 133.3 (CH), 130.5 (d, J=7.9 Hz, CH), 129.2 (CH), 124.1 (CH), 120.6 (Cq), 119.5 (Cq), 116.6 (CH), 115.7 (d, J=20.5 Hz, CH), 111.3 (d, J=15.2 Hz, Cq), 106.9 (CH), 86.8 (d, J=15.2 Hz, Cq). $^{19}$F NMR (376 MHz, CDCl$_3$, 20° C.) δ. −109.3. HRMS (+ESI) calculated for C$_{15}$H$_9$FN$_2$ (M+H+): 237.0822, found: 237.0823.

Example 37. 2-((4-(1-(3-fluoropropyl)piperidin-4-yl)phenyl)ethynyl)-1H-pyrrolo[2,3-b]pyridine 85

2-((4-(1-(3-fluoropropyl)piperidin-4-yl)phenyl)ethynyl)-1H-pyrrolo[2,3-b]pyridine was synthesized in 4 steps. Initially, the corresponding alkyne 86 was prepared in 3 steps and then we did the Sonogashira reaction with azaindole to obtain the final compound.

Example 37.1 Synthesis of 4-(4-ethynylphenyl)-1-(3-fluoropropyl)piperidine 86

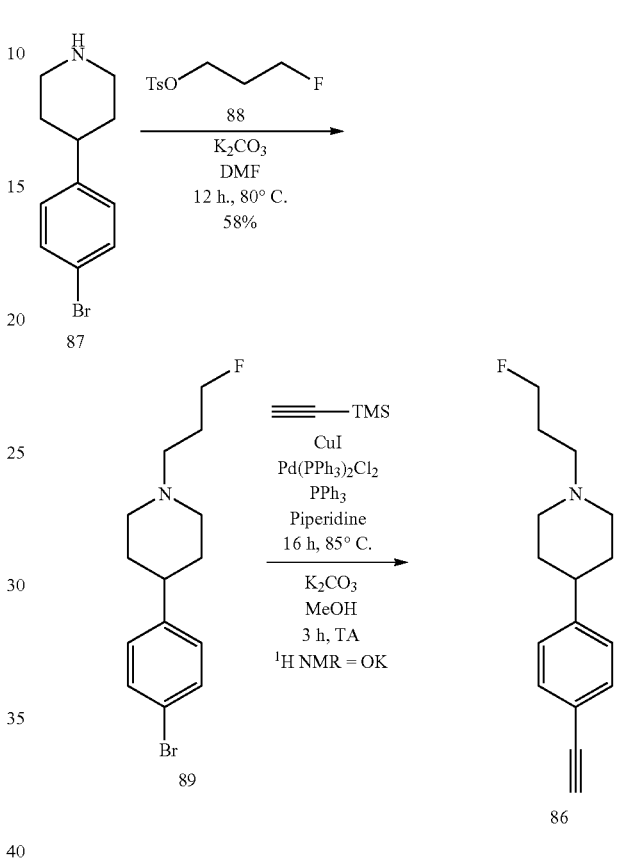

Synthesis of 4-(4-bromophenyl)-1-(3-fluoropropyl)piperidine 89

The bromine 87 (176 mg, 0.635 mmol, 1.2 eq.) and the fluorine 88 (123 mg, 0.529 mmol, 1.0 eq.) are placed in the presence of K$_2$CO$_3$ (219 mg, 0.1.59 mmol, 3.0 eq.) in 10 ml of CH$_3$CN. After 18 h at 90° C., the reaction mixture was cooled to room temperature and the solvent was evaporated under reduced pressure. The crude product is dissolved in 10 ml of ethyl acetate. Then the organic phase was washed with brine (3×10 ml). Then the organic phase is dried, filtered through cotton and evaporated under reduced pressure. After purification on silica gel with an eluent (ethyl acetate/petroleum ether Et$_3$N), the bromine 89 was obtained with a yield of 58% in form of a colorless oil. Rf=0.2 (methanol/dichloromethane=2/48). IR (□, cm$^{-1}$, neat) 3305, 2925, 1639, 1512, 1441, 1376, 1258, 1171, 1124, 1039, 997, 911, 835. $^1$H NMR (250 MHz, CDCl$_3$, 20° C.) δ 7.41 (d, J=8.4 Hz, 2H), 7.10 (d, J=8.4 Hz, 2H), 4.62 (t, J=6.0 Hz, 1H), 4.43 (t, J=6.0 Hz, 1H), 3.23-2.93 (m, 2H), 2.59-2.43 (m, 2H), 2.24-1.60 (m, 10H). $^{13}$C NMR (63 MHz, CDCl$_3$ 20° C.) δ 145.3 (Cq), 131.4 (2×CH), 128.6 (2×CH), 119.7 (Cq), 82.7 (d, J=164.3 Hz, CH$_2$), 54.7 (d, J=5.4 Hz, CH$_2$), 54.3 (CH$_2$), 42.2 (CH$_2$), 33.4 (CH$_2$), 28.0 (d, J=19.6 Hz, CH$_2$). $^{19}$F NMR (235 MHz, CDCl$_3$, 20° C.) δ. −220. HRMS (+ESI) calculated for C$_{14}$H$_{19}$BrFN (M+H+): 300.0757, found: 300.0757.

Synthesis of 4-(4-ethynylphenyl)-1-(3-fluoropropyl)piperidine 86

The alkyne 86 was prepared according to procedure E and purified by flash column chromatography on silica gel (methanol/dichloromethane=2/48) but containing 20% of the bromine 89.

Example 37.2 2-((4-(1-(3-fluoropropyl)piperidin-4-yl)phenyl)ethynyl)-1H-pyrrolo[2,3-b]pyridine

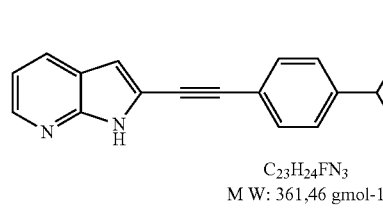

C$_{23}$H$_{24}$FN$_3$
M W: 361,46 gmol-1

The compound was prepared according to procedure C2 and purified by flash column chromatography on silica gel (methanol/dichloromethane/NH$_4$OH=2/48/0.5). White solid (55%), mp 218-220° C., Rf=0.20 (methanol/dichloromethane/NH$_4$OH=2/48/0.5). IR (□, cm$^{-1}$, neat) 3052, 2936, 2777, 2360, 1583, 1534, 1495, 1466, 1432, 1404, 1376, 1356, 1325, 1284, 1133, 1111, 1041, 999, 981, 938, 917, 828, 801, 763. $^1$H NMR (400 MHz, DMSO-d$_6$, 20° C.) δ 12.19 (s, 1H), 8.28 (d, J=4.6 Hz, 1H), 7.96 (d, J=8.0 Hz, 1H), 7.51 (d, J=7.8 Hz, 2H), 7.35 (d, J=8.0 Hz, 2H), 7.10 (dd, J=7.9, 4.7 Hz, 1H), 6.81 (d, J=1.9 Hz, 1H), 4.56 (t, J=6.0 Hz, 1H), 4.44 (t, J=5.9 Hz, 1H), 2.98 (m, 2H), 2.50 (m, 2H), 2.41 (m, 2H), 2.02 (m, 2H), 1.92-1.59 (m, 6H). $^{13}$C NMR (101 MHz, DMSO-d$_6$, 20° C.) 148.8 (Cq), 148.1 (Cq), 144.9 (CH), 131.8 (2×CH), 128.8 (CH), 127.8 (2×CH), 120.0 (Cq), 119.7 (CH), 119.5 (Cq), 116.8 (Cq), 106.6 (CH), 93.3 (Cq), 82.9 (d, J=161.5 Hz, CH$_2$), 82.2 (Cq), 54.3 (d, J=6.0 Hz, CH$_2$), 54.1 (2×CH$_2$), 40.8 (CH$_2$), 33.2 (2×CH$_2$), 28.0 (d, J=19.1 Hz, CH$_2$). $^{19}$F NMR (376 MHz, DMSO-d$_6$, 20° C.) δ. -218.3. HRMS (+ESI) calculated for C$_{23}$H$_{24}$FN$_3$ (M+H+): 361.2027, found: 361.2026.

Example 38. 5-fluoro-2-((4-(4-phenylpiperidin-1-yl)phenyl)ethynyl)-1H-pyrrolo[2,3-b]pyridine 90

5-fluoro-2-((4-(4-phenylpiperidin-1-yl)phenyl)ethynyl)-1H-pyrrolo[2,3-b]pyridine was synthesized in 4 steps. Initially, the corresponding alkyne 91 was prepared in 3 steps and then we did the Sonogashira reaction with azaindole to obtain the final compound.

Example 38.1 Synthesis of 1-(4-ethynylphenyl)-4-phenyl-piperidine 91

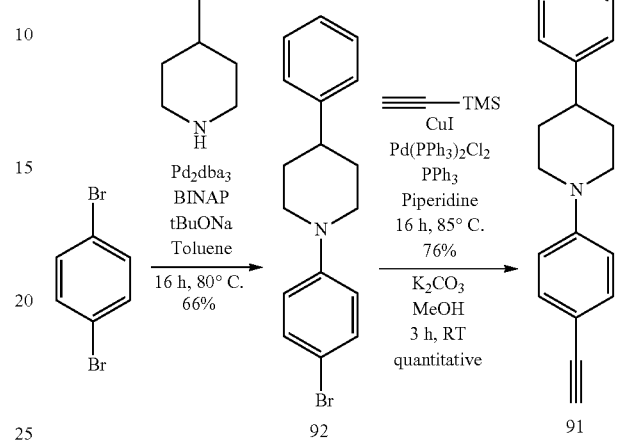

Synthesis of bromine 92

Compound 92 was prepared according to procedure D and purified by flash column chromatography on silica gel (ethyl acetate/petroleum ether=2/48). White solid (97%). $^1$H NMR (250 MHz, CDCl$_3$) δ 7.41-7.20 (m, 6H), 6.92-6.83 (m, 2H), 3.84-3.74 (m, 2H), 2.84 (m, 2H), 2.68 (m, 1H), 2.03-1.83 (m, 4H). CAS Number: 303975-64-6.

Synthesis of 1-(4-ethynylphenyl)-4-phenyl-piperidine 91

The alkyne 91 was prepared according to procedure E and purified by flash column chromatography on silica gel (ethyl acetate/petroleum ether=2/48). White solid (76%), mp 136-138° C., Rf=0.30 (ethyl acetate/petroleum ether=2/48). IR (□, cm$^{-1}$, neat) 3157, 3072, 2893, 2205, 1605, 1541, 1511, 1432, 1273, 1224, 1183, 809, 763, 507. $^1$H NMR (400 MHz, CDCl$_3$, 20° C.) δ 7.46-7.30 (m, 4H), 7.32-7.20 (m, 3H), 6.95-6.87 (m, 2H), 3.96-3.85 (m, 2H), 3.01 (s, 1H), 2.90 (m, 2H), 2.71 (m, 1H), 2.03-1.81 (m, 4H). $^{13}$C NMR (101 MHz, CDCl$_3$, 20° C.) δ 151.5 (Cq), 145.8 (Cq), 133.2 (2×CH), 128.5 (2×CH), 126.8 (2×CH), 126.4 (CH), 115.4 (2×CH), 111.5 (Cq), 84.4 (Cq), 75.3 (CH), 49.5 (2×CH$_2$), 42.5 (CH), 32.9 (2×CH$_2$). HRMS (+ESI) calculated for C$_{19}$H$_{19}$N (M+H+): 262.1590, found: 292.1590.

Example 38.2 5-fluoro-2-((4-(4-phenylpiperidin-1-yl)phenyl)ethynyl)-1H-pyrrolo[2,3-b]pyridine

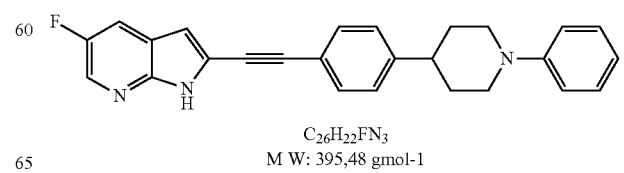

C$_{26}$H$_{22}$FN$_3$
M W: 395,48 gmol-1

The compound was prepared according to procedure C2 and purified by flash column chromatography on silica gel (ethyl acetate/petroleum ether=20/80). White solid (34%), mp>260° C., Rf=0.20 (ethyl acetate/petroleum ether=20/80). IR (□, cm$^{-1}$, neat) 3117, 3063, 2917, 2813, 2734, 2205, 1600, 1586, 1534, 1503, 1462, 1386, 1341, 1292, 1214, 1191, 1154, 1101, 1011, 819. $^1$H NMR (400 MHz, DMSO-d$_6$, 20° C.) δ 12.22 (s, 1H), 8.19 (m, 1H), 7.79 (m, 1H), 7.47-7.09 (m, 7H), 6.99 (d, J=8.8 Hz, 2H), 6.68 (s, 1H), 3.95 (m, 2H), 2.80 (m, 3H), 1.90-1.55 (m, 4H). $^{19}$F NMR (376 MHz, DMSO-d$_6$, 20° C.) δ. −138.5. HRMS (+ESI) calculated for C$_{26}$H$_{22}$FN$_3$ (M+H+): 396.1868, found: 396.1869.

Example 39. 5-((1H-pyrrolo[2,3-b]pyridin-2-yl)ethynyl)-2-fluoro-N,N-dimethylaniline 93

5-((1H-pyrrolo[2,3-b]pyridin-2-yl)ethynyl)-2-fluoro-N,N-dimethylaniline was synthesized in 4 steps. Initially, the corresponding alkyne 94 was prepared in 3 steps and then we did the Sonogashira reaction with azaindole to obtain the final compound.

Example 39.1 Synthesis of 5-ethynyl-2-fluoro-N,N-dimethyl-aniline 94

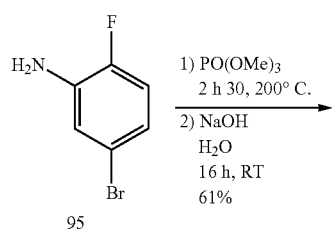

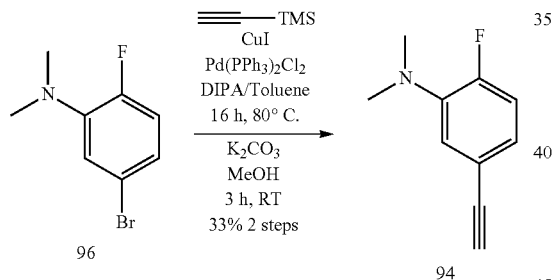

Synthesis of Bromine 96

Bromine 95 (1.0 g, 5.26 mmol, 1.0 eq.) is dissolved in 0.650 ml of trimethyl phosphate (5.52 mmol, 1.05 eq.). After 2 h30 at 200° C., the mixture was cooled to room temperature and 15 ml of a solution of 2M NaOH was added. After one night at room temperature, the organic phase is extracted with dichloromethane (3×15 ml). Then the organic phases are combined, dried and filtered over cotton. After evaporation under reduced pressure, the crude was purified by flash column chromatography on silica gel with eluting agent (ethyl acetate/petroleum ether=2/48) to obtain the compound 96. Colorless oil (61%). 1H NMR (250 MHz, CDCl$_3$) δ 7.01-6.77 (m, 3H), 2.84 (s, 6H). CAS Number: 1352214-46-0.

Synthesis of 5-ethynyl-2-fluoro-N,N-dimethylaniline 94

The catalyst [Pd(PPh$_3$)$_4$] (53 mg, 0.046 mmol, 5 mol %) was added to a degassed solution of bromine derivative 96 (200 mg, 0.92 mmol, 1.0 eq.), ethynyltrimethylsilane (0.152 ml, 0.1 1 mmol, 1.2 eq), CuI (9 mg, 0.046 mmol, 5 mol %) in a mixture of diisopropylamine/toluene (1:3) at a concentration of 0.1 M. The mixture was heated at 80° C. for 16 h under argon. After returning to room temperature, the mixture was concentrated under reduced pressure before being purified by flash column chromatography on silica gel with eluting agent (ethyl acetate/petroleum ether=2/48) to obtain 172 mg of the intermediate alkyne. This latter is reacted with K$_2$CO$_3$ (151 mg, 1.1 mmol, 1.5 eq.) in methanol. After stirring for 3 h at room temperature, the solvent was evaporated. Then, the crude is solubilized in 10 ml of ethyl acetate. Then the organic phase is washed with brine (3×10 ml). Then the organic phase is dried with MgSO$_4$, filtered through cotton and evaporated under reduced pressure.

The crude was purified by flash column chromatography on silica gel with eluent (ethyl acetate/petroleum ether=2/48) to afford the alkyne 94. Colorless oil (33%). Rf=0.30 (ethyl acetate/petroleum ether=15/85). IR (□, cm$^{-1}$, neat) 3290, 2970, 2930, 2853, 2102, 1606, 1511, 1463, 1434, 1356, 1336, 1273, 1245, 1227, 1185, 1140, 1023, 935. $^1$H NMR (400 MHz, CDCl$_3$, 20° C.) δ 7.12-6.81 (m, 3H), 3.00 (s, 1H), 2.84 (s, 6H). $^{13}$C NMR (101 MHz, CDCl$_3$, 20° C.) δ 155.3 (d, J=249.4 Hz, Cq), 140.7 (d, J=9.4 Hz, Cq), 125.0 (d, J=8.2 Hz, CH), 121.9 (d, J=4.2 Hz, CH), 118.1 (d, J=3.8 Hz, Cq), 116.3 (d, J=22.2 Hz, CH), 83.4 (Cq), 76.1 (CH), 42.6 (d, J=4.2 Hz, 2×CH$_3$)$^{19}$F NMR (376 MHz, CDCl$_3$, 20° C.) δ. −119.7. HRMS (+ESI) calculated for C$_{10}$H$_{10}$FN (M+H+): 164.0870, found: 164.0872.

Example 39.2 Synthesis of 5-((1H-pyrrolo[2,3-b]pyridin-2-yl)ethynyl)-2-fluoro-N,N-dimethylaniline 93

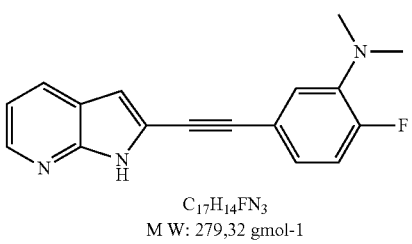 [SMILES: CN(C)c1cc(C#Cc2cc3cccnc3[nH]2)ccc1F]

C$_{17}$H$_{14}$FN$_3$
M W: 279,32 gmol-1

The compound was prepared according to procedure C2 and purified by flash column chromatography on silica gel (ethyl acetate/petroleum ether=45/55). Yellowish solid (79%), mp 170-172° C., Rf=0.20 (ethyl acetate/petroleum ether=30/70). IR (□, cm$^{-1}$, neat) 3157, 3072, 2893, 2205, 1605, 1541, 1511, 1432, 1273, 1224, 1183, 809, 763, 507. $^1$H NMR (400 MHz, CDCl$_3$, 20° C.) δ 10.84 (s, 1H), 8.43-8.31 (m, 1H), 7.93 (d, J=7.9 Hz, 1H), 7.10 (d, J=7.9 Hz, 2H), 7.05-6.93 (m, 1H), 6.76 (s, 1H), 2.90 (s, 6H). $^{13}$C NMR (101 MHz, CDCl$_3$, 20° C.) δ 155.3 (d, J=249.9 Hz, Cq), 148.4 (Cq), 143.9 (CH), 140.9 (d, J=9.4 Hz, Cq), 128.9 (CH), 124.5 (d, J=8.2 Hz, CH), 121.3 (d, J=4.2 Hz, CH), 120.7 (Cq), 119.82 (Cq), 118.5 (Cq), 116.6 (CH), 116.5 (d, J=22.2 Hz, CH), 106.4 (CH), 93.2 (Cq), 80.5 (Cq), 42.7 (CH$_3$), 42.6 (CH$_3$)$_1$$^9$F NMR (376 MHz, CDCl$_3$, 20° C.) δ. −119.3. HRMS (+ESI) calculated for C$_{17}$H$_{14}$FN$_3$ (M+H+): 280.1244, found: 280.1244.

Example 40. 2-((4-(4-((5-fluoro-1H-pyrrolo[2,3-b]pyridin-2 yl)ethynyl)phenoxy)phenyl)(methyl)amino)ethan-1-ol 97 2-((4-(4-((5-fluoro-1H-pyrrolo[2,3-b]pyridin-2-yl)ethynyl)

phenoxy)phenyl)(methyl)amino)ethan-1-ol 97 was synthesized in 6 steps. Initially, the corresponding alkyne 98 was prepared in 4 steps starting from the phenyl ether 99 and then we performed the Sonogashira reaction with azaindole followed by a deprotection reaction with TBAF to obtain the final compound.

Example 40.1 Synthesis of N-[2-[tert-butyl(diphenyl)silyl]oxoethyl]-4-(4-ethynylphenoxy)-N-methyl-aniline 98

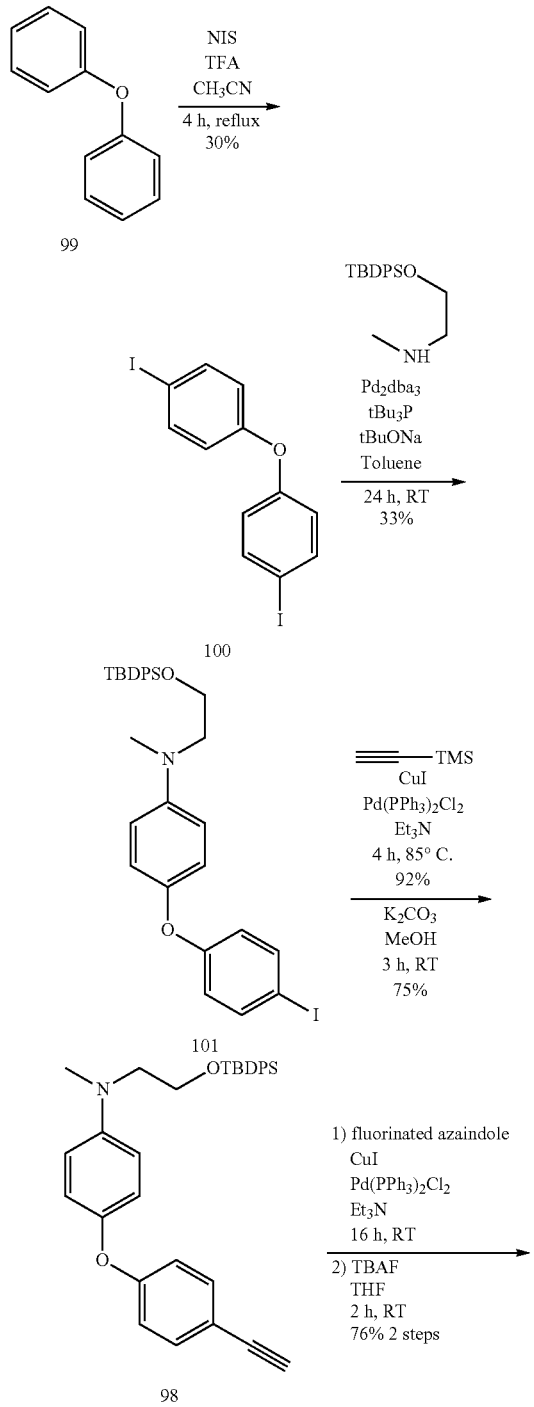

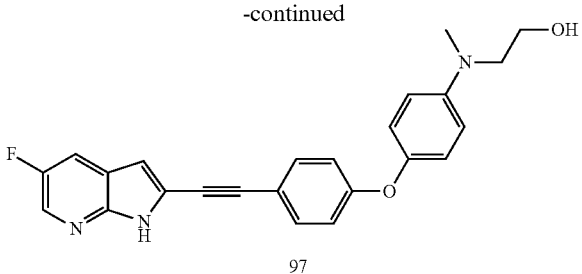

Synthesis of Iodine 100

Under argon, 200 mg of phenyl ether 99 (1.18 mmol, 1.0 eq.) is dissolved in 5 ml of $CH_3CN$. 528 mg of N-iodosuccinimide (2.35 mmol, 2.0 eq.) and 10 µL of TFA are added. After 4 h at reflux, the reaction mixture was cooled to room temperature and 10 ml of sodium thiosulfate solution is added followed by 10 ml of DCM. Then the organic phase was washed with sodium thiosulfate solution (3×10 ml). Then the organic phase was dried with $MgSO_4$, filtered through cotton and evaporated under reduced pressure. The crude product is triturated with diethyl ether, followed by vacuum filtration. The iodine 100 is obtained as a white solid with a yield of 30%. $^1$H NMR (250 MHz, $CDCl_3$) δ 7.70-7.49 (m, 4H), 6.87-6.65 (m, 4H). CAS Number: 28896-49-3.

Synthesis of Compound 101

Under argon, $Pd_2dba_3$ (0.05 eq.) and $tBu_3P$ (0.075 mmol) were added to a degassed anhydrous toluene solution of 0.3M concentration containing the amine (1.0 eq.), the iodine 100 (1.0 eq.) and t-BuONa (1.2 eq.). After 24 h at room temperature, the solvent was evaporated under reduced pressure. Then, the reaction mixture was concentrated under reduced pressure, before being purified by flash column chromatography on silica gel. The compound 101 is obtained as a colorless oil in 33% yield, Rf=0.20 (ethyl acetate/petroleum ether=1/49). IR (□, cm$^{-1}$, neat) 2928, 2856, 1610, 1508, 1477, 1426, 1390, 1273, 1232, 1163, 1105, 1056, 1003, 928, 866, 818. 781. $^1$H NMR (400 MHz, $CDCl_3$, 20° C.) δ 7.65 (dt, J=7.8, 1.3 Hz, 4H), 7.53 (d, J=8.5 Hz, 2H), 7.45-7.33 (m, 6H), 6.85 (d, J=9.0 Hz, 2H), 6.72-6.61 (m, 2H), 6.55 (d, J=9.0 Hz, 2H), 3.81 (t, J=6.2 Hz, 2H), 3.47 (t, J=6.2 Hz, 2H), 2.93 (s, 3H), 1.04 (s, 9H). $^{13}$C NMR (101 MHz, $CDCl_3$, 20° C.) δ 159.4 (Cq), 146.5 (Cq), 145.7 (Cq), 138.3 (2×CH), 135.6 (4×CH), 133.4 (Cq), 129.7 (4×CH), 127.7 (2×CH), 121.2 (2×CH), 119.1 (2×CH), 112.8 (2×CH), 84.0 (Cq), 61.1 ($CH_2$), 54.9 ($CH_2$), 39.3 ($CH_3$), 26.8 (3×$CH_3$). HRMS (+ESI) calculated for $C_{31}H_{34}INO_2Si$ (M+H+): 608.1476, found: 608.1474.

Synthesis N-(2-((tert-butyldiphenylsilyl)ox)ethyl)-4-(4-ethylnlphenoxy)-N-methylaniline 98

Catalyst [Pd(PPh$_3$)$_2$Cl$_2$] (2.8 mg, 0.004 mmol, 0.03 eq.) was added to a degassed solution of iodine 101 (80 mg, 0.131 mmol, 1.0 eq.), ethynyltrimethylsilane (0.027 ml, 0.2 mmol, 1.5 eq.), CuI (1 mg, 0.004 mmol, 0.03 eq.), in the $Et_3N$ at a concentration of 0.3 M. The mixture was stirred at 85° C. for 4 h under argon atmosphere. Then the reaction mixture was concentrated under reduced pressure, before being purified by column flash chromatography on silica gel with eluent (ethyl acetate/petroleum ether=20/80) to obtain 70 mg of the intermediate which reacted with K₂CO₃ (25 mg, 0.181 mmol, 1.5 eq.) in 6 ml of DCM/methanol (1/1). After 3 h stirring at room temperature, the solution is filtered through cotton. After evaporation to dryness, the crude is purified by flash chromatography column on silica gel with eluting agent (ethyl acetate/petroleum ether=30/70) to give alkyne 98 as a brown solid with a yield of 69% yield over 2 steps. mp 170-172° C., Rf=0.20 (ethyl acetate/petroleum ether=30/70). IR (□, cm⁻¹, neat) 3284, 3070, 2929, 2856, 1610, 1513, 1495, 1471, 1427, 1360, 1280, 1234, 1160, 1103, 985, 927, 869. ¹H NMR (250 MHz, CDCl₃, 20° C.) δ 7.65-7.56 (m, 4H), 7.41-7.28 (m, 8H), 6.82 (m, 4H), 6.62-6.45 (m, 2H), 3.87-3.64 (t, J=6.2 Hz, 2H), 3.44 (t, J=6.2 Hz, 2H), 2.97 (s, 1H), 2.91 (s, 3H), 1.01 (s, 9H). ¹³C NMR (63 MHz, CDCl₃, 20° C.) δ 160.2 (2×Cq), 147.2 (Cq), 146.2 (Cq), 136.3 (4×CH), 134.2 (2×CH), 134.1 (Cq), 130.4 (2×CH), 128.4 (4×CH), 122.0 (2×CH), 117.2 (2×CH), 115.8 (Cq), 113.5 (2×CH), 77.9 (Cq) 76.6 (CH), 61.8 (CH₂), 55.5 (CH₂), 39.9 (Cq), 27.5 (3×CH₃), 19.7 (CH₃). HRMS (+ESI) calculated for C₃₃H₃₅NO₂Si (M+H+): 506.2009, found: 506.2009.

Example 40.2 2-((4-(4-((5-fluoro-1H-pyrrolo[2,3-b]pyridin-2-yl)ethynyl)phenoxy)phenyl) (methyl) amino)ethan-1-ol 97

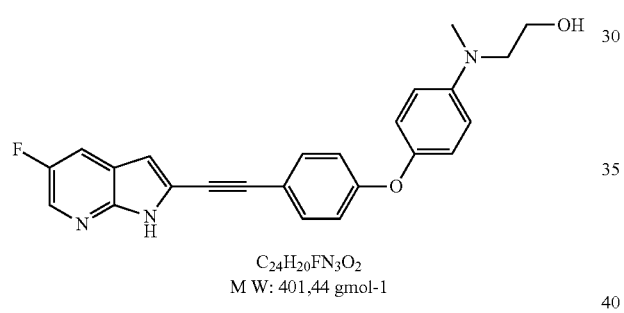

C₂₄H₂₀FN₃O₂
M W: 401,44 gmol-1

The compound was prepared according to procedure C2 followed by procedure F and purified by flash column chromatography on silica gel (methanol/dichloromethliane=2/48). Yellowish solid (76% over 2 steps), mp 172-174° C., Rf=0.20 (methanol/dichloromethane=2/48). IR (□, cm⁻¹, neat) 3122, 2925, 1662, 1610, 1510, 1494, 1436, 1399, 1349, 1296, 1246, 1165, 1120, 1048, 984, 872, 839. ¹H NMR (400 MHz, DMSO-d₆, 20° C.) δ 12.34 (s, 1H), 8.26 (s, 1H), 7.83 (m, 1H), 7.57 (m, 2H), 7.03-6.86 (m, 4H), 6.75 (m, 3H), 4.72-4.60 (t, J=5.9 Hz, 1H), 3.56 (q, J=5.9 Hz, 2H), 3.39 (t, J=6.1 Hz, 2H), 2.93 (s, 3H). ¹³C NMR (101 MHz, DMSO-d₆ 20° C.) δ 155.3 (d, J=239.2 Hz, Cq), 147.9 (Cq), 147.2 (Cq), 145.6 (Cq), 144.9 (Cq), 133.7 (2×CH), 132.8 (d, J=20.9 Hz, CH) 122.1 (Cq), 121.9 (2×CH), 120.2 (d, J=6.2 Hz, Cq), 117.0 (2×CH), 114.9 (Cq), 114.0 (d, J=20.2 Hz, CH), 113.3 (2×CH), 106.4 (d, J=4.0 Hz, CH), 93.7 (Cq), 81.2 (Cq), 58.6 (CH₂), 55.1 (CH₂), 39.2 (CH₃). ¹⁹F NMR (376 MHz, DMSO-d₆, 20° C.) δ. −138.4. HRMS (+ESI) calculated for C₂₄H₂₀FN₃O₂ (M+H+): 402.1612, found: 402.1611.

Example 41. 4-((1H-pyrrolo[2,3-b]pyridin-2-yl)ethynyl)-2-fluoro-N,N-dimethylaniline 103

4-((1H-pyrrolo[2,3-b]pyridin-2-yl)ethynyl)-2-fluoro-N, N-dimethylaniline was synthesized in 4 steps. Initially, the corresponding alkyne 104 was prepared in 3 steps from aldehyde 105 and then we did the Sonogashira reaction with azaindole to obtain the final compound.

Example 41.1 Synthesis of 5-ethynyl-2-fluoro-N,N-dimethylaniline 104

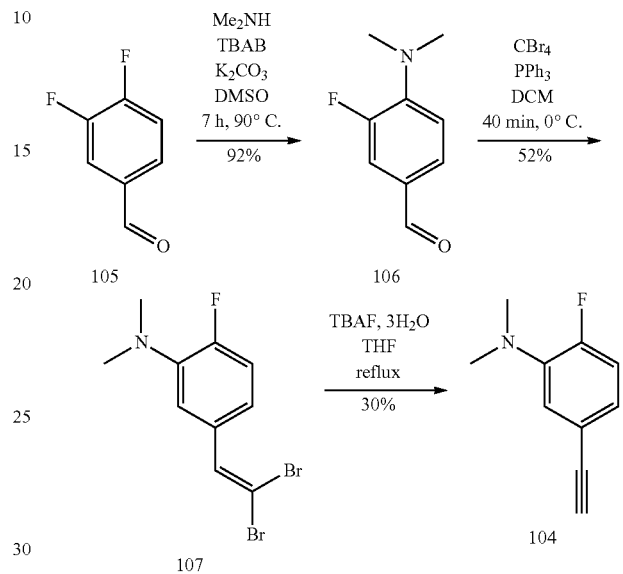

Synthesis of Aldehyde 106

Under argon, the aldehyde 105 (500 mg, 3.52 mmol, 1.0 eq.) was dissolved in 3 ml of DMSO. Then, TBAB (567 mg, 1.76 mmol, 0.5 eq.), K₂CO₃ (486 mg, 3.52 mmol, 1.0 eq.) and dimethylamine (C=2M, 8.8 ml, 17.6 mmol, 5.0 eq.) were added successively. After 7 h at 90° C., 10 ml of a saturated solution of NaHCO₃ is added. The organic phase are extracted with ethyl acetate (3×10 ml) then they are combined, dried with MgSO₄ and filtered through cotton. After evaporation under reduced pressure, the crude was purified by flash column chromatography on silica gel with eluent (ethyl acetate/petroleum ether=30/70) to give the aldehyde 106 as a colorless oil with a yield of 92%. ¹H NMR (250 MHz, CDCl₃) δ 9.72 (s, 1H), 7.57-7.38 (m, 2H), 6.78 (m, 1H), 3.02 (s, 6H). CAS Number: 1021240-69-6.

Synthesis of 5-ethynyl-2-fluoro-N,N-dimethyl-aniline 104

Under argon, CBr₄ (198 mg, 0.6 mmol, 1.0 eq.) is dissolved in 5 ml of DCM. At 0° C., PPh₃ (315 mg, 1.2 mmol, 2.0 eq.) was added in one portion. After 10 minutes, the aldehyde 106 (100 mg, 0.6 mmol, 1.0 eq.) was dissolved in 5 ml of DCM and then added dropwise. After 40 minutes at 0° C., 10 ml of H₂O is added. The organic phase was extracted with ethyl acetate (3×10 ml) and was then combined, dried with MgSO₄ and filtered through cotton. After evaporation under reduced pressure, the crude was purified by flash column chromatography on silica gel with eluent (ethyl acetate/petroleum ether=10/40) to obtain compound 107 as a white solid with a yield of 52%. Then, it was reacted with TBAF, 3H₂O (780 mg, 2.47 mmol, 8.0 eq.) in a mixture of THF/H₂O (2 ml/0.1 ml). After 7 h at 90° C., the mixture was cooled to room temperature and 5 ml of H₂O was added. The organic phase was extracted with ethyl acetate (3×10 ml) and was then combined, dried with MgSO₄ and filtered over cotton. After evaporation under reduced pressure, the crude was purified by flash column chromatography on silica gel with eluent (ethyl acetate/petroleum ether=1/99) to obtain the alkyne 104 as a yellow oil with a yield of 30%. Rf=0.50 (ethyl acetate/ether=1/99 petiole). IR (□, cm⁻¹, neat) 3290, 2970, 2930, 2853, 2102, 1606, 1511, 1463, 1434, 1356, 1336, 1273, 1245, 1227, 1185, 1140, 1023, 935. ¹H NMR (400 MHz, CDCl₃, 20° C.) δ 7.22-7.09 (m, 2H), 6.81-6.69 (m, 1H), 3.00 (s, 1H), 2.89 (s, 6H). ¹³C NMR (101 MHz, CDCl₃, 20° C.) δ 153.5 (d, J=245.3 Hz, Cq), 141.4 (d, J=8.4 Hz, Cq) 128.6 (d, J=3.0 Hz, CH) 119.7 (d, J=23.1 Hz, CH), 117.4 (d, J=4.5 Hz, CH), 113.3 (d, J=9.2 Hz, Cq), 83.0 (d, J=2.7 Hz, Cq), 76.23 (CH), 42.4 (CH₃), 42.4 (CH₃). ¹⁹F NMR (376 MHz, CDCl₃, 20° C.) δ. −122.4. HRMS (+ESI) calculated for C10H10FN (M+H+): 164.0870, found: 164.0872.

Example 41.2 4-((1H-pyrrolo[2,3-b]pyridin-2-yl) ethynyl)-2-fluoro-N,N-dimethylaniline 103

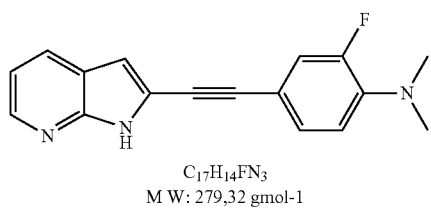 [SMILES: CN(C)c1ccc(C#Cc2cc3cccnc3[nH]2)cc1F]

C₁₇H₁₄FN₃
M W: 279,32 gmol-1

The compound was prepared according to procedure C2 and purified by flash column chromatography on silica gel (ethyl acetate/petroleum ether=45/55). Yellowish solid (79%), mp 180-182° C., Rf=0.20 (ethyl acetate/petroleum ether=30/70). IR (□, cm⁻¹, neat) 3157, 3072, 2893, 2205, 1605, 1541, 1511, 1432, 1273, 1224, 1183, 809, 763, 507. ¹H NMR (400 MHz, DMSO-d₆, 20° C.) δ 12.15 (s, 1H), 8.27 (s, 1H), 7.95 (d, J=7.8 Hz, 1H), 7.46-7.20 (m, 2H), 7.20-7.03 (m, 1H), 6.96 (t, J=9.0 Hz, 1H), 6.78 (s, 1H), 2.89 (s, 6H). ¹³C NMR (101 MHz, DMSO-d₆, 20° C.) δ 152.9 (d, J=243.9 Hz, Cq), 148.5 (Cq), 144.5 (CH), 141.2 (d, J=8.0 Hz, Cq), 128.6 (m, 2×CH), 120.2 (Cq), 119.8 (Cq), 119.6 (d, J=22.8 Hz, CH), 118.2 (d, J=4.7 Hz, CH), 116.6 (CH), 112.2 (d, J=9.7 Hz, Cq), 106.0 (CH), 92.5 (Cq), 81.5 (Cq), 42.2 (CH₃), 42.1 (CH₃). ¹⁹F NMR (376 MHz, DMSO-d₆, 20° C.) δ. −122.1. HRMS (+ESI) calculated for C17H14FN3 (M+H+): 280.1244, found: 280.1245.

Example 42: 2-((4-(1H-pyrazol-1-yl)phenyl)ethynyl)-5-fluoro-1H-pyrrolo[2,3-b]pyridine 108

2-((4-(1H-pyrazol-1-yl)phenyl)ethynyl)-5-fluoro-1H-pyrrolo[2,3-b]pyridine was synthesized in 4 steps. Initially, the corresponding alkyne 109 was prepared in 3 steps from the compound 110 and then we did the Sonogashira reaction with azaindole to obtain the final compound.

Example 42.1 Synthesis of 1-(4-ethynylphenyl)-1H-pyrazole 109

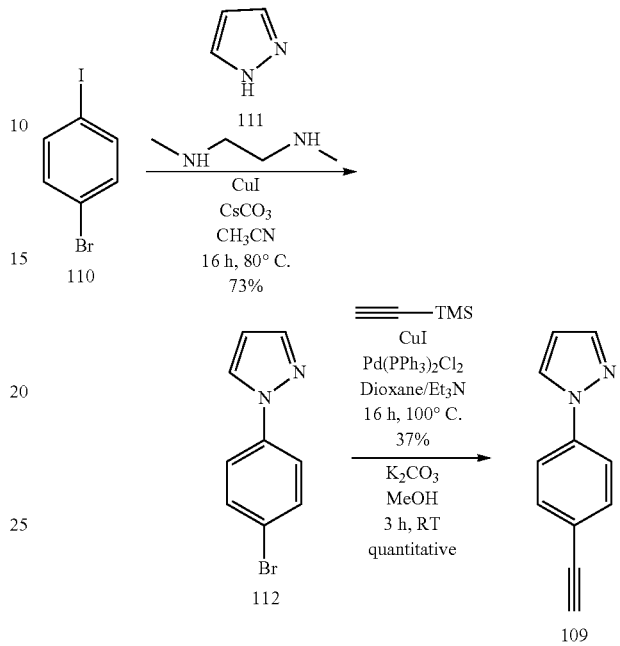

Synthesis of Bromine 112

CuI (27 mg, 0.141 mmol, 20 mol %) was added to a degassed solution of iodine derivative 110 (200 mg, 0.707 mmol, 1.0 eq.), of amine 111 (50.5 mg, 0.742 mmol, 1.05 eq.), N,N'-dimethylethylenediamine (0.026 ml, 0.282 mmol, 20% mol) and CsCO₃ (459 mg, 1.41 mmol, 2.0 eq.) in 3.0 ml of CH₃CN. The mixture was stirred at 80° C. for 16 h under argon. Then the mixture was cooled and filtered through Celite®. The filtrate is evaporated under reduced pressure before being purified by flash column chromatography on silica gel with eluent (ethyl acetate/petroleum ether=25/75) to obtain 115 mg of the bromine 112 in the form of a colorless oil with a yield of 73% yield. ¹H NMR (250 MHz, CDCl₃, 20° C.) δ 7.86 (m, 1H), 7.69 (m, 1H), 7.55 (m, 4H), 6.45 (m, 1H). Numéro CAS Number: 13788-92-6.

Synthesis of 1-(4-ethynylphenyl)-1H-pyrazole 109

Under argon, Pd(PPh₃)₂Cl₂ (6 mg, 0.009 mmol, 0.04 eq.) and CuI (2 mg, 0.009 mmol, 0.04 eq.) were added to a degassed solution of Et₃N/Dioxane (1.5 ml (2/1)) containing ethynyltrimethylsilane (0.155 ml, 1.12 mmol, 5.0 eq.), the bromine derivative 112 (50 mg, 0.224 mmol, 1.0 eq.). After 16 h at 100° C., the solvent was evaporated under reduced pressure. Then, the reaction mixture was purified by flash column chromatography on silica gel. Then, 20 mg of the intermediate alkyne is reacted with K₂CO₃ (17 mg, 0.125 mmol, 1.5 eq.) in 3 ml of methanol. After 3 h at room temperature, the solvent was evaporated under reduced pressure. The crude product is dissolved in 10 ml of ethyl acetate. Then the organic phase is washed with brine (3×10 ml). Then the organic phase is dried with MgSO₄, filtered through cotton and evaporated under reduced pressure to obtain the alkyne 109 as a white solid with a yield of 37% over 2 steps. mp 54-56° C., Rf=0.5 (ethyl acetate/petroleum ether=2/48). IR (□, cm$^{-1}$, neat) 3273, 3232, 3150, 2918, 1606, 1521, 1506, 1390, 1335, 1312, 1248, 1205, 1193, 1205, 1193, 1118, 1045, 1028, 934. $^1$H NMR (250 MHz, CDCl$_3$, 20° C.) δ 7.90 (dd, J=2.5, 0.6 Hz, 1H), 7.71 (dd, J=1.8, 0.6 Hz, 1H), 7.65 (d, J=8.9 Hz, 2H), 7.55 (d, J=8.9 Hz, 2H), 6.45 (dd, J=2.5, 1.8 Hz, 1H), 3.09 (s, 1H). $^{13}$C NMR (63 MHz, CDCl$_3$ 20° C.) δ 141.5 (CH), 140.1 (Cq), 133.3 (2×CH), 126.7 (CH), 120.0 (Cq), 118.7 (2×CH), 108.1 (CH), 82.9 (Cq), 77.9 (CH). HRMS (+ESI) calculated for C$_{11}$H$_9$N$_2$ (M+H+): 169.0760, found: 169.0763.

Example 42.2 2-((4-(1H-pyrazol-1-yl)phenyl)ethynyl)-5-fluoro-1H-pyrrolo[2,3-b]pyridine 108

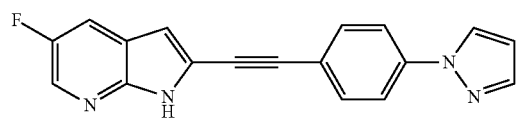

C$_{18}$H$_{11}$FN$_4$
M W: 302,31 gmol-1

The compound was prepared according to procedure C2 and purified by flash column chromatography on silica gel (ethyl acetate/petroleum ether=10/40). Yellowish solid (51%), mp>260° C., Rf=0.1 (ethyl acetate/petroleum ether=10/40). IR (v, cm$^{-1}$, neat) 3157, 3072, 2893, 2205, 1605, 1541, 1511, 1432, 1273, 1224, 1183, 809, 763, 507. $^1$H NMR (400 MHz, DMSO-d$_6$, 20° C.) δ 12.41 (s, 1H), 8.60 (d, J=2.6 Hz, 1H), 8.36-8.21 (m, 1H), 7.96 (d, J=8.7 Hz, 1H), 7.90-7.79 (m, 2H), 7.71 (d, J=8.7 Hz, 2H), 6.84 (d, J=1.9 Hz, 1H), 6.5 (s, 1H). $^{13}$C NMR (101 MHz, DMSO-d$_6$, 20° C.) δ 155.7 (d, J=240.5 Hz, Cq), 145.7 (Cq), 142.1 (CH), 140.3 (Cq), 133.3 (d, J=29.0 Hz, CH), 133.1 (2×CH), 128.5 (CH), 121.6 (Cq), 120.1 (d, J=7.5 Hz, Cq), 119.3 (Cq), 118.9 (2×CH), 114.2 (d, J=20.7 Hz, CH), 108.9 (CH), 106.8 (d, J=4.6 Hz, CH), 93.2 (Cq), 82.7 (Cq). $^{19}$F NMR (376 MHz, DMSO-d$_6$, 20° C.) δ. −122.1. HRMS (+ESI) calculated for C$_{18}$H$_{11}$FN$_4$ (M+H+): 303.1040, found: 303.1039.

Example 43. 2-[2-[4-(4-fluoro-1-piperidyl)phenyl]ethynyl]-1H-pyrrolo[2,3-b]pyridine 113

2-[2-[4-(4-fluoro-1-piperidyl)phenyl]ethynyl]-1H-pyrrolo[2,3-b]pyridine 113 was synthesized in 4 steps. Initially, the corresponding alkyne 114 was prepared in 3 steps from dibromobenzene and then we did the Sonogashira reaction with azaindole to obtain the final compound.

Example 43.1 Synthesis of 1-(4-ethynylphenyl)-4-fluoropiperidine 114

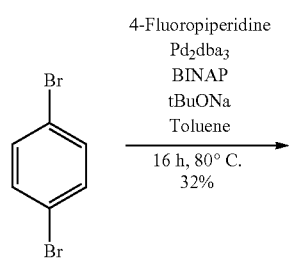

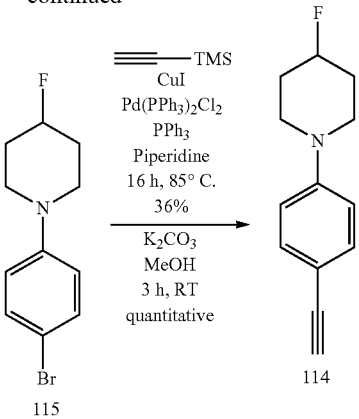

Synthesis of Bromine 115

Compound 115 was prepared according to procedure D and purified by flash column chromatography on silica gel (ethyl acetate/petroleum ether=1/49). Colorless oil (32%). $^1$H MNR (250 MHz, CDCl$_3$) δ 7.33 (d, J=8.9 Hz, 2H), 6.80 (d, J=8.9 Hz, 2H), 4.97-4.61 (m, 1H), 3.41-3.22 (m, 2H), 3.25-3.08 (m, 2H), 2.14-1.86 (m, 4H). CAS Number: 1423130-86-2.

Synthesis of 1-(4-ethynylphenyl)-4-fluoro-piperidine 114

The alkyne 114 was prepared according to procedure E and purified by flash column chromatography on silica gel (ethyl acetate/petroleum ether=2/48). Colorless oil (36% over two steps). IR (v, cm$^{-1}$, neat) 3291, 2962, 2930, 2853, 2102, 1606, 1511, 1463, 1434, 1373, 1356, 1336, 1273, 1245, 1227, 1185, 1141, 1093, 1023, 935. $^1$H NMR (400 MHz, CDCl$_3$, 20° C.) δ 7.40 (d, J=8.8 Hz, 2H), 6.87 (d, J=8.8 Hz, 2H), 4.85 (m, 1H), 3.51-3.37 (m, 2H), 3.34-3.20 (m, 2H), 3.01 (s, 1H), 2.15-1.88 (m, 4H). $^{13}$C NMR (101 MHz, CDCl$_3$, 20° C.) δ 150.9 (Cq), 133.3 (2×CH), 115.4 (2×CH), 111.9 (Cq), 88.1 (d, J=171.3 Hz, CH), 84.2 (Cq), 75.4 (CH), 44.9 (CH$_2$), 44.9 (CH$_2$), 30.9 (CH$_2$), 30.7 (CH$_2$). $^{19}$F NMR (376 MHz, CDCl$_3$, 20° C.) δ. −181.4. HRMS (+ESI) calculated for C$_{13}$H$_{14}$FN (M+H+): 204.1183, found: 204.1181.

Example 43.2 2-[2-[4-(4-fluoro-1-piperidyl)phenyl]ethynyl]-1H-pyrrolo[2,3-b]pyridine 113

C$_{20}$H$_{18}$FN$_3$
M W: 319,38 gmol-1

The compound was prepared according to procedure C1 and purified by flash column chromatography on silica gel (ethyl acetate/petroleum ether=30/70). Yellow solid (quantitative), mp>260° C., Rf=0.20 (ethyl acetate/petroleum ether=30/70). IR (v, cm$^{-1}$, neat) 3113, 3057, 2955, 2932, 2819, 2207, 1600, 1584, 1533, 1505, 1405, 1370, 1354, 1278, 1224, 1189, 1027, 816. $^1$H NMR (250 MHz, DMSO-d$_6$, 20° C.) δ 12.05 (s, 1H), 8.21 (s, 1H), 7.91 (d, J=7.8 Hz, 1H), 7.38 (d, J=8.6 Hz, 2H), 7.09 (m, 1H), 6.98 (d, J=8.6 Hz, 2H), 6.69 (s, 1H), 4.99-4.76 (m, 2H), 3.49 (dt, J=13.5, 5.4 Hz, 2H), 3.33 (dt, J=13.5, 5.4 Hz, 2H), 2.02 (m, 4H). $^{13}$C NMR DEPT (63 MHz, DMSO-d$_6$, 20° C.) δ 144.4 (CH), 132.9 (2×CH), 128.5 (CH), 116.7 (CH), 115.3 (2×CH), 105.8 (CH), 88.8 (d, J=169.2 Hz, CH), 44.4 (d, J=6.8 Hz, 2×CH$_2$), 30.8 (d, J=19.1 Hz, 2×CH$_2$). $^{19}$F NMR (235 MHz, CDCl$_3$, 20° C.) δ. −181.5. HRMS (+ESI) calculated for C$_{20}$H$_{18}$FN$_3$ (M+H+): 320.1157, found: 320.1557.

Example 44. 4'-((5-fluoro-1H-pyrrolo[2,3-b]pyridin-2-yl)ethynyl)-N,N-dimethyl-[1,1'-biphenyl]-4-amine 116

4'-((5-fluoro-1H-pyrrolo[2,3-b]pyridin-2-yl)ethynyl)-N,N-dimethyl-[1,1'-biphenyl]-4-amine was synthesized in 4 steps. Initially, the corresponding alkyne 117 was prepared in 3 steps from the compound 119 and then we did the Sonogashira reaction with azaindole to obtain the final compound.

Example 44.1 Synthesis of 4'-ethynyl-N,N-dimethyl-[1,1'-biphenyl]-4-amine 117

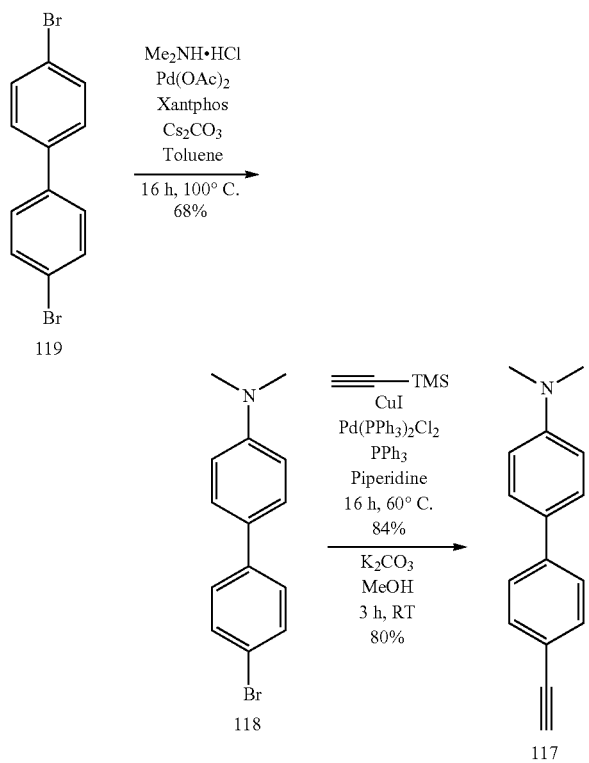

Synthesis of Bromine 118

Under argon, Pd(OAc)$_2$ (0.05 eq.) and Xantphos (0.067 mmol) were added to a degassed anhydrous toluene solution of 0.3M concentration containing dimethylamine hydrochloride (1.0 eq.), The bromine 119 (2.0 eq.) and Cs$_2$CO$_3$ (3.0 eq.). After 16 h at 100° C., the solvent was evaporated under reduced pressure. Then, the reaction mixture was concentrated under reduced pressure before being purified by flash column chromatography on silica gel to obtain the bromine 118 as a white solid with a yield of 68%. $^1$H NMR (250 MHz, CDCl$_3$) δ 7.51-7.34 (m, 6H), 6.76 (d, J=8.9 Hz, 2H), 2.97 (s, 6H). CAS Number: 92194-03-1.

Synthesis of 4-(4-ethynylphenyl)-N,N-dimethyl-aniline 117

The alkyne 117 was prepared according to procedure E and at a temperature of 60° C. and purified by flash column chromatography on silica gel (ethyl acetate/petroleum ether=2/48). Colorless oil (67% over two steps). $^1$H NMR (250 MHz, CDCl$_3$) δ 7.56-7.34 (m, 6H), 6.84-6.67 (m, 2H), 3.31 (s, 1H), 2.97 (s, 6H). CAS Number: 1190376-40-9.

Example 44.2 4'-((5-fluoro-1H-pyrrolo[2,3-b]pyridin-2-yl)ethynyl)-N,N-dimethyl-[1,1'-biphenyl]-4-amine 116

C$_{23}$H$_{18}$FN$_3$
M W: 355,41 gmol-1

The compound was prepared according to procedure C2 and purified by flash column chromatography on silica gel (ethyl acetate/petroleum ether=30/70). Yellow solid (quantitative), mp>260° C., Rf=0.20 (ethyl acetate/petroleum ether=30/70). IR (v, cm$^{-1}$, neat) 3428, 3157, 3072, 2893, 2205, 1605, 1541, 1511, 1432, 1273, 1224, 1183, 809, 763, 507. $^1$H NMR (250 MHz, DMSO-d$_6$, 20° C.) δ 12.38 (s, 1H), 8.28 (s, 1H), 7.86 (dd, J=9.4, 2.7 Hz, 1H), 7.71 (d, J=8.1 Hz, 2H), 7.63-7.53 (m, 4H), 6.86-6.75 (m, 3H), 2.97 (s, 6H). $^{13}$C NMR DEPT (63 MHz, DMSO-d$_6$ 20° C.) δ 133.1 (d, J=29 Hz, CH), 132.3 (2×CH), 127.6 (2×CH), 126.0 (2×CH), 114.1 (d, J=20.8 Hz, CH), 113.03 (2×CH), 106.6 (d, J=4.8 Hz, CH), 40.9 (2×CH3). $^{19}$F NMR (235 MHz, DMSO-d$_6$, 20° C.) δ. −138.5. HRMS (+ESI) calculated for C$_{23}$H$_{18}$FN$_3$ (M+H+): 356.1557, found: 356.1554.

Example 45. (5-((5-fluoro-1H-pyrrolo[2,3-b]pyridin-2-yl)ethynyl)furan-2-yl)methanol 120

(5-((5-fluoro-1H-pyrrolo[2,3-b]pyridin-2-yl)ethynyl)furan-2-yl)methanol was synthesized in 4 steps. Initially, the corresponding alkyne 121 was prepared in 3 steps from the compound 122 and then we did the Sonogashira reaction with azaindole to obtain the final compound.

Example 45.1 Preparation du (5-ethenylfuran-2-yl)methanol 121

The alkyne 121 was prepared in three steps starting with 2-bromo-2-furaldehyde 122. The first step has been described in Organometallics, (Vol. 24, No. 4, 2005, p. 693) and the last step was found in the patent (US2010/63041 A1 p. 30)

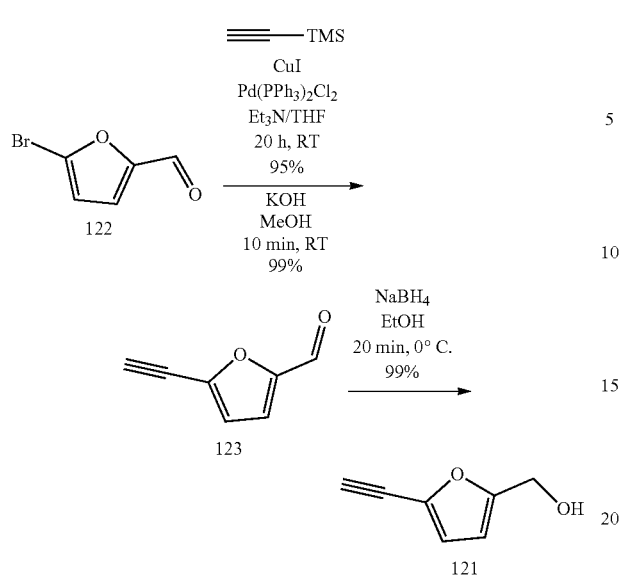

Synthesis of the Aldehyde 123

The compound 123 was prepared according to procedure G. Brown oil (99%), Rf=0.5 (ethyl acetate/petroleum ether=2/98). CAS Number: 153026-71-2.

Synthesis of (5-ethenylfuran-2-yl) methanol 121

100 mg of aldehyde 123 (0.83 mmol, 1.0 eq.) is dissolved with NaBH$_4$ (14 mg, 0.37 mmol, 0.45 eq.) in 2.5 ml of ethanol. After 20 min at 0° C., 10 ml of H$_2$O is added and the organic phase was extracted with ethyl acetate (3×10 ml). The organic phases are combined, dried over MgSO$_4$, filtered through cotton and evaporated under reduced pressure. The alkyne 121 was obtained in the form of a brown oil with a yield of 99%. $^1$H NMR (250 MHz, CDCl$_3$, 20° C.) δ 6.47 (dd, J=3.3, 0.7 Hz, 1H), 6.15 (dd, J=3.3, 0.7 Hz, 1H), 4.45 (s, 2H,), 3.32 (s, 1H). CAS Number: 153026-89-2.

Example 45.2 (5-((5-fluoro-1H-pyrrolo[2,3-b]pyridin-2-yl)ethynyl)furan-2-yl)methanol 120

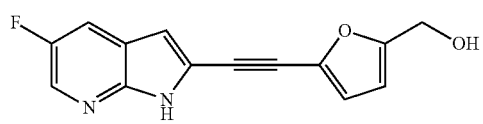

C$_{14}$H$_9$FN$_2$O$_2$
MW: 256.24 gmol-1

The compound was obtained according to procedure C2 and purified by flash column chromatography on silica gel (methanol/dichloromethane/NH$_4$OH=4/94/2). Yellow solid (30%). mp: 216° C. Rf=0.42 (methanol/dichloromethane/NH$_4$OH=4/94/2). IR (v, cm$^{-1}$, neat) 3200, 3059, 2975, 2884, 2206, 1586, 1506, 1401, 1299, 1277, 1158, 1112, 1022, 982, 873. $^1$H NMR (250 MHz, DMSO-d$_6$, 20° C.) δ 12.46 (s, 1H), 8.41-8.18 (m, 1H), 7.87 (dd, J=9.3, 2.7 Hz, 1H), 6.94 (d, J=3.4 Hz, 1H), 6.88 (d, J=1.9 Hz, 1H), 6.45 (d, J=3.3 Hz, 1H), 5.39 (t, J=5.8 Hz, 1H), 4.40 (d, J=5.8 Hz, 2H). $^{13}$C NMR (63 MHz, DMSO-d$_6$, 20° C.) δ 159.9 (d, J=249.9 Hz, Cq), 146.1 (Cq), 145.1 (Cq), 134.6 (CH), 133.8 (Cq), 133.6 (Cq), 120.5 (Cq), 118.2 (CH), 114.2 (d, J=20.6 Hz, CH), 109.0 (CH), 107.5 (d, J=4.5 Hz, CH), 87.8 (Cq), 84.4 (Cq), 58.5 (CH$_2$). $^{19}$F NMR (235 MHz, DMSO-d$_6$, 20° C.) δ −138.16. HRMS (+ESI) calculated for C$_{14}$H$_9$FN$_2$O$_2$ (M+H+): 257.0720, found: 257.0722.

Example 46. 2-((5-((4-fluoropiperidin-1-yl)methyl)thiophen-2-yl)ethynyl)-1H-pyrrolo[2,3-b]pyridine 124

2-((5-((4-fluoropiperidin-1-yl)methyl)thiophen-2-yl)ethynyl)-1H-pyrrolo[2,3-b]pyridine was synthesized in 4 steps. Initially, the corresponding alkyne 125 was prepared in 3 steps from the compound 126 and then we did the Sonogashira reaction with azaindole to obtain the final compound.

Example 46.1 Synthesis of 1-((5-ethynylthiophene-2-yl)methyl)-4-fluoropiperidine 125

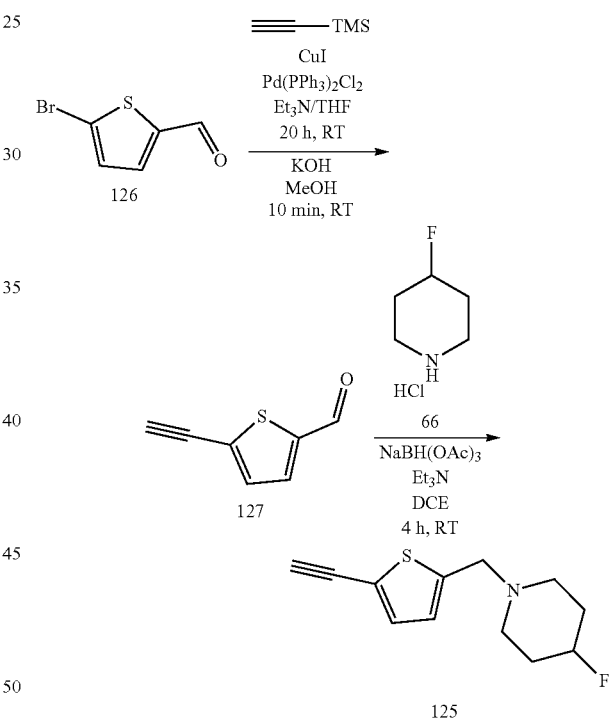

Synthesis of 1-((5-ethynylthiophene-2-yl)methyl)-4-fluoropiperidine 125

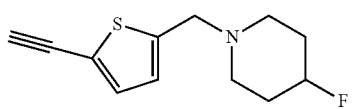

C$_{12}$H$_{14}$FNS
MW: 223.31 gmol-1

The compound was prepared according to procedure H and purified by flash column chromatography on silica gel (ethyl acetate/petroleum ether=10/90). Brown oil (79%). Rf=0.45 (ethyl acetate/petroleum ether=10/90). IR (v, cm⁻¹, neat) 3287, 2949, 1358, 1035, 808, 576, 546, 525. ¹H NMR (250 MHz, CDCl₃, 20° C.) δ 7.09 (dd, J=1.3 Hz, 1H), 6.66-6.78 (m, 1H), 4.48-4.82 (m, 1H), 3.58-3.70 (m, 2H), 3.18-3.37 (m, 1H), 2.74 (m, 4H), 1.68-1.96 (m, 4H). ¹³C NMR (63 MHz, CDCl₃, 20° C.) δ153.4 (Cq), 135.7 (Cq), 116.9 (Cq), 109.8 (Cq), 88.1 (d, J=170.6 Hz, CH), 81.8 (CH), 74.1 (Cq), 54.80 (CH₂), 49.1 (d, J=5.7 Hz, 2×CH₂), 31.3 (d, J=19.7 Hz, 2×CH₂). F¹⁹ NMR (235 MHz, CDCl₃, 20° C.) δ −181. HRMS (+ESI): calculated for C₁₂H₁₄FNS 223.31, found: 223.09.

Example 46.2 2-((5-((4-fluoropiperidin-1-yl)methyl)thiophen-2-yl)ethynyl)-1H-pyrrolo[2,3-b]pyridine 124

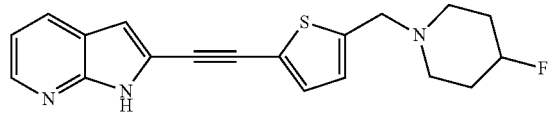

C₁₉H₁₈FN₃S
MW: 339.43 gmol-1

The compound was synthesized according to procedure H and purified by flash column chromatography on silica gel (DCM/MeOH/NH₄OH=94/4/2). Yellowish solid (60%). mp: 148° C. Rf=0.60 (DCM/MeOH/NH₄OH=94/4/2). IR (v, cm⁻¹, neat) 1283, 1123, 1101, 986, 926, 806, 767, 622, 566, 526. ¹H NMR (250 MHz, CDCl₃, 20° C.) δ 10.86 (s, 1H), 8.50-8.31 (m, 1H), 7.95 (d, J=7.8 Hz, 1H), 7.23 (d, J=3.6 Hz, 1H), 7.14 (dd, J=7.8, 4.7 Hz, 1H), 6.87 (d, J=3.6 Hz, 1H), 6.78 (s, 1H), 4.88-4.51 (m, 1H), 3.74 (s, 2H), 2.59 (ddt, J=24.7, 11.0, 4.6 Hz, 4H), 1.94 (ddt, J=24.7, 11.0, 4.6 Hz, 4H). ¹³C NMR (63 MHz, CDCl₃, 20° C.) δ 148.4 (Cq), 145.5 (Cq), 144.1 (Cq), 132.41 (Cq), 129.1 (Cq), 125.7 (Cq), 121.5 (d, J=99.3 Hz, Cq), 120.5 (Cq), 119.5 (Cq), 116.5 (CH), 106.6 (CH), 87.16 (CH), 84.9 (CH), 57.3 (CH₂), 49.2 (d, J=5.7 Hz, CH₂), 49.2 (CH₂), 31.5 (d, J=19.5 Hz, CH₂), 31.3 (CH₂). ¹⁹F NMR (235 MHz, CDCl₃, 20° C.) δ −135.79 (m, 1F). HRMS (+ESI) calculated for C₁₉H₁₈FN₃S (M+H+): 340.1278, found: 340.1273.

Example 47. 2-((5-((4-fluoropiperidin-1-yl)methyl)furan-2-yl)ethynyl)-1H-pyrrolo[2,3-b]pyridine 128

2-((5-((4-fluoropiperidin-1-yl)methyl)furan-2-yl)ethynyl)-1H-pyrrolo[2,3-b]pyridine was synthesized in 4 steps. Initially, the corresponding alkyne 130 was prepared in 3 steps from the compound 122 and then we did the Sonogashira reaction with azaindole to obtain the final compound.

Example 47.1 Synthesis of 1-((5-ethenylfuran-2-yl)methyl)-4-fluoropiperidine 130

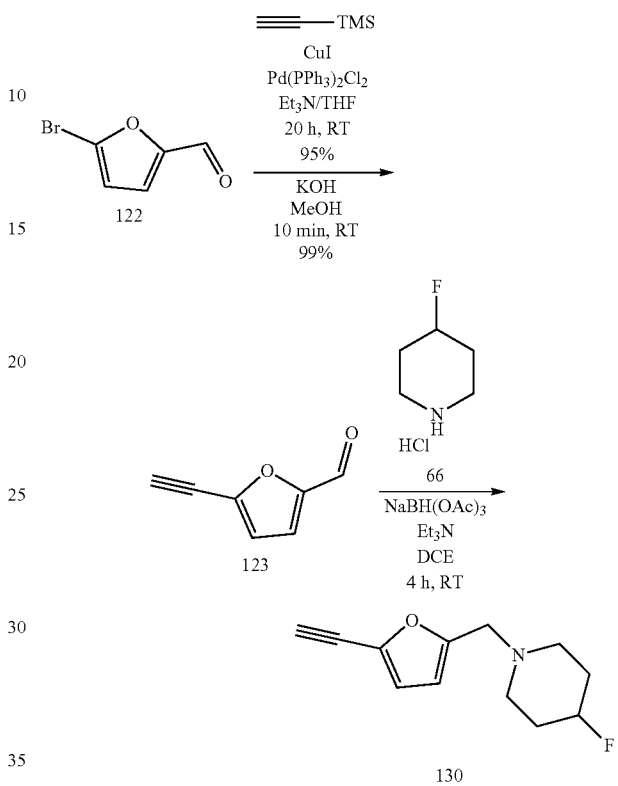

Synthesis of 1-((5-ethenylfuran-2-yl)methyl)-4fluoropiperidine 130

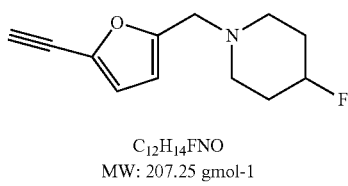

C₁₂H₁₄FNO
MW: 207.25 gmol-1

The compound was prepared according to procedure H and purified by flash column chromatography on silica gel (methanol/dichloromethane=2/98). Brown oil (79%). Rf=0.45 (methanol/dichloromethane=2/98). IR (v, cm⁻¹, neat) 3280, 1425, 1332, 1203, 1018, 795, 537, 520, 506. ¹H NMR (250 MHz, CDCl₃, 20° C.) δ 6.49 (d, 1H, J=3.3 Hz), 6.05-6.17 (m, 1H), 4.42-4.73 (m, 1H), 3.41-3.50 (m, 2H), 3.29-3.37 (m, 1H), 2.22-2.61 (m, 4H), 1.64-1.87 (m, 4H). ¹³C NMR (63 MHz, CDCl₃, 20° C.) δ 153.4 (Cq), 135.7 (Cq), 116.9 (Cq), 109.8 (Cq), 88.1 (d, J=170.6 Hz, CH), 81.8 (CH), 74.1 (Cq), 54.8 (CH₂), 49.1 (d, J=5.7 Hz, 2×CH₂), 31.3 (d, J=19.7 Hz, 2×CH₂). HRMS (+ESI): calculated for C₁₂H₁₄FNO (M+H+): 208.11321, found: 208.11327.

191

Example 47.2 Synthesis of 2-((5-((4-fluoropiperidin-1-yl)methyl)furan-2-yl)ethynyl)-1H-pyrrolo[2,3-b]pyridine 128

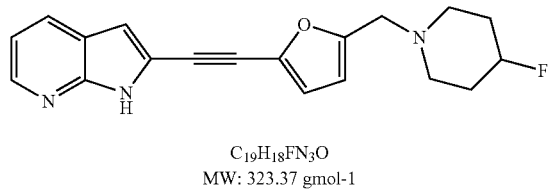 [SMILES: FC1CCN(Cc2ccc(C#Cc3cc4cccnc4[nH]3)o2)CC1]

C₁₉H₁₈FN₃O
MW: 323.37 gmol-1

The compound was synthesized according to procedure C2 and purified by flash column chromatography on silicagel (methanol/dichloromethane/NH₄OH=4/94/2). yellowish solid (77%). mp: 193° C. Rf=0.60 (methanol/dichloromethane/NH₄OH=4/94/2). IR (v, cm⁻¹, neat) 3122, 3053, 2937, 2816, 1584, 1434, 1405, 1352, 1325, 1300, 1132, 1021, 975, 918, 820, 768. ¹H NMR (250 MHz, CDCl₃, 20° C.) δ 10.97 (s, 1H), 8.42 (s, 1H), 7.95 (d, J=7.9 Hz, 1H), 7.13 (dd, J=7.8, 4.5 Hz, 1H), 6.81 (s, 1H), 6.72 (d, J=3.4 Hz, 1H), 6.31 (d, J=3.3 Hz, 1H), 4.84-4.47 (m, 1H), 3.63 (s, 2H), 2.60 (ddt, J=59.6, 11.5, 5.6 Hz, 4H), 1.96 (ddt, J=24.6, 10.8, 4.7 Hz, 4H). ¹³C NMR (63 MHz, CDCl₃, 20° C.) δ 154.1 (Cq), 148.4 (Cq), 144.3 (CH), 136.0 (Cq), 129.2 (CH), 120.4 (Cq), 118.3 (Cq), 117.1 (CH), 116.6 (CH), 110.2 (CH), 107.1 (CH), 88.9 (d, J=170.6 Hz, CH), 85.72 (Cq), 83.7 (Cq), 54.9 (CH₂), 49.1 (d, J=5.5 Hz, 2×CH₂), 31.3 (d, J=19.7 Hz, 2×CH₂). RMN ¹⁹F (235 MHz, CDCl₃, 20° C.) δ −136.58 (m, 1F). HRMS (+ESI) calculated for C₁₉H₁₈FN₃O (M+H+): 340.1278, found: 340.1273.

Example 48. 1-(5-((5-fluoro-1H-pyrrolo[2,3-b]pyridin-2-yl)ethynyl)furan-2-yl)-N,N-dimethylmethanamine 131

1-(5-((5-fluoro-1H-pyrrolo[2,3-b]pyridin-2-yl)ethynyl)furan-2-yl)-N,N-dimethylmethanamine 131 was synthesized in 4 steps. Initially, the corresponding alkyne 132 was prepared in 3 steps from compound 122, followed by a Sonogashira reaction with azaindole for the final compound.

Example 48.1 Synthesis of ((5-ethenylfuran-2-yl)methyl)dimethylamine 132

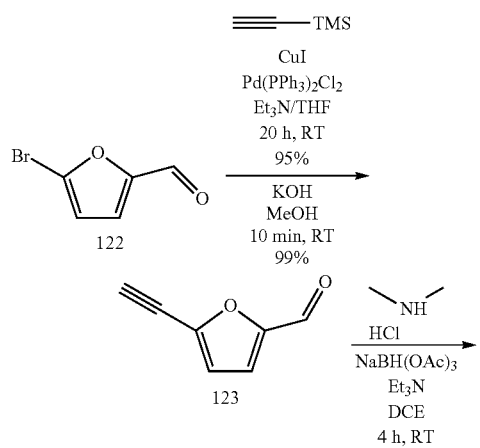

-continued

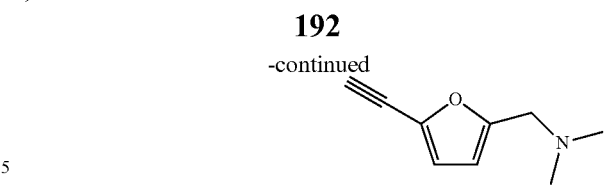

131

Synthesis of 1-(5-ethenylfuran-2-yl)-N,N-dimethylmethanamine 131

The compound was prepared according to procedure H and purified by flash column chromatography on silicagel (methanol/dichloromethane=5/95). brown oil (79%). Rf=0.58 (methanol/dichloromethane=10/90). IR (v, cm⁻¹, neat): 3292, 2945, 2822, 2101, 1602, 1571, 1495, 1326, 1281, 1134, 1017, 992, 972, 936, 841, 792. ¹H NMR (400 MHz, CDCl₃, 20° C.) δ 6.55 (d, J=3.3 Hz, 1H), 6.16 (d, J=3.3 Hz, 1H), 3.50 (s, 2H), 3.35 (s, 1H, CH), 2.24 (d, J=4.4 Hz, 6H). ¹³C NMR (101 MHz, CDCl₃, 20° C.): 6 153.9 (Cq), 135.8 (Cq), 117.1 (CH), 109.7 (CH), 81.9 (Cq), 74.2 (CH), 55.7 (CH₂), 44.9 (3×CH₃). HRMS (+ESI) calculated for C₉H₁₁NO (M+H⁺): 150.0913, found: 150.0915.

Example 48.2 1-(5-((5-fluoro-1H-pyrrolo[2,3-b]pyridin-2-yl)ethynyl)furan-2-yl)-N,N-dimethylmethanamine 131

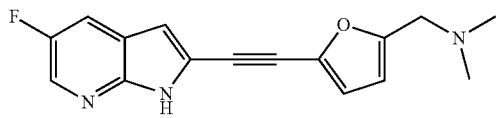

C₁₆H₁₄FN₃O
MW: 283.31 gmol-1

The compound was synthesized according to procedure C2 and purified by flash column chromatography on silicagel (methanol/dichloromethane/NH₄OH=4/94/2). yellowish solid (14%). Rf=0.43 (methanol/dichloromethane/NH₄OH=4/94/2). mp: 144° C. IR (v, cm⁻¹, neat) 2980, 2761, 2202, 1585, 1403, 1358, 1296, 1258, 1223, 1144, 1022, 980, 845, 769, 513. ¹H NMR (400 MHz, DMSO-d₆, 20° C.) δ 12.45 (s, 1H), 8.30 (s, 1H), 7.87 (d, J=8.9 Hz, 1H), 7.02-6.79 (m, 2H), 6.45 (d, J=3.8 Hz, 1H), 3.48 (s, 2H), 2.17 (s, 6H). ¹³C NMR (101 MHz, DMSO-d₆, 20° C.) δ 155.9 (d, J=249.9 Hz, Cq), 155.8 (Cq), 145.7 (Cq), 134.9 (Cq), 133.7 (d, J=29.6 Hz, CH), 120.7 (Cq), 119.9 (d, J=7.5 Hz, Cq), 118.4 (CH), 114.44 (d, J=21.2 Hz, CH), 110.8 (CH), 107.4 (d, J=4.6 Hz, CH), 86.3 (Cq), 83.9 (Cq), 55.40 (CH₂), 45.0 (2×CH₃). ¹⁹F NMR (376 MHz, DMSO-d6, 20° C.) δ. −138.2. HRMS (+ESI): calculated for C₁₆H₁₄FN₃O (284.119367 g/mol), found (284.119244 g/mol).

Example 49. 1-(5-((5-fluoro-1H-pyrrolo[2,3-b]pyridin-2-yl)ethynyl)thiophen-2-yl)-N,N-dimethylmethanamine 133

1-(5-((5-fluoro-1H-pyrrolo[2,3-b]pyridin-2-yl)ethynyl)thiophen-2-yl)-N,N-dimethylmethanamine 133 was synthesized in 4 steps. Initially, the corresponding alkyne 134 was prepared in 3 steps from compound 126, followed by a Sonogashira reaction with azaindole to give the final compound.

Example 49.1 Synthesis of 1-(5-ethynylthiophene-2-yl)-N,N-dimethylmethanamine 134

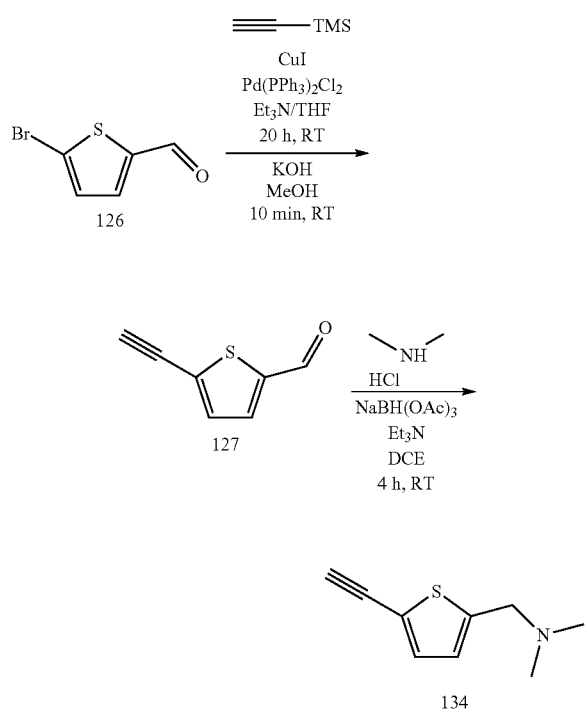

Synthesis of 1-(5-ethynylthiophene-2-yl)-N,N-dimethylmethanamine 134

The compound was prepared according to procedure H and purified by flash column chromatography on silicagel (methanol/dichloromethane=5/95). Brown oil (74%) Rf=0.58 (methanol/dichloromethane=10/90). $^1$H NMR (250 MHz, CDCl$_3$, 20° C.) δ 6.68 (m, 1H), 6.55 (m, 1H), 3.60 (s, 2H) 3.26 (s, 1H), 2.14-2.24 (m, 6H). reaxys number: 10655856.

Example 49.2 1-(5-((5-fluoro-1H-pyrrolo[2,3-b]pyridin-2-yl)ethynyl)thiophen-2-yl)-N,N-dimethylmethanamine 133

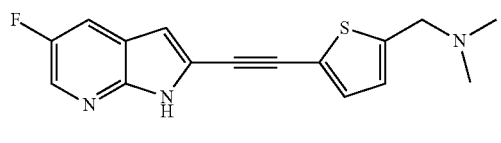

$C_{16}H_{14}FN_3S$
MW: 299.36 gmol-1

The compound was synthesized according to procedure C2 and purified by flash column chromatography on silicagel (methanol/dichloromethane/NH$_4$OH 4/94/2). yellowish solid (14.5%). mp: 162° C. Rf=0.72 (methanol/dichloromethane/NH$_4$OH=4/94/2). IR (v, cm$^{-1}$, neat) 2980, 2761, 2202, 1585, 1503, 1403, 358, 1296, 1258, 1223, 1022, 980, 845, 769, 513. $^1$H NMR (250 MHz, CDCl$_3$, 20° C.) δ 10.27 (d, J=6.4 Hz, 1H), 8.15-8.30 (m, 1H), 7.57 (dd, J=8.7, 2.8 Hz, 1H), 7.19 (d, J=3.7 Hz, 1H), 6.82 (d, J=3.8 Hz, 1H), 6.70 (d, J=2.1 Hz, 1H), 3.63 (s, 2H), 2.29 (d, J=3.4 Hz, 6H). $^{13}$C NMR (63 MHz, CDCl$_3$, 20° C.) 155.9 (d, J=249.9 Hz, Cq), 146.1 (Cq), 145.1 (Cq), 133.0 (Cq), 132.8 (CH), 125.9 (CH), 121.7-119.6 (m, 2×Cq et CH), 114.2 (d, J=20.6 Hz, CH), 106.5 (d, J=4.5 Hz, CH), 87.8 (Cq), 84.4 (Cq), 58.5 (CH$_2$), 45.1 (2×CH$_3$). $^{19}$F NMR (235 MHz, CDCl$_3$, 20° C.) δ −185.73. HRMS (+ESI) calculated for $C_{16}H_{14}FN_3S$ (M+H+): 300.09652, found: 300.09653.

Example 50. Procedure L: (Desylilation of Alkynes)

The silylated alkyne (1.0 eq.) was reacted with K$_2$CO$_3$ (1.5 eq.) in methanol (0.03 M). After 3 h at room temperature, the solvent was evaporated under reduced pressure. The crude product is dissolved in 10 ml of ethyl acetate. Then, the organic phase was washed with brine (3×10 ml), the organic phase is dried with MgSO$_4$ filtered through cotton and evaporated under reduced pressure. Finally, the crude product was purified by flash column chromatography on silicagel eluting with (ethyl acetate/petroleum ether) to yield the true alkyne.

Example 51. Procedure M: (Methylation)

The alcohol derivative (1.0 eq.) is dissolved in THF. NaH (3.5 eq.) and CH$_3$I (1.7 eq.) were added at 0° C. After 2 h at room temperature the mixture was cooled to 0° C. and a saturated solution of NH$_4$Cl is added. The mixture was extracted with dichloromethane (3×10 ml). The organic phases are combined, dried over MgSO$_4$, filtered through cotton and evaporated to dryness.

Example 52: 2-((4'-((5-fluoro-1H-pyrrolo[2,3-b]pyridin-2-yl)ethynyl)-[1,1'-biphenyl]-4-yl)(methyl)amino)ethan-1-ol 134

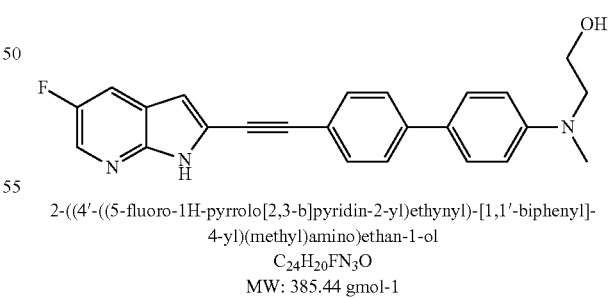

2-((4'-((5-fluoro-1H-pyrrolo[2,3-b]pyridin-2-yl)ethynyl)-[1,1'-biphenyl]-4-yl)(methyl)amino)ethan-1-ol
$C_{24}H_{20}FN_3O$
MW: 385.44 gmol-1

2-((4'-((5-fluoro-1H-pyrrolo[2,3-b]pyridin-2-yl)ethynyl)-[1,1'-biphenyl]-4-yl)(methyl) amino)ethan-1-ol was synthesized in 5 steps. Initially, the corresponding alkyne was prepared in 3 steps and then engaged in a Sonogashira reaction with the azaindole. A deprotection reaction provides the final compound.

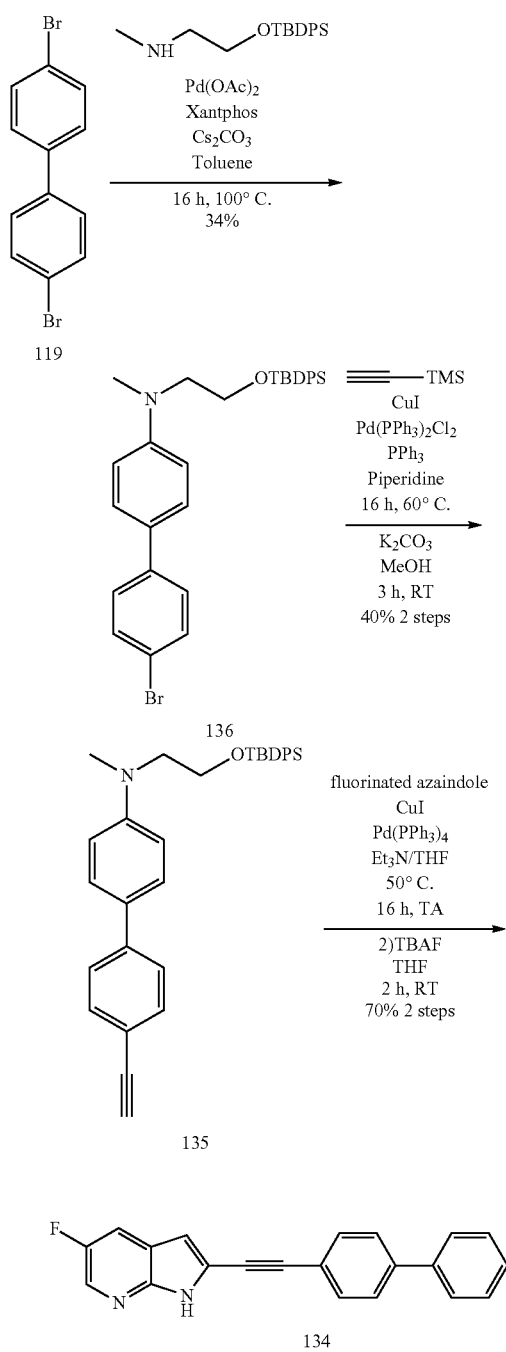

Example 52.1 Synthesis of 4'-bromo-N-(2-((tert-butyldiphenylsilyl)oxy)ethyl)-N-methyl-[1,1'-biphenyl]-4-amine 136

Under argon, Pd(OAc)$_2$ (0.05 eq.) and Xantphos (0.067 mmol) were added to a degassed anhydrous toluene solution at a 0.3 M concentration containing the amine (3.0 eq.), brominated 119 (2.0 eq.) and Cs$_2$CO$_3$ (3.0 eq.). After 16 h at 100° C., the solvent was evaporated under reduced pressure and the reaction mixture was purified by flash column chromatography on silicagel to yield the brominated compound 136 as a white amorphous solid with a yield of 34%, Rf=0.20 (ethyl acetate/petroleum ether=1/99), IR (v, cm$^{-1}$, neat) 3284, 3070, 2929, 2856, 1610, 1513, 1495, 1471, 1427, 1360, 1280, 1234, 1160, 1103, 985, 927, 869. $^1$H NMR (400 MHz, CDCl$_3$, 20° C.) δ 7.65 (d, J=7.2 Hz, 4H), 7.50 (d, J=8.5 Hz, 2H), 7.45-7.32 (m, 10H), 6.62 (d, J=8.5 Hz, 2H), 3.83 (t, J=6.2 Hz, 2H), 3.52 (t, J=6.2 Hz, 2H), 2.99 (s, 3H), 1.05 (s, 9H). $^{13}$C NMR (101 MHz, CDCl$_3$, 20° C.) δ 148.6 (Cq), 140.0 (Cq), 135.4 (4×CH), 133.3 (2×Cq), 131.5 (2×CH), 129.5 (2×CH), 127.5 (6×CH), 127.3 (2×CH), 127.0 (Cq), 119.6 (Cq), 111.9 (2×CH), 60.9 (CH$_2$), 54.3 (CH$_2$), 39.0 (CH$_3$), 26.7 (3×CH$_3$), 18.9 (Cq). HRMS (+ESI) calculated for C$_{31}$H$_{34}$BrNOSi (M+H$^+$): 544.1665, found: 544.1663.

Example 52.2 Synthesis of N-(2-((tert-butyldiphenylsilyl)oxy)ethyl)-4'-ethynyl-N-methyl-[1,1'-biphenyl]-4-amine 135

Alkyne 135 was prepared according to procedure II, at a temperature of 60° C. and purified by flash column chromatography on silicagel (ethyl acetate/petroleum ether=2/48). Yellow oil (40% over two steps), Rf=0.20 (ethyl acetate/petroleum ether=2/48). IR (v, cm$^{-1}$, neat) 3277, 2928, 2855, 1609, 1599, 1532, 1493, 1471, 1426, 1371, 1357, 1292, 1240, 1210, 1194, 1134, 1104, 1087, 1006, 996, 982. $^1$H NMR (400 MHz, CDCl$_3$, 20° C.) δ 7.65 (d, J=7.2 Hz, 4H), 7.50 (sl, 2H), 7.45-7.32 (m, 8H), 6.62 (d, J=8.5 Hz, 2H), 3.83 (t, J=6.2 Hz, 2H), 3.52 (t, J=6.2 Hz, 2H), 3.10 (s, 1H), 2.99 (s, 3H), 1.05 (s, 9H). $^{13}$C NMR (101 MHz, CDCl$_3$, 20° C.) δ 148.6 (Cq), 140.0 (Cq), 135.6 (4×CH), 133.4 (2×Cq), 132.5 (2×CH), 129.7 (2×CH), 127.7 (4×CH), 127.6 (2×CH), 127.4 (Cq), 125.8 (2×CH), 119.6 (Cq), 112.0 (2×CH), 84.0 (Cq), 77.1 (CH), 61.0 (CH$_2$), 54.4 (CH$_2$), 39.1 (CH$_3$), 26.8 (3×CH$_3$), 19.1 (Cq). HRMS (+ESI) calculated for C$_{33}$H$_{35}$NOSi (M+H$^+$): 490.2560, found: 490.2552.

Example 52.3 Preparation of 2-((4'-((5-fluoro-1H-pyrrolo[2,3-b]pyridin-2-yl)ethynyl)-[1,1'-biphenyl]-4-yl)(methyl)amino)ethan-1-ol 134

The compound was prepared according to procedure C1 followed by procedure F and purified by flash column chromatography on silicagel (methanol/dichloromethane=2/48). yellowish solid (70% over 2 steps) mp 172-174° C., Rf=0.20 (methanol/dichloromethane=2/48). IR (u, cm$^{-1}$, neat) 3122, 2925, 1662, 1610, 1510, 1494, 1436, 1399, 1349, 1296, 1246, 1165, 1120, 1048, 984, 872, 839. $^1$H NMR (400 MHz, DMSO-d$_6$, 20° C.) δ 12.38 (s, 1H), 8.28 (s, 1H), 7.86 (dd, J=2 et 9 Hz, 1H), 7.70 (m, 2H), 7.58 (m, 4H), 6.81 (m, 3H), 4.70 (t, J=7.3 Hz, 1H), 3.57 (m, 2H), 3.46 (d, J=7.3 Hz, 2H), 2.99 (s, 3H). $^{13}$C NMR (101 MHz, DMSO-d$_6$ 20° C.) δ 155.3 (d, J=239.2 Hz, Cq), 147.9 (Cq), 145.6 (Cq), 144.9 (Cq), 133.2 (Cq), 132.8 (d, J=20.9 Hz, CH), 132.3 (2×CH), 127.7 (2×CH), 125.9 (2×CH) 125.8 (Cq), 121.9 (Cq), 120.2 (d, J=6.2 Hz, CH), 118.8 (Cq), 114.0 (d, J=20.2 Hz, CH), 112.5 (2×CH), 106.6 (d, J=4.0 Hz, CH), 94.2 (Cq), 82.4 (Cq), 58.6 (CH$_2$), 54.5 (CH$_2$), 39.1 (CH$_3$). $^{19}$F NMR (376 MHz, DMSO-d$_6$, 20° C.) δ. −138.5.

Example 53: 4'-((1H-pyrrolo[2,3-b]pyridine-2-yl)ethynyl)-N-(2-fluoroethyl)-N-methyl-[1,1'-biphenyl]-4-amine 137

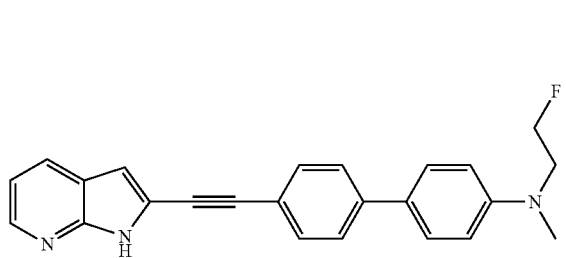

4'-((1H-pyrrolo[2,3-b]pyridin-2-yl)ethynyl)-N-(2-fluoroethyl)-N-methyl-[1,1'-biphenyl]-4-amine 4'-((1H-pyrrolo[2,3-b]pyridin-2-yl)ethynyl)-N-(2-fluoroethyl)-N-methyl-[1,1'-biphenyl]-4-amine 137 was synthesized in 7 steps. In a first step, corresponding alkyne was prepared in 3 steps and then engaged in a Sonogashira reaction with the azaindole and a deprotection reaction. Then, a fluorination reaction with DAST followed by a deprotection reaction of the azaindole leads to the expected compound

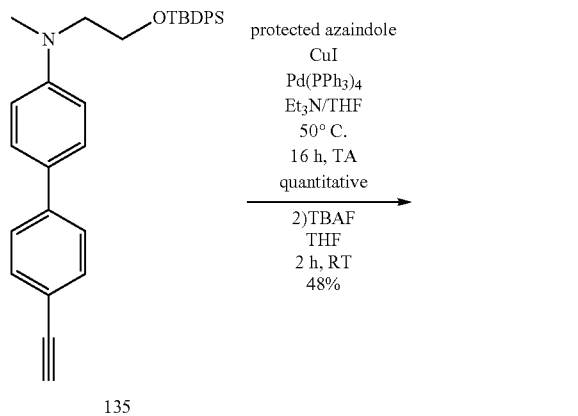

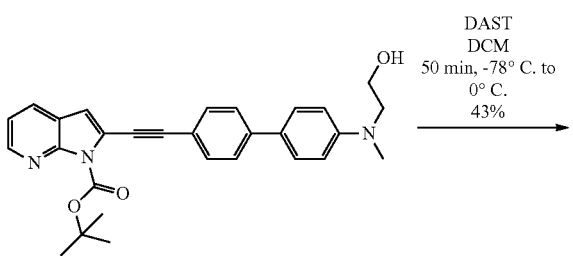

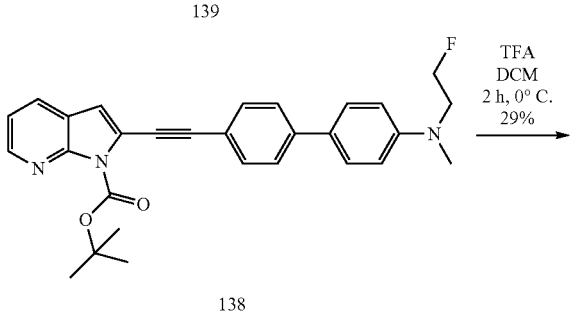

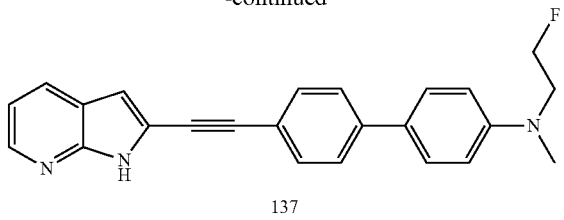

137

Example 53.1 Preparation of tert-butyl 2-((4'-((2-hydroxyethyl)(methyl)amino)-[1,1'-biphenyl]-4-yl)ethynyl)-1H-pyrrolo[2,3-b]pyridine-1-carboxylate 139

The compound was prepared according to procedure C1 followed by procedure F and purified by flash column chromatography on silicagel (methanol/dichloromethane=2/48). Yellowish solid (48% over 2 steps) mp 200-202° C., Rf=0.20 (methanol/dichloromethane=2/48). IR (u, cm$^{-1}$, neat) 2979, 2204, 1742, 1605, 1573, 1544, 1517, 1355, 1306, 1253, 1189, 1154, 1115, 1089, 1041, 979, 813, 774, 527, 510. $^1$H NMR (400 MHz, CDCl$_3$, 20° C.) δ 8.57 (m, 1H), 7.87 (d, J=7.3 Hz, 1H), 7.57 (m, 6H), 7.28 (s, 1H), 7.22 (m, 1H), 6.89 (m, 3H), 3.88 (m, 2H), 3.57 (t, J=5.7 Hz, 2H), 3.07 (s, 3H), 1.73 (s, 9H). $^{13}$C NMR (101 MHz, CDCl$_3$, 20° C.) δ 149.6 (Cq), 148.6 (Cq), 147.9 (Cq), 146.1 (CH), 141.4 (Cq), 131.9 (2×CH), 128.6 (CH), 128.4 (Cq), 127.8 (2×CH), 126.1 (2×CH), 121.4 (Cq), 121.3 (Cq), 120.0 (Cq), 118.9 (CH), 113.0 (2×CH), 112.5 (CH), 105.3 (Cq), 95.9 (Cq), 84.8 (Cq), 81.9 (Cq), 60.2 (CH$_2$), 55.1 (CH$_2$), 38.9 (CH$_3$), 28.2 (3×CH$_3$). HRMS (+ESI) calculated for C$_{29}$H$_{29}$N$_3$O$_3$ (M+H$^+$): 468.2281, found: 468.2287.

Example 53.2 Preparation of 4'-((1H-pyrrolo[2,3-b]pyridin-2-yl)ethynyl)-N-(2-fluoroethyl)-N-methyl-[1,1'-biphenyl]-4-amine 138

To a solution containing compound 139 (0.035 g, 0.075 mmol, 1.0 eq.) in dichloromethane (5 ml), cooled to −78° C. is added dropwise DAST (0.012 ml, 0.089 mmol, 1.2 eq.). Then, the reaction medium is brought to 0° C. and after 50 minutes 1 ml of H$_2$O is added. The aqueous phase is extracted with dichloromethane (2 times 10 ml), the combined organic phases are dried over MgSO$_4$, filtered and concentrated under reduced pressure. The compound is purified by flash column chromatography on silicagel (methanol/dichloromethane=2/98). White solid (22%), mp >260° C., Rf=0.8 (methanol/dichloromethane=4/96). IR (v, cm$^{-1}$, neat) 2924, 1740, 1629, 1597, 1495, 1473, 156, 1400, 1359, 1337, 1301, 1250, 1209, 1153, 1140, 1108, 1086, 1043, 976, 906, 873. $^1$H NMR (250 MHz, CDCl$_3$, 20° C.) δ 8.52 (dd, J=4.8, 1.6 Hz, 1H), 7.82 (dd, J=7.9, 1.6 Hz, 1H), 7.51 (d, J=8.8 Hz, 6H), 7.18 (dd, J=7.9, 4.8 Hz, 3H), 6.86 (s, 1H), 6.78 (d, J=8.8 Hz, 2H), 4.62 (dt, J=47.1, 5.2 Hz, 2H), 3.69 (dt, J=24.3, 5.2 Hz, 2H), 3.06 (s, 3H), 1.68 (s, H). $^{13}$C NMR (63 MHz, CDCl$_3$, 20° C.) δ 148.65 (Cq), 147.48 (Cq), 146.1 (CH), 131.9 (2×CH), 128.6 (CH), 128.31 (Cq), 128.18 (Cq), 127.8 (2×CH), 126.0 (2×CH), 121.43 (Cq), 121.31 (Cq), 120.0 (Cq), 118.9 (CH), 112.6 (CH), 112.5 (2×CH), 96.1 (Cq), 84.8 (Cq), 81.8 (d, J=170.3 Hz, CH$_2$), 80.0 (Cq), 52.6 (d, J=21.2 Hz, CH$_2$), 39.1 (CH$_3$), 28.2 (3×CH$_3$). $^{19}$F NMR (235 MHz, CDCl$_3$, 20° C.) δ −222.2. HRMS (+ESI) calculated for C$_{23}$H$_{25}$FN$_3$O$_2$ (M+H+): 394.1925, found: 394.1925.

Example 53.3 Preparation of 4'-((1H-pyrrolo[2,3-b]pyridin-2-yl)ethynyl)-N-(2-fluoroethyl)-N-methyl-[1,1'-biphenyl]-4-amine 137

Compound 137 was prepared according to procedure F and purified by flash column chromatography on silicagel (ethyl acetate/petroleum ether=20/80). Yellow solid (29%), mp >260° C., Rf=0.28 (ethyl acetate/petroleum ether=20/80). IR (v, cm$^{-1}$, neat) 2882, 2357, 1607, 1595, 1522, 1491, 1431, 1403, 1372, 1355, 1324, 1280, 1247, 1203, 1134, 1112, 1038, 977, 916. $^1$H NMR (400 MHz, DMSO-d$_6$, 20° C.) δ 12.21 (s, 1H), 8.29 (s, 1H), 7.97 (d, J=7.9 Hz, 1H), 7.70 (d, J=8.0 Hz, 2H), 7.60 (d, J=8.0 Hz, 3H), 7.11 (dd, J=7.9, 4.7 Hz, 1H), 6.84 (m, 3H), 4.62 (d, J=47.7, 4.7 Hz, 2H), 3.72 (d, J=26.4, 4.7 Hz, 2H), 3.00 (s, 3H). $^{13}$C NMR (101 MHz, DMSO-d$_6$ 20° C.) δ 149.3 (Cq), 148.8 (Cq), 144.8 (CH), 141.2 (Cq), 132.3 (2×CH), 128.8 (CH), 127.7 (2×CH), 126.6 (Cq), 126.0 (2×CH), 125.9 (Cq), 120.0 (Cq), 119.6 (Cq), 119.2 (Cq), 116.8 (CH), 112.9 (2×CH), 112.5 (Cq), 106.6 (CH), 93.57 (Cq), 82.9 (Cq), 82.8 (d, J=170.3 Hz, CH$_2$), 52.1 (d, J=21.2 Hz, CH$_2$), 38.94 (CH$_3$). $^{19}$F NMR (376 MHz, DMSO-d$_6$, 20° C.) δ. −221.2. HRMS (+ESI) calculated for C$_{24}$H$_{20}$FN$_3$ (M+H+): 370.1714, found: 370.1707.

Example 54: 3-((1H-pyrrolo[2,3-b]pyridin-2-yl)ethynyl)-N-(2-fluoroethyl)-N-methylaniline 140

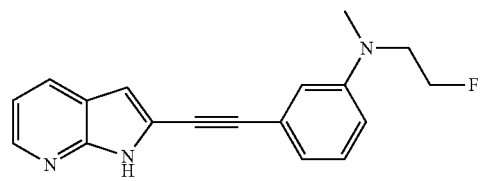

3-((1H-pyrrolo[2,3-b]pyridin-2-yl)ethynyl)-N-(2-fluoroethyl)-N-methylaniline 3-((1H-pyrrolo[2,3-b]pyridin-2-yl)ethynyl)-N-(2-fluoroethyl)-N-methylaniline was synthesized in 4 steps from dibromobenzene. initially, the corresponding alkyne 142 was prepared in 3 steps and the Sonogashira reaction with protected azaindole provides the intermediate 143. then, the alcohol function is liberated using the TBAF and finally compound 140 is obtained after three successive reactions (tosylation, nucleophilic substitution and deprotection).

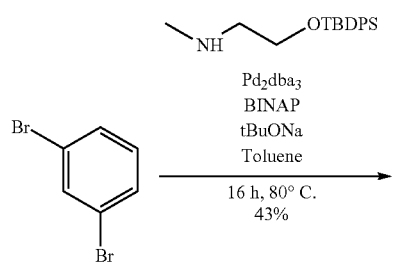

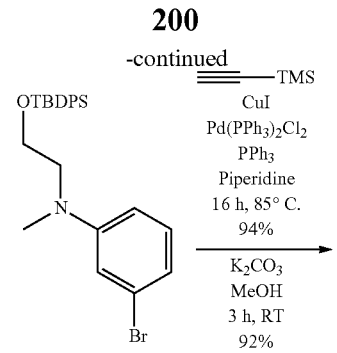

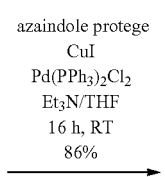

142

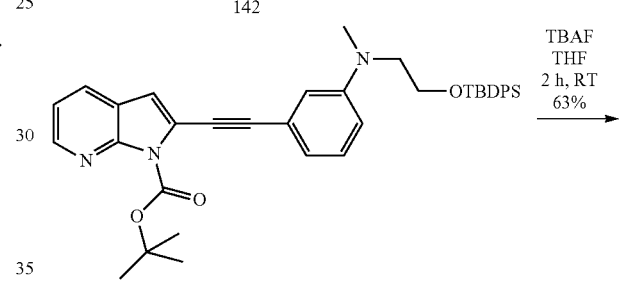

143

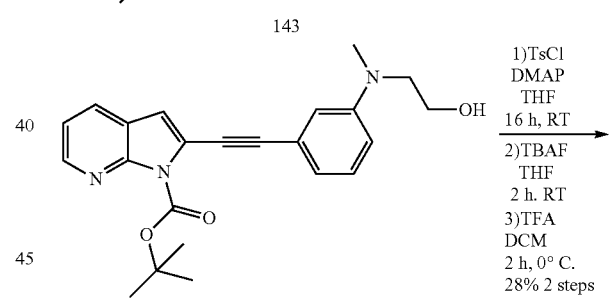

144

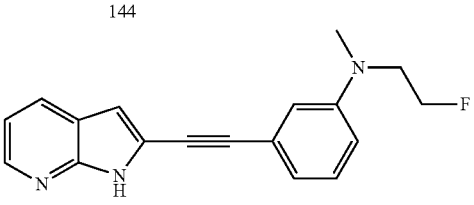

140

Example 54.1 Synthesis of 3-bromo-N-(2-((tert-butyldiphenylsilyl)oxy)ethyl)-N-methylaniline 141

Compound 141 was prepared according to procedure H and purified by flash column chromatography on silicagel (ethyl acetate/petroleum ether=1/49). Colorless oil (43%). IR (v, cm$^{-1}$, neat) 3370, 2929, 2856, 1592, 1496, 1471, 1426, 1370, 1239, 1210, 1189, 1104, 926. $^1$H NMR (250 MHz, CDCl$_3$, 20° C.) δ 7.60 (d, J=6.5 Hz, 4H), 7.50-7.26

(m, 6H), 6.95 (t, J=8.1 Hz, 1H), 6.73 (m, 2H), 6.44 (d, J=7.3 Hz, 1H), 3.76 (t, J=6.0 Hz, 2H), 3.43 (t, J=6.0 Hz, 2H), 2.88 (s, 3H), 1.01 (s, 9H). $^{13}$C NMR (63 MHz, CDCl$_3$, 20° C.) δ 150.4 (Cq), 135.6 (4×CH), 133.3 (2×Cq), 130.2 (CH), 129.7 (CH), 127.7 (5×CH), 123.41 (Cq), 118.6 (CH), 114.2 (CH), 110.4 (CH), 61.1 (CH$_2$), 54.4 (CH$_2$), 39.0 (CH$_3$), 26.79 (2×CH$_3$), 19.06 (Cq). HRMS (+ESI) calculated for C$_{25}$H$_{30}$BrNOSi (M+H+): 468.1352, found: 468.1356.

Example 54.2 Synthesis of N-(2-((tert-butyldiphenylsilyl)oxy)ethyl)-3-ethynyl-N-methylaniline 142

Alkyne 142 was prepared according to procedure II and purified by flash column chromatography on silicagel (ethyl acetate/petroleum ether=2/48). Colorless oil (86% over two steps). IR (v, cm$^{-1}$, neat) 3288, 2929, 2856, 1594, 1570, 1494, 1471, 1427, 1360, 1105, 1003, 822. $^1$H NMR (250 MHz, CDCl$_3$, 20° C.) δ 7.62 (d, J=6.5 Hz, 4H), 7.50-7.26 (m, 6H), 7.08 (t, J=8.1 Hz, 1H), 6.78 (m, 2H), 6.54 (d, J=7.3 Hz, 1H), 3.79 (t, J=6.0 Hz, 2H), 3.47 (t, J=6.0 Hz, 2H), 2.97 (s, 1H), 2.90 (s, 3H), 1.01 (s, 9H). $^{13}$C NMR (63 MHz, CDCl$_3$, 20° C.) δ 150.4 (Cq), 135.6 (4×CH), 133.4 (2×Cq), 129.9 (CH), 129.0 (CH), 127.7 (5×CH), 122.4 (Cq), 119.8 (CH), 115.2 (CH), 112.6 (CH), 84.9 (Cq) 75.8 (CH), 61.1 (CH$_2$), 54.4 (CH$_2$), 39.0 (CH$_3$), 26.79 (2×CH$_3$), 19.06 (Cq). HRMS (+ESI) calculated for C$_{25}$H$_{30}$BrNOSi (M+H$^+$): 468.1352, found: 468.1356.

Example 54.3 Preparation of tert-butyl 2-((3-((2-((tert-butyldiphenylsilyl)oxy)ethyl)(methyl)amino)phenyl)ethynyl)-1H-pyrrolo[2,3-b]pyridine-1-carboxylate 143

Compound 137 was prepared according to procedure C2 and purified by flash column chromatography on silicagel (ethyl acetate/petroleum ether=20/80). Yellow oil (86%), Rf=0.20 (ethyl acetate/petroleum ether=20/80). IR (v, cm$^{-1}$, neat) 2986, 2360, 2198, 1749, 1605, 1544, 1514, 1407, 1348, 1306, 1253, 1187, 1170, 1114, 1092, 1010, 972, 900, 804, 776, 663, 556, 508. $^1$H NMR (400 MHz, CDC$_3$, 20° C.) δ 8.57 (d, J=3.4 Hz, 1H), 7.86 (d, J=8.1 Hz, 1H), 7.66 (d, J=7.8 Hz, 4H), 7.39 (m, 6H), 7.19 (m, 2H), 6.87 (m, 3H), 6.62 (d, J=7.8 Hz, 1H), 3.84 (t, J=5.9 Hz, 2H), 3.54 (t, J=5.9 Hz, 2H), 2.99 (s, 3H), 1.67 (s, 9H), 1.06 (s, 9H). $^{13}$C NMR (101 MHz, CDC$_3$, 20° C.) δ 148.9 (Cq), 148.6 (Cq), 147.9 (Cq), 146.1 (CH), 135.6 (4×CH), 133.4 (Cq), 129.7 (CH), 129.2 (CH), 128.6 (CH), 127.7 (5×CH), 123.0 (Cq), 121.4 (Cq), 119.2 (CH), 118.9 (CH), 114.5 (CH), 112.7 (CH), 112.4 (CH), 96.8 (Cq), 84.7 (Cq), 80.4 (Cq), 61.2 (CH$_2$), 54.4 (CH$_2$), 39.1 (CH$_3$), 28.2 (3×CH$_3$), 26.8 (3×CH$_3$), 19.1 (Cq). HRMS (+ESI) calculated for C$_{39}$H$_{43}$N$_3$O$_3$Si (M+H$^+$): 630.3146, found: 630.3136.

Example 54.4 Preparation of tert-butyl 2-((3-((2-hydroxyethyl)(methyl)amino)phenyl)ethynyl)-1H-pyrrolo[2,3-b]pyridine-1-carboxylate 144

Compound 144 was prepared according to procedure D and purified by flash column chromatography on silicagel (methanol/dichloromethane=4/96). Yellow oil (63%), Rf=0.20 (methanol/dichloromethane=4/96). IR (v, cm$^{-1}$, neat) 3386, 2980, 2926, 2206, 1747, 1603, 1546, 1517, 1473, 1408, 1384, 1343, 1305, 1249, 1194, 1154, 1117, 1085, 980, 847, 831, 814, 776, 746, 643, 525. $^1$H NMR (400 MHz, CDCl$_3$, 20° C.) δ 8.54 (d, J=4.3 Hz, 1H), 7.82 (s, 1H), 7.25-7.16 (m, 2H), 6.99-6.77 (m, 4H), 3.84 (t, J=5.7 Hz, 2H), 3.50 (t, J=5.7 Hz, 2H), 3.00 (s, 3H), 1.69 (s, 9H). $^{13}$C NMR (101 MHz, CDC$_3$, 20° C.) δ 148.8 (Cq), 148.6 (Cq), 147.9 (Cq), 146.1 (CH), 129.3 (CH), 128.6 (CH), 121.4 (Cq), 121.2 (Cq), 120.2 (CH), 118.9 (CH), 115.4 (CH), 113.9 (CH), 112.9 (CH), 112.4 (CH), 96.4 (Cq), 84.7 (Cq), 80.7 (Cq), 60.1 (CH$_2$), 55.2 (CH$_2$), 38.9 (CH$_3$), 28.2 (3×CH$_3$). HRMS (+ESI) calculated for C$_{23}$H$_{25}$N$_3$O$_3$ (M+H$^+$): 392.1968, found: 392.1967.

Example 54.5 Preparation of 3-((1H-pyrrolo[2,3-b]pyridin-2-yl)ethynyl)-N-(2-fluoroethyl)-N-methylaniline 140

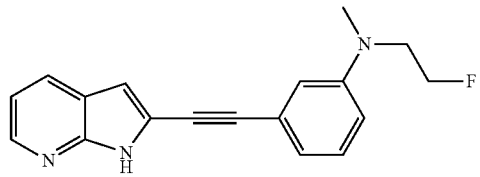

3-((1H-pyrrolo[2,3-b]pyridin-2-yl)ethynyl)-N-(2-fluoroethyl)-N-methylaniline
C$_{18}$H$_{16}$FN$_3$
MW: 293.35 gmol-1

At 0° C., TsCl (0.056 g, 0.294 mmol, 1.2 eq.), triethylamine (0.05 ml, 0.36 mmol, 1.5 eq.) and 4-DMAP (0.003 g, 0.024 mmol, 0, 1 eq.) were added to a solution of 144 (0.96 g, 0.245 mmol, 1.0 eq.) dissolved in DCM (5 ml). The mixture was stirred at room temperature overnight, then the mixture is neutralized with 10 ml of water and the aqueous phase is extracted with dichloromethane (2 times 10 ml). The combined organic phases were dried over MgSO$_4$, filtered and concentrated under reduced pressure. The crude was purified by flash column chromatography on silicagel to afford 73 mg of tosylated compound with a yield of 55%. Then, the product is dissolved in 5 ml of THF and 0.94 ml of TBAF (C=1 M, 0.94 mmol, 7.0 eq.) was added dropwise. After 24 h at RT, 10 ml of H$_2$O were added and the aqueous phase is extracted with dichloromethane (2 times 10 ml). The combined organic phases were dried over MgSO$_4$, filtered and concentrated under reduced pressure. Finally, the crude is dissolved in dichloromethane (0.05 M) and at 0° C., TFA was added dropwise (ratio TFA/dichloromethane=1/2). Stirring at 0° C. is carried out with TLC monitoring. At the end of the reaction, the reaction mixture was evaporated under reduced pressure. The crude is taken up in DCM/NaOH (1M). With stirring, the aqueous phase is extracted with dichloromethane (2 times 10 ml). The combined organic phases were dried over MgSO$_4$, filtered and concentrated under reduced pressure, prior to purifying the crude reaction product by flash column chromatography on silicagel (methanol/dichloromethane=4/96). Yellow solid (28%), Rf=0.15 (methanol/dichloromethane=4/96). IR (v, cm$^{-1}$, neat) 3386, 2980, 2926, 2206, 1747, 1603, 1546, 1517, 1473, 1408, 1384, 1343, 1305, 1249, 1194, 1154, 1117, 1085, 980, 847, 831, 814, 776, 746, 643, 525. $^1$H NMR (250 MHz, DMSO-d$_6$, 20° C.) δ 12.13 (s, 1H), 8.23 (d, J=4.9 Hz, 1H), 7.91 (d, J=7.9 Hz, 1H), 7.20 (t, J=7.9 Hz, 1H), 7.14-7.02 (m, 1H), 6.89-6.70 (m, 4H), 4.56 (dt, J=47.6, 5.0 Hz, 2H), 3.65 (dt, J=26.4, 5.0 Hz, 2H), 2.93 (s, 3H). $^{13}$C NMR (101 MHz, DMSO-d$_6$, 20° C.) δ 148.8 (Cq), 148.6 (Cq), 147.9 (Cq), 144.8 (CH), 129.9 (CH), 128.8 (CH), 121.4 (Cq), 121.2 (Cq), 119.5 (CH), 116.8 (CH), 114.6 (CH), 113.7 (CH), 106.5 (CH), 94.5 (Cq), 82.9 (Cq), 82.8 (d, J=170.3 Hz, $CH_2$), 52.1 (d, J=21.2 Hz, $CH_2$), 38.6 ($CH_3$). $^{19}$F NMR (376 MHz, DMSO-$d_6$, 20° C.) δ −221.03. HRMS (+ESI) calculated for $C_{18}H_{16}FN_3$ (M+H$^+$): 294.1401, found: 294.1401.

Example 55: 2-((3-((5-fluoro-1H-pyrrolo[2,3-b]pyridin-2-yl)ethynyl)phenyl)(methyl) amino)ethan-1-ol 145

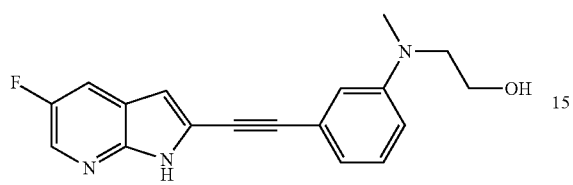

2-((3-((5-fluoro-1H-pyrrolo[2,3-b]pyridin-2-yl)ethynyl)phenyl)(methyl)amino)ethan-1-ol 2-((3-((5-fluoro-1H-pyrrolo[2,3-b]pyridin-2-yl)ethynyl)phenyl)(methyl)amino)ethan-1-ol was synthesized in 2 steps from alkyne 142. Initially, a Sonogashira reaction is performed between the fluorinated azaindole and alkyne 142. Finally, a deprotection reaction using TBAF in is performed to yield the final compound

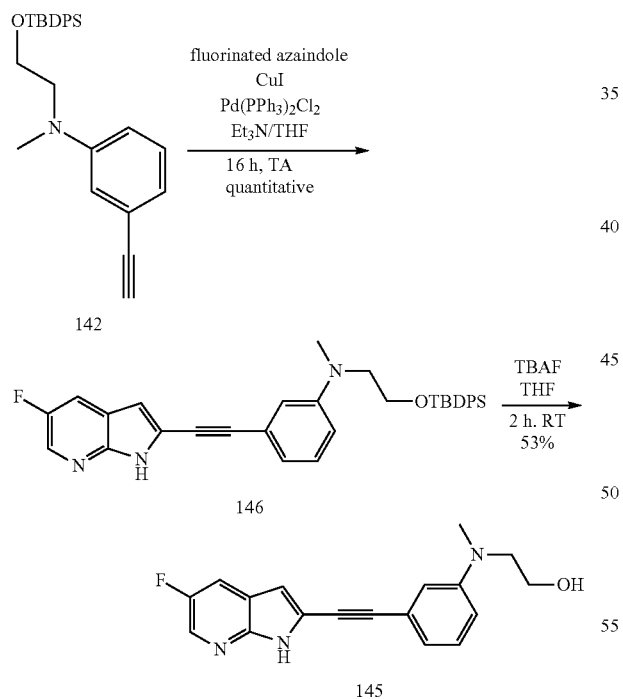

Compound 145 was prepared according to procedure C followed by procedure J and purified by flash column chromatography on silicagel (methanol/dichloromethane=4/96). Yellow solid (53%), Rf=0.10 (methanol/dichloromethane=2/98). mp=158-160° C. IR (v, cm$^{-1}$, neat) 2861, 2809, 1593, 1567, 1489, 1426, 1398, 1365, 1346, 1295, 1221, 1148, 1123, 1052, 1006, 987, 929, 892. $^1$H NMR (400 MHz, DMSO-$d_6$, 20° C.) δ 12.35 (s, 1H), 8.27 (s, 1H), 7.85 (m, 1H), 7.27-7.18 (m, 1H), 6.83 (m, 4H), 4.70 (s, 1H), 3.61-3.52 (m, 2H), 3.46-3.38 (m, 2H), 2.96 (s, 3H). $^{13}$C NMR (101 MHz, CDCl$_3$, 20° C.) δ 154.5 (d, J=239.2 Hz, Cq), 149.6 (Cq), 145.6 (Cq), 132.7 (d, J=29.0 Hz, CH), 129.9 (CH), 122.3 (2×Cq), 120.1 (d, J=7.2 Hz, Cq), 118.9 (CH), 114.8 (CH), 114.1 (d, J=20.8 Hz, CH), 113.9 (CH), 106.5 (d, J=4.0 Hz, CH), 95.0 (Cq), 81.0 (Cq), 58.5 ($CH_2$), 54.5 ($CH_2$), 39.4 ($CH_3$). $^{19}$F NMR (376 MHz, DMSO-$d_6$, 20° C.) δ. −138.5, HRMS (+ESI) calculated for $C_{18}H_{16}FN_3O$ (M+H+): 310.1350; found: 310.1349.

Example 56: N$^1$-(4-((5-fluoro-1H-pyrrolo[2,3-b]pyridin-2-yl)ethynyl)phenyl)-N$^1$,N$^2$,N$^2$-trimethyl-ethane-1,2-diamine 147

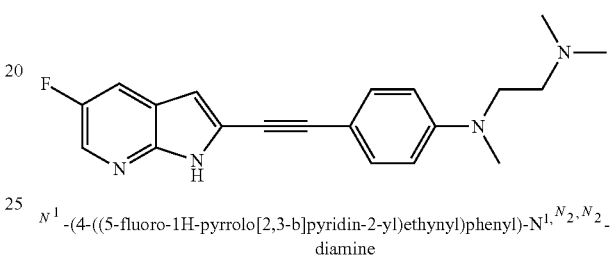

$N^1$-(4-((5-fluoro-1H-pyrrolo[2,3-b]pyridin-2-yl)ethynyl)phenyl)-N$^{1,N_2,N_2}$-diamine N-(4-((5-fluoro-1H-pyrrolo[2,3-b]pyridin-2-yl)ethynyl) phenyl)-N$^1$,N$^2$,N$^2$-trimethylethane-1,2-diamine 147 was synthesized in 4 steps. Initially, the alkyne 148 was prepared in 3 steps from dibromobenzene and Sonogashira reaction with azaindole provides the final compound.

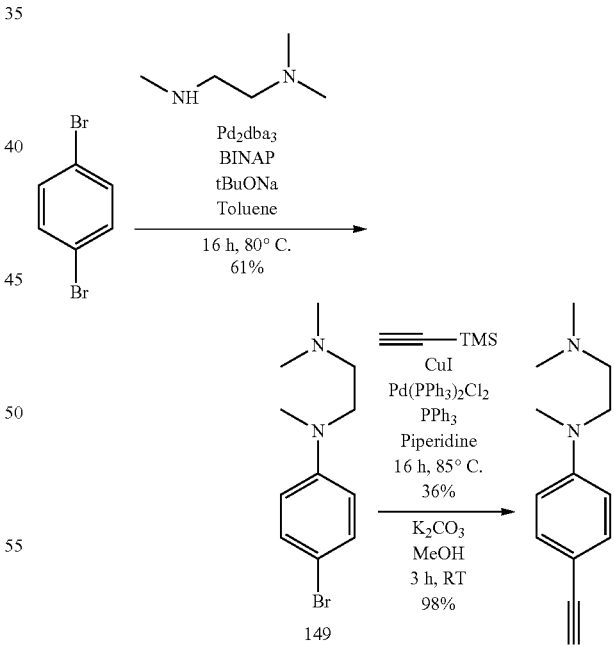

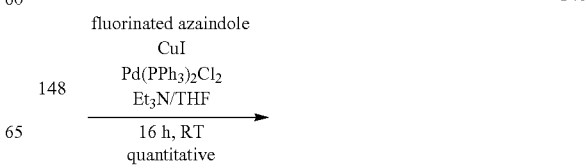

-continued

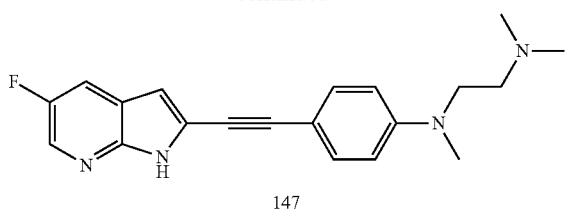

147

Example 56.1 Synthesis of N¹-(4-bromophenyl)-N¹, N²,N²-trimethylethane-1,2-diamine 149

Compound 149 was prepared according to procedure H and purified by flash column chromatography on silicagel (ethyl acetate/petroleum ether=1/49). Orange oil (61%). IR (v, cm⁻¹, neat) 3291, 2962, 2930, 2853, 2102, 1606, 1511, 1463, 1434, 1373, 1356, 1336, 1273, 1245, 1227, 1185, 1141, 1093, 1023, 935. ¹H NMR (250 MHz, CDCl₃, 20° C.) δ 7.25 (d, J=8.7 Hz, 2H), 6.54 (d, J=8.7 Hz, 2H), 3.39 (m, 2H), 2.89 (s, 3H), 2.53-2.35 (m, 2H), 2.25 (s, 6H). ¹³C NMR (63 MHz, CDCl₃, 20° C.) δ 148.1 (Cq), 131.8 (2×CH), 113.7 (2×CH), 108.0 (Cq), 55.8 (CH₂), 51.2 (CH₂), 45.9 (2×CH₃), 38.6 (CH₃). HRMS (+ESI) calculated for C₁₁H₁₇BrN₂ (M+H⁺): 257.0647, found: 257.0646.

Example 56.2 Synthesis of N¹-(4-ethynylphenyl)-N¹,N²,N²-trimethylethane-1,2-diamine 148

Alkyne 148 was prepared according to procedure II and purified by flash column chromatography on silicagel (ethyl acetate/petroleum ether=2/48). yellowish oil (35% over two steps). IR (v, cm⁻¹, neat) 2931, 2819, 2769, 2098, 1606, 1515, 1455, 133, 1324, 1300, 1250, 1215, 1175, 1113. ¹H NMR (400 MHz, CDCl₃, 20° C.) δ 7.37 (d, J=8.5 Hz, 2H), 6.63 (d, J=8.5 Hz, 2H), 3.39 (m, 2H), 2.90 (s, 4H), 2.55-2.41 (m, 2H), 2.31 (s, 6H). ¹³C NMR (101 MHz, CDCl₃, 20° C.) δ 149.1 (Cq), 133.4 (2×CH), 111.4 (2×CH), 108.6 (Cq), 84.8 (Cq), 74.7 (CH), 55.9 (CH₂), 50.9 (CH₂), 45.9 (2×CH₃), 38.5 (CH₃).

Example 56.3 Synthesis of N-(4-((5-fluoro-1H-pyrrolo[2,3-b]pyridin-2-yl)ethynyl)phenyl)-N¹,N², N²-trimethylethanecm-1,2-diamine 147

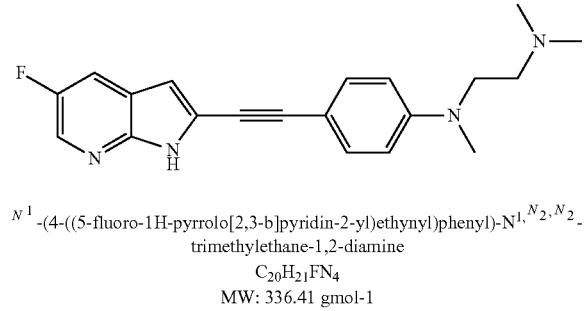

N¹-(4-((5-fluoro-1H-pyrrolo[2,3-b]pyridin-2-yl)ethynyl)phenyl)-N¹,N²,N²-trimethylethane-1,2-diamine
C₂₀H₂₁FN₄
MW: 336.41 gmol-1

The compound was prepared according to procedure C2 and purified by flash column chromatography on silicagel (methanol/dichloromethane/ammonia=4/96/1). yellow solid (80%), mp: 220-222° C., Rf=0.15 (methanol/dichloromethane=4/96). IR (v, cm⁻¹, neat) 2775, 2360, 2342, 1738, 1604, 1583, 1530, 1503, 1462, 1427, 1382, 1295, 1260, 1219, 1186, 1168, 1155, 1118, 1104, 1063, 1040, 1016, 981, 971, 957, 885. ¹H NMR (400 MHz, DMSO-d₆, 20° C.) δ 12.23 (s, 1H), 8.23 (m, 1H), 7.80 (dd, J=9.5, 2.5 Hz, 1H), 7.38 (d, J=8.6 Hz, 2H), 6.76-6.67 (m, 3H), 3.49 (t, J=7.1 Hz, 2H), 2.97 (s, 3H), 2.43 (t, J=7.1 Hz, 2H), 2.23 (s, 6H). ¹³C NMR (101 MHz, DMSO-d₆, 20° C.) δ 155.8 (d, J=239.4 Hz, Cq), 149.7 (Cq), 145.6 (Cq), 133.1 (2×CH), 132.1 (d, J=27.4 Hz, CH), 122.9 (Cq), 120.3 (d, J=7.5 Hz, Cq), 113.7 (2×CH), 112.0 (d, J=20.8 Hz, CH), 107.4 (Cq), 105.4 (d, J=4.0 Hz, CH), 95.5 (Cq), 80.1 (Cq), 55.4 (CH₂), 49.9 (CH₂), 45.9 (2×CH₃), 38.6 (CH₃). ¹⁹F NMR (376 MHz, CDCl₃, 20° C.) δ. -138.4. HRMS (+ESI) calculated for C₂₀H₂₁FN₄ (M+H⁺): 337.1823, found: 337.1821.

Example 57: 8-(4-((5-fluoro-1H-pyrrolo[2,3-b] pyridin-2-yl)ethynyl)phenyl)-8-azaspiro[4.5]decane 150

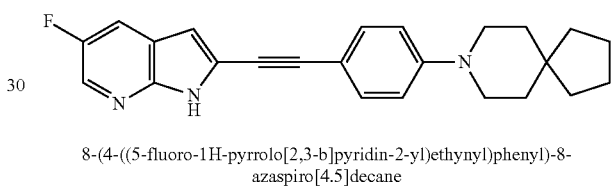

8-(4-((5-fluoro-1H-pyrrolo[2,3-b]pyridin-2-yl)ethynyl)phenyl)-8-azaspiro[4.5]decane 8-(4-((5-fluoro-1H-pyrrolo[2,3-b]pyridin-2-yl)ethynyl) phenyl)-8-azaspiro[4.5]decane 150 was synthesized in 3 steps. Initially, the corresponding alkyne 151 was prepared from brominated 152 then a Sonogashira reaction was performed on the azaindole to obtain the final compound

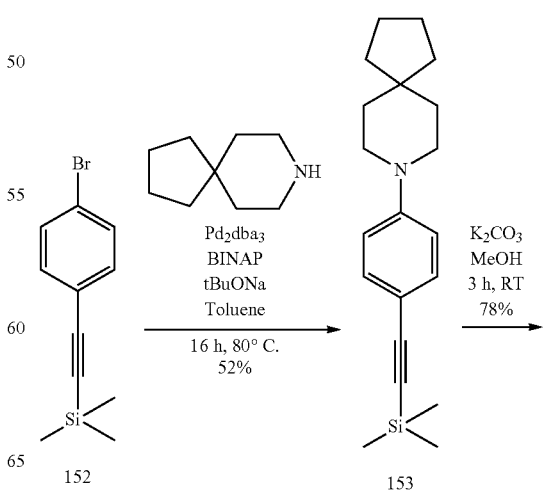

152     153

Example 57.1 Synthesis of 8-(4-ethynylphenyl)-8-azaspiro[4.5]decane 151

Compound 151 was prepared according to procedure H followed by procedure L and purified by flash column chromatography on silicagel (ethyl acetate/petroleum ether=1/49). pale yellow amorphous solid (41% over 2 steps). IR (v, cm$^{-1}$, neat) 3302, 2915, 2849, 2096, 1729, 1678, 1602, 1554, 1508, 1463, 1448, 1389, 1345, 1309, 1248, 1193, 1137, 1067, 998, 951, 899, 858. $^1$H NMR (400 MHz, CDCl$_3$, 20° C.) δ 7.38 (d, J=8.7 Hz, 2H), 6.85 (d, J=8.7 Hz, 2H), 3.29-3.20 (m, 4H), 2.99 (s, 1H), 1.72-1.58 (m, 8H), 1.49 (m, 4H). $^{13}$C NMR (101 MHz, CDCl$_3$, 20° C.) δ 151.6 (Cq), 133.2 (2×CH), 114.9 (2×CH), 110.9 (Cq), 84.5 (Cq), 75.1 (Cq), 46.3 (2×CH$_2$), 40.7 (Cq), 37.7 (2×CH$_2$), 37.0 (2×CH$_2$), 24.3 (2×CH$_2$). HRMS (+ESI) calculated for C$_{17}$H$_{21}$N (M+H$^+$): 240.1745, found: 240.1746.

Example 57.2 Synthesis of 8-(4-((5-fluoro-1H-pyrrolo[2,3-b]pyridin-2-yl)ethynyl)phenyl)-8-azaspiro[4.5]decane 150

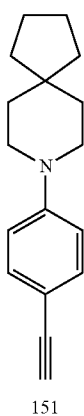

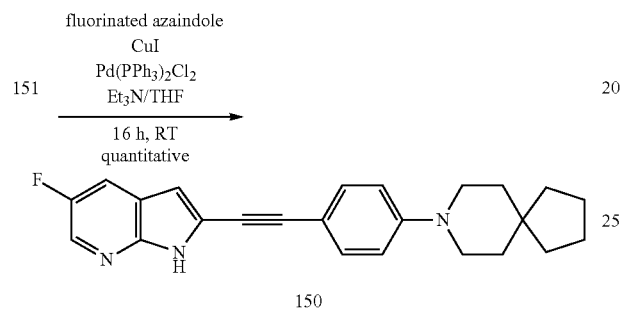

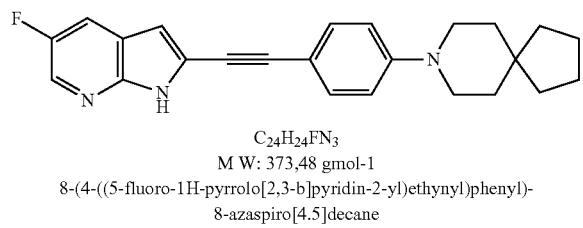 [SMILES: Fc1cnc2[nH]c(C#Cc3ccc(N4CCC5(CCCC5)CC4)cc3)cc2c1]

C$_{24}$H$_{24}$FN$_3$
M W: 373,48 gmol-1
8-(4-((5-fluoro-1H-pyrrolo[2,3-b]pyridin-2-yl)ethynyl)phenyl)-8-azaspiro[4.5]decane The compound was prepared according to procedure C2 and purified by silicagel column chromatography (methanol/dichloromethane=2/98). Yellow solid (40%), mp>260° C., Rf=0.22 (methanol/dichloromethane=2/98). IR (v, cm$^{-1}$, neat) 3119, 3058, 2921, 2827, 2200, 1601, 1585, 1533, 1504, 1462, 1385, 1344, 1287, 1243, 1226, 1186, 1155, 1138, 1107, 998, 984, 952, 898, 878. $^1$H NMR (400 MHz, DMSO-d$_6$, 20° C.) δ 12.26 (s, 1H), 8.24 (s, 1H), 7.81 (m, 1H), 7.39 (d, J=8.9 Hz, 2H), 6.97 (d, J=8.9 Hz, 2H), 6.72 (s, 1H), 3.34-3.24 (m, 4H), 1.61 (s, 4H), 1.54-1.40 (m, 8H). $^{13}$C NMR (101 MHz, DMSO-d$_6$, 20° C.) δ 155.6 (d, J=239.4 Hz, Cq), 150.6 (Cq), 144.7 (Cq), 132.0 (2×CH), 131.6 (d, J=27.4 Hz, CH), 121.8 (Cq), 119.4 (d, J=7.5 Hz, Cq), 114.1 (2×CH), 112.8 (d, J=20.8 Hz, CH), 108.6 (Cq), 104.8 (d, J=4.0 Hz, CH), 94.2 (Cq), 79.4 (Cq), 44.63 (2×CH$_2$), 40.1 (Cq), 36.7 (2×CH$_2$), 35.9 (2×CH$_2$), 24.4 (2×CH$_2$). $^{19}$F NMR (376 MHz, CDCl$_3$, 20° C.) δ. -138.4. HRMS (+ESI) calculated C$_{24}$H$_{24}$FN$_3$ (M+H$^+$): 374.2027, found: 374.2027.

Example 58 4-(4-((5-fluoro-1H-pyrrolo[2,3-b]pyridin-2-yl)ethynyl)phenoxy)-N,N-dimethylaniline 154

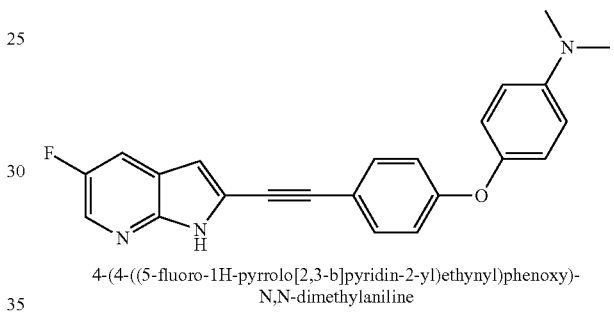

4-(4-((5-fluoro-1H-pyrrolo[2,3-b]pyridin-2-yl)ethynyl)phenoxy)-N,N-dimethylaniline 4-(4-((5-fluoro-1H-pyrrolo[2,3-b]pyridin-2-yl)ethynyl)phenoxy)-N,N-dimethylaniline 154 was synthesized in 5 steps. Initially, the alkyne 155 was prepared in 4 steps starting from the phenyl ether 99. The Sonogashira reaction was carried out with the fluorinated azaindole to yield the final compound

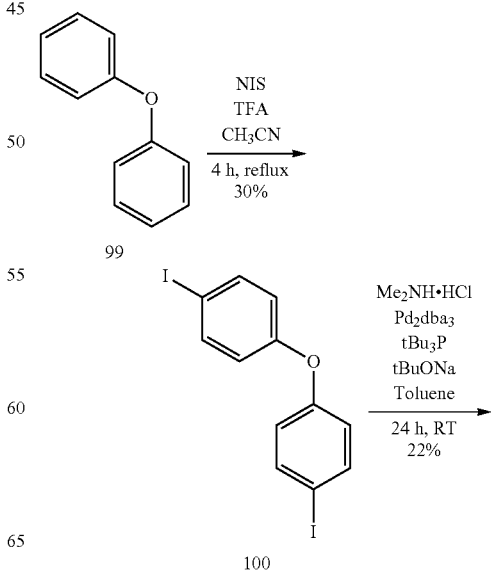

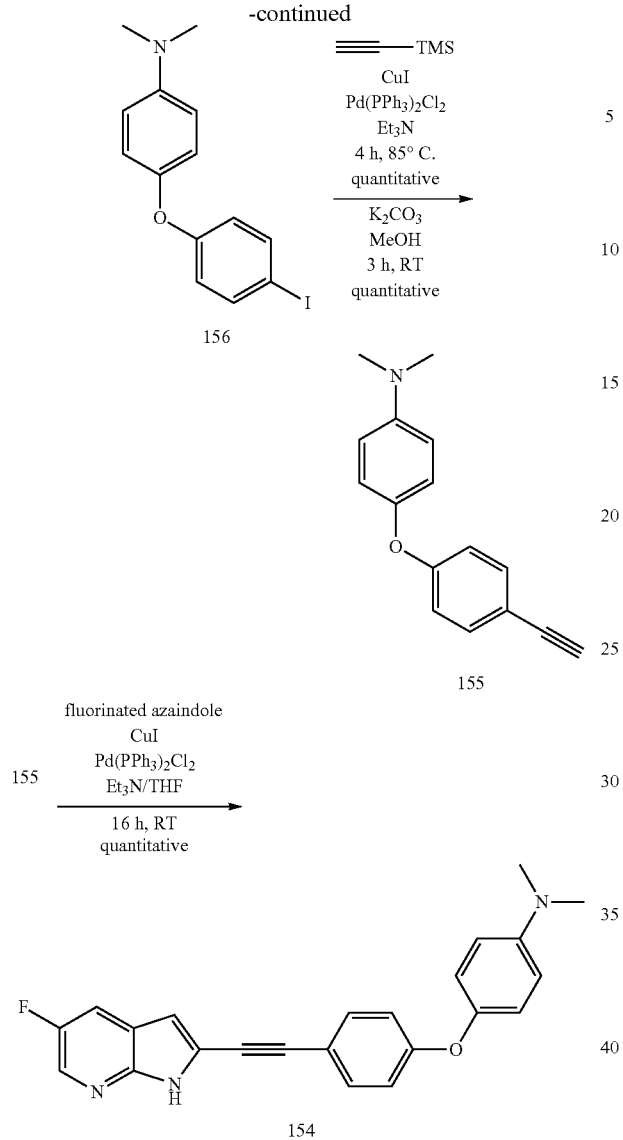

Example 58.1 Synthesis of 4-(4-iodophenoxy)-N,N-dimethylaniline 156

Under argon, $Pd_2dba_3$ (0.05 eq.) and $tBu_3P$ (0.075 mmol) were added to a degassed anhydrous toluene solution of 0.3M concentration containing the amine (1.0 eq.), the iodine 100 (1.0 eq.) and t-BuONa (1.2 eq.). After 24 h at room temperature, the solvent was evaporated under reduced pressure. Then, the reaction mixture was concentrated under reduced pressure before being purified by flash column chromatography on silica gel. Compound 156 is obtained as a colorless oil with a yield of 22%., Rf=0.20 (ethyl acetate/petroleum ether=1/49). IR (v, cm$^{-1}$, neat) 3044, 2844, 2793, 1578, 1508, 1475, 1439, 1395, 1344, 1276, 1223, 1163, 1125, 1056, 1001, 947. $^1$H NMR (250 MHz, CDCl$_3$, 20° C.) δ 7.52 (d, J=8.9 Hz, 2H), 6.91 (d, J=8.9 Hz, 2H), 6.74-6.62 (m, 4H), 2.91 (s, 6H). $^{13}$C NMR DEPT (63 MHz, CDCl$_3$, 20° C.) δ 138.5 (2×CH), 121.2 (2×CH), 119.4 (2×CH), 114.1 (2×CH), 41.4 (2×CH$_3$). HRMS (+ESI) calculated for $C_{14}H_{14}INO$ (M+H$^+$): 340.0192, found: 340.0191.

Example 58.2 Synthesis of 4-(4-ethynylphenoxy)-N,N-dimethylaniline 155

The catalyst [Pd(PPh$_3$)$_2$Cl$_2$] (1.5 mg, 0.002 mmol, 0.03 eq.) was added to a degassed solution of iodine 156 (80 mg, 0.131 mmol, 1.0 eq), ethynyltrimethylsilane (0.016 ml, 0.1 mmol, 1.5 eq.), CuI (1 mg, 0.002 mmol, 0.03 eq.), in the Et$_3$N at a concentration of 0.3 M. The mixture was stirred at 85° C. for 4 h under argon atmosphere. Then, the reaction mixture was concentrated under reduced pressure before being purified by flash column chromatography on silicagel with eluent (ethyl acetate/petroleum ether=20/80) to obtain 28 mg of the intermediate which reacted with K$_2$CO$_3$ (19 mg, 0.140 mmol, 1.5 eq.) in 4 ml of DCM/methanol (1/1). After 3 h stirring at room temperature, the solution is filtered through cotton. After evaporation to dryness, the crude is purified by flash column chromatography on silica gel with eluent (ethyl acetate/petroleum ether=4/96) to obtain the alkyne 155 as a colorless oil in quantitative yield over 2 steps. Rf=0.20 (ethyl acetate/petroleum ether=4/96). IR (v, cm$^{-1}$, neat) 3284, 3070, 2929, 2856, 1610, 1513, 1495, 1471, 1427, 1360, 1280, 1234, 1160, 1103, 985, 927, 869. $^1$H NMR (400 MHz, CDCl$_3$, 20° C.) δ 7.40 (d, J=8.6 Hz, 2H), 6.96 (d, J=9.0 Hz, 2H), 6.85 (d, J=8.6 Hz, 2H), 6.74 (d, J=9.0 Hz, 2H), 3.00 (s, 1H), 2.94 (s, 6H). $^{13}$C NMR (101 MHz, CDCl$_3$, 20° C.) δ 159.8 (Cq), 148.0 (Cq), 146.3 (Cq), 133.6 (2×CH), 121.3 (2×CH), 116.7 (2×CH), 115.3 (Cq), 113.8 (2×CH), 83.5 (Cq), 77.3 (CH), 41.1 (2×CH$_3$). HRMS (+ESI) calculated for $C_{16}H_{15}NO$ (M+Na+): 280.1308, found: 280.1312.

Example 58.3 Synthesis of 4-(4-((5-fluoro-1H-pyrrolo[2,3-b]pyridin-2-yl)ethynyl)phenoxy)-N,N-dimethylaniline 154

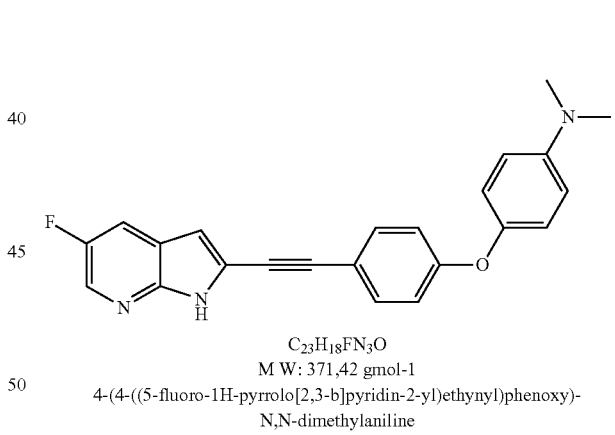

$C_{23}H_{18}FN_3O$
M W: 371,42 gmol-1
4-(4-((5-fluoro-1H-pyrrolo[2,3-b]pyridin-2-yl)ethynyl)phenoxy)-N,N-dimethylaniline The compound was prepared according to procedure C2 and purified by flash column chromatography on silica gel (methanol/dichloromethane=2/98). Yellow solid (31%), mp: 228-230° C., Rf=0.22 (methanol/dichloromethane=2/98). IR (v, cm$^{-1}$, neat) 3119, 3060, 2970, 2850, 2799, 1586, 1515, 1504, 1493, 1455, 1443, 1427, 1396, 1347, 1293, 1277, 1250, 1222, 1162, 1126, 1102, 1060, 985, 946, 893. $^1$H NMR (250 MHz, DMSO-d$_6$, 20° C.) δ 12.30 (s, 1H), 8.22 (s, 1H), 7.79 (m, 1H), 7.50 (d, J=8.4 Hz, 2H), 6.92 (2×d, J=8.4 Hz, 4H), 6.75 (d, J=7.7 Hz, 3H), 2.86 (s, 6H). $^{13}$C NMR DEPT (63 MHz, DMSO-d$_6$, 20° C.) δ 133.7 (2×CH), 132.9 (d, J=27.4 Hz, CH), 121.7 (2×CH), 117.1 (2×CH), 114.2 (2×CH), 113.8 (d, J=20.8 Hz, CH), 106.4 (d, J=4.0 Hz, CH), 41.00 (2×CH$_3$). $^{19}$F NMR (235 MHz, CDCl$_3$, 20° C.)

δ. −138.5. HRMS (+ESI) calculated for $C_{23}H_{18}FN_3O$ (M+H$^+$): 372.1506, found: 372.1505.

Example 59: 5-fluoro-2-((4-(4-(methylsulfonyl)piperazin-1-yl)phenyl)ethynyl)-1H-pyrrolo[2,3-b]pyridine 157

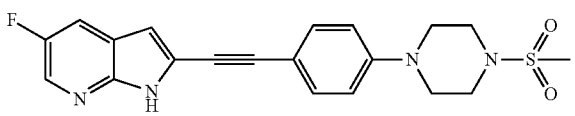

5-fluoro-2-((4-(4-(methylsulfonyl)piperazin-1-yl)phenyl)ethynyl)-1H-pyrrolo[2,3-b]pyridine 157 was synthesized in 3 steps. Initially, the alkyne 158 was prepared in 2 steps from the bromine 152 then the Sonogashira reaction with azaindole allowed to obtain the final compound.

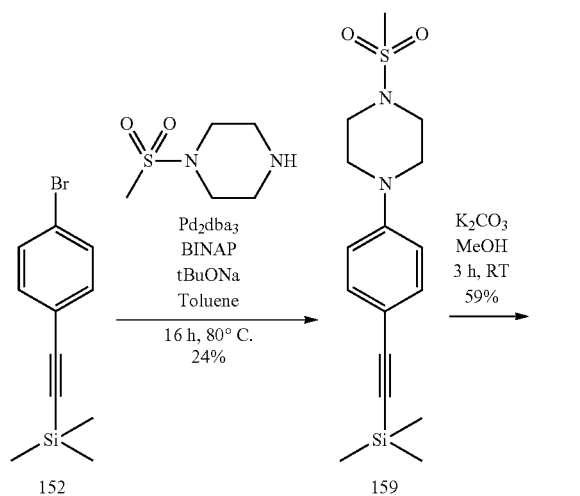

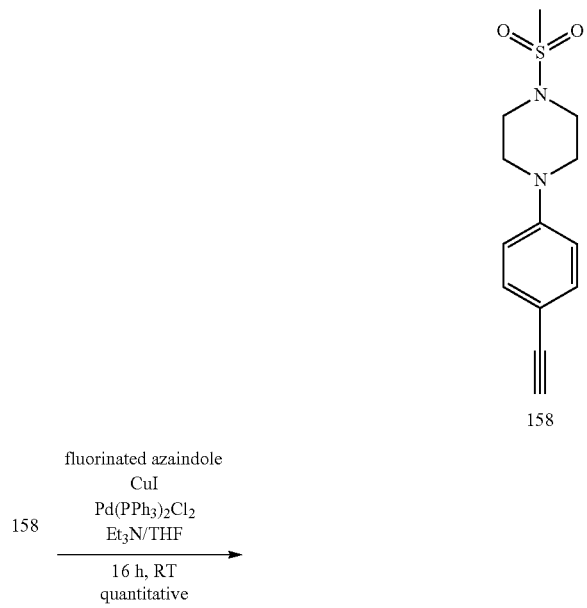

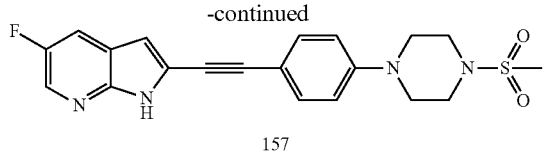

157

Example 59.1 Synthesis of 1-(4-ethynylphenyl)-4-(methylsulfonyl)piperazine 158

The compound 158 was prepared according to procedure H followed by Procedure L and purified by flash column chromatography on silica gel (ethyl acetate petroleum ether=30/70). White solid (14% over 2 steps), mp. 208-210° C., Rf=0.5 (ethyl acetate/petroleum ether=30/70). IR (v, cm$^{-1}$, neat) 3245, 2928, 2836, 1605, 1508, 1448, 1389, 1374, 1340, 1329, 1319, 1286, 1263, 1237, 1204, 1179, 1156, 1139, 1114, 1065, 1049, 948, 908. $^1$H NMR (400 MHz, CDCl$_3$, 20° C.) δ 7.39 (d, J=8.7 Hz, 2H), 6.82 (d, J=8.7 Hz, 2H), 3.34 (s1, 8H), 2.98 (s, 1H), 2.80 (s, 3H). $^{13}$C NMR (101 MHz, CDCl$_3$, 20° C.) δ 150.5 (Cq), 133.3 (2×CH), 115.9 (2×CH), 113.5 (Cq), 83.8 (Cq), 75.9 (Cq), 48.5 (2×CH$_2$), 45.6 (2×CH$_2$), 34.5 (CH$_3$). HRMS (+ESI) calculated for $C_{13}H_{16}N_2O_2S$ (M+H$^+$): 265.1006, found: 265.1005.

Example 59.2 Synthesis of 5-fluoro-2-((4-(4-(methylsulfonyl)piperazin-1-yl)phenyl)ethynyl)-1H-pyrrolo[2,3-b]pyridine 157

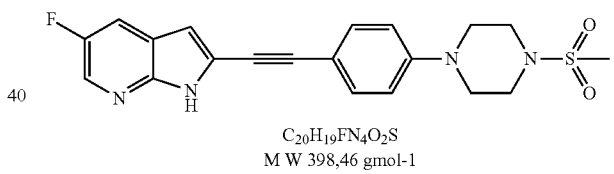

$C_{20}H_{19}FN_4O_2S$
M W 398,46 gmol-1

The compound was prepared according to procedure C2 and purified by flash column chromatography on silica gel (ethyl acetate/petroleum ether=30/70). Yellow solid (33%), mp>260° C., Rf=0.33 (ethyl acetate/petroleum ether=30/70). IR (v, cm$^{-1}$, neat) 2971, 2901, 2361, 1729, 1606, 1559, 1541, 1507, 1448, 1393, 1373, 1323, 1291, 1259, 1223, 1186, 1174, 1132, 115, 1088, 1066, 1012, 937, 833, 817, 803. $^1$H NMR (400 MHz, DMSO-d$_6$, 20° C.) δ 12.28 (s, 1H), 8.25 (s, 1H), 7.83 (d, J=9.1 Hz, 1H), 7.45 (d, J=8.5 Hz, 2H), 7.04 (d, J=8.7 Hz, 2H), 6.75 (s, 1H), 3.38 (d, J=5.0 Hz, 4H), 3.25 (d, J=5.0 Hz, 4H), 2.93 (s, 3H). $^{13}$C NMR (101 MHz, DMSO-d$_6$, 20° C.) δ 155.6 (d, J=239.4 Hz, Cq), 150.9 (Cq), 145.6 (Cq), 133.0 (2×CH), 132.6 (d, J=27.4 Hz, CH), 122.5 (Cq), 120.3 (d, J=7.5 Hz, Cq), 115.7 (2×CH), 113.9 (d, J=20.8 Hz, CH), 111.3 (Cq), 105.9 (d, J=4.0 Hz, CH), 94.7 (Cq), 80.7 (Cq), 47.4 (2×CH$_2$), 45.6 (2×CH$_2$), 34.4 (CH$_3$). $^{19}$F NMR (376 MHz, DMSO-d$_6$, 20° C.) δ. −138.6. HRMS (+ESI) calculated for $C_{20}H_{19}FN_4O_2S$ (M+H$^+$): 399.1285, found: 399.1285.

Example 60: 2-((4-((5-fluoro-1H-pyrrolo[2,3-b]pyridin-2-yl)ethynyl)phenyl)(methyl) amino)ethan-1-ol 160

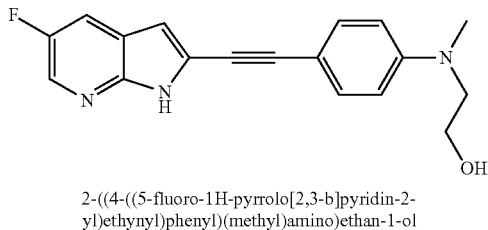 [SMILES: CN(CCO)c1ccc(C#Cc2cc3cc(F)cnc3[nH]2)cc1]

2-((4-((5-fluoro-1H-pyrrolo[2,3-b]pyridin-2-yl)ethynyl)phenyl)(methyl)amino)ethan-1-ol 2-((4-((5-fluoro-1H-pyrrolo[2,3-b]pyridin-2-yl)ethynyl)phenyl)(methyl)amino)ethan-1-ol 160 was synthesized in 4 steps. Initially, the alkyne 161 was prepared in 2 steps from the bromine 152 then the Sonogashira reaction with azaindole followed by deprotection allows to obtain the final compound.

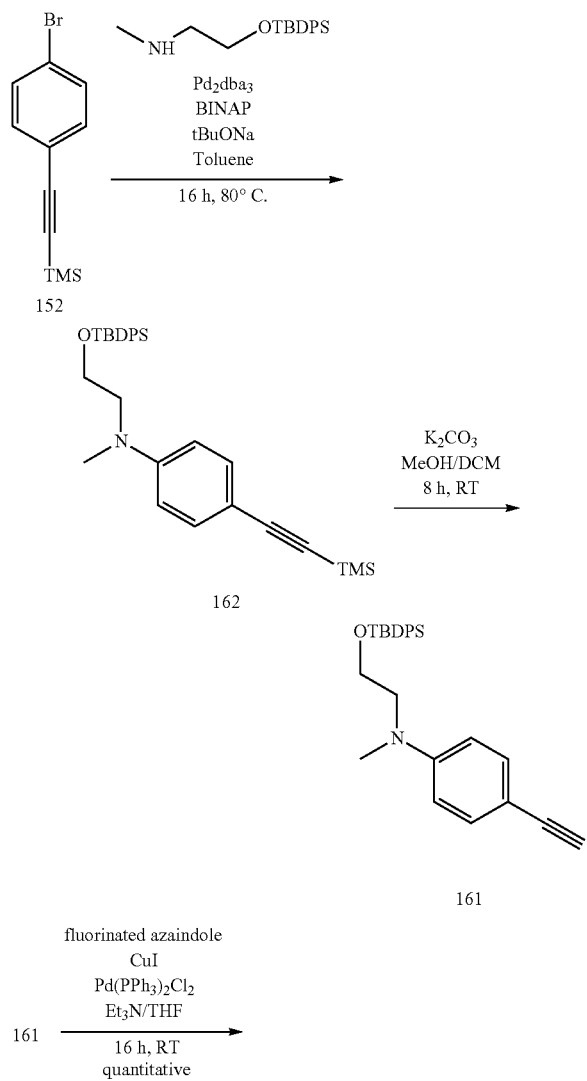

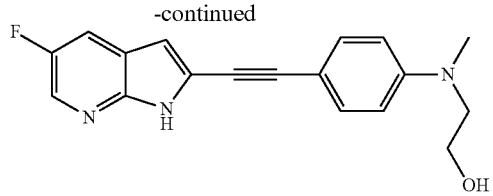

160

Example 60.1 Synthesis of N-(2-((tert-butyldiphenylsilyl)oxy)ethyl)-4-ethynyl-N-methylaniline 161

Compound 161 was prepared according to procedure H followed by procedure L and purified by flash column chromatography on silica gel (ethyl acetate/petroleum ether=10/90). Yellow oil (44% over 2 steps). Rf=0.4 (ethyl acetate/petroleum ether=10/90). IR (v, cm$^{-1}$, neat) 3291, 2962, 2930, 2853, 2102, 1606, 1511, 1463, 1434, 1373, 1356, 1336, 1273, 1245, 1227, 1185, 1141, 1093, 1023, 935.1H NMR (400 MHz, CDCl$_3$, 20° C.) δ 7.68 (d, J=6.8 Hz, 3H), 7.40 (td, J=12.3, 11.8, 6.0 Hz, 7H), 6.49 (d, J=8.8 Hz, 2H), 3.83 (t, J=6.2 Hz, 2H), 3.52 (d, J=6.1 Hz, 2H), 2.98 (d, J=5.3 Hz, 3H), 1.09 (s, 9H).

Example 60.2 Synthesis of N-(2-((tert-butyldiphenylsilyl)oxy)ethyl)-4-((5-fluoro-1H-pyrrolo[2,3-b]pyridin-2-yl)ethynyl)-N-methylaniline 163

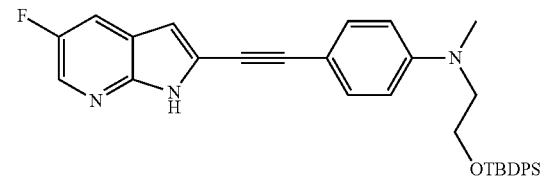

Compound 163 was prepared according to procedure C2 and purified by flash column chromatography on silicagel (ethyl acetate/petroleum ether=10/90). Yellow solid (78%), Rf=0.10 (ethyl acetate/petroleum ether=10/90). mp=182-184° C. IR (v, cm$^{-1}$, neat) 2922, 2852, 2198, 2008, 1605, 1584, 1537, 1504, 1470, 1426, 1377, 1349, 1294, 1233, 1188, 1154, 1107, 1007, 976, 871. $^1$H NMR (400 MHz, CDCl$_3$, 20° C.) δ 8.23 (s, 1H), 7.66 (d, J=7.5 Hz, 4H), 7.59 (d, J=8.5 Hz, 1H), 7.46 (t, J=7.5 Hz, 2H), 7.39 (t, J=7.5 Hz, 6H), 6.68 (s, 1H), 6.55 (d, J=8.5 Hz, 2H), 3.84 (t, J=6.2 Hz, 2H), 3.54 (t, J=6.2 Hz, 2H), 3.01 (s, 3H), 1.07 (s, 9H). $^{13}$C NMR DEPT (101 MHz, CDCl$_3$, 20° C.) δ133.0 (4×CH), 132.8 (2×CH), 132.3 (d, J=27.4 Hz, CH), 129.8 (2×CH), 127.8 (4×CH), 113.6 (d, J=20.8 Hz, CH), 111.5 (2×CH), 106.4 (d, J=4.0 Hz, CH), 60.7 (CH$_2$), 54.2 (CH$_2$), 39.2 (CH$_3$), 26.8 (3×CH$_3$). $^{19}$F NMR (376 MHz, CDCl$_3$, 20° C.) δ. −138.54, HRMS (+ESI) calculated for C$_{34}$H$_{34}$FN$_3$OSi (M+H$^+$): 548.2527; found: 548.2528.

Example 60.3 Synthesis of 2-((4-((5-fluoro-1H-pyrrolo[2,3-b]pyridin-2-yl)ethynyl)phenyl)(methyl)amino)ethan-1-ol 160

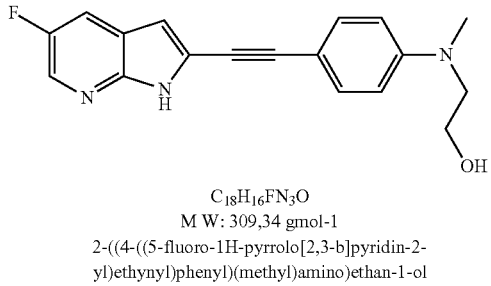 [SMILES: CN(CCO)c1ccc(C#Cc2cc3cc(F)cnc3[nH]2)cc1]

C$_{18}$H$_{16}$FN$_3$O
MW: 309,34 gmol-1
2-((4-((5-fluoro-1H-pyrrolo[2,3-b]pyridin-2-yl)ethynyl)phenyl)(methyl)amino)ethan-1-ol Compound 160 was prepared according to procedure E and purified by flash column chromatography on silica gel (methanol/dichloromethane=4/96). Yellow solid (45%), Rf=0.10 (methanol/dichloromethane=2/98). mp=192-194° C. IR (v, cm$^{-1}$, neat) 3126, 2921, 2852, 2198, 1729, 1603, 1585, 1540, 1507, 1449, 1432, 1372, 1321, 1287, 1260, 1241, 1219, 1185, 1153, 1120, 1100, 1078, 1052, 978, 930, 917, 889, 892, 832. $^1$H NMR (400 MHz, DMSO-d$_6$, 20° C.) δ 12.22 (s, 1H), 8.22 (s, 1H), 7.80 (m, 1H), 7.37 (d, J=8.5 Hz, 2H), 6.80-6.60 (m, 3H), 4.71 (s, 1H), 3.56 (m, 2H), 3.50-3.39 (m, 2H), 2.99 (s, 3H). $^{13}$C NMR (101 MHz, DMSO-d6, 20° C.) δ 155.6 (d, J=239.4 Hz, Cq), 150.0 (Cq), 145.6 (Cq), 133.0 (2×CH), 132.6 (d, J=27.4 Hz, CH), 123.3 (Cq), 120.3 (d, J=7.5 Hz, Cq), 113.4 (d, J=20.8 Hz, CH), 112.0 (2×CH), 107.2 (Cq), 106.3 (d, J=4.0 Hz, CH), 95.6 (Cq), 80.6 (Cq), 58.5 (CH$_2$), 54.3 (CH$_2$), 39.2 (CH$_3$). $^{19}$F NMR (376 MHz, DMSO-d$_6$, 20° C.) δ. -138.4, HRMS (+ESI) calculated for C$_{18}$H$_{16}$FN$_3$O (M+H$^+$): 310.1350; found: 310.1349.

Example 61: 3-((4-((5-fluoro-1H-pyrrolo[2,3-b]pyridin-2-yl)ethynyl)phenyl)(methyl) amino)propan-1-ol 164

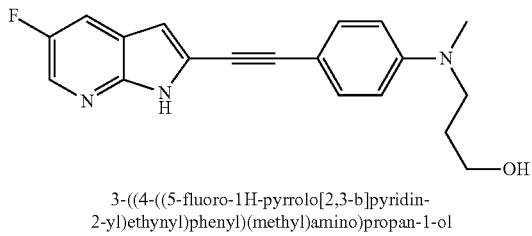 [SMILES: CN(CCCO)c1ccc(C#Cc2cc3cc(F)cnc3[nH]2)cc1]

3-((4-((5-fluoro-1H-pyrrolo[2,3-b]pyridin-2-yl)ethynyl)phenyl)(methyl)amino)propan-1-ol 3-((4-((5-fluoro-1H-pyrrolo[2,3-b]pyridin-2-yl)ethynyl)phenyl)(methyl)amino)propan-1-ol 164 was synthesized in 4 steps. Initially, the alkyne 165 was prepared in 3 steps from the bromine 152 then the Sonogashira reaction with azaindole followed by deprotection provides the final compound

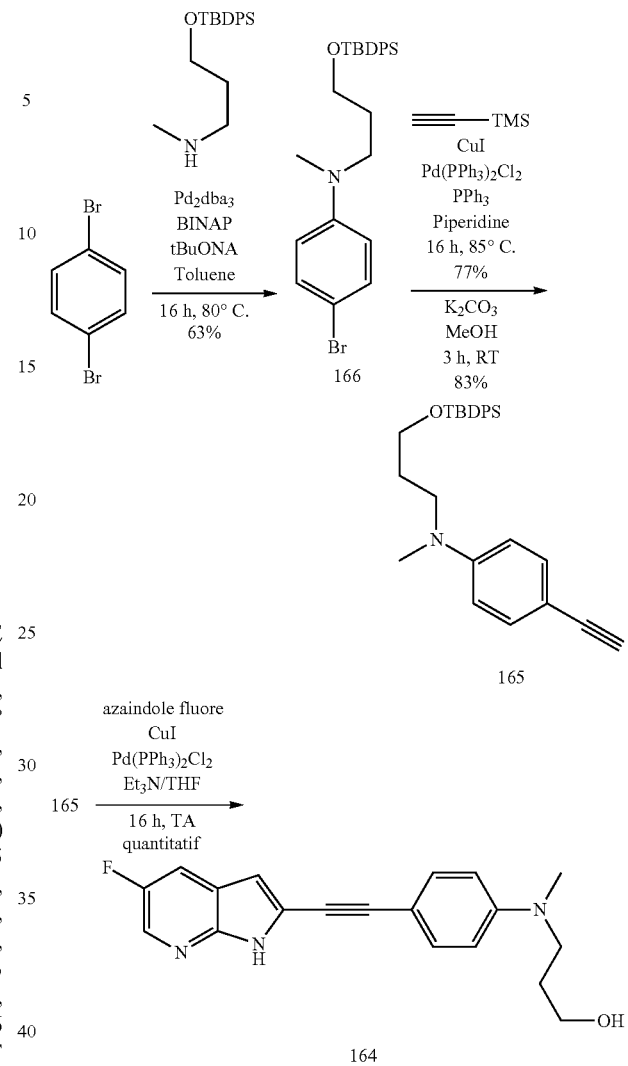

Example 61.1 Synthesis of 4-bromo-N-(3-((tert-butyldiphenylsilyl)oxy)propyl)-N-methylaniline 166

Compound 166 was prepared according to procedure H and purified by flash column chromatography on silica gel (ethyl acetate/petroleum ether=2/48). Orange oil (64%). Rf=0.55 (ethyl acetate/petroleum ether=2/48). IR (v, cm$^{-1}$, neat) 33070, 2929, 2856, 1592, 1496, 1471, 1426, 1370, 1239, 1210, 1189, 1104, 926. $^1$H NMR (400 MHz, CDCl$_3$, 20° C.) δ 7.69 (d, J=7.2 Hz, 4H), 7.42 (m, 6H), 7.29 (m, 2H), 6.62 (d, J=8.5 Hz, 2H), 3.73 (t, J=7.3 Hz, 2H), 3.49 (t, J=7.3 Hz, 2H), 2.91 (s, 3H), 1.79 (p, J=6.5 Hz, 2H), 1.11 (s, 9H). $^{13}$C NMR (101 MHz, CDCl$_3$, 20° C.) δ 148.3 (Cq), 135.6 (4×CH), 133.7 (2×Cq), 131.7 (2×CH), 129.7 (2×CH), 127.7 (4×CH), 113.8 (2×CH), 107.7 (Cq) δ1.3 (CH$_2$), 49.4 (CH$_2$), 38.3 (CH$_3$), 29.4 (CH$_2$), 26.9 (3×CH$_3$), 19.2 (Cq). HRMS (+ESI) calculated for C$_{26}$H$_{32}$BrNOSi (M+): 482.1509, found: 482.1509.

Example 61.2 Synthesis of N-(3-((tert-butyldiphenylsilyl)oxy)propyl)-4-ethynyl-N-methylaniline 165

The alkyne 165 was prepared according to procedure 11 and purified by flash column chromatography on silica gel (ethyl acetate/petroleum ether=2/48). Yellowish oil (35% over two steps). Rf=0.50 (ethyl acetate/petroleum ether=2/48). IR (v, cm$^{-1}$, neat) 3288, 2929, 2856, 1594, 1570, 1494, 1471, 1427, 1360, 1105, 1003, 822. $^1$H NMR (250 MHz, CDCl$_3$, 20° C.) δ 7.70-7.60 (m, 4H), 7.48-7.30 (m, 8H), 6.63 (d, J=8.9 Hz, 2H), 3.70 (t, J=5.7 Hz, 2H), 3.58-3.47 (m, 2H), 2.97 (s, 1H), 2.93 (s, 3H), 1.78 (s, 2H), 1.08 (s, 9H). $^{13}$C NMR (101 MHz, CDCl$_3$, 20° C.) δ 13C NMR (63 MHz, CDCl3) δ 149.3 (Cq), 135.6 (4×CH), 133.7 (2×Cq), 133.3 (2×CH), 129.7 (2×CH), 127.7 (4×CH), 111.4 (CH), 108.2 (Cq) 84.9 (Cq), 74.6 (CH), 61.2 (CH$_2$) 49.1 (CH$_2$), 38.2 (CH$_3$), 29.6 (CH$_2$), 26.9 (3×CH$_3$), 19.2 (Cq). HRMS (+ESI) calculated for C$_{28}$H$_{33}$N$_2$OSi (M+H$^+$): 428.2404, found: 428.2399.

Example 61.3 Synthesis of 3-((4-((5-fluoro-1H-pyrrolo[2,3-b]pyridin-2 yl)ethynyl)phenyl)(methyl)amino)propan-1-ol 164

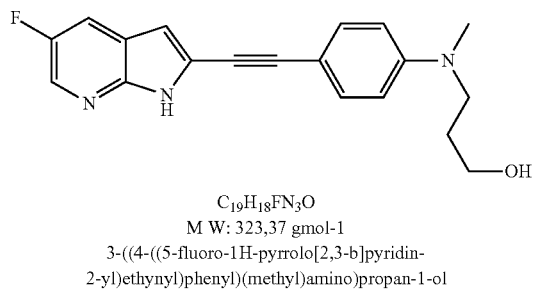 [SMILES: CN(CCCO)c1ccc(C#Cc2cc3cc(F)cnc3[nH]2)cc1]

C$_{19}$H$_{18}$FN$_3$O
M W: 323,37 gmol-1
3-((4-((5-fluoro-1H-pyrrolo[2,3-b]pyridin-2-yl)ethynyl)phenyl)(methyl)amino)propan-1-ol The compound 164 was prepared according to procedure C2 followed by procedure E and purified by flash column chromatography on silica gel (methanol/dichloromethane=4/96). Yellow solid (48% over 2 steps), Rf=0.10 (methanol/dichloromethane=2/98). mp=192-194° C. IR (v, $^{-1}$, neat) 3126, 2921, 2852, 2198, 1729, 1603, 1585, 1540, 1507, 1449, 1432, 1372, 1321, 1287, 1260, 1241, 1219, 1185, 1153, 1120, 1100, 1078, 1052, 978, 930, 917, 889, 892, 832. $^1$H NMR (400 MHz, DMSO-d$_6$, 20° C.) δ 12.23 (s, 1H), 8.22 (s, 1H), 7.80 (d, J=9.5 Hz, 1H), 7.37 (d, J=8.5 Hz, 2H), 6.77-6.67 (m, 3H), 4.58-4.51 (m, 1H), 3.51-3.39 (m, 4H), 2.95 (s, 3H), 1.68 (p, J=6.5 Hz, 2H). $^{13}$C NMR (101 MHz, DMSO-d6, 20° C.) δ 155.6 (d, J=239.4 Hz, Cq), 150.0 (Cq), 145.6 (Cq), 133.0 (2×CH), 132.6 (d, J=27.4 Hz, CH), 123.3 (Cq), 120.3 (d, J=7.5 Hz, Cq), 113.4 (d, J=20.8 Hz, CH), 112.0 (2×CH), 107.2 (Cq), 106.3 (d, J=4.0 Hz, CH), 95.7 (Cq), 80.0 (Cq), 58.7 (CH$_2$), 48.9 (CH$_2$), 39.2 (CH$_3$), 29.9 (CH$_2$). $^{19}$F NMR (376 MHz, CDCl$_3$, 20° C.) δ. –138.54. HRMS (+ESI) calculated for C$_{19}$H$_{18}$FN$_3$O (M+H$^+$): 324.1505; found: 324.1504.

Example 62: (1-(2-((4-((5-fluoro-1H-pyrrolo[2,3-b]pyridin-2-yl)ethynyl)phenyl)(methyl)amino)ethyl)-1H-1,2,3-triazol-4-yl)methanol 167

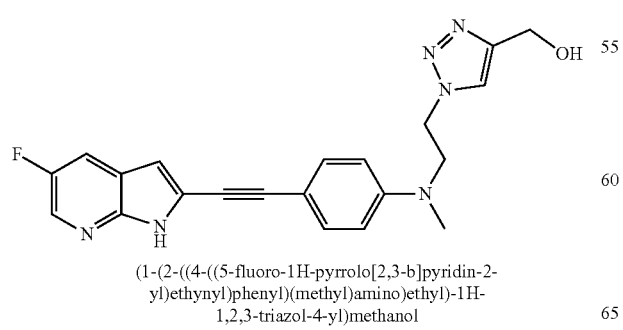

(1-(2-((4-((5-fluoro-1H-pyrrolo[2,3-b]pyridin-2-yl)ethynyl)phenyl)(methyl)amino)ethyl)-1H-1,2,3-triazol-4-yl)methanol (1-(2-((4-((5-fluoro-1H-pyrrolo[2,3-b]pyridin-2-yl)ethynyl)phenyl)(methyl)amino)ethyl)-1H-1,2,3-triazol-4-yl) methanol 167 was synthesized in 10 steps. Initially, the corresponding alkyne 168 was prepared in 8 steps from 1,4-dibromobenzene and then the Sonogashira reaction with azaindole followed by a deprotection reaction allowed to obtain the final compound.

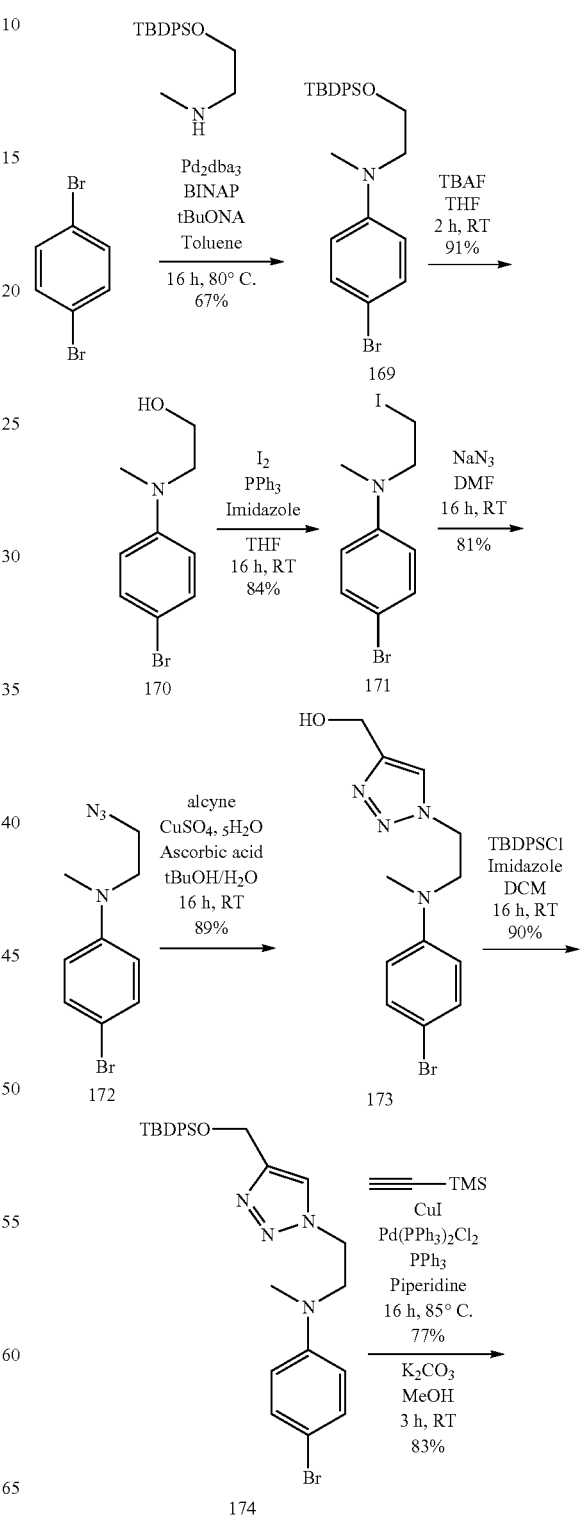

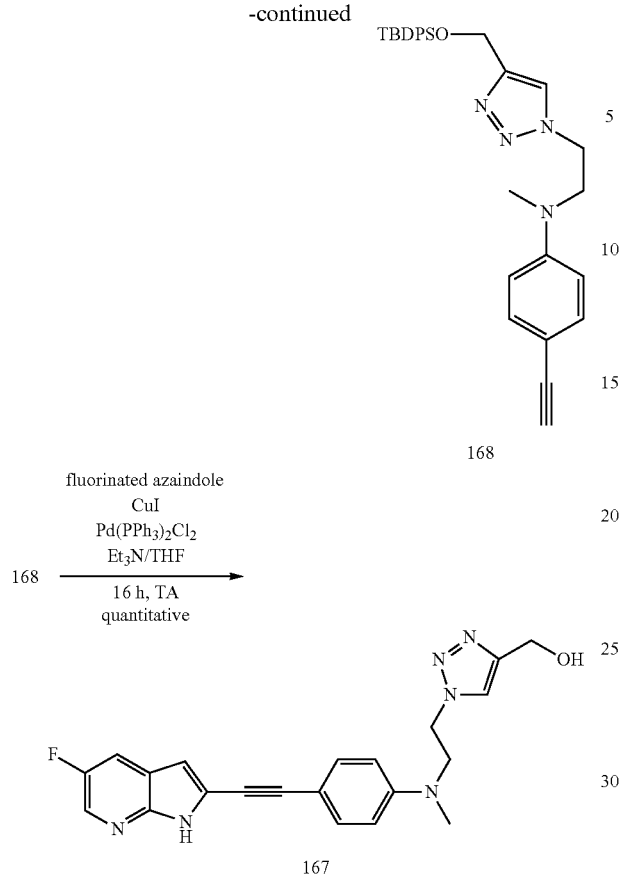

Example 62.1 Synthesis of 4-bromo-N-(2-((tert-butyldiphenylsilyl)oxy)ethyl)-N-methylaniline 169

Compound 169 was prepared according to procedure H and purified by column flash chromatography on silica gel (ethyl acetate/petroleum ether=5/45). Orange oil (67%). Rf=0.65 (ethyl acetate/petroleum ether=1/49). IR (v, cm$^{-1}$, neat) 2929, 2855, 1588, 1496, 1471, 1427, 1356, 1314, 1253, 1218, 1190, 1141, 1105, 1079, 1045, 997, 936. $^1$H NMR (400 MHz, CDCl$_3$, 20° C.) δ 7.69 (d, J=7.2 Hz, 4H), 7.42 (m, 6H), 7.29 (m, 2H), 6.62 (d, J=8.5 Hz, 2H), 3.73 (t, J=7.3 Hz, 2H), 3.49 (t, J=7.3 Hz, 2H), 2.91 (s, 3H), 1.11 (s, 9H). $^{13}$C NMR (101 MHz, CDCl$_3$, 20° C.) δ 148.3 (Cq), 135.6 (4×CH), 133.7 (2×Cq), 131.7 (2×CH), 129.7 (2×CH), 127.7 (4×CH), 113.8 (2×CH), 107.7 (Cq) δ0.8 (CH$_2$), 54.5 (CH$_2$), 38.3 (CH$_3$), 26.9 (3×CH$_3$), 19.2 (Cq). HRMS (+ESI) calculated for C$_{25}$H$_{30}$BrNOSi (M+): 468.1352, found: 468.1353.

Example 62.2 Synthesis of 2-((4-bromophenyl)(methyl)amino)ethan-1-ol 170

Compound 170 was prepared according to procedure E and purified by flash column chromatography on silica gel (methanol/dichloromethane=4/96). Colorless oil (91%). $^1$H NMR (400 MHz, CDCl$_3$) δ 7.30 (d, J=8.3 Hz, 2H), 6.75-6.53 (d, J=8.3 Hz, 2H), 3.80 (m, 2H), 3.45 (m, 2H), 2.94 (s, 3H). CAS Number: 252949-11-4.

Example 62.3 Synthesis of 4-bromo-N-(2-iodoethyl)-N-methylaniline 171

Under argon, 400 mg of 2-((4-bromophenyl) (methyl) amino)ethan-1-ol 170 (1.74 mmol, 1 0.0 eq) were dissolved in 18 ml of THF. At 0° C., 190 mg of imidazole (2.80 mmol, 1.6 eq.), 616 mg of triphenylphosphine (2.35 mmol, 1.35 eq.) and 574 mg of iodine (2.26 mmol, 1.3 eq.) were added. After 5 minutes at 0° C., the reaction mixture is brought to room temperature. 'I After 6 h stirring, 30 ml of saturated thiosulfate solution is added. The organic phase was extracted with ethyl acetate (3×30 ml). The organic phases are combined and washed with a saturated NaCl solution and then dried over MgSO$_4$ filtered through cotton and evaporated to dryness. The crude was purified by flash column chromatography on silica gel (ethyl acetate/petroleum ether=2/98) to obtain compound 171 (497 mg, 84%) as a colorless oil. Rf=0.9 (ethyl acetate/petroleum ether=20/80). IR (v, cm$^{-1}$, neat) 2873, 2820, 1588, 1492, 1427, 1369, 1339, 1311, 1289, 1269, 1216, 1169, 1109, 1089, 971. $^1$H NMR (400 MHz, CDCl$_3$, 20° C.) δ 7.31 (d, J=9.0 Hz, 2H), 6.56 (d, J=9.0 Hz, 2H), 3.73-3.65 (m, 2H), 3.23-3.17 (m, 2H), 2.96 (s, 3H). $^{13}$C NMR (101 MHz, CDCl$_3$, 20° C.) δ 146.9 (Cq), 132.1 (2×CH), 113.7 (2×CH), 109.0 (Cq), 55.5 (CH$_2$), 38.4 (CH$_3$), 1.8 (CH$_2$). HRMS (+ESI) calculated for C$_9$H$_{11}$IBrN (M+H$^+$): 341.9172, found: 341.9170.

Example 62.4 Synthesis of N-(2-azidoethyl)-4-bromo-N-methylaniline 172

Under argon, 460 mg of 4-bromo-N-(2-iodoethyl)-N-methyl aniline 171 (1.35 mmol, 1.0 eq.) are dissolved in 5 ml of DMF. Then, 102 mg of azide (1.62 mmol, 1.2 eq.) were added. After 16 h stirring at room temperature, 30 ml of H$_2$O are added. The organic phase was extracted with ethyl acetate (3×30 ml). The organic phases are combined and washed with a saturated NaCl solution and then dried over MgSO$_4$, filtered through cotton and evaporated to dryness. The crude was purified by flash column chromatography on silica gel (ethyl acetate/petroleum ether=4/96) to afford compound 171 (280 mg, 81%) as a colorless oil. Rf=0.85 (ethyl acetate/petroleum ether=10/90). IR (v, cm$^{-1}$, neat) 3292, 2940, 2870, 1594, 1570, 1494, 1480, 1435, 1370, 1155, 1003, 822. $^1$H NMR (400 MHz, CDCl$_3$, 20° C.) δ 7.34 (d, J=9.0 Hz, 2H), 6.62 (d, J=9.0 Hz, 2H), 3.54 (t, J=5.8 Hz, 2H), 3.47 (t, J=5.8 Hz, 2H), 3.00 (s, 3H). $^{13}$C NMR (101 MHz, CDCl$_3$, 20° C.) δ 147.6 (Cq), 132.0 (2×CH), 113.9 (2×CH), 109.0 (Cq), 55.5 (CH$_2$), 48.7 (CH$_2$), 38.9 (CH$_3$). HRMS (+ESI) calculated for C$_9$H$_{11}$BrN$_4$ (M): 255.0239, found: 255.0238.

Example 62.5 Synthesis of (1-(2-((4-bromophenyl)(methyl)amino)ethyl)-1H-1,2,3-triazol-4-yl)methanol 173

Under argon, 240 mg of N-(2-azidoethyl)-4-bromo-N-methylaniline 170 (0.94 mmol, 1.0 eq.) are dissolved in 1 ml of t-butanol/water (2/1). At room temperature, 0.055 ml of propargyl alcohol (0.94, 1.0 eq.), 25 mg of CuSO$_4$, 5H$_2$O (0.094 mmol, 0.1 eq.) and 19 mg of sodium ascorbate (0.094 mmol, 0.1 eq.) were added. After 16 h of stirring, 30 ml of water are added. The organic phase is extracted with dichloromethane (3×30 ml). The organic phases are combined and washed with a saturated NaCl solution and then dried over MgSO$_4$, filtered through cotton and evaporated to dryness. The crude was purified by flash column chromatography on silica gel (methanol/dichloromethane=4/96) to afford compound 173 (260 mg, 89%) as a colorless oil. Rf=0 (ethyl acetate/petroleum ether=20/80). IR (v, cm$^{-1}$, neat) 2873, 1588, 1494, 1449, 1430, 1355, 1314, 1255, 1215, 1191, 1141, 1113, 1079, 1038, 1009, 959. $^1$H NMR (250 MHz, CDCl$_3$, 20° C.) δ 7.33 (m, 3H), 6.48 (d, J=9.0 Hz, 2H), 6.5 (s, 2H), 3.73-3.65 (m, 2H), 3.23-3.17 (m, 2H), 2.76 (s, 3H). $^{13}$C NMR (63 MHz, CDCl$_3$, 20° C.) δ 147.9 (Cq), 147.1 (Cq), 132.1 (2×CH), 122.6 (CH), 113.7 (2×CH), 109.0 (Cq), 56.5 (CH$_2$), 53.0 (CH$_2$), 47.5 (CH$_2$), 38.8 (CH$_3$).

Example 62.6 Synthesis of 4-bromo-N-(2-(4-(((tert-butyldiphenylsilyl)oxy)methyl)-1H-1,2,3-triazol-1-yl)ethyl)-N-methylaniline 174

Under argon, the (1-(2-((4-bromophenyl) (methyl)amino) ethyl)-1H-1,2,3-triazol-4-yl)methanol 173 (735 mg, 2.35 mmol, 1.0 eq.) is dissolved in 50 ml of DCM. At 0° C., 0.7 ml of TBDPSCl (2.82 mmol, 1.2 eq.)), and 192 mg of imidazole (2.80 mmol, 1.2 eq.) were added. After 5 minutes at 0° C., the reaction mixture is brought to room temperature. After 16 h of stirring, 30 ml of water is added. The organic phase is extracted with dichloromethane (3×30 ml). The organic phases are combined and washed with a saturated NaCl solution and then dried over MgSO$_4$, filtered through cotton and evaporated to dryness. The crude was purified by flash column chromatography on silica gel (ethyl acetate/petroleum ether=20/80) to obtain compound 174 (1.2 g, 90%) as a colorless oil. Rf=0.25 (ethyl acetate/petroleum ether=20/80). IR (v, cm$^{-1}$, neat) 2929, 2855, 1588, 1496, 1471, 1427, 1356, 1314, 1253, 1218, 1190, 1141, 1105, 1079, 1045, 997, 936. $^1$H NMR (250 MHz, CDCl$_3$, 20° C.) δ 7.65 (d, J=6.5 Hz, 4H), 7.48-7.27 (m, 8H), 7.19 (s, 1H), 6.49 (d, J=9.0 Hz, 2H), 4.85 (s, 2H), 4.51 (t, J=6.1 Hz, 2H), 3.81 (t, J=6.1 Hz, 2H), 2.73 (s, 3H), 1.05 (s, 9H). $^{13}$C NMR (63 MHz, CDCl$_3$, 20° C.) δ 148.4 (Cq), 147.0 (Cq), 135.5 (4×CH), 133.2 (2×Cq), 132.1 (2×CH), 129.8 (2×CH), 127.8 (4×CH), 122.6 (CH), 113.8 (2×CH), 109.4 (Cq), 58.53 (CH$_2$), 53.0 (CH$_2$), 47.3 (CH$_2$), 38.8 (CH$_3$), 26.8 (3×CH$_3$), 19.2 (Cq). HRMS (+ESI) calculated for C$_{28}$H$_{33}$BrN$_4$OSi (M+H$^+$): 551.1660, found: 551.1664.

Example 62.7 Synthesis of N-(2-(4-(((tert-butyldiphenylsilyl)oxy)methyl)-1H-1,2,3-triazol-1-yl)ethyl)-4-ethynyl-N-methylaniline 168

The alkyne 168 was prepared according to procedure 12 and purified by flash chromatographie column on silica gel (ethyl acetate/petroleum ether=30/70). Brown oil (38% over two steps). Rf=0.55 (ethyl acetate/petroleum ether=40/60). IR (v, cm$^{-1}$, neat) 3280, 2928, 2930, 2855, 2098, 1606, 1514, 1459, 1426, 1375, 1355, 1273, 1256, 1220, 1174, 1141. $^1$H NMR (250 MHz, CDCl$_3$, 20° C.) δ 7.65 (d, J=6.5 Hz, 4H), 7.48-7.27 (m, 8H), 7.18 (s, 1H), 6.55 (d, J=9.0 Hz, 2H), 4.85 (s, 2H), 4.50 (t, J=6.1 Hz, 2H), 3.86 (t, J=6.1 Hz, 2H), 2.76 (s, 1H), 2.76 (s, 3H), 1.05 (s, 9H). $^{13}$C NMR DEPT (63 MHz, CDCl$_3$, 20° C.) δ 135.5 (4×CH), 133.6 (2×CH), 129.8 (2×CH), 127.8 (4×CH), 122.6 (CH), 111.6 (2×CH), 75.3 (CH), 58.5 (CH$_2$), 52.7 (CH$_2$), 47.3 (CH$_2$), 38.8 (CH$_3$), 26.8 (3×CH$_3$), 19.2 (Cq). HRMS (+ESI) calculated for C$_{30}$H$_{34}$N$_4$OS (M+H$^+$): 495.2573, found: 495.2575.

Example 62.8 Synthesis of (1-(2-((4-((5-fluoro-1H-pyrrolo[2,3-b]pyridin-2-yl)ethynyl)phenyl)(methyl)amino)ethyl)-1H-1,2,3-triazol-4-yl)methanol 167

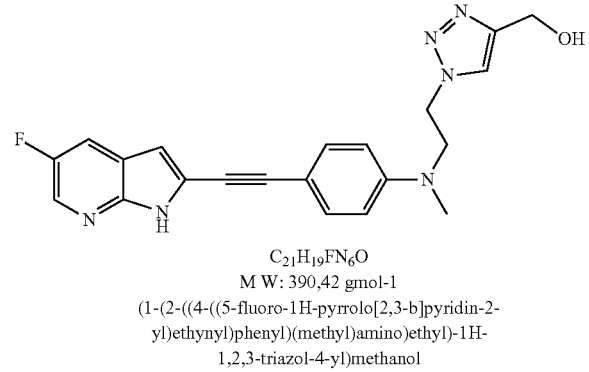 [SMILES: CN(CCn1cc(CO)nn1)c1ccc(C#Cc2cc3cc(F)cnc3[nH]2)cc1]

C$_{21}$H$_{19}$FN$_6$O
M W: 390,42 gmol-1
(1-(2-((4-((5-fluoro-1H-pyrrolo[2,3-b]pyridin-2-yl)ethynyl)phenyl)(methyl)amino)ethyl)-1H-1,2,3-triazol-4-yl)methanol Compound 167 was prepared according to procedure C2 followed by procedure E and purified by flash column chromatography on silica gel (methanol/dichloromethane=4/96). Yellow solid (74% over 2 steps), Rf=0.30 (methanol/dichloromethane=4/96). mp=222-224° C. IR (v, cm$^{-1}$, neat) 3311, 3121, 2901, 2202, 1605, 1585, 1540, 1508, 1475, 1448, 1431, 1378, 1357, 1323, 1291, 1257, 1231, 1185, 1156, 1109, 1073, 1052, 1036, 1012, 983, 965, 937, 869. $^1$H NMR (400 MHz, DMSO-d$_6$, 20° C.) δ 12.22 (s, 1H), 8.22 (s, 1H), 7.99 (s, 1H), 7.80 (dd, J=8.8, 2.8 Hz, 1H), 7.37 (d, J=8.8 Hz, 2H), 6.72 (m, 3H), 5.14 (t, J=5.6 Hz, 1H), 4.52 (m, 4H), 3.85 (t, J=6.2 Hz, 2H), 2.79 (s, 3H). $^{13}$C NMR (63 MHz, DMSO-d6, 20° C.) δ 155.6 (d, J=239.4 Hz, Cq), 149.3 (Cq), 148.6 (Cq), 145.63 (Cq), 133.0 (2×CH), 132.6 (d, J=27.4 Hz, CH), 123.6 (CH), 122.9 (Cq), 120.4 (d, J=7.5 Hz, Cq), 113.7 (d, J=20.8 Hz, CH), 112.2 (2×CH), 108.7 (Cq), 105.9 (d, J=4.0 Hz, CH), 95.3 (Cq), 80.0 (Cq), 55.5 (CH$_2$), 52.01 (CH$_2$), 47.1 (CH$_2$), 39.2 (CH$_3$). $^{19}$F NMR (376 MHz, CDCl$_3$, 20° C.) δ. -138.54. HRMS (+ESI) calculated for C$_{21}$H$_{19}$FN$_6$O (M+H$^+$): 391.1675, found: 391.1677.

Example 63: 4-((3-((dimethylamino)methyl)-1H-pyrrolo[2,3-b]pyridin-2-yl)ethynyl)-N-(2-fluoroethyl)-N-methylaniline 175

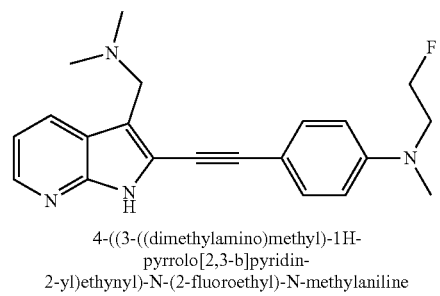 [SMILES: CN(C)Cc1c(C#Cc2ccc(N(C)CCF)cc2)[nH]c2ncccc12]

4-((3-((dimethylamino)methyl)-1H-pyrrolo[2,3-b]pyridin-2-yl)ethynyl)-N-(2-fluoroethyl)-N-methylaniline 4-((3-((dimethylamino)methyl)-1H-pyrrolo[2,3-b]pyridin-2-yl)ethynyl)-N-(2-fluoroethyl)-N-methylaniline 175 was synthesized in 2 steps. Initially, the azaindole 176 is obtained by the Mannich reaction followed by the Sonogoshira reaction to obtain the desired final compound

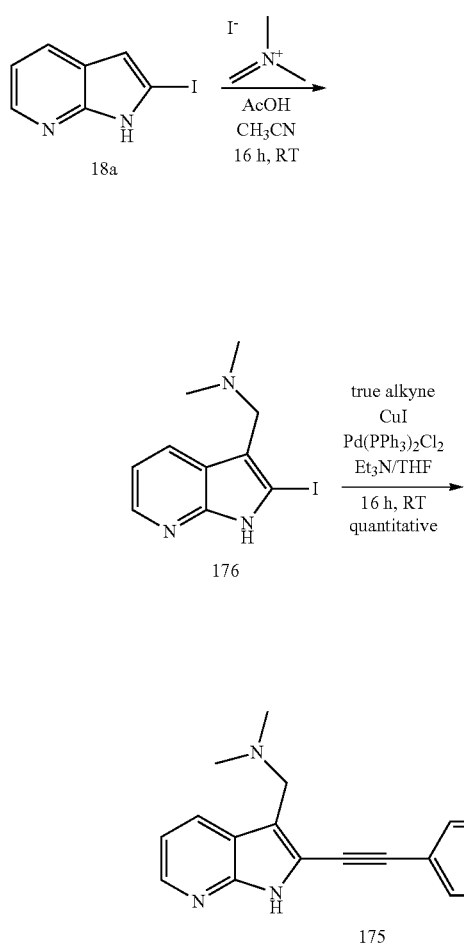

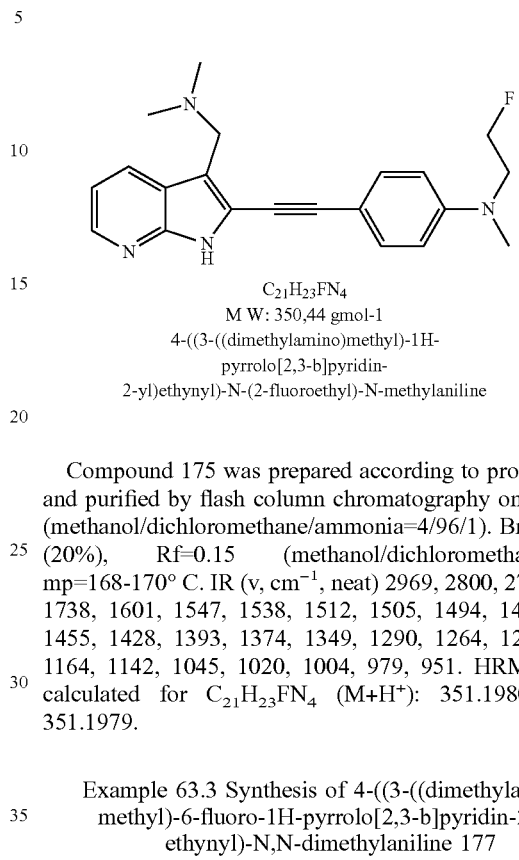

C$_{21}$H$_{23}$FN$_4$
M W: 350,44 gmol-1
4-((3-((dimethylamino)methyl)-1H-
pyrrolo[2,3-b]pyridin-
2-yl)ethynyl)-N-(2-fluoroethyl)-N-methylaniline

Example 63.1 Synthesis of 1-(2-iodo-1H-pyrrolo[2,3-b]pyridin-3-yl)-N,N-dimethylmethanamine 176

In a vial, 2-iodo-1H-pyrrolo[2,3-b] pyridine 18a (200 mg, 0.82 mmol, 1 eq.) was dissolved in 8 ml of acetonitrile. Then 0.4 ml of acetic acid followed by 182 mg of Eschenmoser's salt (0.98 mmol, 1.2 eq.) were added. After sealing the vial, the reaction mixture is stirred for 20 h at room temperature. 15 ml of a 2M solution of potassium hydroxide is added slowly and then the organic phase was extracted with ethyl acetate (3×20 ml). The organic phases are combined and then dried over MgSO$_4$, filtered through cotton and evaporated to dryness. Finally, the crude is triturated with pentane and then vacuum filtered to obtain compound 174 (190 mg, 77%) as a yellow solid. Rf=0.10 (methanol/dichloromethane=2/98) mp=142-144° C. IR (v, cm$^{-1}$, neat) 2957, 2932, 2851, 2812, 2768, 1603, 1580, 1514, 1489, 1448, 1407, 1369, 1354, 1328, 1287, 1273, 1248, 1206, 1167, 1147, 1121, 1094, 1036, 1004, 978, 905, 842. $^1$H NMR (400 MHz, CDCl$_3$, 20° C.) δ 13.08 (s1, 1H), 8.41 (dd, J=4.9, 1.4 Hz, 1H), 8.09 (dd, J=7.9, 1.4 Hz, 1H), 7.11 (dd, J=7.9, 4.8 Hz, 1H), 3.60 (s 2H), 2.33 (s, 6H). $^{13}$C NMR (101 MHz, CDCl$_3$, 20° C.) δ 151.0 (Cq), 142.0 (CH), 127.4 (CH), 121.3 (Cq), 116.7 (Cq), 115.8 (CH), 82.9 (Cq) 56.1 (CH$_2$), 45.4 (2×CH$_3$). HRMS (+ESI) calculated for C$_{10}$H$_{12}$IN$_3$ (M+H$^+$): 302.0148, found: 302.0148.

Example 63.2 Synthesis of 4-((3-((dimethylamino)methyl)-1H-pyrrolo[2,3-b]pyridin-2-yl)ethynyl)-N-(2-fluoroethyl)-N-methylaniline 175

Compound 175 was prepared according to procedure C2 and purified by flash column chromatography on silica gel (methanol/dichloromethane/ammonia=4/96/1). Brown solid (20%), Rf=0.15 (methanol/dichloromethane=4/96). mp=168-170° C. IR (v, cm$^{-1}$, neat) 2969, 2800, 2755, 2358, 1738, 1601, 1547, 1538, 1512, 1505, 1494, 1470, 1463, 1455, 1428, 1393, 1374, 1349, 1290, 1264, 1216, 1187, 1164, 1142, 1045, 1020, 1004, 979, 951. HRMS (+ESI) calculated for C$_{21}$H$_{23}$FN$_4$ (M+H$^+$): 351.1980; found: 351.1979.

Example 63.3 Synthesis of 4-((3-((dimethylamino)methyl)-6-fluoro-1H-pyrrolo[2,3-b]pyridin-2-yl)ethynyl)-N,N-dimethylaniline 177

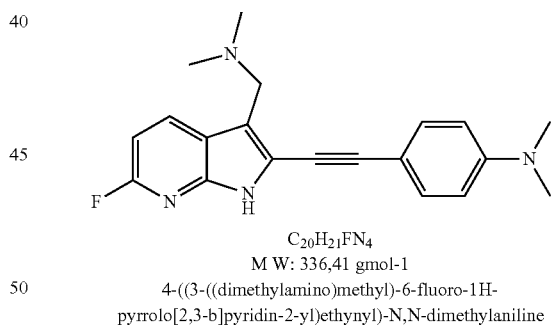

C$_{20}$H$_{21}$FN$_4$
M W: 336,41 gmol-1
4-((3-((dimethylamino)methyl)-6-fluoro-1H-
pyrrolo[2,3-b]pyridin-2-yl)ethynyl)-N,N-dimethylaniline Compound 177 was prepared according to procedure C2 and purified by flash column chromatography on silica gel (methanol/dichloromethane/ammonia=4/96/1). Greenish solid (36%), Rf=0.25 (methanol/dichloromethane=4/96). mp=182-184° C. IR (v, cm$^{-1}$, neat) 3157, 3072, 2893, 2205, 1605, 1541, 1511, 1432, 1273, 1224, 1183, 809, 763, 507. $^1$H NMR (400 MHz, CDCl$_3$, 20° C.) 9.42 (s, 1H), 8.09 (t, J=8.0 Hz, 1H), 7.45 (d, J=8.7 Hz, 2H), 6.71 (m, 3H), 3.76 (s, 2H), 3.03 (s, 6H), 2.35 (s, 6H). $^{13}$C NMR (101 MHz, DMSO-d6, 20° C.) δ 161.0 (d, J=238.0 Hz, Cq), 150.5 (Cq), 144.7 (d, J=18.3 Hz, CH), 132.7 (2×CH), 132.5 (d, J=9.3 Hz, Cq)), 119.40 (d, J=4.4 Hz, Cq), 118.13 (d, J=2.7 Hz, Cq), 116.2 (Cq), 111.8 (2×CH), 108.8 (Cq), 101.82 (d, J=37.8 Hz, CH), 97.7 (Cq), 78.0 (Cq), 54.1 (CH$_2$), 45.4 (2×CH$_3$), 40.2

(2×CH$_3$). $^{19}$F NMR (376 MHz, DMSO-d6, 20° C.) δ. −76.0. HRMS (+ESI) calculated for C$_{20}$H$_{21}$FN$_4$ (M+H$^+$): 337.1823; found: 337.1822.

Example 64: 4-((3-((dimethylamino)methyl)-5-fluoro-1H-pyrrolo[2,3-b]pyridin-2-yl)ethynyl)-N,N-dimethylaniline 179

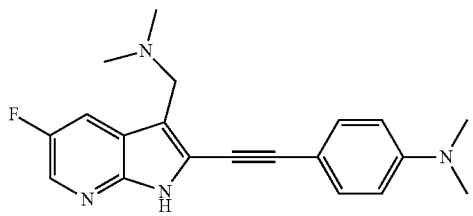

4-((3-((dimethylamino)methyl)-5-fluoro-1H-pyrrolo[2,3-b]pyridin-2-yl)ethynyl)-N,N-dimethylaniline 4-((3-((dimethylamino)methyl)-5-fluoro-1H-pyrrolo[2,3-b]pyridin-2-yl)ethynyl)-N,N-dimethylaniline 179 was synthesized in 2 steps. Initially, the azaindole 180 is obtained by the Mannich reaction followed by the Sonogoshira reaction to obtain the desired final compound

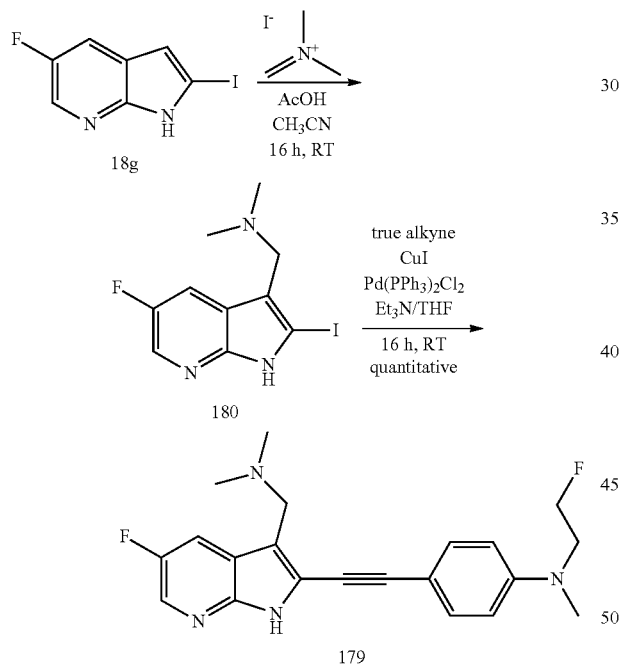

Example 64.1 Synthesis of 1-(5-fluoro-2-iodo-1H-pyrrolo[2,3-b]pyridin-3-yl)-N,N-dimethylmethanamine 180

In a vial, 5-fluoro-2-iodo-1H-pyrrolo[2,3-b] pyridine 18 g (200 mg, 0.82 mmol, 1 eq.) was dissolved in 8 ml of acetonitrile. Then 0.4 ml of acetic acid, followed by 182 mg of salt of Esclienmoser (0.98 mmol, 1.2 eq.) were added. After sealing the vial, the reaction mixture is stirred for 20 h at room temperature. 15 ml of a 2M solution of potassium hydroxide is added slowly and then the organic phase was extracted with ethyl acetate (3×20 ml). The organic phases are combined and then dried over MgSO$_4$, filtered through cotton and evaporated to dryness. Finally, the crude is triturated with pentane and then vacuum filtered to obtain compound 180 (180 mg, 77%) as a brown solid. Rf=0.10 (methanol/dichloromethane=2/98). mp=180-182° C. IR (v, cm$^{-1}$, neat) 2934, 2857, 2818, 2773, 2703, 1491, 152, 1395, 1368, 1333, 1322, 1295, 1261, 1250, 1218, 1183, 1168, 1146, 1068, 1006, 951, 871, 842. $^1$H NMR (250 MHz, CDCl$_3$, 20° C.) δ 8.21 (s, 1H), 7.77 (dd, J=8.9, 2.4 Hz, 1H), 3.50 (s, 2H), 2.26 (s, 6H). $^{13}$C NMR (250 MHz, CDCl$_3$, 20° C.) δ 155.34 (d, J=242.4 Hz, Cq), 147.8 (Cq), 130.6 (d, J=30.2 Hz, CH), 121.02 (d, J=7.0 Hz, Cq), 117.10 (d, J=4.2 Hz, Cq), 113.27 (d, J=21.0 Hz, CH), 84.4 (Cq) 56.3 (CH$_2$), 45.4 (2×CH$_3$). $^{19}$F NMR (235 MHz, CDCl$_3$, 20° C.) δ. −138.0. HRMS (+ESI) calculated for C$_{10}$H$_{12}$FIN$_3$ (M+H$^+$): 320.0054, found: 320.0054.

Example 64.2 Synthesis of 4-((3-((dimethylamino)methyl)-5-fluoro-1H-pyrrolo[2,3-b]pyridin-2-yl)ethynyl)-N,N-dimethylaniline 179

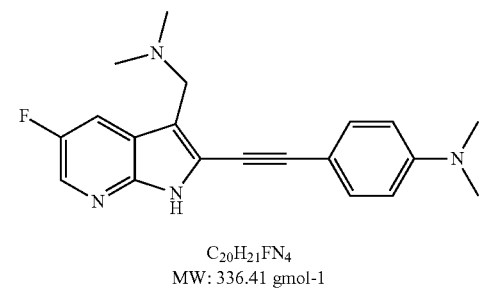 [SMILES: CN(C)Cc1c(C#Cc2ccc(N(C)C)cc2)[nH]c2ncc(F)cc12]

C$_{20}$H$_{21}$FN$_4$
MW: 336.41 gmol-1

Compound 177 was prepared according to procedure C2 and purified by flash column chromatography on silica gel (methanol/dichloromethane/ammonia=4/96/1). Brown solid (28%), Rf=0.25 (methanol/dichloromethane=4/96). mp=188-190° C. IR (v, cm$^{-1}$, neat) 2933, 2875, 2851, 2766, 2766, 2708, 1604, 1587, 1574, 1539, 1515, 1494, 1462, 1455, 1445, 1397, 1368, 1355, 1334, 1307, 1283, 1224, 1166, 1126, 1116, 1090, 1017, 982, 949, 906, 863507. $^1$H NMR (250 MHz, CDCl$_3$, 20° C.) δ 9.89 (s, 1H), 8.20 (m, 1H), 7.75 (dd, J=8.9, 2.7 Hz, 1H), 7.44 (d, J=8.9 Hz, 2H), 6.68 (d, J=8.9 Hz, 2H), 3.72 (s, 2H), 3.02 (s, 6H), 2.32 (s, 6H). $^{19}$F NMR (376 MHz, CDCl$_3$, 20° C.) δ. −138.0. HRMS (+ESI) calculated for C$_{20}$H$_{21}$FN$_4$ (M+H$^+$): 337.1823; found: 337.1822.

Example 65: N-(2-fluoroethyl)-N-methyl-4-((3-methyl-1H-pyrrolo[2,3-b]pyridin-2-yl)ethynyl)aniline 181

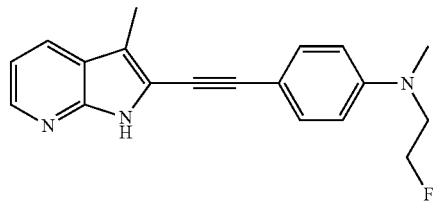

N-(2-fluoroethyl)-N-methyl-4-((3-methyl-1H-pyrrolo[2,3-b]pyridin-2yl)ethynyl)aniline N-(2-fluoroethyl)-N-methyl-4-((3-methyl-1H-pyrrolo[2,3-b]pyridin-2-yl)ethynyl)aniline 179 was synthesized in 6 steps. Initially, the azaindole 182 is obtained by five successive steps starting from 7-azaindole and the last step consists of the Sonogoshira reaction with alkyne to give the expected final compound

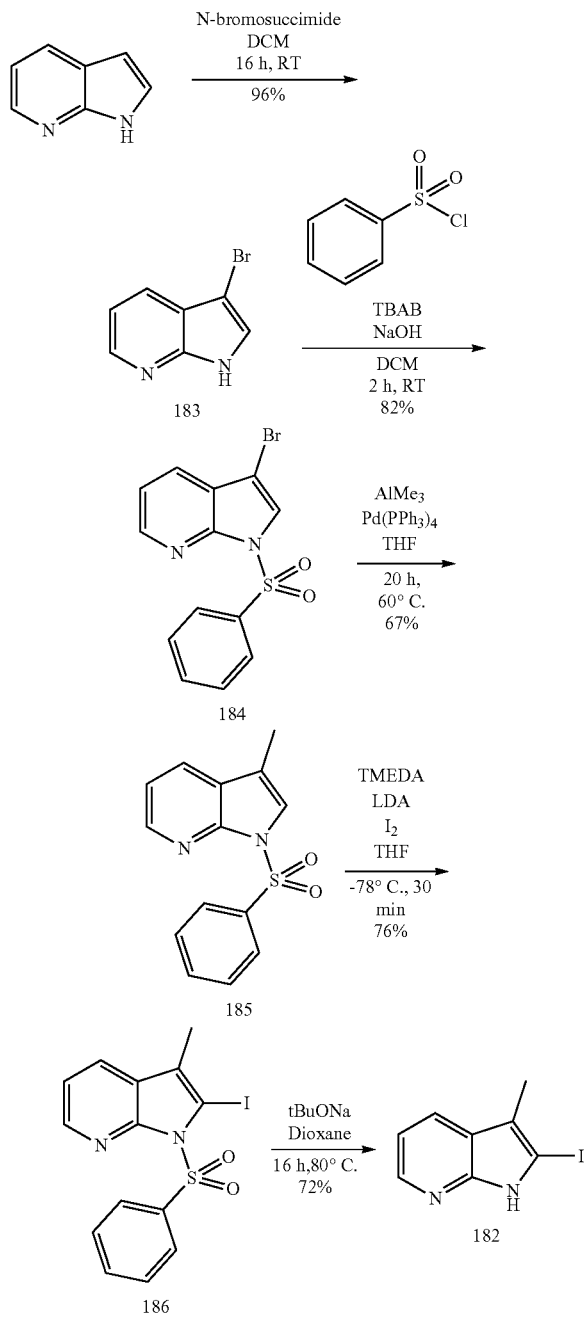

Example 65.1 Synthesis of 3-bromo-1H-pyrrolo[2,3-b]pyridine 183

At room temperature, N-bromosuccimide (1.65 g, 9.31 mmol, 1.1 eq.) was added on the 7-azaindole (1 g, 8.46 mmol, 1 eq.) dissolved in 20 ml of DCM. After 16 h stirring at room temperature, a saturated aqueous NaHCO$_3$ (20 ml) was added. The aqueous phase is extracted with dichloromethane (2 times). Then the combined organic phases were dried over MgSO$_4$ and concentrated under reduced pressure. The crude is purified by flash column chromatography on silica gel (ethyl acetate/petroleum ether=1/1) to obtain the compound 183 (1.6 g, 96%) as a brown solid. $^1$H NMR (400 MHz, DMSO-d$_6$, 20° C.) δ 11.45 (br, 1H), 8.38 (dd, J=5.1, 1.2 Hz, 1H), 8.06 (dd, J=7.8, 1.2 Hz, 1H), 7.48 (s, 1H), 7.28 (dd, J=7.8, 5.1 Hz, 1H). CAS Number: 74420-15-8.

Example 65.2 Synthesis of 3-bromo-1-(phenylsulfonyl)-1H-pyrrolo[2,3-b]pyridine 184

Under argon, 1 g of 3-bromo-1H-pyrrolo[2,3-b]pyridine 184 (5.07 mmol, 1.0 eq.) was dissolved in 30 ml of DCM. At room temperature, 49 mg of TBAB (0.15 mmol, 0.03 eq.) and 608 mg of iodine (15.21 mmol, 3.0 eq.) were added. Then, the reaction mixture was placed at 0° C. and then 0.81 ml of benzosulfonyle chloride was added dropwise. After 2 h of stirring at room temperature, 30 ml of water are added. The organic phases were extracted with dichloromethane (3×30 ml). The organic phases are combined and washed with a saturated NaCl solution and then dried over MgSO$_4$, filtered through cotton and evaporated to dryness. The crude product is triturated with diethyl ether to obtain compound 184 (1.4 g, 82%) as an orange solid. $^1$H NMR (400 MHz, CDCl$_3$, 20° C.) δ 8.48 (dd, J=4.8, 1.5 Hz, 1H), 8.24-8.17 (m, 2H), 7.82 (dd, J=8.0, 1.5 Hz, 1H), 7.79 (s, 1H), 7.60 (dd, J=7.5 Hz, 1H), 7.54-7.46 (m, 2H), 7.27 (m, 1H). CAS Number: 880769-95-9.

Example 65.3 Synthesis of 3-methyl-1-(phenylsulfonyl)-1H-pyrrolo[2,3-b]pyridine 185

3-bromo-1-(phenylsulfonyl)-1H-pyrrolo[2,3-b]pyridine 184 (500 mg, 1.48 mmol) was dissolved in THF (10 ml) under argon. After degassing 10 minutes, Pd(PPh$_3$) (85 mg, 0.074 mmol, 0.05 eq.) was then added and this is followed by addition of a solution of trimethylaluminium in toluene (2M, 1.48 ml, 2.96 mmol, 2.0 eq.) dropwise. Then the mixture is heated at 60° C. for 20 h. After cooling, 30 ml of a saturated solution of NaHCO$_3$ are added dropwise. The organic phase was extracted with ethyl acetate (3×30 ml). The organic phases are combined and washed with saturated NaCl solution and then dried over MgSO$_4$, filtered through cotton and evaporated to dryness. The crude was purified by flash column chromatography on silica gel (ethyl acetate/petroleum ether=20/80) to obtain compound 185 (270 g, 67%) as a yellowish solid. $^1$H NMR (400 MHz, CDCl$_3$, 20° C.) δ 11.45 (br, 1H), 8.38 (dd, J=5.1, 1.2 Hz, 1H), 8.06 (dd, J=7.8, 1.2 Hz, 1H), 7.48 (s, 1H), 7.28 (dd, J=7.8, 5.1 Hz, 1H), 2.32 (s, 3H). Reaxys Number: 28959361.

Example 65.4 Synthesis of 2-iodo-3-methyl-1-(phenylsulfonyl)-1H-pyrrolo[2,3-b]pyridine 186

Under an argon atmosphere, at a solution of 3-methyl-1-(phenylsulfonyl)-1H-pyrrolo[2,3-b]pyridine 185 (270 mg, 0.99 mmol, 1.0 eq.) and of TMEDA (0.163 ml, 1.09 mmol, 1.1 eq.) in THF (0.1 M), cooled to −78° C., was added a solution of LDA (2M in THF, 0.6 ml, 1.19 mmol, 1.2 eq.) drop by drop.

After 30 min, a solution of iodine (502.5 mg, 1.98 mmol, 2.0 eq.) in THF (0.5M) was slowly added via cannula to the reaction medium. After 30 min stirring at −78° C., 20 ml of water are added and the reaction medium is brought back to room temperature slowly. The organic phases were extracted with ethyl acetate (3 times 20 ml), combined, dried over MgSO$_4$, extruding and then concentrated under reduced pressure. The crude was purified by flash column chromatography on silica gel (ethyl acetate/petroleum ether=20/80) to obtain compound 186 (300 g, 76%) as a yellowish solid. Rf=0.10 (ethyl acetate/petroleum ether=20/80). mp=178-180° C. IR (v, cm$^{-1}$, neat) 2955, 2172, 2137, 2104, 2025, 1966, 1618, 1586, 1562, 1501, 1479, 1435, 1383, 1337, 1277, 1248, 1190, 1157, 1119, 1071, 1001, 973, 962, 933. $^1$H NMR (250 MHz, CDCl$_3$, 20° C.) δ 8.37 (d, J=4.3 Hz, 1H), 8.14 (d, J=7.3 Hz, 2H), 7.68 (dd, J=8.7, 0.8 Hz, 1H), 7.57-7.35 (m, 3H), 7.12 (dd, J=7.8, 4.8 Hz, 1H), 2.22 (s, 3H). $^{13}$C NMR (63 MHz, CDCl$_3$, 20° C.) δ 6 150.5 (Cq) 144.7 (CH), 138.8 (Cq), 133.9 (CH), 128.9 (2×CH), 127.9 (2×CH), 126.8 (CH), 125.2 (Cq), 123.3 (Cq), 119.1 (CH), 80.0 (Cq), 13.5 (CH$_3$). HRMS (+ESI) calculated for C$_{14}$H$_{11}$N$_2$O$_2$S (M+H$^+$): 398.9658, found: 398.9657.

Example 65.5 Synthesis of 2-iodo-3-methyl-1H-pyrrolo[2,3-b]pyridine 182

2-iodo-3-methyl-1-(phenylsulfonyl)-1H-pyrrolo[2,3-b]pyridine 186 (125 mg, 0.314 mmol, 1.0 eq.) was dissolved in 7 ml of dioxane. 45 mg of sodium t-butoxide (0.47 mmol, 1.5 eq.) were added. After 16 h at 80° C., the reaction medium was cooled to temperature and the solvent was evaporated under reduced pressure. The residue was dissolved in 30 ml ethyl acetate and 30 ml of water. Then, the organic phase is extracted with ethyl acetate (3 times). The combined organic phases were dried over MgSO$_4$ and concentrated under reduced pressure. The crude was purified by flash column chromatography on silica gel (ethyl acetate/petroleum ether=20/80) to obtain compound 182 (58 mg, 72%) as a yellowish solid. Rf=0.25 (ethyl acetate/petroleum ether=20/80). mp=188-190° C. IR (v, cm$^{-1}$, neat) 2707, 1580, 1455, 1405, 1381, 1336, 1325, 1281, 1205, 1130, 903, 784. $^1$H NMR (400 MHz, DMSO-d$_6$, 20° C.) δ 11.93 (s, 1H), 8.13 (dd, J=4.6, 0.8 Hz, 1H), 7.87 (dd, J=7.5, 0.8 Hz, 1H), 7.01 (dd, J=7.5, 4.6 Hz, 1H), 2.19 (s, 3H). $^{13}$C NMR (250 MHz, DMSO-d$_6$, 20° C.) δ 151.0 (Cq), 142.9 (CH), 126.0 (CH), 120.5 (Cq), 115.7 (CH), 114.9 (Cq), 83.4 (Cq), 11.9 (CH$_3$). HRMS (+ESI) calculated for C$_8$H$_7$IN$_2$ (M+H$^+$), found:

Example 65.6 Synthesis of N-(2-fluoroethyl)-N-methyl-4-((3-methyl-1H-pyrrolo[2,3-b]pyridin-2-yl)ethynyl)aniline 181

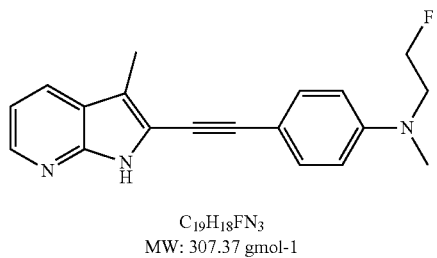 [SMILES: Cc1c(C#Cc2ccc(N(C)CCF)cc2)[nH]c2ncccc12]

C$_{19}$H$_{18}$FN$_3$
MW: 307.37 gmol-1

Compound 181 was prepared according to procedure C2 and purified by flash column chromatography on silica gel (ethyl acetate/petroleum ether=20/80). Yellowish solid (28%), Rf=0.25 (ethyl acetate/petroleum ether=20/80). mp=212-214° C. IR (v, cm$^{-1}$, neat) 3033, 2910, 2777, 2358, 2341, 2196, 1603, 1581, 1539, 1513, 1446, 1434, 1407, 1368, 1352, 1284, 1266, 1233, 1212, 1180, 1132, 1076, 1036, 976. $^1$H NMR (400 MHz, DMSO-d$_6$, 20° C.) δ 11.75 (s1, 1H), 8.29 (s1, 1H), 7.91 (d, J=7.8 Hz, 1H), 7.60 (s1, 1H), 7.39 (d, J=8.6 Hz, 2H), 7.07 (s1, 1H), 6.79 (d, J=8.6 Hz, 2H), 4.61 (dt, J=47.6, 5.0 Hz, 2H), 3.73 (dt, J=26.4, 5.0 Hz, 2H), 3.32 (s, 3H), 2.35 (s, 3H). $^{13}$C NMR (101 MHz, DMSO-d$_6$, 20° C.) δ 149.5 (Cq), 148.4 (Cq), 144.3 (Cq), 132.9 (2×CH), 131.9 (Cq), 129.1 (Cq), 127.0 (CH), 118.1 (Cq), 114.3 (CH), 112.4 (2×CH), 108.7 (CH), 97.4 (Cq), 83.2 (d, J=161.5 Hz, CH$_2$) 79.6 (Cq), 51.8 (d, J=19.8 Hz, CH$_2$), 38.9 (CH$_3$), 9.9 (CH$_3$). $^{19}$F NMR (376 MHz, DMSO-d$_6$, 20° C.) δ. −221.3. HRMS (+ESI) calculated for C$_{19}$H$_{18}$FN$_3$ (M+H+): 308.1557; found: 308.1558.

Example 66: N-(2-fluoroethyl)-N-methyl-4-((6-morpholino-1H-pyrrolo[2,3-b]pyridin-2-yl)ethynyl)aniline 187

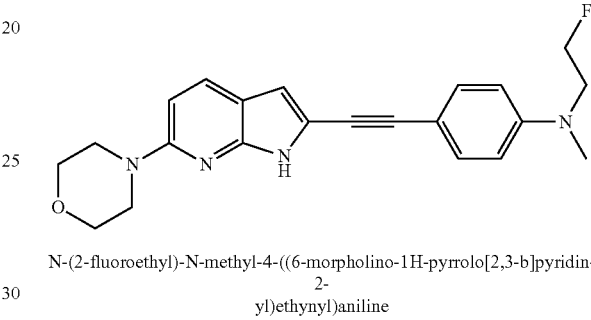

N-(2-fluoroethyl)-N-methyl-4-((6-morpholino-1H-pyrrolo[2,3-b]pyridin-2-yl)ethynyl)aniline N-(2-fluoroethyl)-N-methyl-4-((6-morpholino-1H-pyrrolo[2,3-b]pyridin-2-yl)ethynyl)aniline N-(2-fluoroethyl)-N-methyl-4-((6-morpholino-1H-pyrrolo[2,3-b]pyridin-2-yl)ethynyl)aniline 187 was synthesized in 4 steps. Initially, the alkyne 188 was obtained in two successive steps starting from 6-bromo-2-iodo-1H-pyrrolo[2,3-b]pyridine 18j and then followed by the Buchwald reaction with an amine. Finally, the deprotection reaction provided the expected final compound

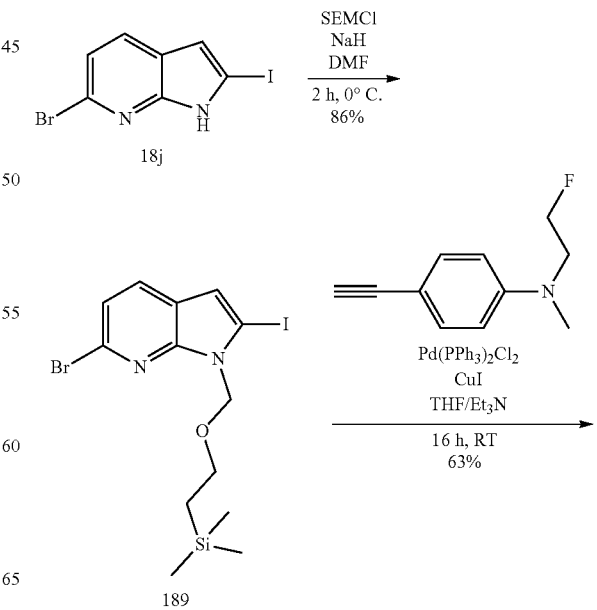

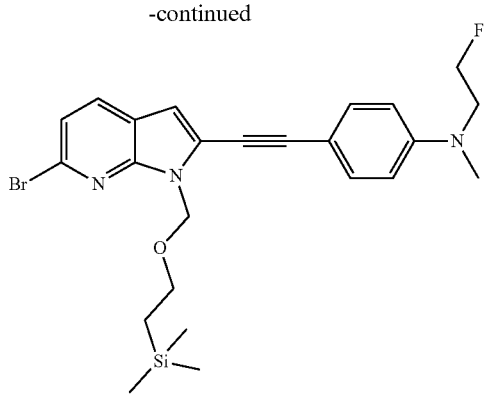

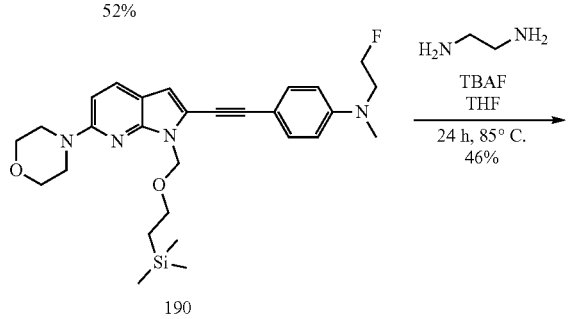

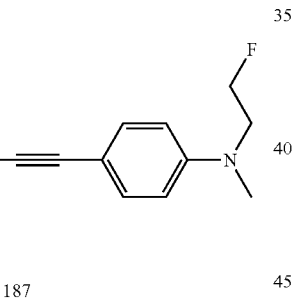

Example 66.1 Synthesis of 6-bromo-2-iodo-1-((2-(trimethylsilyl)ethoxy)methyl)-1H-pyrrolo[2,3-b]pyridine 189

Under argon, 6-bromo-2-iodo-1H-pyrrolo[2,3-b]pyridine 18j (500 mg, 1.55 mmol, 1 eq.) was dissolved in 10 ml of DMF. At 0° C., NaH (50% in mineral oil, 89 mg, 1.86 mmol, 1.2 eq.) was added portionwise. After 1 h stirring, SEMCl (0.33 ml, 1.86 mmol, 1.2 eq.) was added dropwise. After 2 hours of reaction, 10 ml of water was added slowly. The organic phases are extracted with ethyl acetate (3×10 ml). The combined organic phases were washed with NaCl, dried over MgSO$_4$ and concentrated reduced pressure. The crude was purified by flash column chromatography on silica gel (ethyl acetate/petroleum ether=20/80) to obtain compound 189 (603 g, 86%) as a colorless oil. Rf=0.9 (ethyl acetate/petroleum ether=20/80). IR (v, cm$^{-1}$, neat) 2949, 1568, 1463, 1448, 1418, 1394, 1376, 1310, 1259, 1246, 1217, 1202, 1119, 1110, 1076, 992, 969, 943, 915, 855. $^1$H NMR (400 MHz, CDCl$_3$, 20° C.) δ 7.65 (d, J=8.1 Hz, 1H), 7.20 (d, J=8.1 Hz, 1H), 6.82 (s, 1H), 5.68 (s, 2H), 3.63-3.54 (m, 2H), 0.98-0.88 (m, 2H), 0.0 (s, 9H). $^{13}$C NMR (101 MHz, CDCl$_3$, 20° C.) δ 148.5 (Cq), 135.1 (Cq), 129.2 (CH), 120.6 (CH), 112.2 (CH), 91.6 (Cq), 83.8 (Cq), 73.1 (CH$_2$), 66.4 (CH$_2$), 17.8 (CH$_2$), −1.46 (3×CH$_3$). HRMS (+ESI) calculated for C$_{13}$H$_{18}$BrIN$_2$OSi (M+H$^+$): 452.9489 found: 452.9487.

Example 66.2 Synthesis of 4-((6-bromo-1-((2-(trimethylsilyl)ethoxy)methyl)-1H-pyrrolo[2,3-b]pyridin-2-yl)ethynyl)-N-(2-fluoroethyl)-N-methylaniline 188

The compound was prepared according to procedure C2 and purified by flash column chromatography on silica gel (ethyl acetate/petroleum ether=10/90). Yellowish solid (63%), mp 106-108° C., Rf=0.7 (dichloromethane). IR (v, cm$^{-1}$, neat) 2891, 2198, 1607, 1557, 1538, 1510, 1447, 1417, 1360, 1293, 1266, 1243, 1223, 1186, 1130, 1114, 1072, 1044, 979, 933, 895. $^1$H NMR (400 MHz, CDCl$_3$, 20° C.) δ 7.68 (d, J=7.9 Hz, 1H), 7.44 (d, J=8.7 Hz, 2H), 7.25 (d, J=7.9 Hz, 1H), 6.76-6.62 (m, 3H), 5.77 (s, 2H), 4.62 (dt, J=47.1, 5.1 Hz, 2H), 3.78-3.61 (m, 4H), 3.07 (s, 3H), 1.01-0.91 (m, 2H), 0.00 (s, 9H). $^{13}$C NMR (101 MHz, CDCl$_3$, 20° C.) δ 149.2 (Cq), 147.7 (Cq), 135.9 (Cq), 133.0 (2×CH), 130.3 (CH), 123.6 (Cq), 120.7 (CH), 118.9 (Cq), 111.7 (2×CH$_2$), 109.2 (Cq), 105.8 (CH), 98.0 (Cq), 81.60 (d, J=170.2 Hz, CH$_2$), 78.2 (Cq), 71.1 (CH$_2$), 66.6 (CH$_2$), 52.35 (d, J=21.1 Hz, CH$_2$), 39.0 (CH$_3$), 17.8 (CH$_2$), −0.00 (3×CH$_3$). $^{19}$F NMR (376 MHz, DMSO-d$_6$, 20° C.) δ. −222.3. HRMS (+ESI) calculated for C$_{24}$H$_{29}$BrFN$_3$OSi (M+H$^+$): 502.1320, found: 502.1318.

Example 66.3 Synthesis of N-(2-fluoroethyl)-N-methyl-4-((6-morpholino-1-((2-(trimethylsilyl)ethoxy) methyl)-1H-pyrrolo[2,3-b]pyridin-2-yl)ethynyl)aniline 190

Under argon, Pd(OAc)$_2$ (0.05 eq) and Xantphos (0.075 mmol) were added to a degassed anhydrous dioxane solution of 0.05 M concentration containing 4-((6-bromo-1-((2-(trimethylsilyl)ethoxy)methyl)-1H-pyrrolo[2,3-b]pyridin-2-yl)ethynyl)-N-(2-fluoroethyl)-N-methylaniline 188 (1.0 eq.), morpholine (1.0 eq.) and CsCO$_3$ (1.2 eq.). After 1 h30 at 110° C., the solvent was evaporated under reduced pressure. Then, the reaction mixture was concentrated under reduced pressure before being purified by flash column chromatography on silica gel (ethyl acetate/petroleum ether=20/80) to get the compound 190 (21 mg, 52%) as a greenish solid. Rf=0.1 (dichloromethane). mp: 110-112° C. IR (v, cm$^{-1}$, neat) 2952, 2890, 2851, 1602, 1568, 1538, 1507, 1489, 1443, 1431, 1403, 1374, 1338, 1324, 1293, 1246, 1229, 1190, 1156, 1120, 1104, 1071, 1046, 980, 941, 907. $^1$H NMR (400 MHz, CDCl$_3$, 20° C.) δ 8.19 (s, 1H), 7.49-7.37 (m, 3H), 6.75-6.60 (m, 3H), 5.77 (s, 2H), 4.62 (dt, J=47.1, 5.1 Hz, 2H), 3.98-3.87 (m, 4H), 3.76-3.63 (m, 4H), 3.19-3.12 (m, 3H), 3.07 (s, 3H), 0.92 (m 2H), −0.08 (s, 9H). $^{13}$C NMR (101 MHz, CDCl$_3$, 20° C.) δ 154.8 (Cq), 149.0 (Cq), 144.2 (Cq), 143.5 (Cq), 137.7 (CH), 132.9 (2×CH), 123.8 (Cq), 120.2 (Cq), 115.6 (CH), 111.8 (2×CH), 109.5 (Cq), 105.2 (CH), 97.5 (Cq), 81.60 (d, J=170.2 Hz, CH$_2$), 78.7 (Cq), 71.2 (CH$_2$), 67.0 (2×CH$_2$), 66.2 (CH$_2$), 52.5 (d, J=21.1 Hz, CH$_2$), 51.6 (2×CH$_2$), 39.0 (CH$_3$), 17.8 (CH$_2$), −0.00 (3×CH$_3$). HRMS (+ESI) calculated for C$_{28}$H$_{37}$FN$_4$O$_2$Si (M+H$^+$): 509.2739, found: 509.2743.

Example 66.4 Synthesis of N-(2-fluoroethyl)-N-methyl-4-((6-morpholino-1H-pyrrolo[2,3-b]pyridin-2-yl)ethynyl)aniline 187

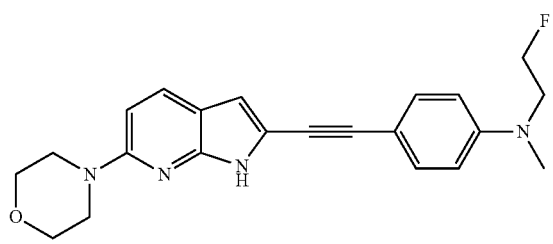

C$_{22}$H$_{23}$FN$_4$O
MW: 378.45 gmol-1

At room temperature and under argon, a solution of TBAF in THF (C=1 M, 0.19 ml, 0.19 mmol, 5.0 eq.) was added dropwise to the reaction medium containing N-(2-fluoroethyl)-N-methyl-4-((6-morpholino-1-((2-(trimethylsilyl)ethoxy)methyl)-1H-pyrrolo[2,3-b]pyridin-2-yl)ethynyl)aniline 190 (20 mg, 0.04 mmol, 1.0 eq.) and ethylenediamine (0.004 ml, 0.06 mmol, 1.2 eq.) diluted in 2 ml of THF. After 24 h at 80° C., the reaction mixture was cooled and 10 ml of water, followed by 10 ml of ethyl acetate are successively added. The organic phases were extracted 3 times with ethyl acetate. Then, they were combined, dried with MgSO$_4$, filtered through cotton and evaporated under reduced pressure. Finally, the crude was purified by flash column chromatography on silica gel with eluent (ethyl acetate/petroleum ether=20/80) to get the final compound (7 mg, 46%) as a greenish solid. Rf=0.5 (ethyl acetate/petroleum ether=20/80). mp>260° C. IR (v, cm$^{-1}$, neat) 3289, 2918, 2851, 1604, 1573, 1539, 1506, 1449, 1424, 1374, 1293, 1257, 1230, 1184, 1136, 1108, 1067, 1055, 1038, 992, 900. $^1$H NMR (400 MHz, CDCl$_3$, 20° C.) δ 8.39 (s, 1H), 7.71 (d, J=8.8 Hz, 1H), 7.42 (m, 2H), 6.69 (d, J=8.5 Hz, 1H), 6.59 (s, 1H), 4.69 (m, 1H), 4.57 (m, 1H), 3.87 (m, 4H), 3.74 (m, 1H), 3.68 (m, 1H), 3.55 (m, 4H), 3.08 (s, 3H). $^{13}$C NMR DEPT (101 MHz, CDCl$_3$, 20° C.) δ 131.4 (2×CH), 130.3 (CH), 111.6 (2×CH), 106.3 (CH), 101.9 (CH), 81.60 (d, J=170.2 Hz, CH$_2$), 78.7 (Cq), 65.0 (2×CH$_2$), 52.5 (d, J=21.1 Hz, CH$_2$), 46.4 (2×CH$_2$), 39.0 (CH$_3$). HRMS (+ESI) calculated for C$_{22}$H$_{23}$FN$_4$O (M+H+): 379.1924, found: 379.1928.

Example 67: 1-(6-bromo-2-((4-(dimethylamino)phenyl)ethynyl)-1H-pyrrolo[2,3-b]pyridin-1-yl)ethan-1-one 191

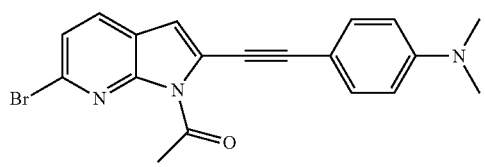

1-(6-bromo-2-((4-(dimethylamino)phenyl)ethynyl)-1H-pyrrolo[2,3-b]pyridin-1-yl)ethan-1-one 1-(6-bromo-2-((4-(dimethylamino)phenyl)ethynyl)-1H-pyrrolo[2,3-b]pyridin-1-yl)ethan-1-one 191 was synthesized in 2 steps. Initially, 6-bromo-2-iodo-1H-pyrrolo[2,3-b]pyridine 18j was protected with an acetate type protecting group and the the Sonogoshira reaction was performed to get the final compound. Then radiolabeling tests with fluorine 18 may be made on the position 6 of azaindolique nucleous to give after deprotection the radiolabelled compound 22f.

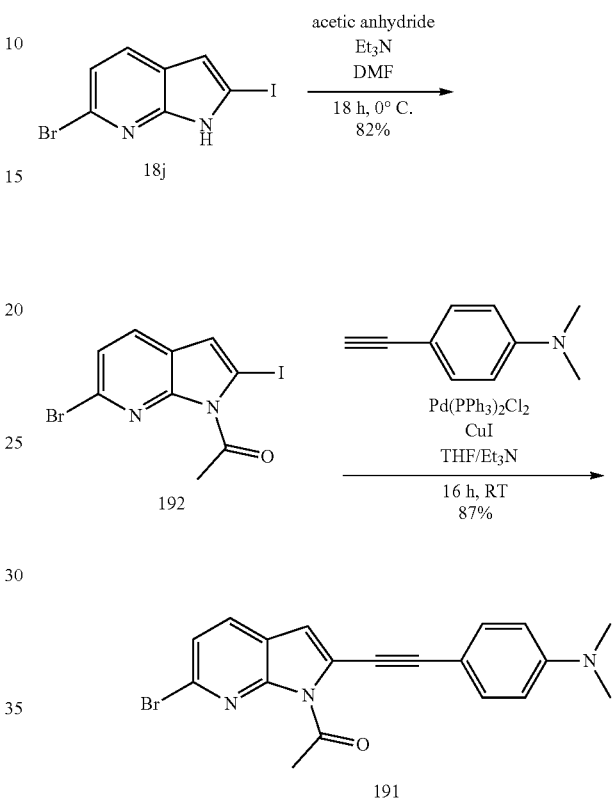

Example 67.1 Synthesis of 1-(6-bromo-2-iodo-1H-pyrrolo[2,3-b]pyridin-1-yl)ethan-1-one 192

Under argon, 6-bromo-2-iodo-1H-pyrrolo[2,3-b]pyridine 18j (200 mg, 0.62 mmol, 1 eq.) was dissolved in 5 ml of DMF. Acetic anhydride (0.088 ml, 0.93 mmol, 1.5 eq.) and triethylamine (0.129 ml, 0.93 mmol, 1 0.5 eq) were added successively. After 18 h stirring at room temperature, 10 ml of water was added slowly. The organic phases were extracted with ethyl acetate (3×10 ml). The combined organic phases were washed with NaCl, dried over MgSO$_4$, filtered and concentrated under reduced pressure. The crude is purified by flash column chromatography on silica gel (dichloromethane/petroleum ether=20/40) to provide compound 192 (186 mg, 82%) as a white solid Rf=0.6 (dichloromethane), mp:126-128° C. IR (v, cm$^{-1}$, neat) 1718, 1590, 1558, 1489, 1429, 1404, 1368, 1294, 1254, 1218, 1205, 1134, 1113, 1090, 1025, 991, 905, 829, 807. $^1$H NMR (400 MHz, CDCl$_3$, 20° C.) δ 7.62 (d, J=8.1 Hz, 1H), 7.34 (d, J=8.1 Hz, 1H), 6.99 (s, 1H), 3.05 (s, 3H). $^{13}$C NMR DEPT (250 MHz, CDCl$_3$, 20° C.) δ 129.2 (CH), 122.9 (CH), 119.7 (CH), 27.9 (CH$_3$). HRMS (+ESI) calculated for C$_9$H$_6$BrIN$_2$O (M+Na+): 386.8600, found: 386.8599.

Example 67.2 Synthesis of 1-(6-bromo-2-((4-(dimethylamino)phenyl)ethynyl)-1H-pyrrolo[2,3-b]pyridin-1-yl)ethan-1-one 191

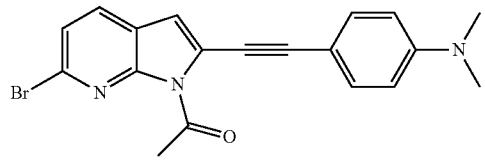

C₁₉H₁₆BrN₃O
MW: 382.26 gmol-1

The compound was prepared according to procedure C2 and purified by flash column chromatography on silica gel (dichloromethane/petroleum ether=50/50). Yellowish solid (87%), mp 194-196° C., Rf=0.5 (dichloromethane/petroleum ether=40/60). IR (v, cm$^{-1}$, neat) 2918, 2852, 2188, 1728, 1604, 1561, 1541, 1508, 1448, 1431, 1393, 1364, 1322, 1305, 1290, 1258, 1221, 1185, 1131, 1099, 1067, 1037, 1010, 936, 900. $^1$H NMR (250 MHz, CDCl₃, 20° C.) δ 7.64 (d, J=8.0 Hz, 1H), 7.45 (d, J=8.9 Hz, 2H), 7.33 (d, J=8.0 Hz, 1H), 6.77 (s, 1H), 6.63 (d, J=8.9 Hz, 2H), 3.03 (s, 3H), 2.98 (s, 6H). $^{13}$C NMR (63 MHz, CDCl₃, 20° C.) δ 169.0 (Cq), 150.5 (Cq), 146.6 (Cq). 135.5 (Cq), 133.0 (2×CH), 130.2 (CH), 123.0 (CH), 122.7 (Cq), 120.9 (Cq), 111.7 (2×CH), 111.2 (CH), 109.0 (Cq), 98.9 (Cq), 79.8 (Cq), 40.1 (2×CH₃), 27.4 (CH₃). HRMS (+ESI) calculated for C₁₉H₁₆BrN₃O (M+Na⁺): 404.0368, found: 404.0369.

Example 68: N-(2-fluoroethyl)-N-methyl-4-((5-morpholino-1H-pyrrolo[2,3-b]pyridin-2-yl)ethynyl)aniline 193

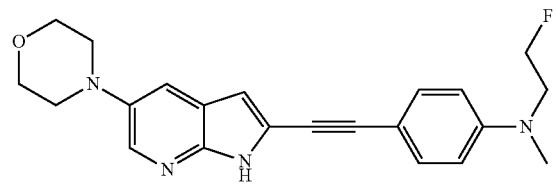

N-(2-fluoroethyl)-N-methyl-4-((5-morpholino-1H-pyrrolo[2,3-b]pyridin-2-yl)ethynyl)aniline N-(2-fluoroethyl)-N-methyl-4-((6-morpholino-1H-pyrrolo[2,3-b]pyridin-2-yl)ethynyl) aniline 193 was synthesized in 4 steps. Initially, the alkyne 194 was obtained in 2 successive steps starting from 5-bromo-2-iodo-1H-pyrrolo[2,3-b]pyridine 18k then the Buchwald reaction with an amine is carried out. Finally, a deprotection reaction led to the expected final compound.

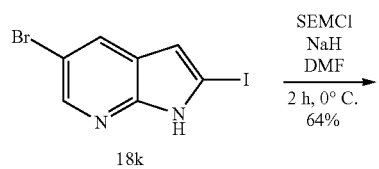

18k

SEMCl
NaH
DMF
———→
2 h, 0° C.
64%

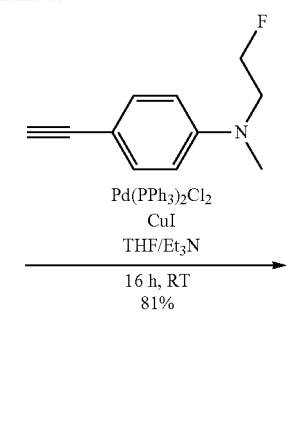

195

Pd(PPh₃)₂Cl₂
CuI
THF/Et₃N
———→
16 h, RT
81%

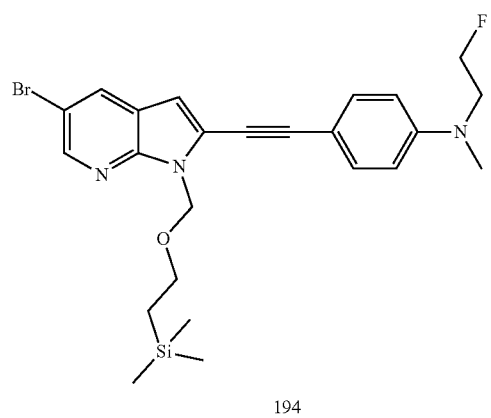

194

Morpholine
Pd₂(dba)₃
Xantphos
tBuONa
Toluene
———→
2 h,
110° C.
45%

194

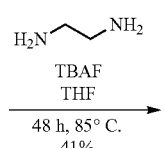

TBAF
THF
———→
48 h, 85° C.
41%

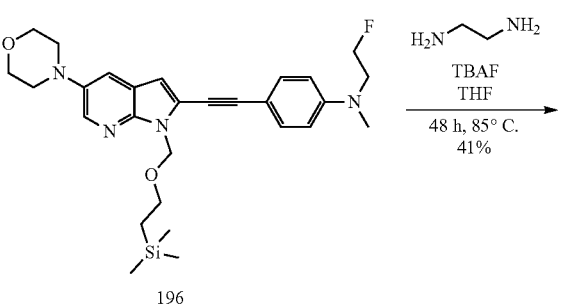

196

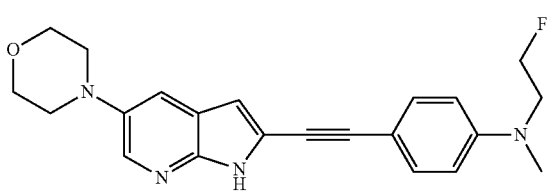

193

Example 68.1 Synthesis of 5-bromo-2-iodo-1-((2-(trimethylsilyl)ethoxy)methyl)-1H-pyrrolo[2,3-b]pyridine 195

Under argon, 5-bromo-2-iodo-1H-pyrrolo[2,3-b]pyridine 18k (594 mg, 1.84 mmol, 1 eq.) was dissolved in 10 ml of DMF. At 0° C., NaH (50% in mineral oil, 105 mg, 2.21 mmol, 1.2 eq.) was added portionwise. After 1 h of stirring, SEMCl (0.39 ml, 2.21 mmol, 1.2 eq.) was added dropwise. After 2 hours of reaction, 10 ml of water were added slowly. The organic phases were extracted with ethyl acetate (3×10 ml). The combined organic phases were washed with NaCl, dried over MgSO$_4$, filtered and concentrated under reduced pressure. The crude was purified by flash column chromatography on silica gel (ethyl acetate/petroleum ether=5/95) to afford compound 195 (534 g, 64%) as a colorless oil. Rf=0.9 (ethyl acetate/petroleum ether=5/95). IR (v, cm$^{-1}$, neat) 2949, 1568, 1463, 1448, 1418, 1394, 1376, 1310, 1259, 1246, 1217, 1202, 1119, 1110, 1076, 992, 969, 943, 915, 855. $^1$H NMR (400 MHz, CDCl$_3$, 20° C.) δ 8.27 (d, J=2.3 Hz, 1H), 7.93 (d, J=2.3 Hz, 1H), 6.77 (s, 1H), 5.68 (s, 2H), 3.63-3.54 (m, 2H), 0.98-0.88 (m, 2H), 0.00 (s, 9H). $^{13}$C NMR (101 MHz, CDCl$_3$, 20° C.) δ 147.6 (Cq), 143.6 (CH), 129.1 (CH), 123.3 (Cq), 112.7 (Cq), 111.3 (CH), 91.6 (Cq), 85.8 (Cq), 73.1 (CH$_2$), 66.4 (CH$_2$), 17.8 (CH$_2$), -1.46 (3×CH$_3$). HRMS (+ESI) calculated for C$_{13}$H$_{18}$BrIN$_2$OSi (M+H$^+$): 452.9489 found: 452.9487.

Example 68.2 Synthesis of 4-((5-bromo-1-((2-(trimethylsilyl)ethoxy)methyl)-1H-pyrrolo[2,3-b]pyridin-2-yl)ethynyl)-N-(2-fluoroethyl)-N-methylaniline 194

The compound was prepared according to procedure C2 and purified by flash column chromatography on silica gel (ethyl acetate/petroleum ether=10/90). Yellowish solid (63%). mp 84-86° C., Rf=0.25 (ethyl acetate petroleum ether=20/80). IR (v, cm$^{-1}$, neat) 2891, 2198, 1607, 1557, 1538, 1510, 1447, 1417, 1360, 1293, 1266, 1243, 1223, 1186, 1130, 1114, 1072, 1044, 979, 933, 895. $^1$H NMR (400 MHz, CDCl$_3$, 20° C.) δ 8.37 (d, J=2.3 Hz, 1H), 7.97 (d, J=2.3 Hz, 2H), 7.44 (d, J=7.9 Hz, 1H), 6.76-6.62 (m, 3H), 5.78 (s, 2H), 4.62 (dt, J=47.1, 5.1 Hz, 2H), 3.78-3.61 (m, 4H), 3.00 (s, 3H), 1.01-0.91 (m, 2H), 0.00 (s, 9H). $^{13}$C NMR (101 MHz, CDCl$_3$, 20° C.) δ 149.2 (Cq), 146.6 (Cq), 144.5 (CH), 133.0 (2×CH), 130.2 (CH), 124.9 (Cq), 121.8 (Cq), 112.8 (Cq), 112.8 (2×CH$_2$), 109.0 (Cq), 105.4 (CH), 98.0 (Cq), 81.60 (d, J=170.2 Hz, CH$_2$), 78.2 (Cq), 71.1 (CH$_2$), 66.6 (CH$_2$), 52.35 (d, J=21.1 Hz, CH$_2$), 39.0 (CH$_3$), 17.8 (CH$_2$), -0.00 (3×CH$_3$). $^{19}$F NMR (376 MHz, DMSO-d$_6$, 20° C.) δ. -222.3. HRMS (+ESI) calculated for C$_{24}$H$_{29}$BrFN$_3$OSi (M+H$^+$): 502.1320, found: 502.1318.

Example 68.3 Synthesis of N-(2-fluoroethyl)-N-methyl-4-((5-morpholino-1-((2-(trimethylsilyl)ethoxy) methyl)-1H-pyrrolo[2,3-b]pyridin-2-yl)ethynyl)aniline 196

Under argon, Pd$_2$(dba)$_3$ (2 mg, 0.002 mmol, 0.02 eq.) and Xantphos (4 mg, 0.006 mmol, 0.06 eq.) were added to a degassed anhydrous toluene solution of 0.1 M concentration containing the 4-((5-bromo-1-((2-(trimethylsilyl)ethoxy) methyl)-1H-pyrrolo[2,3-b]pyridin-2-yl)ethynyl)-N-(2-fluoroethyl)-N-methylaniline 188 (50 mg, 0.1 mmol, 1.0 eq.), morpholine (0.012 ml, 0.12 mmol, 1.2 eq.) and the tBuONa (14 mg, 0.15 mmol, 1.5 eq.). After 2 h at 110° C., the solvent was evaporated under reduced pressure. Then, the reaction mixture was concentrated under reduced pressure before being purified by flash column chromatography on silica gel (ethyl acetate/petroleum ether=20/80) to get compound 196 (23 mg, 45%) as a greenish oil. Rf=0.25 (ethyl acetate/petroleum ether=20/80). IR (v, cm$^{-1}$, neat) 2952, 2890, 2851, 1602, 1568, 1538, 1507, 1489, 1443, 1431, 1403, 1374, 1338, 1324, 1293, 1246, 1229, 1190, 1156, 1120, 1104, 1071, 1046, 980, 941, 907. $^1$H NMR (400 MHz, CDCl$_3$, 20° C.) δ 8.19 (s, 1H), 7.43 (d, J=8.6 Hz, 2H), 7.39 (s, 1H), 6.72-6.61 (m, 3H), 5.77 (s, 2H), 4.62 (dt, J=47.2, 5.1 Hz, 2H), 3.94-3.88 (m, 4H), 3.73 (m, 4H), 3.14 (m, 4H), 3.07 (s, 3H), 0.97-0.89 (m, 2H), -0.08 (s, 9H). $^{13}$C NMR (101 MHz, CDCl$_3$, 20° C.) δ 148.9 (Cq), 144.00 (Cq), 143.4 (Cq), 137.5 (CH), 132.8 (2×CH), 123.6 (Cq), 120.0 (Cq), 115.5 (CH), 111.6 (2×CH$_2$), 109.3 (Cq), 105.0 (CH), 97.3 (Cq), 81.60 (d, J=170.2 Hz, CH$_2$), 78.2 (Cq), 71.0 (CH$_2$), 66.9 (2×CH$_2$), 66.1 (CH$_2$), 52.3 (d, J=21.1 Hz, CH$_2$), 52.1 (2×CH$_2$), 38.9 (CH$_3$), 17.7 (CH$_2$), -0.00 (3×CH$_3$). $^{19}$F NMR (376 MHz, CDCl$_3$, 20° C.) δ. -222.0 HRMS (+ESI) calculated for C$_{28}$H$_{37}$FN$_4$O$_2$Si (M+H$^+$): 509.2739, found: 509.2743.

Example 68.4 Synthesis of N-(2-fluoroethyl)-N-methyl-4-((5-morpholino-1H-pyrrolo[2,3-b]pyridin-2-yl)ethynyl)aniline 193

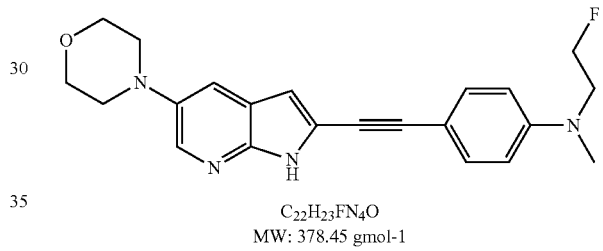

C$_{22}$H$_{23}$FN$_4$O
MW: 378.45 gmol-1

At room temperature and under argon, a solution of TBAF in THF (C=1 M, 0.23 ml, 0.23 mmol, 5.0 eq.) was added dropwise to the reaction medium containing N-(2-fluoroethyl)-N-methyl-4-((6-morpholino-1-((2-(trimethylsilyl) ethoxy)methyl)-1H-pyrrolo[2,3-b]pyridin-2-yl)ethynyl)aniline 190 (23 mg, 0.045 mmol, 1.0 eq.) and ethylenediamine (0.005 ml, 0.07 mmol, 1.2 eq.) diluted in 2 ml of THF. After 48 h at 80° C., the reaction mixture was cooled and 10 ml of water, then 10 ml of ethyl acetate are successively added. The organic phases were extracted 3 times with ethyl acetate (30 ml), combined, dried over MgSO$_4$ filtered through cotton and evaporated under reduced pressure. Finally, the crude is purified by flash column chromatography on silica gel with eluent (ethyl acetate/petroleum ether=30/70) to get the final compound (7 mg, 41%) as a solid greenish. Rf=0.1 (ethyl acetate/petroleum ether=30/70). mp>260° C. IR (v, cm$^{-1}$, neat) 3289, 2918, 2851, 1604, 1573, 1539, 1506, 1449, 1424, 1374, 1293, 1257, 1230, 1184, 1136, 1108, 1067, 1055, 1038, 992, 900. $^1$H NMR (400 MHz, CDCl$_3$, 20° C.) δ 9.01 (s, 1H), 8.15 (s, 1H), 7.45 (m, 3H), 6.67 (m, 3H), 4.62 (m, 2H), 3.93 (m, 4H), 3.70 (m, 2H), 3.16 (m, 4H), 3.07 (s, 3H). $^{13}$C NMR (101 MHz, CDCl$_3$, 20° C.) δ 149.1 (Cq), 143.9 (Cq), 143.8 (Cq), 137.3 (CH), 132.9 (2×CH), 123.4 (Cq), 121.7 (Cq), 116.0 (CH), 111.8 (2×CH$_2$), 109.3 (Cq), 105.4 (CH), 94.8 (Cq), 81.60 (d, J=170.2 Hz, CH$_2$), 78.2 (Cq), 67.1 (2×CH$_2$), 52.3 (d, J=21.1 Hz, CH$_2$), 51.6 (2×CH$_2$), 38.9 (CH$_3$). $^{19}$F NMR (376 MHz, CDCl$_3$, 20° C.) δ. -222. HRMS (+ESI) calculated for C$_8$H$_7$IN$_2$ (M+H$^+$): 379.1929, found: 379.1928.

Example 69: 4-(2-((4-((2-fluoroethyl)(methyl) amino)phenyl)ethynyl)-1-((2-(trimethylsilyl)ethoxy) methyl)-1H-pyrrolo[2,3-b]pyridin-5-yl)benzonitrile 198

4-((5-bromo-1-((2-(trimethylsilyl)ethoxy)methyl)-1H-pyrrolo[2,3-b]pyridin-2-yl)ethynyl)-N-(2-fluoroethyl)-N-methylaniline 198 was obtained from 194 by a Suzuki reaction with the corresponding boronic acid. Deprotection of the silyl derivative will give the final deprotected product 197

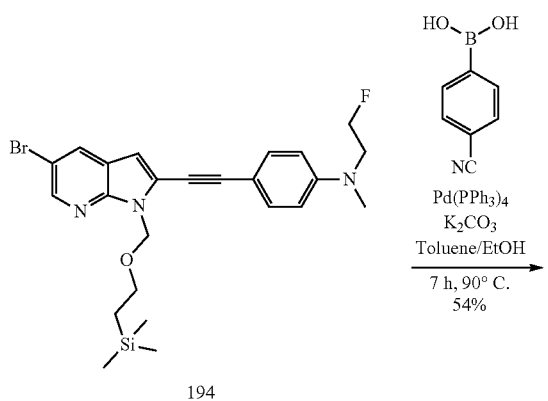

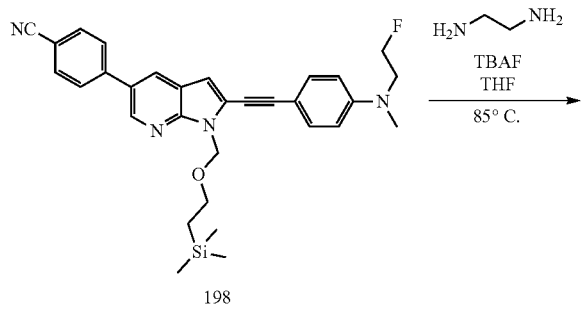

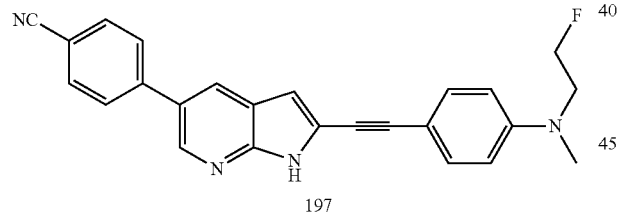

Under argon, 4-((5-bromo-1-((2-(trimethylsilyl) ethoxy) methyl)-1H-pyrrolo[2,3-b] pyridin-2-yl) ethynyl)-N-(2-fluoroethyl)-N-methylaniline 194 (25 mg, 0.05 mmol, 1 eq.) was dissolved in a mixture toluene/EtOH (1/1) then the addition of 4-cyanophenylboronic acid (9 mg, 0.06 mmol, 1.2 eq.) and $K_2CO_3$ (21 mg, 0.15 mmol, 3 eq.) is performed. Then, the reaction medium was degassed for 10 minutes before adding [Pd(PPh$_3$)$_4$] (5.8 mg, 0.005 mmol, 0.1 eq.). The reaction mixture was heated to 90° C. for 7 h. After cooling, the solvents are evaporated under reduced pressure. Finally, the crude is purified by flash column chromatography on silica gel with eluent (ethyl acetate/petroleum ether=20/80) to get the final compound (14 mg, 54%) as a yellow is solid h. Rf=0.2 (dichloromethane) mp. 158-160° C. IR (v, cm$^{-1}$, neat) 2949, 2224, 2197, 1606, 1541, 1514, 1474, 1450, 1422, 1377, 1353, 1317, 1291, 1261, 1247, 1215, 1196, 1182, 1135, 1114, 1097, 1066, 1047, 982, 941, 897, 857. $^1$H NMR (400 MHz, CDCl$_3$, 20° C.) 8.59 (d, J=1.6 Hz, 1H), 8.04 (d, J=1.6 Hz, 1H),), 7.75 (m, 4H), 7.45 (d, J=8.1 Hz, 2H), 6.79 (s, 1H), 6.69 (d, J=8.1 Hz, 2H), 5.85 (s, 2H), 4.63 (dt, J=47.2, 5.1 Hz, 2H), 3.71 (m, 4H), 3.08 (s, 3H), 0.97-0.89 (m, 2H), −0.08 (s, 9H). $^{13}$C NMR (101 MHz, CDCl$_3$, 20° C.) δ 149.2 (Cq), 148.3 (Cq), 144.1 (Cq), 143.2 (CH), 133.0 (2×CH), 132.8 (2×CH), 128.7 (Cq), 127.8 (2×CH), 126.8 (CH), 124.8 (Cq), 120.0 (Cq), 118.8 (Cq), 111.8 (2×CH), 110.7 (Cq), 109.1 (Cq), 105.9 (CH), 98.4 (Cq), 81.60 (d, J=170.2 Hz, CH$_2$), 78.3 (Cq), 71.0 (CH$_2$), 66.5 (CH$_2$), 52.3 (d, J=21.1 Hz, CH$_2$), 38.9 (CH$_3$), 17.8 (CH$_2$), −0.00 (3×CH$_3$). HRMS (+ESI) calculated for $C_{31}H_{33}FN_4OSi$ (M+H$^+$): 398.9658, found: 398.9657.

Example 70: N,N-dimethyl-4-((5-(4,4,5,5-tetramethyl-1,3,2-dioxaborolan-2-yl)-1H-pyrrolo[2,3-b] pyridin-2-yl)ethynyl)aniline 199

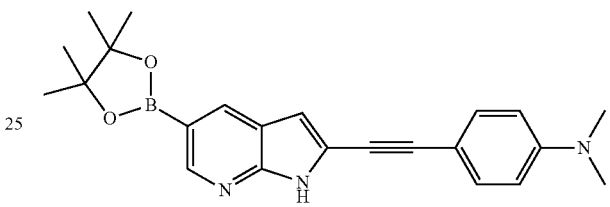

N,N-dimethyl-4-((5-(4,4,5,5-tetramethyl-1,3,2-dioxaborolan-2-yl)-H-pyrrolo[2,3-b]pyridin-2-yl)ethynyl)aniline 193 was synthesized in 4 steps. Initially, the alkyne 201 was obtained in 2 successive steps starting from 5-bromo-2-iodo-1H-pyrrolo[2,3-b]pyridine 18k and the Sonogashira reaction with the corresponding alkyne was carried out and finally the deprotection reaction provided the expected final compound. This will be a precursor in order to use in radiolabeling

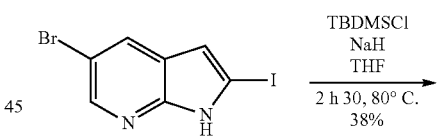

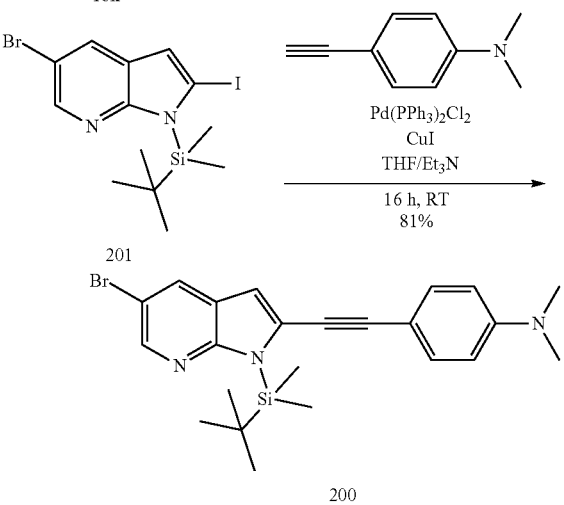

-continued

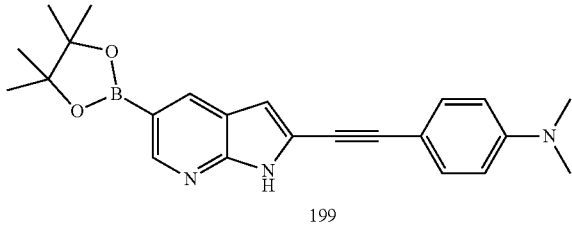

Example 70.1 Synthesis of 5-bromo-1-(tert-butyldimethylsilyl)-2-iodo-1H-pyrrolo[2,3-b]pyridine 201

Under argon, 5-bromo-2-iodo-1H-pyrrolo[2,3-b]pyridine 18k (230 mg, 0.71 mmol, 1 eq.) was dissolved in 10 ml of THF. At 0° C., NaH (50% in mineral oil, 41 mg, 0.86 mmol, 1.2 eq.) was added portionwise. After 30 h stirring at temperature, the mixture was returned to 0° C. and TBDMSCl (129 mg, 0.86 mmol, 1.2 eq.) was added portionwise. Then the mixture was carried out at 80° C. for 2 h30. After cooling to 0° C., 10 ml of water was added slowly and the organic phases were extracted with the ethyl acetate (3×10 ml). The combined organic phases were washed with NaCl, dried over $MgSO_4$, filtered and concentrated under reduced pressure. The crude was purified by flash column chromatography on silica gel (ethyl acetate/petroleum ether=5/95) to provide compound 201 (117 g, 38%) as a colorless oil. Rf=0.9 (ethyl acetate/petroleum ether=5/95). IR (v, $cm^{-1}$, neat) 2951, 2925, 2854, 1587, 1541, 1484, 1460, 1444, 1353, 1339, 1307, 1253, 1215, 1175, 1114, 1066, 997, 917, 846. $^1$H NMR (250 MHz, $CDCl_3$, 20° C.) δ 8.16 (d, J=2.3 Hz, 1H), 7.82 (d, J=2.3 Hz, 1H), 6.80 (s, 1H), 0.94 (s, 9H), 0.81 (s, 6H). $^{13}$C NMR DEPT (63 MHz, $CDCl_3$, 20° C.) δ 142.2 (CH), 127.7 (CH), 116.7 (CH), 27.1 (3×$CH_2$), −0.65 (2×$CH_3$). HRMS (+ESI) calculated for $C_{13}H_{18}BrN_2Si$ $(M+H^+)$: 436.9540 found: 436.9538.

Example 70.2 Synthesis of 4-((5-bromo-1-(tert-butyldimethylsilyl)-1H-pyrrolo[2,3-b]pyridin-2-yl)ethynyl)-N,N-dimethylaniline 200

The compound was prepared according to procedure C2 and purified by flash column chromatography on silica gel (dichloromethane/petroleum ether=20/80). Yellowish amorphous solid (62%), Rf=0.5 (ethyl acetate/petroleum ether=20/80). IR (v, $cm^{-1}$, neat) 2952, 2890, 2851, 1603, 1568, 1538, 1507, 1489, 1443, 1431, 1403, 1374, 1338, 1324, 1293, 1246, 1229, 1191, 1157, 1120, 1104, 1071, 1046, 980, 942, 907. $^1$H NMR (400 MHz, $CDCl_3$, 20° C.) δ 8.28 (d, J=2.3 Hz, 1H), 7.91 (d, J=2.3 Hz, 2H), 6.76-6.62 (m, 3H), 3.00 (s, 6H), 0.99 (s, 9H), 0.82 (s, 6H). $^{13}$C NMR DEPT (101 MHz, $CDCl_3$, 20° C.) δ 143.4 (CH), 132.4 (2×CH), 128.9 (CH), 111.9 (2×$CH_2$), 109.7 (CH), 40.2 (2×$CH_3$), 26.7 (3×$CH_3$), −1.58 (2×$CH_3$). HRMS (+ESI) calculated for $C_2H_{28}BrN_3Si$ $(M+H^+)$: 454.1308, found: 454.1309.

Example 70.3 Synthesis of N,N-dimethyl-4-((5-(4,4,5,5-tetramethyl-1,3,2-dioxaborolan-2-yl)-1H-pyrrolo[2,3-b]pyridin-2-yl)ethynyl)aniline 199

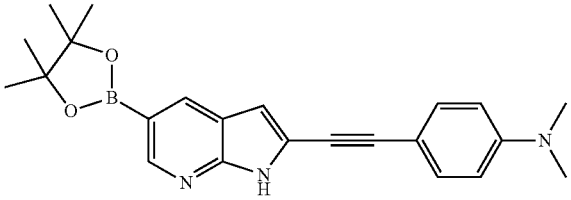

$C_{23}H_{26}BN_3O_2$
MW/387.29 gmol-1

Under argon, 4-((5-bromo-1-(tert-butyldimethylsilyl)-1H-pyrrolo[2,3-b]pyridin-2-yl)ethynyl)-N,N-dimethylaniline 200 (50 mg, 0.11 mmol, 1.0 eq.) was dissolved in dioxane (1 ml) followed by the addition of bis (pinacolato) diboron (56 mg, 0.22 mmol, 2.0 eq.) and KOAc (32 mg, 0.33 mmol, 3.0 eq.) was carried out. Then, the reaction medium is degassed for 10 minutes before adding $Pd(dppf)_2Cl_2.DCM$ (9.0 mg, 0.011 mmol, 0.1 eq.). The reaction mixture was heated at 100° C. for 4 h.

After cooling, the solvent was evaporated under reduced pressure. Finally, the crude was purified by flash column chromatography on silica gel with eluent (dichloromethane/petroleum ether=30/70) to provide the intermediate. Then the crude product was directly dissolved in 5 ml of THF. At 0° C., a solution of TBAF in THF (C=1 M, 0.05 ml, 0.05 mmol, 0.2 eq.) was added dropwise. After 40 minutes at 0° C., 10 ml of water and 10 ml of ethyl acetate were successively added. The organic phases were extracted 3 times with ethyl acetate, combined, dried with $MgSO_4$, filtered through cotton and evaporated under reduced pressure. The crude was purified by flash column chromatography on silica gel (ethyl acetate/petroleum ether=20/80) to procided the compound 199 (10 mg, 64%) as a yellow solid. Rf=0.1 (ethyl acetate/petroleum ether=10/90). mp>260° C. IR (v, $cm^{-1}$, neat) 3291, 2962, 2930, 2853, 2102, 1606, 1511, 1463, 1434, 1373, 1356, 1336, 1273, 1245, 1227, 1185, 1141, 1093, 1023, 935. $^1$H NMR (400 MHz, DMSO-$d_6$, 20° C.) δ 12.20 (s, 1H), 8.46 (s, 1H), 8.18 (s, 1H), 7.39 (d, J=8.6 Hz, 2H), 6.74 (m, 3H), 2.97 (s, 6H), 1.32 (s, 12H). $^{13}$C NMR (63 MHz, $CDCl_3$, 20° C.) δ 150.9 (Cq), 150.3 (Cq), 149.8 (Cq), 135.2 (CH), 133.0 (2×CH), 120.9 (Cq), 120.9 (Cq), 119.9 (Cq), 112.5 (2×CH), 110.7 (Cq), 107.9 (Cq), 106.0 (CH), 95.4 (Cq), 84.1 (2×Cq), 80.6 (Cq), 40.2 (2×$CH_3$), 25.2 (4×$CH_3$). HRMS (+ESI) calculated for $C_{23}H_{26}BN_3O_2$ $(M+H^+)$: 388.2190, found: 388.2193.

Example 71: N,N-dimethyl-4-((4-(4,4,5,5-tetramethyl-1,3,2-dioxaborolan-2-yl)-1H-pyrrolo[2,3-b]pyridin-2-yl)ethynyl)aniline 202

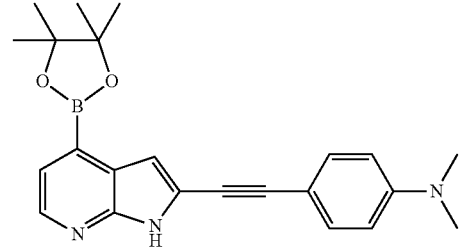

243

N,N-dimethyl-4-((4-(4,4,5,5-tetramethyl-1,3,2-dioxaborolan-2-yl)-1H-pyrrolo[2,3-b]pyridin-2-yl)ethynyl)aniline 202 was synthesized in 6 steps. Initially, the alkyne 204 was obtained in 5 successive steps starting from 4-bromo-1H-pyrrolo[2,3-b]pyridine and the Sonogashira reaction with the corresponding alkyne was carried out and finally the deprotection reaction provided the expected final compound. The compounds 207 and 202 are precursors for radiolabeling

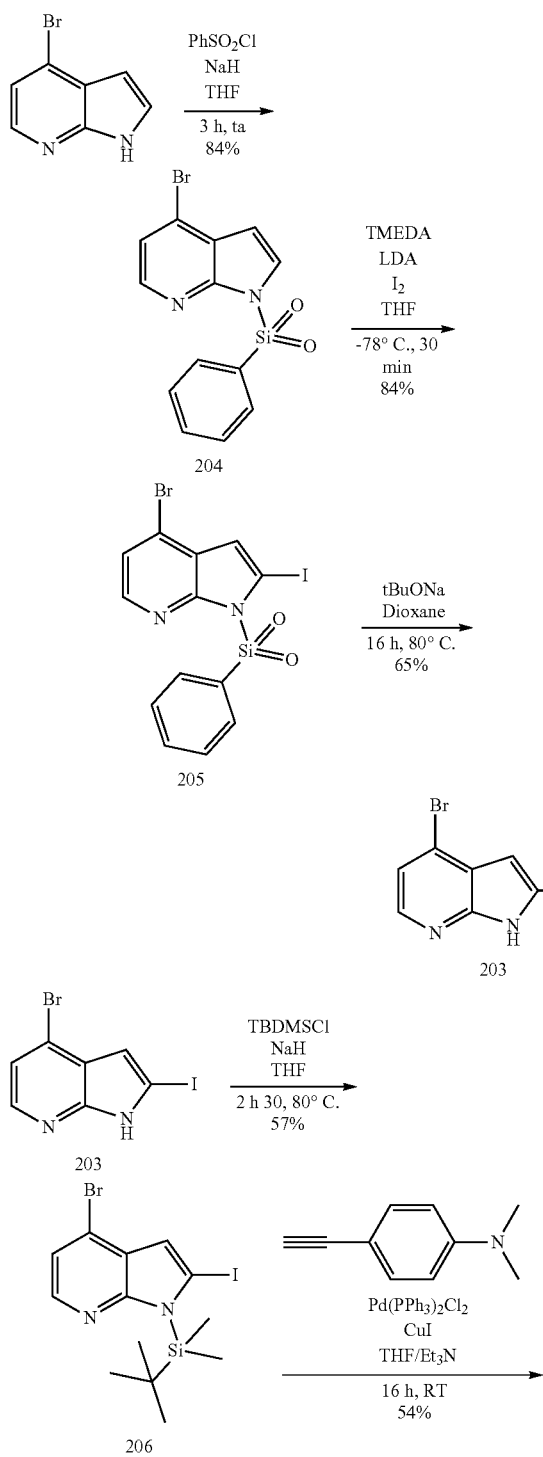

244

Example 71. Synthesis of 4-bromo-1-(phenylsulfonyl)-1H-pyrrolo[2,3-b]pyridine 205

To a solution of NaH (1.46 g, 30.4 mmol, 1.2 eq.) in THF under argon and at 0° C. was slowly added a solution of 4-bromo-7-azaindole (5 g, 25.4 mmol, 1.0 eq.) in THF (1 M). The mixture was stirred at room temperature for 30 min. Return to 0° C., benzenesulfonyl chloride (3.5 ml, 27.9 mmol, 1.1 eq.) was added drop by drop. After 3 h stirring at room temperature the mixture was poured into a vial filled with ice. Once the medium back to room temperature, the phases were separated. The aqueous phase was extracted with ethyl acetate. The combined organic phases were washed with NaCl, dried over $MgSO_4$ and concentrated under reduced pressure. The crude product was triturated with pentane and vacuum filtered to obtain compound 205 (7.2 g, 84%) as a brown solid. $^1$H NMR (400 MHz, $CDCl_3$, 20° C.) δ 8.18 (d, J=7.8 Hz, 3H), 7.52 (m, 4H), 7.30 (m, 1H), 7.02 (s, 1H). CAS Number: 889939-25-7.

Example 71.2 Synthesis of 4-bromo-2-iodo-1-(phenylsulfonyl)-1H-pyrrolo[2,3-b]pyridine 205

Under argon atmosphere, to a solution of 4-bromo-1-(phenylsulfonyl)-1H-pyrrolo[2,3-b] pyridine 205 (7 g, 0.99 mmol, 1.0 eq.) and TMEDA (3.42 ml, 22.8 mmol, 1.1 eq.) in THF (0.1 M), cooled to −78° C., was added a solution of LDA (2M in THF, 12.5 ml, 24.8 mmol, 1.2 eq.) dropwise. After 30 min, a solution of iodine (1.5 1 g, 45.5 mmol, 2.2 eq.) In THF (0.5M) was slowly added via cannula to the reaction medium. After 30 min stirring at −78° C., 20 ml of water are additonnes and the reaction medium is brought back to room temperature slowly. The organic phases are extracted with ethyl acetate (3 times 20 ml), combined, dried over $MgSO_4$, filtered and then concentrated under reduced pressure. The crude was purified by flash column chromatography on silicagel (ethyl acetate/petroleum ether=20/80)

to yield compound 205 (8.1 g, 76%) as a brown solid. Rf (0.10 (ethyl acetate/petroleum ether=20/80). M.P. 144-146° C. IR (v, cm$^{-1}$, neat) 3383, 2359, 1635, 1588, 1567, 1485, 1449, 1430, 1370, 1333, 1275, 1235, 1207, 1175, 1129, 1114, 1087, 1011, 918, 826, 755, 723, 697, 684, 623, 585, 557, 537, 502. $^{1}$H NMR (250 MHz, CDCl$_3$, 20° C.) δ 8.19 (t, J=6.5 Hz, 3H), 7.65-7.44 (m, 3H), 7.32 (d, J=5.5 Hz, 1H), 7.05 (s, 1H). $^{13}$C NMR (63 MHz, CDCl$_3$, 20° C.) δ 149.1 (Cq), 144.7 (CH), 138.3 (Cq), 134.4 (CH), 129.1 (2×CH), 128.2 (2×CH), 125.3 (2×Cq), 123.7 (Cq), 122.5 (CH), 119.6 (CH). HRMS (+ESI) calculated for C$_{13}$H$_9$BrIN$_2$O$_2$S (M+H+): 464.8587, found: 464.8581.

Example 71.3 Synthesis of 4-bromo-2-iodo-1H-pyrrolo[2,3-b]pyridine 203

4-bromo-2-iodo-1-(phenylsulfonyl)-1H-pyrrolo[2,3-e]pyridine 205 (8.1 g, 17.5 mmol, 1.0 eq.) was dissolved in 250 ml of dioxane and 2.6 g of tert sodium t-butoxide (26.3 mmol, 1.5 eq.) were added. After 16 h at 80° C., the reaction medium is cooled to temperature and the solvent was evaporated under reduced pressure. The residue was dissolved in 100 ml of ethyl acetate and 100 ml of water are added. Then, the organic phase is extracted with ethyl acetate (3 times 20 ml). The combined organic phases were dried over MgSO$_4$ and concentrated under reduced pressure. The crude is triturated with dichloromethane and then vacuum filtration allows to produce compound 203 (58 g, 72%) as a yellowish solid. Rf=0.25 (ethyl acetate/petroleum ether=20/80). Mp>260° C. IR (v, cm$^{-1}$, neat) 3898, 3851, 3819, 3800, 3749, 3742, 3731, 3687, 3674, 3668, 3646, 3627, 3565, 3099, 3019, 2930, 2844, 2798, 2588, 2216, 1912, 1595, 1567, 1473, 1406, 1382, 1330, 1282, 1263, 1206, 1120, 1098, 964, 953, 920, 813, 751, 670, 621, 603, 536, 524, 517, 506. $^{1}$H NMR (250 MHz, DMSO-d$_6$, 20° C.) δ 12.60 (s, 1H), 7.97 (d, J=5.2 Hz, 1H), 7.26 (d, J=5.2 Hz, 1H), 6.62 (s, 1H). $^{13}$C NMR (63 MHz, DMSO-d$_6$, 20° C.) δ 150.7 (Cq), 143.5 (CH), 123.2 (Cq), 121.9 (Cq), 119.3 (CH), 109.4 (CH), 83.2 (Cq). HRMS (+ESI) calculated for C$_7$H$_4$BrIN$_2$ (M+H$^+$): 322.8675, found: 322.8673.

Example 71.4 Synthesis of 4-bromo-1-(tert-butyldimethylsilyl)-2-iodo-1H-pyrrolo[2,3-b]pyridine 206

Under argon, 4-bromo-2-iodo-1H-pyrrolo[2,3-b]pyridine 203 (386 mg, 1.19 mmol, 1.0 eq.) was dissolved in 20 ml of THF. At 0° C., NaH (50% in mineral oil, 68 mg, 1.43 mmol, 1.2 eq.) was added portionwise. After stirring for 30 minutes at temperature, the mixture was returned to 0° C. and TBDMSCl (215 mg, 1.43 mmol, 1.2 eq.) Was added in portions. Then the mixture is at 80° C. for 2 h30. After cooling to 0° C., 10 ml of water are slowly added and the organics were extracted with ethyl acetate (3×10 ml). The combined organic phases were washed with NaCl, dried over MgSO$_4$, filtered and concentrated under reduced pressure. The crude is purified by column flash chromatographie on silicagel (ethyl acetate/petroleum ether=5/95) to yield compound 205 (300 g, 57%) as a colorless oil. Rf=0.9 (ethyl acetate/petroleum ether=5/95 IR (v, cm$^{-1}$, neat) 2951, 2925, 2854, 1587, 1541, 1484, 1460, 1444, 1353, 1339, 1307, 1253, 1215, 1175, 1116, 1066, 997, 917, 846. $^{1}$H NMR (400 MHz, CDCl$_3$, 20° C.) δ 7.98 (d, J=5.0 Hz, 1H), 7.18 (d, J=5.0 Hz, 1H), 6.98 (s, 1H), 0.99 (s, 9H), 0.87 (s, 6H). $^{13}$C NMR (101 MHz, CDCl$_3$, 20° C.) δ 156.0 (Cq), 141.9 (CH), 125.2 (Cq), 121.7 (Cq), 119.5 (CH), 117.3 (CH), 84.6 (Cq), 29.7 (3×CH$_3$), 27.1 (Cq), 0.7 (2×CH$_3$). HRMS (+ESI) calculated for C$_{13}$H$_{18}$BrIN$_2$Si (M+H+): 436.9540 found: 436.9538.

Synthesis of 4-((4-bromo-1-(tert-butyldimethylsilyl)-1H-pyrrolo[2,3-b]pyridin-2-yl)ethynyl)-N,N-dimethylaniline 207

The compound was prepared according to procedure C2 and purified by flash column chromatography on silicagel (dichloromethane/petroleum ether=20/80). yellowish amorphous solid (54%), Rf=0.5 (ethyl acetate/petroleum ether=20/80). mp: 120-122° C. IR (υ, cm$^{-1}$, neat) 2952, 2890, 2851, 1603, 1568, 1538, 1507, 1489, 1443, 1431, 1403, 1374, 1338, 1324, 1293, 1246, 1229, 1191, 1157, 1120, 1104, 1071, 1046, 980, 942, 907. $^{1}$H NMR (250 MHz, CDCl$_3$, 20° C.) δ 8.02 (d, J=5.2 Hz, 1H), 7.46 (d, J=8.9 Hz, 2H), 7.17 (d, J=5.2 Hz, 2H), 6.84 (s, 1H), 6.66 (d, J=8.9 Hz, 2H), 2.99 (s, 6H), 0.95 (s, 9H), 0.79 (s, 6H). $^{13}$C NMR (63 MHz, CDCl$_3$, 20° C.) δ 154.2 (Cq), 150.4 (Cq), 143.0 (CH), 132.4 (2×CH), 127.2 (Cq), 123.6 (Cq), 123.1 (Cq), 119.5 (CH), 111.9 (2×CH), 110.3 (CH), 109.3 (Cq), 96.8 (Cq), 82.3 (Cq), 40.2 (2×CH$_3$), 26.8 (3×CH$_3$), 19.9 (Cq), −1.5 (3×CH$_3$). HRMS (+ESI) calculated for C$_2$H$_{28}$BrN$_3$Si (M+H+): 454.1308, found: 454.1309.

Example 71.5 Synthesis of N,N-dimethyl-4-((4-((4-(4,5,5-tetramethylcm-1,32-dioxaborolan-2-yl)-1H-pyrrolo[2,3-b]pyridin-2-yl)ethynyl)aniline 202

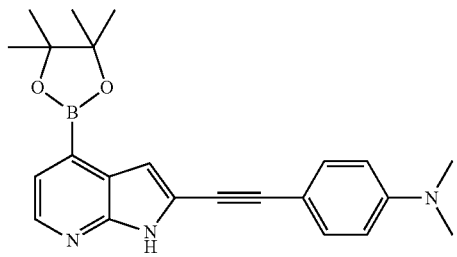

C$_{23}$H$_{26}$BN$_3$O$_2$
MW: 387.29 gmol-1

Under argon, 4-((4-bromo-1-(tert-butyldimethylsilyl)-1H-pyrrolo[2,3-b]pyridin-2-yl)ethynyl)-N,N-dimethyl aniline 207 (100 mg, 0.22 mmol, 1.0 eq.) was dissolved in dioxane (1 ml) followed by addition of bis(pinacolato)diboron (1 12 mg, 0.44 mmol, 2.0 eq.) and KOAc (64 mg, 0.66 mmol, 3.0 eq.). Then, the reaction medium is degassed for 10 minutes before adding Pd(dppf)$_2$Cl$_2$.dcm (18 mg, 0.022 mmol, 0.1 eq.). The reaction mixture was heated at 100° C. for 4 h. After cooling, the solvent was evaporated under reduced pressure. Finally, the crude is purified by flash column chromatography on silicagel eluting with (dichloromethane/petroleum ether=20/80) to yield the intermediate but with 10% of bis (pinacolato) diboron). Then, the crude is dissolved in 5 ml of THF. At 0° C., a solution of TBAF in THF (C=1 M, 0.09 ml, 0.09 mmol, 1.2 eq.) was added dropwise. After 1 h at 0° C., 10 ml of water and 10 ml of ethyl acetate are successively added. The organic phases are extracted 3 times with ethyl acetate (30 ml). Together, they are dried with MgSO$_4$, filtered through cotton and evaporated under reduced pressure. The crude was purified by flash column chromatography on silicagel (ethyl acetate/ petroleum ether=20/80) to yield compound 199 (20 mg, 24% over 2 steps) as a solid yellow. Rf=0.1 (ethyl acetate/petroleum ether=10/90). mp>260° C. IR (v, cm⁻¹, neat) 3291, 2962, 2930, 2853, 2102, 1606, 1511, 1463, 1434, 1373, 1356, 1336, 1273, 1245, 1227, 1185, 1141, 1093, 1023, 935. $^1$H NMR (250 MHz, DMSO-$d_6$, 20° C.) 12.06 (s, 1H), 8.21 (m, 1H), 7.33 (m, 3H), 6.84 (s, 1H), 6.71 (d, J=8.7 Hz, 2H), 2.93 (s, 6H), 1.31 (s, 12H). $^{13}$C NMR (63 MHz, DMSO-$d_6$, 20° C.) δ 150.7 (Cq), 148.4 (2×Cq), 143.5 (CH), 132.9 (2×CH), 124.4 (Cq), 122.2 (CH), 121.4 (Cq), 112.4 (2×CH), 107.9 (Cq), 107.0 (CH), 95.6 (Cq), 84.4 (Cq), 80.5 (2×Cq), 40.7 (2×CH$_3$), 25.2 (4×CH$_3$). HRMS (+ESI) calculated for $C_{23}H_{26}BN_3O_2$ (M+H+): 388.2190, found 388.2193.

Example 72: 5-Fluoro-2-((5-(methoxymethyl)furan-2-yl)ethynyl)-1H-pyrrolo[2,3-b] pyridine 215

215

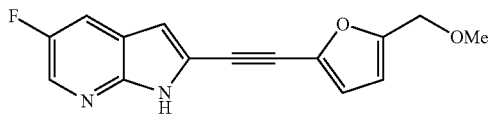

5-Fluoro-2-((5-(methoxymethyl)furan-2-yl)ethynyl)-1H-pyrrolo[2,3-b]pyridine 215 was synthesized in two steps by methylation reaction of true alkyne 212 followed by a Sonogashira reaction from the halogenoazaindole

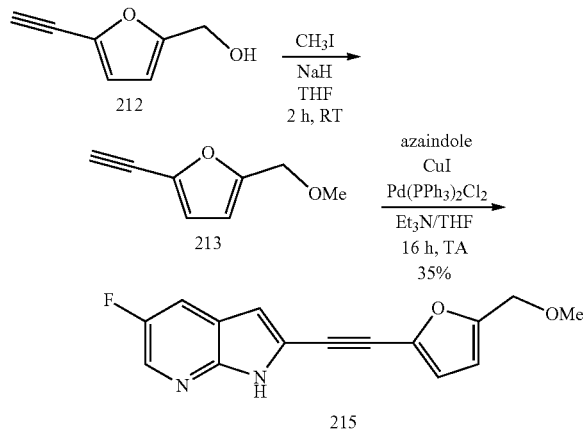

Example 72.1 Synthesis of 2-ethynyl-5-(methoxymethyl)furane 213

Compound 213 was prepared according to procedure M from 212 and isolated as a brown oil (90%). Rf=0.25 (petroleum ether/ethyl acetate=9/1). IR (v, cm⁻¹, neat) 3517, 3165, 2896, 2179, 1654, 1560, 1370, 1111, 957, 770. $^1$H NMR (250 MHz, CDCl$_3$, 20° C.) δ 6.58 (m, 1H), 6.45-6.28 (d, J 0.6 Hz, 1H), 4.35 (d, J 0.6 Hz, 2H), 3.36 (s, 3H), 3.23 (s, 1H). $^{13}$C NMR (63 MHz, CDCl$_3$, 20° C.) δ 170.4 (Cq), 129.8 (CH), 114.6 (CH$_2$), 109.4 (Cq), 102.1 (CH), 78.9 (CH), 76.8 (Cq), 61.3 (CH$_3$). HRMS (+ESI) calculated for $C_{14}H_9FN_2O_2$ (M+H+): 137,1738 found: 137,1278.

Example 72.2 Synthesis of 5-Fluoro-2-((5-(methoxymethyl)furan-2-yl)ethynyl)-1H-pyrrolo[2,3-b]pyridine 215

Compound 215 was synthesized according to procedure C2 and purified by flash column chromatography on silicagel (ethyl acetate/petroleum ether=1/9). The compound was obtained as a yellow solid (35%). mp: 162-164° C. Rf=0.31 (ethyl acetate/petroleum ether=1/9). IR (v, cm⁻¹, neat) 3117, 3059, 2981, 2890, 2727, 1584, 1505, 1433, 1374, 1360, 1346, 1297, 1251, 1179, 1157, 1087, 1020, 981, 935, 963, 876, 855, 758, 628. $^1$H NMR (400 MHz, DMSO-$d_6$, 20° C.) δ 12.43 (s, 1H), 8.26 (m, 1H), 7.83 (m, 1H), 6.97-6.85 (m, 2H), 6.56 (m, 1H), 4.35 (s, 2H), 3.23 (s, 3H). $^{13}$C NMR (101 MHz, DMSO-$d_6$, 20° C.) δ154.7 (Cq), 145.7 (Cq), 135.5 (Cq), 133.6 (CH), 120.7 (Cq), 119.7 (d, J=47.8 Hz, CH), 117.57 (Cq), 114.5 (d, J=23.6 Hz, CH), 114.2 (Cq), 111.6 (CH), 107.6 (CH), 86.3 (Cq), 83.8 (Cq), 65.7 (CH$_2$), 58.4 (CH$_3$). $^{19}$F NMR (376 MHz, DMSO-$d_6$, 20° C.) δ −138.1 (m, 1F).

HRMS (+ESI) calculated for $C_{14}H_9FN_2O_2$ (M+H$^+$): 271, 087732, found: 271,087812.

Example 73: 5-(2-(5-Fluoro-1H-pyrrolo[2,3-b]pyridin-2-yl)ethynyl)furan-2-yl)methanol 221

221

$C_{14}H_{10}N_2OS$
M.W.: 254,31g.mol⁻¹

5-(2-(5-Fluoro-1H-pyrrolo[2,3-b]pyridin-2-yl)ethynyl) furan-2-yl)methanol 221 was synthesized in one step by Sonogashira reaction from true alkyne

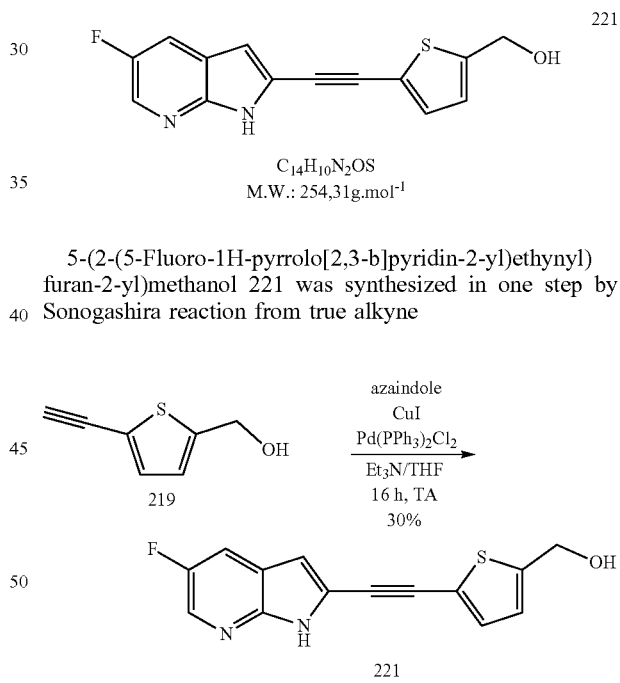

Compound 221 was prepared according to procedure C2 and purified by flash column chromatography on silicagel (methanol/dichloromethane/ammonia=4/94/2). The compound was obtained as a yellow solid (30%). mp: 240-242° C. Rf=0.42 (methanol/dichloromethane/ammonia=4/94/2) IR (v, cm⁻¹, neat) 3136, 2220, 2186, 2021, 1993, 1966, 1589, 1504, 1408, 1300, 1237, 1208, 1142, 1008, 985, 870, 800, 768, 611. $^1$H NMR (400 MHz, DMSO-$d_6$, 20° C.) δ 12.38 (s, 1H), 8.28 (d, J=2.2 Hz, 1H), 7.85 (m, 1H), 7.35 (m, 1H), 6.98 (d, J=2.2 Hz, 1H), 6.84 (d, J=2.2 Hz, 1H), 4.71-4.52 (m, 2H), 3.17 (m, 1H). $^{13}$C NMR (101 MHz, DMSO-$d_6$, 20° C.) δ 151.1 (Cq), 145.6 (Cq), 133.7 (Cq), 133.4 (m, J=29.3 Hz, 2×CH), 124.8 (CH), 121.3 (Cq), 119.7 (Cq), 114.1 (d, J=20.6 Hz, CH), 106.9 (d, J=4.5 Hz, CH), 87.4 (Cq), 85.4 (Cq), 58.8 (CH$_2$), 31.1 (Cq). $^{19}$F NMR (376 MHz, DMSO-d$_6$, 20° C.) δ −138.3 (m, 1F). HRMS (+ESI) calculée pour C$_{14}$H$_9$FN$_2$O$_2$ (M+H+): 273,0492 trouvée: 273,0489.

Example 74: 5-Fluoro-2-((5-(methoxymethyl)furan-2-yl)ethynyl)-1H-pyrrolo[2,3-b]pyridine 222

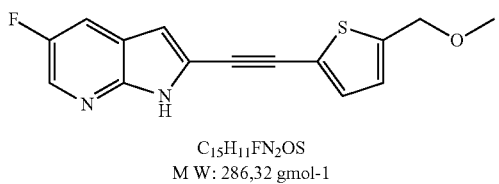 [SMILES: COCc1ccc(C#Cc2cc3cc(F)cnc3[nH]2)s1]

C$_{15}$H$_{11}$FN$_2$OS
M W: 286,32 gmol-1

5-Fluoro-2-((5-(methoxymethyl)furan-2-yl)ethynyl)-1H-pyrrolo[2,3-b]pyridine 222 was synthesized in 2 steps by an methylation reaction of the primary alcohol followed by a Sonogashira reaction starting rom the true alkyne and corresponding halogenated azaindole

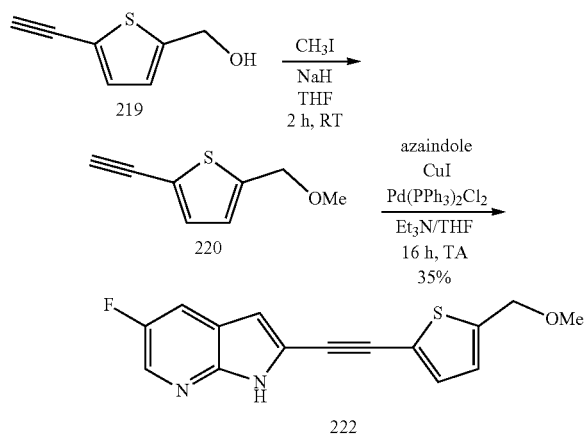

Example 74.1 Synthesis of 2-Ethynyl-5-(methoxymethyl)thiophene 220

Compound 220 was prepared according to procedure M as a brown oil (90%). Rf=0.25 (petroleum ether/ethyl acetate=9/1). IR (v, cm$^{-1}$, neat) 3400, 3250, 2980, 2052, 1620, 1433, 1269, 1087, 922, 831. $^1$H NMR (250 MHz, CDCl$_3$, 20° C.) δ 7.16-7.05 (m, 1H), 6.84-6.74 (m, 1H), 4.58-4.45 (m, 2H), 3.35 (s, 3H), 3.30 (s, 1H). $^{13}$C NMR (63 MHz, CDCl$_3$, 20° C.) δ 167.1 (Cq), 131.9 (CH), 117.1 (CH$_2$), 108.2 (Cq), 103.8 (CH), 79.1 (CH), 77.1 (Cq), 60.2 (CH$_3$). HRMS (+ESI) calculated for C$_{14}$H$_9$FN$_2$O$_2$ (M+H$^+$): 153,08976 found: 153,09459.

Example 74.2 Synthesis of 5-Fluoro-2-((5-(methoxymethyl)thiophen-2-yl)ethynyl)-1H-pyrrolo[2,3-b]pyridine 222

Compound 222 was synthesized according to procedure C2 and purified by flash column chromatography on silicagel (ethyl acetate/petroleum ether=1/9). The compound was obtained as a yellow solid (35%). mp: 154-156° C. Rf=0.31 (ethyl acetate/petroleum ether=1/9). IR (v, cm$^{-1}$, neat) 3114, 3047, 2929, 2855, 2203, 1587, 1523, 1503, 1471, 1427, 1394, 1375, 1295, 1242, 1219, 1175, 1142, 1087, 1007, 980, 950, 799, 769, 643, 566. $^1$H NMR (400 MHz, CDCl$_3$, 20° C.) δ 10.95 (s, 1H), 8.29 (s, 1H), 7.64 (m, 1H), 7.32-7.19 (m, 2H), 6.96 (m, 1H), 6.76 (s, 1H), 4.64 (s, 3H), 3.44 (s, 4H). $^{13}$C NMR (101 MHz, CDCl$_3$, 20° C.) δ 157.1 (Cq), 154.6 (Cq), 145.1 (Cq), 144.3 (Cq), 132.8 (Cq), 132.6 (d, J 16.2 Hz, CH), 126.3 (CH), 121.8 (d, J 47.8 Hz, CH), 120.6 (Cq), 114.4 (d, J 20.9 Hz, CH), 106.5 (d, J 4.5 Hz, CH), 87.4 (Cq), 84.8 (Cq), 69.1 (CH$_2$), 58.1 (CH$_3$). $^{19}$F NMR (376 MHz, DMSO-d$_6$, 20° C.) δ −137.3 (m, 1F). HRMS (+ESI) calculée pour C$_{14}$H$_9$FN$_2$O$_2$ (M+H$^+$): 287,06488 trouvée: 287,06469

Example 75: 4-({[4-(2-{5-Fluoro-1H-pyrrolo[2,3-b]pyridin-2-yl}ethynyl)phenyl]methoxy}methyl)piperidine 223

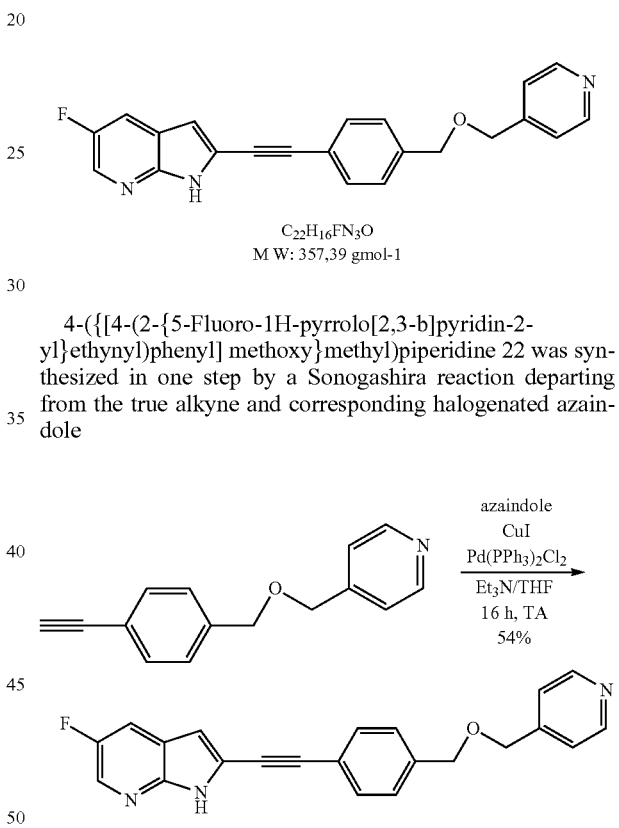

C$_{22}$H$_{16}$FN$_3$O
M W: 357,39 gmol-1

4-({[4-(2-{5-Fluoro-1H-pyrrolo[2,3-b]pyridin-2-yl}ethynyl)phenyl] methoxy}methyl)piperidine 22 was synthesized in one step by a Sonogashira reaction departing from the true alkyne and corresponding halogenated azaindole Compound 223 was synthesized according to procedure C2 from 4-{[(4-ethynylphenyl)methoxy]methyl}pyridine and purified by flash column chromatography on silicagel (ethyl acetate/petroleum ether=3/7). The compound was obtained as a yellow solid (54%). mp:>260° C. Rf=0.29 (ethyl acetate/petroleum ether=3/7). IR (v, cm$^{-1}$, neat) 2678, 1610, 1535, 1497, 1397, 1296, 1150, 1085, 1028, 880, 808, 760, 737, 591, 563. $^1$H NMR (400 MHz, DMSO-d$_6$, 20° C.) 12.40 (sl, 1H), 8.60 (s, 2H), 8.28 (m, 1H), 7.86 (m, 1H), 7.60 (d, J=7.8 Hz, 2H), 7.49 (d, J=7.8 Hz, 2H), 7.40 (sl, 2H), 6.84 (d, J 2.0 Hz, 1H), 4.64 (2 s, 4H). $^{13}$C NMR (101 MHz, DMSO-d$_6$, 20° C.) δ 156.8 (Cq), 154.34 (Cq), 150.1 (Cq), 147.7 (Cq), 145.6 (Cq), 139.9 (Cq), 133.4 (CH), 133.13 (CH), 131.8 (2×CH), 128.3 (2×CH), 121.6 (CH), 120.78 (CH), 120.1 (d, J 7.5 Hz, Cq), 114.3 (CH), 114.1 (CH), 106.7 (d, J 4.6 Hz, CH), 93.6 (Cq), 82.2 (Cq), 71.8 (CH$_2$), 70.4

(CH$_2$)$^{19}$F NMR (376 MHz, DMSO-d$_6$, 20° C.) δ −137.8 (m, 1F). HRMS (+ESI) calculated for C$_{14}$H$_9$FN$_2$O$_2$ (M+H$^+$): 258,135027, found: 258.135169.

Example 76: 2-[2-(4-Fluorophenyl)ethynyl]-1H-pyrrolo[2,3-b]pyridine 224

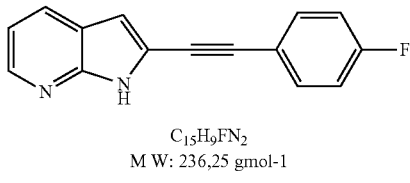 [SMILES: Fc1ccc(C#Cc2cc3cccnc3[nH]2)cc1]

C$_{15}$H$_9$FN$_2$
M W: 236,25 gmol-1

2-[2-(4-Fluorophenyl)ethynyl]-1H-pyrrolo[2,3-b]pyridine 224 was synthesized in one step by a Sonogashira reaction departing from the true alkyne

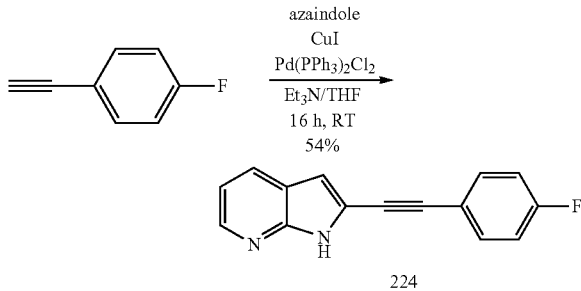

Compound 224 was synthesized according to procedure C2 from 1-ethynyl-4-fluoro-benzene and purified by flash column chromatography on silicagel (ethyl acetate/petroleum ether=3/7). The compound was obtained as a yellow solid (81%). mp:>260° C. Rf=0.29 (ethyl acetate/petroleum ether=3/7). IR (v, cm$^{-1}$, neat) 3117, 3056, 2979, 2877, 2817, 2703, 1536, 1397, 1359, 1228, 1197, 1155, 1020, 979, 935, 918, 833, 760, 652, 597. $^1$H NMR (400 MHz, DMSO-d$_6$, 20° C.) δ 12.23 (s, 1H), 8.29 (dd, J 4.6, 1.6 Hz, 1H), 7.97 (dd, J 7.9, 1.6 Hz, 1H), 7.71-7.61 (m, 2H), 7.37-7.27 (m, 2H), 7.11 (dd, J 7.9, 4.6 Hz, 1H), 6.83 (d, J 1.6 Hz, 1H). $^{13}$C NMR (101 MHz, DMSO-d$_6$, 20° C.) δ 163.9 (Cq), 161.4 (Cq), 148.8 (CH), 144.9 (CH), 134.1 (d, J=8.7 Hz, CH), 128.9 (CH), 119.9 (Cq), 119.2 (Cq), 118.59 (d, J=3.4 Hz, CH), 116.87 (d, J=5.9 Hz, CH), 116.6 (CH), 106.8 (CH), 99.9 (Cq), 92.1 (Cq), 82.4 (Cq). $^{19}$F NMR (376 MHz, DMSO-d$_6$, 20° C.) δ −109.7 (m, 1F). HRMS (+ESI) calculated for C$_{14}$H$_9$FN$_2$O$_2$ (M+H$^+$): 237,082253, for 237,082117.

Example 77: 2-((1H-Indol-4-yl)ethynyl)-5-fluoro-1H-pyrrolo[2,3-b]pyridine 225

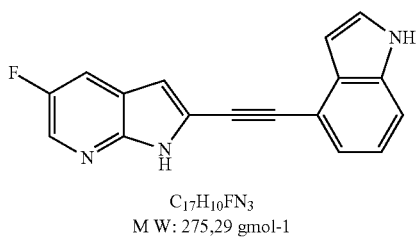 [SMILES: Fc1cnc2[nH]c(C#Cc3cccc4[nH]ccc34)cc2c1]

C$_{17}$H$_{10}$FN$_3$
M W: 275,29 gmol-1

2-((1H-Indol-4-yl)ethynyl)-5-fluoro-1H-pyrrolo[2,3-b]pyridine 225 was synthesized in one step by a Sonogashira reaction of true alkyne

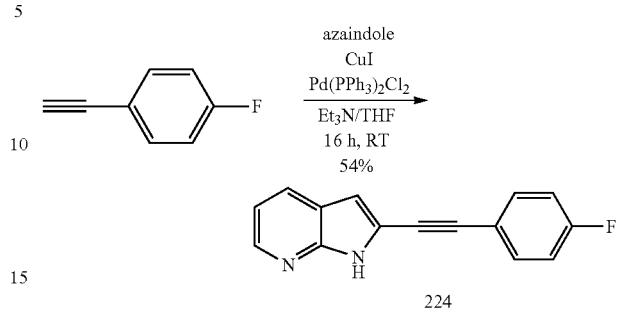

Compound 225 was synthesized according to procedure A from 4-ethynyl-1H-indole and purified by flash column chromatography on silicagel (ethyl acetate/petroleum ether=3/7). The compound was obtained as a yellow solid (15%). mp:>260° C. Rf=0.29 (ethyl acetate/petroleum ether=3/7 IR (v, cm$^{-1}$, neat) 3400, 3111, 3054, 2980, 2792, 2205, 1732, 1607, 1582, 1531, 1499, 1462, 1416, 1394, 1344, 1310, 1259, 1227, 1196, 1138, 1099, 1066, 985, 887, 803, 726, 604, 556. $^1$H NMR (400 MHz, DMSO-d$_6$, 20° C.) δ 12.30 (sl, 1H), 11.38 (sl, 1H), 8.25 (s, 1H), 7.83 (dt, J=6.5 Hz, 2H), 7.46 (dd, J=6.5 Hz, 2H), 7.30 (d, J=1.6 Hz, 1H), 6.77 (d, J=1.6 Hz, 1H), 6.53-6.48 (m, 1H). $^{13}$C NMR (101 MHz, DMSO-d$_6$, 20° C.) 145.6 (Cq), 136.4 (Cq), 132.6 (CH), 132.4 (CH), 128.1 (Cq), 127.4 (CH), 124.76 (CH), 124.33 (CH), 122.7 (Cq), 120.34 (Cq), 113.8 (d, J=20.9 Hz, CH), 112.5 (Cq), 111.8 (CH), 105.8 (CH), 102.1 (CH), 96.1 (Cq), 79.5 (Cq). $^{19}$F NMR (376 MHz, DMSO-d$_6$, 20° C.) δ −138.7 (m, 1F). HRMS (+ESI) calculated for C$_{14}$H$_9$FN$_2$O$_2$ (M+H$^+$): 276,093152, found 276,093345.

The invention claimed is:
1. Compound of formula II

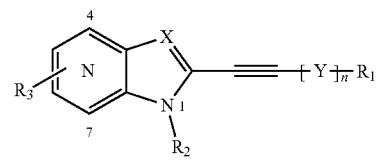

(II)

X being selected from N or C—R$_4$

Y being selected from an alkene or an alkyne, an aryl or a heteroaryl, an alkane comprising from 1 to 7 carbon atoms, n being an integer equal to 0 or 1;

R$_1$ being selected from aryl or heteroaryl selected from phenyl, pyrimidine, pyridine, thiophene, furan, triazole, oxazole, (aza)indole, (aza)indoline, (aza)benzimidazole optionally substituted at one or more positions with a group selected from:

Halogen, NO$_2$, CN, dimethyltriazene, trimethylammonium, aryliodonium,

NR$^a$R$^b$, SO$_2$NR$^a$R$^b$, CONR$^a$R$^b$, NR$^c$SO$_2$NR$^a$R$^b$, NR$^c$-CONR$^a$R$^b$, NR$^a$COR$^b$;

R$^a$, R$^b$ and R$^c$ are independently of each other H, (C$_1$-C$_7$) alkyl, aryl, heteroaryl, (C$_3$-C$_7$) carbocyclyl, (C$_1$-C$_7$) alkyl-aryl, (C$_1$-C$_7$) alkyl-heteroaryl, or R$^a$ and R$^b$ together form a (C$_3$-C$_7$) heterocyclyl;

Sn (Alkyl)$_3$, Alkyl is selected from methyl or n-butyl;

B(OH)$_2$, B(pinacol);

R$^d$, CH$_2$R$^d$;

R$^d$ represents H, (C$_1$-C$_7$)alkyl, aryl, heteroaryl, (C$_3$-C$_7$) heterocyclyl, (C$_3$-C$_7$) carbocyclyle, (C$_1$-C$_7$)alkyl-aryl, (C$_1$-C$_7$) alkyl-heteroaryl, (C$_1$-C$_7$) alkyl-(C$_3$-C$_7$) heterocyclyl, [(C$_1$-C$_7$) alkyl]$_n$-Z or a [(C$_1$-C$_7$) alkyl-Z]$_n$, Z being a heteroatom selected from N, O or S, in particular selected from NR$^a$R$^b$ or OR$^e$, and n being an integer comprised from 1 to 7;

OR$^e$, OAc, OTs, OTf, SR$^e$, SO$_2$R$^e$, COR$^e$, NR$^e$SO$_2$R$^e$, NHCOOR$^e$;

R$^e$ is H, (C$_1$-C$_7$)alkyl, aryl, heteroaryl, (C$_3$-C$_7$) heterocyclyl, (C$_3$-C$_7$) carbocyclyl, (C$_1$-C$_7$) alkyl-aryl, (C$_1$-C$_7$) alkyl-heteroaryl or (C$_1$-C$_7$) alkyl-(C$_3$-C$_7$) heterocyclyl;

R$_2$ being selected from:

H, SO$_2$Ph, COR$^e$, NR$^c$CONR$^a$R$^b$, COOR$^e$, OH, R$^d$;

R$_3$ being selected from:

Halogen, NO$_2$, CN, dimethyltriazene, trimethylammonium, aryliodonium,

NR$^a$R$^b$, SO$_2$NR$^a$R$^b$, CONR$^a$R$^b$, NR$^c$SO$_2$NR$^a$R$^b$, NR$^c$CONR$^a$R$^b$, NR$^a$COR$^b$;

Sn(Alkyl)$_3$, Alkyl being selected from methyl or n-butyl;

B(OH)$_2$, B (pinacol);

R$^d$, CH$_2$R$^d$;

OR$^e$, OAc, OTs, OTf, O(heteroaryl), especially O(HOBt), SR$^e$, SO$_2$R$^e$, COR$^e$, NR$^a$SO$_2$R$^e$, NHCOOR$^e$;

R$_4$ being selected from:

Halogen, CH$_2$NR$^a$R$^b$, R$^a$, COOR$^e$, CHO, CH$_2$OR$^e$;

wherein at least one of the substituents R$_1$, R$_2$, R$_3$ or R$_4$ comprises a radioelement selected from $^{18}$F, $^{11}$C, $^{123}$I and $^{124}$I.

2. A compound according to claim 1 of the general formula II-1:

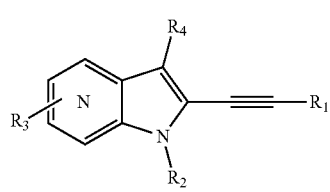

(II-1)

R$_1$, R$_2$, R$_3$ and R$_4$ being as previously defined in formula II; wherein at least one of the substituents R$_1$, R$_2$, R$_3$ or R$_4$ comprises a radioelement selected from $^{18}$F, $^{11}$C, $^{123}$I and $^{124}$I.

3. Compound according to claim 1, said compound being of general formula II-1:

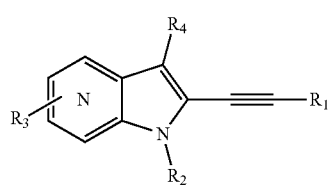

(II-1)

R$_2$, R$_3$ and R$_4$ being as previously defined in formula II;

R$_1$ being optionally labeled and selected from

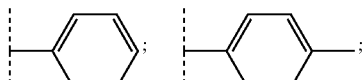

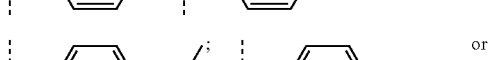

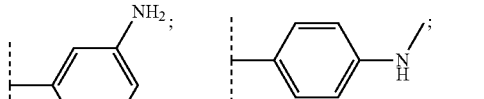

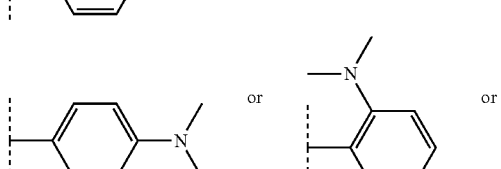

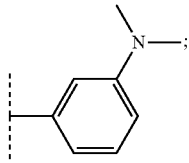

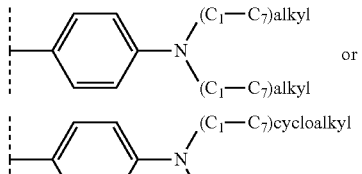

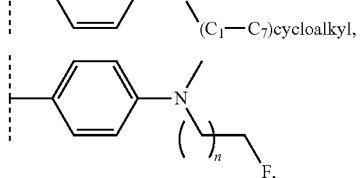

n being in particular comprised from 0 to 6;

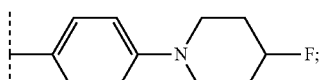

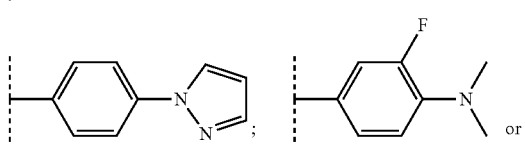

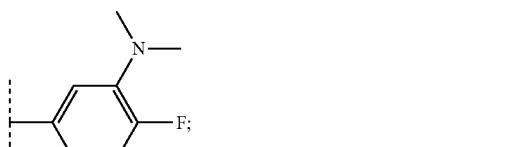

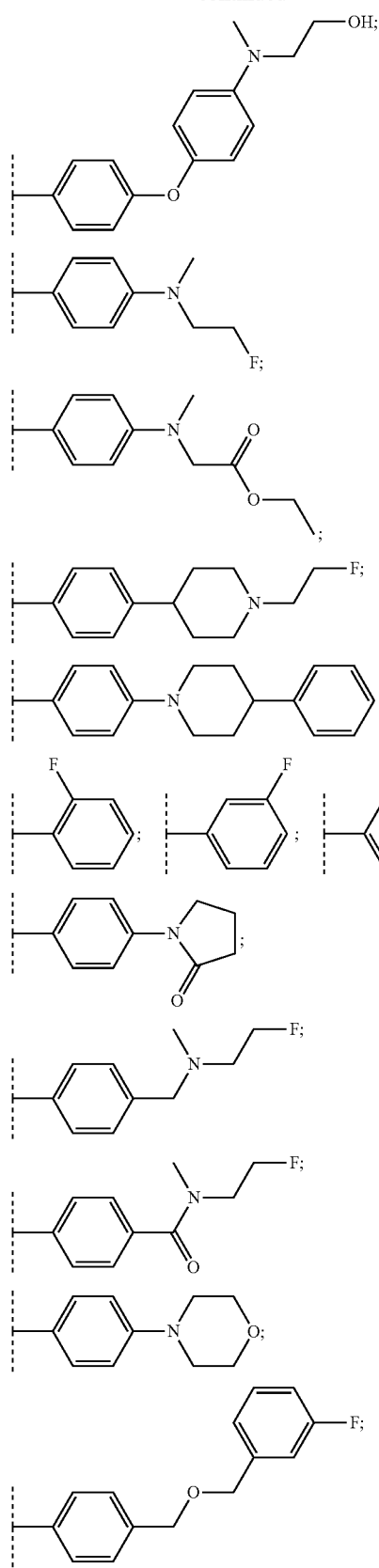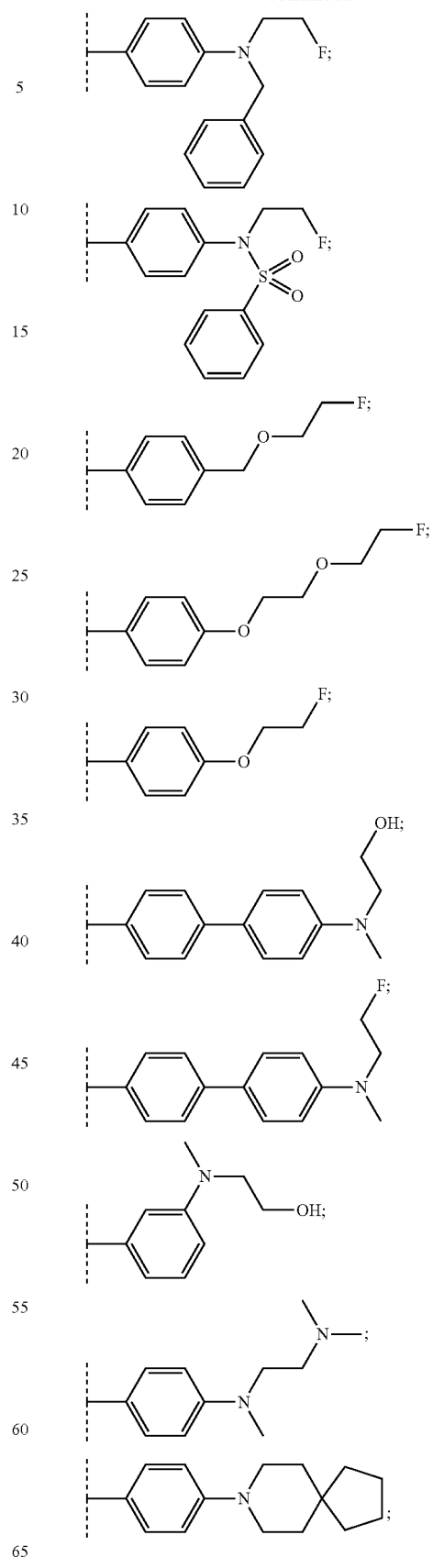

-continued

[chemical structures]

4. Compound according to claim 1, said compound being of general formula II-1:

(II-1)

[structure of formula II-1]

$R_1$, $R_3$ and $R_4$ being as previously defined in formula II;

$R_2$ being optionally labeled and selected from
- H;
- $(CH_2CH_2O)_n$—$CH_2CH_2F$, n being an integer equal to 0, 1 or 2;
- $SO_2Ph$;
- $COO^tBu$;
- $CH_2OCH_3$;
- $CH_2O(CH_2)_2OCH_3$;
- $COCH_3$;

[silyl group structure]

5. Compound according to claim 1, said compound being of general formula II-1:

(II-1)

[structure of formula II-1]

$R_1$, $R_2$ and $R_4$ being as previously defined in formula II;
$R_3$ is optionally labeled and selected from
- 6-Cl;
- 6-F;
- 5-F;
- 4-F;
- 6-(2-thienyl);
- 6-(3-thienyl);
- 6-(6-fluoro-3-pyridyl);
- 5-OMe;
- 6-morpholino;
- 5-morpholino;
- 6-Br;
- 4-Br;
- 4-Bpin;
- 5-Bpin.

6. Compound according to one of claim 1, said compound being of general formula II-1:

(II-1)

[structure of formula II-1]

$R_1$, $R_2$ et $R_3$ being as previously defined in formula II;
$R_4$ is selected from
- H;
- $(CH_2)_n$—N-alkyl, n being an integer equal to 0, 1 or 2.

7. Compound according to claim 1, said compound being of general formula II-1a:

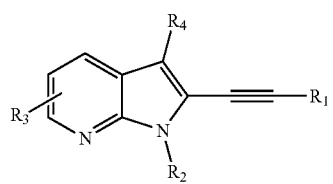
(II-1a)
$R_2$, $R_3$ and $R_4$ being as previously defined in formula II;
$R_1$ being optionally labeled and is selected from
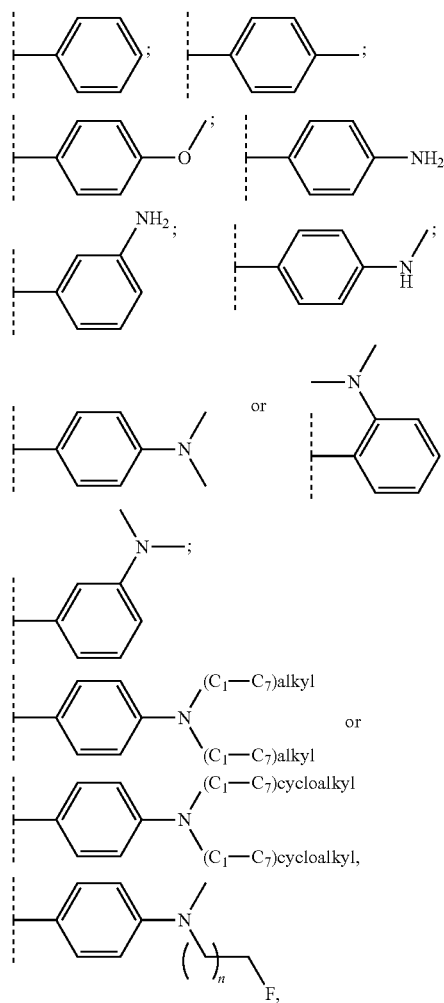
n being in particular from 0 to 6
-continued
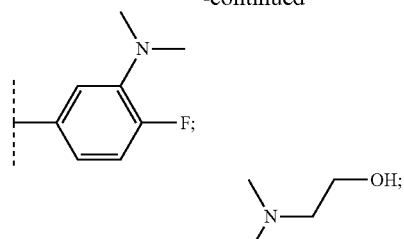
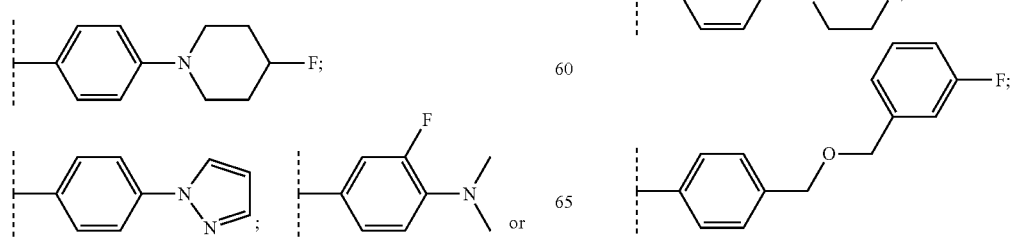

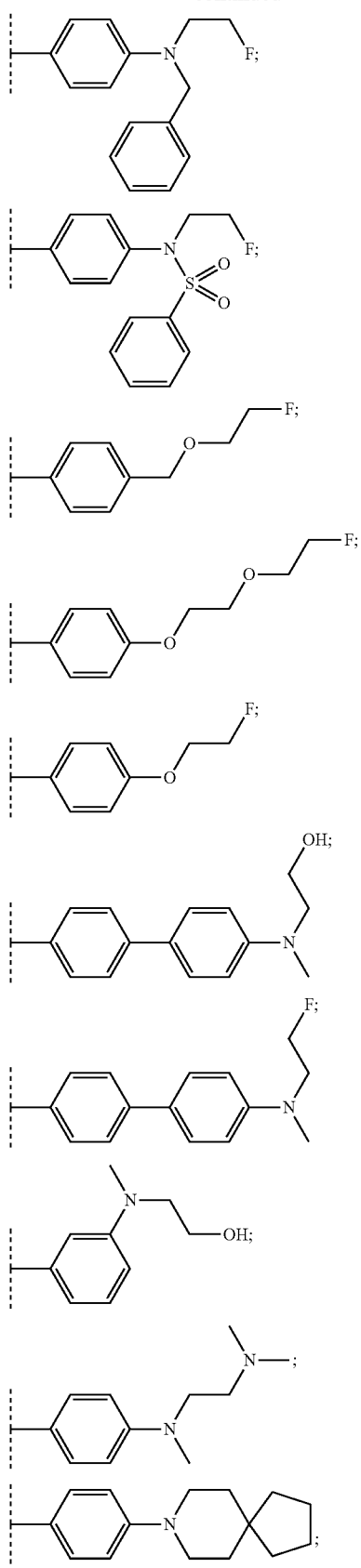
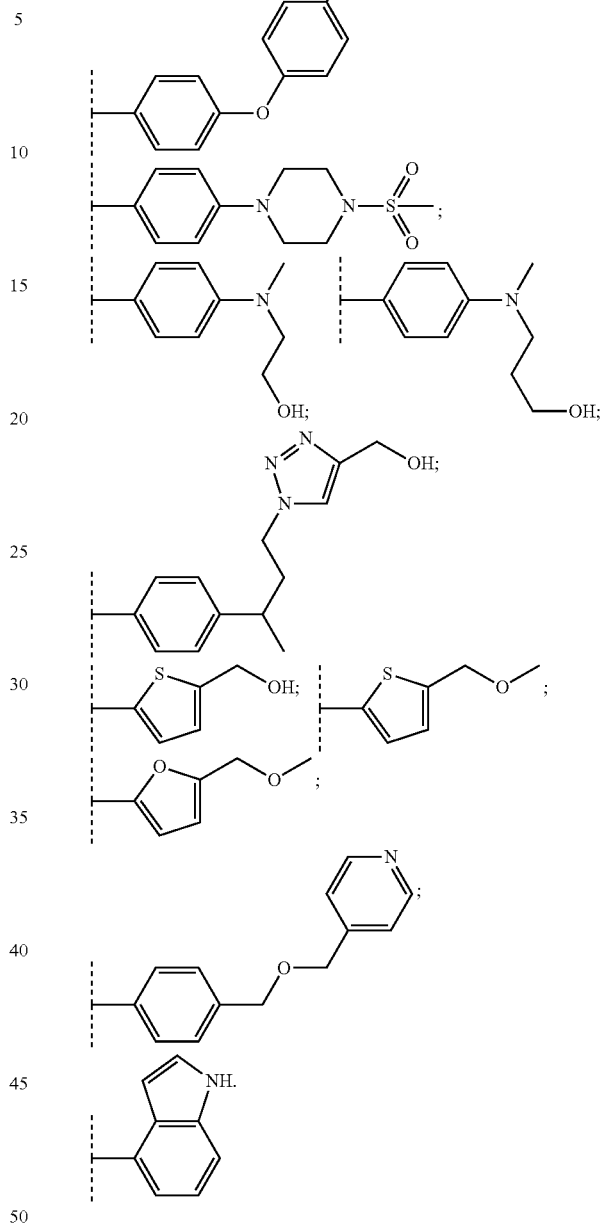
8. Compound according claim 1, said compound being of general formula II-2
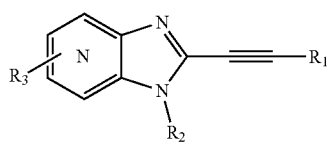
(II-2)
$R_1$, $R_2$ or $R_3$ being as defined above in formula II;
wherein at least one of the substituents $R_1$, $R_2$ or $R_3$ comprises a radioelement selected from $^{18}F$, $^{11}C$, $^{123}I$ and $^{124}I$.

9. Compound according to claim 1, said compound of formula II being chosen from compounds of the following formulas:
22a
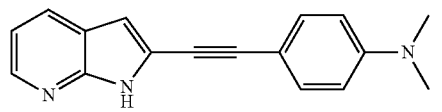
22b
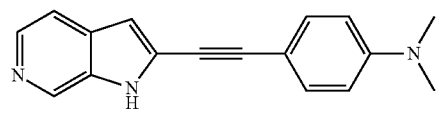
22c
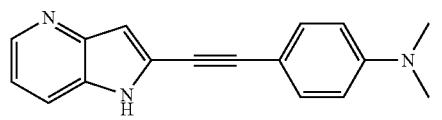
22d
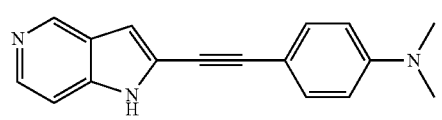
22e
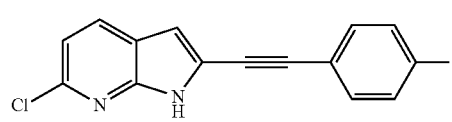
22f
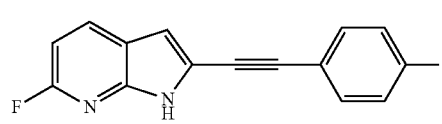
22g
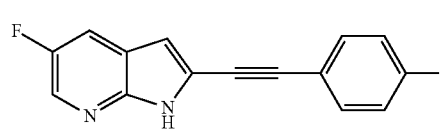
22h
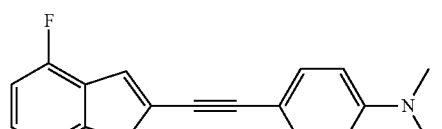
22i
22k
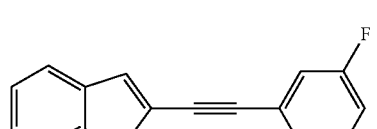
22m
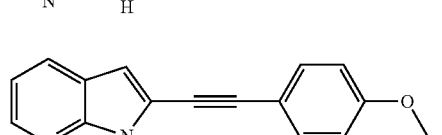
-continued
22n
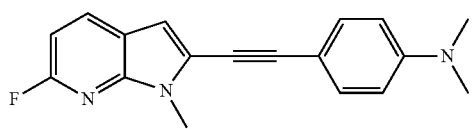
25a
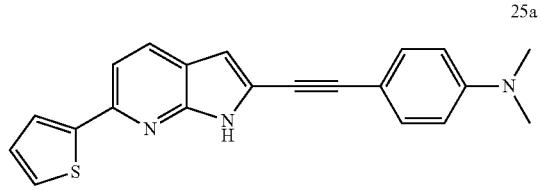
25b
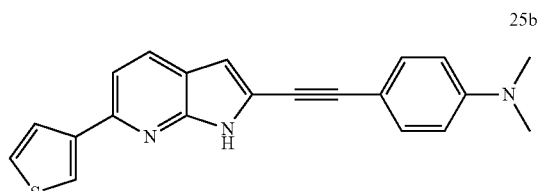
25c
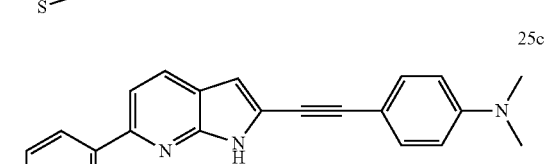
28
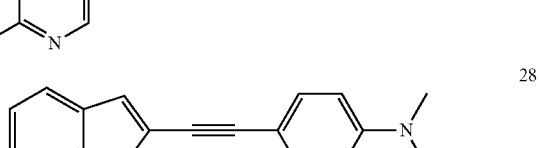
35
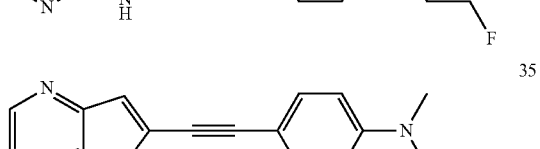
37
38
131
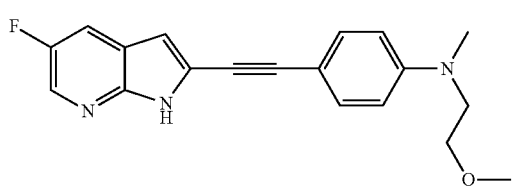

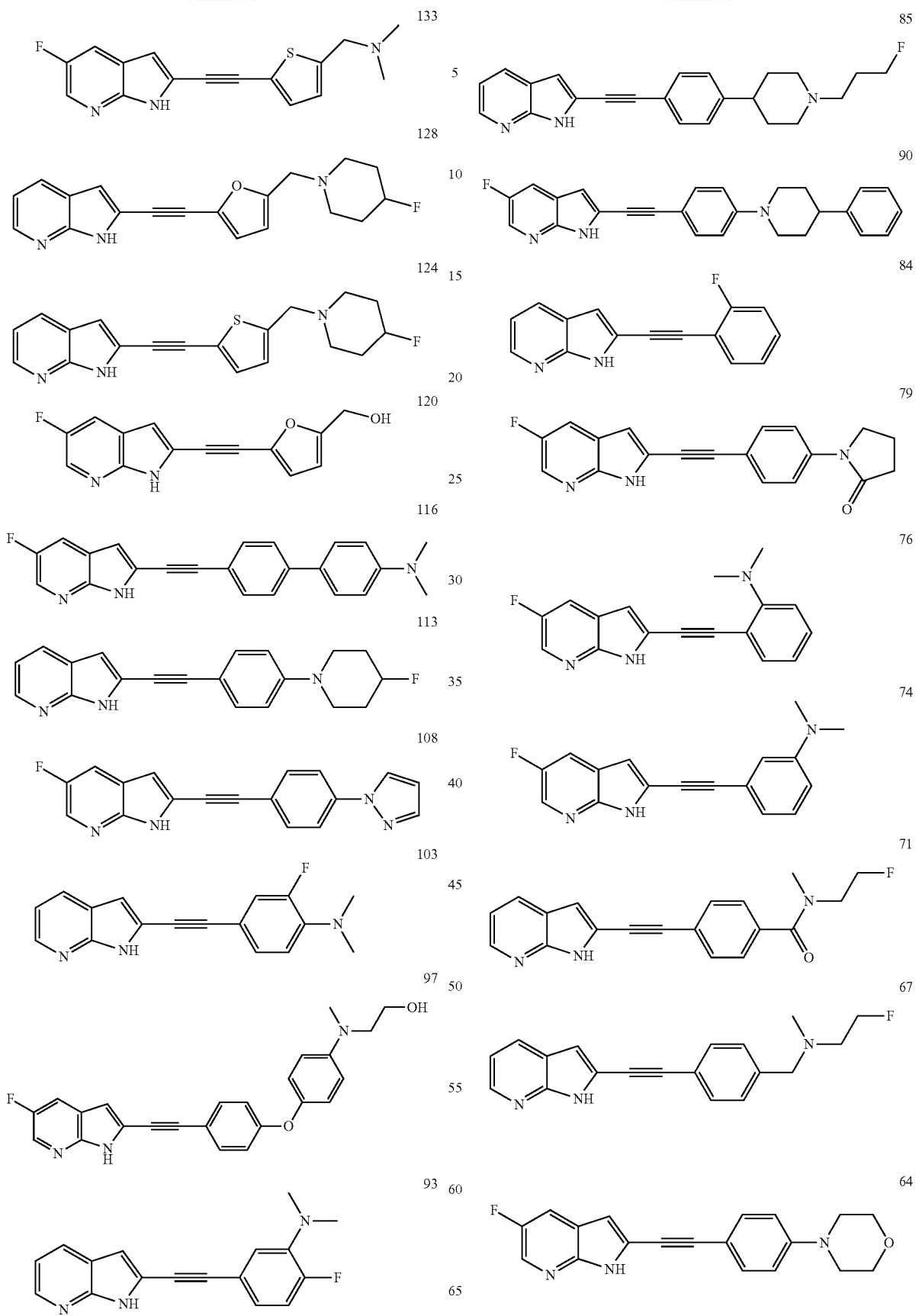

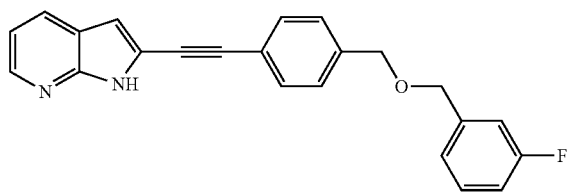
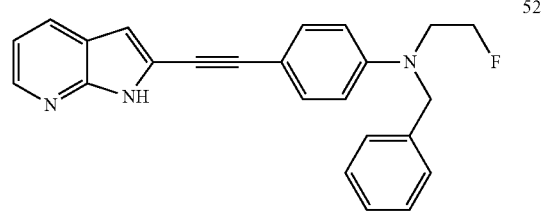
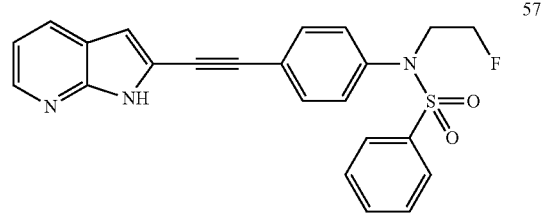
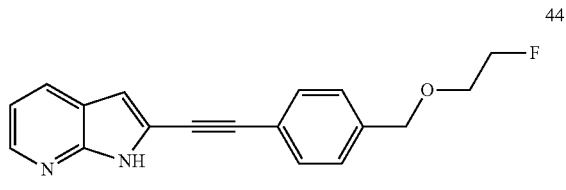
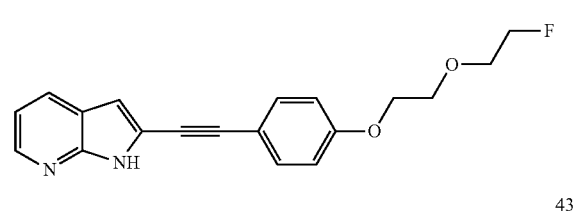
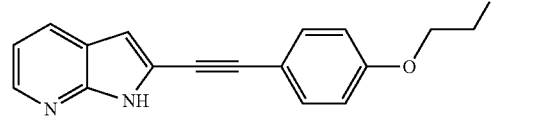
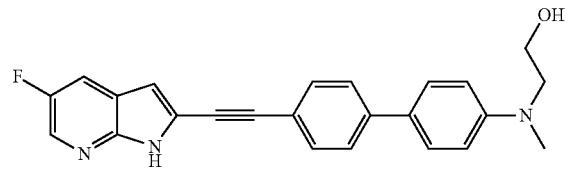
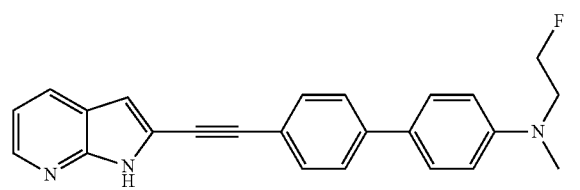
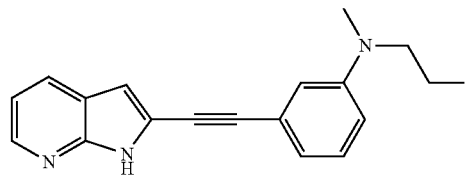
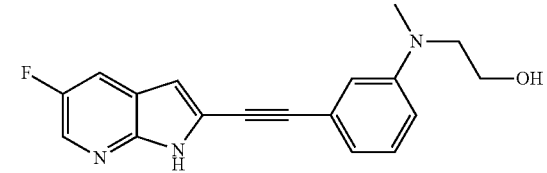
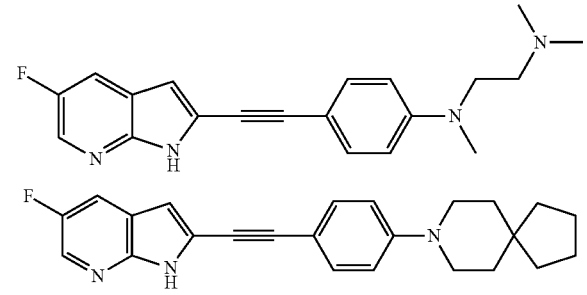
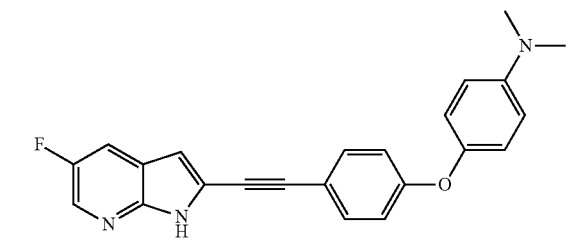
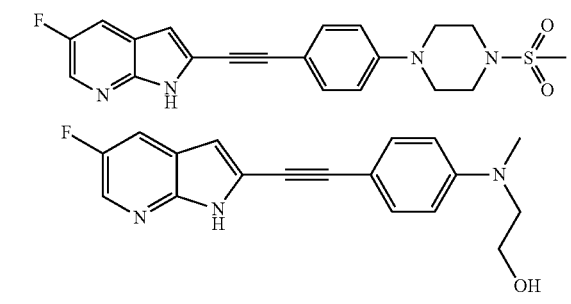
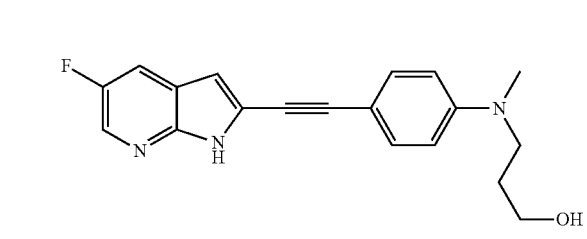
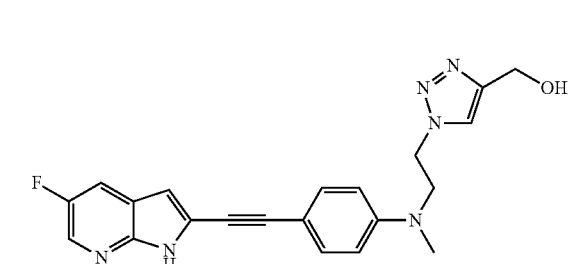

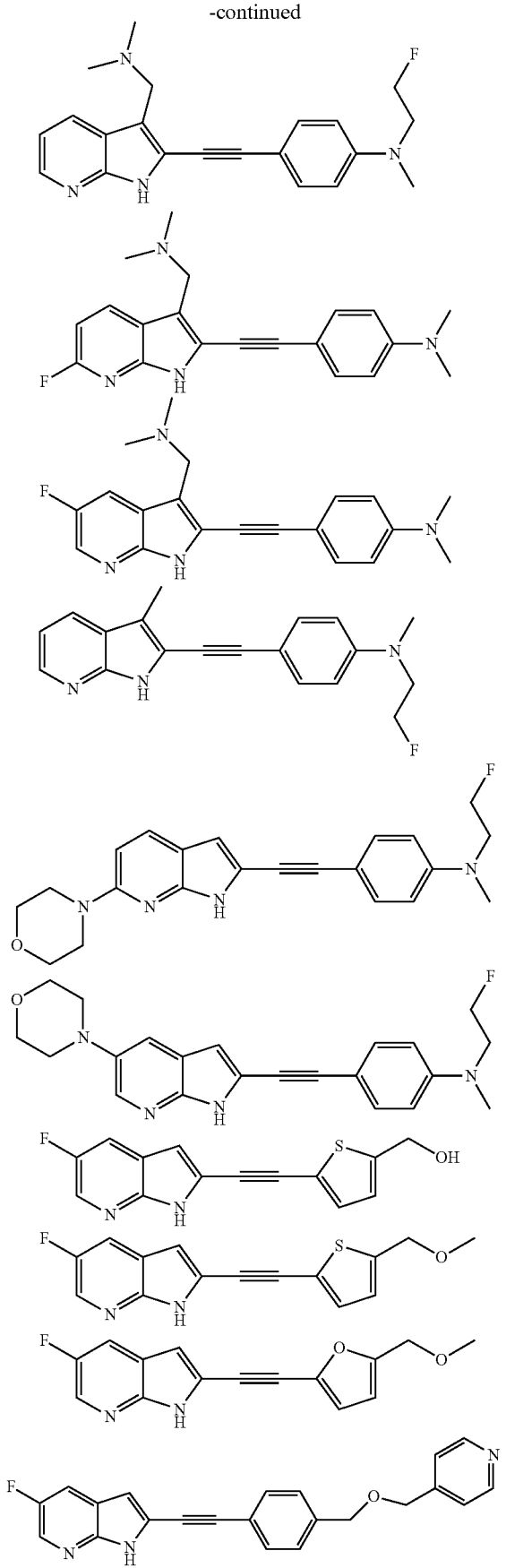
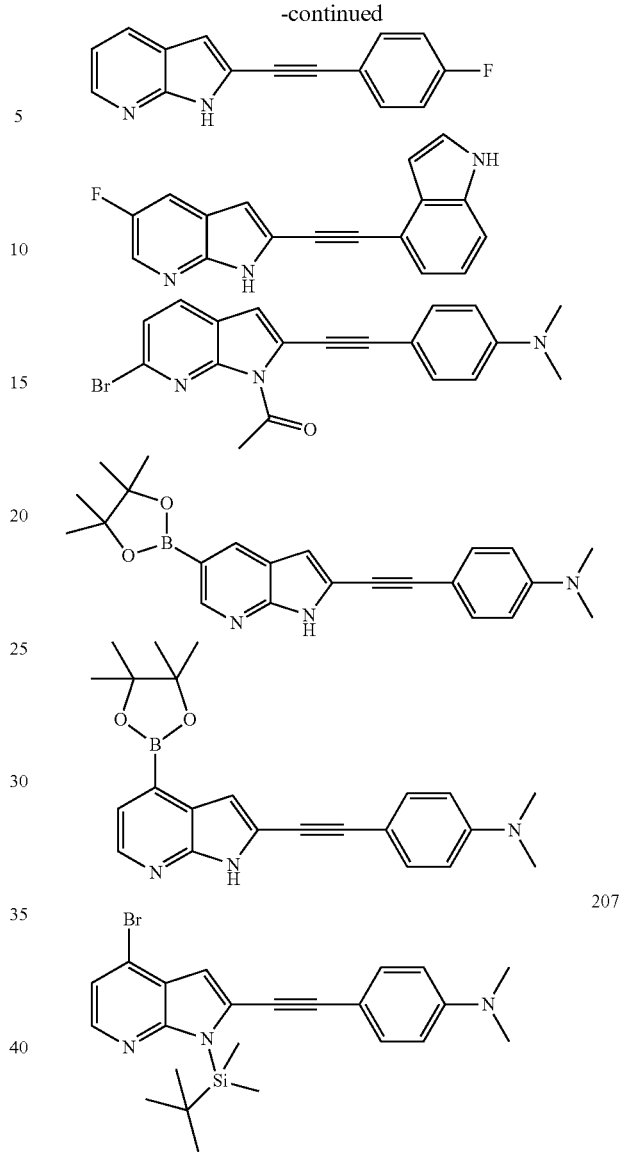

in a radio labelled state.

10. Method for diagnosing or in vivo imaging a subject having a neurodegenerative disease, comprising administering a compound of formula π wherein at least one of the substituents $R_1$, $R_2$, $R_3$ or $R_4$ comprises a radioelement selected from $^{18}F$, $^{11}C$, $^{123}I$ and $^{124}I$ according to claim 1, to said subject.

11. Method for diagnosing or in vivo imaging a subject having a neurodegenerative disease, comprising administering a compound of formula II wherein at least one of the substituents $R_1$, $R_2$, $R_3$ or $R_4$ comprises a radioelement selected from $^{18}F$, $^{11}C$, $^{123}I$ and $^{124}I$ according to claim 1, to said subject, wherein the in vivo imaging method is positron emission tomography or single photon emission tomography.

12. Method for diagnosing or in vivo imaging a subject having a neurodegenerative disease, comprising administering a compound of formula II wherein at least one of the substituents $R_1$, $R_2$, $R_3$ or $R_4$ comprises a radioelement selected from $^{18}F$, $^{11}C$, $^{123}I$ and $^{124}I$ according to claim 1, to said subject, wherein said neurodegenerative disease is amyloidopathy, alpha-synucleinopathy or tauopathy.

* * * * *